(12) United States Patent
Luo et al.

(10) Patent No.: US 11,242,395 B2
(45) Date of Patent: *Feb. 8, 2022

(54) ANTI-CD137 MOLECULES AND USE THEREOF

(71) Applicant: Adagene Inc., Grand Cayman (KY)

(72) Inventors: Peter Peizhi Luo, Suzhou (CN); Fangyong Du, Suzhou (CN); Yan Li, Suzhou (CN); Guizhong Liu, Suzhou (CN); Jun Chen, Suzhou (CN); Xiaohong She, Suzhou (CN); Peter Cheung, Suzhou (CN)

(73) Assignee: Adagene Inc., Grand Cayman (KY)

( * ) Notice: Subject to any disclaimer, the term of this patent is extended or adjusted under 35 U.S.C. 154(b) by 210 days.

This patent is subject to a terminal disclaimer.

(21) Appl. No.: 16/108,018

(22) Filed: Aug. 21, 2018

(65) Prior Publication Data
US 2019/0055314 A1    Feb. 21, 2019

Related U.S. Application Data

(63) Continuation-in-part of application No. PCT/CN2017/098332, filed on Aug. 21, 2017.

(51) Int. Cl.
| C07K 16/28 | (2006.01) |
| A61K 39/395 | (2006.01) |
| A61K 39/00 | (2006.01) |
| A61P 35/00 | (2006.01) |
| A61K 45/06 | (2006.01) |

(52) U.S. Cl.
CPC ...... *C07K 16/2878* (2013.01); *A61K 39/3955* (2013.01); *A61K 39/39591* (2013.01); *A61P 35/00* (2018.01); *C07K 16/2818* (2013.01); *A61K 45/06* (2013.01); *A61K 2039/505* (2013.01); *A61K 2039/545* (2013.01); *C07K 2317/21* (2013.01); *C07K 2317/33* (2013.01); *C07K 2317/52* (2013.01); *C07K 2317/55* (2013.01); *C07K 2317/56* (2013.01); *C07K 2317/75* (2013.01); *C07K 2317/76* (2013.01); *C07K 2317/92* (2013.01); *C07K 2317/94* (2013.01)

(58) Field of Classification Search
CPC .......... A61K 39/39541; A61K 39/3955; A61K 2039/505; C07K 16/2896; C07K 16/287; C07K 16/2818; C07K 2317/92; C07K 2317/33; C07K 2317/55; C07K 14/70596
See application file for complete search history.

(56) References Cited

U.S. PATENT DOCUMENTS

| 4,399,216 A | 8/1983 | Axel et al. |
| 4,634,665 A | 1/1987 | Axel et al. |
| 4,816,567 A | 3/1989 | Cabilly et al. |
| 5,179,017 A | 1/1993 | Axel et al. |
| 5,648,237 A | 7/1997 | Carter |
| 5,677,425 A | 10/1997 | Axel et al. |
| 5,994,619 A | 11/1999 | Axel et al. |
| 6,172,197 B1 | 1/2001 | Axel et al. |
| 6,291,158 B1 | 9/2001 | Bodmer et al. |
| 6,582,915 B1 | 6/2003 | Stice et al. |
| 6,593,081 B1 | 7/2003 | McCafferty et al. |
| 6,696,245 B2 | 2/2004 | Winter et al. |
| 6,765,087 B1 | 7/2004 | Casterman et al. |
| 6,838,254 B1 | 1/2005 | Hamers et al. |
| 6,887,673 B2 | 5/2005 | Kunkel et al. |
| 6,933,368 B2 | 8/2005 | Co et al. |
| 7,138,500 B1 | 11/2006 | Goodwin et al. |
| 7,214,493 B2 | 5/2007 | Kunkel et al. |
| 7,288,638 B2 | 10/2007 | Jure-Kunkel et al. |
| 7,659,384 B2 | 2/2010 | Jure-Kunkel et al. |
| 8,137,667 B2 | 3/2012 | Jure-Kunkel et al. |
| 8,337,850 B2 | 12/2012 | Ahrens et al. |
| 8,716,452 B2 | 5/2014 | Jure-Kunkel et al. |
| 8,821,867 B2 | 9/2014 | Ahrens et al. |
| 9,382,328 B2 | 7/2016 | Jure-Kunkel et al. |
| 9,468,678 B2 | 10/2016 | Ahrens et al. |
| 10,174,122 B2 | 1/2019 | Kwon et al. |
| 10,279,038 B2 | 5/2019 | Bobrowicz et al. |
| 10,279,039 B2 | 5/2019 | Bobrowicz et al. |
| 10,279,040 B1 | 5/2019 | Bobrowicz et al. |
| 10,350,292 B1 | 7/2019 | Bobrowicz et al. |
| 2003/0118588 A1 | 6/2003 | Diehl et al. |

(Continued)

FOREIGN PATENT DOCUMENTS

| AU | 2013202755 A1 | 5/2013 |
| CN | 1357009 | 7/2002 |

(Continued)

OTHER PUBLICATIONS

Paul. Fundamental Immunology, 3rd Edition, Raven Press, New York, Chapter 8, pp. 292-295, 1993 (Year: 1993).*
MacCallum et al. Journal of Molecular Biology, 262:732-745, 1996 (Year: 1996).*
Casset et al. Biochemical and Biophysical Research Communications, 307:198-205, 2003 (Year: 2003).*
Vajdos et al. Journal of Molecular Biology, Jul. 5, 2002;320(2):415-28 (Year: 2002).*
Ferrara et al. mABs, 2015; 7(1): 32-41 (Year: 2015).*
Bird et al., (1988). "Single-chain antigen-binding proteins," Science, 242(4877):423-426.
Broll, (2001). "CD137 Expression in Tumor Vessel Walls: High Correlation With Malignant Tumors," Amer. J. Clin. Pathol., 115(4):543-549.

(Continued)

*Primary Examiner* — Vanessa L. Ford
*Assistant Examiner* — Sandra E Dillahunt
(74) *Attorney, Agent, or Firm* — Morrison Foerster LLP

(57) ABSTRACT

The present disclosure provides antibodies that bind to human CD137 or antigen binding fragments thereof, nucleic acid encoding the same, therapeutic compositions thereof, and their use to enhance T-cell function to upregulate cell-mediated immune responses and for the treatment of T cell dysfunctional disorders, such as tumor immunity, and for the treatment of cancer.

29 Claims, 55 Drawing Sheets

Specification includes a Sequence Listing.

(56) References Cited

U.S. PATENT DOCUMENTS

| | | |
|---|---|---|
| 2006/0153808 A1 | 7/2006 | Cristofanilli et al. |
| 2007/0117809 A1 | 5/2007 | Fridman |
| 2011/0059045 A1 | 3/2011 | Bermejo et al. |
| 2016/0145604 A1 | 5/2016 | Du et al. |
| 2016/0368998 A1 | 12/2016 | Jure-Kunkel et al. |
| 2018/0194851 A1 | 7/2018 | Ahrens et al. |
| 2018/0344870 A1 | 12/2018 | Xiao et al. |
| 2019/0015508 A1 | 1/2019 | Bobrowicz et al. |
| 2019/0241662 A1 | 8/2019 | Luo et al. |
| 2019/0241886 A1 | 8/2019 | Du et al. |
| 2020/0369776 A1 | 11/2020 | Luo et al. |
| 2020/0377608 A1 | 12/2020 | Luo et al. |
| 2021/0207126 A1 | 7/2021 | Luo et al. |

FOREIGN PATENT DOCUMENTS

| | | | |
|---|---|---|---|
| CN | 1749270 | A | 3/2006 |
| CN | 1867585 | A * | 11/2006 |
| CN | 1867585 | B * | 2/2011 |
| CN | 102482347 | A | 5/2012 |
| CN | 105296433 | A | 2/2016 |
| CN | 106163556 | A | 11/2016 |
| CN | 109963873 | A | 7/2019 |
| CN | 110546166 | A | 12/2019 |
| EP | 0368684 | B1 | 3/1994 |
| EP | 0338841 | B1 | 3/1995 |
| EP | 0616640 | B1 | 9/2004 |
| EP | 2161336 | A1 | 3/2010 |
| WO | WO-1987004462 | A1 | 7/1987 |
| WO | WO-1989001036 | A1 | 2/1989 |
| WO | WO-1996032495 | A1 | 10/1996 |
| WO | WO-2000029445 | A1 | 5/2000 |
| WO | WO-2002053596 | A2 | 7/2002 |
| WO | WO-2002055106 | A2 | 7/2002 |
| WO | WO-2003002609 | A2 | 1/2003 |
| WO | WO-2003015711 | A2 | 2/2003 |
| WO | WO-2003040170 | A2 | 5/2003 |
| WO | WO-2003048731 | A2 | 6/2003 |
| WO | WO-2003074678 | A2 | 9/2003 |
| WO | WO-2004003019 | A3 | 1/2004 |
| WO | WO-2004010947 | A2 | 2/2004 |
| WO | WO-2004016805 | A2 | 2/2004 |
| WO | WO-2004058821 | A2 | 7/2004 |
| WO | WO-2004081026 | A2 | 9/2004 |
| WO | WO-2004101790 | A1 | 11/2004 |
| WO | WO-2005035572 | A2 | 4/2005 |
| WO | WO-2005035584 | A1 | 4/2005 |
| WO | WO-2005120568 | A1 | 12/2005 |
| WO | WO-2006029220 | A2 | 3/2006 |
| WO | WO-2006066568 | A2 | 6/2006 |
| WO | WO-2006079372 | A1 | 8/2006 |
| WO | WO-2006129163 | A1 | 12/2006 |
| WO | WO-2007059782 | A1 | 5/2007 |
| WO | WO-2009022215 | A1 | 2/2009 |
| WO | WO-2009025846 | A2 | 2/2009 |
| WO | WO-2009079335 | A1 | 6/2009 |
| WO | WO-2010081173 | A2 | 7/2010 |
| WO | WO-2015/094123 | A1 | 6/2015 |
| WO | WO-2016130898 | A2 | 8/2016 |
| WO | WO-2016130986 | A1 | 8/2016 |
| WO | WO-2016134358 | A1 | 8/2016 |
| WO | WO-2016200645 | A1 | 12/2016 |
| WO | WO-2017011580 | A3 | 1/2017 |
| WO | WO-2017049452 | A1 | 3/2017 |
| WO | WO-2017/112811 | A1 | 6/2017 |
| WO | WO-2017106372 | A1 | 6/2017 |
| WO | WO-2017106656 | A1 | 6/2017 |
| WO | WO-2017140826 | A1 | 8/2017 |
| WO | WO-2017/151940 | A2 | 9/2017 |
| WO | WO-2017194265 | A1 | 11/2017 |
| WO | WO-2018091740 | A2 | 5/2018 |
| WO | 2018127787 | A1 † | 7/2018 |
| WO | WO-2018191502 | A2 | 10/2018 |
| WO | WO-2018/199595 | A1 | 11/2018 |
| WO | WO-2018202649 | A1 | 11/2018 |
| WO | WO-2018209701 | A1 | 11/2018 |
| WO | WO-2019014328 | A2 | 1/2019 |
| WO | WO-2019020774 | A2 | 1/2019 |
| WO | WO-2019/036855 | A1 | 2/2019 |
| WO | WO-2019/037711 | A1 | 2/2019 |
| WO | WO-2019036842 | A1 | 2/2019 |
| WO | WO-2019036856 | A1 | 2/2019 |
| WO | WO-2019105468 | A1 | 6/2019 |
| WO | WO-2019148445 | A1 | 8/2019 |

OTHER PUBLICATIONS

Cheuk et al., (2004). "Role of 4-1BB:4-1BB ligand in cancer immunotherapy," Cancer Gene Therapy, 11(3): 215-226.

Croft, (2009). "The role of TNF superfamily members in T-cell function and diseases," Nat Rev Immunol., 9:271-285.

Drenkard, (2007). "CD137 is expressed on blood vessel walls at sites of Inflammation and enhances monocyte migratory activity," FASEB Journal, 21: 456-463.

Feldhaus et al., (2003). "Flow-cytometric isolation of human antibodies from a non-immune Saccharomyces cerevisiae surface display library," Nat Biotechnol, 21(2):163-170.

International Search Report and Written Opinion of the International Searching Authority dated Feb. 27, 2019, issued for PCT/CN2018/118631, filed Nov. 30, 2018, 15 pages.

International Search Report and Written Opinion of the International Searching Authority dated May 25, 2018, issued for PCT/CN2017/098332, filed Aug. 21, 2017, 20 pages.

International Search Report and Written Opinion of the International Searching Authority dated Nov. 14, 2018, issued for PCT/CN2018/101501, filed Aug. 21, 2018, 12 pages.

International Search Report and Written Opinion of the International Searching Authority dated Sep. 7, 2018, issued for PCT/CN2017/0114247, filed Dec. 1, 2017, 14 pages.

Li, (2014). "Expression of human CD137 and CD28 proteins and preparation of their specific monoclonal antibodies," Chinese Master's Theses Full-Text Database Medicine And Health Sciences 2:E059-133; pp. 1-73. English Abstract Only.

Lynch (2008). "The promise of 4-1BB (CD137)-mediated immunomodulation and the immunotherapy of cancer," Immunol Rev., 222(1):277-286.

Martinez-Forero et al., (2013). "T cell costimulation with anti-CD137 monoclonal antibodies is mediated by K63-polyubiquitin-dependent signals from endosomes," J Immunol., 190(12):6694-706.

Narazaki et al., (2010). "CD137 agonist antibody prevents cancer 1-50 recurrence: contribution of CD 13 7 on both hematopoietic and nonhematopoietic cells," Immunobiology. 10(115):1941-1948.

Olofsson, (2008). "CD137 is expressed in human atherosclerosis and promotes development of plaque inflammation in hypercholesterolemic mice," Circulation, 117(10):1292-1301.

Peters et al., (2012). "Engineering an improved IgG4 molecule with reduced disulfide bond heterogeneity and increased Fab domain thermal stability," J Biol Chem. 287(29):24525-33.

Seaman, (2007). "Genes that distinguish physiological and pathological angiogenesis," Cancer Cell, 11(6): 539-554.

Shi et al., (2006). "Augmented antitumor effects of radiation therapy by 4-1BB antibody (BMS-469492) treatment," Anticancer Res., 26(5A):3445-53.

Tian et al., (2015). "In-depth analysis of subclass-specific conformational preferences of IgG antibodies," IUCrJ. 2(Pt 1):9-18.

Vinay et al., (2006). "Dual immunoregulatory pathways of 4-1BB signaling," J Mol Med, 84(9):726-736.

Wang et al., (2009). "Immune regulation by 4-1BB and 4-1BBL: complexities and challenges," Immunological Reviews, 229(1):192-215.

Wei et al., (2013). "Combinatorial PD-1 blockade and CD137 activation has therapeutic efficacy in murine cancer models and synergizes with cisplatin," PLoS One. 8(12):1-11.

Xiao et al., (2007). "Soluble PD-1 facilitates 4-1BBL-triggered antitumor immunity against murine H22 hepatocarcinoma in vivo," Clin Cancer Res., 13(6):1823-30.

(56) References Cited

OTHER PUBLICATIONS

Yi et al., (2009). "Major Region Localization and Structural Analysis of Ligand Recognition in Mouse 4-1 BB Molecule," Chin. J. Microbiol. Immunol. 4(29):343-344. Abstract Only.
Yonezawa et al., (2015) "Boosting Cancer Immunotherapy with 1-3, 6-33 Anti-CD137 Antibody Therapy," Clinical Cancer Research. 14(21):3113-3120.
Guinn et al., (1999). "4-1BBL Cooperates With B7-1 and B7-2 in Converting a B Cell Lymphoma Cell Line Into a Long-Lasting Antitumor Vaccine," J. Immunol., 162(8):5003-10.
International Search Report and Written Opinion of the International Searching Authority dated Sep. 4, 2020, issued for PCT/CN2020/094371, filed Jun. 4, 2020, 14 pages.
Martinet et al., (2000). "Immunomodulatory Gene Therapy With Interleukin 12 and 4-1BB Ligand: Long-Term Remission of Liver Metastases in a Mouse Model," J Natl Cancer Inst., 92(11):931-6.
Melero et al., (1998). "Amplification of Tumor Immunity by Gene Transfer of the Co-Stimulatory 4-1BB Ligand: Synergy With the CD28 Co-Stimulatory Pathway," Eur. J. Immunol., 28(3):1116-21.
Shao et al., (2011). "CD137 Ligand, a member of the tumor necrosis factor family, regulates immune responses via reverse signal transduction," J. Leukoc. Biol., 89: 21-29.
Shao et al., (2015). "Trogocytic CD137 transfer causes an internalization of CD137 ligand on murine APCs leading to reduced T cell costimulation," J. Leukocyte Biol., 97:909-919.
Tolcher et al., (2017). "Phase Ib Study of Utomilumab (PF-05082566), a 4-1BB/CD137 Agonist, in Combination with Pembrolizumab (MK-3475) in Patients with Advanced Solid Tumor," Clin Cancer Res., 23(18):5349-5357.
Xiang, (1999). "Expression Of Co-Stimulatory 4-1bb Ligand Induces Significant Tumor Regression And Protective Immunity," Cancer Biother. Radiopharm., 14(5):353-61.
ClinicalTrials.org, (2019). "Adagene (Suzhou) Limited, NCT03802955: Study of ADG106 With Advanced or Metastatic Solid Tumors and/or Non-Hodgkin Lymphoma," Available online at <https://clinicaltrials.gov/ct2/show/NCT0380295514> obtained on May 21, 2021, 5 pages.
Committee for Medicinal Products for Human Use (CHMP). Assessment Report For Yervoy (ipilirnumab). CHMP assessment report EMNCHMP/557664/2011. May 19, 2011(May 19, 2011) pp. 1-71.
Extended European Sear Report and Opinion for European Patent Application No. 18847500.8, dated Apr. 22, 2021, 8 pages.
Extended European Sear Report and Opinion for European Patent Application No. 18683687.6, dated Jul. 30, 2021, 10 pages.
Ferrara et al., (2018). "Anti-CTLA-4 immunotherapy does not deplete FOXP3+ regulatory T cells (Tregs) in human cancers—Letter," Clin. Cancer Res, 25(11):3468.
Gerspach et al., (2006). "Target-selective activation of a TNF prodrug by urokinase-type plasminogen activator (uPA) mediated proteolytic processing at the cell surface," Cancer Immunol Immunother, 55(12):1590-1600.
Ha et al., (2019). "Differential control of human Treg and effector T cells in tumor immunity by Fc-engineered anti-CTLA-4 antibody," PNAS, 116(2):609-618.
He et al., (2017). "Remarkably similar CTLA-4 binding properties of therapeutic ipilirnumab and tremelimumab antibodies," Oncotarget 8:67129-67139.
Hurwitz et al., (1998). "CTLA-4 blockade synergizes with tumor-derived granulocyte-macrophage colony-stimulating factor for treatment of an experimental mammary carcinoma," Proc Natl Acad Sci USA 95 (17):10067-71.
International Search Report and Written Opinion of the International Searching Authority dated Apr. 28, 2019, issued for PCT/CN2019/074580, filed Feb. 2, 2019, 15 pages.
International Search Report and Written Opinion of the International Searching Authority dated Feb. 18, 2021, issued for PCT/CN2020/094278, filed Jun. 4, 2020, 17 pages.
International Search Report and Written Opinion of the International Searching Authority dated Jan. 27, 2021, issued for PCT/CN2020/090073, filed May 13, 2020, 16 pages.
International Search Report and Written Opinion of the International Searching Authority dated Jan. 27, 2021, issued for PCT/CN2020/115795, filed Sep. 17, 2020, 14 pages.
International Search Report and Written Opinion of the International Searching Authority dated May 8, 2019, issued for PCT/CN2019/074581, filed Feb. 2, 2019, 13 pages.
International Search Report and Written Opinion of the International Searching Authority dated Nov. 6, 2018, issued for PCT/CN2018/075065, filed Feb. 2, 2018, 16 pages.
International Search Report and Written Opinion of the International Searching Authority dated Nov. 7, 2018, issued for PCT/CN2018/075064, filed Feb. 2, 2018, 17 pages.
International Search Report and Written Opinion of the International Searching Authority dated Aug. 18, 2021, issued for PCT/CN2021/093511, filed May 13, 2021, 15 pages.
Jiang et al., (2004). "Tumor imaging by means of proteolytic activation of cell-penetrating peptides," Proc Natl Acad Sci USA 101(51):17867-72.
Ke et al., (1997). "Optimal Subsite Occupancy and Design of a Selective Inhibitor of Urokinase," J Biol Chem 272(33):20456-62.
Keler et al., (2003). "Activity and Safety of CTLA-4 Blockade Combined with Vaccines in Cynomolgus," The Journal of Immunology, 171:6251-59.
Kwon et al., (1997). "Manipulation of T cell costimulatory and inhibitory signals for immunotherapy of prostate cancer," Proc Natl Acad Sci USA, 94(15):8099-8103.
Labiano et al., (2016). "Hypoxia-induced soluble CD137 in malignant cells blocks CD137L-costimulation as an immune escape mechanism," Oncoimmunology, 5:e1062967, 10 pages.
Lee et al., (2016). "Structural basis of checkpoint blockade by monoclonal antibodies in cancer immunotherapy," Nat Commun 7(13354):1-10.
Lei et al., (1987). "Characterization of the Erwinia carotovora pelB gene and its product pectate lyase," J. Bacteriol., 169:4379-83.
Palma et al., (2004). "CD137 and CD137 Ligand Constitutively Coexpressed On Human T And B Leukemia Cells Signal Proliferation And Survival," International Journal Of Cancer, 108:390-398.
Ramagopal et al., (2017). "Structural basis for cancer immunotherapy by the first-in-class checkpoint inhibitor ipilimumab," Proc Natl Acad Sci USA 114(21): 4223-4232.
Ribas et al., (2007). "Tremelimumab (CP-675, 206), a Cytotoxic T 1-61 Lymphocyte-Associated Antigen 4 Blocking Monoclonal Antibody in Clinical Development for Patients with Cancer," The Oncologist, 12:873-883.
Schwartz et al., (2001). "Structural basis for co-stimulation by the human CTLA-4/B7-2 complex," Nature 410(6828): 604-606.
Segal et al., (2018). "Phase I Study of Single-Agent Utomilumab (PF-05082566), a 4-1BB/CD137 Agonist, in Patients with Advanced Cancer," Clinical Cancer Research, 24:1816-1823.
Sharma et al., (2019; epub 2018). "Anti-CTLA-4 Immunotherapy Does Not Deplete FOXP3+ Regulatory T Cells (Tregs) in Human Cancers," Clin. Cancer Res., 25:1233-1238.
Stamper et al., (2001). "Crystal structure of the B7-1/CTLA-4 complex that inhibits human immune responses," Nature 410(6828): 608-611.
Tolcher et al., (2019). "A phase 1, first-in-human, dose-escalation study of ADG106, a fully human anti-CD137 agonistic antibody, in subjects with advanced or metastatic solid tumors and/or relapsed/refractory non-Hodgkin lymphoma," Molecular Targets And Cancer Therapeutics, 18:A082, 2 pages. (Abstract Only).
Xu et al., (2012). "Preparation and characterization of a chimeric anti-human CTLA-4 monoclonal antibody," Current Immunology, 5(32):359-364. English Abstract Only.
Yang et al., (1997). "Enhanced induction of antitumor T-cell responses by cytotoxic T lymphocyte-associated molecule-4 blockade: the effect is manifested only at the restricted tumor-bearing stages," Cancer Res 57(18):4036-41.
Ye et al., (2020). "CD137, an attractive candidate for the immunotherapy of lung cancer," Cancer Science, 111:1461-1467.
Zhang et al., (2020). "Phase 1, dose-escalation study of ADG106, a fully human anti-CD137 agonistic antibody, in subjects with advanced

(56) References Cited

OTHER PUBLICATIONS solid tumors or relapsed/refractory non-Hodgkin lymphoma," Journal Of Clinical Oncology, 38:A3105, 2 pages. (Abstract Only).
ABY47575.1, 1 page, Dec. 5, 2008.†
AAH06196.1, Jul. 15, 2006.†
S. Michael Chin et al., Structure of the 4-1BB/4-1BBL complex and distinct binding and functional properties of utomilumab and urelumab, 13 pages, Nov. 8, 2018.†
Shi-Yan Li et al., Immunotherapy of melanoma with the immune costimulatory monoclonal antibodies targeting CD137, 7 pages, Aug. 30, 2013, Dovepress.†

\* cited by examiner
† cited by third party

FIG. 7B

```
                                                                          CRD1                                                           CRD2
CD137_HUMAN   MGNSCYNIVATLLLVLNFERTRSLQDPCSNCPAGTFCDNNRNQICSPCPPNSFSSAGGQR
CD137_MONKEY  ----------------------LQDLCSNCPAGTFCDNNRSQICSPCPPNSFSSAGGQR
CD137_MOUSE   MGNNCYNVVVIVLLLVGCEKVGAVQNSCDNCQPGTFCRK-YNPVCKSCPPSTFSSIGGQP
                                     *:::** :**** *:*** ** .** .*.****:*.* **.

CD137_HUMAN   TCDICRQCKGVFRTRKECSSTSNAECDCTPGFHCLGAGCSMCEQDCKQGQELTKKGCKDC
CD137_MONKEY  TCDICRQCKGVFKTRKECSSTSNAECDCISGYHCLGAECSMCEQDCKQGQELTKKGCKDC
CD137_MOUSE   NCNICRVCAGYFRFKKFCSSTHNAECECIEGFHCLGPQCTRCEKDCRPGQELTKQGCKTC
               *:***.*.* *: :* ****:****:*  *:**** *: **:**: *:***.*:**.*
                                                                          CRD3
CD137_HUMAN   CFGTFNDQK-RGICRPWTNCSLDGKSVLVNGTKERDVVCGPSPADLSPGASSVTPPAPAR
CD137_MONKEY  CFGTFNDQK-RGICRPWTNCSLDGKSVLVNGTKERDVVCGPSPADLSPGASSATPPAPAR
CD137_MOUSE   SLGTFNDQNGTGVCRPWTNCSLDGRSVLKTGTTEKDVVCGPPVVSFSPSTTISVTP-EGG
              . ******:  ..*********:***  **.*:******.  .:**..:: *.**  .*
                                          CRD4
```

ANTI-CD137 MOLECULES AND USE THEREOF

CROSS REFERENCE TO RELATED APPLICATIONS

This application is a continuation-in-part of International Patent Application Serial No. PCT/CN2017/098332, filed Aug. 21, 2017, which is hereby incorporated by reference in its entirety.

REFERENCE TO SEQUENCE LISTING

The content of the following submission on ASCII text file is incorporated herein by reference in its entirety: a computer readable form (CRF) of the Sequence Listing (file name: 695402000320SEQLIST.TXT, date recorded: Aug. 21, 2018, size: 542 KB).

FIELD OF THE INVENTION

The present disclosure relates to antibodies that bind to human CD137 or antigen binding fragments thereof, nucleic acid encoding the same, therapeutic compositions thereof, and their anti-tumor use.

BACKGROUND

CD137 (also referred to as CD137 receptor, 4-1BB, TNFRSF9, etc.) is a transmembrane protein of the Tumor Necrosis Factor Receptor Superfamily (TNFRS). Current understanding of CD137 indicates that its expression is generally activation dependent and is present in a broad subset of immune cells including activated NK and NKT cells, regulatory T cells, dendritic cells (DC), stimulated mast cells, differentiating myeloid cells, monocytes, neutrophils, and eosinophils (Wang, 2009, Immunological Reviews 229: 192-215). CD137 expression has also been demonstrated on tumor vasculature (Broll, 2001, Amer. J. Clin. Pathol. 115(4):543-549; Seaman, 2007, Cancer Cell 11: 539-554) and at sites of inflamed or atherosclerotic endothelium (Drenkard, 2007 FASEB J. 21: 456-463; Olofsson, 2008, Circulation 117: 1292-1301). The ligand that stimulates CD137, i.e., CD137 Ligand (CD137L), is expressed on activated antigen-presenting cells (APCs), myeloid progenitor cells, and hematopoietic stem cells.

Human CD137 is a 255 amino acid protein (GenBank Accession No. NM_001561; NP_001552; SEQ ID NO.: 1). The protein comprises a signal sequence (amino acid residues 1-17), followed by an extracellular domain (169 amino acids), a transmembrane region (27 amino acids), and an intracellular domain (42 amino acids) (Cheuk A T C et al. 2004 Cancer Gene Therapy 11: 215-226). The receptor is expressed on the cell surface in monomer and dimer forms and likely trimerizes with CD137 ligand to signal.

Numerous studies of murine and human T cells indicate that CD137 promotes enhanced cellular proliferation, survival, and cytokine production (Croft, 2009, Nat Rev Immunol 9:271-285). Studies have indicated that some CD137 agonist mAbs increase costimulatory molecule expression and markedly enhance cytolytic T lymphocyte responses, resulting in anti-tumor efficacy in various models. CD137 agonist mAbs have demonstrated efficacy in prophylactic and therapeutic settings. Further, CD137 monotherapy and combination therapy tumor models have established durable anti-tumor protective T cell memory responses (Lynch, 2008, Immunol Rev. 22: 277-286). CD137 agonists also have been shown to inhibit autoimmune reactions in a variety of art-recognized autoimmunity models (Vinay, 2006, J Mol Med 84:726-736). This dual activity of CD137 offers the potential to provide anti-tumor activity while dampening autoimmune side effects that can be associated with immunotherapy approaches that break immune tolerance.

There is a long-felt unmet need for antibodies that bind human CD137, increase a CD137-mediated response, and thereby provide a potential therapeutics for treatment of various diseases and conditions, including cancer and autoimmune diseases. Furthermore, a need exists for anti-CD137 antibody that is cross-reactive among different species such as human and experimental animals (mouse, monkey, dog, etc.) to enable animal model studies and provide therapeutic candidates at the same time.

SUMMARY

It is an object of the disclosure to provide an isolated binding molecule that binds to human CD137, such as an antibody or a binding fragment thereof, or derivative thereof. It is another object of the disclosure to provide a composition comprising a binding molecule that binds to CD137. It is also an object of the present disclosure to provide methods for treating a disease and/or condition associated with or mediated by CD137 signaling by using one or more binding molecules of the disclosure. These and other objects of the disclosure are more fully described herein.

Accordingly, in one aspect, provided herein is one or more antibodies (e.g., isolated antibodies), or one or more antigen-binding fragments thereof, that binds to an extracellular domain of human CD137, and which comprise one or more (e.g., one or more, two or more, three or more, four or more, five or more, six or more, seven or more, eight or more, nine or more, or all 10) of the following functional characteristics: (a) binds one or more amino acid residues within amino acid residues 34-108 of SEQ ID NO:1; (b) does not bind to one or more amino acid residues within amino acid residues 109-112, 125, 126, 135-138, 150 and 151 of SEQ ID NO:1; (c) binds to human CD137 with a $K_D$ of 100 nM or less; (d) has agonist activity on human CD137; (e) does not bind to human OX40, CD40, GITR and/or CD27 receptor at concentration up to 1000 nM; (0 is cross-reactive with monkey, mouse, rat, and/or dog CD137; (g) does not induce ADCC effect; (h) is capable of inhibiting tumor cell growth; (i) has therapeutic effect on a cancer; and/or (j) blocks binding between CD137 and CD137L.

Accordingly, in one aspect, provided herein is an antibody (e.g., an isolated antibody), or antigen-binding fragment thereof, that binds to an extracellular domain of human CD137. In some embodiments, the antibody or antigen-binding fragment comprises a heavy chain variable region and a light chain variable region, wherein the heavy chain variable region comprises an HVR-H1, an HVR-H2, and an HVR-H3, wherein the HVR-H1 comprises an amino acid sequence according to a formula selected from the group consisting of: Formula (I): $X_1TFX_2X_3YX_4IHWV$ (SEQ ID NO:2), wherein X1 is F or Y, X2 is S or T, X3 is G, N, or S, and X4 is A, G, or W; Formula (II): $YSIX_1SGX_2X_3WX_4WI$ (SEQ ID NO:3), wherein X1 is S or T, X2 is H or Y, X3 is H or Y, and X4 is A, D, G, N, S, or T; and Formula (III): $FSLSTX_1GVX_2VX_3WI$ (SEQ ID NO:4), wherein X1 is G or S, X2 is A or G, and X3 is A, G, S, or T; wherein the HVR-H2 comprises an amino acid sequence according to a formula selected from the group consisting of: Formula (IV): LALIDWX1X2DKX3YSX4SLKSRL (SEQ ID NO:5), wherein X1 is A, D, or Y, X2 is D or G, X3 is R, S, or Y, and X4 is P or T; Formula (V): IGX1IYHSGX2TYYX3PSLKSRV (SEQ ID NO:6), wherein X1 is D or E, X2 is N or S, and X3 is N or S; and Formula (VI): VSX1ISGX2GX3X4TYYADSVKGRF (SEQ ID NO:7), wherein X1 is A, G, S, V, or Y, X2 is A, D, S, or Y, X3 is D, G, or S, and X4 is S or T; and wherein the HVR-H3 comprises an amino acid sequence according to Formula (VII): ARX1GX2X3X4VX5GDWFX6Y (SEQ ID NO:8), wherein X1 is E or G, X2 is E or S, X3 is D or T, X4 is A, T, or V, X5 is A, I, L, T, or V, and X6 is A, D, or G.

In some embodiments, provided herein is an antibody (e.g., an isolated antibody), or antigen-binding fragment thereof, that binds to an extracellular domain of human CD137 comprising a heavy chain variable region and a light chain variable region, wherein the heavy chain variable region comprises an HVR-H1, an HVR-H2, and an HVR-H3, wherein the HVR-H1 comprises an amino acid sequence according to a formula selected from the group consisting of: Formula (XII): X1TFSX2YWIHWV (SEQ ID NO:853), wherein X1 is F or Y, and X2 is N, or S; Formula (XIII): YSIX1SGX2X3WX4WI (SEQ ID NO:854), wherein X1 is S or T, X2 is H or Y, X3 is H or Y, and X4 is A, D, G, N, or S; and Formula (XIV): FSLSTX1GVX2VX3WI (SEQ ID NO:855), wherein X1 is G or S, X2 is A or G, and X3 is A, G, or S; wherein the HVR-H2 comprises an amino acid sequence according to a formula selected from the group consisting of: Formula (IV): LALIDWX1X2DKX3YSX4SLKSRL (SEQ ID NO:5), wherein X1 is A, D, or Y, X2 is D or G, X3 is R, S, or Y, and X4 is P or T; and Formula (XV): VSX1ISGX2GX3X4TYYADSVKGRF (SEQ ID NO:856), wherein X1 is G, S, V, or Y, X2 is A, D, S, or Y, X3 is D, G, or S, and X4 is S or T; and wherein the HVR-H3 comprises an amino acid sequence according to Formula (VII): ARX1GX2X3X4VX5GDWFX6Y (SEQ ID NO:8), wherein X1 is E or G, X2 is E or S, X3 is D or T, X4 is A, T, or V, X5 is A, I, L, T, or V, and X6 is A, D, or G.

In another aspect, provided herein is an antibody (e.g., an isolated antibody), or antigen-binding fragment thereof, that binds to an extracellular domain of human CD137. In some embodiments, the antibody or antigen-binding fragment comprises a heavy chain variable region and a light chain variable region, wherein the light chain variable region comprises an HVR-L1, an HVR-L2, and an HVR-L3, wherein the HVR-L1 comprises an amino acid sequence according to Formula (VIII): X1ASQX2X3X4X5X6X7X8 (SEQ ID NO:9), wherein X1 is Q or R, X2 is D, G, or S, X3 is I or V, X4 is G, R, S, or T, X5 is P, R, S, or T, X6 is A, D, F, S, V, or Y, X7 is L or V, and X8 is A, G, or N; wherein the HVR-L2 comprises an amino acid sequence according to Formula (IX): X1ASX2X3X4X5GX6 (SEQ ID NO:10), wherein X1 is A or D, X2 is N, S, or T, X3 is L or R, X4 is A, E, or Q, X5 is S or T, and X6 is I or V; and wherein the HVR-L3 comprises an amino acid sequence according to a formula selected from the group consisting of: Formula (X): YCQQX1YX2X3X4T (SEQ ID NO:11), wherein X1 is A, G, S, or Y, X2 is Q, S, or Y, X3 is I, L, T, or Y, and X4 is I, S, V, or W; and Formula (XI): YCX1QX2X3X4X5PX6T (SEQ ID NO:12), wherein X1 is E or Q, X2 is P, S, or Y, X3 is D, L, S, T, or Y, X4 is D, E, H, S, or T, X5 is D, L T, or W, and X6 is L, P, R, or V.

In some embodiments, provided herein is an antibody (e.g., an isolated antibody), or antigen-binding fragment thereof, that binds to an extracellular domain of human CD137 comprising a heavy chain variable region and a light chain variable region, wherein the light chain variable region comprises an HVR-L1, an HVR-L2, and an HVR-L3, wherein the HVR-L1 comprises an amino acid sequence according to Formula (XVI): X1ASQX2X3X4X5X6X7X8 (SEQ ID NO:857), wherein X1 is Q or R, X2 is D, G, or S, X3 is I or V, X4 is G, R, S, or T, X5 is P, R, S, or T, X6 is A, F, S, V, or Y, X7 is L or V, and X8 is A or G; wherein the HVR-L2 comprises an amino acid sequence according to Formula (XVII): X1ASX2X3X4X5GX6 (SEQ ID NO:858), wherein X1 is A or D, X2 is N or S, X3 is L or R, X4 is A, E, or Q, X5 is S or T, and X6 is I or V; and wherein the HVR-L3 comprises an amino acid sequence according to Formula (XVIII): YCQQX1YX2X3WT (SEQ ID NO:859), wherein X1 is A or G, X2 is S or Y, and X3 is I, L, or T.

In another aspect, provided herein is an antibody (e.g., an isolated antibody), or antigen-binding fragment thereof, that binds to an extracellular domain of human CD137. In some embodiments, the antibody or antigen-binding fragment comprises a heavy chain variable region and a light chain variable region, wherein the heavy chain variable region comprises the HVR-H1, HVR-H2, and HVR-H3 of: VH1, VH2, VH3, VH4, VH5, VH6, VH7, VH8, VH9, VH10, VH11, VH12, VH13, VH14, VH15, VH16, VH17, VH18, VH19, VH20, VH21, VH22, VH23, VH24, VH25, VH26, VH27, VH28, VH29, VH30, VH31, VH32, VH33, VH34, VH35, VH36, VH37, VH38, VH39, VH40, VH41, VH42, VH43, VH44, VH45, VH46, VH47, VH48, VH49, VH50, VH51, VH52, VH53, VH54, VH55, VH56, VH57, VH58, VH59, or VH60; and/or the light chain variable region comprises the HVR-L1, HVR-L2, and HVR-L3 of: VL1, VL2, VH3, VL4, VH5, VL6, VL7, VL8, VL9, VL10, VL11, VL12, VL13, VL14, VL15, VL16, VL17, VL18, VL19, VL20, VL21, VL22, VL23, VL24, VL25, VL26, VL27, VL28, VL29, VL30, VL31, VL32, VL33, VL34, VL35, VL36, VL37, VL38, VL39, VL40, VL41, VL42, VL43, VL44, VL45, VL46, VL47, VL48, VL49, VL50, VLSI, VL52, VL53, VL54, VL55, VL56, VL57, VL58, VL59, or VL60 (as shown in Table 1c). In some embodiments, the antibody or antigen-binding fragment comprises a heavy chain variable region and a light chain variable region, wherein the heavy chain variable region and light chain variable region comprise the HVR-H1, HVR-H2, HVR-H3, HVR-L1, HVR-L2, and HVR-L3 of: VH1 and VL1, VH2 and VL2, VH3 and VL3, VH4 and VL4, VH5 and VL5, VH6 and VL6, VH7 and VL7, VH8 and VL8, VH9 and VL9, VH10 and VL10, VH11 and VL11, VH12 and VL12, VH13 and VL13, VH14 and VL14, VH15 and VL15, VH16 and VL16, VH17 and VL17, VH18 and VL18, VH19 and VL19, VH20 and VL20, VH21 and VL21, VH22 and VL22, VH23 and VL23, VH24 and VL24, VH25 and VL25, VH26 and VL26, VH27 and VL27, VH28 and VL28, VH29 and VL29, VH30 and VL30, VH31 and VL31, VH32 and VL32, VH33 and VL33, VH34 and VL34, VH35 and VL35, VH36 and VL36, VH37 and VL37, VH38 and VL38, VH39 and VL39, VH40 and VL40, VH41 and VL41, VH42 and VL42, VH43 and VL43, VH44 and VL44, VH45 and VL45, VH46 and VL46, VH47 and VL47, VH48 and VL48, VH49 and VL49, VH50 and VL50, VH51 and VL51, VH52 and VL52, VH53 and VL53, VH54 and VL54, VH55 and VL55, VH56 and VL56, VH57 and VL57, VH58 and VL58, VH59 and VL59, or VH60 and VL60 (as shown in Table 1c).

In another aspect, provided herein is an antibody (e.g., an isolated antibody), or antigen-binding fragment thereof, that binds to an extracellular domain of human CD137. In some embodiments, the antibody or antigen-binding fragment comprises a heavy chain variable region and a light chain variable region, wherein the heavy chain variable region comprises the heavy chain variable region of: VH1, VH2, VH3, VH4, VH5, VH6, VH7, VH8, VH9, VH10, VH11, VH12, VH13, VH14, VH15, VH16, VH17, VH18, VH19, VH20, VH21, VH22, VH23, VH24, VH25, VH26, VH27, VH28, VH29, VH30, VH31, VH32, VH33, VH34, VH35, VH36, VH37, VH38, VH39, VH40, VH41, VH42, VH43, VH44, VH45, VH46, VH47, VH48, VH49, VH50, VH51, VH52, VH53, VH54, VH55, VH56, VH57, VH58, VH59, or VH60; and/or the light chain variable region comprises the light chain variable region of: VL1, VL2, VH3, VL4, VH5, VL6, VL7, VL8, VL9, VL10, VL11, VL12, VL13, VL14, VL15, VL16, VL17, VL18, VL19, VL20, VL21, VL22, VL23, VL24, VL25, VL26, VL27, VL28, VL29, VL30, VL31, VL32, VL33, VL34, VL35, VL36, VL37, VL38, VL39, VL40, VL41, VL42, VL43, VL44, VL45, VL46, VL47, VL48, VL49, VL50, VLSI, VL52, VL53, VL54, VL55, VL56, VL57, VL58, VL59, or VL60 (as shown in Table 1c). In some embodiments, the antibody or antigen-binding fragment comprises a heavy chain variable region and a light chain variable region, wherein the heavy chain variable region and light chain variable region comprise the heavy chain variable region and light chain variable region of: VH1 and VL1, VH2 and VL2, VH3 and VL3, VH4 and VL4, VH5 and VL5, VH6 and VL6, VH7 and VL7, VH8 and VL8, VH9 and VL9, VH10 and VL10, VH11 and VL11, VH12 and VL12, VH13 and VL13, VH14 and VL14, VH15 and VL15, VH16 and VL16, VH17 and VL17, VH18 and VL18, VH19 and VL19, VH20 and VL20, VH21 and VL21, VH22 and VL22, VH23 and VL23, VH24 and VL24, VH25 and VL25, VH26 and VL26, VH27 and VL27, VH28 and VL28, VH29 and VL29, VH30 and VL30, VH31 and VL31, VH32 and VL32, VH33 and VL33, VH34 and VL34, VH35 and VL35, VH36 and VL36, VH37 and VL37, VH38 and VL38, VH39 and VL39, VH40 and VL40, VH41 and VL41, VH42 and VL42, VH43 and VL43, VH44 and VL44, VH45 and VL45, VH46 and VL46, VH47 and VL47, VH48 and VL48, VH49 and VL49, VH50 and VL50, VH51 and VL5I, VH52 and VL52, VH53 and VL53, VH54 and VL54, VH55 and VL55, VH56 and VL56, VH57 and VL57, VH58 and VL58, VH59 and VL59, or VH60 and VL60 (as shown in Table 1c).

In another aspect, provided herein is an antibody (e.g., an isolated antibody), or antigen-binding fragment thereof, that binds to an extracellular domain of human CD137. In some embodiments, the antibody or the antigen-binding fragment thereof binds to one or more amino acid residues within amino acid residues 34-108 of SEQ ID NO:1. In some embodiments, the antibody or antigen-binding fragment binds to one or more amino acid residues within amino acid residues 34-93 of SEQ ID NO:1. In some embodiments, the antibody or antigen-binding fragment binds to one or more amino acid residues selected from the group consisting of amino acid residues 34-36, 53-55, and 92-93 of SEQ ID NO:1. In some embodiments, the antibody or antigen-binding fragment binds to one or more of amino acid residues 34-36, one or more of amino acid residues 53-55, and one or more or amino acid residues 92-93 of SEQ ID NO:1. In some embodiments, the antibody or antigen-binding fragment does not bind to one or more of amino acid residues selected from the group consisting of amino acid residues 109-112, 125, 126, 135-138, 150 and 151 of SEQ ID NO:1. In some embodiments, the antibody or antigen-binding fragment does not bind to amino acid residues 109-112, 125, 126, 135-138, 150 and 151 of SEQ ID NO:1. In some embodiments, the antibody or antigen-binding fragment is cross-reactive with a CD137 polypeptide from at least one non-human species selected from cynomolgus monkey, mouse, rat and/or dog. In some embodiments, the antibody or antigen-binding fragment binds to cynomolgus monkey CD137.

In some embodiments, the antibody or antigen-binding fragment comprises a heavy chain variable region and a light chain variable region, wherein the heavy chain variable region comprises an HVR-H1 comprising the amino acid sequence of SEQ ID NO:711, an HVR-H2 comprising the amino acid sequence of SEQ ID NO:735, and an HVR-H3 comprising the amino acid sequence of SEQ ID NO:759; and/or wherein the light chain variable region comprises an HVR-L1 comprising the amino acid sequence of SEQ ID NO:783, an HVR-L2 comprising the amino acid sequence of SEQ ID NO:807, and an HVR-L3 comprising the amino acid sequence of SEQ ID NO:831. In some embodiments, the heavy chain variable region comprises the amino acid sequence of SEQ ID NO:41, and/or the light chain variable region comprises the amino acid sequence of SEQ ID NO:42. In some embodiments, the antibody comprises a heavy chain and a light chain, and wherein the heavy chain comprises the amino acid sequence of SEQ ID NO:617, and/or the light chain comprises the amino acid sequence of SEQ ID NO:618.

In some embodiments, the antibody or antigen-binding fragment comprises a heavy chain variable region and a light chain variable region, wherein the heavy chain variable region comprises an HVR-H1 comprising the amino acid sequence of SEQ ID NO:712, an HVR-H2 comprising the amino acid sequence of SEQ ID NO:736, and an HVR-H3 comprising the amino acid sequence of SEQ ID NO:760; and/or wherein the light chain variable region comprises an HVR-L1 comprising the amino acid sequence of SEQ ID NO:784, an HVR-L2 comprising the amino acid sequence of SEQ ID NO:808, and an HVR-L3 comprising the amino acid sequence of SEQ ID NO:832. In some embodiments, the heavy chain variable region comprises the amino acid sequence of SEQ ID NO:61, and/or the light chain variable region comprises the amino acid sequence of SEQ ID NO:62. In some embodiments, the antibody comprises a heavy chain and a light chain, wherein the heavy chain comprises the amino acid sequence of SEQ ID NO:619, and/or the light chain comprises the amino acid sequence of SEQ ID NO:620.

In some embodiments, the antibody or antigen-binding fragment comprises a heavy chain variable region and a light chain variable region, wherein the heavy chain variable region comprises an HVR-H1 comprising the amino acid sequence of SEQ ID NO:731, an HVR-H2 comprising the amino acid sequence of SEQ ID NO:755, and an HVR-H3 comprising the amino acid sequence of SEQ ID NO:779; and/or wherein the light chain variable region comprises an HVR-L1 comprising the amino acid sequence of SEQ ID NO:803, an HVR-L2 comprising the amino acid sequence of SEQ ID NO:827, and an HVR-L3 comprising the amino acid sequence of SEQ ID NO:851. In some embodiments, the heavy chain variable region comprises the amino acid sequence of SEQ ID NO:71, and/or the light chain variable region comprises the amino acid sequence of SEQ ID NO:72. In some embodiments, the antibody comprises a heavy chain and a light chain, wherein the heavy chain comprises the amino acid sequence of SEQ ID NO:657, and/or the light chain comprises the amino acid sequence of SEQ ID NO:658.

In another aspect, provided herein is an antibody (e.g., an isolated antibody), that binds to an extracellular domain of human CD137, comprising a heavy chain variable region and a light chain variable region, wherein the heavy chain variable region comprises an HVR-H1, an HVR-H2, and an HVR-H3, wherein the HVR-H1 comprises an amino acid sequence according to a formula selected from the group consisting of: Formula (I), Formula (II), and Formula (III); the HVR-H2 comprises an amino acid sequence according to a formula selected from the group consisting of: Formula (IV), Formula (V), and Formula (VI); and the HVR-H3 comprises an amino acid sequence according to Formula (VII); and/or the light chain variable region comprises an HVR-L1, an HVR-L2, and an HVR-L3, wherein the HVR-L1 comprises an amino acid sequence according to Formula (VIII); the HVR-L2 comprises an amino acid sequence according to Formula (IX); and the HVR-L3 comprises an amino acid sequence according to a formula selected from the group consisting of: Formula (X) and Formula (XI). In some embodiments, provided herein is an antibody (e.g., an isolated antibody), that binds to an extracellular domain of human CD137, comprising a heavy chain variable region and a light chain variable region, wherein the heavy chain variable region comprises an HVR-H1, an HVR-H2, and an HVR-H3, wherein the HVR-H1 comprises an amino acid sequence according to a formula selected from the group consisting of: Formula (XIII) and Formula (XVI); the HVR-H2 comprises an amino acid sequence according to a formula selected from the group consisting of: Formula (IV) and Formula (XV); and the HVR-H3 comprises an amino acid sequence according to Formula (VII); and/or the light chain variable region comprises an HVR-L1, an HVR-L2, and an HVR-L3, wherein the HVR-L1 comprises an amino acid sequence according to Formula (XVI); the HVR-L2 comprises an amino acid sequence according to Formula (XVII); and the HVR-L3 comprises an amino acid sequence according to Formula (XVIII).

In some embodiments, the HVR-H1 comprises an amino acid sequence selected from the group consisting of SEQ ID NOs: 253-312, the HVR-H2 comprises an amino acid sequence selected from the group consisting of SEQ ID NOs: 313-372, the HVR-H3 comprises an amino acid sequence selected from the group consisting of SEQ ID NOs: 373-432, the HVR-L1 comprises the amino acid sequence selected from the group consisting of SEQ ID NOs: 433-492, the HVR-L2 comprises the amino acid sequence selected from the group consisting of SEQ ID NOs: 493-552, and/or the HVR-L3 comprises an amino acid sequence selected from the group consisting of SEQ ID NOs: 553-612. In some embodiments, the heavy chain variable region comprises an amino acid sequence selected from the group consisting of SEQ ID NOS:13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, and 131, and/or the light chain variable region comprises an amino acid sequence selected from the group consisting of SEQ ID NOS:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, and 132.

In some embodiments, the HVR-H1 comprises an amino acid sequence according to a formula selected from the group consisting of Formula (XII), Formula (XIII), and Formula (XIV); the HVR-H2 comprises an amino acid sequence according to Formula (IV) or Formula (XV); and the HVR-H3 comprises an amino acid sequence according to Formula (VII); and/or wherein the HVR-L1 comprises an amino acid sequence according to Formula (XVI); the HVR-L2 comprises an amino acid sequence according to Formula (XVII); and the HVR-L3 comprises an amino acid sequence according to Formula (XVIII). In some embodiments, the HVR-H1 comprises an amino acid sequence selected from the group consisting of SEQ ID NOS:709-732, the HVR-H2 comprises an amino acid sequence selected from the group consisting of SEQ ID NOS:733-756, the HVR-H3 comprises an amino acid sequence selected from the group consisting of SEQ ID NOS:757-780, the HVR-L1 comprises an amino acid sequence selected from the group consisting of SEQ ID NOS:781-804, the HVR-L2 comprises an amino acid sequence selected from the group consisting of SEQ ID NOS:805-828, and the HVR-L3 comprises an amino acid sequence selected from the group consisting of SEQ ID NOS:829-852. In some embodiments, the heavy chain variable region comprises an amino acid sequence selected from the group consisting of SEQ ID NOS:15, 17, 31, 33, 35, 37, 39, 41, 43, 45, 47, 49, 53, 61, 63, 65, 67, 71, 73, 75, 79, 83, 85, and 87, and/or the light chain variable region comprises an amino acid sequence selected from the group consisting of SEQ ID NOS:16, 18, 32, 34, 36, 38, 40, 42, 44, 46, 48, 50, 54, 62, 64, 66, 68, 72, 74, 76, 80, 84, 86, and 88. In some embodiments, the antibody comprises a heavy chain and a light chain, wherein the heavy chain comprises an amino acid sequence selected from the group consisting of SEQ ID NOs: 613, 615, 617, 619, 621, 623, 625, 627, 629, 631, 633, 635, 637, 639, 641, 643, 645, 647, 649, 651, 653, 655, 657, and 659, and/or the light chain comprises an amino acid sequence selected from the group consisting of SEQ ID NOs: 614, 616, 618, 620, 622, 624, 626, 628, 630, 632, 634, 636, 638, 640, 642, 644, 646, 648, 650, 652, 654, 656, 658, and 660.

In some embodiments, the HVR-H1 comprises an amino acid sequence of SEQ ID NO:711 or 731, the HVR-H2 comprises an amino acid sequence of SEQ ID NO:735 or 755, the HVR-H3 comprises an amino acid sequence of SEQ ID NO:759 or 779, the HVR-L1 comprises an amino acid sequence of SEQ ID NO:783 or 803, the HVR-L2 comprises an amino acid sequence or SEQ ID NO:807 or 827, and the HVR-L3 comprises an amino acid sequence of SEQ ID NO:831 or 851. In some embodiments, the heavy chain variable region comprises an amino acid sequence of SEQ ID NO:41 or 71, and the light chain variable region comprises an amino acid sequence of SEQ ID NO:42 or 72. In some embodiments, the antibody comprises a heavy chain and a light chain, wherein the heavy chain comprises an amino acid sequence of SEQ ID NO: 617 or 657, and the light chain comprises an amino acid sequence of SEQ ID NO: 618 or 658.

In some embodiments, the HVR-H1 comprises an amino acid sequence of SEQ ID NO:712, the HVR-H2 comprises an amino acid sequence of SEQ ID NO:736, the HVR-H3 comprises an amino acid sequence of SEQ ID NO:760, the HVR-L1 comprises an amino acid sequence of SEQ ID NO:784, the HVR-L2 comprises an amino acid sequence or SEQ ID NO:808, and the HVR-L3 comprises an amino acid sequence of SEQ ID NO:832. In some embodiments, the heavy chain variable region comprises an amino acid sequence of SEQ ID NO:61, and the light chain variable region comprises an amino acid sequence of SEQ ID NO:62. In some embodiments, the antibody comprises a heavy chain and a light chain, wherein the heavy chain comprises an amino acid sequence of SEQ ID NO: 619, and the light chain comprises an amino acid sequence of SEQ ID NO:620.

In some embodiments that may be combined with any of the preceding embodiments, the antibody or antigen-binding fragment binds human CD137 with a $K_D$ of 100 nM or less (e.g., as measured by surface plasmon resonance). In some embodiments, the antibody or antigen-binding fragment binds human CD137 with a $K_D$ of 50 nM or less (e.g., as measured by surface plasmon resonance).

In some embodiments that may be combined with any of the preceding embodiments, the antibody or antigen-binding fragment is cross-reactive with a CD137 polypeptide from at least one non-human species selected from cynomolgus monkey (e.g., GenBank Gene ID 102127961), mouse (e.g., GenBank Gene ID 21942), rat (e.g., GenBank Gene ID 500590) and/or dog (e.g., GenBank Gene ID 608274). In some embodiments, the antibody or antigen-binding fragment binds to cynomolgus monkey CD137.

In some embodiments that may be combined with any of the preceding embodiments, an activity of human CD137 (e.g., when expressed on a cell such as a human cell) is decreased when contacted with the antibody or antigen-binding fragment.

In some embodiments that may be combined with any of the preceding embodiments, the antibody or antigen-binding fragment has a half maximal inhibitory concentration ($IC_{50}$) of about 100 nM or less for blocking binding of human CD137 to human CD137L in vitro. In some embodiments, the antibody or antigen-binding fragment completely blocks binding of human CD137 to human CD137L in vitro when the antibody or antigen-binding fragment is provided at a concentration of about 1 μM or greater. In some embodiments that may be combined with any of the preceding embodiments, an activity of human CD137 (e.g., when expressed on a cell such as a human cell) is increased when contacted with the antibody or antigen-binding fragment. In some embodiments, contacting CD137 (e.g., expressed on a human cell) with the antibody or antigen-binding fragment results in increased NF-κB-dependent transcription. In some embodiments of any of the above embodiments, the antibody or antigen-binding fragment blocks one or more aspects of CD137 signaling stimulated by CD137L, e.g., CD137L-stimulated NF-κB-dependent transcription, in a cell that expresses CD137.

In some embodiments that may be combined with any of the preceding embodiments, the antibody comprises a human IgG2 Fc region. In some embodiments that may be combined with any of the preceding embodiments, the antibody comprises a human IgG4 Fc region. In some embodiments, the human IgG4 Fc region comprises an S241P mutation, wherein numbering is according to Kabat. In some embodiments, the antibody or antigen-binding fragment does not induce ADCC effects.

In another aspect, provided herein are antibody heavy chain variable regions encoded by a polynucleotide comprising a sequence selected from SEQ ID NOs: 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, and 251, and/or antibody light chain variable regions encoded by a polynucleotide comprising a sequence selected from SEQ ID NOs: 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, and 252. In some embodiments, provided herein are antibody heavy chains encoded by a polynucleotide comprising a sequence selected from SEQ ID NOs:661, 663, 665, 667, 669, 671, 673, 675, 677, 679, 681, 683, 685, 687, 689, 691, 693, 695, 697, 699, 701, 703, 705, and 707, and/or antibody light chains encoded by a polynucleotide comprising a sequence selected from SEQ ID NOs:662, 664, 666, 668, 670, 672, 674, 676, 678, 680, 682, 684, 686, 688, 690, 692, 694, 696, 698, 700, 702, 704, 706, and 708.

In some embodiments, the HVRs are according to Kabat. In some embodiments, the antibody comprises a heavy chain variable (VH) domain comprising an HVR-H1 comprising the sequence GFSLSTSGVGVG (SEQ ID NO:866), an HVR-H2 comprising the sequence LIDWDDDKYYSPSLKS (SEQ ID NO:867), and an HVR-H3 comprising the sequence GGSDTVLGDWFAY (SEQ ID NO:868); and/or a light chain variable (VL) domain comprising an HVR-L1 comprising the sequence RASQSVSPYLA (SEQ ID NO:869), an HVR-L2 comprising the sequence DASSLES (SEQ ID NO:870), and an HVR-L3 comprising the sequence QQGYSLWT (SEQ ID NO:871).

In some embodiments, the HVRs are according to Kabat. In some embodiments, the antibody comprises a heavy chain variable (VH) domain comprising an HVR-H1 comprising the sequence GYSITSGHYWA (SEQ ID NO:872), an HVR-H2 comprising the sequence SISGYGSTTYYADSVKG (SEQ ID NO:873), and an HVR-H3 comprising the sequence GGSDAVLGDWFAY (SEQ ID NO:874); and/or a light chain variable (VL) domain comprising an HVR-L1 comprising the sequence RASQGIGSFLA (SEQ ID NO:875), an HVR-L2 comprising the sequence DASNLET (SEQ ID NO:876), and an HVR-L3 comprising the sequence QQGYYLWT (SEQ ID NO:877).

In some embodiments, the HVRs are according to Kabat. In some embodiments, the antibody comprises a heavy chain variable (VH) domain comprising an HVR-H1 comprising the sequence GFSLSTGGVGVG (SEQ ID NO:878), an HVR-H2 comprising the sequence LIDWADDKYYSPSLKS (SEQ ID NO:879), and an HVR-H3 comprising the sequence GGSDTVIGDWFAY (SEQ ID NO:880); and/or a light chain variable (VL) domain comprising an HVR-L1 comprising the sequence RASQSIGSYLA (SEQ ID NO:881), an HVR-L2 comprising the sequence DASNLET (SEQ ID NO:882), and an HVR-L3 comprising the sequence QQGYYLWT (SEQ ID NO:883).

In some embodiments of any of the above embodiments, an antibody of the present disclosure is a multimeric antibody (e.g., a bispecific antibody). In some embodiments of any of the above embodiments, an antibody of the present disclosure is an IgM antibody, e.g., comprises an IgM Fc region (e.g., a human IgM Fc region).

In another aspect, provided herein is a polynucleotide encoding any of the antibodies or antigen-binding fragments described herein. In some embodiments, provided herein is a polynucleotide comprising a sequence selected from SEQ ID NOs:133-252.

In another aspect, provided herein is a vector comprising any of the polynucleotides described above. In some embodiments, the vector is an expression vector.

In another aspect, provided herein is a host cell (e.g., a bacterial cell, a yeast cell, an insect cell, a mammalian cell (such as a CHO cell or a 293T cell), etc.) comprising any of the polynucleotides or vectors described herein. In some embodiments, provided herein is a method of making an antibody or antigen-binding fragment comprising culturing the host cell under conditions suitable for producing the antibody or antigen-binding fragment. In some embodiments, the method further comprises recovering the antibody or antigen-binding fragment produced by the host cell.

In another aspect, provided herein is a pharmaceutical composition comprising any of the antibodies or antigen-binding fragments described herein (or any derivatives thereof) and a pharmaceutically acceptable carrier.

In another aspect, provided herein are methods of treating abnormal cell growth (e.g., a cancer) in a subject in need thereof, comprising administering to the subject a therapeutically effective amount of any of the antibodies, antigen-binding fragments, and/or pharmaceutical compositions described herein. In some embodiments, provided herein are methods of reducing tumor cell metastasis in a subject, comprising administering to said subject a therapeutically effective amount of any of the antibodies, antigen-binding fragments, and/or pharmaceutical compositions described herein. In some embodiments, the methods further comprise administering to the subject a therapeutically effective amount of at least one (e.g., at least one, at least two, at least three, at least four, at least five, at least 10, etc.) additional therapeutic agent. In some embodiments, the at least one additional therapeutic agent is selected from the group consisting of viral gene therapy, immune checkpoint inhibitors, target therapies, radiation therapies, and chemotherapies. In some embodiments, the at least one additional therapeutic agent is selected from the group consisting of pomalyst, revlimid, lenalidomide, pomalidomide, thalidomide, a DNA-alkylating platinum-containing derivative, cisplatin, 5-fluorouracil, cyclophosphamide, an anti-CTLA4 antibody, an anti-PD-1 antibody, an anti-PD-L1 antibody, an anti-CD20 antibody, an anti-CD40 antibody, an anti-DR5 antibody, an anti-CD1d antibody, an anti-TIM3 antibody, an anti-SLAMF7 antibody, an anti-MR receptor antibody, an anti-OX40 antibody, an anti-HER2 antibody, an anti-ErbB-2 antibody, an anti-EGFR antibody, cetuximab, rituximab, trastuzumab, pembrolizumab, radiotherapy, single dose radiation, fractionated radiation, focal radiation, whole organ radiation, IL-12, IFNα, GM-CSF, a chimeric antigen receptor, adoptively transferred T cells, an anti-cancer vaccine, and an oncolytic virus. Also provided herein is the use of any of the pharmaceutical compositions, antibodies, and/or antigen-binding fragments described herein (or any derivatives thereof) for the treatment of abnormal cell growth (e.g., a cancer) and/or the reduction of tumor cell metastasis in a subject in need thereof. Also provided herein is the use of any of the antibodies or antigen-binding fragments described herein (or any derivatives thereof) for the manufacture of a medicament for the treatment of abnormal cell growth (e.g., a cancer) and/or the reduction of tumor cell metastasis in a subject in need thereof.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIG. 7B shows a multiple sequence alignment of a portion of human (SEQ ID NO:1), cynomolgus monkey (SEQ ID NO:860), and mouse (SEQ ID NO:861) CD137, with CD137 sequences/regions of interest (annotated) that were identified from the epitope mapping experiments.

DETAILED DESCRIPTION

A. Definitions

Figures 1A, 1B:
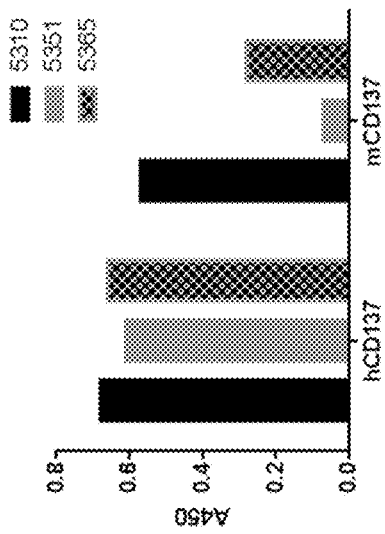
FIG. 1A shows hyper-variable region (HVR) definition as compared to the Kabat CDR definition for an exemplary heavy chain variable region (VH) (SEQ ID NO:13) and an exemplary light chain variable region (VL) (SEQ ID NO:14).
FIG. 1B shows selection of Fab hits that are cross-reactive with mouse CD137.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, antibody engineering, immunotherapy, cell and tissue culture, molecular biology, immunology, microbiology, genetics and protein and nucleic acid chemistry described herein are those well-known and commonly used in the art.

As used herein, each of the following terms has the meaning associated with it in this section.

The articles "a" and "an" refer to one or to more than one (i.e., to at least one) of the grammatical object of the article. By way of example, "an element" means one element or more than one element.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and 0-phosphoserine. The term "amino acid analogs" refers to compounds that have the same basic chemical structure as a naturally occurring amino acid but the C-terminal carboxy group, the N-terminal amino group, or side chain functional group has been chemically modified to another functional group. The term "amino acid mimetics" refers to chemical compounds that have a structure that is different from the general chemical structure of an amino acid, but that functions similarly to a naturally occurring amino acid.

The term "antibody" is used herein in the broadest sense and specifically covers monoclonal antibodies (including full length monoclonal antibodies), polyclonal antibodies, multispecific antibodies (e.g., bispecific antibodies), and antibody fragments (e.g., a single-chain variable fragment or scFv) so long as they exhibit the desired biological activity.

The term "antibody" is an art-recognized term and may refer to an antigen-binding protein (i.e, immunoglobulin) having a basic four-polypeptide chain structure consisting of two identical heavy (H) chains and two identical light (L) chains. Each L chain is linked to an H chain by one covalent disulfide bond, while the two H chains are linked to each other by one or more disulfide bonds depending on the H chain isotype. Each heavy chain has, at the N-terminus, a variable region (abbreviated herein as $V_H$) followed by a constant region. The heavy chain constant region is comprised of three domains, $C_{H1}$, $C_{H2}$ and $C_{H3}$. Each light chain has, at the N-terminus, a variable region (abbreviated herein as $V_L$) followed by a constant region at its other end. The light chain constant region is comprised of one domain, $C_L$. The $V_L$ is aligned with the $V_H$ and the $C_L$ is aligned with the first constant domain of the heavy chain (CH1). The pairing of a $V_H$ and $V_L$ together forms a single antigen-binding site. An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain.

The $V_H$ and $V_L$ regions can be further subdivided into regions of hypervariability, termed hyper-variable regions (HVR) based on the structural and sequence analysis. HVRs are interspersed with regions that are more conserved, termed framework regions (FW). For comparison, the Kabat CDR definition by Yvonne Chen, et al. (Selection and Analysis of an Optimized Anti-VEGF Antibody: Crystal Structure of an Affinity-matured Fab in Complex with Antigen, J. Mol. Biol. (1999) 293, 865-881) is listed below (see also FIG. 1a). Each $V_H$ and $V_L$ is composed of three HVRs and four FWs, arranged from amino-terminus to carboxy-terminus in the following order: FW1, HVR1, FW2, HVR2, FW3, HVR3, FW4. Throughout the present disclosure, the three HVRs of the heavy chain are referred to as HVR H1, HVR H2, and HVR H3. Similarly, the three HVRs of the light chain are referred to as HVR L1, HVR L2, and HVR L3.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. Within light and heavy chains, the variable and constant regions are joined by a "J" region of about 12 or more amino acids, with the heavy chain also including a "D" region of about 10 or more amino acids. See generally, Fundamental Immunology Ch. 7 (Paul, W., ed., $2^{nd}$ ed. Raven Press, N.Y. (1989)).

The L chain from any vertebrate species can be assigned to one of two clearly distinct types, called kappa and lambda, based on the amino acid sequences of their constant domains. Depending on the amino acid sequence of the constant domain of their heavy chains (CH), antibodies can be assigned to different classes or isotypes. There are five classes of antibodies: IgA, IgD, IgE, IgG, and IgM, having heavy chains designated α (alpha), δ (delta), ε (epsilon), γ (gamma), and μ (mu), respectively. The IgG class of antibody can be further classified into four subclasses IgG1, IgG2, IgG3, and IgG4 by the gamma heavy chains, Y1-Y4, respectively.

The term "antibody derivative" or "derivative" of an antibody refers to a molecule that is capable of binding to the same antigen (e.g., CD137) that the antibody binds to and comprises an amino acid sequence of the antibody linked to an additional molecular entity. The amino acid sequence of the antibody that is contained in the antibody derivative may be a full-length heavy chain, a full-length light chain, any portion or portions of a full-length heavy chain, any portion or portions of the full-length light chain of the antibody, any other fragment(s) of an antibody, or the complete antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional molecular entity by chemical coupling, genetic fusion, noncovalent association, or otherwise. The term "antibody derivative" also encompasses chimeric antibodies, humanized antibodies, and molecules that are derived from modifications of the amino acid sequences of a CD137 antibody, such as conservation amino acid substitutions, additions, and insertions.

The term "antigen-binding fragment" or "antigen binding portion" of an antibody refers to one or more portions of an antibody that retain the ability to bind to the antigen that the antibody bonds to (e.g., CD137). Examples of "antigen-binding fragment" of an antibody include (i) a Fab fragment, a monovalent fragment consisting of the $V_L$, $V_H$, $C_L$ and $C_m$ domains; (ii) a F(ab')$_2$ fragment, a bivalent fragment comprising two Fab fragments linked by a disulfide bridge at the hinge region; (iii) a Fd fragment consisting of the $V_H$ and $C_m$ domains; (iv) a Fv fragment consisting of the $V_L$ and $V_H$ domains of a single arm of an antibody, (v) a dAb fragment (Ward et al., Nature 341:544-546 (1989)), which consists of a $V_H$ domain; and (vi) an isolated complementarity determining region (CDR).

The term "binding molecule" encompasses (1) antibody, (2) antigen-binding fragment of an antibody, and (3) derivative of an antibody, each as defined herein.

The term "binding CD137," "binds CD137," "binding to CD137," or "binds to CD137" refers to the binding of a binding molecule, as defined herein, to the human CD137 in an in vitro assay, such as a Biacore assay as described in Example 4, with an affinity ($K_D$) of 100 nM or less.

The terms "CD137" and "CD137 receptor" are used interchangeably in the present application, and include the human CD137 receptor, as well as variants, isoforms, and species homologs thereof. Accordingly, a binding molecule, as defined and disclosed herein, may also bind CD137 from species other than human. In other cases, a binding molecule may be completely specific for the human CD137 and may not exhibit species or other types of cross-reactivity.

The term "CD137 antibody" refers to an antibody, as defined herein, capable of binding to human CD137 receptor.

The term "chimeric antibody" refers to an antibody that comprises amino acid sequences derived from different animal species, such as those having a variable region derived from a human antibody and a murine immunoglobulin constant region.

The term "compete for binding" refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The term "epitope" refers to a part of an antigen to which an antibody (or antigen-binding fragment thereof) binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope can include various numbers of amino acids in a unique spatial conformation. Methods of determining spatial conformation of epitopes include, for example, x-ray crystallography, 2-dimensional nuclear magnetic resonance, deuterium and hydrogen exchange in combination with mass spectrometry, or site-directed mutagenesis, or all methods used in combination with computational modeling of antigen and its complex structure with its binding antibody and its variants. See, e.g., Epitope Mapping Protocols in Methods in Molecular Biology, Vol. 66, G. E. Morris, Ed. (1996). Once a desired epitope of an antigen is determined, antibodies to that epitope can be generated, e.g., using the techniques described herein. The generation and characterization of antibodies may also elucidate information about desirable epitopes. From this information, it is then possible to competitively screen antibodies for binding to the same epitope. An approach to achieve this is to conduct cross-competition studies to find antibodies that competitively bind with one another, i.e., the antibodies compete for binding to the antigen. A high throughput process for "binning" antibodies based upon their cross-competition is described in PCT Publication No. WO 03/48731. The term "germline" refers to the nucleotide sequences of the antibody genes and gene segments as they are passed from parents to offspring via the germ cells. The germline sequence is distinguished from the nucleotide sequences encoding antibodies in mature B cells which have been altered by recombination and hypermutation events during the course of B cell maturation.

The term "glycosylation sites" refers to amino acid residues which are recognized by a eukaryotic cell as locations for the attachment of sugar residues. The amino acids where carbohydrate, such as oligosaccharide, is attached are typically asparagine (N-linkage), serine (0-linkage), and threonine (0-linkage) residues. The specific site of attachment is typically signaled by a sequence of amino acids, referred to herein as a "glycosylation site sequence". The glycosylation site sequence for N-linked glycosylation is: -Asn-X-Ser- or -Asn-X-Thr-, where X may be any of the conventional amino acids, other than proline. The terms "N-linked" and "O-linked" refer to the chemical group that serves as the attachment site between the sugar molecule and the amino acid residue. N-linked sugars are attached through an amino group; O-linked sugars are attached through a hydroxyl group. The term "glycan occupancy" refers to the existence of a carbohydrate moiety linked to a glycosylation site (i.e., the glycan site is occupied). Where there are at least two potential glycosylation sites on a polypeptide, either none (0-glycan site occupancy), one (1-glycan site occupancy) or both (2-glycan site occupancy) sites can be occupied by a carbohydrate moiety.

The term "host cell" refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; or human tissues or hybridoma cells, yeast cells, and insect cells, and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

The term "human antibody" refers to an antibody in which the entire amino acid sequences of the light chains and heavy chains are from the human immunoglobulin genes. A human antibody may contain murine carbohydrate chains if produced in a mouse, in a mouse cell or in a hybridoma derived from a mouse cell. Human antibodies may be prepared in a variety of ways known in the art.

The term "humanized antibody" refers to a chimeric antibody that contains amino acid residues derived from human antibody sequences. A humanized antibody may contain some or all of the CDRs or HVRs from a non-human animal or synthetic antibody while the framework and constant regions of the antibody contain amino acid residues derived from human antibody sequences.

The term "illustrative antibody" refers to any one of the antibodies described in the disclosure and designated as those listed in Tables 1a and 1b. These antibodies may be in any class (e.g., IgA, IgD, IgE, IgG, and IgM). Thus, each antibody identified above encompasses antibodies in all five classes that have the same amino acid sequences for the $V_L$ and $V_H$ regions. Further, the antibodies in the IgG class may be in any subclass (e.g., IgG1 IgG2, IgG3, and IgG4). Thus, each antibody identified above in the IgG subclass encompasses antibodies in all four subclasses that have the same amino acid sequences for the $V_L$ and $V_H$ regions. The amino acid sequences of the heavy chain constant regions of human antibodies in the five classes, as well as in the four IgG subclasses, are known in the art. The amino acid sequence of the full length heavy chain and light chain for the IgG4 subclass of each of the illustrative antibodies shown in Table 1b is provided in the disclosure.

The term "isolated antibody" or "isolated binding molecule" refers to an antibody or a binding molecule, as defined herein, that: (1) is not associated with naturally associated components that accompany it in its native state; (2) is free of other proteins from the same species; (3) is expressed by a cell from a different species; or (4) does not occur in nature. Examples of isolated antibodies include a CD137 antibody that has been affinity purified using CD137, a CD137 antibody that has been generated by hybridomas or other cell line in vitro, and a CD137 antibody derived from a transgenic animal.

The term "isolated nucleic acid" refers to a nucleic acid molecule of genomic, cDNA, or synthetic origin, or a combination thereof, which is separated from other nucleic acid molecules present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid of interest.

The term "$k_a$" refers to the association rate constant of a particular antibody-antigen interaction, whereas the term "$k_d$" refers to the dissociation rate constant of a particular antibody-antigen interaction.

The term "$K_D$" refers to the equilibrium dissociation constant of a particular antibody-antigen interaction. It is obtained from the ratio of $k_d$ to $k_a$ (i.e., $k_d/k_a$) and is expressed as a molar concentration (M). $K_D$ is used as a measure for the affinity of an antibody's binding to its binding partner. The smaller the $K_D$, the more tightly bound the antibody is, or the higher the affinity between antibody and the antigen. For example, an antibody with a nanomolar (nM) dissociation constant binds more tightly to a particular antigen than an antibody with a micromolar (µM) dissociation constant. $K_D$ values for antibodies can be determined using methods well established in the art. One method for determining the $K_D$ of an antibody is by using surface plasmon resonance, typically using a biosensor system such as a Biacore® system. An assay procedure using the BIACORE™ system (BIAcore assay) is described in the Examples section of this disclosure.

The term "mammal" refers to any animal species of the Mammalia class. Examples of mammals include: humans; laboratory animals such as rats, mice, simians and guinea pigs; domestic animals such as cats, dogs, rabbits, cattle, sheep, goats, horses, and pigs; and captive wild animals such as lions, tigers, elephants, and the like.

The term "prevent" or "preventing," with reference to a certain disease condition in a mammal, refers to preventing or delaying the onset of the disease, or preventing the manifestation of clinical or subclinical symptoms thereof.

As used herein, "sequence identity" between two polypeptide sequences indicates the percentage of amino acids that are identical between the sequences. The amino acid sequence identity of polypeptides can be determined conventionally using known computer programs such as Bestfit, FAST A, or BLAST (see, e.g. Pearson, *Methods Ezymol.* 183:63-98 (1990); Pearson, *Methods Mol. Biol.* 132:185-219 (2000); Altschul et al., *J. Mol. Biol.* 215:403-410 (1990); Altschul et al., *Nucleic Acids Res.* 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

The term "specifically binds" or "specifically binds to," in reference to the interaction of a binding molecule, as defined herein, (e.g., an antibody) with its binding partner (e.g., an antigen), refers to the ability of the binding molecule to discriminate between an antigen of interest from an animal species and the antigen orthologue from a different animal species under a given set of conditions. A CD137 binding molecule is said to specifically bind to human CD137 if it binds to human CD137 at an EC50 that is below 50 percent of the EC50 at which it binds CD137 of rat or mouse as determined in an in vitro assay. Binding specificity of an antibody can be determined using methods known in the art. Examples of such methods include FACS using PHA stimulated primary cells, Western blots, ELISA-, RIA-, ECL-, IRMA-tests and peptide scans.

The term "selectively binds" or "selectively binds to," in reference to the interaction of a binding molecule, as defined herein, (e.g., an antibody) with its binding partner (e.g., an antigen), refers to the ability of the binding molecule to discriminate between an antigen of interest from an animal species (such as human CD137) and a different antigen from the same animal species (such as human CD40) under a given set of conditions. A CD137 binding molecule is said to selectively bind to human CD137 if it binds to human CD137 at an EC50 that is below 10 percent of the EC50 at which it binds to human CD40 or human CD134 as determined in an in vitro assay.

The term "treat", "treating", or "treatment", with reference to a certain disease condition in a mammal, refers causing a desirable or beneficial effect in the mammal having the disease condition. The desirable or beneficial effect may include reduced frequency or severity of one or more symptoms of the disease (i.e., tumor growth and/or metastasis, or other effect mediated by the numbers and/or activity of immune cells, and the like), or arrest or inhibition of further development of the disease, condition, or disorder. In the context of treating cancer in a mammal, the desirable or beneficial effect may include inhibition of further growth or spread of cancer cells, death of cancer cells, inhibition of reoccurrence of cancer, reduction of pain associated with the cancer, or improved survival of the mammal. The effect can be either subjective or objective. For example, if the mammal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

The term "vector" refers to a nucleic acid molecule capable of transporting a foreign nucleic acid molecule. The foreign nucleic acid molecule is linked to the vector nucleic acid molecule by a recombinant technique, such as ligation or recombination. This allows the foreign nucleic acid molecule to be multiplied, selected, further manipulated or expressed in a host cell or organism. A vector can be a plasmid, phage, transposon, cosmid, chromosome, virus, or virion. One type of vectors can be integrated into the genome of a host cell upon introduction into the host cell, and thereby are replicated along with the host genome (e.g., non-episomal mammalian vectors). Another type of vector is capable of autonomous replication in a host cell into which it is introduced (e.g., bacterial vectors having a bacterial origin of replication and episomal mammalian vectors). Another specific type of vector capable of directing the expression of expressible foreign nucleic acids to which they are operatively linked is commonly referred to as "expression vectors." Expression vectors generally have control sequences that drive expression of the expressible foreign nucleic acids. Simpler vectors, known as "transcription vectors," are only capable of being transcribed but not translated: they can be replicated in a target cell but not expressed. The term "vector" encompasses all types of vectors regardless of their function. Vectors capable of directing the expression of expressible nucleic acids to which they are operatively linked are commonly referred to "expression vectors."

The methods and techniques of the present disclosure are generally performed according to methods well known in the art and as described in various general and more specific references that are cited and discussed throughout the present specification unless otherwise indicated. Such references include, e.g., Sambrook and Russell, Molecular Cloning, *A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane *Antibodies: A Laboratory Manual*, Cold Spring Harbor Laboratory Press, Cold Spring Harbor, N.Y. (1990). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)).

B. Binding Molecules that Bind to Human CD137

The present disclosure provides isolated binding molecules that bind to human CD137, including CD137 antibodies, antigen-binding fragments of the CD137 antibodies, and derivatives of the CD137 antibodies. In some embodiments, the binding molecules are any of the antibodies described herein, including antibodies described with reference to epitope binding and antibodies described with reference to specific amino acid sequences of HVRs, variable regions (VL, VH), and IgG (e.g., IgG4) light and heavy chains. In some embodiments, the present disclosure relates to binding molecules that bind to human CD137, and have at least one (e.g., at least one, at least two, at least three, at least four, at least five, at least six, at least seven, eight, or all nine) of the following functional properties: (a) bind to human CD137 with a KD of 500 nM or less; (b) have agonist activity on human CD137; (c) do not bind to human OX40, CD40, GITR and/or CD27 receptor at concentration up to 1000 nM; (d) is cross-reactive with monkey, mouse, rat, or dog CD137; (e) do not induce ADCC effects; (f) are capable of inhibiting tumor cell growth; (g) have therapeutic effect on a cancer; (h) blocks binding between CD137 and CD137L; and (i) blocks CD137 signaling stimulated by CD137L (e.g., CD137L-stimulated NF-κB-dependent transcription) in a cell that expresses CD137. In some embodiments, the antibodies disclosed herein can also block, e.g., completely block, the binding between CD137 and its ligand CD137L. Also provided herein are one or more anti-CD137 antibodies or antigen-binding fragments that cross-compete for binding to human CD137 with one or more of the antibodies or antigen-binding fragments as described herein.

In some embodiments, the antibodies or the antigen-binding fragments thereof bind to one or more amino acid residues within amino acid residues 34-108 of SEQ ID NO:1. In some embodiments, the antibodies or antigen-binding fragments bind to one or more amino acid residues within amino acid residues 34-93 of SEQ ID NO:1. In some embodiments, the antibodies or antigen-binding fragments bind to one or more amino acid residues selected from the group consisting of amino acid residues 34-36, 53-55, and 92-93 of SEQ ID NO:1. In some embodiments, the antibodies or antigen-binding fragments bind to one or more of amino acid residues 34-36, one or more of amino acid residues 53-55, and one or more or amino acid residues 92-93 of SEQ ID NO:1. In some embodiments, the antibodies or antigen-binding fragments do not bind to one or more of amino acid residues selected from the group consisting of amino acid residues 109-112, 125, 126, 135-138, 150 and 151 of SEQ ID NO:1. In some embodiments, the antibodies or antigen-binding fragments do not bind to amino acid residues 109-112, 125, 126, 135-138, 150 and 151 of SEQ ID NO:1. Methods of measuring an antibody or antigen-binding fragment's ability to bind a target antigen may be carried out using any method known in the art, including for example, by surface plasmon resonance, an ELISA, isothermal titration calorimetry, a filter binding assay, an EMSA, etc. In some embodiments, the ability of the antibody or antigen-binding fragment to bind a target antigen is measured by surface plasmon resonance (See e.g., Example 1 below).

In some embodiments, the antibodies or antigen-binding fragments bind to human CD137 with a KD of about 500 nM or less (e.g., about 500 nM or less, about 400 nM or less, about 300 nM or less, about 200 nM or less, about 150 nM or less, about 100 nM or less, about 90 nM or less, about 80 nM or less, about 75 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the antibodies or antigen-binding fragments bind to human CD137 with a KD of about 100 nM or less. In some embodiments, the antibodies or antigen-binding fragments bind to human CD137 with a KD of about 50 nM or less. Methods of measuring the KD of an antibody or antigen-binding fragment may be carried out using any method known in the art, including for example, by surface plasmon resonance, an ELISA, isothermal titration calorimetry, a filter binding assay, an EMSA, etc. In some embodiments, the KD is measured by surface plasmon resonance (See e.g., Example 1 below).

Anti-CD137 antibodies need to be cross-linked to become agonistic. For example, crosslinking is achieved in vivo through Fcgamma receptors, while typically polyclonal anti-Fc antibodies are used in cell-based experiments in vitro. In some embodiments, the antibodies or antigen-binding fragments described herein have agonist activity on human CD137. In some embodiments, the antibodies or antigen-binding fragments induce one or more (e.g., one or more, two or more, three or more, etc.) activities of human CD137 when a cell (e.g., a human cell) expressing human CD137 is contacted by the antibody or antigen binding fragment. Various CD137 activities are known in the art and may include, without limitation, induction of NF-κB-dependent transcription, induction of T cell proliferation, prolonging T cell survival, co-stimulation of activated T cells, induction of cytokine secretion (such as IL-2), and induction of monocyte activation. In some embodiments, the one or more CD137 activities is not CD137 binding to its ligand. Methods of measuring CD137 activity (e.g., the induction of NF-κB-dependent transcription and/or T cell proliferation, etc.) are known in the art, including, for example, via the methods described in Examples 8 and 9 below. In some embodiments, the antibodies or antigen-binding fragments increase NF-κB dependent transcription in cells (e.g., human cells) expressing human CD137. In some embodiments, NF-κB dependent transcription is increased by about 10% or more, about 20% or more, about 30% or more, about 40% or more, about 50% or more, about 60% or more, about 70% or more, about 80% or more, about 90% or more, or about 99% or more in cells (e.g., human cells) expressing CD137 contacted with the antibody or antigen-binding fragment, relative to a corresponding cell not contacted with the antibody or antigen-binding fragment (e.g., a corresponding cell not contacted with an antibody, or contacted with an isotype control antibody).

In some embodiments, NF-κB dependent transcription is increased by about 2-fold, 3-fold, 4-folr, 5-fold, 6-fold, 7-fold, 8-fold, 9-fold, 10-fold, 100-fold, 1000-fold or more in cells (e.g., human cells) expressing CD137 contacted with the antibody or antigen-binding fragment, relative to a corresponding cell not contacted with the antibody or antigen-binding fragment (e.g., a corresponding cell not contacted with an antibody, or contacted with an isotype control antibody).

In some embodiments, the antibodies or antigen-binding fragments are cross-reactive with monkey (e.g., cynomolgus monkey), mouse, rat, and/or dog CD137. In some embodiments, the antibodies or antigen-binding fragments are cross-reactive with monkey CD137. In some embodiments, the antibodies or antigen-binding fragments are cross-reactive with mouse CD137. In some embodiments, the antibodies or antigen-binding fragments are cross-reactive with rat CD137. In some embodiments, the antibodies or antigen-binding fragments are cross-reactive with dog CD137. In some embodiments, the antibodies or antigen binding fragments are cross reactive with monkey and mouse CD137; monkey and rat CD137; monkey and dog CD137; mouse and rat CD137; mouse and dog CD137; rat and dog CD137; monkey, mouse, and rat CD137; monkey, mouse, and dog CD137; monkey, rat, and dog CD137; mouse, rat, and dog CD137; or monkey, mouse, rat, and dog CD137. In some embodiments, the antibodies or antigen-binding fragments are cross-reactive at about 100 nM (e.g., at about 1 nM, at about 10 nM, at about 25 nM, at about 50 nM, at about 75 nM, at about 100 nM). Methods of measuring antibody cross-reactivity are known in the art, including, without limitation, surface plasmon resonance, an ELISA, isothermal titration calorimetry, a filter binding assay, an EMSA, etc. In some embodiments, the cross-reactivity is measured by ELISA (See e.g., Example 2 below).

In some embodiments, the antibodies do not induce ADCC effects. Methods of measuring ADCC effects (e.g., in vivo methods) are known in the art, including, without limitation, via the methods described in Example 11 below. In some embodiments, the antibodies do not ADCC effects by more than about 10% (do not induce ADCC by more than about 10%, more than about 5%, more than about 1%, more than about 0.1%, more than about 0.01%) relative to a control.

In some embodiments, the antibodies or antigen-binding fragments are capable of inhibiting tumor cell growth/proliferation. In some embodiments, the tumor cell growth/proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the antibodies or antigen-binding fragments relative to corresponding tumor cells not contacted with the antibodies or antigen-binding fragments. In some embodiments, the antibodies or antigen-binding fragments are capable of reducing tumor volume in a subject when the subject is administered the antibodies or antigen-binding fragments. In some embodiments, the antibodies or antigen-binding fragments are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the antibodies or antigen-binding fragments). Methods of monitoring tumor cell growth/proliferation, tumor volume, and/or tumor inhibition are known in the art, including, for example, via the methods described in Example 10 below.

In some embodiments, the antibodies or antigen-binding fragments have therapeutic effect on a cancer. In some embodiments, the antibodies or antigen-binding fragments reduce one or more signs or symptoms of a cancer. In some embodiments, a subject suffering from a cancer goes into partial or complete remission when administered the antibodies or antigen-binding fragments.

In another aspect, the disclosure provides isolated antibodies that compete or cross-compete for binding to human CD137 with any of the illustrative antibodies of the disclosure, such as AG10058, AG10059, and/or AG10131. In a particular embodiment, the disclosure provides isolated antibodies that compete or cross-compete for binding to the same epitope on the human CD137 with any of the illustrative antibodies of the disclosure. The ability of an antibody to compete or cross-compete for binding with another antibody can be determined using standard binding assays known in the art, such as BIAcore analysis, ELISA assays, or flow cytometry. For example, one can allow an illustrative antibody of the disclosure to bind to human CD137 under saturating conditions and then measure the ability of the test antibody to bind to the CD137. If the test antibody is able to bind to the CD137 at the same time as the illustrative antibody, then the test antibody binds to a different epitope as the illustrative antibody. However, if the test antibody is not able to bind to the CD137 at the same time, then the test antibody binds to the same epitope, an overlapping epitope, or an epitope that is in close proximity to the epitope bound by the illustrative antibody. This experiment can be performed using various methods, such as ELISA, RIA, FACS or surface plasmon resonance.

In some embodiments, the antibodies or antigen-binding fragments block the binding between CD137 and its ligand (e.g., human CD137 and human CD137L). In some embodiments, the antibodies or antigen-binding fragments block the binding between CD137 and its ligand in vitro. In some embodiments, the antibody or antigen-binding fragment has a half maximal inhibitory concentration (IC50) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for blocking binding of CD137 its ligand. In some embodiments, the antibody or antigen-binding fragment has a half maximal inhibitory concentration (IC50) of about 100 nM or less for blocking binding of CD137 its ligand. In some embodiments, the antibody or antigen-binding fragment completely blocks binding of human CD137 to its ligand when provided at a concentration of about 100 nM or greater (e.g., about 100 nM or greater, about 500 nM or greater, about 1 µM or greater, about 1004 or greater, etc.). As used herein, the term "complete blocking" or "completely blocks" refers to the antibody or antigen-binding fragment's ability to reduce binding between a first protein and a second protein by at least about 80% (e.g., at least about 80%, at least about 85%, at least about 90%, at least about 95%, at least about 99%, etc.). Methods of measuring the ability of an antibody or antigen-binding fragment to block binding of a first protein (e.g., a CD137) and a second protein (e.g., CD137L) are known in the art, including, without limitation, via BIAcore analysis, ELISA assays, and flow cytometry (See e.g., Example 6 below).

B-1. CD137 Antibodies

In some aspects, the present disclosure provides an isolated antibody that binds to human CD137 at an epitope within amino acid residues 34-108 or 34-93 of SEQ ID NO.: 1. The antibody, in some embodiments, binds human CD137 with a $K_D$ of 50 nM or less as measured by surface plasmon resonance. In certain embodiments, the antibody can be cross-reactive with at least one non-human species selected from the list consisting of cynomolgus monkey, mouse, rat and dog.

In one aspect, the present disclosure provides an isolated antibody comprising a heavy chain variable region and a light chain variable region, a) wherein the heavy chain variable region comprises an HVR-H1, an HVR-H2, and an HVR-H3, wherein the HVR-H1 comprises an amino acid sequence according to a formula selected from the group consisting of: Formula (I): X1TFX2X3YX4IHWV (SEQ ID NO:2), wherein X1 is F or Y, X2 is S or T, X3 is G, N, or S, and X4 is A, G, or W; Formula (II): YSIX1SGX2X3WX4WI (SEQ ID NO:3), wherein X1 is S or T, X2 is H or Y, X3 is H or Y, and X4 is A, D, G, N, S, or T; and Formula (III): FSLSTX1GVX2VX3WI (SEQ ID NO:4), wherein X1 is G or S, X2 is A or G, and X3 is A, G, S, or T; wherein the HVR-H2 comprises an amino acid sequence according to a formula selected from the group consisting of: Formula (IV): LALIDWX1X2DKX3YSX4SLKSRL (SEQ ID NO:5), wherein X1 is A, D, or Y, X2 is D or G, X3 is R, S, or Y, and X4 is P or T; Formula (V): IGX1IYHSGX2TYYX3PSLKSRV (SEQ ID NO:6), wherein X1 is D or E, X2 is N or S, and X3 is N or S; and Formula (VI): VSX1ISGX2GX3X4TYYADSVKGRF (SEQ ID NO:7), wherein X1 is A, G, S, V, or Y, X2 is A, D, S, or Y, X3 is D, G, or S, and X4 is S or T; and wherein the HVR-H3 comprises an amino acid sequence according to Formula (VII): ARX1GX2X3X4VX5GDWFX6Y (SEQ ID NO:8), wherein X1 is E or G, X2 is E or S, X3 is D or T, X4 is A, T, or V, X5 is A, I, L, T, or V, and X6 is A, D, or G; and/or b) wherein the light chain variable region comprises an HVR-L1, an HVR-L2, and an HVR-L3, wherein the HVR-L1 comprises an amino acid sequence according to Formula (VIII): X1ASQX2X3X4X5X6X7X8 (SEQ ID NO:9), wherein X1 is Q or R, X2 is D, G, or S, X3 is I or V, X4 is G, R, S, or T, X5 is P, R, S, or T, X6 is A, D, F, S, V, or Y, X7 is L or V, and X8 is A, G, or N; wherein the HVR-L2 comprises an amino acid sequence according to Formula (IX): X1ASX2X3X4X5GX6 (SEQ ID NO:10), wherein X1 is A or D, X2 is N, S, or T, X3 is L or R, X4 is A, E, or Q, X5 is S or T, and X6 is I or V; and wherein the HVR-L3 comprises an amino acid sequence according to a formula selected from the group consisting of: Formula (X): YCQQX1YX2X3X4T (SEQ ID NO:11), wherein X1 is A, G, S, or Y, X2 is Q, S, or Y, X3 is I, L, T, or Y, and X4 is I, S, V, or W; and Formula (XI): YCX1QX2X3X4X5PX6T (SEQ ID NO:12), wherein X1 is E or Q, X2 is P, S, or Y, X3 is D, L, S, T, or Y, X4 is D, E, H, S, or T, X5 is D, L T, or W, and X6 is L, P, R, or V.

In some embodiments, the antibody can comprise an HVR_H1 having the amino acid sequence selected from the group consisting of SEQ ID NOs: 253-312, an HVR_H2 having the amino acid sequence selected from the group consisting of SEQ ID NOs: 313-372, an HVR_H3 having the amino acid sequence selected from the group consisting of SEQ ID NOs: 373-432, an HVR_L1 having the amino acid sequence selected from the group consisting of SEQ ID NOs: 433-492, an HVR_L2 having the amino acid sequence selected from the group consisting of SEQ ID NOs: 493-552, and/or an HVR_L3 having the amino acid sequence selected from the group consisting of SEQ ID NOs: 553-612.

In certain embodiments, the antibody can comprise a VL and/or VH having the amino acid sequence selected from the group consisting of SEQ ID NOs:13-132, which can preferably be encoded by the DNA sequence selected from the group consisting of SEQ ID NOs: 133-252, respectively.

In some embodiments, the antibody can comprise an HVR_H1 having the amino acid sequence selected from the group consisting of SEQ ID NOs: 709-732, an HVR_H2 having the amino acid sequence selected from the group consisting of SEQ ID NOs: 733-756, an HVR_H3 having the amino acid sequence selected from the group consisting of SEQ ID NOs: 757-780, an HVR_L1 having the amino acid sequence selected from the group consisting of SEQ ID NOs: 781-804, an HVR_L2 having the amino acid sequence selected from the group consisting of SEQ ID NOs: 805-828, and/or an HVR_L3 having the amino acid sequence selected from the group consisting of SEQ ID NOs: 829-852.

In certain embodiments, the antibody can comprise a light chain and/or heavy chain (e.g., those of IgG such as IgG4) having the amino acid sequences selected from the group consisting of SEQ ID NOs: 613-660, which can be preferably encoded by the DNA sequence selected from the group consisting of SEQ ID NOs: 661-708, respectively.

In some embodiments, the HVRs are according to Kabat. In some embodiments, the antibody comprises a heavy chain variable (VH) domain comprising an HVR-H1 comprising the sequence GFSLSTSGVGVG (SEQ ID NO:866), an HVR-H2 comprising the sequence LIDWDDDKYYSPSLKS (SEQ ID NO:867), and an HVR-H3 comprising the sequence GGSDTVLGDWFAY (SEQ ID NO:868); and/or a light chain variable (VL) domain comprising an HVR-L1 comprising the sequence RASQSVSPYLA (SEQ ID NO:869), an HVR-L2 comprising the sequence DASSLES (SEQ ID NO:870), and an HVR-L3 comprising the sequence QQGYSLWT (SEQ ID NO:871).

In some embodiments, the HVRs are according to Kabat. In some embodiments, the antibody comprises a heavy chain variable (VH) domain comprising an HVR-H1 comprising the sequence GYSITSGHYWA (SEQ ID NO:872), an HVR-H2 comprising the sequence SISGYGSTTYYADSVKG (SEQ ID NO:873), and an HVR-H3 comprising the sequence GGSDAVLGDWFAY (SEQ ID NO:874); and/or a light chain variable (VL) domain comprising an HVR-L1 comprising the sequence RASQGIGSFLA (SEQ ID NO:875), an HVR-L2 comprising the sequence DASNLET (SEQ ID NO:876), and an HVR-L3 comprising the sequence QQGYYLWT (SEQ ID NO:877).

In some embodiments, the HVRs are according to Kabat. In some embodiments, the antibody comprises a heavy chain variable (VH) domain comprising an HVR-H1 comprising the sequence GFSLSTGGVGVG (SEQ ID NO:878), an HVR-H2 comprising the sequence LIDWADDKYYSPSLKS (SEQ ID NO:879), and an HVR-H3 comprising the sequence GGSDTVIGDWFAY (SEQ ID NO:880); and/or a light chain variable (VL) domain comprising an HVR-L1 comprising the sequence RASQSIGSYLA (SEQ ID NO:881), an HVR-L2 comprising the sequence DASNLET (SEQ ID NO:882), and an HVR-L3 comprising the sequence QQGYYLWT (SEQ ID NO:883).

The CD137 antibodies described herein can be in any class, such as IgG, IgM, IgE, IgA, or IgD. It is preferred that the CD137 antibodies are in the IgG class, such as IgG1, IgG2, IgG3, or IgG4 subclass. A CD137 antibody can be converted from one class or subclass to another class or subclass using methods known in the art. An exemplary method for producing an antibody in a desired class or subclass comprises the steps of isolating a nucleic acid encoding a heavy chain of an CD137 antibody and a nucleic acid encoding a light chain of a CD137 antibody, isolating the sequence encoding the $V_H$ region, ligating the $V_H$ sequence to a sequence encoding a heavy chain constant region of the desired class or subclass, expressing the light chain gene and the heavy chain construct in a cell, and collecting the CD137 antibody.

Further, the antibodies provided by the present disclosure can be monoclonal or polyclonal, but preferably monoclonal.

Examples of specific isolated antibodies provided by the present disclosure include those listed in Tables 1a and 1b. The nucleotide and amino acid sequences of the heavy chain variable region, full length heavy chain for the IgG2 and IgG4 subclass, light chain variable region, and full length light chain of these antibodies are also provided hereunder.

Antibodies of the present disclosure can be produced by techniques known in the art, including conventional monoclonal antibody methodology e.g., the standard somatic cell hybridization technique (See e.g., Kohler and Milstein, *Nature* 256:495 (1975), viral or oncogenic transformation of B lymphocytes, or recombinant antibody technologies as described in detail herein below.

Hybridoma production is a very well-established procedure. The common animal system for preparing hybridomas is the murine system. Immunization protocols and techniques for isolation of immunized splenocytes for fusion are known in the art. Fusion partners (e.g., murine myeloma cells) and fusion procedures are also known. One well-known method that may be used for making human CD137 antibodies provided by the present disclosure involves the use of a XenoMouse™ animal system. XenoMouse™ mice are engineered mouse strains that comprise large fragments of human immunoglobulin heavy chain and light chain loci and are deficient in mouse antibody production. See, e.g., Green et al., Nature Genetics 7:13-21 (1994) and WO2003/040170. The animal is immunized with a CD137 antigen. The CD137 antigen is isolated and/or purified CD137, preferably CD137. It may be a fragment of CD137, such as the extracellular domain of CD137, particularly a CD137 extracellular domain fragment comprising amino acid resides 34-108 or 34-93 of SEQ ID NO: 1. Immunization of animals can be carried out by any method known in the art. See, e.g., Harlow and Lane, Antibodies: A Laboratory Manual, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. The CD137 antigen may be administered with an adjuvant to stimulate the immune response. Exemplary adjuvants include complete or incomplete Freund's adjuvant, RIBI (muramyl dipeptides) or ISCOM (immunostimulating complexes). After immunization of an animal with a CD137 antigen, antibody-producing immortalized cell lines are prepared from cells isolated from the immunized animal. After immunization, the animal is sacrificed and lymph node and/or splenic B cells are immortalized. Methods of immortalizing cells include, but are not limited to, transferring them with oncogenes, inflecting them with the oncogenic virus cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using CD137, a portion thereof, or a cell expressing CD137. CD137 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

Antibodies of the disclosure can also be prepared using phage display or yeast display methods. Such display methods for isolating human antibodies are established in the art, such as Achim Knappik, et al., "Fully Synthetic Human Combinatorial Antibody Libraries (HuCAL) Based on Modular Consensus Frameworks and CDRs Randomized with Trinucleotides." J. Mol. Biol. (2000) 296, 57-86; and Michael J. Feldhaus, et al, "Flow-cytometric isolation of human antibodies from a non-immune *Saccharomyces cerevisiae* surface display library" Nat Biotechnol (2003) 21:163-170.

B-2. Antigen Binding Fragments

In some other aspects, the present disclosure provides antigen-binding fragments of any of the CD137 antibodies provided by the present disclosure.

The antigen-binding fragment may comprise any sequences of the antibody. In some embodiments, the antigen-binding fragment comprises the amino acid sequence of: (1) a light chain of a CD137 antibody; (2) a heavy chain of a CD137 antibody; (3) a variable region from the light chain of a CD137 antibody; (4) a variable region from the heavy chain of a CD137 antibody; (5) one or more HVRs (two, three, four, five, or six HRVs) of a CD137 antibody; or (6) three HVRs from the light chain and three HVRs from the heavy chain of a CD137 antibody.

In some particular embodiments, the disclosure provides an antigen-binding fragment of an antibody selected from those listed in Tables 1a and 1b.

In some other particular embodiments, the antigen-binding fragments of an CD137 antibody include: (i) a Fab fragment, which is a monovalent fragment consisting of the $V_L$, $V_H$, $C_L$ and $C_H1$ domains; (ii) a F(ab')$_2$ fragment, which is a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated CDR, and (vii) single chain antibody (scFv), which is a polypeptide comprising a $V_L$ region of an antibody linked to a $V_H$ region of an antibody. Bird et al., (1988) Science 242:423-426 and Huston et al., (1988) Proc. Natl. Acad. Sci. USA 85:5879-5883.

In some particular embodiments, the antigen-binding fragment is a Fab fragment selected from those listed in Table 1a.

B-3. Antibody Derivatives

In some further aspects, the present disclosure provides derivatives of any of the CD137 antibodies provided by the present disclosure.

In one aspect, the antibody derivative is derived from modifications of the amino acid sequences of an illustrative antibody ("parent antibody") of the disclosure while conserving the overall molecular structure of the parent antibody amino acid sequence. Amino acid sequences of any regions of the parent antibody chains may be modified, such as framework regions, HVR regions, or constant regions. Types of modifications include substitutions, insertions, deletions, or combinations thereof, of one or more amino acids of the parent antibody.

In some embodiments, the antibody derivative comprises a $V_L$ or $V_H$ region that is at least 65%, at least 75%, at least 85%, at least 90%, at least 95%, at least 96%, at least 97%, at least 98%, or at least 99% identical to an amino acid sequence as set forth in any of SEQ ID NOs: 13-132. In some embodiments, the antibody derivative comprises an HVR_H1 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 253-312. In some embodiments, the antibody derivative comprises an HVR_H2 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 313-372. In some embodiments, the antibody derivative comprises an HVR_H3 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 373-432. In some embodiments, the antibody derivative comprises an HVR_L1 amino acid sequences for all Fab hits shown in Table 1a can be found in SEQ ID NOs: 433-492. In some embodiments, the antibody derivative comprises an HVR_L2 amino acid sequences for all Fab hits shown in Table 1a can be found in SEQ ID NOs: 493-552.

In some embodiments, the antibody derivative comprises an HVR_L3 amino acid sequences for all Fab hits shown in Table 1a can be found in SEQ ID NOs: 553-612. In some particular embodiments, the derivative comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to an amino acid sequence as set forth in any of SEQ ID NOs: 13-132 and 253-612.

In some embodiments, the antibody derivative comprises a light chain or heavy chain that is at least 65%, at least 75%, at least 85%, at least 90%, at least 95%, at least 96%, at least 97%, at least 98%, or at least 99% identical to an amino acid sequence as set forth in any of SEQ ID NOs: 613-660.

In some embodiments, the antibody derivative comprises an HVR_H1 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 709-732. In some embodiments, the antibody derivative comprises an HVR_H2 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 733-756. In some embodiments, the antibody derivative comprises an HVR_H3 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 757-780. In some embodiments, the antibody derivative comprises an HVR_L1 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 781-804. In some embodiments, the antibody derivative comprises an HVR_L2 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 805-828. In some embodiments, the antibody derivative comprises an HVR_L3 amino acid sequence region that is at least 65%, at least 75%, at least 85%, at least 90%, at least 95%, at least 96%, at least 97%, at least 98%, or at least 99% identical to an amino acid sequence as set forth in any of SEQ ID NOs: 829-852. In some particular embodiments, the derivative comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to an amino acid sequence as set forth in any of SEQ ID NOs: 613-660 and 709-852.

Amino acid substitutions encompass both conservative substitutions and non-conservative substitutions. The term "conservative amino acid substitution" means a replacement of one amino acid with another amino acid where the two amino acids have similarity in certain physico-chemical properties such as polarity, charge, solubility, hydrophobicity, hydrophilicity, and/or the amphipathic nature of the residues involved. For example, substitutions typically may be made within each of the following groups: (a) nonpolar (hydrophobic) amino acids, such as alanine, leucine, isoleucine, valine, proline, phenylalanine, tryptophan, and methionine; (b) polar neutral amino acids, such as glycine, serine, threonine, cysteine, tyrosine, asparagine, and glutamine; (c) positively charged (basic) amino acids, such as arginine, lysine, and histidine; and (d) negatively charged (acidic) amino acids, such as aspartic acid and glutamic acid.

The modifications may be made in any positions of the amino acid sequences of the antibody, including the HVRs, framework regions, or constant regions. In one embodiment, the present disclosure provides an antibody derivative that contains the $V_H$ and $V_L$ HVR sequences of an illustrative antibody of this disclosure, yet contains framework sequences different from those of the illustrative antibody. Such framework sequences can be obtained from public DNA databases or published references that include germline antibody gene sequences. For example, germline DNA sequences for human heavy and light chain variable region genes can be found in the Genbank database or in the "VBase" human germline sequence database (Kabat, E. A., et al., Sequences of Proteins of Immunological Interest, Fifth Edition, U.S. Department of Health and Human Services, NIH Publication No. 91-3242 (1991); Tomlinson, I. M., et al., *J. Mol. Biol.* 227:776-798 (1992); and Cox, J. P. L. et al., *Eur. J. Immunol.* 24:827-836 (1994)). Framework sequences that may be used in constructing an antibody derivative include those that are structurally similar to the framework sequences used by illustrative antibodies of the disclosure, e.g., similar to the $V_H$ 3-23 framework sequences and/or the $V_L\lambda 3$ or $\lambda 1$-13 framework sequences used by illustrative antibodies of the disclosure. For example, the HVR_H1, HVR_H2, and HVR_H3 sequences, and the HVR_L1, HVR_L2, and HVR_L3 sequences of an illustrative antibody can be grafted onto framework regions that have the identical sequence as that found in the germline immunoglobulin gene from which the framework sequence derive, or the HVR sequences can be grafted onto framework regions that contain one or more mutations as compared to the germline sequences.

In a particular embodiment, the antibody derivative is a chimeric antibody which comprises an amino acid sequence of an illustrative antibody of the disclosure. In one example, one or more HVRs from one or more illustrative human antibodies are combined with HVRs from an antibody from a non-human animal, such as mouse or rat. In another example, all of the HVRs of the chimeric antibody are derived from one or more illustrative antibodies. In some particular embodiments, the chimeric antibody comprises one, two, or three HVRs from the heavy chain variable region or from the light chain variable region of an illustrative antibody. Chimeric antibodies can be generated using conventional methods known in the art.

Another type of modification is to mutate amino acid residues within the HRV regions of the $V_H$ and/or $V_L$ chain. Site-directed mutagenesis or PCR-mediated mutagenesis can be performed to introduce the mutation(s) and the effect on antibody binding, or other functional property of interest, can be evaluated in in vitro or in vivo assays known in the art. Typically, conservative substitutions are introduced. The mutations may be amino acid additions and/or deletions. Moreover, typically no more than one, two, three, four or five residues within a HVR region are altered. In some embodiments, the antibody derivative comprises 1, 2, 3, or 4 amino acid substitutions in the heavy chain HVRs and/or in the light chain HVRs. In another embodiment, the amino acid substitution is to change one or more cysteines in an antibody to another residue, such as, without limitation, alanine or serine. The cysteine may be a canonical or non-canonical cysteine. In one embodiment, the antibody derivative has 1, 2, 3, or 4 conservative amino acid substitutions in the heavy chain HVR regions relative to the amino acid sequences of an illustrative antibody.

Modifications may also be made to the framework residues within the $V_H$ and/or $V_L$ regions. Typically, such framework variants are made to decrease the immunogenicity of the antibody. One approach is to "back mutate" one or more framework residues to the corresponding germline sequence. An antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back mutated" to the germline sequence by, for example, site-directed mutagenesis or PCR-mediated mutagenesis.

In addition, modifications may also be made within the Fc region of an illustrative antibody, typically to alter one or more functional properties of the antibody, such as serum half-life, complement fixation, Fc receptor binding, and/or antigen-dependent cellular cytotoxicity. In one example, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody. In another case, the Fc hinge region of an antibody is mutated to decrease the biological half-life of the antibody.

Furthermore, an antibody of the disclosure may be modified to alter its potential glycosylation site or pattern in accordance with routine experimentation known in the art. In another aspect, the present disclosure provide an derivative of an CD137 antibody of the disclosure that contains at least one mutation in an variable region of a light chain or heavy chain that changes the pattern of glycosylation in the variable region. Such an antibody derivative may have an increased affinity and/or a modified specificity for binding an antigen. The mutations may add a novel glycosylation site in the V region, change the location of one or more V region glycosylation site(s), or remove a pre-existing V region glycosylation site. In one embodiment, the present disclosure provides a derivative of a CD137 antibody having a potential N-linked glycosylation site at asparagine in the heavy chain variable region, wherein the potential N-linked glycosylation site in one heavy chain variable region is removed. In another embodiment, the present disclosure provides a derivative of a CD137 antibody having a potential N-linked glycosylation site at asparagine in the heavy chain variable region, wherein the potential N-linked glycosylation site in both heavy chain variable regions is removed. Method of altering the glycosylation pattern of an antibody is known in the art, such as those described in U.S. Pat. No. 6,933,368, the disclosure of which incorporated herein by reference.

In another aspect, the present disclosure provides an antibody derivative that comprises a CD137 antibody, or antigen-binding fragment thereof, as described herein, linked to an additional molecular entity. Examples of additional molecular entities include pharmaceutical agents, peptides or proteins, detection agent or labels, and antibodies.

In some embodiments, the antibody derivative comprises an antibody of the disclosure linked to a pharmaceutical agent. Examples of pharmaceutical agents include cytotoxic agents or other cancer therapeutic agents, and radioactive isotopes. Specific examples of cytotoxic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for linking an antibody to a pharmaceutical agent are known in the art, such as using various linker technologies. Examples of linker types include hydrazones, thioethers, esters, disulfides and peptide-containing linkers. For further discussion of linkers and methods for linking therapeutic agents to antibodies, see also Saito et al., *Adv. Drug Deliv. Rev.* 55:199-215 (2003); Trail, et al., *Cancer Immunol. Immunother.* 52:328-337 (2003); Payne, *Cancer Cell* 3:207-212 (2003); Allen, *Nat. Rev. Cancer* 2:750-763 (2002); Pastan, I. and Kreitman, *Curr. Opin. Investig. Drugs* 3:1089-1091 (2002); Senter, P. D. and Springer, C. J. (2001) *Adv. Drug Deliv. Rev.* 53:247-264.

In a particular embodiment, the antibody derivative is a CD137 antibody multimer, which is a multimeric form of a CD137 antibody, such as antibody dimers, trimers, or higher-order multimers of monomeric antibodies. Individual monomers within an antibody multimer may be identical or different. In addition, individual antibodies within a multimer may have the same or different binding specificities. Multimerization of antibodies may be accomplished through natural aggregation of antibodies. For example, some percentage of purified antibody preparations (e.g., purified IgG4 molecules) spontaneously form protein aggregates containing antibody homodimers, and other higher-order antibody multimers. Alternatively, antibody homodimers may be formed through chemical linkage techniques known in the art, such as through using crosslinking agents. Suitable crosslinkers include those that are heterobifunctional, having two distinctly reactive groups separated by an appropriate spacer (such as m-maleimidobenzoyl-N-hydroxysuccinimide ester, succinimidyl 4-(maleimidomethyl)cyclohexane-1-carboxylate, and N-succinimidyl S-acethylthioacetate) or homobifunctional (such as disuccinimidyl suberate). Such linkers are commercially available from, for example, Pierce Chemical Company, Rockford, Ill. Antibodies can also be made to multimerize through recombinant DNA techniques known in the art.

In some embodiments, an antibody of the present disclosure is a multimeric antibody (e.g., a bispecific antibody). In some embodiments, an antibody of the present disclosure is an IgM antibody, e.g., comprises an IgM Fc region (e.g., a human IgM Fc region).

Examples of other antibody derivatives provided by the present disclosure include single chain antibodies, diabodies, domain antibodies, nanobodies, and unibodies. A "single-chain antibody" (scFv) consists of a single polypeptide chain comprising a $V_L$ domain linked to a $V_H$ domain wherein $V_L$ domain and $V_H$ domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "diabody" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609). Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (See e.g., U.S. Pat. Nos. 6,765,087, 6,838,254, WO 06/079372). Unibodies consist of one light chain and one heavy chain of an IgG4 antibody. Unibodies may be made by the removal of the hinge region of IgG4 antibodies. Further details of unibodies and methods of preparing them may be found in WO2007/059782.

C. Nucleic Acids, Vectors, Host Cells, and Recombinant Methods of Producing CD137 Antibodies Another aspect of the disclosure provides an isolated nucleic acid molecule that comprises a nucleotide sequence encoding an amino acid sequence of a binding molecule provided by the present disclosure. The amino acid sequence encoded by the nucleotide sequence may be any portion of an antibody, such as a HVR, a sequence comprising one, two, or three HVRs, a variable region of a heavy chain, variable region of a light chain, or may be a full-length heavy chain or full length light chain. A nucleic acid of the disclosure can be, for example, DNA or RNA, and may or may not contain intronic sequences. Typically, the nucleic acid is a cDNA molecule.

In some embodiments, the disclosure provides an isolated nucleic acid molecule that comprises or consists of a nucleotide sequence encoding an amino acid sequence selected from the group consisting of: (1) amino acid sequence of a HVR_H3 or HVR_L3 of an illustrative antibody; (2) a variable region of a heavy chain or variable region of a light chain of an illustrative antibody; or (3) a full length heavy chain or full length light chain of an illustrative antibody.

In other embodiments, the nucleic acid molecule comprises or consists of a nucleotide sequence that encodes an amino acid sequence as set forth in any one of SEQ ID NOs: 13-132, 253-612, 613-660 and 709-852.

In still other embodiments, the nucleic acid molecule comprises or consists of nucleotide sequence selected from the group consisting of SEQ ID NOs: 133-252 and 661-708.

Nucleic acids of the disclosure can be obtained using any suitable molecular biology techniques. For antibodies expressed by hybridomas, cDNAs encoding the light and heavy chains of the antibody made by the hybridoma can be obtained by PCR amplification or cDNA cloning techniques. For antibodies obtained from an immunoglobulin gene library (e.g., using phage display techniques), the nucleic acid encoding the antibody can be recovered from the library.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG4 or IgG2 constant region without ADCC effect. The IgG4 constant region sequence can be any of the various alleles or allotypes known to occur among different individuals. These allotypes represent naturally occurring amino acid substitution in the IgG4 constant regions. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al., Science 242:423-426 (1988); Huston et al., Proc. Natl. Acad. Sci. USA 85:5879-5883 (1988); and McCafferty et al., Nature 348:552-554 (1990)).

The present disclosure further provides a vector that comprises a nucleic acid molecule provided by the present disclosure. The nucleic acid molecule may encode a portion of a light chain or heavy chain (such as a CDR or a HVR), a full-length light or heavy chain, polypeptide that comprises a portion or full-length of a heavy or light chain, or an amino acid sequence of an antibody derivative or antigen-binding fragment. In some embodiments, the vector is an expression vector useful for the expression of a binding molecule, such as an antibody or an antigen binding fragment thereof. In some embodiments, provided herein are vectors, wherein a first vector comprises a polynucleotide sequence encoding a heavy chain variable region as described herein, and a second vector comprises a polynucleotide sequence encoding a light chain variable region as described herein. In some embodiments, a single vector comprises polynucleotides encoding a heavy chain variable region as described herein and a light chain variable region as described herein.

To express a binding molecule of the disclosure, DNAs encoding partial or full-length light and heavy chains are inserted into expression vectors such that the DNA molecules are operatively linked to transcriptional and translational control sequences. In this context, the term "operatively linked" means that an antibody gene is ligated into a vector such that transcriptional and translational control sequences within the vector serve their intended function of regulating the transcription and translation of the DNA molecule. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by any suitable methods (e.g., ligation of complementary restriction sites on the antibody gene fragment and vector, or homologous recombination-based DNA ligation). The light and heavy chain variable regions of the antibodies described herein can be used to create full-length antibody genes of any antibody isotype and subclass by inserting them into expression vectors already encoding heavy chain constant and light chain constant regions of the desired isotype and subclass such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the expression vectors of the disclosure typically carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SR promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by any suitable techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the disclosure in either prokaryotic or eukaryotic host cells, expression of antibodies in eukaryotic cells, and typically mammalian host cells, is most typical.

The present disclosure further provides a host cell containing a nucleic acid molecule provided by the present disclosure. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Introduction of the recombinant nucleic acid construct into the host cell can be effected by calcium phosphate transfection, DEAE, dextran mediated transfection, electroporation or phage infection.

Suitable prokaryotic hosts for transformation include *E. coli, Bacillus subtilis, Salmonella typhimurium* and various species within the genera *Pseudomonas, Streptomyces*, and *Staphylococcus*.

Mammalian host cells for expressing a binding molecule of the disclosure include, for example, Chinese Hamster Ovary (CHO) cells (including dhfr-CHO cells, described in Urlaub and Chasin, *Proc. Natl. Acad. Sci. USA* 77:4216-4220 (1980), used with a DHFR selectable marker, e.g., as described in Kaufman and Sharp, *J. Mol. Biol.* 159:601-621 (1982), NSO myeloma cells, COS cells and Sp2 cells. In particular, for use with NSO myeloma or CHO cells, another expression system is the GS (glutamine synthetase) gene expression system disclosed in WO 87/04462, WO 89/01036 and EP 338,841. When expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using any suitable protein purification methods.

D. Compositions

In other aspects, the present disclosure provides a composition containing a binding molecule provided by the disclosure. In one aspect, the composition is a pharmaceutical composition comprising a binding molecule and a pharmaceutically acceptable carrier. The compositions can be prepared by conventional methods known in the art.

In some embodiments, present disclosure provides a composition comprising an antibody, or an antigen-binding fragment thereof, provided by the present disclosure and a pharmaceutically acceptable carrier, wherein said antibody comprises a variable domain comprising the HVR amino acid sequence disclosed herein, and wherein said composition comprises not more than about 11%, 10%, 8%, 5%, 3%, or 2% of said antibody, or antigen-binding portion, that is glycosylated at the asparagine of said amino acid sequence compared with the total amount of antibody, or antigen-binding portion thereof, present in said composition. In another embodiment, the composition comprises at least about 2% of said antibody, or antigen-binding portion, that is glycosylated at the asparagine of said amino acid sequence compared with the total amount of antibody, or antigen-binding portion thereof, present in said composition.

The term "pharmaceutically acceptable carrier" refers to any inactive substance that is suitable for use in a formulation for the delivery of a binding molecule. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride.

The compositions may be in any suitable forms, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering a binding molecule is a sterile liquid, such as a solution, suspension, or dispersion, for injection or infusion. Sterile solutions can be prepared by incorporating the antibody in the required amount in an appropriate carrier, followed by sterilization microfiltration. Generally, dispersions are prepared by incorporating the antibody into a sterile vehicle that contains a basic dispersion medium and other carriers. In the case of sterile powders for the preparation of sterile liquid, methods of preparation include vacuum drying and freeze-drying (lyophilization) to yield a powder of the active ingredient plus any additional desired ingredient from a previously sterile-filtered solution thereof. The various dosage forms of the compositions can be prepared by conventional techniques known in the art.

The relative amount of a binding molecule included in the composition will vary depending upon a number of factors, such as the specific binding molecule and carriers used, dosage form, and desired release and pharmacodynamic characteristics. The amount of a binding molecule in a single dosage form will generally be that amount which produces a therapeutic effect, but may also be a lesser amount. Generally, this amount will range from about 0.01 percent to about 99 percent, from about 0.1 percent to about 70 percent, or from about 1 percent to about 30 percent relative to the total weight of the dosage form.

In addition to the binding molecule, one or more additional therapeutic agents may be included in the composition. Examples of additional therapeutic agents are described herein below. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent which produces a therapeutic effect, but may be a lesser amount as well.

E. Use of the Binding Molecules and Pharmaceutical Compositions

Binding molecules and pharmaceutical compositions provided by the present disclosure are useful for therapeutic, diagnostic, or other purposes, such as modulating an immune response, treating cancer, enhancing efficacy of other cancer therapy, enhancing vaccine efficacy, or treating autoimmune diseases. Thus, in other aspects, the present disclosure provides methods of using the binding molecules or pharmaceutical compositions. In one aspect, the present disclosure provides a method of treating a disorder in a mammal, which comprises administering to the mammal in need of treatment a therapeutically effective amount of a binding molecule provided by the disclosure. The binding molecule may be a CD137 agonist or antagonist. In some embodiments, the binding molecule is a CD137 agonist. In some embodiments, the mammal is a human.

In some embodiments, the disorder is a cancer. A variety of cancers where CD137 is implicated, whether malignant or benign and whether primary or secondary, may be treated or prevented with a method provided by the disclosure. Examples of such cancers include lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblastic, myelomonocytic)

leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas.

In some other embodiments, the disorder is an autoimmune disease. Examples of autoimmune diseases that may be treated with the binding molecules include autoimmune encephalomyelitis, lupus erythematosus, and rheumatoid arthritis. The binding molecule may also be used to treat inflammation (such as allergic asthma) and chronic graft-versus-host disease, In another aspect, the present disclosure provides a method of enhancing an immune response in a mammal, which comprises administering to the mammal a therapeutically effective amount of a binding molecule provided by the disclosure. In some embodiments, the binding molecule is a CD137 antibody or antigen-binding fragment thereof and the mammal is a human. In a further embodiment, the binding molecule is CD137 agonist antibody or an antigen-binding fragment thereof. The term "enhancing immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or a mammal not treated using the claimed methods. In one embodiment, the binding molecule is used to enhance the immune response of a human to a microbial pathogen (such as a virus). In another embodiment, the binding molecule is used to enhance the immune response of a human to a vaccine. The binding molecule may be a CD137 agonist or antagonist. In some embodiments, the binding molecule is a CD137 agonist. In one embodiment, the method enhances a cellular immune response, particularly a cytotoxic T cell response. In another embodiment, the cellular immune response is a T helper cell response. In still another embodiment, the immune response is a cytokine production, particularly IL-2 production. The binding molecule may be used to enhance the immune response of a human to a microbial pathogen (such as a virus) or to a vaccine. The binding molecule may be a CD137 agonist or antagonist. In some embodiments, the binding molecule is a CD137 agonist.

In practicing the therapeutic methods, the binding molecules may be administered alone as monotherapy, or administered in combination with one or more additional therapeutic agents or therapies. Thus, in another aspect, the present disclosure provides a combination therapy, which comprises a binding molecule in combination with one or more additional therapies or therapeutic agents for separate, sequential or simultaneous administration. The term "additional therapy" refers to a therapy which does not employ a binding molecule provided by the disclosure as a therapeutic agent. The term "additional therapeutic agent" refers to any therapeutic agent other than a binding molecule provided by the disclosure. In one particular aspect, the present disclosure provides a combination therapy for treating cancer in a mammal, which comprises administering to the mammal a therapeutically effective amount of a binding molecule provided by the disclosure in combination with one or more additional therapeutic agents. In a further embodiment, the mammal is a human.

A wide variety of cancer therapeutic agents may be used in combination with a binding molecule provided by the present disclosure. One of ordinary skill in the art will recognize the presence and development of other cancer therapies which can be used in combination with the methods and binding molecules of the present disclosure, and will not be restricted to those forms of therapy set forth herein. Examples of categories of additional therapeutic agents that may be used in the combination therapy for treating cancer include (1) chemotherapeutic agents, (2) immunotherapeutic agents, and (3) hormone therapeutic agents.

The term "chemotherapeutic agent" refers to a chemical or biological substance that can cause death of cancer cells, or interfere with growth, division, repair, and/or function of cancer cells. Examples of chemotherapeutic agents include those that are disclosed in WO 2006/129163, and US 20060153808, the disclosures of which are incorporated herein by reference. Examples of particular chemotherapeutic agents include: (1) alkylating agents, such as chlorambucil (LEUKERAN), mcyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME); (2) alkaloids or plant vinca alkaloids, including cytotoxic antibiotics, such as doxorubicin (ADRIAMYCIN), epirubicin (ELLENCE, PHARMORUBICIN), daunorubicin (CERUBIDINE, DAUNOXOME), nemorubicin, idarubicin (IDAMYCIN PFS, ZAVEDOS), mitoxantrone (DHAD, NOVANTRONE). dactinomycin (actinomycin D, COSMEGEN), plicamycin (MITHRACIN), mitomycin (MUTAMYCIN), and bleomycin (BLENOXANE), vinorelbine tartrate (NAVELBINE)), vinblastine (VELBAN), vincristine (ONCOVIN), and vindesine (ELDISINE); (3) antimetabolites, such as capecitabine (XELODA), cytarabine (CYTOSAR-U), fludarabine (FLUDARA), gemcitabine (GEMZAR), hydroxyurea (HYDRA), methotrexate (FOLEX, MEXATE, TREXALL), nelarabine (ARRANON), trimetrexate (NEUTREXIN), and pemetrexed (ALIMTA); (4) Pyrimidine antagonists, such as 5-fluorouracil (5-FU); capecitabine (XELODA), raltitrexed (TOMUDEX), tegafur-uracil (UFTORAL), and gemcitabine (GEMZAR); (5) taxanes, such as docetaxel (TAXOTERE), paclitaxel (TAXOL); (6) platinum drugs, such as cisplatin (PLATINOL) and carboplatin (PARAPLATIN), and oxaliplatin (ELOXATIN); (7) topoisomerase inhibitors, such as irinotecan (CAMPTOSAR), topotecan (HYCAMTIN), etoposide (ETOPOPHOS, VEPESSID, TOPOSAR), and teniposide (VUMON); (8) epipodophyllotoxins (podophyllotoxin derivatives), such as etoposide (ETOPOPHOS, VEPESSID, TOPOSAR); (9) folic acid derivatives, such as leucovorin (WELLCOVORIN); (10) nitrosoureas, such as carmustine (BiCNU), lomustine (CeeNU); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA), erlotinib (TARCEVA), bortezomib (VELCADE), imatinib mesylate (GLEEVEC), genefitinib, lapatinib, sorafenib, thalidomide, sunitinib (SUTENT), axitinib, rituximab (RITUXAN, MABTHERA), trastuzumab (HERCEPTIN), cetuximab (ERBITUX), bevacizumab (AVASTIN), and ranibizumab (LUCENTIS), lym-1 (ONCOLYM), antibodies to insulin-like growth factor-1 receptor (IGF-1R) that are disclosed in WO2002/053596); (12) angiogenesis inhibitors, such as bevacizumab (AVASTIN), suramin (GERMANIN), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE).

The term "immunotherapeutic agents" refers to a chemical or biological substance that can enhance an immune response of a mammal. Examples of immunotherapeutic agents include: *bacillus* Calmette-Guerin (BCG); cytokines such as interferons; vaccines such as MyVax personalized immunotherapy, Onyvax-P, Oncophage, GRNVAC1, Favld, Provenge, GVAX, Lovaxin C, BiovaxlD, GMXX, and NeuVax; and antibodies such as alemtuzumab (CAMPATH), bevacizumab (AVASTIN), cetuximab (ERBITUX), gemtuzumab ozogamicin (MYLOTARG), ibritumomab tiuxetan (ZEVALIN), panitumumab (VECTIBIX), rituximab (RITUXAN, MABTHERA), trastuzumab (HERCEPTIN), tositumomab (BEXXAR), ipilimumab (YERVOY) tremelimumab, CAT-3888, agonist antibodies to OX40 receptor (such as those disclosed in WO2009/079335), agonist antibodies to CD40 receptor (such as those disclosed in WO2003/040170, and TLR-9 agonists (such as those disclosed in WO2003/015711, WO2004/016805, and WO2009/022215).

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), and leuprolide (LUPRON). The binding molecules of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

The combination therapy for treating cancer also encompasses the combination of a binding molecule with surgery to remove a tumor. The binding molecule may be administered to the mammal before, during, or after the surgery.

The combination therapy for treating cancer also encompasses combination of a binding molecule with radiation therapy, such as ionizing (electromagnetic) radiotherapy (e.g., X-rays or gamma rays) and particle beam radiation therapy (e.g., high linear energy radiation). The source of radiation can be external or internal to the mammal. The binding molecule may be administered to the mammal before, during, or after the radiation therapy.

The binding molecules and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The antibodies and compositions of the disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art The term "therapeutically effective amount" of a binding molecule refers to an amount that is effective for an intended therapeutic purpose. For example, in the context of enhancing an immune response, a "therapeutically effective amount" is any amount that is effective in stimulating, evoking, increasing, improving, or augmenting any response of a mammal's immune system. In the context of treating a disease, a "therapeutically effective amount" is any amount that is sufficient to cause any desirable or beneficial effect in the mammal being treated. Specifically, in the treatment of cancer, examples of desirable or beneficial effects include inhibition of further growth or spread of cancer cells, death of cancer cells, inhibition of reoccurrence of cancer, reduction of pain associated with the cancer, or improved survival of the mammal. The therapeutically effective amount of a CD137 antibody usually ranges from about 0.001 to about 500 mg/kg, and more usually about 0.01 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the therapeutically effective amount of a CD137 antibody is in the range of about 0.01-30 mg/kg of body weight of the mammal. In some other embodiments, the therapeutically effective amount of a CD137 antibody is in the range of about 0.05-15 mg/kg of body weight of the mammal. The precise dosage level to be administered can be readily determined by a person skilled in the art and will depend on a number of factors, such as the type, and severity of the disorder to be treated, the particular binding molecule employed, the route of administration, the time of administration, the duration of the treatment, the particular additional therapy employed, the age, sex, weight, condition, general health and prior medical history of the patient being treated, and like factors well known in the medical arts.

A binding molecule or composition is usually administered on multiple occasions. Intervals between single doses can be, for example, weekly, monthly, every three months or yearly. An exemplary treatment regimen entails administration once per week, once every two weeks, once every three weeks, once every four weeks, once a month, once every three months or once every three to six months. Typical dosage regimens for a CD137 antibody include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims. The contents of all figures and all references, patents and published patent applications cited throughout this disclosure are expressly incorporated herein by reference in their entirety.

EXAMPLES

Example 1

Generation of Primary Fabs that Specifically Binds to Human CD137

Proprietary phagemid libraries (See PCT International Application titled "Dynamic Human Antibody Light Chain Libraries" filed concurrently herewith under International Patent Application No. PCT/CN2017/098333, incorporated herein by reference in its entirety; See also PCT International Application titled "Dynamic Human Heavy Chain Antibody Libraries" filed concurrently herewith under International Patent Application No. PCT/CN2017/098333, incorporated herein by reference in its entirety) were employed to pan against human CD137 antigens. A total of three or four rounds of panning were conducted. After the final round of panning, single-colony supernatant ELISA was performed to identify the primary hits that specifically recognize human CD137. The primary hits were defined as those whose ELISA signals were at least twice that of background. They were sequenced, the unique clones were expressed and purified for affinity measurement by ForteBio and Biacore. The list was refined to 124 in Fab with both ELISA positive hits and unique sequences. Following the criteria of $K_D$ response signal R>0.1, $R^2$>0.9 and affinity $K_D$<100 nM, the list was further refined to 60 hits (Table 1a). 24 of them were then converted into IgG (Table 1b) for detailed biophysical and functional characterization.

The Fabs corresponding to the unique hits were expressed in *E. coli* and purified. Their affinities against human CD137 were measured by ForteBio Octet RED96 Systems. Briefly, the AHC sensors (Anti-Human IgG Fc Capture Dip and Read Biosensors) were used to capture CD137-hisFc fusion protein (Sino Biological #Cat 10041-H03H), and dipped into wells containing purified Fabs that were diluted to 5-10 μg/ml with kinetic buffer (10 mM HEPES, 150 mM NaCl, 3 mM EDTA, 0.005% v/v Surfactant P20, pH 7.4). The acquired ForteBio data were processed with Data Acquisition software 7.1, and kinetic data were fitted to a 1:1 Langmuir binding model. The affinity and kinetic parameters (with background subtracted) are listed in Table 1a. The affinity of their corresponding IgGs to human CD137 was measured by Biacore and shown in Table 1b.

TABLE 1a

Affinity of selected Fabs against human CD137 and corresponding amino acid sequences (in SEQ ID NO.)

| Hit ID | KD (nM) | kon (1/Ms) | koff (1/s) | SEQ ID NO. (upper row VH; lower row VL) |
|---|---|---|---|---|
| 3760 | 1.26E−08 | 3.52E+05 | 4.44E−03 | 13 |
|  |  |  |  | 14 |
| 4072 | 6.95E−09 | 1.54E+05 | 1.07E−03 | 15 |
|  |  |  |  | 16 |
| 4074 | 1.95E−08 | 4.80E+04 | 9.37E−04 | 17 |
|  |  |  |  | 18 |
| 4076 | 7.44E−09 | 6.38E+04 | 4.75E−04 | 19 |
|  |  |  |  | 20 |
| 4079 | 3.15E−08 | 6.93E+04 | 2.19E−03 | 21 |
|  |  |  |  | 22 |
| 4134 | 1.30E−08 | 5.93E+04 | 7.69E−04 | 23 |
|  |  |  |  | 24 |
| 4137 | <1.0E−12 | 8.56E+04 | <1.0E−07 | 25 |
|  |  |  |  | 26 |
| 4139 | 1.65E−09 | 4.96E+04 | 8.17E−05 | 27 |
|  |  |  |  | 28 |
| 4140 | <1.0E−12 | 2.57E+04 | <1.0E−07 | 29 |
|  |  |  |  | 30 |
| 4217 | 9.67E−08 | 5.64E+05 | 5.45E−02 | 31 |
|  |  |  |  | 32 |
| 5299 | 1.37E−08 | 5.55E+05 | 7.60E−03 | 33 |
|  |  |  |  | 34 |
| 5300 | 1.53E−08 | 5.96E+05 | 9.10E−03 | 35 |
|  |  |  |  | 36 |
| 5302 | 1.21E−09 | 3.54E+05 | 4.26E−04 | 37 |
|  |  |  |  | 38 |
| 5303 | 5.12E−09 | 9.95E+05 | 5.09E−03 | 39 |
|  |  |  |  | 40 |
| 5310 | 5.72E−09 | 8.13E+05 | 4.65E−03 | 41 |
|  |  |  |  | 42 |
| 5314 | 8.39E−09 | 2.10E+05 | 1.77E−03 | 43 |
|  |  |  |  | 44 |
| 5316 | 1.14E−08 | 140600 | 0.001605 | 45 |
|  |  |  |  | 46 |
| 5318 | 1.90E−08 | 1.41E+05 | 2.69E−03 | 47 |
|  |  |  |  | 48 |
| 5323 | 1.04E−08 | 7.82E+05 | 8.12E−03 | 49 |
|  |  |  |  | 50 |
| 5341 | 2.93E−08 | 6.42E+04 | 1.88E−03 | 51 |
|  |  |  |  | 52 |
| 5342 | 3.89E−08 | 1.57E+05 | 6.12E−03 | 53 |
|  |  |  |  | 54 |
| 5346 | 1.61E−08 | 6.05E+05 | 9.77E−03 | 55 |
|  |  |  |  | 56 |
| 5348 | 1.02E−08 | 1.31E+06 | 1.33E−02 | 57 |
|  |  |  |  | 58 |
| 5349 | 6.20E−09 | 1.62E+05 | 1.01E−03 | 59 |
|  |  |  |  | 60 |
| 5351 | 7.29E−09 | 4.66E+05 | 3.40E−03 | 61 |
|  |  |  |  | 62 |
| 5353 | 1.61E−08 | 3.70E+05 | 5.97E−03 | 63 |
|  |  |  |  | 64 |
| 5359 | 7.10E−10 | 4.64E+05 | 3.30E−04 | 65 |
|  |  |  |  | 66 |

TABLE 1a-continued

Affinity of selected Fabs against human CD137 and corresponding amino acid sequences (in SEQ ID NO.)

| Hit ID | KD (nM) | kon (1/Ms) | koff (1/s) | SEQ ID NO. (upper row VH; lower row VL) |
|---|---|---|---|---|
| 5360 | 2.41E−08 | 1.20E+05 | 2.89E−03 | 67 |
|  |  |  |  | 68 |
| 5363 | 9.87E−09 | 8.37E+04 | 8.26E−04 | 69 |
|  |  |  |  | 70 |
| 5365 | 2.56E−09 | 7.01E+05 | 1.79E−03 | 71 |
|  |  |  |  | 72 |
| 5367 | 1.49E−08 | 4.07E+05 | 6.08E−03 | 73 |
|  |  |  |  | 74 |
| 5370 | 1.91E−09 | 5.24E+05 | 1.00E−03 | 75 |
|  |  |  |  | 76 |
| 5371 | 3.97E−09 | 1.21E+06 | 4.79E−03 | 77 |
|  |  |  |  | 78 |
| 5404 | 3.30E−09 | 3.95E+05 | 1.30E−03 | 79 |
|  |  |  |  | 80 |
| 5407 | 1.76E−09 | 2.48E+05 | 4.37E−04 | 81 |
|  |  |  |  | 82 |
| 5408 | 2.36E−08 | 3.18E+05 | 7.50E−03 | 83 |
|  |  |  |  | 84 |
| 5409 | 1.70E−08 | 2.51E+05 | 4.27E−03 | 85 |
|  |  |  |  | 86 |
| 5413 | 9.93E−10 | 5.55E+05 | 5.51E−04 | 87 |
|  |  |  |  | 88 |
| 5417 | 4.04E−08 | 5.72E+04 | 2.31E−03 | 89 |
|  |  |  |  | 90 |
| 7077 | 1.88E−08 | 4.98E+05 | 9.34E−03 | 91 |
|  |  |  |  | 92 |
| 7078 | 2.52E−08 | 3.45E+05 | 8.70E−03 | 93 |
|  |  |  |  | 94 |
| 7079 | 2.99E−08 | 1.00E+05 | 3.00E−03 | 95 |
|  |  |  |  | 96 |
| 7080 | 2.44E−08 | 3.06E+05 | 7.46E−03 | 97 |
|  |  |  |  | 98 |
| 7081 | 4.31E−08 | 2.87E+05 | 1.23E−02 | 99 |
|  |  |  |  | 100 |
| 7087 | 6.96E−08 | 1.23E+05 | 8.55E−03 | 101 |
|  |  |  |  | 102 |
| 7088 | 4.36E−08 | 2.55E+05 | 1.11E−02 | 103 |
|  |  |  |  | 104 |
| 7090 | 5.55E−08 | 3.12E+05 | 1.73E−02 | 105 |
|  |  |  |  | 106 |
| 7092 | 4.57E−08 | 4.31E+05 | 1.97E−02 | 107 |
|  |  |  |  | 108 |
| 7097 | 2.43E−08 | 5.42E+05 | 1.32E−02 | 109 |
|  |  |  |  | 110 |
| 7100 | 3.50E−08 | 4.62E+05 | 1.62E−02 | 111 |
|  |  |  |  | 112 |
| 7105 | 3.33E−08 | 3.30E+05 | 1.10E−02 | 113 |
|  |  |  |  | 114 |
| 7109 | 3.20E−08 | 1.73E+05 | 5.55E−03 | 115 |
|  |  |  |  | 116 |
| 7120 | 3.45E−08 | 2.64E+05 | 9.11E−03 | 117 |
|  |  |  |  | 118 |
| 7128 | 3.97E−08 | 3.09E+05 | 1.23E−02 | 119 |
|  |  |  |  | 120 |
| 7131 | 3.04E−08 | 2.66E+05 | 8.10E−03 | 121 |
|  |  |  |  | 122 |
| 7133 | 4.03E−08 | 1.01E+05 | 4.05E−03 | 123 |
|  |  |  |  | 124 |
| 7135 | 3.17E−08 | 1.02E+05 | 3.22E−03 | 125 |
|  |  |  |  | 126 |
| 7159 | 3.79E−08 | 1.06E+05 | 4.03E−03 | 127 |
|  |  |  |  | 128 |
| 7163 | 1.26E−08 | 2.99E+05 | 3.78E−03 | 129 |
|  |  |  |  | 130 |
| 7166 | 1.24E−08 | 3.45E+05 | 4.29E−03 | 131 |
|  |  |  |  | 132 |

The corresponding DNA sequences encoding the amino acid sequences of SEQ ID NOs:13-132 can be found in SEQ ID NOs: 133-252, respectively. The HVR_H1 amino acid sequences for all Fab hits shown in Table 1a can be found in SEQ ID NOs: 253-312, respectively. The HVR_H2 amino acid sequences for all Fab hits shown in Table 1a can be found in SEQ ID NOs: 313-372, respectively. The HVR_H3 amino acid sequences for all Fab hits shown in Table 1a can be found in SEQ ID NOs: 373-432, respectively. The HVR_L1 amino acid sequences for all Fab hits shown in Table 1a can be found in SEQ ID NOs: 433-492, respectively. The HVR_L2 amino acid sequences for all Fab hits shown in Table 1a can be found in SEQ ID NOs: 493-552, respectively. The HVR_L3 amino acid sequences for all Fab hits shown in Table 1a can be found in SEQ ID NOs: 553-612, respectively (See also, Table 1c).

TABLE 1b

Affinity of Fabs and the corresponding IgGs against human CD137

| | Fab | | | | IgG | | | IgG SEQ ID NO. (upper row heavy chain; lower row light chain) |
|---|---|---|---|---|---|---|---|---|
| Hits ID | KD (M) | ka(1/Ms) | kd(1/s) | IgG ID | KD (M) | Ka(1/Ms) | kd (1/s) | |
| 4072 | 7.0E−09 | 1.5E+05 | 1.1E−03 | AG10054 | 1.3E−08 | 1.4E+05 | 1.9E−03 | 613 |
|  |  |  |  |  |  |  |  | 614 |
| 5303 | 5.1E−09 | 1.0E+06 | 5.1E−03 | AG10057 | 7.9E−09 | 7.7E+05 | 6.1E−03 | 615 |
|  |  |  |  |  |  |  |  | 616 |
| 5310 | 5.7E−09 | 8.1E+05 | 4.7E−03 | AG10058 | 5.9E−09 | 4.1E+05 | 2.4E−03 | 617 |
|  |  |  |  |  |  |  |  | 618 |
| 5351 | 7.3E−09 | 4.7E+05 | 3.4E−03 | AG10059 | 3.8E−08 | 1.6E+05 | 6.3E−03 | 619 |
|  |  |  |  |  |  |  |  | 620 |
| 5359 | 7.1E−10 | 4.6E+05 | 3.3E−04 | AG10060 | 1.1E−09 | 2.2E+05 | 2.5E−04 | 621 |
|  |  |  |  |  |  |  |  | 622 |
| 5370 | 1.9E−09 | 5.2E+05 | 1.0E−03 | AG10061 | 3.6E−09 | 2.2E+05 | 7.8E−04 | 623 |
|  |  |  |  |  |  |  |  | 624 |
| 5404 | 3.3E−09 | 4.0E+05 | 1.3E−03 | AG10062 | 5.9E−09 | 1.6E+05 | 9.4E−04 | 625 |
|  |  |  |  |  |  |  |  | 626 |
| 5413 | 9.9E−10 | 5.6E+05 | 5.5E−04 | AG10063 | 9.9E−10 | 3.9E+05 | 3.9E−04 | 627 |
|  |  |  |  |  |  |  |  | 628 |

TABLE 1b-continued

Affinity of Fabs and the corresponding IgGs against human CD137

| | Fab | | | | IgG | | | IgG SEQ ID NO. (upper row heavy chain; lower row light chain) |
|---|---|---|---|---|---|---|---|---|
| Hits ID | KD (M) | ka(1/Ms) | kd(1/s) | IgG ID | KD (M) | Ka(1/Ms) | kd (1/s) | |
| 4074 | 2.0E−08 | 4.8E+04 | 9.4E−04 | AG10079 | 1.4E−09 | 1.9E+05 | 2.7E−04 | 629 630 |
| 4217 | 9.7E−08 | 5.6E+05 | 5.5E−02 | AG10080 | 1.0E−08 | 1.2E+06 | 1.2E−02 | 631 632 |
| 5299 | 1.4E−08 | 5.6E+05 | 7.6E−03 | AG10081 | 6.9E−09 | 2.4E+05 | 1.7E−03 | 633 634 |
| 5300 | 1.5E−08 | 6.0E+05 | 9.1E−03 | AG10082 | 1.3E−08 | 5.6E+05 | 7.2E−03 | 635 636 |
| 5323 | 1.0E−08 | 7.8E+05 | 8.1E−03 | AG10083 | 1.2E−08 | 5.7E+05 | 6.9E−03 | 637 638 |
| 5360 | 2.4E−08 | 1.2E+05 | 2.9E−03 | AG10084 | 4.3E−08 | 6.6E+04 | 2.8E−03 | 639 640 |
| 5367 | 1.5E−08 | 4.1E+05 | 6.1E−03 | AG10085 | 5.4E−08 | 1.5E+05 | 7.9E−03 | 641 642 |
| 5409 | 1.7E−08 | 2.5E+05 | 4.3E−03 | AG10086 | 4.6E−08 | 1.0E+05 | 4.5E−03 | 643 644 |
| 5302 | 1.2E−09 | 3.5E+05 | 4.3E−04 | AG10124 | 6.0E−09 | 5.0E+05 | 3.0E−03 | 645 646 |
| 5314 | 8.4E−09 | 2.1E+05 | 1.8E−03 | AG10125 | 1.5E−08 | 1.1E+05 | 1.7E−03 | 647 648 |
| 5316 | 1.1E−08 | 1.4E+05 | 1.6E−03 | AG10126 | 1.4E−08 | 5.4E+09 | 7.3E+01 | 649 650 |
| 5318 | 1.9E−08 | 1.4E+05 | 2.7E−03 | AG10127 | 9.6E−09 | 3.0E+05 | 2.9E−03 | 651 652 |
| 5342 | 3.9E−08 | 1.6E+05 | 6.1E−03 | AG10128 | 3.0E−09 | 1.2E+05 | 3.7E−04 | 653 654 |
| 5353 | 1.6E−08 | 3.7E+05 | 6.0E−03 | AG10129 | 1.9E−08 | 3.1E+05 | 6.0E−03 | 655 656 |
| 5365 | 2.6E−09 | 7.0E+05 | 1.8E−03 | AG10131 | 3.7E−09 | 5.1E+05 | 1.9E−03 | 657 658 |
| 5408 | 2.4E−08 | 3.2E+05 | 7.5E−03 | AG10132 | 6.9E−08 | 2.0E+05 | 1.4E−02 | 659 660 |

The corresponding DNA sequences encoding the amino acid sequences of SEQ ID NOs: 613-660 can be found in SEQ ID NOs: 661-708, respectively. The HVR_H1 amino acid sequences for all IgG sequences shown in Table 1b can be found in SEQ ID NOs: 709-732, respectively. The HVR_H2 amino acid sequences for all IgG sequences shown in Table 1b can be found in SEQ ID NOs: 733-756, respectively. The HVR_H3 amino acid sequences for all IgG sequences shown in Table 1b can be found in SEQ ID NOs: 757-780, respectively. The HVR_L1 amino acid sequences for all IgG sequences shown in Table 1b can be found in SEQ ID NOs: 781-804, respectively. The HVR_L2 amino acid sequences for all IgG sequences shown in Table 1b can be found in SEQ ID NOs: 805-828, respectively. The HVR_L3 amino acid sequences for all IgG sequences shown in Table 1b can be found in SEQ ID NOs: 829-852, respectively.

TABLE 1c

CDR sequences of Fabs

| Hit ID | VH/VL | HVR-H1 SEQ ID NO. | HVR-H2 SEQ ID NO. | HVR-H3 SEQ ID NO. | HVR-L1 SEQ ID NO. | HVR-L2 SEQ ID NO. | HVR-L31 SEQ ID NO. |
|---|---|---|---|---|---|---|---|
| 3760 | VH1/VL1 | 253 | 313 | 373 | 433 | 493 | 553 |
| 4072 | VH2/VL2 | 254 | 314 | 374 | 434 | 494 | 554 |
| 7074 | VH3/VL3 | 255 | 315 | 375 | 435 | 495 | 555 |
| 4076 | VH4/VL4 | 256 | 316 | 376 | 436 | 496 | 556 |
| 4079 | VH5/VL5 | 257 | 317 | 377 | 437 | 497 | 557 |
| 4134 | VH6/VL6 | 258 | 318 | 378 | 438 | 498 | 558 |
| 4137 | VH7/VL7 | 259 | 319 | 379 | 439 | 499 | 559 |
| 4139 | VH8/VL8 | 260 | 320 | 380 | 440 | 500 | 560 |
| 4140 | VH9/VL9 | 261 | 321 | 381 | 441 | 501 | 561 |
| 4217 | VH10/VL10 | 262 | 322 | 382 | 442 | 502 | 562 |
| 5299 | VH11/VL11 | 263 | 323 | 383 | 443 | 503 | 563 |
| 5300 | VH12/VL12 | 264 | 324 | 384 | 444 | 504 | 564 |
| 5302 | VH13/VL13 | 265 | 325 | 385 | 445 | 505 | 565 |
| 5303 | VH14/VL14 | 266 | 326 | 386 | 446 | 506 | 566 |
| 5310 | VH15/VL15 | 267 | 327 | 387 | 447 | 507 | 567 |
| 5314 | VH16/VL16 | 268 | 328 | 388 | 448 | 508 | 568 |
| 5316 | VH17/VL17 | 269 | 329 | 389 | 449 | 509 | 569 |
| 5318 | VH18/VL18 | 270 | 330 | 390 | 450 | 510 | 570 |

TABLE 1c-continued

CDR sequences of Fabs

| Hit ID | VH/VL | HVR-H1 SEQ ID NO. | HVR-H2 SEQ ID NO. | HVR-H3 SEQ ID NO. | HVR-L1 SEQ ID NO. | HVR-L2 SEQ ID NO. | HVR-L31 SEQ ID NO. |
|---|---|---|---|---|---|---|---|
| 5323 | VH19/VL19 | 271 | 331 | 391 | 451 | 511 | 571 |
| 5341 | VH20/VL20 | 272 | 332 | 392 | 452 | 512 | 572 |
| 5342 | VH21/VL21 | 273 | 333 | 393 | 453 | 513 | 573 |
| 5346 | VH22/VL22 | 274 | 334 | 394 | 454 | 514 | 574 |
| 5348 | VH23/VL23 | 275 | 335 | 395 | 455 | 515 | 575 |
| 5349 | VH24/VL24 | 276 | 336 | 396 | 456 | 516 | 576 |
| 5351 | VH25/VL25 | 277 | 337 | 397 | 457 | 517 | 577 |
| 5353 | VH26/VL26 | 278 | 338 | 398 | 458 | 518 | 578 |
| 5359 | VH27/VL27 | 279 | 339 | 399 | 459 | 519 | 579 |
| 5360 | VH28/VL28 | 280 | 340 | 400 | 460 | 520 | 580 |
| 5363 | VH29/VL29 | 281 | 341 | 401 | 461 | 521 | 581 |
| 5365 | VH30/VL30 | 282 | 342 | 402 | 462 | 522 | 582 |
| 5367 | VH31/VL31 | 283 | 343 | 403 | 463 | 523 | 583 |
| 5370 | VH32/VL32 | 284 | 344 | 404 | 464 | 524 | 584 |
| 5371 | VH33/VL33 | 285 | 345 | 405 | 465 | 525 | 585 |
| 5404 | VH34/VL34 | 286 | 346 | 406 | 466 | 526 | 586 |
| 5407 | VH35/VL35 | 287 | 347 | 407 | 467 | 527 | 587 |
| 5408 | VH36/VL36 | 288 | 348 | 408 | 468 | 528 | 588 |
| 5409 | VH37/VL37 | 289 | 349 | 409 | 469 | 529 | 589 |
| 5413 | VH38/VL38 | 290 | 350 | 410 | 470 | 530 | 590 |
| 5417 | VH39/VL39 | 291 | 351 | 411 | 471 | 531 | 591 |
| 7077 | VH40/VL40 | 292 | 352 | 412 | 472 | 532 | 592 |
| 7078 | VH41/VL41 | 293 | 353 | 413 | 473 | 533 | 593 |
| 7079 | VH42/VL42 | 294 | 354 | 414 | 474 | 534 | 594 |
| 7080 | VH43/VL43 | 295 | 355 | 415 | 475 | 535 | 595 |
| 7081 | VH44/VL44 | 296 | 356 | 416 | 476 | 536 | 596 |
| 7087 | VH45/VL45 | 297 | 357 | 417 | 477 | 537 | 597 |
| 7088 | VH46/VL46 | 298 | 358 | 418 | 478 | 538 | 598 |
| 7090 | VH47/VL47 | 299 | 359 | 419 | 479 | 539 | 599 |
| 7092 | VH48/VL48 | 300 | 360 | 420 | 480 | 540 | 600 |
| 7097 | VH49/VL49 | 301 | 361 | 421 | 481 | 541 | 601 |
| 7100 | VH50/VL50 | 302 | 362 | 422 | 482 | 542 | 602 |
| 7105 | VH51/VL51 | 303 | 363 | 423 | 483 | 543 | 603 |
| 7109 | VH52/VL52 | 304 | 364 | 424 | 484 | 544 | 604 |
| 7120 | VH53/VL53 | 305 | 365 | 425 | 485 | 545 | 605 |
| 7128 | VH54/VL54 | 306 | 366 | 426 | 486 | 546 | 606 |
| 7131 | VH55/VL55 | 307 | 367 | 427 | 487 | 547 | 607 |
| 7133 | VH56/VL56 | 308 | 368 | 428 | 488 | 548 | 608 |
| 7135 | VH57/VL57 | 309 | 369 | 429 | 489 | 549 | 609 |
| 7159 | VH58/VL58 | 310 | 370 | 430 | 490 | 550 | 610 |
| 7163 | VH59/VL59 | 311 | 371 | 431 | 491 | 551 | 611 |
| 7166 | VH60/VL60 | 312 | 372 | 432 | 492 | 552 | 612 |

Example 2

Selection of Fab Hits that are Cross-Reactive with Mouse CD137

The species cross-reactivity of Fab hits was determined using ELISA. Briefly, 200 μL 5 μg/mL anti-human IgG (Fab specific) (Sigma #15260) was coated on Maxisorp microplate (Thermo Scientific 446469) at 4° C. overnight. After blocking, 100 ρL Fab 5310 (5 μg/mL), 5351 (2.8 μg/mL) and 5365 (5 μg/mL) were added and incubated for 1 hr. After washing for three times, serial dilutions of human or mouse CD137 antigens fused with human FC fragments were added and incubated for 1 hr. After washing, HRP labelled goat anti-human FC were diluted 1:2000 with PBS, and added to each well for 1 hr incubation. Plates were washed three times and incubated with TMB substrate for 20 min at room temperature. Absorbance at 450 nm was measured after the reaction was stopped. The result is presented in FIG. 1b, lower panel showing that Fab 5310 and 5365 bind to both human and mouse CD137, whereas Fab 5351 binds to human CD137, but not to mouse CD137.

Example 3

IgG Conversion and Expression: AG10058, AG10059 and AG10131

The heavy chains and light chains of the Fabs 5310, 5351, and 5365 were cloned into the mammalian expression vector pCDNA3.3 (Thermo Fisher Scientific) separately in IgG4 isotype with S241P mutation. The heavy and light chains of two reference antibodies were also cloned into pCDNA3.3 in IgG4 and IgG2 isotype respectively.

The heavy chain variable region used in reference antibody AC1097 comprised the sequence EVQLVQSGAEVKKPGESLRISCKGSGYSFSTYWISWVRQMPGKGLEWMGKIYPGDSYTNYSPSFQGQVTISADKSISTAYLQWSSLKASDTAMYYCARGYGIFDYWGQGTLVTVSS (SEQ ID NO: 862), and the light chain variable region in reference antibody AC1097 comprised the sequence SYELTQPPSVSVSPGQTASITCSGDNIGDQYAHWYQQKPGQSPVLVIYQDKNRPSGIPERFSGSNSGNTATLTISGTQAMDEADYYCATYTGFGSLAVFGGGTKLTVL (SEQ ID NO: 863). The heavy chain variable region used in reference antibody AC1121 comprised the sequence QVQLQQWGAGLLKP-SETLSLTCAVYGGSFSGYYWSWIRQS-PEKGLEWIGEINHGGYVTYN PSLESRVTISVDTSKNQFSLKLSSVTAADTAVYY-CARDYGPGNYDWYFDLWGRGTLVTVS S (SEQ ID NO: 864), and the light chain variable region in reference antibody AC1121 comprised the sequence EIVLTQSPATLSLSPGERATLSCRASQSVSSY-LAWYQQKPGQAPRLLIYDASNRATGIPARF SGSGSGTDFTLTISSLEPEDFAVYYCQQRSNWPPAL-TFGGGTKVEIK (SEQ ID NO: 865). IgGs used in herein are shown in Table 2.

TABLE 2

List of IgGs

| IgG | Fab | Isotype | Description |
|---|---|---|---|
| AC1097 | Reference 1 | IgG2 | Reference Ab |
| AC1121 | Reference 2 | IgG4 (S241P) | Reference Ab |
| AG10058 | 5310 | IgG4 (S241P) | Adagene mAb |
| AG10059 | 5351 | IgG4 (S241P) | Adagene mAb |
| AG10131 | 5365 | IgG4 (S241P) | Adagene mAb |
| AG10154 | | IgG4 (S241P) | Isotype control |

Pairs of plasmids were transiently transfected into HEK293F cells following manufacturer's instructions. The supernatants were harvested, cleared by centrifugation and filtration, and IgGs were purified with standard protein A affinity chromatography (MabSelect SuRe, GE Healthcare). The proteins were eluted and neutralized, and buffer exchanged into PB buffer (20 mM sodium phosphate, 150 mM NaCl, pH 7.0). Protein concentrations were determined by UV-spectrophotometry, and IgG purity was analyzed under denaturing, reducing and non-reducing conditions by SDS-PAGE or SEC-HPLC.

Example 4

Binding Affinity to Human, Monkey and Mouse CD137

The binding affinity of IgGs to human, monkey and mouse CD137 were measured by BIAcore, ELISA and flow cytometry. The results were summarized in Table 3.

4a. Measurement of Binding Affinity and Kinetics by SPR

Binding affinity and kinetics of antibodies against human, monkey and mouse CD137 protein were examined by surface plasmon resonance (SPR) analysis using a Biacore™ T200 instrument (Biacore AB, Uppsala, Sweden) according to the manufacturer's guidelines. Anti-Human IgG (Fc) antibody from Human Antibody Capture Kit (GE BR-1008-39) was immobilized on CM5 chips by coupling of its amine groups onto carboxylated surfaces of sensor chips according to the instructions of Amine Coupling kit (GE Biacore #BR-1000-50). The immobilized Anti-Human IgG (Fc) antibody was used to capture AG10058, AG10059, AG10131, AC1121 and AC1097. Finally, six concentrations (3.13, 6.25, 12.5, 25, 50, 100) (nM) (diluted in running buffer) of human CD137-His6 (Sino Biological #10041-H08H) were injected at a flow rate of 30 µl/min for 300 seconds, and the dissociation time was 300 seconds. The running buffer used was 1×HBS-EP (10 mM HEPES, 150 mM NaCl, 3 mM EDTA, 0.005% v/v Surfactant P20, pH 7.4 at 25° C.). Corresponding controls were conducted in each case using a blank flow cell with no protein immobilized for "background" subtraction. The association and dissociation curves were fitted to a 1:1 Langmuir binding model using Biacore T200 Evaluation Software (Biacore AB, Uppsala, Sweden) according to the manufacturer's guidelines. As shown in Table 3, all antibodies bind to human CD137. AG10058 and AG10059 show higher affinity than both reference antibodies. Except AC1121 reference mAb, all antibodies bind to monkey CD137. Only AG10058 and AG10131 bind to mouse and rat CD137. AG10058 has higher affinity (15.2 nM) than AG10131 (64.5 nM).

4b. Measurement of Binding Affinity to Soluble CD137 Using ELISA Assay

Figure 2:
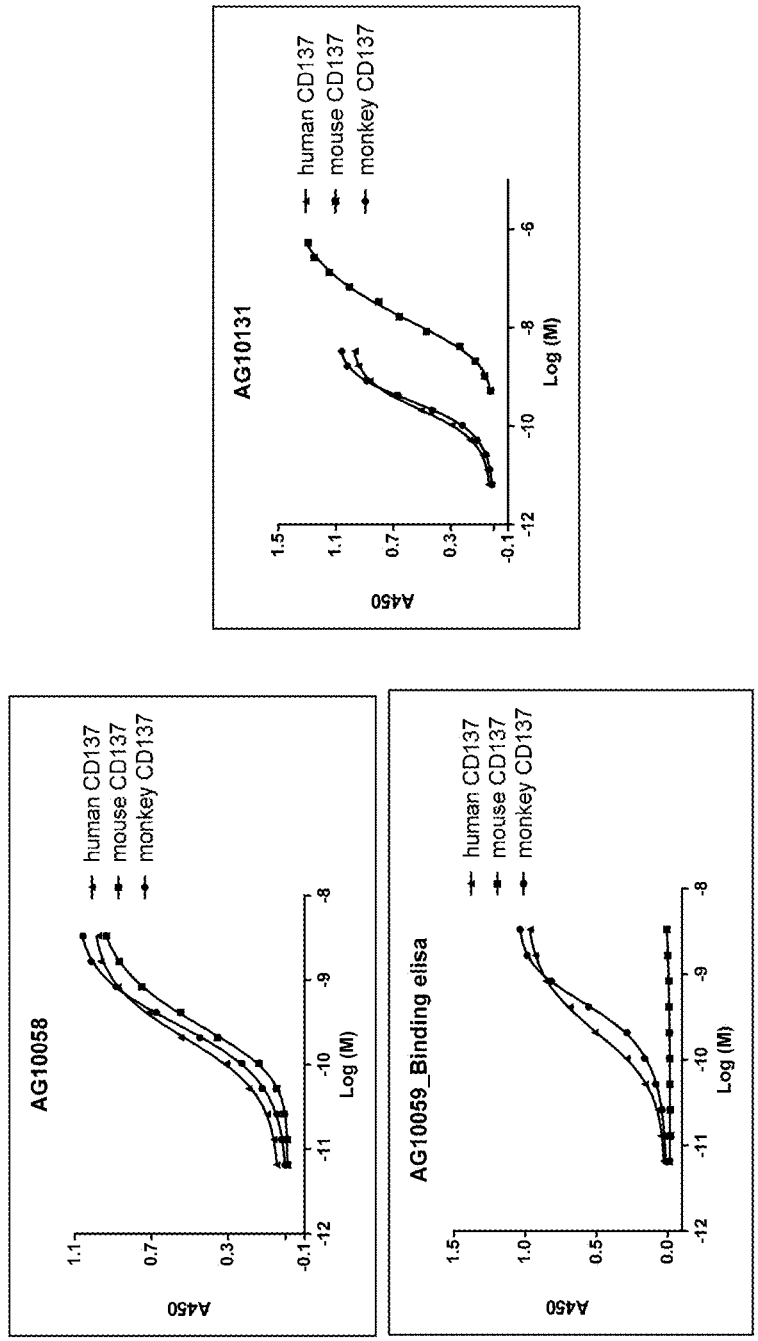
FIG. 2 shows ELISA binding assays to human, monkey and mouse CD137 of exemplary antibodies. Each panel is for a different antibody as indicated at top of the panel.

A serial dilution of human, monkey or mouse CD137 fused with human FC fragment were prepared and used to coat the ELISA plate at 37° C. for 1 hr. After blocking, 100 pt IgGs (5 µg/mL) were added and incubated at 37° C. for 1 hr. Plates were washed for three times and then incubated with HRP-conjugated protein L (1:2000 dilution) at 37° C. for 1 hr. Plates were washed again for three times and incubated with TMB substrate for 20 min at room temperature. Absorbance at 450 nm was measured after the reaction was stopped. The data was analyzed by Graphpad Prism 6 with nonlinear fitting. As shown in FIG. 2, all antibodies bind to human CD137 (FC fusion protein) with similar sub nM affinity. Except AC1121 reference mAb, all antibodies bind to monkey CD137 with similar sub nM affinity. Consistent with results from Biacore, only AG10058 and AG10131 bind to mouse CD137. AG10058 has higher affinity (0.3 nM) than AG10131 (23.9 nM).

TABLE 3

Binding affinity of antibodies to human, monkey and mouse CD137

| KD (nM) | Biacore | | | ELISA | | | HEK293F Cell surface | | |
|---|---|---|---|---|---|---|---|---|---|
| | Human | Cyno | Mouse | Human | Cyno | Mouse | Human | Cyno | Mouse |
| AG10131 | 3.7 | 12.5 | 64.5 | 0.2 | 0.3 | 23.9 | 1.3 | 1.2 | 49.4 |
| AG10058 | 5.9 | 9.3 | 15.2 | 0.2 | 0.3 | 0.3 | 1.8 | 2 | 10.1 |
| AG10059 | 24.2 | 23.1 | NC | 0.8 | 0.4 | NC | 5 | 2.6 | NC |
| AC1097 | 20.9 | 37.6 | NC | 0.2 | 0.4 | NC | 1.9 | 2.9 | NC |
| AC1121 | 9.6 | NC | NC | 0.2 | | NC | 3.3 | NC | NC |

NC: not cross-reactive

Figure 3A:
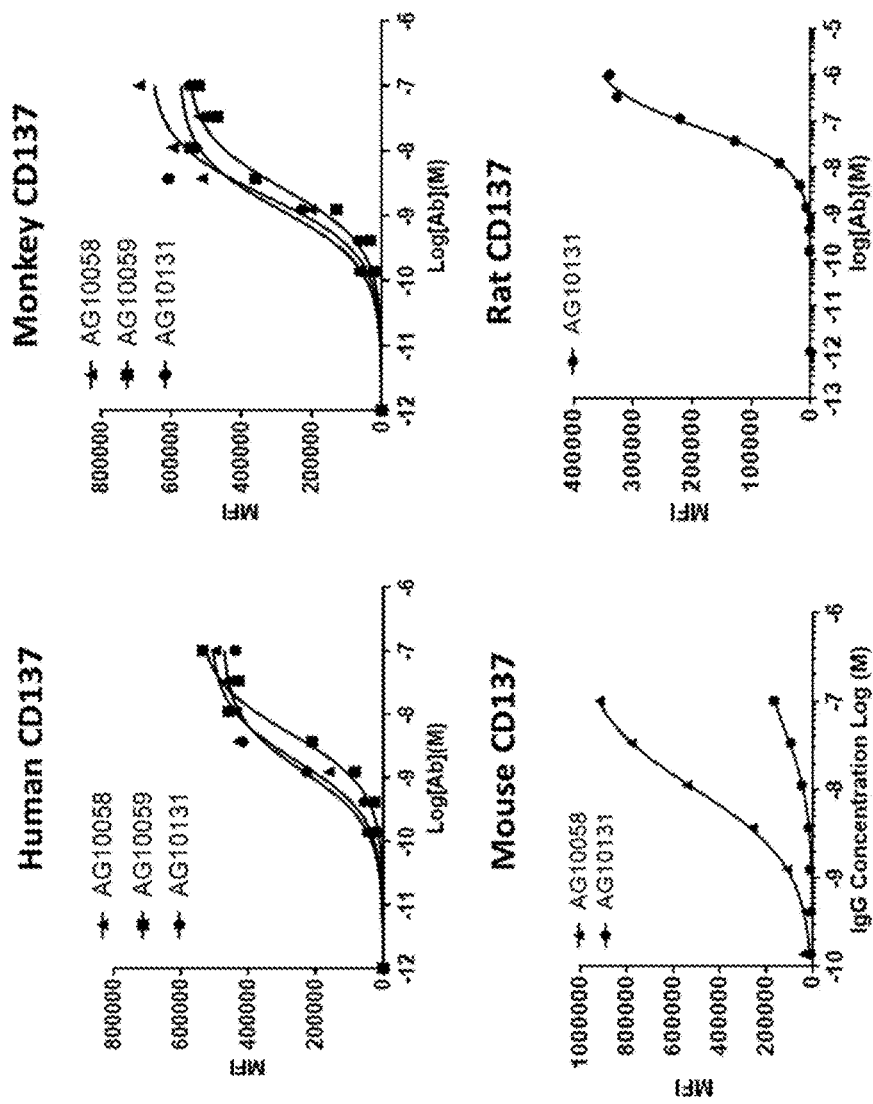
FIG. 3A shows FACS-based binding assays to human, monkey, mouse and rat CD137 of exemplary antibodies. Each panel is for a different antigen as indicated at top of the panel.
Figure 3B:
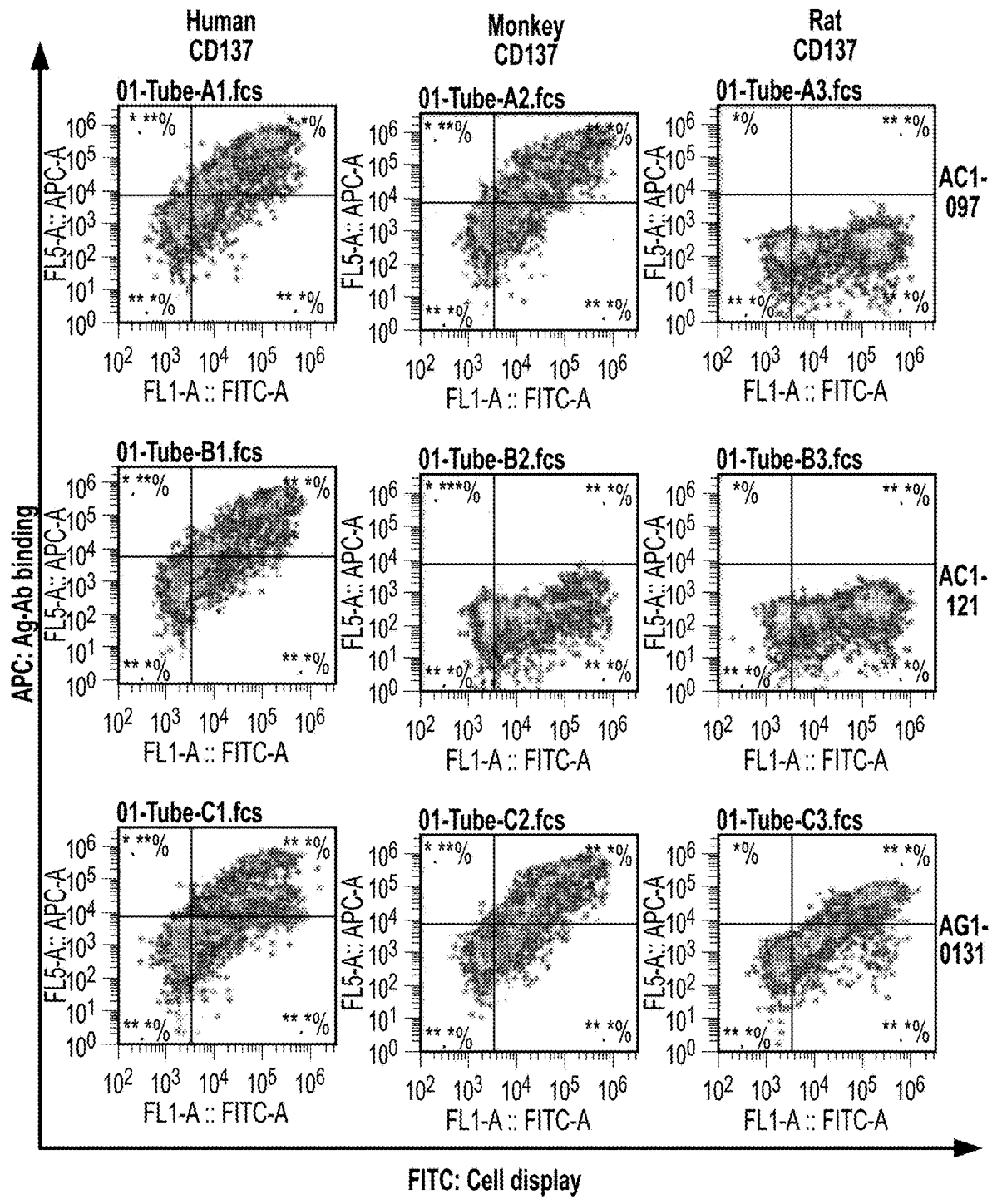
FIG. 3B shows a comparison of species cross-reactivity among exemplary antibodies and reference antibodies.
Figure 3B:
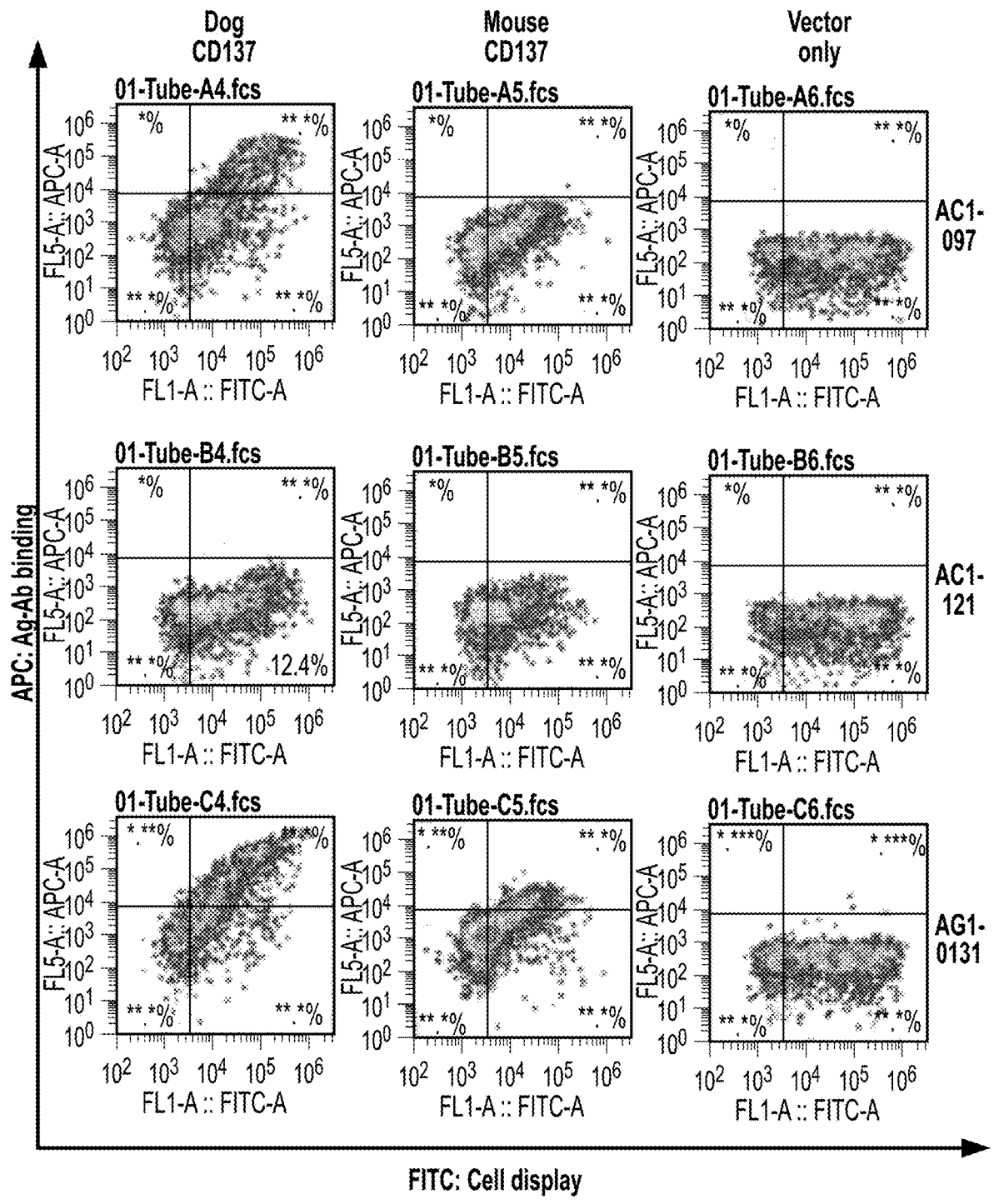
Figure 3B:
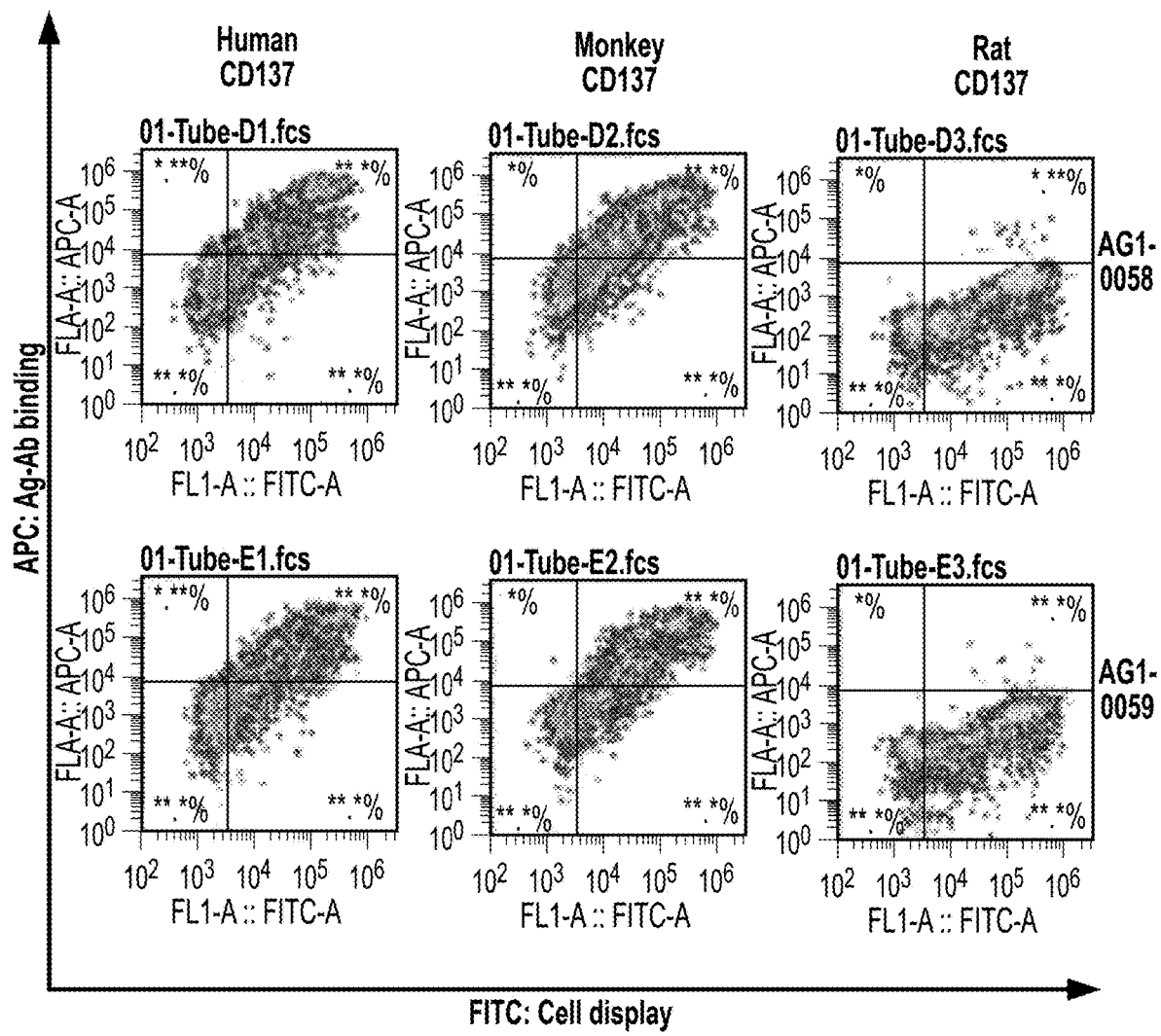
Figure 3B:
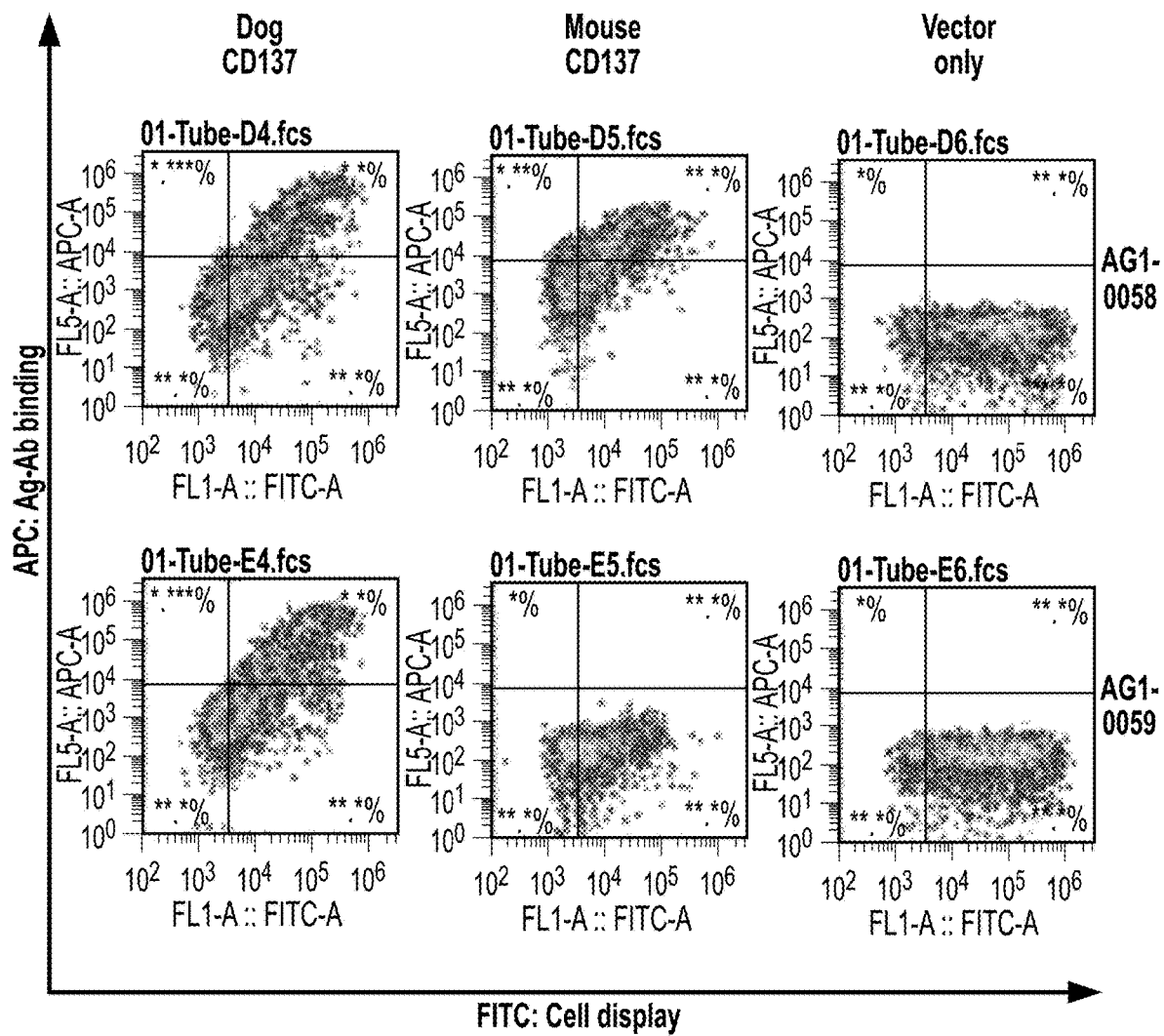

4c. Measurement of Binding Affinity to CD137 Overexpressed on Cell Surface by Flow Cytometry The affinity of antibodies were also assessed against human, monkey and mouse CD137 that are transiently expressed on the surface of HEK293F cells. Briefly, HEK293F cells were transfected with a plasmid expressing full-length human, monkey or mouse CD137 from a bicistronic IRES vector, EGFP was used to identify the transfected cells. After 48 hrs, the transfected cells were harvested and then washed once with cold FACS buffer (PBS supplemented with 1% BSA). Cells were then incubated with various IgGs (each at 100 nM) for 1 hr on ice, washed twice with pre-chilled FACS buffer, and incubated with Alexa Fluor® 647 conjugated mouse anti-human FC antibodies for 30 min on ice. The cells were washed once prior to analysis by flow cytometry (Beckman® CytoFlex). As shown in FIG. 3a, all antibodies bind to human CD137 expressed on cell surface with low nM affinity. AG10058, AG10059 and AG10131 are slightly better than both reference antibodies. Except AC1121 reference mAb, all antibodies bind to monkey CD137 with low nM affinity, AG10058, AG10059 and AG10131 are slightly better than AC1097 reference antibody. Consistent with results from Biacore and ELISA, only AG10058 and AG10131 bind to mouse and rat CD137. AG10058 has higher affinity than AG10131 against mouse CD137. Additionally, AG10058 and AG10131 (each at 100 nM) also bind to rat and canine CD137 overexpressed on HEK293F cell surface (FIG. 3b).

4d. Binding of IgGs to Activated Human, Monkey, Mouse and Rat T Cells.

The species-cross reactivity of the exemplary antibodies was further confirmed using PMA and Ionomycin stimulated PBMC or T cells of human, monkey, mouse and rat. Human and cynomolgus monkey PBMC were isolated by Ficoll-density gradient centrifugation. Briefly, fresh whole blood from healthy donors or cynomolgus monkeys were diluted with equal volume of PBS and carefully loaded on to the top of Histopaque 1077 (14 ml in 50 ml centrifuge tube). Centrifuge at 1,200×g for 30 minutes at room temperature with brake off. After centrifugation, carefully aspirate the upper layer with a pipette to within 0.5 cm of the opaque interface containing mononuclear cells.

Discard upper layer. Carefully transfer the opaque interface (about 3-5 ml) with a pipette into a clean 50 ml conical centrifuge tube. Wash the cells with 20 ml of PBS, collect cells by centrifuge at 400×g for 5 minutes, and resuspend cells into 20 ml of PBS. Count the cells with hemocytometer, and collect cells again by centrifuge at 400×g for 5 minutes. Mouse or rat splenocytes were isolated by passing spleens through a 45 µm cell strainer attached to a 50-mL conical tube to get single cell suspension, and wash cells through the strainer with PBS. Centrifuge at 1600 rpm for 5 min and discard the supernatant. Resuspend cell pellet in 2 ml red blood cell lysing solution for 2 min. Add in excess of 10-fold volume PBS and collect cells at 1600 rpm centrifugation for 5 min. Discard supernatant and resuspend splenocytes in RPMI1640/10% FBS. Pan-T cells were enriched from PBMC (human/monkey), or splenocytes (mouse/rat) by negative selection with magnetic beads in commercial kits (Stemcell Technologies) specific for human, monkey, mouse and rat, respectively. Activation of human/monkey PBMC, or mouse/rat splenocytes was performed by incubating cells with 50 ng/ml PMA+1 µM Ionomycin at 37° C., 5% CO2 for overnight.

Figure 4A:
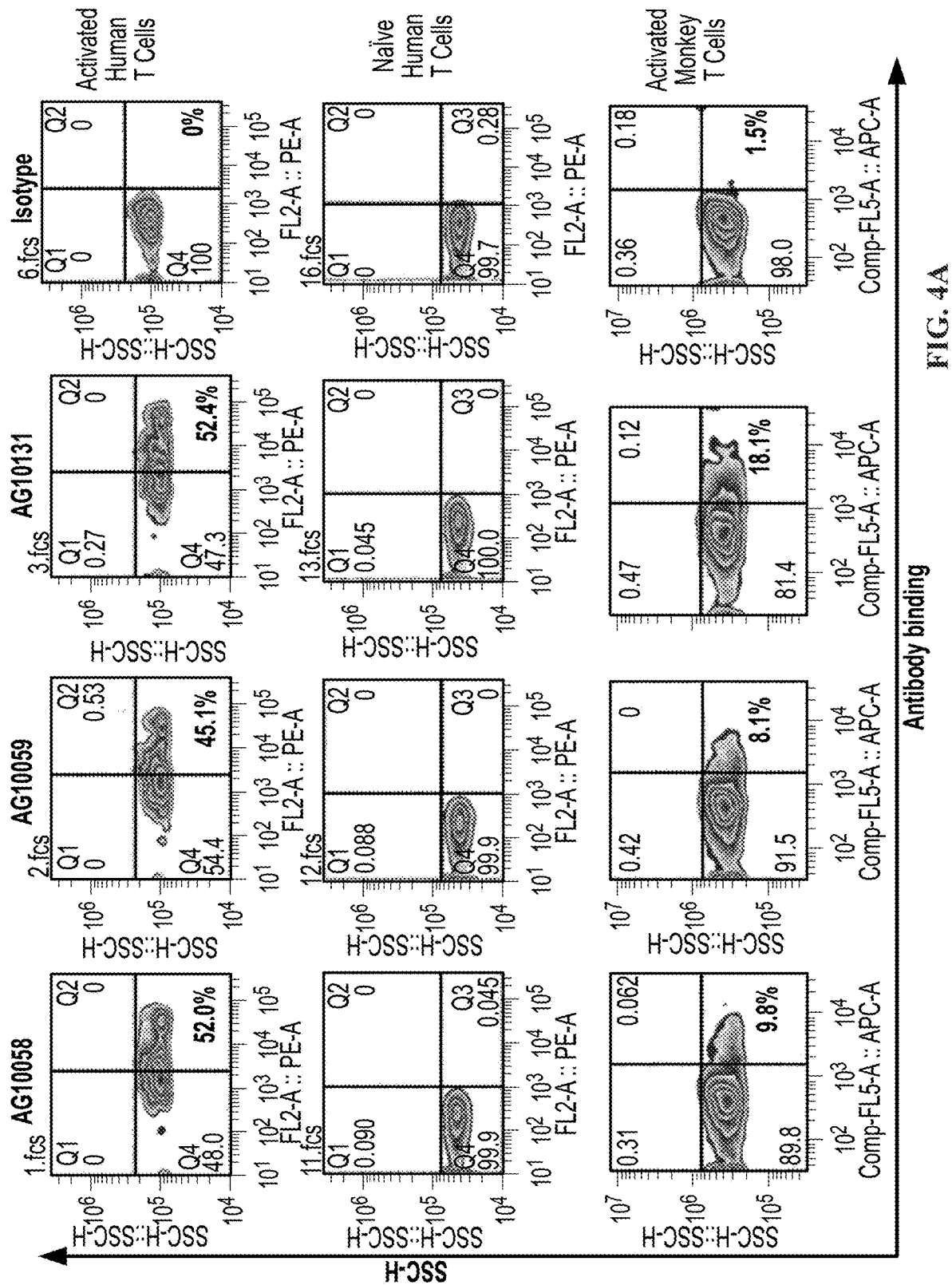
FIG. 4A shows exemplary antibodies binding to activated human and monkey T cells, but not naïve human T cells.
Figure 4B:
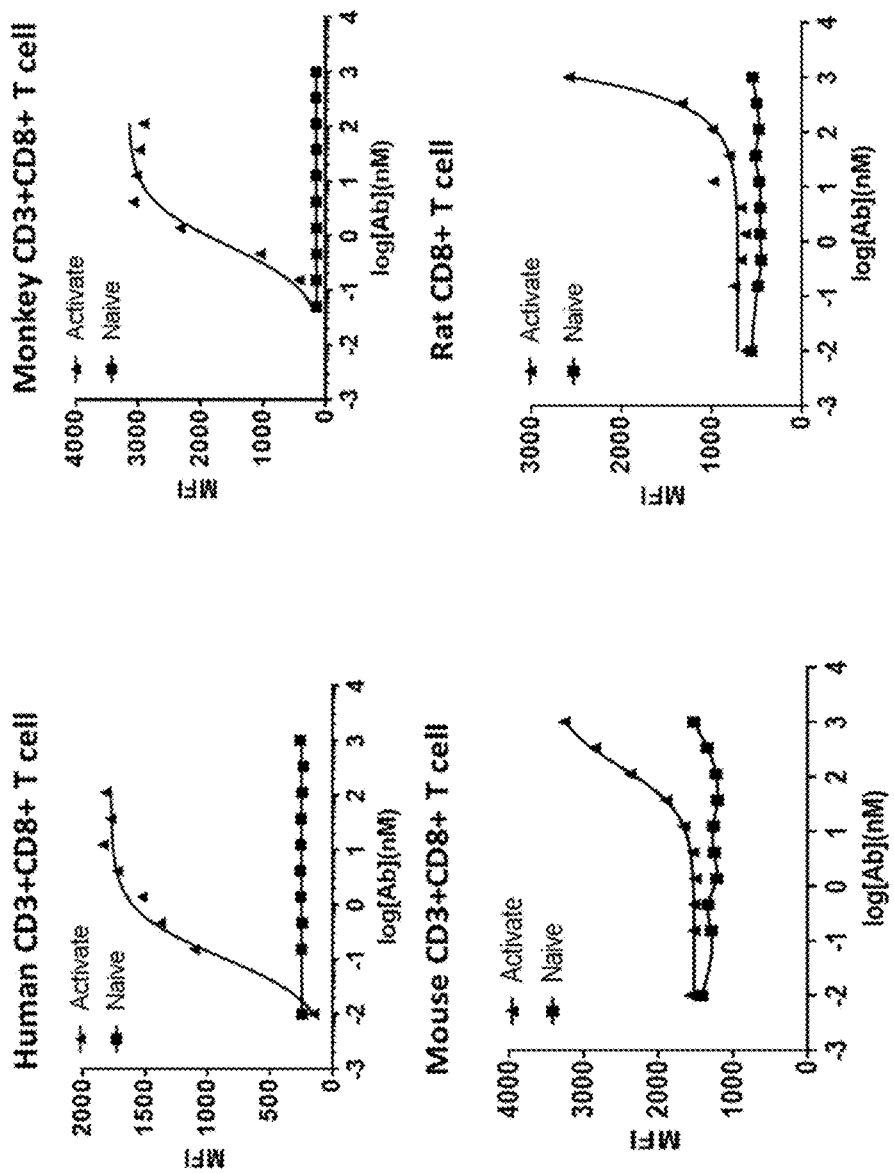
FIG. 4B shows binding of AG10131 to activated human, monkey, mouse and rat T cells.

Activated cells (~2×10$^5$ cells/tube) were washed in pre-chilled staining buffer (PBS supplemented with 2% FBS) and incubated with 100 nM tested antibodies for 1 hr on ice. Cells were then washed twice using 1 mL staining buffer and resuspended in 100 µL staining buffer containing Alexa Fluor® 647 conjugated mouse anti-human FC antibody and the species-specific T cell marker antibodies. The T cell marker antibodies were used as follows: CD3, CD4 or CD8. The cells were washed twice with staining buffer after incubation in dark for 30 minutes. Finally, cells were resuspended in 300 µL staining buffer and analyzed by Beckman CytoFlex. The data analysis was performed using Flowjo 10 software. As shown in FIG. 4a, all tested antibodies bind to both activated human and monkey T cells, but not to the naïve human T cells. The binding ability of AG10131 to activated mouse and rat T cells were further evaluated (FIG. 4b). AG10131 binds to both activated mouse and rat T cells.

In summary, AG10058 and AG10131 antibodies show higher affinity to human and monkey CD137. They exhibit broad species-cross reactivity, including human, cynomolgus monkey, mouse, rat and dog for AG10131, but human, cynomolgus monkey, mouse, and dog for AG10058, allowing quick assessment of in vivo efficacy in mouse syngeneic models.

Example 5

Binding Selectivity of Antibodies for CD137

Figure 5:
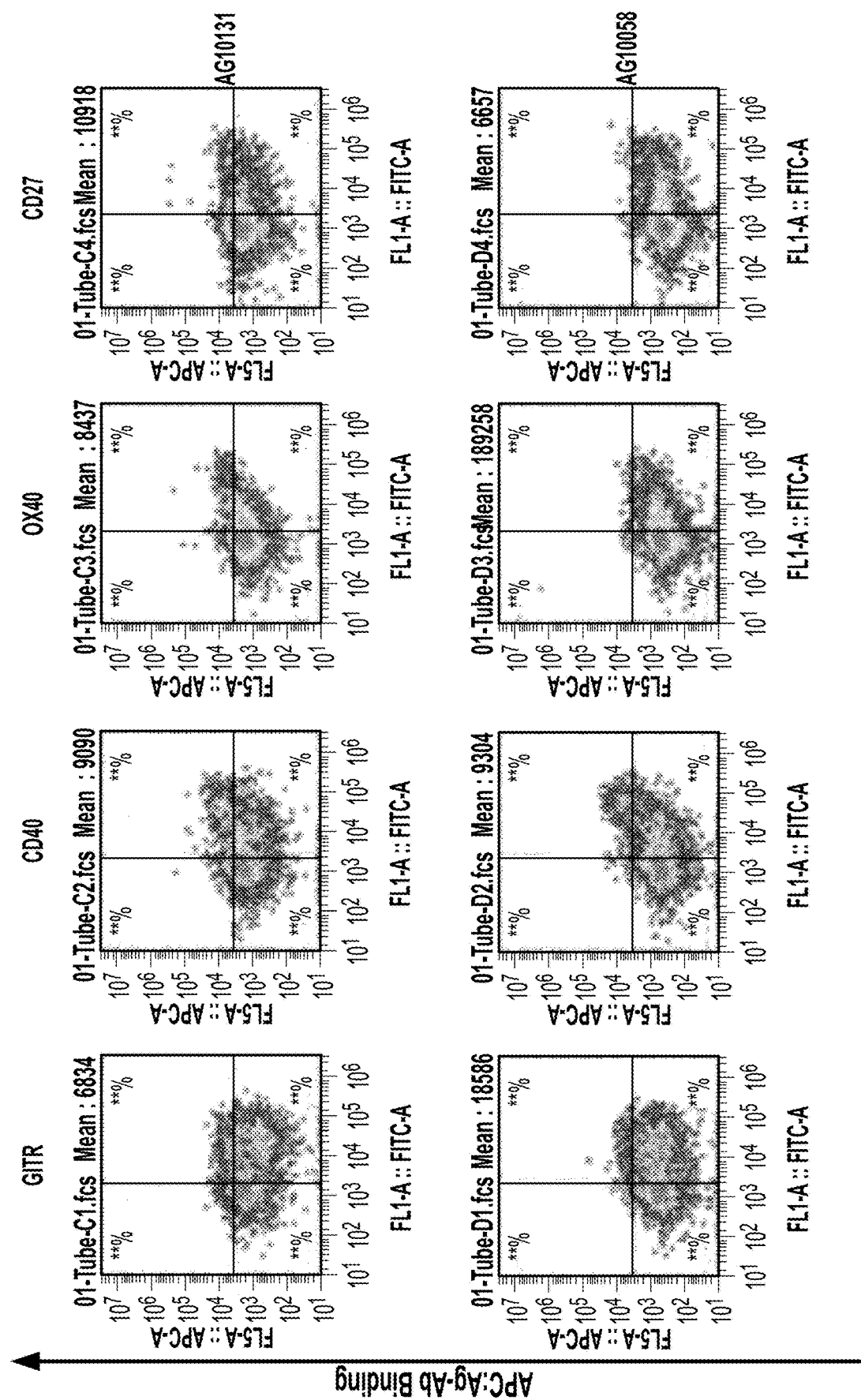
FIG. 5 shows binding specificity of exemplary antibodies to CD137, but to other TNFR family members.
Figure 5:
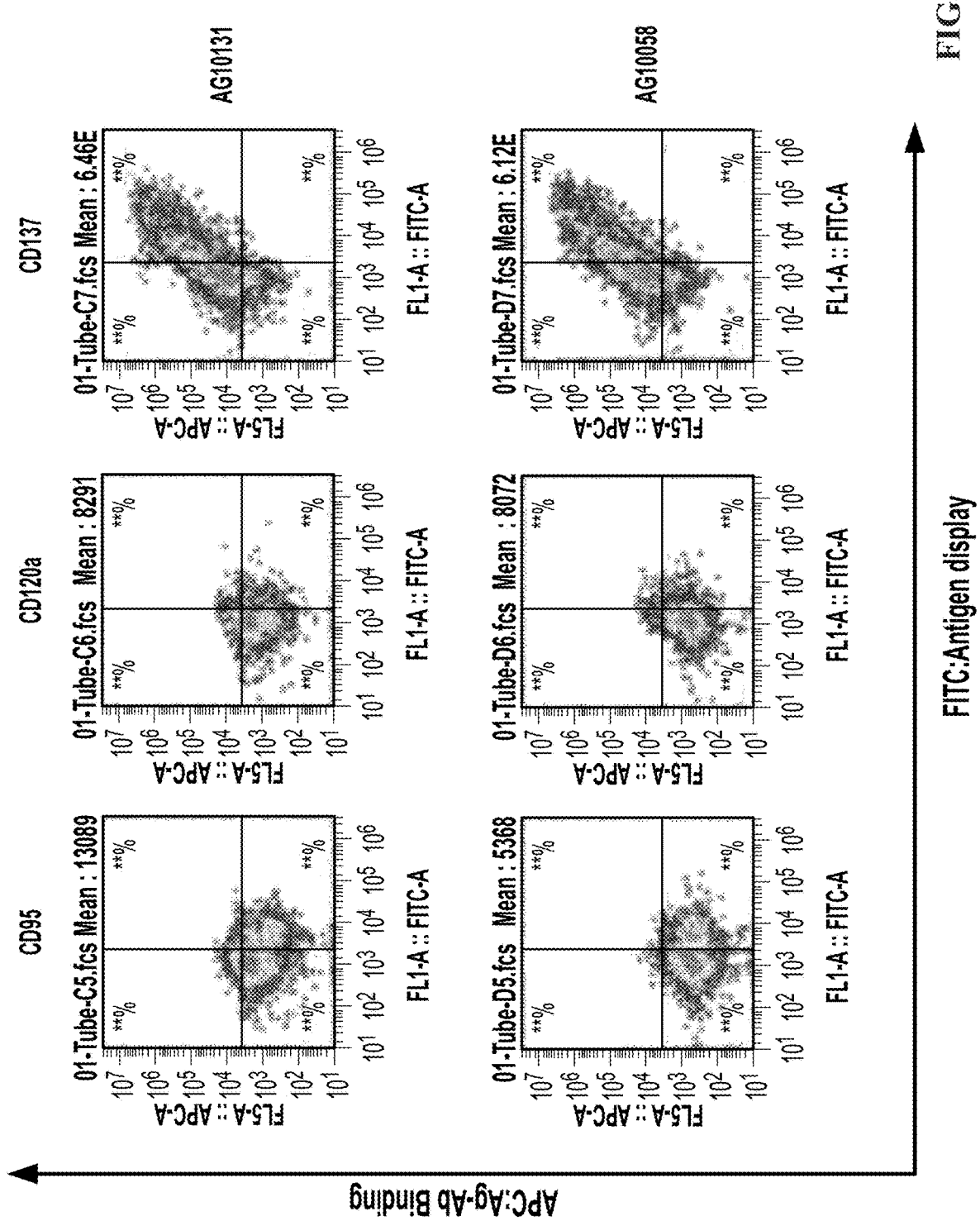
Figure 5:
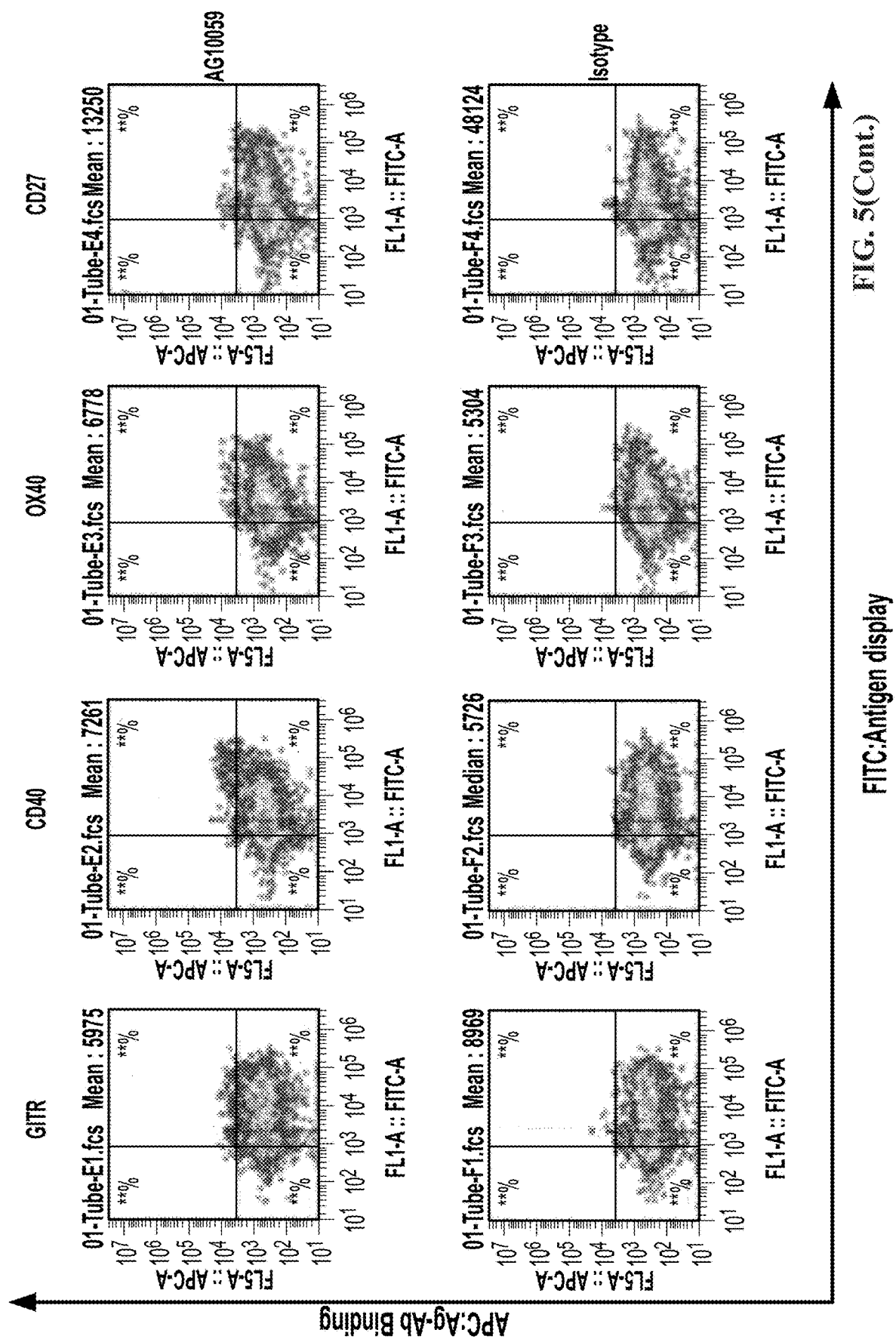
Figure 5:
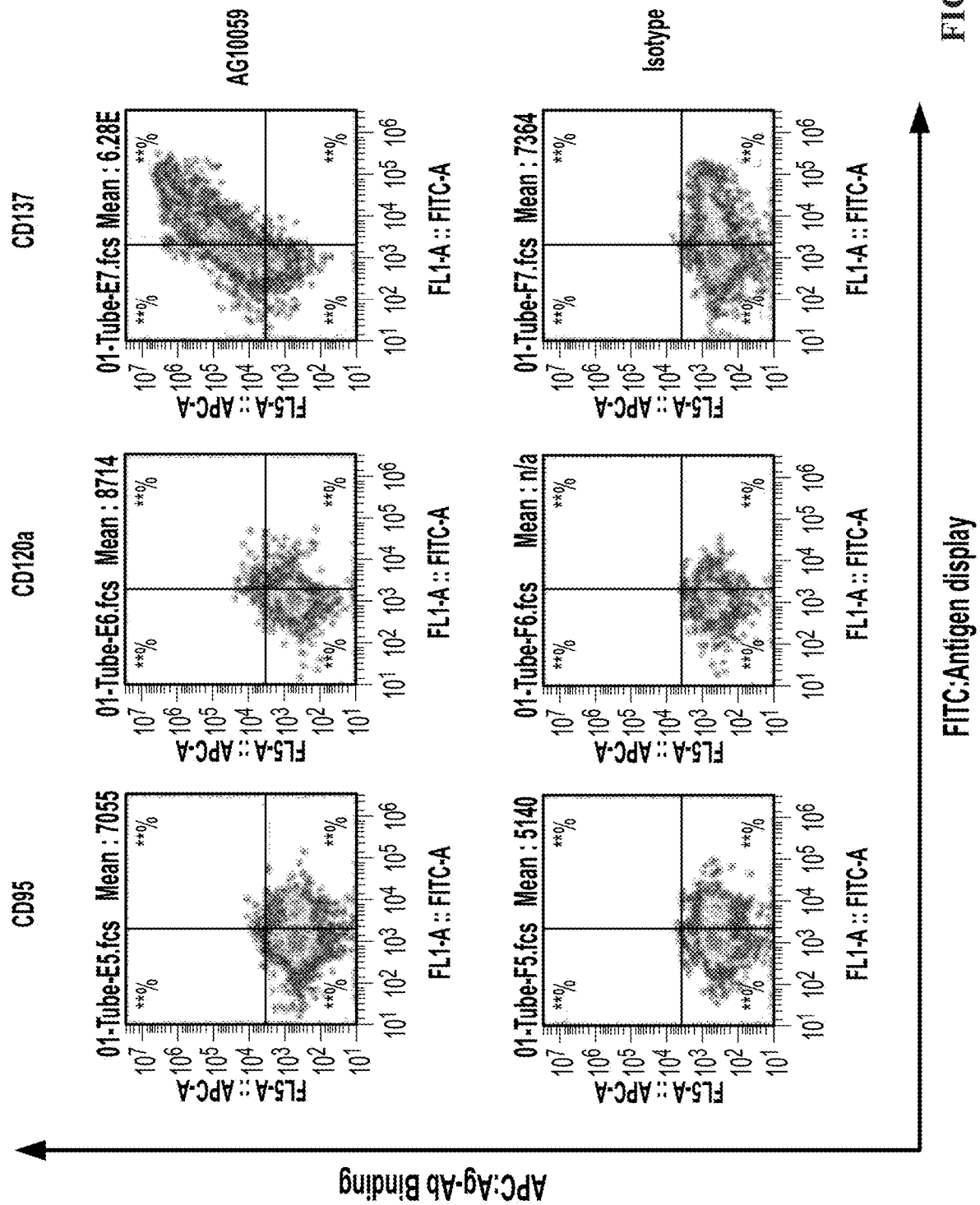

The selectivity of antibodies for CD137 was evaluated using flow cytometry analysis of their binding ability to members of TNFR superfamily. The TNFRSF receptors including CD137, OX40, CD40, GITR and CD27 were transiently overexpressed on the surface of HEK293F cells. Transfected cells were washed in pre-chilled staining buffer (PBS supplemented with 2% FBS), then incubated with 100 nM test antibodies for 1 hr on ice. Cells were washed twice with staining buffer, and Alexa Fluor® 647 conjugated mouse anti-human FC antibodies were added and incubated for 30 min on ice. Samples were washed once with staining buffer prior to analysis by flow cytometry. As shown in FIG. 5, AG10058, AG10059 and AG10131 bind specifically to CD137, not to any other tested family members or parent cells transfected with empty vectors.

Example 6

Ligand Competition Using ELISA and Flow Cytometry

Figure 6A:
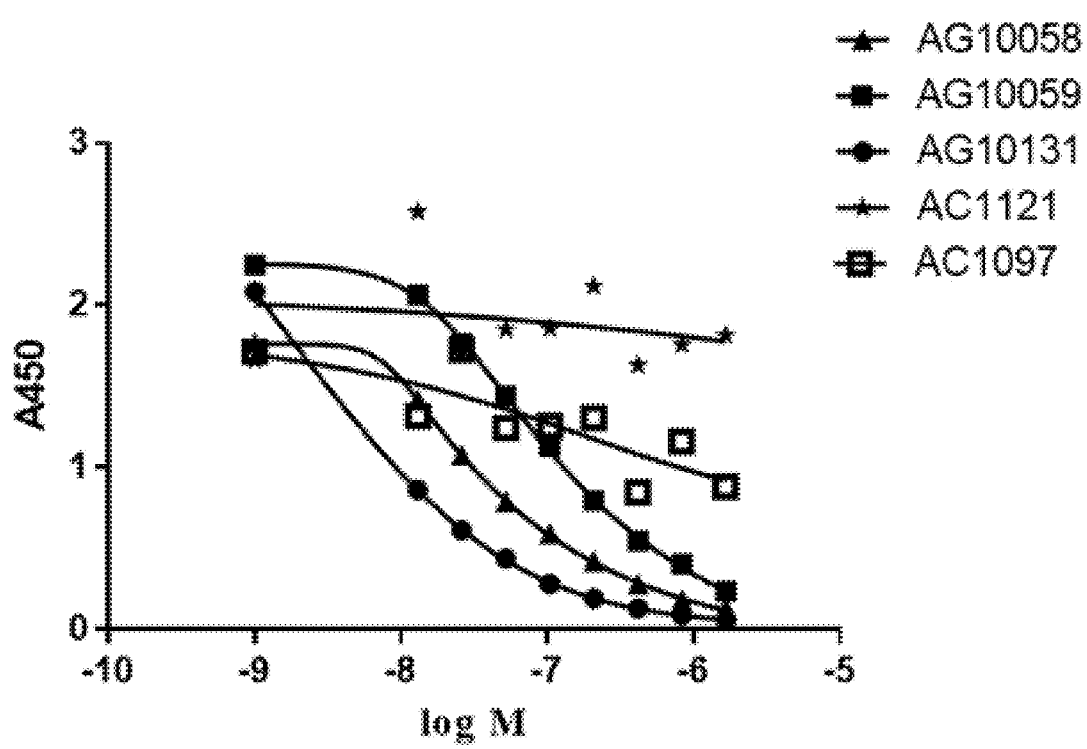
FIG. 6A and FIG. 6B show that exemplary antibodies block the binding of CD137 and its cognate ligand CD137L by both ELISA (FIG. 6A) and flow cytometry assay (FIG. 6B).
Figure 6B:
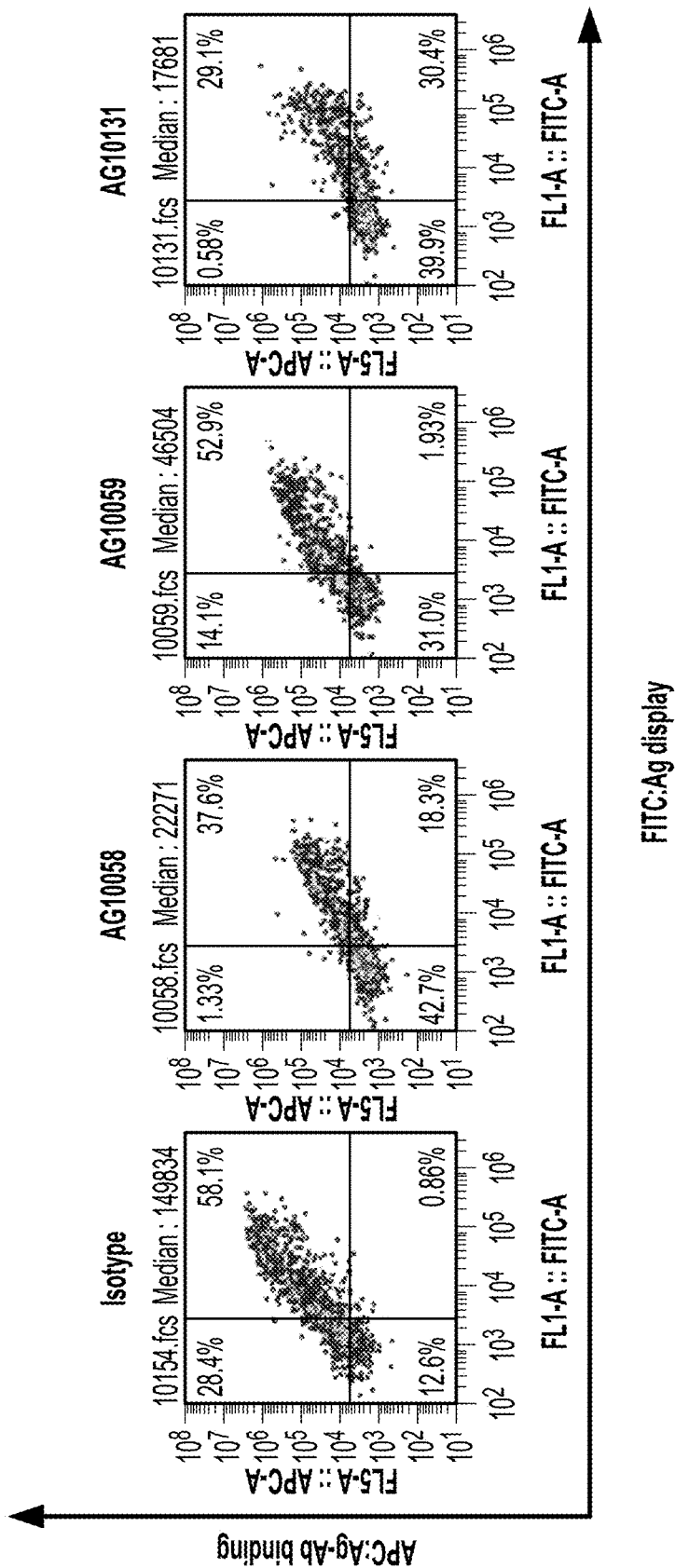

Antibodies were tested for their ability to block the binding of CD137 to its cognate ligand CD137L by both ELISA and flow cytometry assay. As shown in FIGS. 6a and 6b, all tested antibodies block the binding of CD137 and CD137L.

6a. Ligand Competition Binding by ELISA

Recombinant human CD137 (fused with human Fc and His tag) was diluted to 1 µg/mL in PBS and coated on Maxisorp plate at 4° C. overnight. Plates were blocked with PBS supplemented with 3% non-fat milk at 37° C. for 1 hr. After washing, a total volume of 100 uL mixture of 50 uL biotinylated CD137L (4 µg/mL) and various concentrations of test antibodies (eight 1:2 serial dilutions ranging from 500 µg/mL to 2 µg/mL) were added to each well and incubated at 37° C. for 1 hr. Plates were washed three times and 100 µL HRP conjugated neutravidin (1:1000) were added to each well and incubated at 37° C. for 1 hr. Plates were washed as previously described and 50 µL TMB substrate solution was added and incubated at room temperature for 20 minutes before the reaction was stopped by 50 pt H$_2$SO$_4$. As shown in FIG. 6a, all test antibodies AG10058, AG10059 and AG10131 block the binding of CD137 to CD137L.

AG10131 shows the strongest or complete blocking ability, at about uM range, followed by AG10058 for significant blocking at >uM; and AG10059 for effective blocking at uM range. These data suggest that, under the conditions tested and with the reagents used, the broad species cross-reactive antibodies AG10131 and AG10058 are highly effective inhibitors of the interaction between CD137 and its ligand CD137L, whereas AG10059 only shows moderately effective blocking of the interaction between CD137 and its ligand CD137L. It should be noted that the reference antibody AC1097, which cross-reacts with both human and monkey CD137, while AC1121, which only reacts with human CD137, shows almost no blocking at all.

6b. Ligand Competition Binding by Flow Cytometry

The plasmid encoding full-length human CD137 was transiently expressed in HEK293F cells. Cells were washed with staining buffer (PBS supplemented with 1% BSA) and resuspended in staining buffer containing 100 nM test antibodies. After incubation on ice for 30 min, 33 nM biotinylated CD137L were added to each well and incubated for another 1 hr on ice. Cells were washed with staining buffer twice, and 50 µL staining buffer containing Alexa fluor 647 conjugated streptavidin were added and incubated on ice for 30 min. Cells were washed once and analyzed by CytoFlex flow cytometry. As shown in FIG. 6b, all three tested antibodies can block binding between CD137 and CD137L in a concentration dependent manner. AG10131 shows the strongest blocking capability, followed by AG10058 with significant blocking; and AG10059 with less effective blocking. These data suggest that the broad species cross-reactive antibodies AG10131 and AG10058 are highly effective in blocking the interaction between CD137 and its ligand CD137L, while AG10059 shows partial blocking of the interaction between CD137 and its ligand CD137L. In contrast, the AC1097 reference antibody, which cross-reacts with both human and monkey CD137, shows only partial blocking, while the AC1121 reference antibody, which only reacts with human CD137, shows no blocking.

Example 7

Epitope Mapping

Figure 7A:
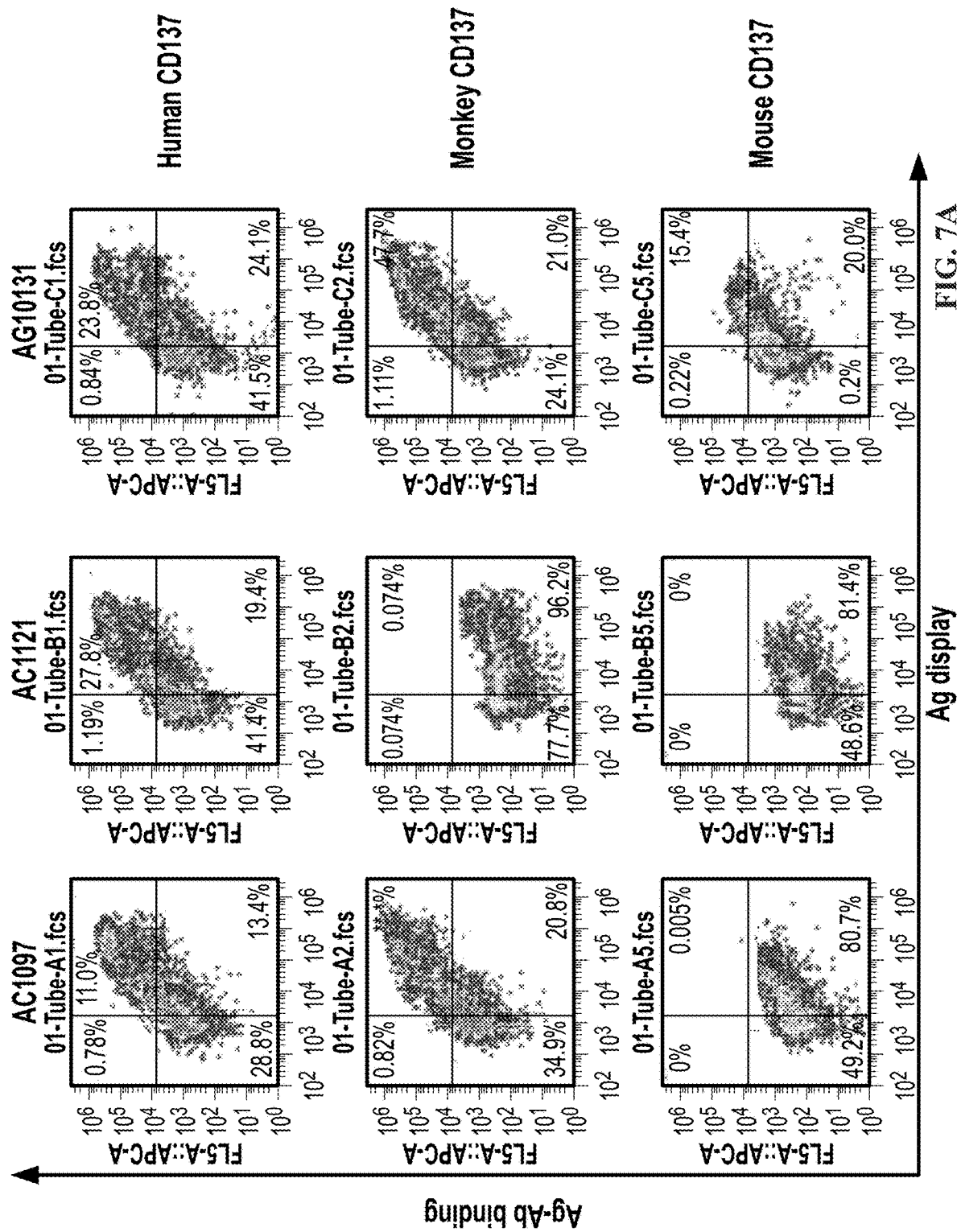
FIG. 7A shows epitope mapping results by flow cytometry.
Figure 7A:
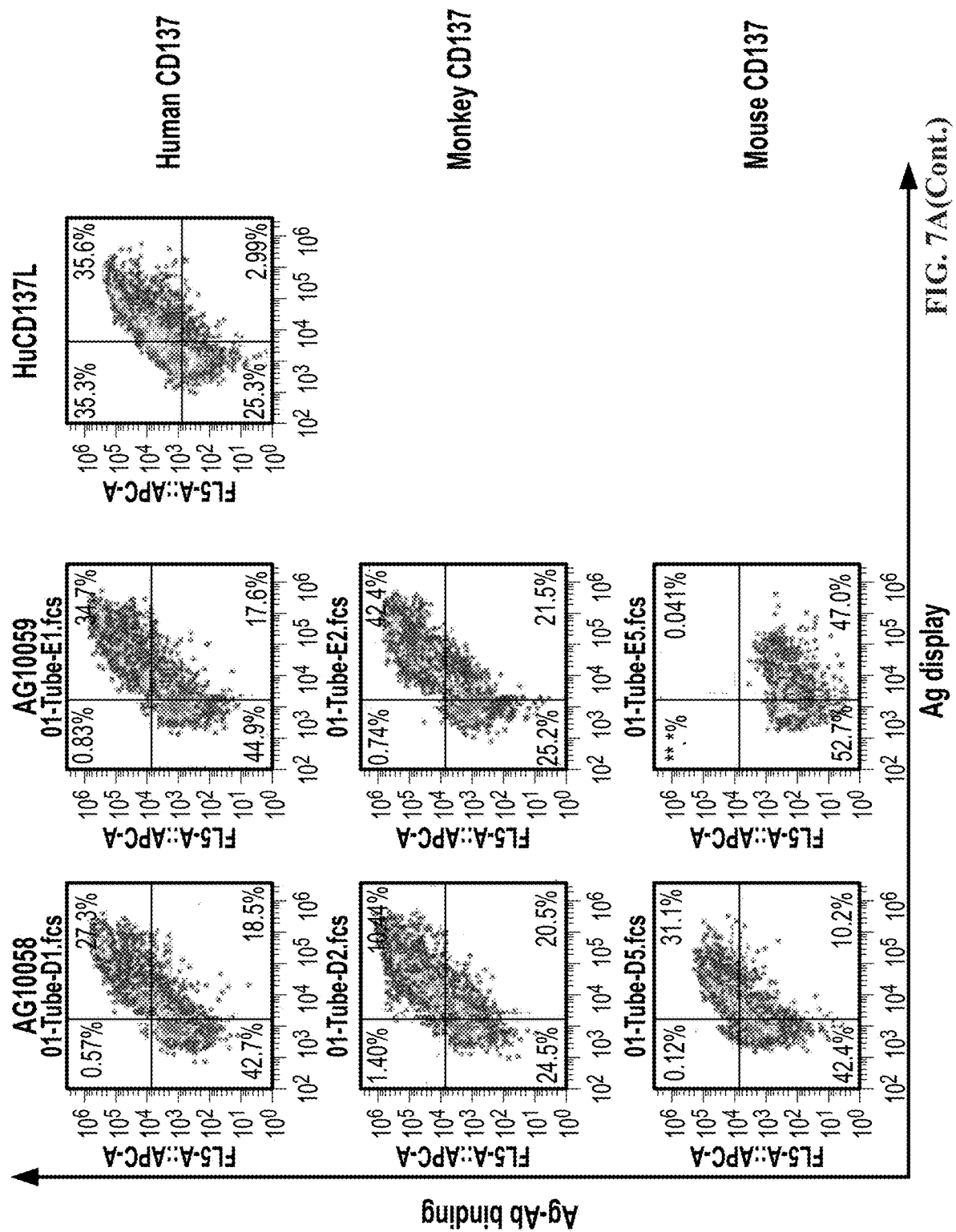
Figure 7A:
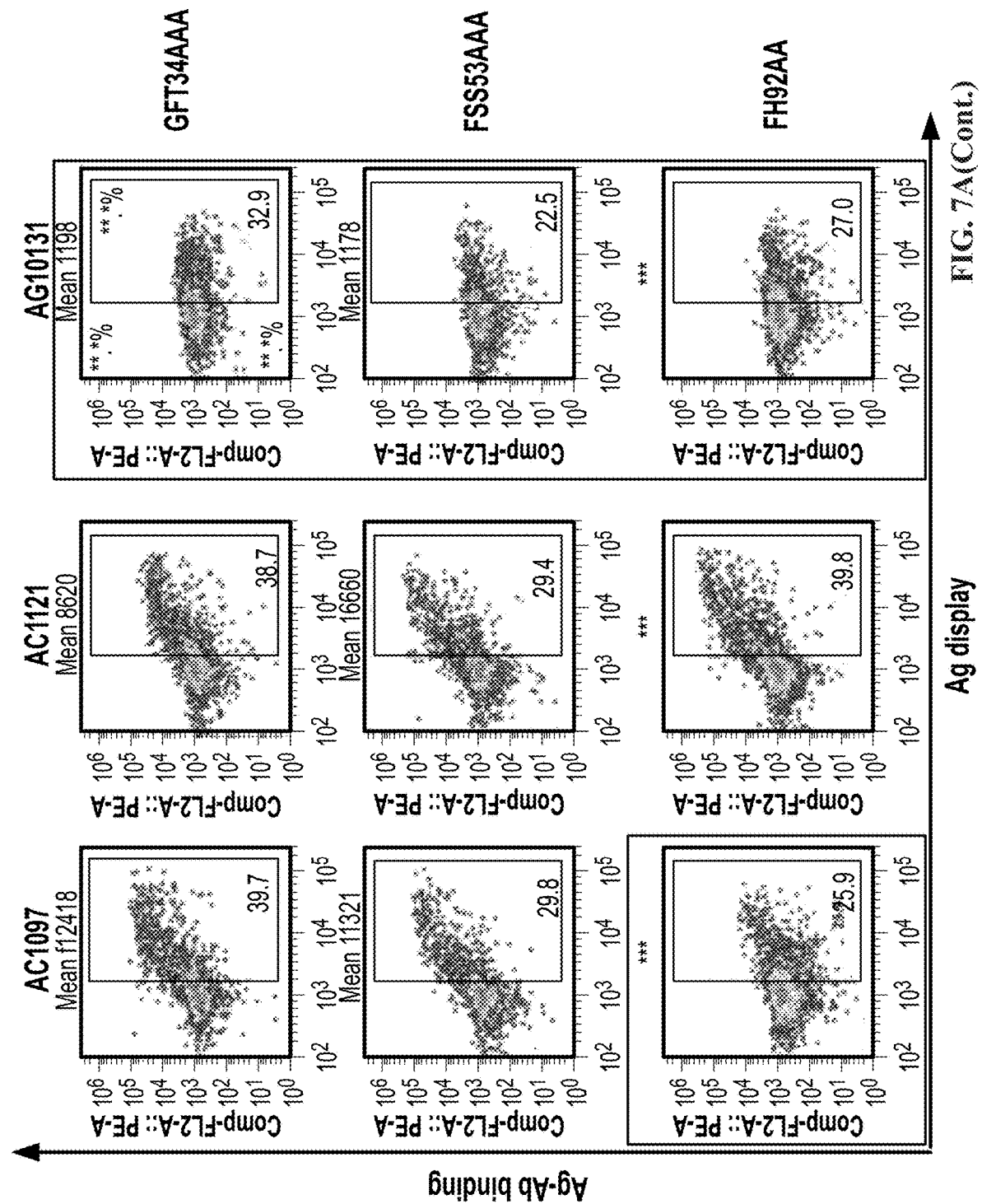
Figure 7A:
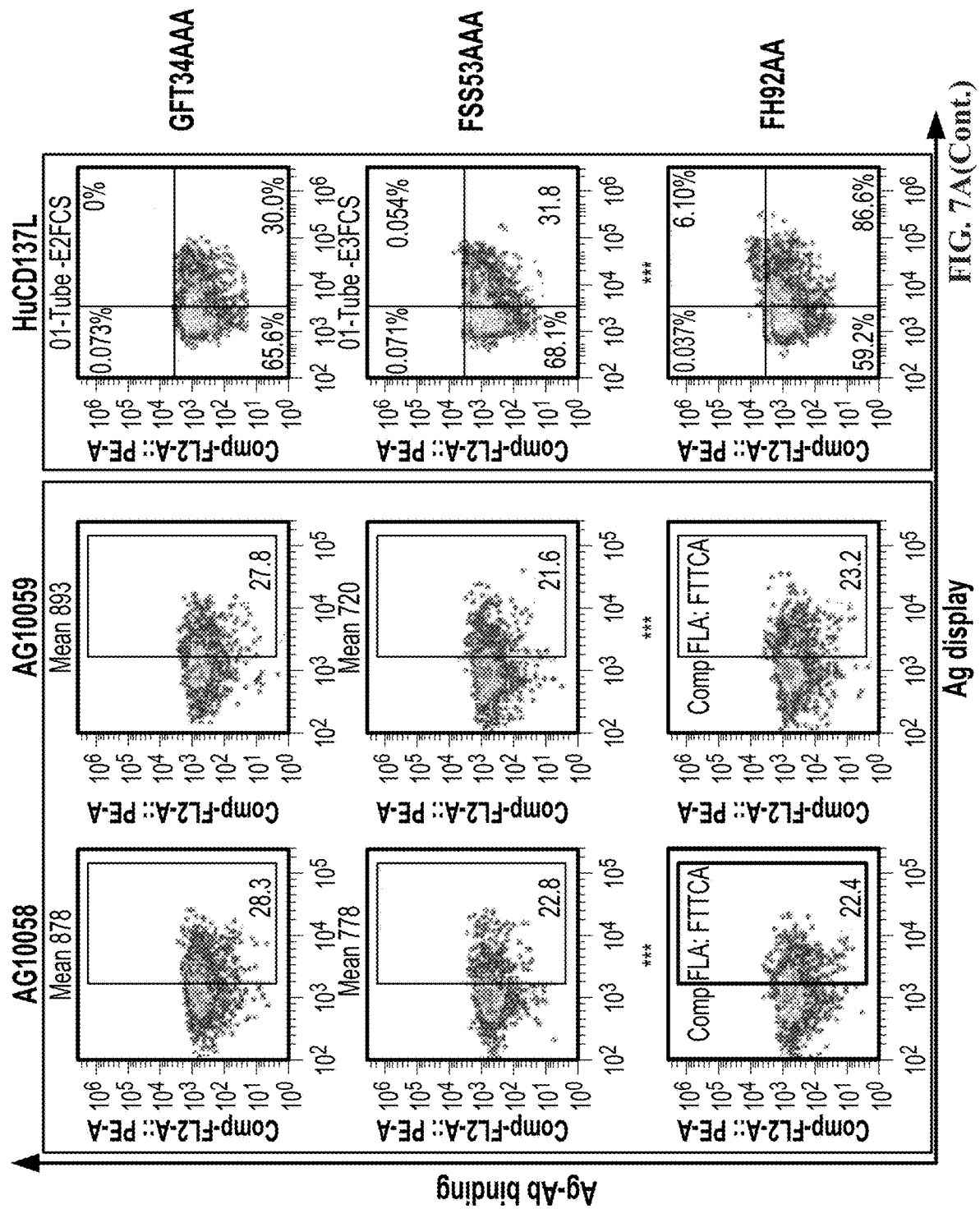
Figure 7A:
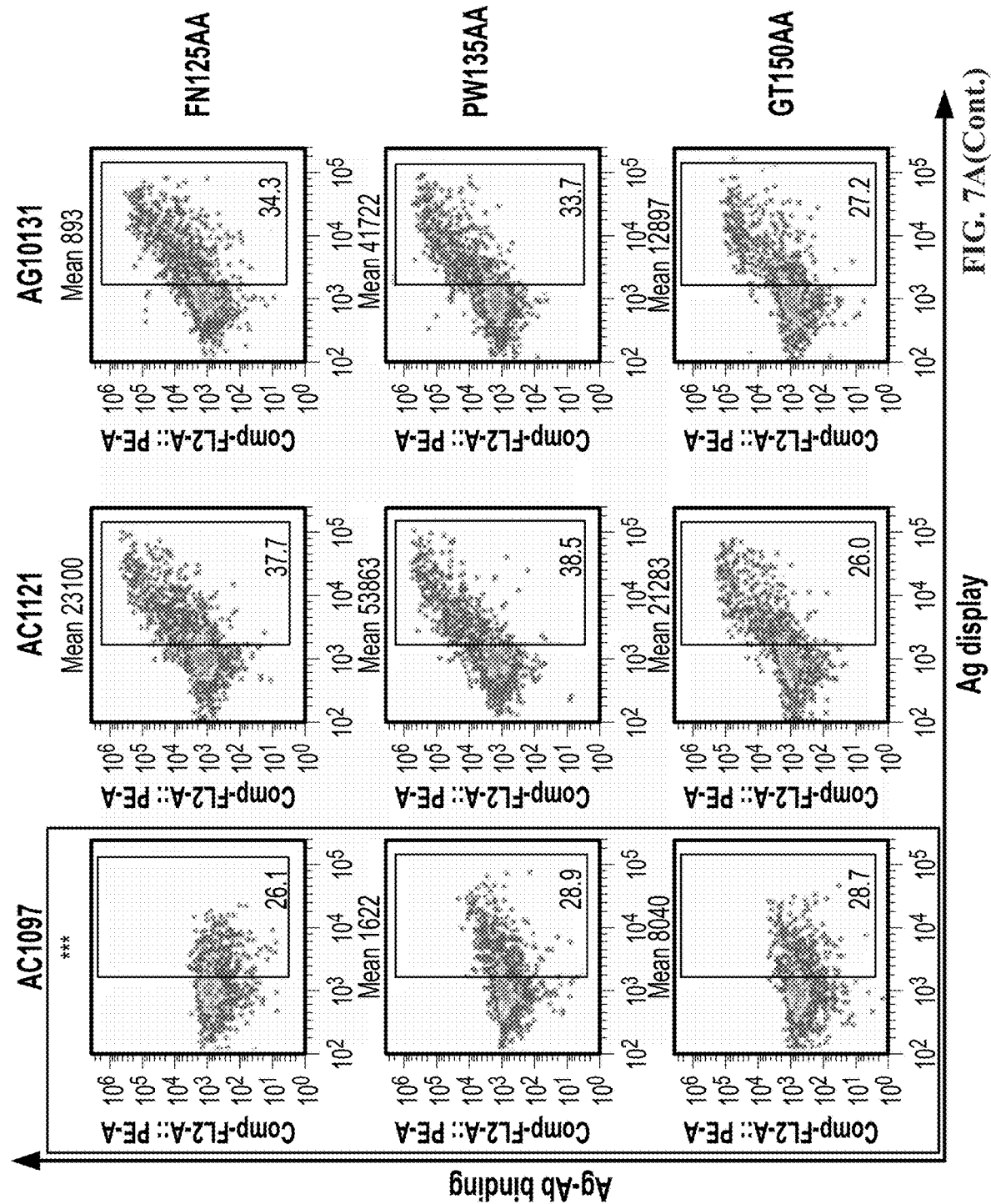
Figure 7A:
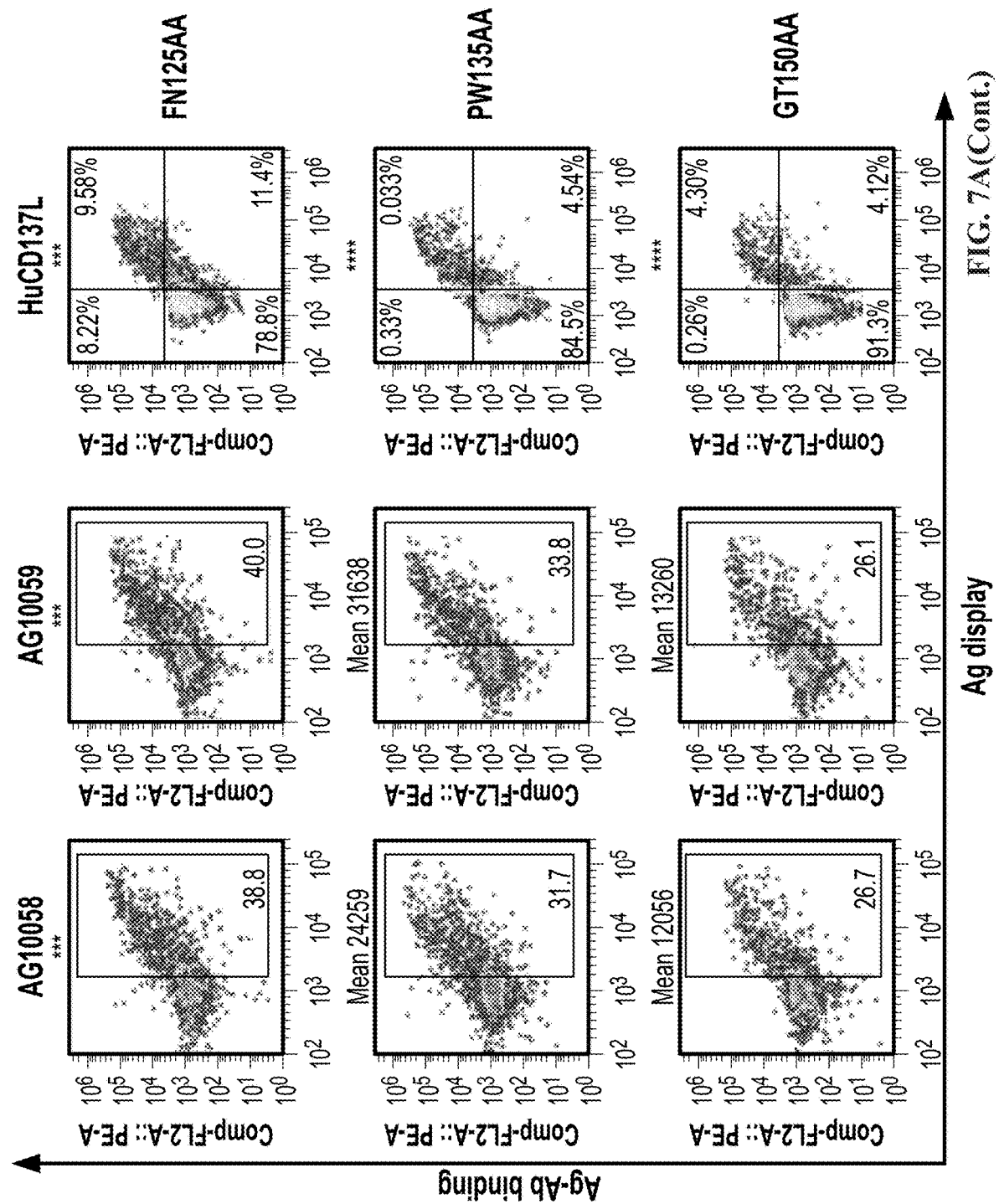

To determine the binding regions of the tested antibodies at amino acid residue level, a series of mutations (Table 5) were made at the extracellular domain of human CD137. These CD137 mutation plasmids were used to transfect HEK293F cells. The binding of antibodies to the human CD137 mutants were assessed by flow cytometry analysis as previously described in Example 5 and shown in FIG. 7A. The results are summarized in Table 5, together with the cross-reactivity of these antibodies with human, monkey, mouse, and rat CD137 in interesting differentiation, indicating the fine epitopes from hits derived from Adagene libraries. AG10131 binds to all 4 species, whereas AG10058 binds all 3 CD137 but not rat CD137. AG10058, AG10059 and AG10131 lost the binding ability to GFT34AAA, FSS53AAA, and FH92AA mutations, indicating that their binding epitopes are within these regions, e.g., amino acid residues 34-93 or 34-108 of SEQ ID NO.: 1 (See also, FIG. 7B). AG10058 and AG10131 may bind the same or highly similar epitope, while AG10059 may bind different epitopes from AG10058 and AG10131.

The mutant constructs were meant to differentiate the epitopes by AG10058, AG10059 and AG10131 from the reference antibodies by AC1121 and AC1097. It is clear that all three antibodies AG10058, AG10059 and AG10131 target very different epitopes from AC1121 and AC1097. AG10058, AG10059 and AG10131 differ from AC1121 in regions defined by mutants Hu FH92AA and Hu FSS53AAA and possibly Hu GTF34AAA, whereas AG10058, AG10059 and AG10131 differ from AC1097 in regions defined by most of the mutants used, except for Hu FH92AA and their species cross-reactivity with Monkey but different in other species cross-reactivity such as mouse, rat and dog CD137. In some embodiments, AG10058, AG10059 and AG10131 or other antibodies disclosed herein do not bind to an epitope located within amino acid residues 115-156 of SEQ ID NO.: 1. Also shown in FIG. 7A and Table 5 is that binding of the human CD137 ligand to the wild-type vs. mutant human CD137 matches well with binding pattern of the tested antibodies, consisting with the observation that these antibodies block CD137 ligand binding to its receptor.

TABLE 5

| | Epitope Mapping | | | | | |
|---|---|---|---|---|---|---|
| Mutations | AG10058 | AG10059 | AG10131 | AC1121 | AC1097 | HuCD137L |
| Hu_WT | + | + | + | + | + | + |
| Cyno_WT | + | + | + | − | + | |
| Mouse_WT | + | − | + | − | − | |
| Rat_WT | − | − | + | − | − | |
| Hu_GTF34AAA | − | − | − | −/+ | + | − |
| Hu_FSS53AAA | − | − | − | + | + | − |
| Hu_FH92AA | − | − | − | + | − | − |
| Hu_GQ109AA | + | + | + | + | − | + |
| Hu_EL111AA | + | + | + | + | − | + |
| Hu_F125A | + | + | + | + | − | + |
| Hu_FN125AA | + | + | + | + | − | + |
| Hu_PW135AA | + | + | + | + | − | + |
| Hu_TN137AA | + | + | + | + | − | + |
| Hu_GT150AA | + | + | + | + | − | + |

Example 8

Agonist Activity of Antibodies in NFκB Luciferase Reporter Assay

Figure 8:
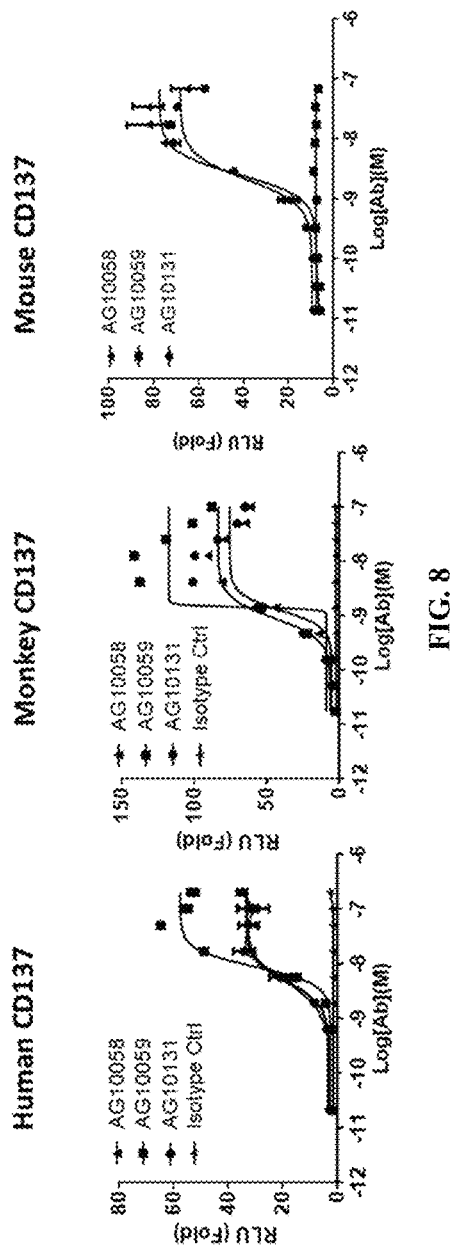
FIG. 8 shows agonist activity of exemplary antibodies in NFκB reporter assay.

Agonist activity of antibodies was evaluated using NFκB reporter assay. 293T cells were transfected with plasmid expressing human, monkey or mouse CD137 along with NFκB luciferase reporter plasmids. After 4h, 50 µL cells were plated into each assay well of a 96-well plate at density of 0.4×10$^6$/mL. A total volume of 50 µL antibody mixture containing test antibodies and 3:1 ratio of cross linking antibody (Fab' goat anti-human IgG FC) was added and incubated for 18h. After medium is removed, 50 μL Passive Lysis Buffer (Promega E1980) were added and incubated at 37° C. for 30 min. 20 ρt lysate were transferred to a white plate and the luciferase substrates were added. The luminescence signal of firefly and Renina was measured and their ratio was used for data analysis by GraphPad Prism 6.0 software. As shown in FIG. 8, compare to isotype control antibody, all test antibodies activate NFκB reporter gene expression when human and monkey CD137 is expressed. When mouse CD137 is expressed, AG10058 and AG10131, but not AG10059, activate NFκB reporter gene expression. This is consistent with the prior observation that AG10058 and AG10131 bind to mouse CD137 whereas AG10059 does not.

Example 9

Agonist Activity of Antibodies in T Cell Activation Assay

Figure 9:
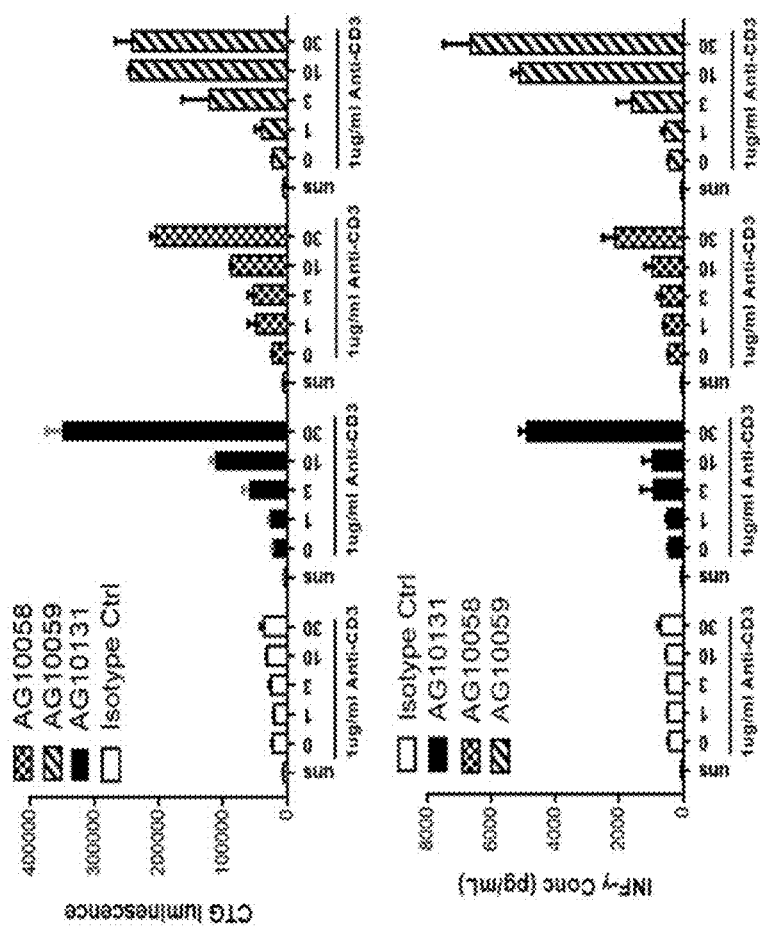
FIG. 9 shows agonist activity of exemplary antibodies in CD8+ T cell proliferation (top panel) and INF-γ secretion (bottom panel).

Agonist activity of antibodies was further confirmed in the T cell activation assay. 96-well cell culture plates were coated with 50 μL of the anti-CD3 antibody (2 μg/ml) alone or along with 50 μL of the test antibodies (60 μg/mL, 20 μg/mL, 6 μg/mL, 2 μg/mL, and 0 μg/mL) in 1×PBS at 4° C. overnight. CD8+ T cells were isolated using protocols according to the manufacture's instruction. Cells were prepared at density of $1\times10^7$ cells/mL in RPMI1640 media supplemented with 10% FBS. 200 μL cells were plated to each assay well and incubated for 4 days in a 37° C., 5% CO2 incubator. Cells were checked daily under microscope for proliferation. After 96 hr incubation, 100 μL of supernatant were transferred to a new 96-well plate for IFN-γ detection. T cell proliferation was assayed using Cell Titer Glow kit (Promega). As shown in FIG. 9, compared to isotype control antibody, all tested antibodies induced both CD8+ T cell proliferation and IFN-γ secretion in a dose-dependent manner.

Example 10

Anti-Tumor Activity in Mouse Syngeneic Models

The species cross-reactivity with mouse CD137 allows quick in vivo functional assessment. AG10058 and AG10131 have been tested in multiple mouse syngeneic models. BALB/c mice (n=8 per group) were transplanted subcutaneously with $2\times10^6$ H22 liver cancer cells (Xiao et.al, Soluble PD-1 facilitates 4-1BBL-triggered antitumor immunity against murine H22 hepatocarcinoma in vivo. Clin Cancer Res. 2007; 13(6):1823-30.), $5\times10^5$ CT26 colon cancer cells, or $5\times10^5$ EMT6 breast cancer cells. When tumors were established (>50 $mm^3$), treatment began with isotype control antibody, AG10058, or AG10131 by intraperitoneal injection, twice a week for up to 3 weeks. Tumor growth was monitored twice a week and reported as the mean tumor volume±s.e.m. over time. As shown in FIGS. 10-13, compared to the isotype control antibody, both AG10058 and AG10131 exhibited potent in vivo anti-tumor activity in these different syngeneic mouse tumor models.

Figure 10:
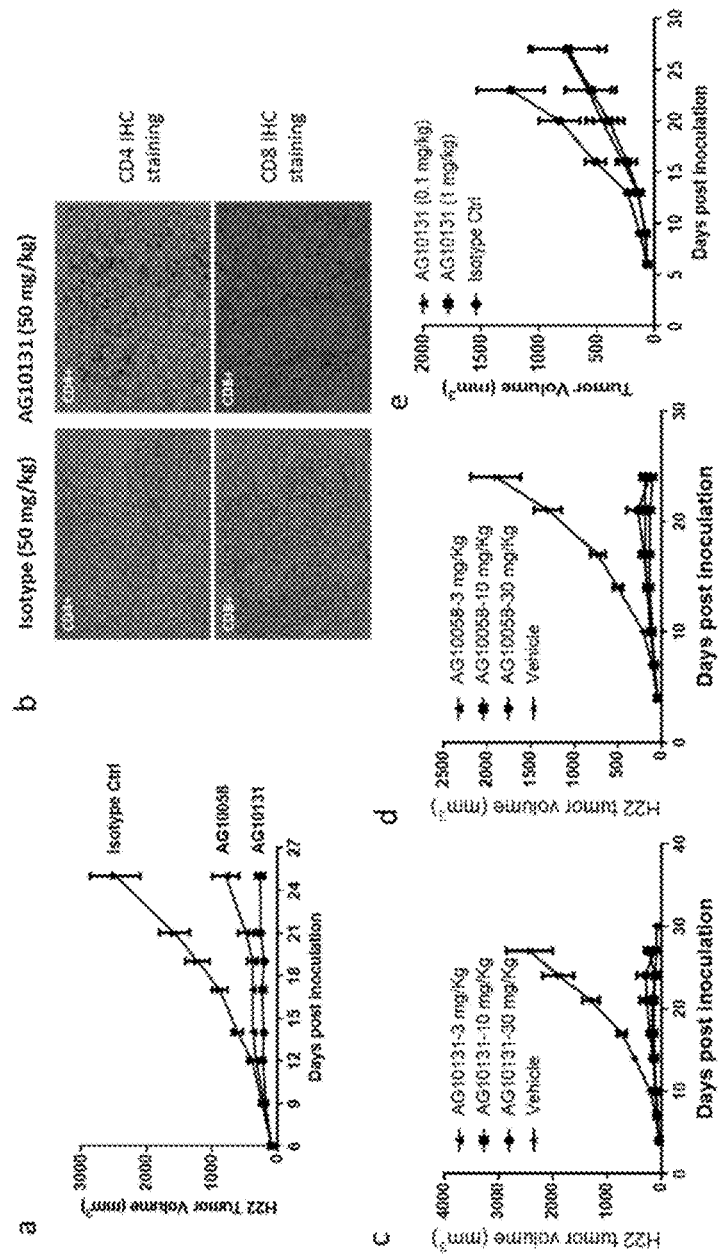
FIG. 10 shows anti-tumor efficacy of exemplary antibodies, as well as infiltration of $CD4^+$ and $CD8^+$ T cells into tumors, in H22 mouse liver cancer model.
Figure 11:
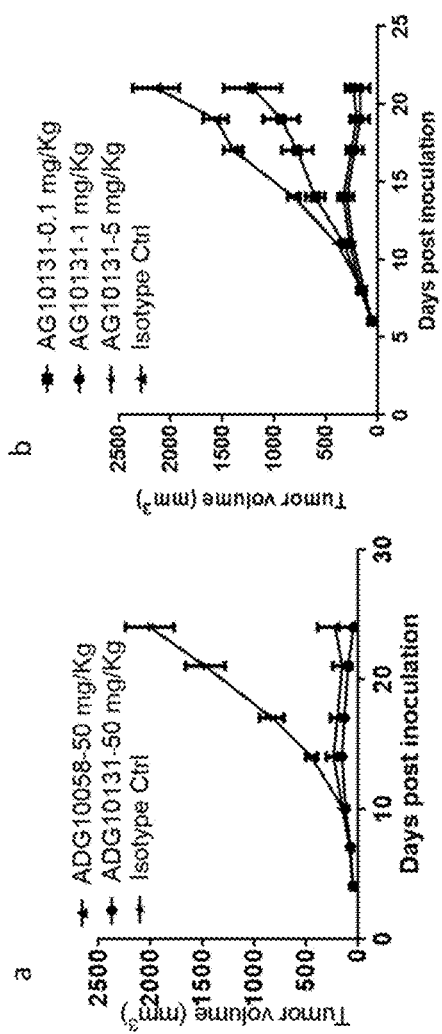
FIG. 11 shows anti-tumor efficacy of exemplary antibodies in CT26 mouse colon cancer model.

10a. CD137 Agonist Antibodies Exhibit Anti-Tumor Efficacy in H22 Mouse Liver Cancer Model First, AG10058 or AG10131 was administrated twice a week for 3 weeks at dosage of 50 mg/kg. Both molecules showed almost 100% TGI (tumor growth inhibition) (FIG. 10, panel a). Immunohistochemistry staining of CD4 and CD8 markers showed that AG10131 significantly increased the infiltration of both CD4+ and CD8+ T cells in H22 tumor (Xiao et.al, Soluble PD-1 facilitates 4-1BBL-triggered anti-tumor immunity against murine H22 hepatocarcinoma in vivo. Clin Cancer Res. 2007; 13(6):1823-30.) microenvironment (FIG. 10, panel b). Further dose titrations down to 3 mg/kg still showed ~100% TGI, suggesting both molecules have potent anti-tumor activity (FIG. 10, panels c and d). Further dose titration of AG10131 down to 1 and 0.1 mg/kg showed greater than 50% TGI at 0.1 mg/kg and 1 mg/kg (FIG. 10, panel e).

10b. CD137 Agonist Antibodies Exhibit Anti-Tumor Efficacy in CT26 Mouse Colon Cancer Model As shown in FIG. 10, both AG10058 and AG10131 showed almost 100% TGI (tumor growth inhibition) at dose of 50 mg/kg (FIG. 11, panel a) in CT26 mouse colon cancer model (Martinez-Forero et.al, T cell costimulation with anti-CD137 monoclonal antibodies is mediated by K63-polyubiquitin-dependent signals from endosomes. J Immunol. 2013; 190(12):6694-706). Further dose titration of AG10131 (FIG. 11, panel b) showed almost 100% TGI at doses of 5 mg/kg and 1 mg/kg. At 0.1 mg/kg dosage, approximately 40% TGI was achieved, indicating a dose-dependent anti-tumor activity.

10c. EMT6 Breast Cancer Model

Figure 12:
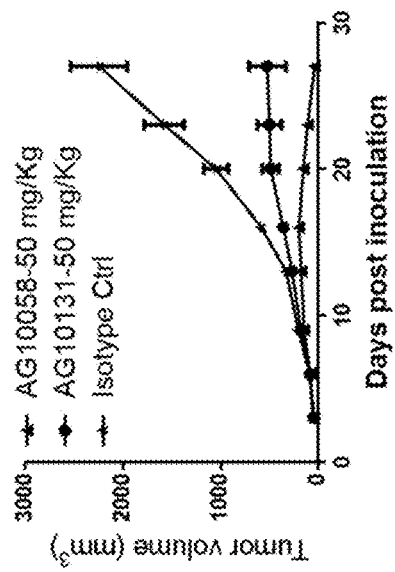
FIG. 12 shows anti-tumor efficacy of exemplary antibodies in EMT6 mouse breast cancer model.

Anti-tumor activity is further evaluated in EMT6 mouse breast cancer syngeneic model (Shi and Siemann, Augmented antitumor effects of radiation therapy by 4-1BB antibody (BMS-469492) treatment. Anticancer Res. 2006; 26:3445-53) (FIG. 12). Both AG10058 and AG10131 exhibited almost ~100% tumor growth inhibition.

Figure 13:
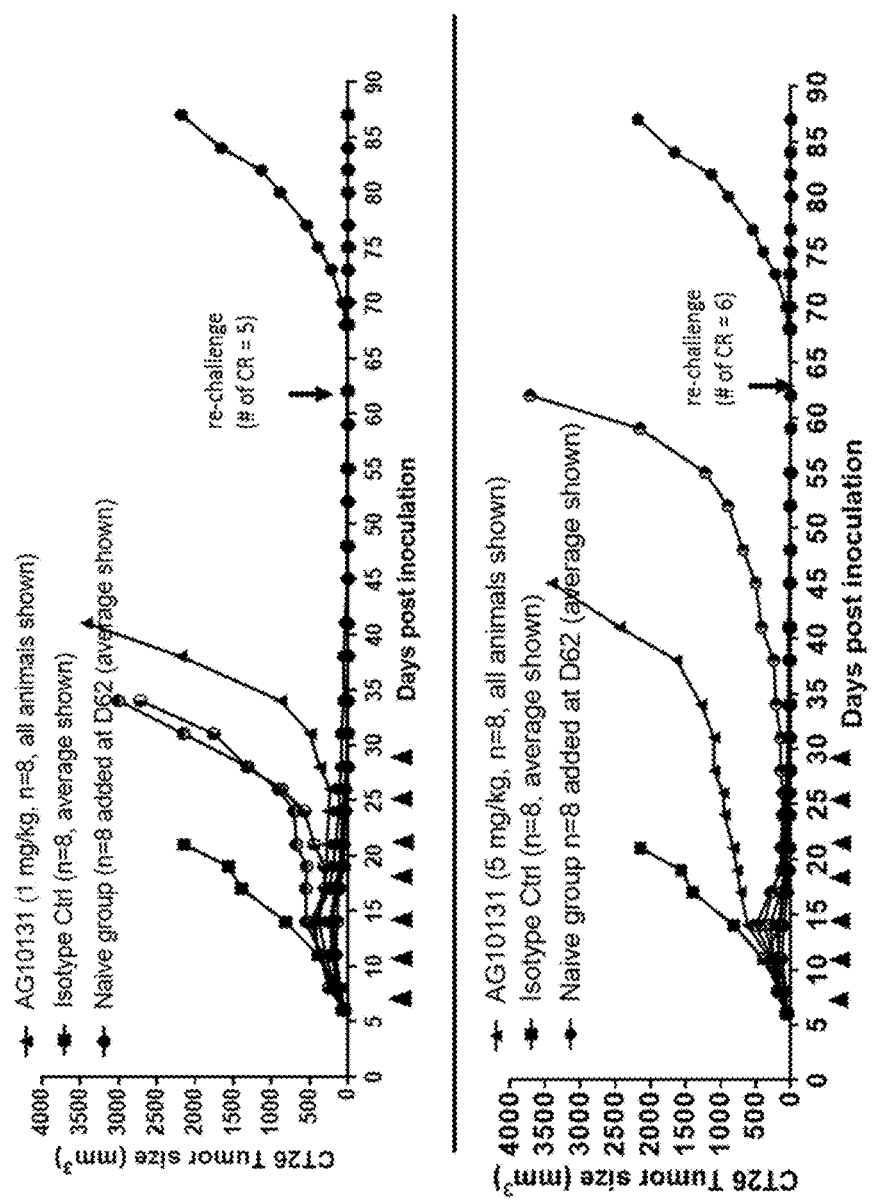
FIG. 13 shows CT26 mice treated with exemplary antibodies maintained tumor free after re-challenging with the same tumor cells.

10d Mice with Complete Response to CD137 Agonist Antibody Treatment Maintain Tumor Free after Re-Challenge with New Tumor Cells After treatment with AG10058 or AG10131 for 3 weeks in the CT26 tumor model, the mice with complete tumor regression were maintained without treatment for over an additional month. Mice that maintained complete response were then re-challenged on Day 62 subcutaneously with $5\times10^5$ CT26 tumor cells in the opposite flank, and monitored for tumor growth. Re-challenge control group was set up at the same time with naïve mice inoculated with the same number of CT26 tumor cells. As shown in FIG. 13, treatment with AG10131 (at 1 and 5 mg/kg, see FIG. 13, top and bottom panel, respectively) exhibited potent antitumor activity in CT26 tumor model, 5/8 in AG10131 (1 mg/kg group), 6/8 in AG10131 (5 mg/kg group) showing complete response over 60 days before re-challenged with CT26 tumor cells again. Furthermore, these mice remained tumor free after re-challenge with the same tumor cells, suggesting that specific anti-tumor memory was developed in these mice.

Figure 14:
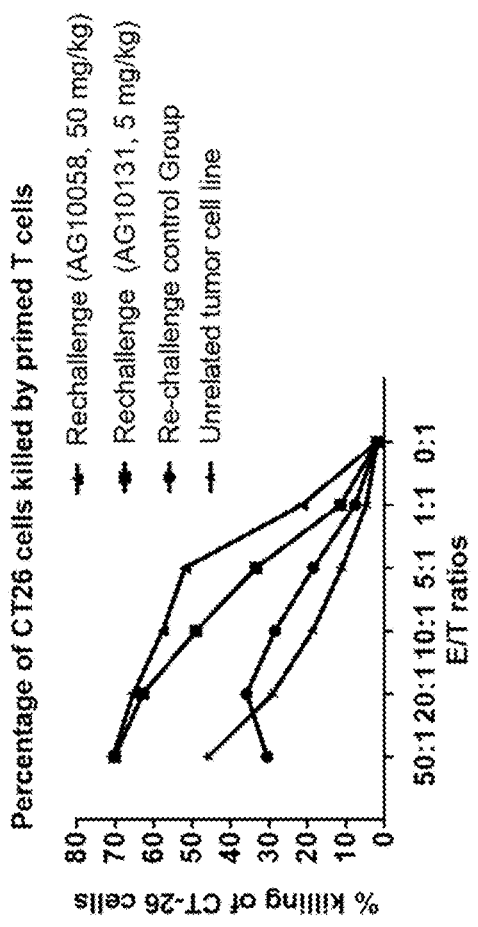
FIG. 14 shows tumor cell killing with splenocytes from tumor-rejecting re-challenged mice.

To prove this hypothesis, splenocytes were collected from these tumor-rejecting re-challenged mice and control mice and co-cultivated with the mitomycin C-arrested CT26 tumor cells in vitro for 7 days to amplify the tumor-specific memory T cells. These splenocytes were then recovered and mixed with fluorescence labeled live CT26 tumor cells at different E/T ratio for 4h and tumor cell killing was detected by the live/dead staining and FACS analysis. As shown in FIG. 14, significantly increased tumor cell killing was observed with splenocytes from tumor-rejecting re-challenged mice with prior treatment of both AG10058 and AG10131.

Example 11

AG10131-IgG4 does not Induce ADCC Effect

Figure 15:
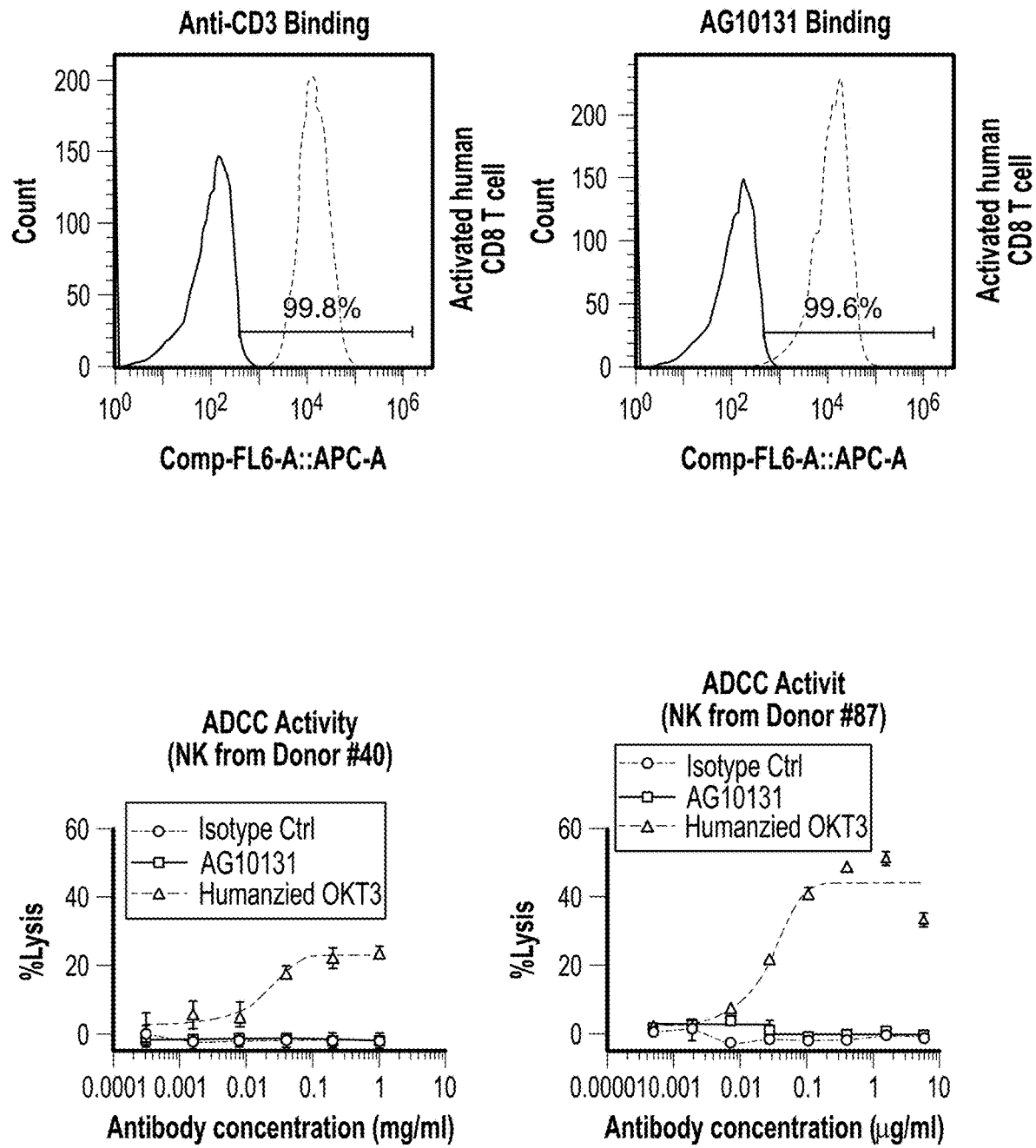
FIG. 15 shows that AG10131 does not show ADCC effects.

Human CD8+ T cells were isolated from peripheral blood from a healthy donor with the EasySep human CD8+ T cell enrichment kit (StemCell Technologies), and then stimulated with PMA (50 ng/ml)+Ionomycin (1 uM) for 18 hours in vitro. These activated CD8+ T cells were then labeled with Calcein-AM and served as the target cells. NK cells from different healthy donors were isolated with the human NK isolation kit (StemCell Technologies), and served as effector cells. For the antibody-dependent cytotoxicity (ADCC) assay, effector (NK) and target (activated CD8+ T) cells were mixed at 5:1 ratio in a 96-well plate in the absence and presence of serially diluted antibodies for 4 hours under culture condition. Supernatant from each well was then collected, and fluorescence signal was detected by plate-reader SpectraMax i3× (Ex 488 nm, Em 520 nm). An isotype hIgG4 mAb was used as a negative control, whereas the humanized OKT3 (an anti-CD3 hIgG1 from Novoprotein) was used as a positive control. The % lysis was then calculated using the following formula: % Lysis=[(Experimental Release)−Ave (Target+ NK)]/[Ave (Target Max)−Ave (Target only)]×100% (FIG. 15).

Example 12

Developability Profile of Antibodies

For developability assessment, purified AG10058, AG10059, AG10131 and AC1097 were exchanged into PB buffer (20 mM PB, 150 mM NaCl, pH 7.0). All experiments, including filtration, concentration, accelerated stress tests, were performed in PB buffer. For all the SEC-HPLC analyses, the TSKgel columns (Tosoh Bioscience G3000SWx1) were used.

12a. Solubility

Figure 16:
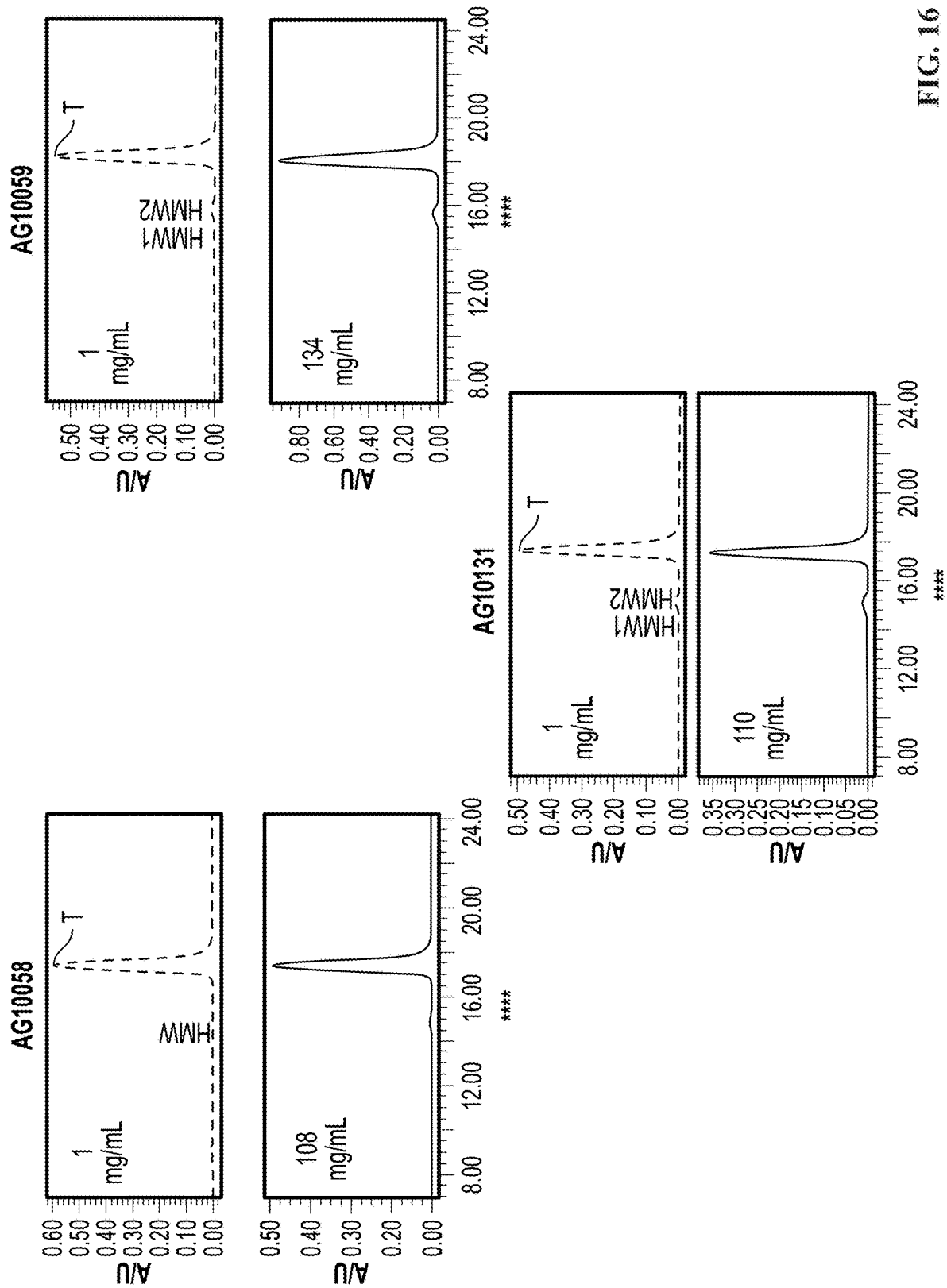
FIG. 16 shows exemplary antibodies displayed little aggregation at high concentration.

All three antibodies can be concentrated to higher than 100 mg/ml in PB buffer without obvious precipitation (Table 6). Antibodies then were adjusted to 20 mg/ml in PB buffer. Samples (10 μg each) were then assayed through SEC-HPLC for detection of high molecular weight (HMW) aggregate. As shown in the chromatograms (FIG. 16), no increase of HMW aggregate was observed at high concentration (20 mg/ml) for all test antibodies.

TABLE 6

Solubility of antibodies

| Sample | Concentration/(mg/mL) | Aggregation (HMW %) |
|---|---|---|
| AG10058 | 108 | 1.0 |
| AG10059 | 134 | 1.4 |
| AG10131 | 110 | 2.0 |

12b. Antibody Stability Under Accelerated Stress Conditions

Figure 17:
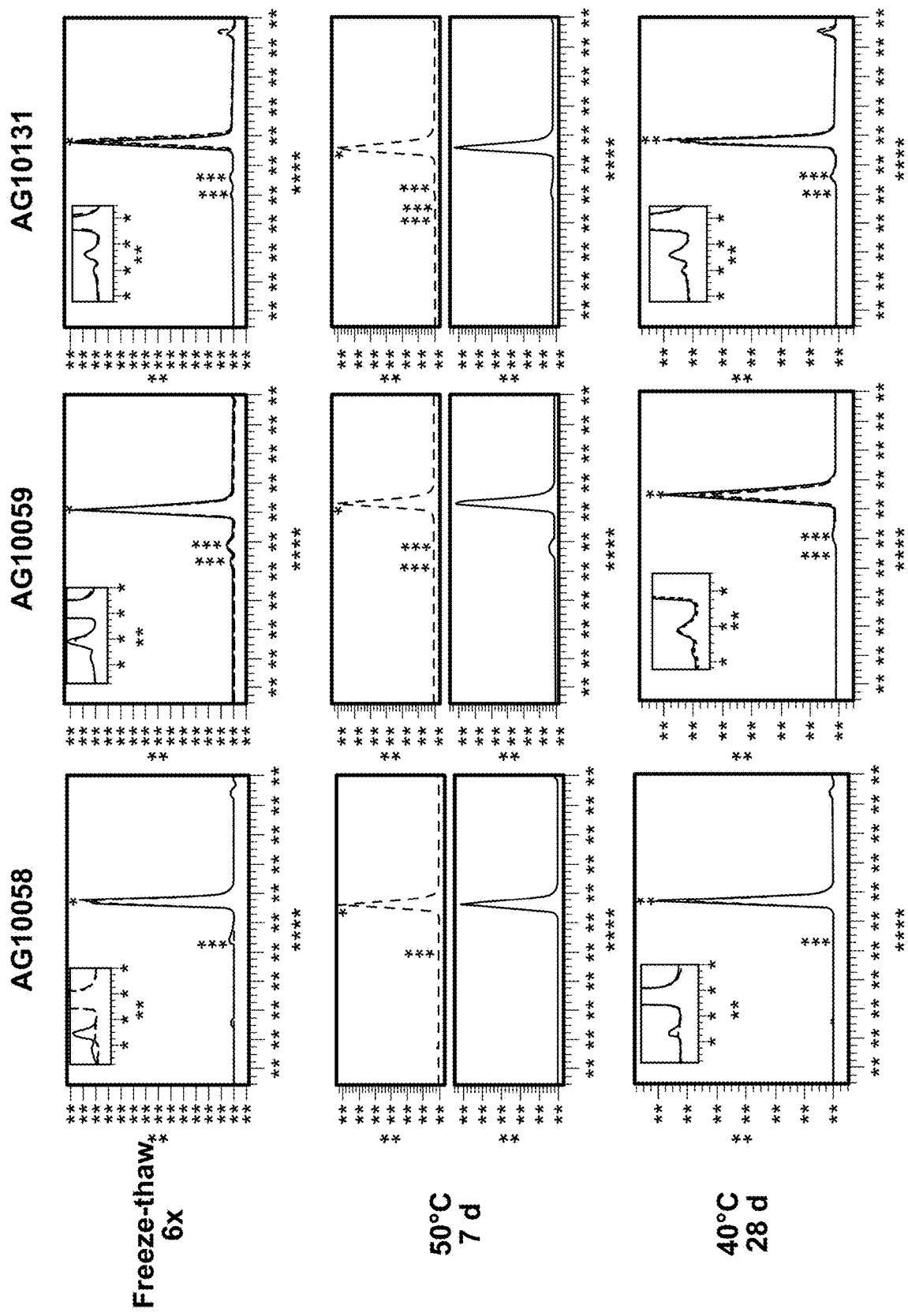
FIG. 17 shows stability of exemplary antibodies under accelerated stress conditions.

Antibody stabilities were also examined under accelerated stress conditions, result is summarized in Table 7. All antibodies remain stable after six cycles of freezing (−80° C.) and thawing (Room temperature) (FIG. 17). After seven days at 50° C., there was little change of HMW aggregate or LMW fragments (FIG. 17). In longer-term time course experiments (40° C. for up to 28 days), all antibodies remain stable, and there were no significant increase of HMW aggregate or LMW fragments (FIG. 17).

TABLE 7

Changes of HMW under accelerated conditions

| | AG10058 | AG10059 | AG10131 |
|---|---|---|---|
| Freeze-thaw 6X | 4.6% | 1.2% | 0.4% |
| 50° C. 7 d | 0.7% | 1.2% | 0% |
| 40° C. 28 d | 0.9% | 0% | 0% |

Figure 18:
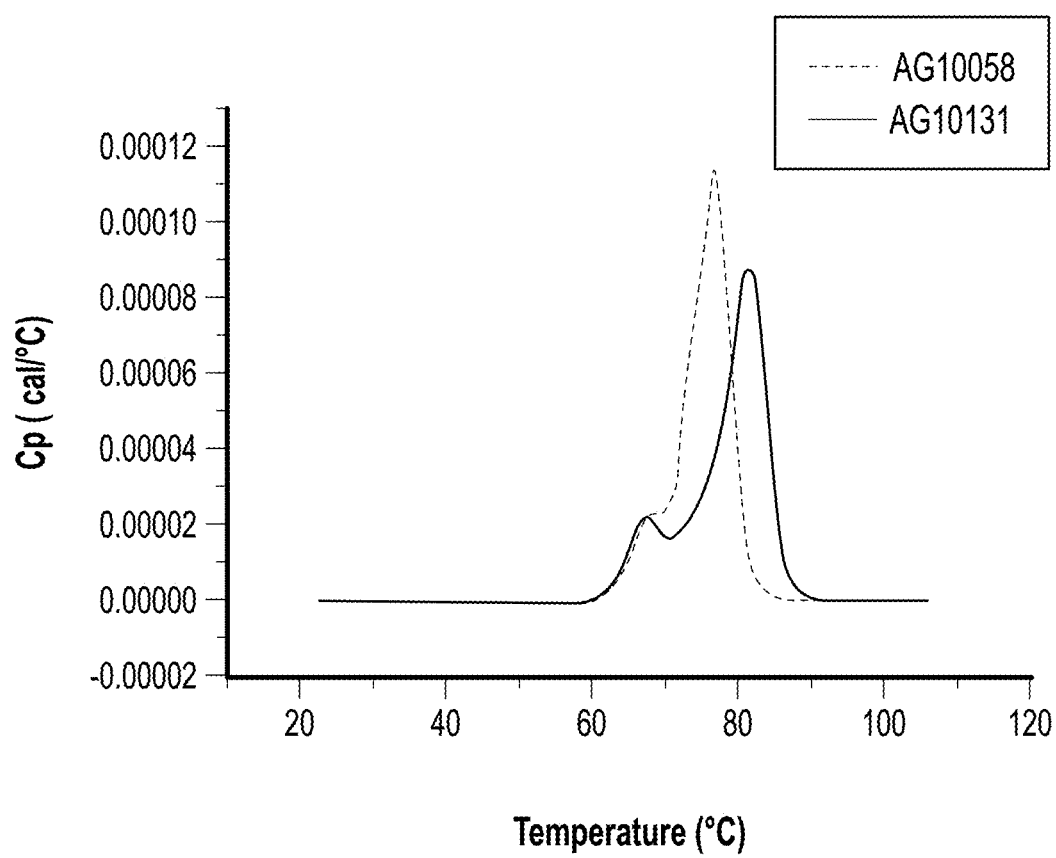
FIG. 18 shows thermostability.

Furthermore, thermostability as measured by differential scanning cALorimetry (DSC) shows that both AG10131 and AG10058 are stable up to at least about 59° C. The transition midpoint, Tm (the characteristic temperature at which the unfolding transition for almost all protein domains occur) is shown in FIG. 18 and Table 8 below.

TABLE 8

Thermostability by DSC

| | Tm onset (° C.) | Tm1 (° C.) | Tm2 (° C.) |
|---|---|---|---|
| AG10058 | 61.5 | 67.3 | 76.9 |
| AG10131 | 59.3 | 67.6 | 81.5 |

In addition, the highest achievable concentration of AG10131 and AG10058 after centrifugation was over 180 mg/mL and over 220 mg/mL, respectively.

Example 13

Safety Profile in Relevant Species: Mouse and Cynomolgus Monkey

13a. Repeated Dosing Toxicity Studies of AG10131 in Normal C57BL/6 Mice.

Repeated dosing toxicity of AG10131 was conducted in normal C57BL/6 mice. Vehicle, AG10131 (100 mg/kg) was administered i.p. (10 mL/kg) on Day1, Day4, Day8, and Day11. Five female mice (7-8 weeks old) were included in each group. Mice were monitored daily for abnormal behaviors and symptoms, and measured daily for food intake and body weight. On day14, animals were euthanized for post-mortem examination and other analysis. Blood was collected from each animal, with 2 blood samples per group used for hematology (RBC, platelet, WBC, WBC differential) and the other 3 blood samples in the group for blood biochemistry (AL, AST, ALB, GLB, A/G, TBIL, ALP, GGT, and LDH) analysis. The following organs from each mouse were collected and preserved in FFPE: Heart, lung, thymus, liver, spleen, and kidneys. FFPE blocks for liver tissues were prepared, sectioned and H&E stained for histopathology analysis.

Figure 19:
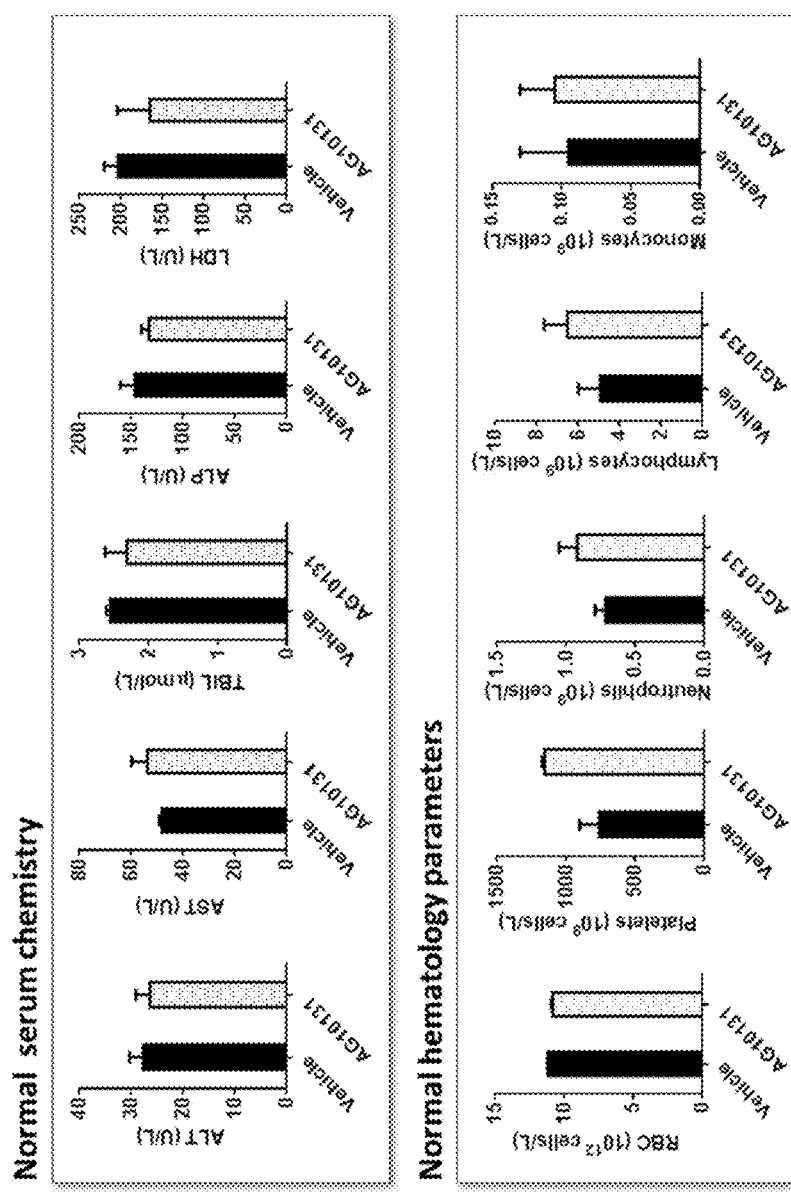
FIG. 19 shows that AG10131 has no hematological toxicity in normal mice up to 100 mg/kg bi-weekly (BIW)×2.
Figure 20:
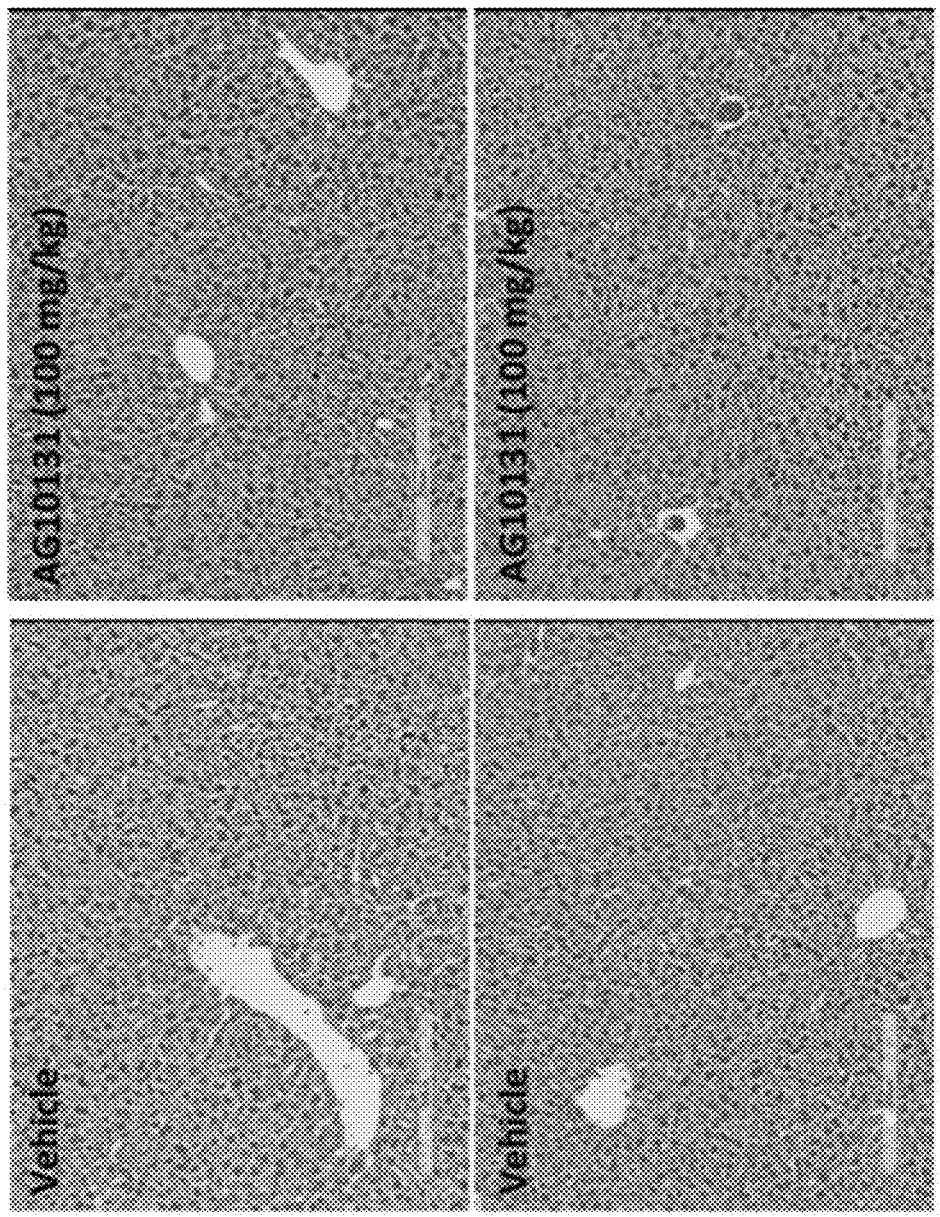
FIG. 20 shows that AG10131 has no histological liver abnormality in normal mice up to 100 mg/kg bi-weekly (BIW)×2.

During the in-life period of the whole study, there was no abnormal behavior observed or un-scheduled animal death. Compared to the vehicle treatment, AG10131 did not affect the food intake and body weight. Post-mortem examination also did not show any obvious lesions in mice of the treatment groups with both AG10131. Hematology analysis did not show any significant changes, so as to the blood biochemistry parameters tested in mice treated with AG10131 (FIG. 19). No obvious abnormalities were found in the histopathology sections of the liver from all these mice (FIG. 20). Overall, AG10131 was well tolerated in this study and no significant toxicity was observed in mice.

13b. Repeated Dosing Studies of AG10131 in Cynomolgus Monkeys

Repeated dosing study of AG10131 was conducted in normal cynomolgus monkeys. Human IgG4 Isotype control (10 mg/kg), AG10131 (0.5 and 10 mg/kg) was administered i.v. (1 mL/kg) on Day0, Day7, Day14, and Day22. One male and one female cynomolgus monkeys (3-5 years old) were included in each group. Animals were monitored daily for abnormal behaviors and clinical signs, and measured daily for food intake. Body weight was measured on predose Day (−15), Day (−5), and postdose Day6, Day13, Day18 and Day26. Hematology and blood chemistry parameters were measured on predose Day (−12), Day (−5), and postdose Day7, Day14, Day19, and Day27 (10 mg/kg group only), urinalysis was conducted on predose Day (−12), Day (−5), and postdose Day6, Day13, Day18. Animals in the 10 mg/kg groups were euthanized for post-mortem examination and other analysis on Day27. Major organs were dissected and weighed. FFPE liver tissue blocks were prepared, sectioned and H&E stained for histopathology analysis.

Figure 21:
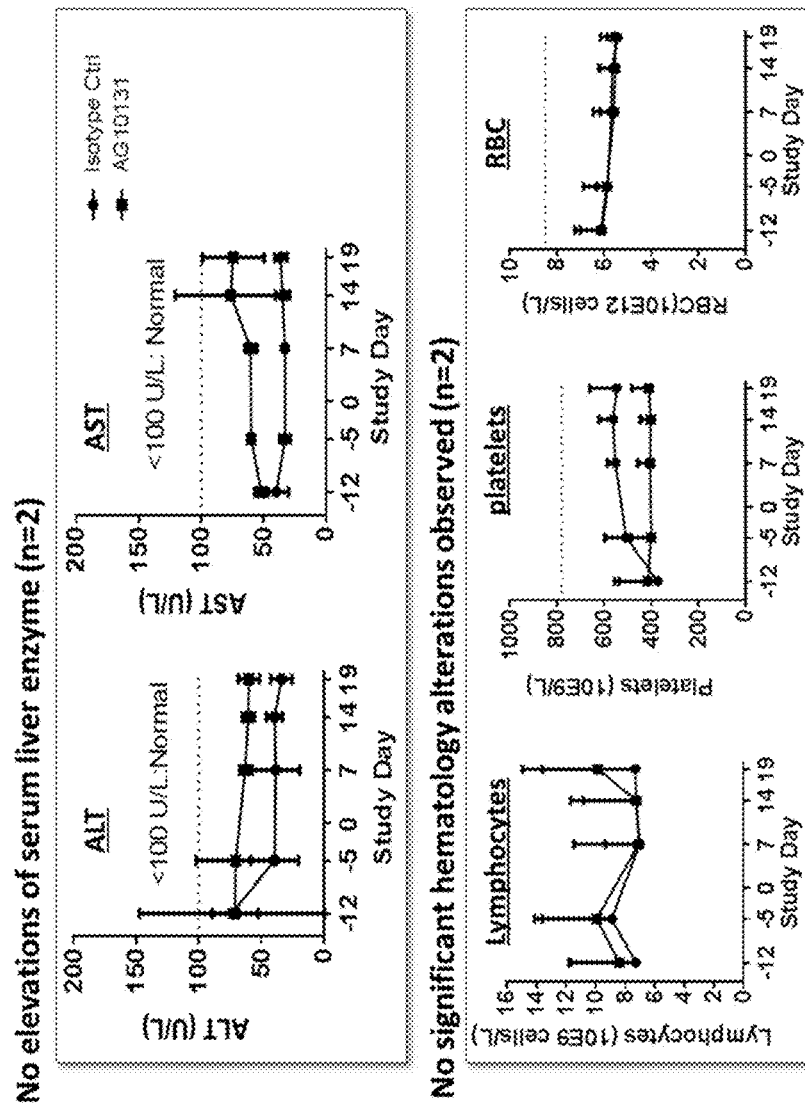
FIG. 21 shows that AG10131 has no hematological toxicity in cynomolgus monkeys at 10 mg/kg/week×4.
Figure 22:
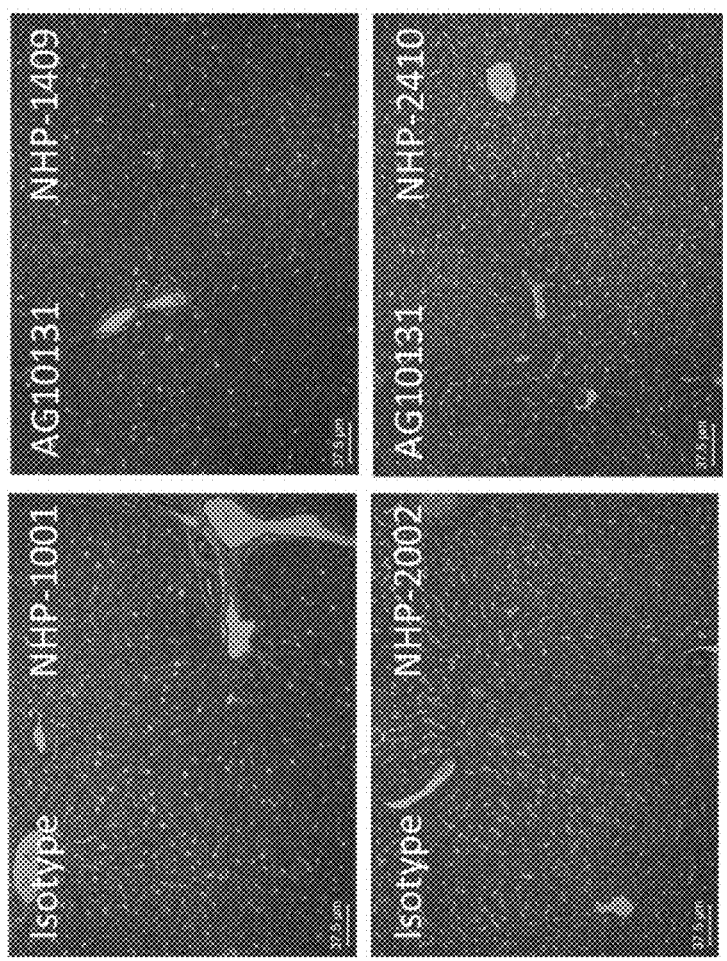
FIG. 22 shows that AG10131 has no liver toxicity in monkey at 10 mg/kg/week×4.

During the in-life period of the whole study, there was no abnormal behavior observed or un-scheduled animal death in all groups. Compared to the vehicle treatment, AG10131 treatment at 10 mg/kg did not affect the food intake and body weight. No clinical signs were noted including injection site reactions as well. Post-mortem examinations did not show any obvious lesions and weight abnormalities in all organs examined in cynomolgus monkeys treated with AG10131 at 10 mg/kg. Hematology, blood chemistry and urine parameters are also within normal ranges in all treatment groups (FIG. 21). Histopathology analysis of the liver did not show any obvious abnormalities including lymphocyte infiltration after repeated dosing of AG10131 at 10 mg/kg (FIG. 22). Overall, AG10131 was well tolerated at up to 10 mg/kg weekly doses in cynomolgus monkeys and no obvious toxicity was detected.

Example 14

Pharmacokinetics of AG10131 in Cynomolgus Monkey

14a. Pharmacokinetics of AG10131 in Cynomolgus Monkey

A pharmacokinetics study of AG10131 was conducted in naive cynomolgus monkeys. Three dose levels of AG10131 (10 mg/kg, 30 mg/kg and 100 mg/kg) were intravenous bolus administrated to three groups of monkeys. Each group contains 3 males and 3 females. Serum samples were collected pre-dose, 0.083, 0.25, 0.5, 1, 2, 6, 12, 24, 36, 48, 72, 96, 120, 144, 168, 240, 336, 408, 504, 672 and 840 hours post dosing. Serum concentrations of AG10131 were determined by ELISA.

Figure 23:
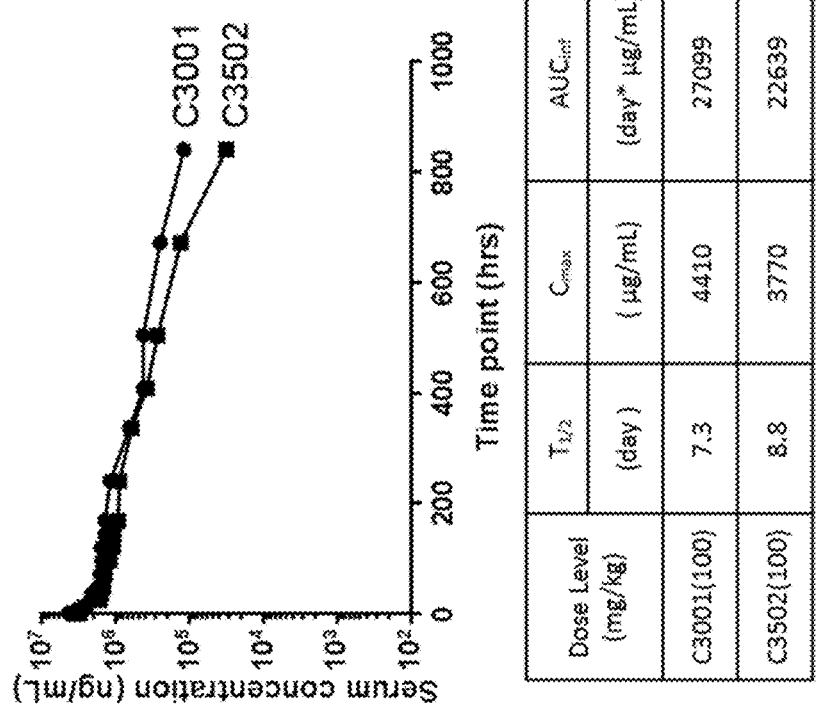
FIG. 23 shows the pharmacokinetics profiles of AG10131 in monkey.

AG10131 was rapidly cleared at day 14 (336 hrs) in 12 out of 16 animals, i.e., all animals from low and medium dose groups and 2 of 6 animals from high dose group. On day 21, 2 more animals from high dose group showed a rapid clearance. Serum concentrations in these 14 animals are low or below the limit of the quantification. This is consistent with the observation of anti-drug antibody generation in these animals. Data from the two animals with potentially unaffected pharmacokinetics from the high dose group were fitted to predict the pharmacokinetics parameters (FIG. 23). The half-life of AG10131 ranges from 7.3 to 8.8 days.

14b. Pharmacokinetics of AG10131 in Rat

A pharmacokinetics study of AG10131 was conducted in naïve SD rats. Three dose levels of AG10131 (10 mg/kg, 30 mg/kg and 100 mg/kg) were intravenous bolus administrated to three groups of animals. Each group contains 15 males and 15 females. Serum samples were collected from 3 animals each time point: pre-dose, 0.083, 0.25, 0.5, 1, 2, 6, 12, 24, 36, 48, 72, 96, 120, 144, 168, 240, 336, 408, 504, 672 and 840 hours post dosing. Serum concentrations of AG10131 were determined by ELISA and the data were analyzed by Phoenix Professional V6.3.

Figure 24:
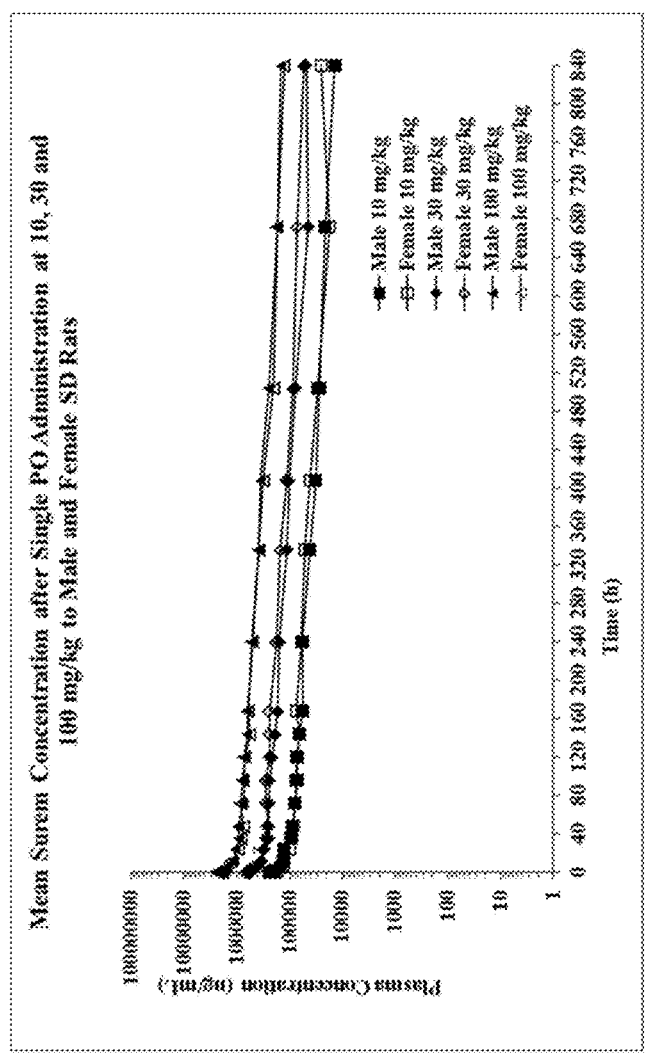
FIG. 24 shows the pharmacokinetics profiles of AG10131 in rat.

Results: The PK parameters from low, mid and high doses are similar (FIG. 24). The clearance rate of AG10131 is about 0.004 ml/kg/min. The half-life of AG10131 ranges from 11.5 to 14.6 days.

14c. Pharmacokinetics of AG10131 in Mouse

A pharmacokinetics study of AG10131 was conducted in BALB/c mice at about 8-week age. 3 female BALB/c mice per dosing group were intravenously injected the test antibodies including AG10131 at 1 mg/kg through the tail vein. Blood samples (~100 µl per sample) were collected at 1h, 8, 48, 168, and 336 hours post dosing. Blank control blood was collected from 3 naive female mice without antibody administration. Serum concentrations of each test antibody including AG10131 were determined by ELISA, in which the anti-human IgG (Fc specific) antibody was used for capture and the HRP-labeled anti-human IgG (Fab specific) antibody for detection.

Figure 25:
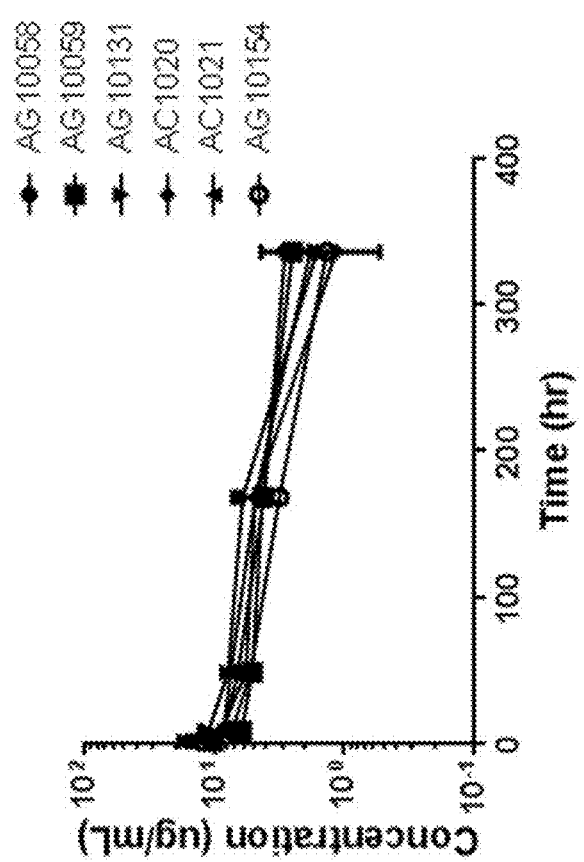
FIG. 25 shows the pharmacokinetics profiles of various antibodies in mouse.

All test antibodies including the isotype control (AG10154), two benchmark antibodies (AC1020 and AC1021), and three Adagene antibodies (AG10131, AG10058, and AG10059) exhibit comparable pharmacokinetics in mice (FIG. 25).

Example 15

Further Epitope Mapping

Figure 27:
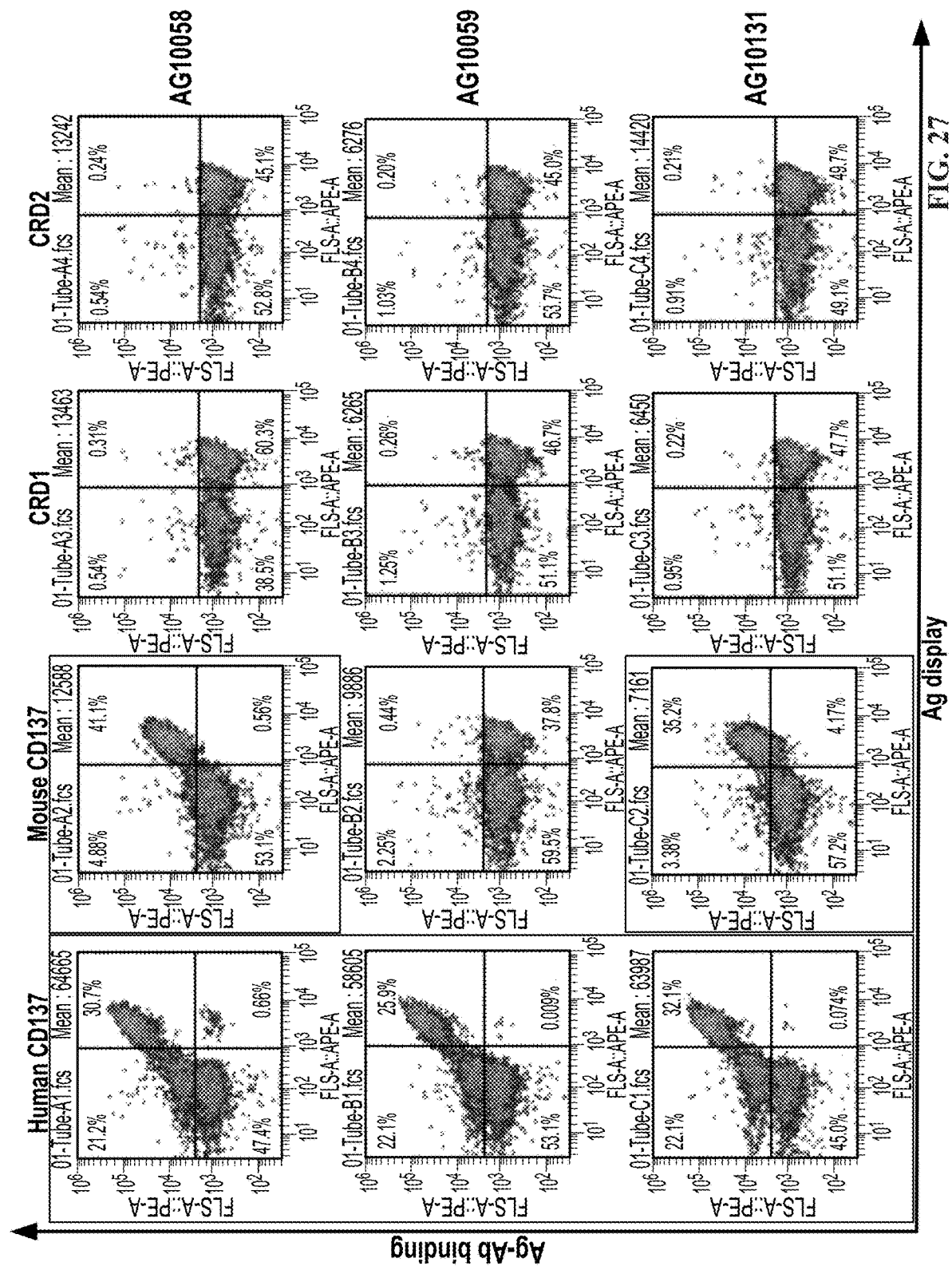
FIG. 27 shows the epitope mapping of the indicated anti-CD137 antibody binding to the indicated human CD137 CRDs by flow cytometry.
Figure 27:
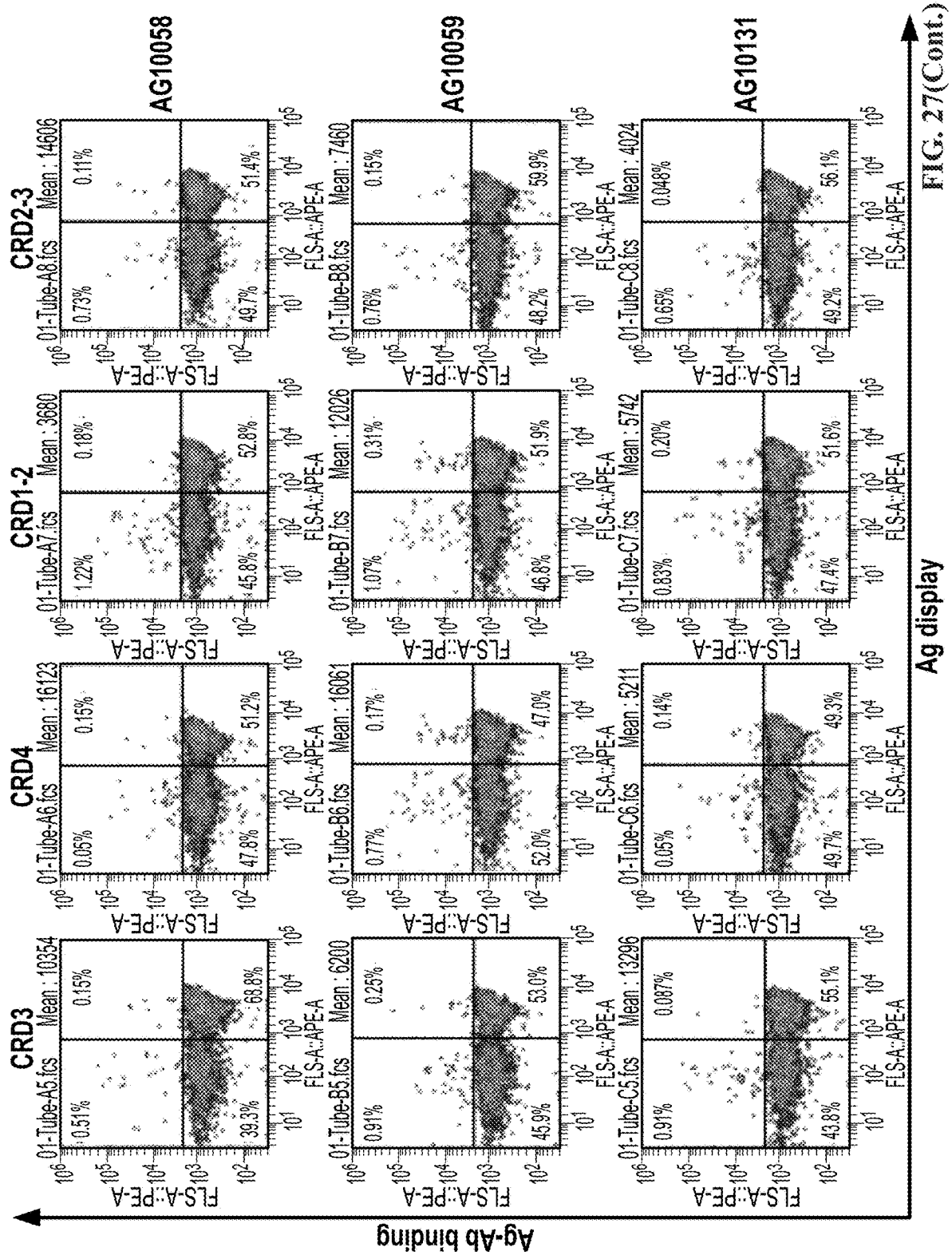
Figure 27:
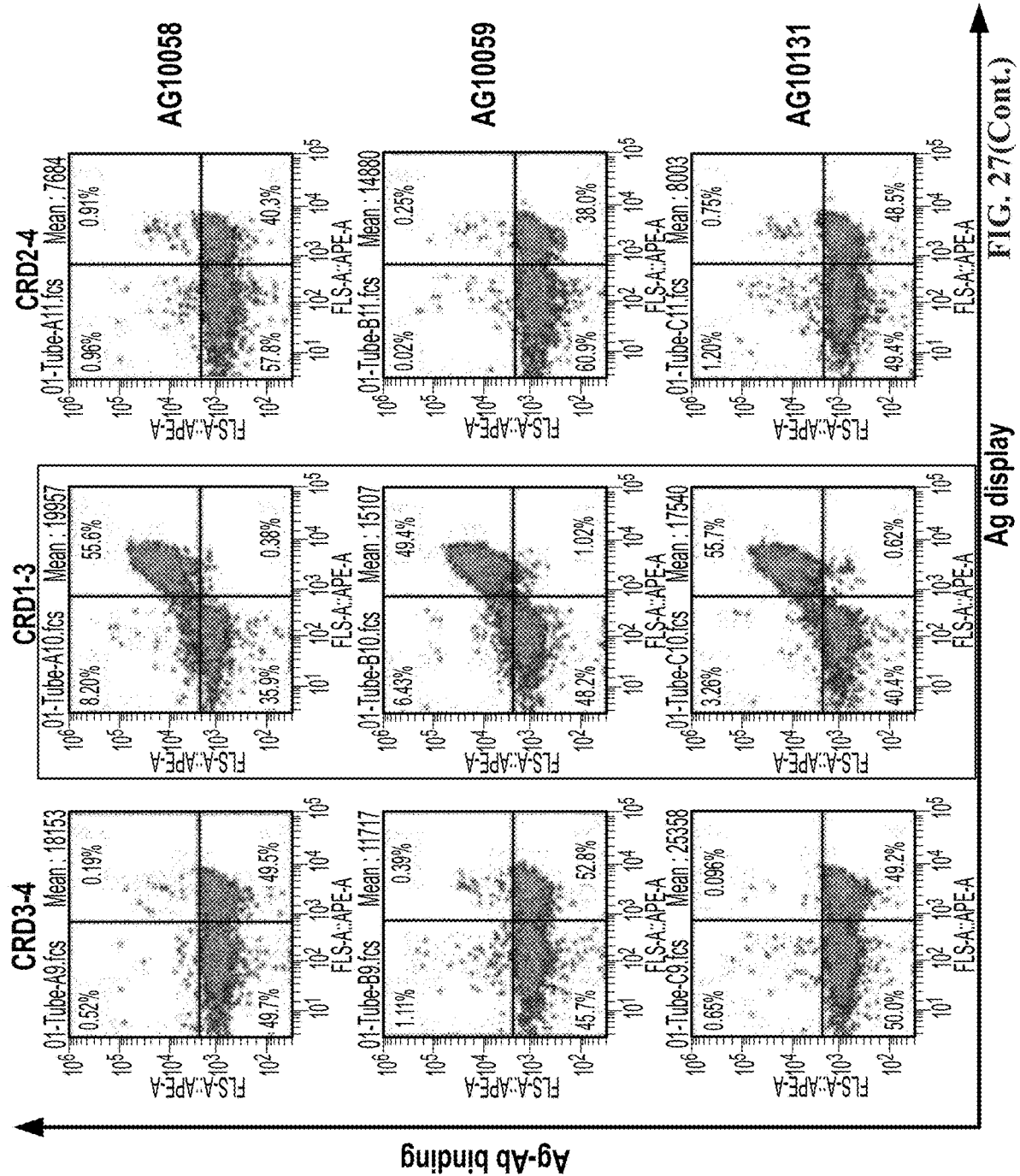
Figure 27:
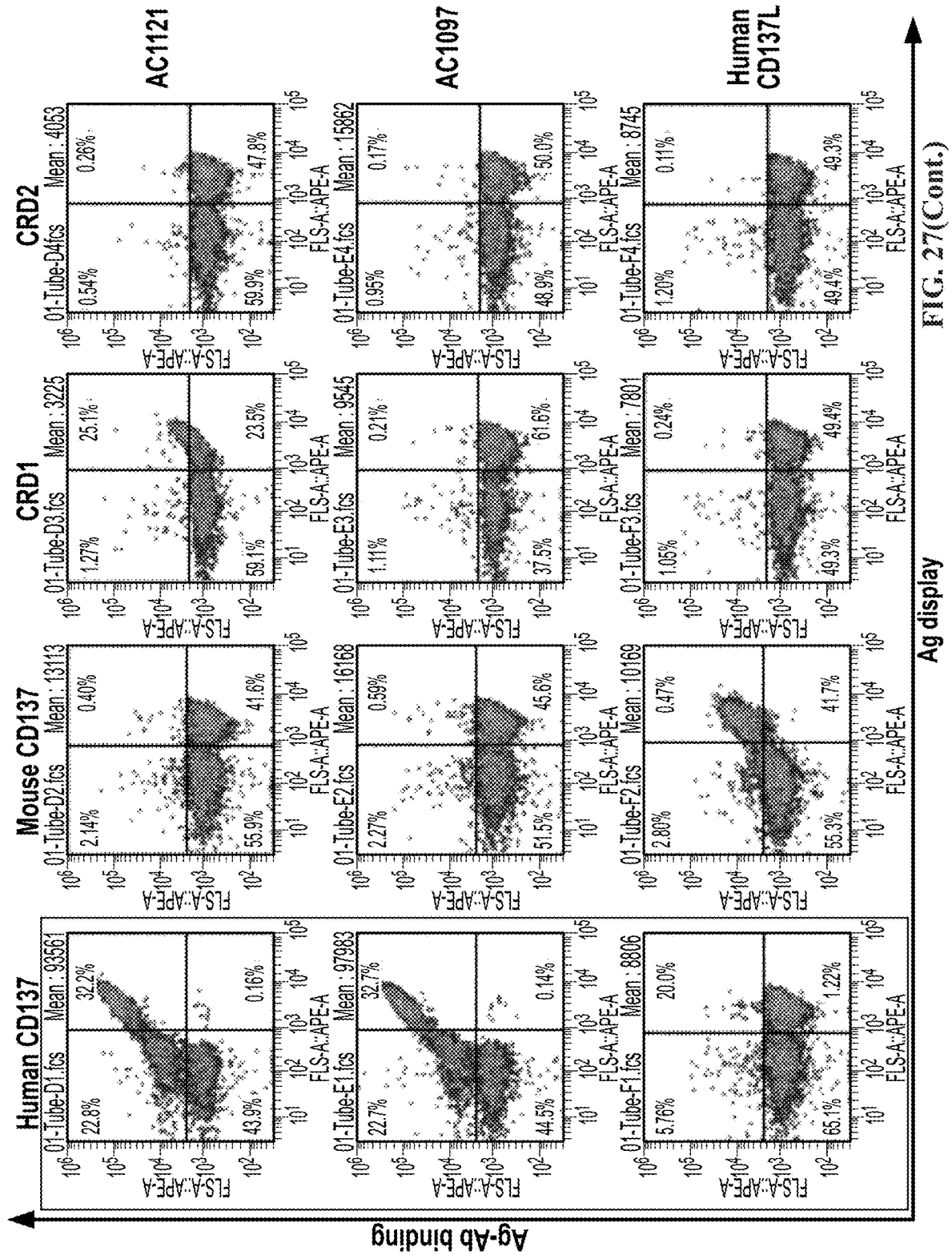
Figure 27:
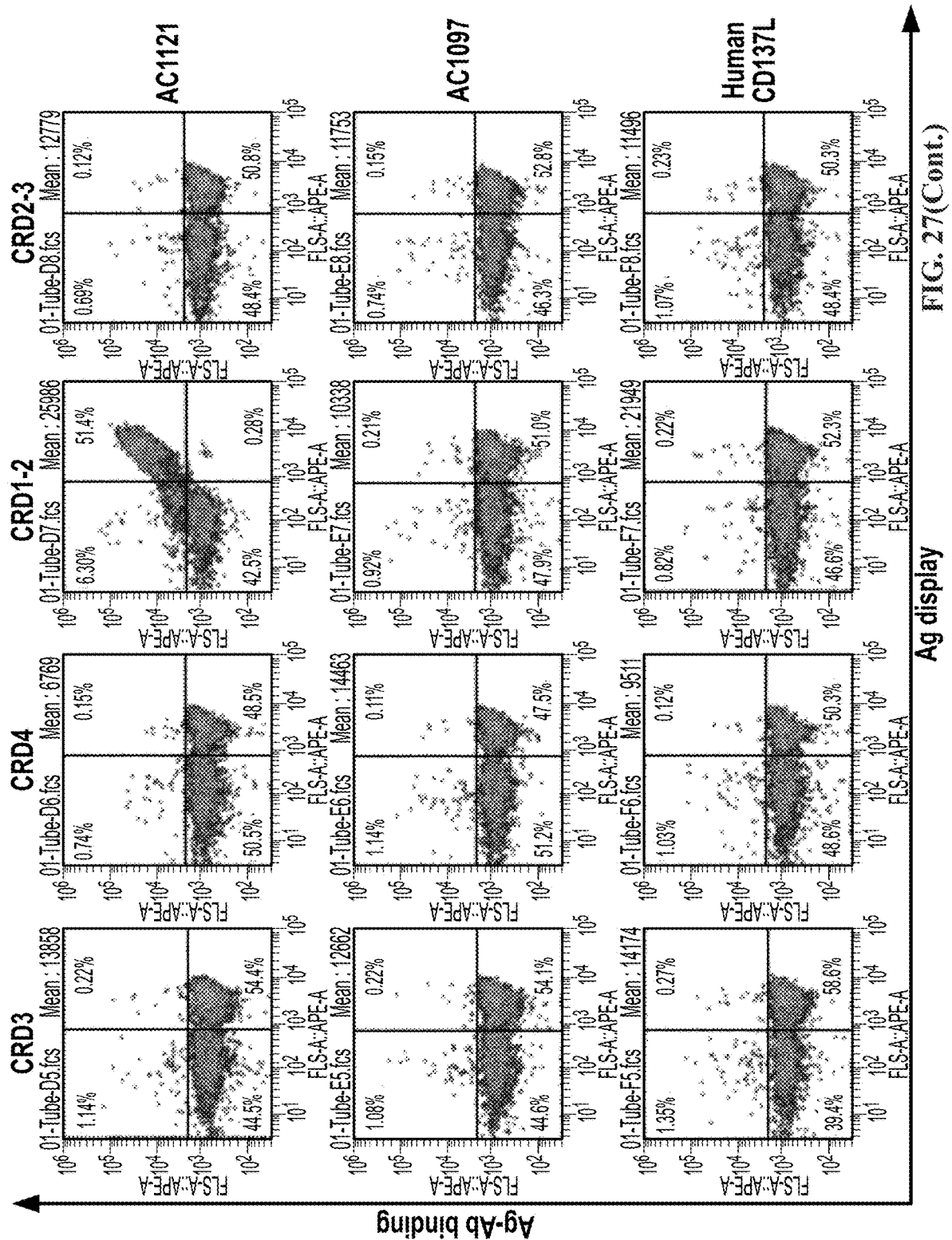
Figure 27:
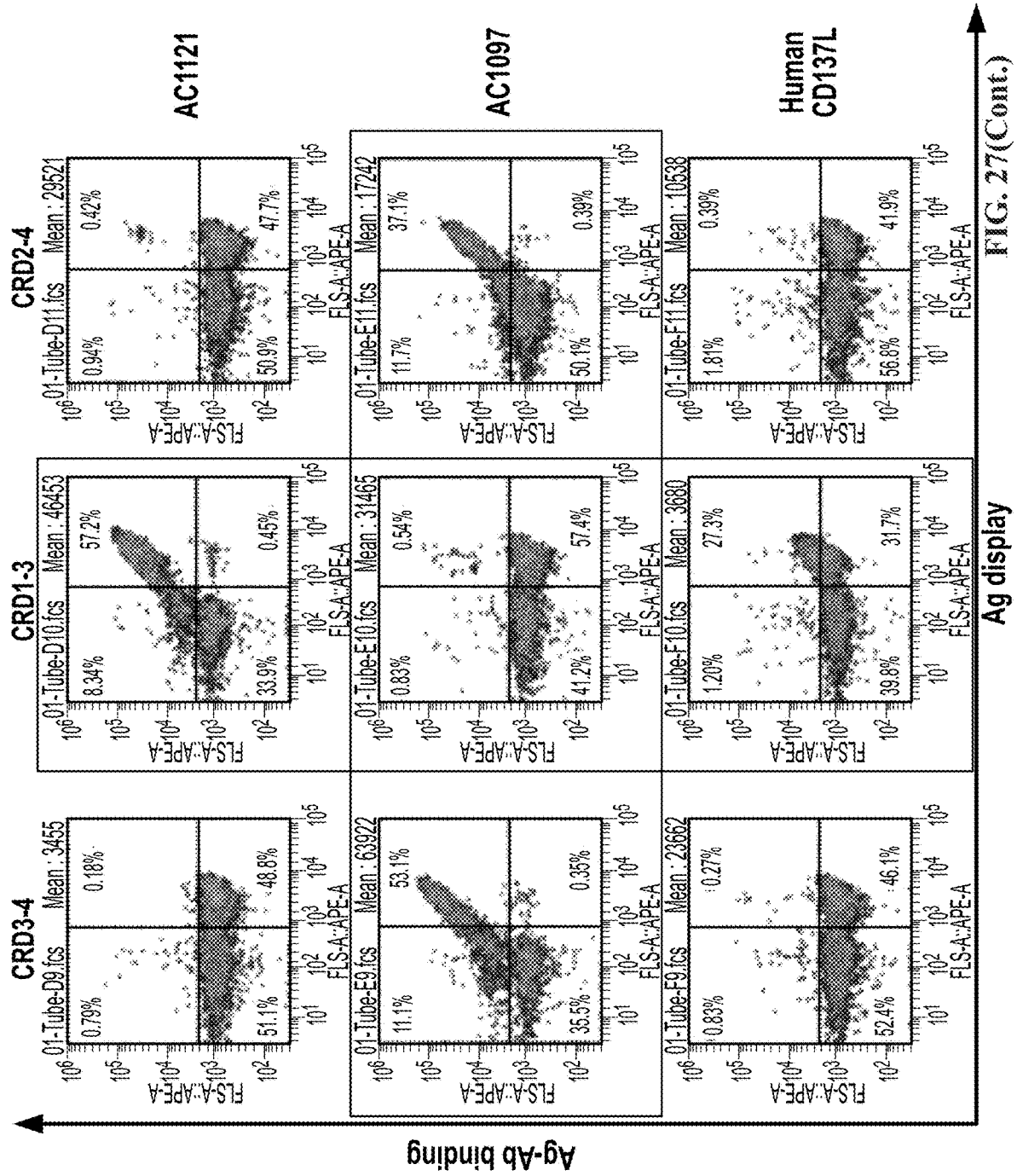
Figure 27:
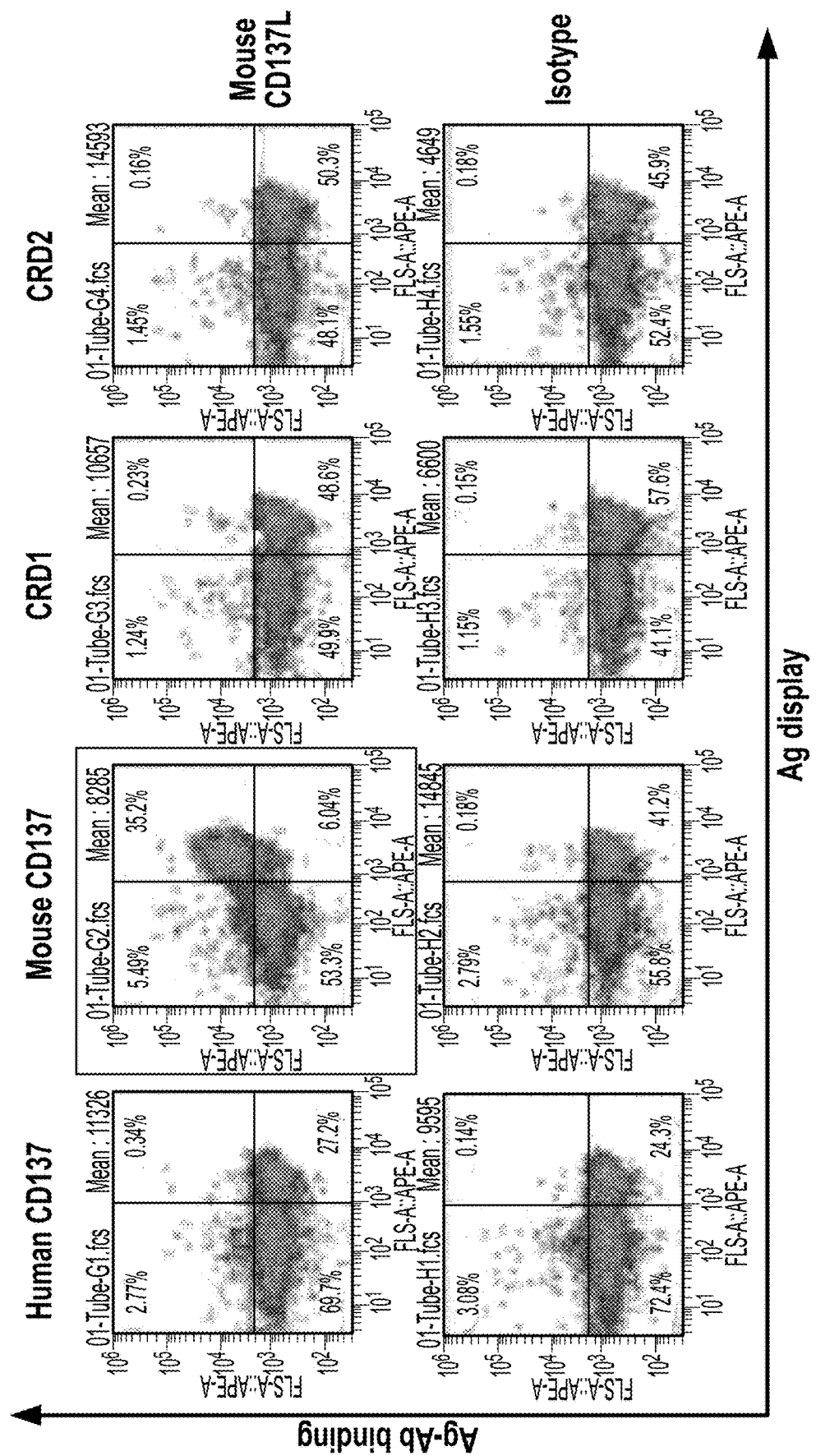
Figure 27:
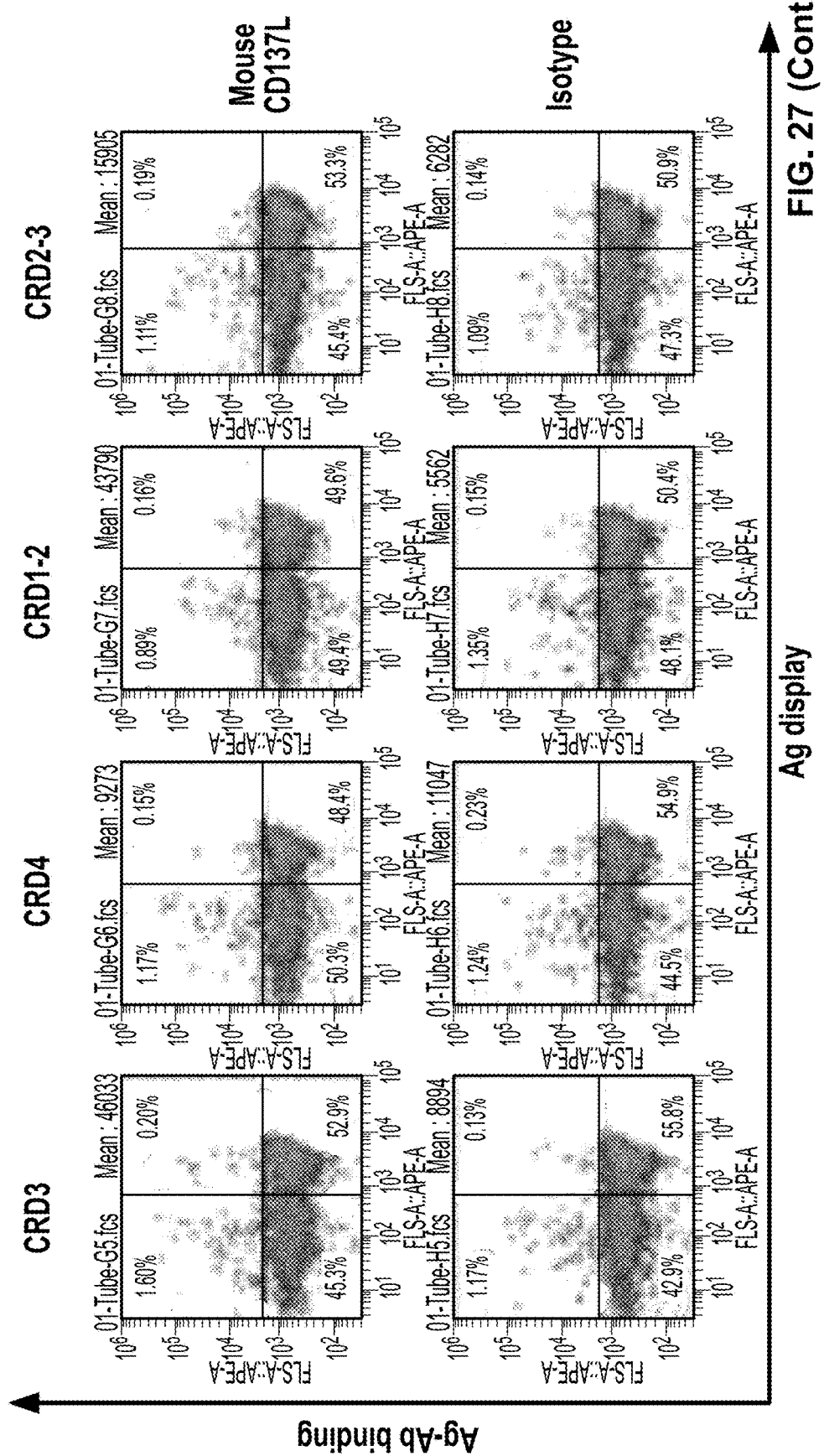
Figure 27:
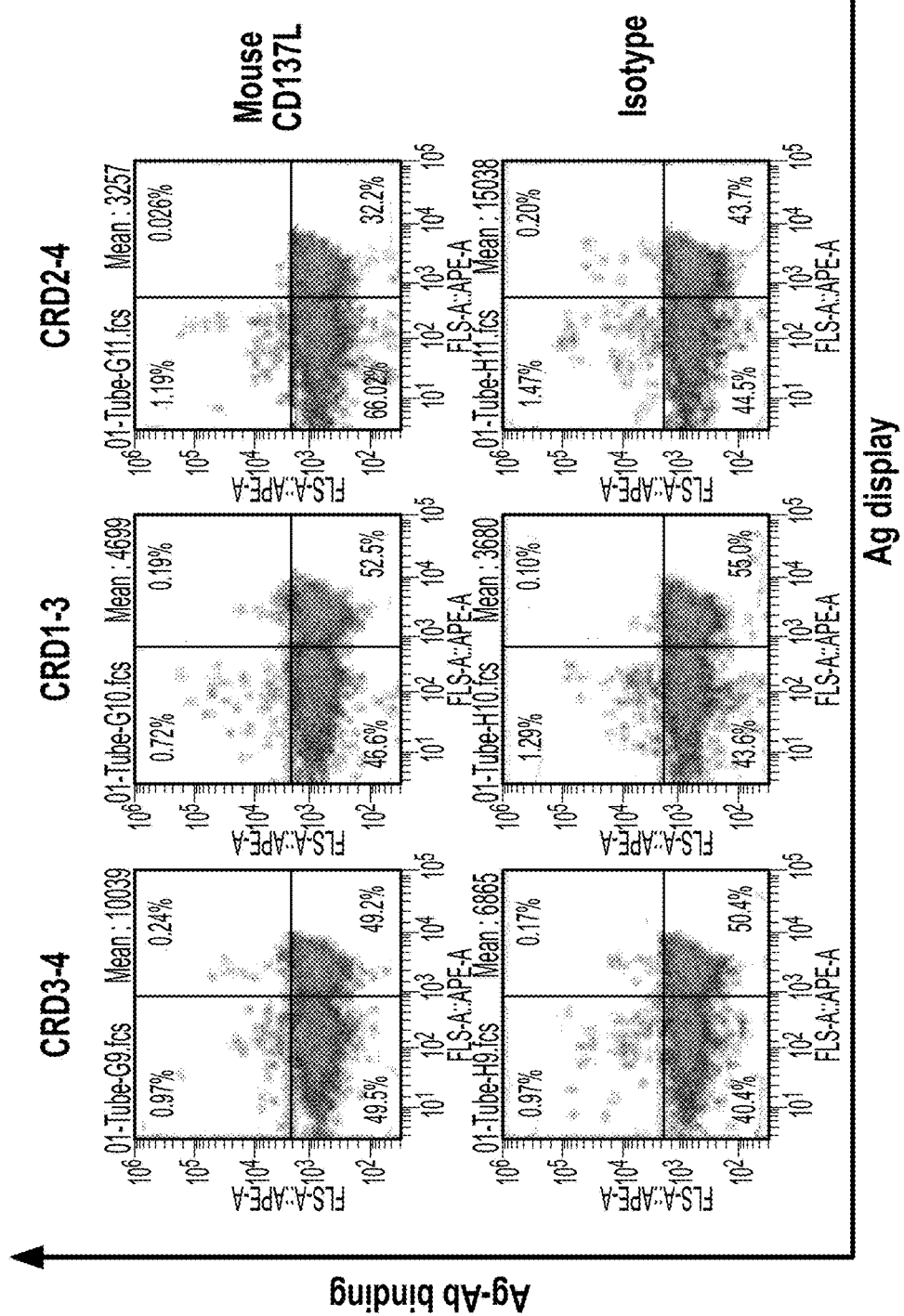

To determine the binding epitope of the antibodies shown herein by Adagene and other reference antibodies, we have taken a systematic approach to dissecting the epitopes by three levels of resolution: domain, motif, and residues. The extra cellular domain of CD137 containing 4 CRD motifs and CD137 from 4 different species such as human, monkey, mouse, and rat CD137 were used (Table 9). A series of human CD137 CRD motif (cysteine rich domain) and their constructs containing one, two, and three units of human CRD motifs (Table 9) were displayed. A low copy number, CEN/ARS-based vector was used to express the human CD137 CRDs under the control of the inducible GAL1-10 promoter in the yeast *S. cerevisiae* (Boder and Wittrup (1997) Nat Biotechnol 15(6):553-7). The binding of antibodies to the human CD137 CRDs were assessed by flow cytometry analysis and other technology as previously described in Example 5 and shown in FIG. 27.

The results are summarized in Table 9, these antibodies only bind selectively to CD137 target, but none of the non-CD137 targets listed in the table; however, their species-specific cross-reactivity by these antibodies with CD137 from human, monkey, mouse, and rat species are striking, highlighting the fine epitope coverage by diverse hits screened from Adagene Dynamic Precision Libraries. For example, AG10131 binds to CD137 from human, monkey, mouse, rat, and dog (not shown); AG10058 binds human, monkey, mouse CD137, but not rat CD137; whereas AG10059 binds both human and monkey CD137. In contrast, the reference antibody AC1121 from transgenic mouse only binds to human CD137; whereas another reference antibody by morphosys phage library binds to both human and monkey CD137. For comparison, it should be noted that the human ligand CD137L only interacts with human CD137 receptor, not mouse CD137, and mouse CD137L only interact with mouse CD137 not human CD137 (see table 9).

TABLE 9

|  | AG10058 | AG10059 | AG10131 | AC1121 | AC1097 | Human CD137L | Mouse CD137L |
|---|---|---|---|---|---|---|---|
| Human_WT | + | + | + | + | + | + | − |
| Mouse_WT | + | − | + | − | − | − | + |
| Cyno_WT | + | + | + | − | + |  | NA |
| Rat_WT | − | − | + | − | − |  | NA |

Figure 26:
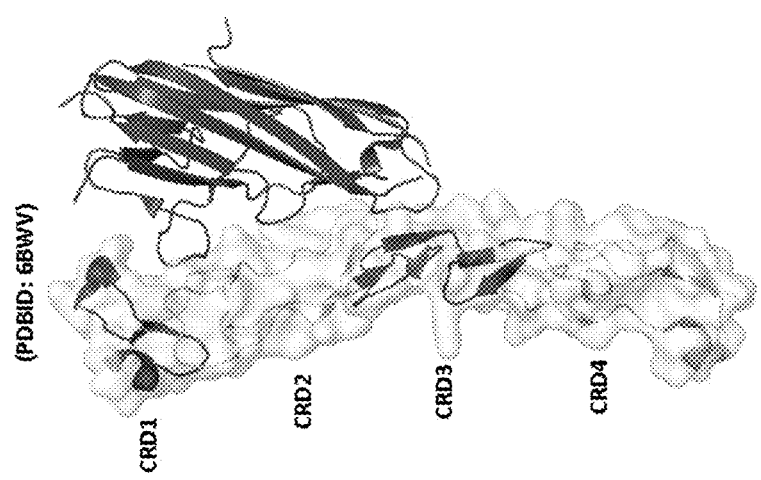
FIG. 26 shows a crystal structure of the human CD137-CD137L complex with the CD137 cysteine rich domains (CRDs) indicated.

To further dissect the binding motifs of these antibodies to human CD137 target as summarized in Table 9, distinguished binding sites by Adagene, other reference antibodies, in comparison with CD137 ligand binding with the dissected CD137 CRD motifs and their combination are well separated and noted: AG10058, AG10059 and AG10131 antibodies and human CD137 ligand does not bind to the single CRD or two CRD units (CRD2-CRD3) of human CD137. AG10058, AG10059, and AG10131 antibodies, similar to the human CD137 ligand, can bind to three CRD units (CRD1-CRD2-CRD3) of human CD137. Although the reference antibody AC1121 can also bind to three CRD units (CRD1-CRD2-CRD3) of human CD137, however, it is the specific two CRD units (CRD1-CRD2) of human CD137. In comparison, the three CRD units (CRD1-CRD2-CRD3) of human CD137 are required for binding by AG10058, AG10059, AG10131 antibodies, and the human CD137 ligand. Reference antibody AC1097 can bind two CRD units (CRD3-CRD4), including three CRD units (CRD2-CRD3-CRD4) of human CD137. These indicate Adagene AG10058, AG10059, AG10131 antibodies bind the epitopes covered by the three CRD units (CRD1-CRD2-CRD3) of human CD137, similar to human CD137 ligand, but they are very different from the reference antibody AC1121 that binds to two CRD units (CRD1-CRD2) of human CD137 and reference antibody AC1097 which binds to two CRD units (CRD3-CRD4) of human CD137. In conclusion, the binding epitope of CD137 by Adagene's antibodies is different from the epitope by the two reference antibodies (AC1121 with CRD1-CRD2; and AC1097 with CRD3-CRD4) as shown by the distinction in terms of the specific CRDs used and their number of CRD units required (see Table 9B) by highly similar, if not overlapping, to the CD137 epitope by human CD137L ligand; the epitope between CD137-CD137L is confirmed by the recently reported crystal structure complex, as is shown in FIG. 26 (Gilbreth, R. N., Oganesyan, V. Y., Amdouni, H., Novarra, S., Grinberg, L., Barnes, A., Baca, M. (2018) J. Biol. Chem. 293: 9880-9891).

To determine the binding epitope of Adagene's and reference antibodies at amino acid residue level, a series of mutations (Table 5) were made at the extracellular domain of human CD137. These CD137 mutation plasmids were used to transfect HEK293F cells. The binding of antibodies to the human CD137 mutants were assessed by flow cytometry analysis as previously described in Example 5 and shown in FIG. 7A. The results are summarized in Table 5, together with the cross-reactivity of these antibodies with human, monkey, mouse, and rat CD137 in interesting differentiation, indicating the fine epitopes from hits derived from Adagene libraries. AG10131 binds to human, monkey, mouse, and rat CD137, whereas AG10058 binds human, monkey and mouse CD137, but not rat CD137. The binding epitope of CD137 by AG10058, AG10059 and AG10131 was mapped onto CRD1-CRD2-CRD3 units of CD137, they lost their binding ability to GFT34AAA, FSS53AAA, and FH92AA mutations, indicating that their binding epitopes are within these regions, e.g., amino acid residues 34-93 or 34-108 of SEQ ID NO.: 1 (See also, FIG. 7B). AG10058 and AG10131 may bind the same or highly similar epitope, while AG10059 may bind different epitopes from AG10058 and AG10131. Single mutants such as T35A, F36A, F53A, R66A, F72A, N83A, and F92A show that the loss of binding by Adagene antibodies AG10058, AG10059 and AG10131 with human CD137, together with the binding by CD137L except for R66A which still maintains the binding of CD137 by its ligand. Single mutants, P32A and P49A, however, that the binding between CDL137L and CD137 is lost but its impact on the interaction between antibody and CD137 are varied. F125A shows AC1097 does not bind to CD137 anymore, but with no effects on the binding by other antibodies including human CD137L. In conclusion, the overall binding pattern by mutants across CD137 does show a clear message that Adagene antibodies and their reference antibodies are distinguished in terms of their binding sites. The mutant constructs were meant to differentiate the epitopes by AG10058, AG10059 and AG10131 from the reference antibodies by AC1121 and AC1097. Three antibodies AG10058, AG10059 and AG10131 target very different epitopes from AC1121 and AC1097. AG10058, AG10059 and AG10131 differ from AC1121 in regions

TABLE 9B

|  | AG10058 | AG10059 | AG10131 | AC1121 | AC1097 | Human CD137L | Mouse CD137L |
|---|---|---|---|---|---|---|---|
| Hu_CRD1 | − | − | − | − | − | − | − |
| Hu_CRD2 | − | − | − | − | − | − | − |
| Hu_CRD3 | − | − | − | − | − | − | − |
| Hu_CRD4 | − | − | − | − | − | − | − |
| Hu_CRD1-CRD2 | − | − | − | + | − | − | − |
| Hu_CRD2-CRD3 | − | − | − | − | − | − | − |
| Hu_CRD1-CRD2-CRD3 | + | + | + | + | − | + | − |
| Hu_CRD3-CRD4 | − | − | − | − | + | − | − |
| Hu_CRD2-CRD3-CRD4 | − | − | − | − | + | − | − | defined by mutants Hu_FH92AA and Hu FSS53AAA and possibly Hu_GTF34AAA, whereas AG10058, AG10059 and AG10131 differ from AC1097 in regions defined by most of the mutants used, except for Hu_FH92AA and their species cross-reactivity with Monkey but different in other species cross-reactivity such as mouse, rat and dog CD137. In some embodiments, AG10058, AG10059 and AG10131 or other antibodies disclosed herein do not bind to an epitope located within amino acid residues 115-156 of SEQ ID NO.: 1. Also shown in FIG. 7A and Table 5 is that binding of the human CD137 ligand to the wild-type vs. mutant human CD137 matches well with binding pattern of the tested antibodies, consisting with the observation that these antibodies block CD137 ligand binding to its receptor.

luciferase units (RLUs) were calculated vs. the levels of luciferase expressed in 293T cells in the absence of antibody treatment.

Figure 28:
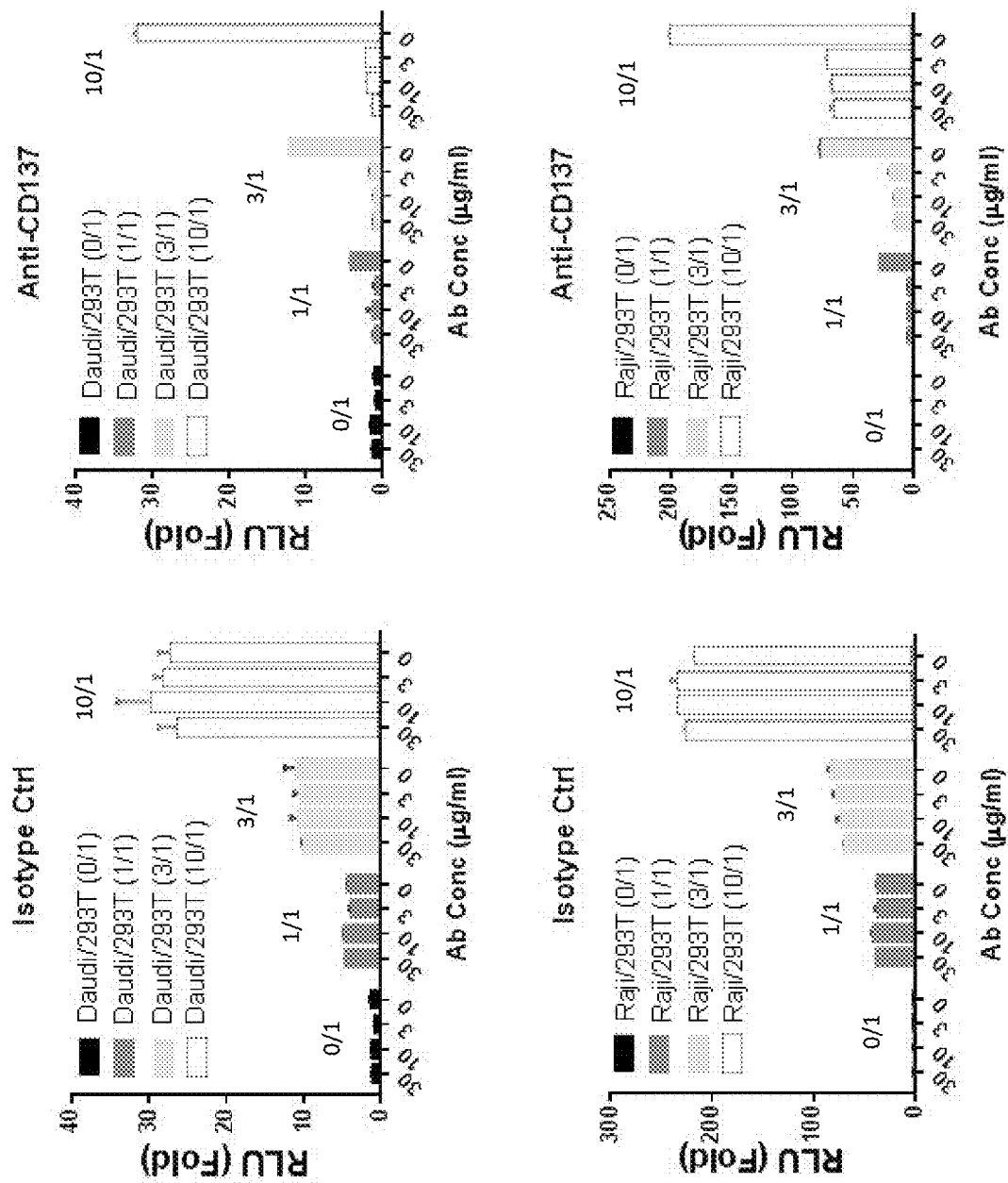
FIG. 28 shows that the anti-CD137 antibody AG10131 blocks CD137L-stimulated CD137 signaling. Results are from a cellular NFκB luciferase reporter assay in which 293T cells stably expressing an NFκB luciferase reporter were transfected with a DNA construct expressing human CD137 were co-cultivated with the human B-cell lymphoma cells Daudi (top row) or Raji (bottom row) at the indicated ratios, then incubated with serial dilutions (as indicated) of isotype control (left column) or ligand-blocking anti-CD137 antibodies (right column) overnight, followed by measurement of luciferase activity.

As shown in FIG. 28, both Daudi (top row) and Raji (bottom row) cells expressed functional CD137 ligand to activate the NFκB luciferase reporter in 293T cells. Compared to the isotype control antibody (left column), addition of AG10131 to the co-culture system (right column) significantly inhibited the NFκB signaling stimulated by both cell types, suggesting that AG10131 antibody can functionally block the CD137 signaling stimulated from CD137 ligand expressed on both Daudi and Raji B lymphoma cells.

|  | AG10058 | AG10059 | AG10131 | AC1121 | AC1097 | Human CD137L | Mouse CD137L |
|---|---|---|---|---|---|---|---|
| Human WT | + | + | + | + | + | + | − |
| Mouse_WT | + | − | + | − | − | − | + |
| Cyno_WT | + | + | + | − | + | − | NA |
| Rat_WT | − | − | + | − | − |  | NA |
| Hu_N30A | + | + | + | + | + | + | − |
| Hu_P32A | + | + | + | − | + | − | − |
| Hu_GTF34AAA | − | − | − | −/+ | + | − | − |
| Hu_T35A | − | − | − | − | + | − | − |
| Hu_F36A | − | − | − | − | + | − | − |
| Hu_P49A | + | − | + | + | + | − | − |
| Hu_P50A | + | + | + | + | + | + | − |
| Hu_F53A | − | − | − | − | + | − | − |
| Hu_FSS53AAA | − | − | − | + | + | − | − |
| Hu_Q59A | + | + | + | + | + | + | − |
| Hu_I64A | + | + | + | + | + | + | − |
| Hu_R66A | − | − | − | + | + | + | − |
| Hu_F72A | − | − | − | + | + | − | − |
| Hu_N83A | − | − | − | + | + | − | − |
| Hu_F92A | − | − | − | + | + | − | − |
| Hu_L95A | + | + | + | + | + | + | − |
| Hu_FH92AA | − | − | − | + | − | − | − |
| Hu_GQ109AA | + | + | + | + | + | + | − |
| Hu_EL111AA | + | + | + | + | − | + | − |
| Hu_F125A | + | + | + | + | − | + | − |
| Hu_FN125AA | + | + | + | + | − | + | − |
| Hu_PW135AA | + | + | + | + | − | + | − |
| Hu_TN137AA | + | + | + | + | − | + | − |
| Hu_GT150AA | + | + | + | + | − | + | − |
| Hu_CRD1 | − | − | − | − | − | − | − |
| Hu_CRD2 | − | − | − | − | − | − | − |
| Hu_CRD3 | − | − | − | − | − | − | − |
| Hu_CRD4 | − | − | − | − | − | − | − |
| Hu_CRD1-CRD2 | − | − | − | + | − | − | − |
| Hu_CRD2-CRD3 | − | − | − | − | − | − | − |
| Hu_CRD1-CRD2-CRD3 | + | + | + | + | − | + | − |
| Hu_CRD3-CRD4 | − | − | − | − | + | − | − |
| Hu_CRD2-CRD3-CRD4 | − | − | − | − | + | − | − |

Example 16

Native CD137L Signaling is Blocked by AG10131

An in vitro binding assay by ELISA demonstrated that AG10131 can block recombinant CD137 and its ligand interaction. To further functionally validate this ligand-blocking activity of AG10131, a cellular NFκB luciferase reporter assay was conducted. Briefly, 293T cells stably expressing an NFκB luciferase reporter were transfected with a DNA construct expressing human CD137, and the cells were co-cultivated with the human B-cell lymphoma cells Daudi or Raji at different ratios. The cell mixture was incubated with serial dilutions of isotype control or ligand-blocking anti-CD137 antibodies overnight, and luciferase activity was measured using the Promega luciferase assay kit according to manufacturer's instructions. Relative Example 17

Anti-CD137 Antibody Crosslinking in an NFκB Reporter Assay

Figure 29:
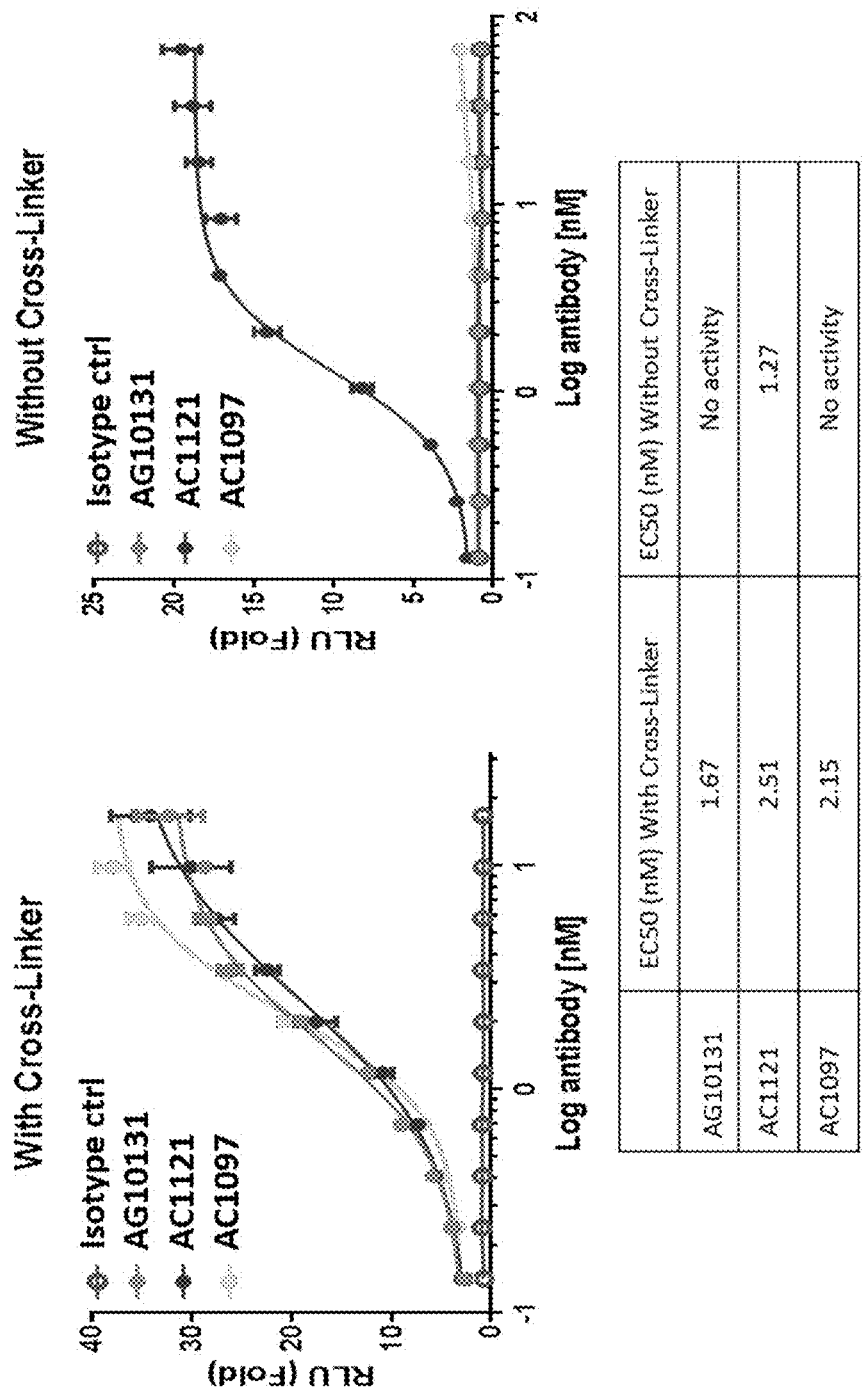
FIG. 29 shows the activation of human CD137-mediated NFκB signaling by anti-CD137 antibodies AG10131, AC1121, or AC1097 in the presence or absence of cross-linking antibody. The EC50 (nM) for each antibody against NFκB signaling activation (in the presence or absence of crosslinking) is indicated.

Using the functional cellular NFκB reporter assay, three anti-CD137 antibodies (AG10131, AC1121 and AC1097) were tested. As shown in FIG. 29, when crosslinked, all three anti-CD137 antibodies were capable of stimulating human CD137 receptor signaling in a dose-dependent manner at comparable levels. The EC50s of the antibody induced NFκB signaling activation response were at similar range for all three anti-CD137 antibodies. However, AC1121 displayed a unique property that is different from AG10131 and AC1097. AC1121 was able to activate human CD137 receptor signaling significantly in the absence of crosslinking, whereas AG10131 and AC1097 were unable to do so. The EC50 of AC1121 with or without crosslinking in the stimulation of the CD137 receptor signaling was found to be at similar levels.

Example 18

AG10131 does not Induce CDC

Figure 30:
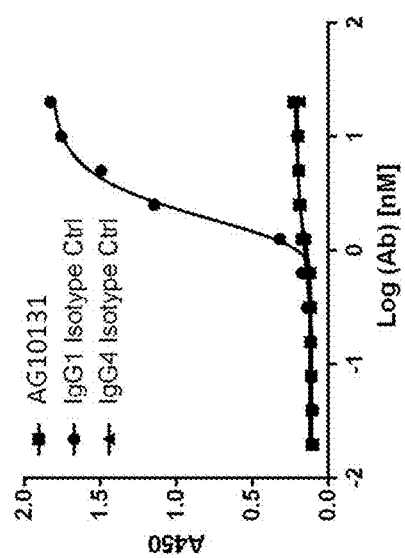
FIG. 30 shows AG10131 and its human IgG4 isotype control antibody lack the ability to bind to human complement C1q component in the concentration range tested, whereas a human IgG1 isotype control antibody is able to bind to C1q.

The CDC activity of AG10131 was determined by the direct binding of AG10131 with the purified C1q component of the human complement with ELISA. As shown in FIG. 30, AG10131 and its human IgG4 isotype control antibody lack the ability to bind to human complement C1q component in the concentration range tested, whereas a human IgG1 isotype control antibody is able to bind to C1q. This result suggests that AG10131 is also unlikely to induce complement dependent cytotoxicity, consistent with its IgG4 isotype framework.

Example 19

Anti-CD137 Antibody AG10131 Enhances Tumor-Infiltrating T-Lymphocytes

The in vivo anti-tumor efficacy studies in the syngeneic mouse H22 liver cancer, EMT6 breast cancer, and CT26 colon cancer models shown in Example 10 demonstrated that AG10131 treatment strongly inhibits tumor growth. AG10131 is an agonistic antibody that activates T cells, and thus AG10131 treatment is expected to stimulate tumor infiltrating T cells into the tumor micro-environment, thereby mediating an anti-tumor effect in vivo. To evaluate the effect of AG10131 treatment on the tumor infiltrating lymphocytes, tumors from the in vivo anti-tumor efficacy study of AG10131 in mouse H22, EMT6, and CT26 cancer models were collected at the end of studies.

Figure 31:
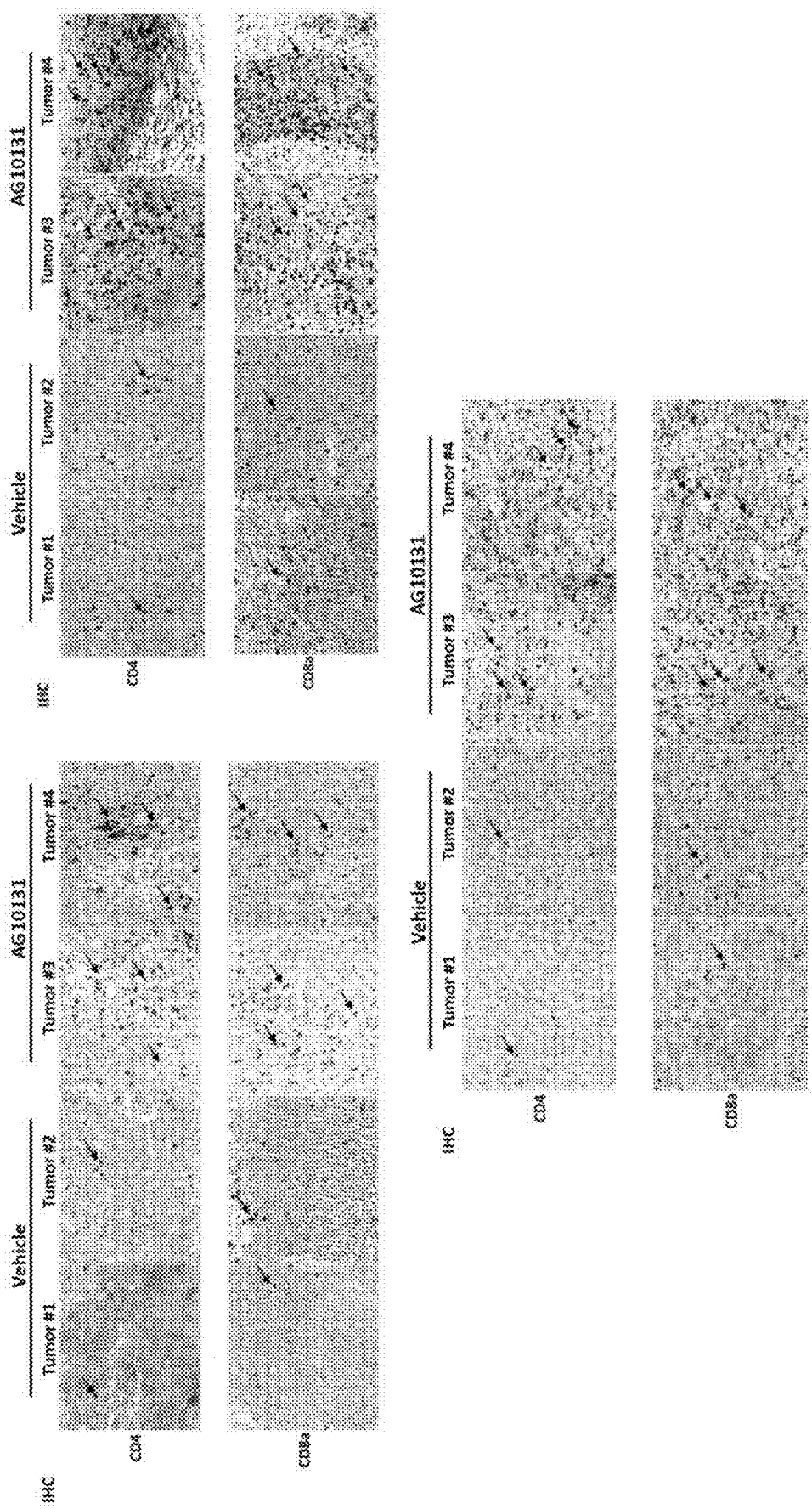
FIG. 31 shows the enhancement of tumor-infiltrating T lymphocytes by AG10131 treatment in various tumor models. Top left: representative IHC staining images of mouse CD4+(upper panels) and CD8+(lower panels) T cells in H22 tumors after treatment. Top right: representative IHC staining images of mouse CD4+(upper panels) and CD8+(lower panels) T cells in EMT6 tumors after treatment. Bottom center: representative IHC staining images of mouse CD4+ (upper panels) and CD8+(lower panels) T cells in CT26 tumors after treatment. CD4+ or CD8+ T cells were stained in black in the background of nuclear counterstain by Hematoxylin. CD4+ and CD8+ T cells are indicated by black arrows.
Figure 32:
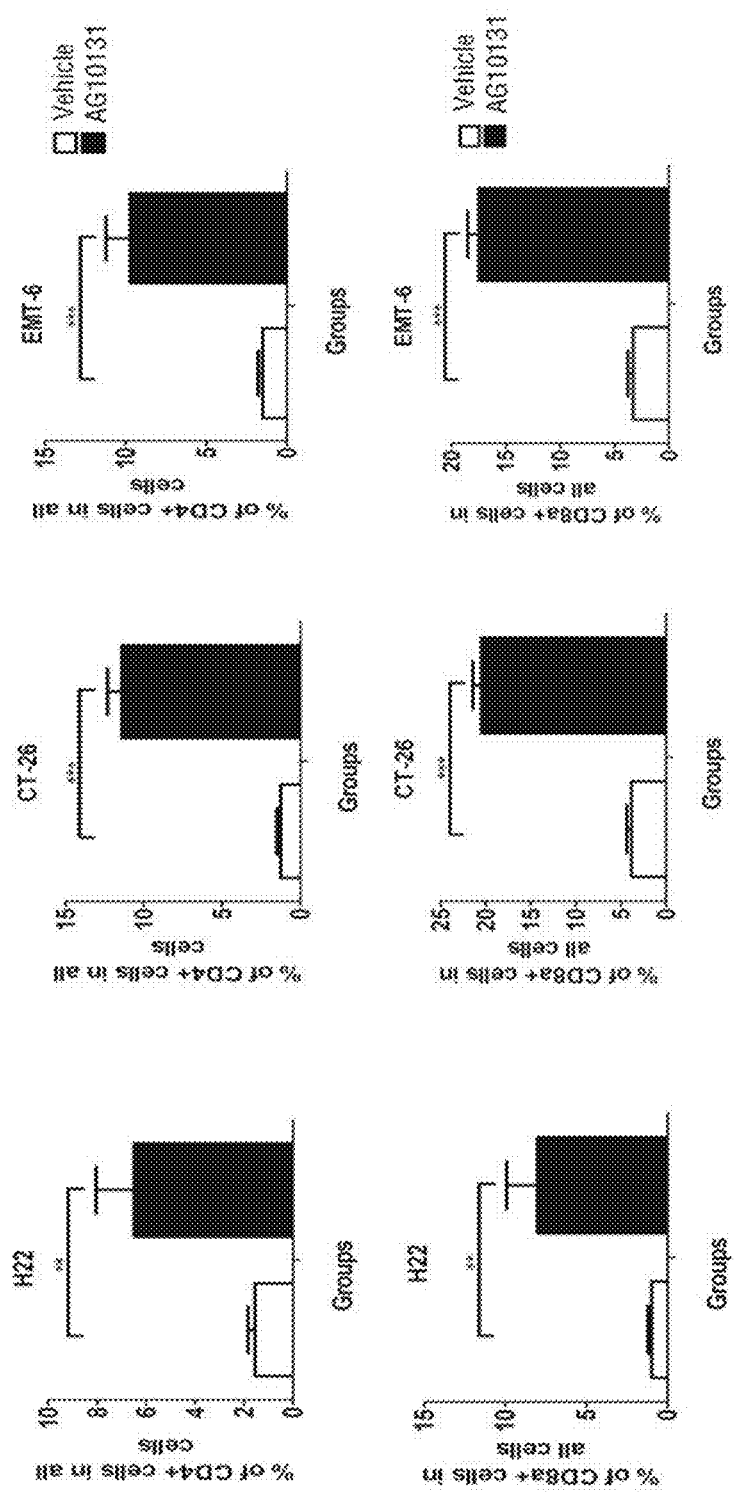
FIG. 32 quantifies numbers of tumor infiltrating T lymphocytes from the experiments shown in FIG. 31. The % $CD4^+$ (top row) and $CD8^+$ T cells (bottom row) in tumors from H22, EMT6, and CT26 tumor samples were compared between vehicle and AG10131 treated groups. , p<0.01; *, p<0.001.

FIG. 31 shows representative IHC staining images of mouse CD4+ and CD8+ T cells in H22 tumors (top left), EMT6 tumors (top right), and CT26 tumors (bottom center). As shown in FIG. 32, few T lymphocytes (either CD4+ or CD8+ T cells) were present in the vehicle control treated H22, EMT6, and CT26 tumors, whereas AG10131 treatment significantly stimulated the infiltration of both CD4+ and CD8+ T cells (indicated by black arrows in FIG. 31) into the tumors. These data are consistent with the function of AG10131 as an immune agonist by stimulating T cell proliferation, activation, and infiltration into the tumor micro-environment to mediate an antitumor effect.

Example 20

Enhanced Anti-Tumor Efficacy by Combining Anti-CD137 Antibody AG10131 and Anti-PD1 Antibody in the CT26 Colon Cancer Model The effect of combining the anti-CD137 antibody AG10131 with an anti-PD1 antibody was next tested in the CT26 colon cancer model. Each female BALB/c mouse was inoculated subcutaneously at the right lower flank region with CT26 tumor cells ($3\times10^5$) for tumor development. When the mean tumor volume reached 98 mm³, 10 mice were assigned to each experimental group. These groups received either vehicle (PBS), AG10131 at 5 or 10 mg/kg, anti-PD-1 at 10 mg/kg, or a combination of 5 or 10 mg/kg of AG10131 and 10 mg/kg of anti-PD-1 mAb by i.p. injection twice weekly for 3 weeks. Tumor volumes were measured and each mouse was euthanized when its tumor reached the endpoint volume of 2000 mm³, or on the final day (Day 42), whichever came first.

Figure 33:
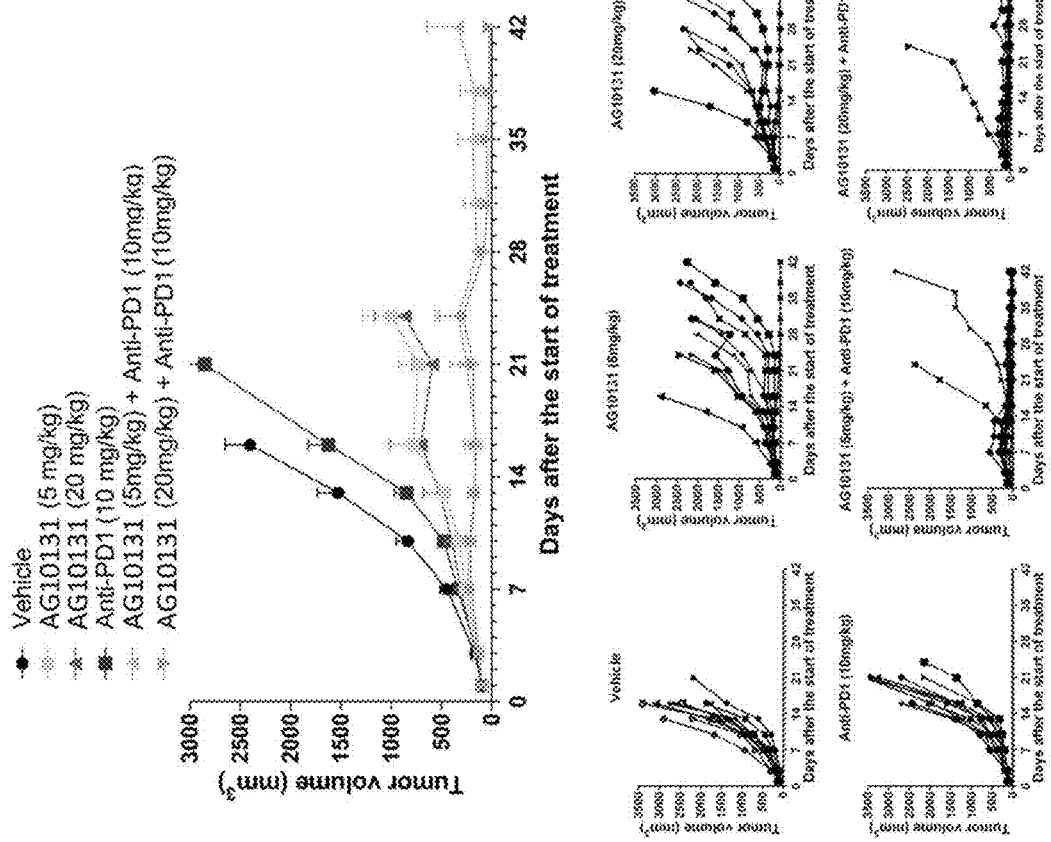
FIG. 33 shows the anti-tumor effects of AG10131 and anti-PD-1 antibody, alone and in combination, in the established mouse CT26 colon cancer syngeneic model. Top panel: plot with average tumor growth for each treatment group. Bottom panels: spider plots with individual tumor growth for each group.

As shown in FIG. 33, both AG10131 (5 mg/kg or 20 mg/kg) and anti-PD1 (10 mg/kg) delayed tumor progression, though AG10131 delayed tumor progression by a few more days, and in rare cases, resulted in tumor shrinkage. However, nearly all mice treated with either AG10131 or anti-PD1 eventually died of tumor progression. Importantly, when AG10131 (5 mg/kg or 20 mg/kg) was administered in combination with anti-PD1 (10 mg/kg), most of the mice were essentially cured of tumor, with only 2 (out of 10) or 1 (out of 10) escaped tumor suppression in the combinations of AG10131 (5 mg/kg) with anti-PD1 (10 mg/kg) or AG10131 (20 mg/kg) with anti-PD1 (10 mg/kg) respectively. These results demonstrated the strong synergistic effect of AG10131 and anti-PD1, suggesting that the combination of AG10131 with anti-PD1 could be effective in anti-PD1 resistance tumors.

What is claimed is:

1. An isolated antibody, or antigen-binding fragment thereof, that binds to an extracellular domain of human CD137, comprising a heavy chain variable region and a light chain variable region,
wherein:
(i) the heavy chain variable region comprises an HVR-H1 comprising the amino acid sequence of SEQ ID NO:731, an HVR-H2 comprising the amino acid sequence of SEQ ID NO:755, and an HVR-H3 comprising the amino acid sequence of SEQ ID NO:779; and
(ii) the light chain variable region comprises an HVR-L1 comprising the amino acid sequence of SEQ ID NO:803, an HVR-L2 comprising the amino acid sequence of SEQ ID NO:827, and an HVR-L3 comprising the amino acid sequence of SEQ ID NO:851.

2. The antibody or antigen-binding fragment of claim 1, wherein the antibody or antigen-binding fragment binds human CD137 with a $K_D$ of 0.1 pM to 100 nM, as measured by surface plasmon resonance.

3. The antibody or antigen-binding fragment of claim 2, wherein the antibody or antigen-binding fragment binds human CD137 with a $K_D$ of 0.1 pM to 50 nM, as measured by surface plasmon resonance.

4. The antibody or antigen-binding fragment of claim 1, wherein the antibody or antigen-binding fragment is cross-reactive with a CD137 polypeptide from at least one non-human species selected from the group consisting of cynomolgus monkey, mouse, rat and dog.

5. The antibody or antigen-binding fragment of claim 4, wherein the antibody or antigen-binding fragment binds to cynomolgus monkey CD137.

6. The antibody or antigen-binding fragment of claim 1, wherein an activity of human CD137 expressed on a human cell is decreased when contacted with the antibody or antigen-binding fragment.

7. The antibody or antigen-binding fragment of claim 1, wherein the antibody or antigen-binding fragment has a half maximal inhibitory concentration ($IC_{50}$) of 0.1 pM to 100 nM for blocking binding of human CD137 to human CD137L in vitro.

8. The antibody or antigen-binding fragment of claim 1, wherein the antibody or antigen-binding fragment completely blocks binding of human CD137 to human CD137L in vitro when the antibody or antigen-binding fragment is provided at a concentration of about 1 µM or greater.

9. The antibody or antigen-binding fragment of claim 1, wherein the antibody or antigen-binding fragment blocks CD137 signaling stimulated by CD137L in a cell that expresses CD137.

10. The antibody or antigen-binding fragment of claim 1, wherein an activity of human CD137 expressed on a human cell is increased when contacted with the antibody or antigen-binding fragment.

11. The antibody or antigen-binding fragment of claim 10, wherein contacting a human cell expressing CD137 with the antibody or antigen-binding fragment results in increased NF-κB-dependent transcription.

12. The antibody or antigen-binding fragment of claim 1, wherein the antibody comprises a human IgG2 Fc region.

13. The antibody or antigen-binding fragment of claim 1, wherein the antibody comprises a human IgG4 Fc region.

14. The antibody or antigen-binding fragment of claim 13, wherein the human IgG4 Fc region comprises an S241P mutation, wherein numbering is according to Kabat.

15. A pharmaceutical composition comprising the antibody or antigen-binding fragment of claim 1 and a pharmaceutically acceptable carrier.

16. The antibody or antigen-binding fragment of claim 1, wherein the antibody or antigen-binding fragment binds to one or more amino acid residues within amino acid residues 34-93 of SEQ ID NO:1.

17. The antibody or antigen-binding fragment of claim 1, wherein the antibody or antigen-binding fragment binds to one or more amino acid residues selected from the group consisting of amino acid residues 34-36, 53-55, and 92-93 of SEQ ID NO:1.

18. The antibody or antigen-binding fragment of claim 17, wherein the antibody or antigen-binding fragment binds to one or more of amino acid residues 34-36, one or more of amino acid residues 53-55, and one or more or amino acid residues 92-93 of SEQ ID NO:1.

19. The antibody or antigen-binding fragment of claim 1, wherein the antibody or antigen-binding fragment does not bind to one or more of amino acid residues selected from the group consisting of amino acid residues 109-112, 125, 126, 135-138, 150 and 151 of SEQ ID NO:1.

20. The antibody or antigen-binding fragment of claim 19, wherein the antibody or antigen-binding fragment does not bind to amino acid residues 109-112, 125, 126, 135-138, 150 and 151 of SEQ ID NO:1.

21. An isolated antibody, or antigen-binding fragment thereof, that binds to an extracellular domain of human CD137, comprising a heavy chain variable region and a light chain variable region, wherein the heavy chain variable region comprises an amino acid sequence of SEQ ID NO:71, and the light chain variable region comprises an amino acid sequence of SEQ ID NO:72.

22. An isolated antibody, or antigen-binding fragment thereof, that binds to an extracellular domain of human CD137, wherein the antibody comprises a heavy chain and a light chain, wherein the heavy chain comprises an amino acid sequence of SEQ ID NO: 657, and the light chain comprises an amino acid sequence of SEQ ID NO: 658.

23. The antibody or antigen-binding fragment of claim 1, wherein the antibody or antigen-binding fragment does not induce ADCC effect.

24. The antibody or antigen-binding fragment of claim 1, wherein the antigen-binding fragment is selected from the group consisting of a Fab fragment, a F(ab')2 fragment, a Fv fragment, and a single chain antibody (scFv).

25. The antibody or antigen-binding fragment of claim 21, wherein the antibody comprises a human IgG4 Fc region.

26. The antibody or antigen-binding fragment of claim 25, wherein the human IgG4 Fc region comprises an S241P mutation, wherein numbering is according to Kabat.

27. The antibody or antigen-binding fragment of claim 21, wherein the antigen-binding fragment is selected from the group consisting of a Fab fragment, a F(ab')2 fragment, a Fv fragment, and a single chain antibody (scFv).

28. A pharmaceutical composition comprising the antibody or antigen-binding fragment of claim 21 and a pharmaceutically acceptable carrier.

29. A pharmaceutical composition comprising the antibody or antigen-binding fragment of claim 22 and a pharmaceutically acceptable carrier.

* * * * *

SEQUENCE LISTING

```
<160> NUMBER OF SEQ ID NOS: 883

<210> SEQ ID NO 1
<211> LENGTH: 255
<212> TYPE: PRT
<213> ORGANISM: Homo sapiens

<400> SEQUENCE: 1

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80
```

-continued

```
Thr Ser Asn Ala Glu Cys Asp Cys Thr Pro Gly Phe His Cys Leu Gly
             85                  90                  95
Ala Gly Cys Ser Met Cys Glu Gln Asp Cys Lys Gln Gly Gln Glu Leu
        100                 105                 110
Thr Lys Lys Gly Cys Lys Asp Cys Cys Phe Gly Thr Phe Asn Asp Gln
    115                 120                 125
Lys Arg Gly Ile Cys Arg Pro Trp Thr Asn Cys Ser Leu Asp Gly Lys
130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
                165                 170                 175
Pro Ala Arg Glu Pro Gly His Ser Pro Gln Ile Ile Ser Phe Phe Leu
            180                 185                 190
Ala Leu Thr Ser Thr Ala Leu Leu Phe Leu Leu Phe Phe Leu Thr Leu
        195                 200                 205
Arg Phe Ser Val Val Lys Arg Gly Arg Lys Lys Leu Leu Tyr Ile Phe
    210                 215                 220
Lys Gln Pro Phe Met Arg Pro Val Gln Thr Thr Gln Glu Glu Asp Gly
225                 230                 235                 240
Cys Ser Cys Arg Phe Pro Glu Glu Glu Glu Gly Gly Cys Glu Leu
                245                 250                 255

<210> SEQ ID NO 2
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)..(1)
<223> OTHER INFORMATION: X1 : F or Y
<220> FEATURE:
<221> NAME/KEY: VARIANT
<222> LOCATION: (4)..(4)
<223> OTHER INFORMATION: X2 : S or T
<220> FEATURE:
<221> NAME/KEY: VARIANT
<222> LOCATION: (5)..(5)
<223> OTHER INFORMATION: X3 : G or N or S
<220> FEATURE:
<221> NAME/KEY: VARIANT
<222> LOCATION: (7)..(7)
<223> OTHER INFORMATION: X4 : A or G or W

<400> SEQUENCE: 2

Xaa Thr Phe Xaa Xaa Tyr Xaa Ile His Trp Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (4)..(4)
<223> OTHER INFORMATION: X1 : S or T
<220> FEATURE:
<221> NAME/KEY: VARIANT
<222> LOCATION: (7)..(7)
<223> OTHER INFORMATION: X2 : H or Y
<220> FEATURE:
<221> NAME/KEY: VARIANT
```

-continued

```
<222> LOCATION: (8)..(8)
<223> OTHER INFORMATION: X3 : H or Y
<220> FEATURE:
<221> NAME/KEY: VARIANT
<222> LOCATION: (10)..(10)
<223> OTHER INFORMATION: X4 : A or D or G or N or S or T

<400> SEQUENCE: 3

Tyr Ser Ile Xaa Ser Gly Xaa Xaa Trp Xaa Trp Ile
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (6)..(6)
<223> OTHER INFORMATION: X1 : G or S
<220> FEATURE:
<221> NAME/KEY: VARIANT
<222> LOCATION: (9)..(9)
<223> OTHER INFORMATION: X2 : A or G
<220> FEATURE:
<221> NAME/KEY: VARIANT
<222> LOCATION: (11)..(11)
<223> OTHER INFORMATION: X3 : A or G or S or T

<400> SEQUENCE: 4

Phe Ser Leu Ser Thr Xaa Gly Val Xaa Val Xaa Trp Ile
1               5                   10

<210> SEQ ID NO 5
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (7)..(7)
<223> OTHER INFORMATION: X1 : A or D or Y
<220> FEATURE:
<221> NAME/KEY: VARIANT
<222> LOCATION: (8)..(8)
<223> OTHER INFORMATION: X2 : D or G
<220> FEATURE:
<221> NAME/KEY: VARIANT
<222> LOCATION: (11)..(11)
<223> OTHER INFORMATION: X3 : R or S or Y
<220> FEATURE:
<221> NAME/KEY: VARIANT
<222> LOCATION: (14)..(14)
<223> OTHER INFORMATION: X4 : P or T

<400> SEQUENCE: 5

Leu Ala Leu Ile Asp Trp Xaa Xaa Asp Lys Xaa Tyr Ser Xaa Ser Leu
1               5                   10                  15

Lys Ser Arg Leu
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (3)..(3)
```

```
<223> OTHER INFORMATION: X1 : D or E
<220> FEATURE:
<221> NAME/KEY: VARIANT
<222> LOCATION: (9)..(9)
<223> OTHER INFORMATION: X2 : N or S
<220> FEATURE:
<221> NAME/KEY: VARIANT
<222> LOCATION: (13)..(13)
<223> OTHER INFORMATION: X3 : N or S

<400> SEQUENCE: 6

Ile Gly Xaa Ile Tyr His Ser Gly Xaa Thr Tyr Tyr Xaa Pro Ser Leu
1               5                   10                  15

Lys Ser Arg Val
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (3)..(3)
<223> OTHER INFORMATION: X1 : A or G or S or V or Y
<220> FEATURE:
<221> NAME/KEY: VARIANT
<222> LOCATION: (7)..(7)
<223> OTHER INFORMATION: X2 : A or D or S or Y
<220> FEATURE:
<221> NAME/KEY: VARIANT
<222> LOCATION: (9)..(9)
<223> OTHER INFORMATION: X3 : D or G or S
<220> FEATURE:
<221> NAME/KEY: VARIANT
<222> LOCATION: (10)..(10)
<223> OTHER INFORMATION: X4 : S or T

<400> SEQUENCE: 7

Val Ser Xaa Ile Ser Gly Xaa Gly Xaa Xaa Thr Tyr Tyr Ala Asp Ser
1               5                   10                  15

Val Lys Gly Arg Phe
            20

<210> SEQ ID NO 8
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (3)..(3)
<223> OTHER INFORMATION: X1 : E or G
<220> FEATURE:
<221> NAME/KEY: VARIANT
<222> LOCATION: (5)..(5)
<223> OTHER INFORMATION: X2 : E or S
<220> FEATURE:
<221> NAME/KEY: VARIANT
<222> LOCATION: (6)..(6)
<223> OTHER INFORMATION: X3 : D or T
<220> FEATURE:
<221> NAME/KEY: VARIANT
<222> LOCATION: (7)..(7)
<223> OTHER INFORMATION: X4 : A or T or V
<220> FEATURE:
<221> NAME/KEY: VARIANT
<222> LOCATION: (9)..(9)
<223> OTHER INFORMATION: X5 : A or I or L or T or V
<220> FEATURE:
<221> NAME/KEY: VARIANT
```

```
<222> LOCATION: (14)..(14)
<223> OTHER INFORMATION: X6 : A or D or G

<400> SEQUENCE: 8

Ala Arg Xaa Gly Xaa Xaa Xaa Val Xaa Gly Asp Trp Phe Xaa Tyr
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)..(1)
<223> OTHER INFORMATION: X1 : Q or R
<220> FEATURE:
<221> NAME/KEY: VARIANT
<222> LOCATION: (5)..(5)
<223> OTHER INFORMATION: X2 : D or G or S
<220> FEATURE:
<221> NAME/KEY: VARIANT
<222> LOCATION: (6)..(6)
<223> OTHER INFORMATION: X3 : I or V
<220> FEATURE:
<221> NAME/KEY: VARIANT
<222> LOCATION: (7)..(7)
<223> OTHER INFORMATION: X4 : G or R or S or T
<220> FEATURE:
<221> NAME/KEY: VARIANT
<222> LOCATION: (8)..(8)
<223> OTHER INFORMATION: X5 : P or R or S or T
<220> FEATURE:
<221> NAME/KEY: VARIANT
<222> LOCATION: (9)..(9)
<223> OTHER INFORMATION: X6 : A or D or F or S or V or Y
<220> FEATURE:
<221> NAME/KEY: VARIANT
<222> LOCATION: (10)..(10)
<223> OTHER INFORMATION: X7 : L or V
<220> FEATURE:
<221> NAME/KEY: VARIANT
<222> LOCATION: (11)..(11)
<223> OTHER INFORMATION: X8 : A or G or N

<400> SEQUENCE: 9

Xaa Ala Ser Gln Xaa Xaa Xaa Xaa Xaa Xaa Xaa
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)..(1)
<223> OTHER INFORMATION: X1 : A or D
<220> FEATURE:
<221> NAME/KEY: VARIANT
<222> LOCATION: (4)..(4)
<223> OTHER INFORMATION: X2 : N or S or T
<220> FEATURE:
<221> NAME/KEY: VARIANT
<222> LOCATION: (5)..(5)
<223> OTHER INFORMATION: X3 : L or R
<220> FEATURE:
<221> NAME/KEY: VARIANT
<222> LOCATION: (6)..(6)
<223> OTHER INFORMATION: X4 : A or E or Q
<220> FEATURE:
<221> NAME/KEY: VARIANT
<222> LOCATION: (7)..(7)
```

```
<223> OTHER INFORMATION: X5 : S or T
<220> FEATURE:
<221> NAME/KEY: VARIANT
<222> LOCATION: (9)..(9)
<223> OTHER INFORMATION: X6 : I or V

<400> SEQUENCE: 10

Xaa Ala Ser Xaa Xaa Xaa Xaa Gly Xaa
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (5)..(5)
<223> OTHER INFORMATION: X1 : A or G or S or Y
<220> FEATURE:
<221> NAME/KEY: VARIANT
<222> LOCATION: (7)..(7)
<223> OTHER INFORMATION: X2 : Q or S or Y
<220> FEATURE:
<221> NAME/KEY: VARIANT
<222> LOCATION: (8)..(8)
<223> OTHER INFORMATION: X3 : I or L or T or Y
<220> FEATURE:
<221> NAME/KEY: VARIANT
<222> LOCATION: (9)..(9)
<223> OTHER INFORMATION: X4 : I or S or V or W

<400> SEQUENCE: 11

Tyr Cys Gln Gln Xaa Tyr Xaa Xaa Xaa Thr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (3)..(3)
<223> OTHER INFORMATION: X1 : E or Q
<220> FEATURE:
<221> NAME/KEY: VARIANT
<222> LOCATION: (5)..(5)
<223> OTHER INFORMATION: X2 : P or S or Y
<220> FEATURE:
<221> NAME/KEY: VARIANT
<222> LOCATION: (6)..(6)
<223> OTHER INFORMATION: X3 : D or L or S or T or Y
<220> FEATURE:
<221> NAME/KEY: VARIANT
<222> LOCATION: (7)..(7)
<223> OTHER INFORMATION: X4 : D or E or H or S or T
<220> FEATURE:
<221> NAME/KEY: VARIANT
<222> LOCATION: (8)..(8)
<223> OTHER INFORMATION: X5 : D or L or T or W
<220> FEATURE:
<221> NAME/KEY: VARIANT
<222> LOCATION: (10)..(10)
<223> OTHER INFORMATION: X6 : L or P or R or V

<400> SEQUENCE: 12

Tyr Cys Xaa Gln Xaa Xaa Xaa Xaa Pro Xaa Thr
1               5                   10

<210> SEQ ID NO 13
```

<211> LENGTH: 117
<212> TYPE: PRT
<213> ORGANISM: Artificial Sequence
<220> FEATURE:
<223> OTHER INFORMATION: Synthetic sequence

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Gly Ile His Trp Val Arg Gln Ala Pro Gly Lys Gly Leu Glu Trp Val
        35                  40                  45

Ser Gly Ile Ser Gly Ala Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Glu Arg Asp Tyr Asp Phe Asp Tyr Trp Gly Gln Gly Thr Leu
            100                 105                 110

Val Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: Synthetic sequence

<400> SEQUENCE: 14

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser His
                85                  90                  95

Thr Phe Gly Gln Gly Thr Lys Val Glu Ile Lys Arg
            100                 105

<210> SEQ ID NO 15
<211> LENGTH: 123
<212> TYPE: PRT
<213> ORGANISM: Artificial Sequence
<220> FEATURE:
<223> OTHER INFORMATION: Synthetic sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

```
Gly Val Ala Val Ser Trp Ile Arg Gln Ala Pro Gly Lys Gly Leu Glu
            35                  40                  45

Trp Ile Gly Ile Ile Asn Pro Asn Phe Gly Asp Thr Asn Tyr Ala Gln
 50                  55                  60

Lys Phe Gln Gly Arg Val Thr Ile Ser Arg Asp Asn Ser Lys Asn Thr
 65                  70                  75                  80

Leu Tyr Leu Gln Leu Asn Ser Leu Arg Ala Glu Asp Thr Ala Val Tyr
                85                  90                  95

Tyr Cys Ala Arg Asp Glu Tyr Tyr Gly Ser Tyr Tyr Phe Asp Tyr
                100                 105                 110

Trp Gly Gln Gly Thr Leu Val Thr Val Ser Ser
            115                 120
```

<210> SEQ ID NO 16
<211> LENGTH: 108
<212> TYPE: PRT
<213> ORGANISM: Artificial Sequence
<220> FEATURE:
<223> OTHER INFORMATION: Synthetic sequence

<400> SEQUENCE: 16

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Val Arg Thr Ala
            20                  25                  30

Val Ala Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asp Trp Pro Pro
                85                  90                  95

Thr Phe Gly Gln Gly Thr Lys Val Glu Ile Lys Arg
            100                 105
```

<210> SEQ ID NO 17
<211> LENGTH: 121
<212> TYPE: PRT
<213> ORGANISM: Artificial Sequence
<220> FEATURE:
<223> OTHER INFORMATION: Synthetic sequence

<400> SEQUENCE: 17

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Thr Gly
            20                  25                  30

Gly Val Gly Val Ser Trp Ile Arg Gln Ala Pro Gly Lys Gly Leu Glu
         35                  40                  45

Trp Val Ser Ser Ile Ser Gly Ser Gly Gly Thr Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Leu Asn Ser Leu Arg Ala Glu Asp Thr Ala Val Tyr
                85                  90                  95

Tyr Cys Ala Arg Asp Asp Leu Tyr Ser Trp Tyr Phe Asp Val Trp Gly
                100                 105                 110
```

```
Gln Gly Thr Leu Val Thr Val Ser Ser
        115                 120
```

<210> SEQ ID NO 18
<211> LENGTH: 107
<212> TYPE: PRT
<213> ORGANISM: Artificial Sequence
<220> FEATURE:
<223> OTHER INFORMATION: Synthetic sequence

<400> SEQUENCE: 18

```
Asp Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Gly Ser Ser
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Thr Trp Thr
                85                  90                  95

Phe Gly Gln Gly Thr Lys Val Glu Ile Lys Arg
            100                 105
```

<210> SEQ ID NO 19
<211> LENGTH: 120
<212> TYPE: PRT
<213> ORGANISM: Artificial Sequence
<220> FEATURE:
<223> OTHER INFORMATION: Synthetic sequence

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr His Trp Gly Trp Ile Arg Gln Ala Pro Gly Lys Gly Leu Glu Trp
        35                  40                  45

Val Ser Ala Ile Ser Gly Ala Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Gly Tyr Gly Ser Tyr Phe Asp Tyr Trp Gly Gln
            100                 105                 110

Gly Thr Leu Val Thr Val Ser Ser
        115                 120
```

<210> SEQ ID NO 20
<211> LENGTH: 107
<212> TYPE: PRT
<213> ORGANISM: Artificial Sequence
<220> FEATURE:
<223> OTHER INFORMATION: Synthetic sequence

<400> SEQUENCE: 20

```
Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Thr Phe
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Ile Trp Thr
                85                  90                  95

Phe Gly Gln Gly Thr Lys Val Glu Ile Lys Arg
            100                 105
```

<210> SEQ ID NO 21
<211> LENGTH: 120
<212> TYPE: PRT
<213> ORGANISM: Artificial Sequence
<220> FEATURE:
<223> OTHER INFORMATION: Synthetic sequence

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Trp Ile His Trp Val Arg Gln Ala Pro Gly Lys Gly Leu Glu Trp Val
            35                  40                  45

Gly Arg Ile Arg Ser Lys Thr Asp Gly Tyr Thr Thr Glu Tyr Ala Ala
    50                  55                  60

Pro Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Leu Gly Gly His Trp Tyr Phe Asp Val Trp Gly Gln
            100                 105                 110

Gly Thr Leu Val Thr Val Ser Ser
        115                 120
```

<210> SEQ ID NO 22
<211> LENGTH: 108
<212> TYPE: PRT
<213> ORGANISM: Artificial Sequence
<220> FEATURE:
<223> OTHER INFORMATION: Synthetic sequence

<400> SEQUENCE: 22

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Glu Gln Pro Leu Glu Leu Pro Arg
                85                  90                  95

Thr Phe Gly Gln Gly Thr Lys Val Glu Ile Lys Arg
            100                 105

<210> SEQ ID NO 23
<211> LENGTH: 122
<212> TYPE: PRT
<213> ORGANISM: Artificial Sequence
<220> FEATURE:
<223> OTHER INFORMATION: Synthetic sequence

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His His Trp Gly Trp Ile Arg Gln Ala Pro Gly Lys Gly Leu Glu Trp
        35                  40                  45

Val Ser Gly Ile Ser Gly Tyr Gly Asp Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Pro Tyr Ser Ser Gly Ser Gly Tyr Phe Asp Tyr Trp
            100                 105                 110

Gly Gln Gly Thr Leu Val Thr Val Ser Ser
        115                 120

<210> SEQ ID NO 24
<211> LENGTH: 107
<212> TYPE: PRT
<213> ORGANISM: Artificial Sequence
<220> FEATURE:
<223> OTHER INFORMATION: Synthetic sequence

<400> SEQUENCE: 24

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Tyr Thr Trp Thr
                85                  90                  95

Phe Gly Gln Gly Thr Lys Val Glu Ile Lys Arg
            100                 105

<210> SEQ ID NO 25
<211> LENGTH: 117
<212> TYPE: PRT
<213> ORGANISM: Artificial Sequence
<220> FEATURE:
<223> OTHER INFORMATION: Synthetic sequence
```

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr Tyr Trp Gly Trp Ile Arg Gln Ala Pro Gly Lys Gly Leu Glu Trp
        35                  40                  45

Val Ser Gly Ile Ser Gly Ser Gly Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Thr Tyr Ser Phe Asp Val Trp Gly Gln Gly Thr Leu
            100                 105                 110

Val Thr Val Ser Ser
            115

<210> SEQ ID NO 26
<211> LENGTH: 107
<212> TYPE: PRT
<213> ORGANISM: Artificial Sequence
<220> FEATURE:
<223> OTHER INFORMATION: Synthetic sequence

<400> SEQUENCE: 26

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Ile Thr
                85                  90                  95

Phe Gly Gln Gly Thr Lys Val Glu Ile Lys Arg
            100                 105

<210> SEQ ID NO 27
<211> LENGTH: 117
<212> TYPE: PRT
<213> ORGANISM: Artificial Sequence
<220> FEATURE:
<223> OTHER INFORMATION: Synthetic sequence

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Gly Tyr
            20                  25                  30

Ala Ile His Trp Val Arg Gln Ala Pro Gly Lys Gly Leu Glu Trp Val
        35                  40                  45

Ser Ala Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gly Tyr Arg Gly Tyr Phe Asp Tyr Trp Gly Gln Gly Thr Leu
            100                 105                 110

Val Thr Val Ser Ser
        115

<210> SEQ ID NO 28
<211> LENGTH: 109
<212> TYPE: PRT
<213> ORGANISM: Artificial Sequence
<220> FEATURE:
<223> OTHER INFORMATION: Synthetic sequence

<400> SEQUENCE: 28

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Thr Ser Thr
            20                  25                  30

Tyr Leu Ala Trp Tyr Gln Gln Lys Pro Gly Lys Ala Pro Lys Leu Leu
        35                  40                  45

Ile Tyr Asp Ala Ser Asn Leu Glu Thr Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Ser Asp Trp Pro
                85                  90                  95

Pro Thr Phe Gly Gln Gly Thr Lys Val Glu Ile Lys Arg
            100                 105

<210> SEQ ID NO 29
<211> LENGTH: 123
<212> TYPE: PRT
<213> ORGANISM: Artificial Sequence
<220> FEATURE:
<223> OTHER INFORMATION: Synthetic sequence

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Asn Trp Ile Arg Gln Ala Pro Gly Lys Gly Leu Glu Trp
        35                  40                  45

Val Ser Ser Ile Ser Gly Ser Gly Ser Thr Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Pro Asn Tyr Tyr Ser Ser Gly Ser Tyr Phe Asp Tyr
            100                 105                 110

Trp Gly Gln Gly Thr Leu Val Thr Val Ser Ser
        115                 120

```
<210> SEQ ID NO 30
<211> LENGTH: 107
<212> TYPE: PRT
<213> ORGANISM: Artificial Sequence
<220> FEATURE:
<223> OTHER INFORMATION: Synthetic sequence

<400> SEQUENCE: 30
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Phe
            20                  25                  30

Leu Gly Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Leu Trp Thr
                85                  90                  95

Phe Gly Gln Gly Thr Lys Val Glu Ile Lys Arg
            100                 105

```
<210> SEQ ID NO 31
<211> LENGTH: 121
<212> TYPE: PRT
<213> ORGANISM: Artificial Sequence
<220> FEATURE:
<223> OTHER INFORMATION: Synthetic sequence

<400> SEQUENCE: 31
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr Tyr Trp Asp Trp Ile Arg Gln Ala Pro Gly Lys Gly Leu Glu Trp
        35                  40                  45

Val Ser Ser Ile Ser Gly Asp Gly Asp Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Tyr Tyr Gly Tyr Gly Tyr Ala Leu Asp Tyr Trp Gly
            100                 105                 110

Gln Gly Thr Leu Val Thr Val Ser Ser
        115                 120

```
<210> SEQ ID NO 32
<211> LENGTH: 108
<212> TYPE: PRT
<213> ORGANISM: Artificial Sequence
<220> FEATURE:
<223> OTHER INFORMATION: Synthetic sequence

<400> SEQUENCE: 32
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 33
<211> LENGTH: 119
<212> TYPE: PRT
<213> ORGANISM: Artificial Sequence
<220> FEATURE:
<223> OTHER INFORMATION: Synthetic sequence

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His Tyr Trp Gly Trp Ile Arg Gln Ala Pro Gly Lys Gly Leu Glu Trp
        35                  40                  45

Leu Ala Leu Ile Asp Trp Tyr Gly Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Asp Tyr Tyr Gly Ser His Phe Asp Tyr Trp Gly Gln Gly
            100                 105                 110

Thr Leu Val Thr Val Ser Ser
        115

<210> SEQ ID NO 34
<211> LENGTH: 112
<212> TYPE: PRT
<213> ORGANISM: Artificial Sequence
<220> FEATURE:
<223> OTHER INFORMATION: Synthetic sequence

<400> SEQUENCE: 34

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Asp
            20                  25                  30

Gly Phe Ser Phe Leu Ala Trp Tyr Gln Gln Lys Pro Gly Lys Ala Pro
        35                  40                  45

Lys Leu Leu Ile Tyr Asp Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Thr Leu Pro Arg Thr Phe Gly Gln Gly Thr Lys Val Glu Ile Lys Arg

<210> SEQ ID NO 35
<211> LENGTH: 122
<212> TYPE: PRT
<213> ORGANISM: Artificial Sequence
<220> FEATURE:
<223> OTHER INFORMATION: Synthetic sequence

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asn Tyr
            20                  25                  30

Trp Ile His Trp Val Arg Gln Ala Pro Gly Lys Gly Leu Glu Trp Val
        35                  40                  45

Ser Tyr Ile Ser Gly Asp Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
            85                  90                  95

Ala Arg Glu Gly Ser Thr Thr Val Ala Gly Asp Trp Phe Ala Tyr Trp
            100                 105                 110

Gly Gln Gly Thr Leu Val Thr Val Ser Ser
            115                 120

<210> SEQ ID NO 36
<211> LENGTH: 107
<212> TYPE: PRT
<213> ORGANISM: Artificial Sequence
<220> FEATURE:
<223> OTHER INFORMATION: Synthetic sequence

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Phe
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Leu Val Thr
            85                  90                  95

Phe Gly Gln Gly Thr Lys Val Glu Ile Lys Arg
            100                 105

<210> SEQ ID NO 37
<211> LENGTH: 124
<212> TYPE: PRT
<213> ORGANISM: Artificial Sequence
<220> FEATURE:
<223> OTHER INFORMATION: Synthetic sequence

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Ala Trp Ile Arg Gln Ala Pro Gly Lys Gly Leu Glu
        35                  40                  45

Trp Val Ser Ser Ile Ser Gly Tyr Gly Ser Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Ala Val Leu Gly Asp Trp Phe Gly
                100                 105                 110

Tyr Trp Gly Gln Gly Thr Leu Val Thr Val Ser Ser
            115                 120

<210> SEQ ID NO 38
<211> LENGTH: 107
<212> TYPE: PRT
<213> ORGANISM: Artificial Sequence
<220> FEATURE:
<223> OTHER INFORMATION: Synthetic sequence

<400> SEQUENCE: 38

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Thr Thr Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys Arg
                100                 105

<210> SEQ ID NO 39
<211> LENGTH: 123
<212> TYPE: PRT
<213> ORGANISM: Artificial Sequence
<220> FEATURE:
<223> OTHER INFORMATION: Synthetic sequence

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr

```
                  85                  90                  95

Cys Ala Arg Glu Gly Ser Asp Ala Val Leu Gly Asp Trp Phe Ala Tyr
            100                 105                 110

Trp Gly Gln Gly Thr Leu Val Thr Val Ser Ser
        115                 120

<210> SEQ ID NO 40
<211> LENGTH: 107
<212> TYPE: PRT
<213> ORGANISM: Artificial Sequence
<220> FEATURE:
<223> OTHER INFORMATION: Synthetic sequence

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Phe
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Ile Trp Thr
                85                  90                  95

Phe Gly Gln Gly Thr Lys Val Glu Ile Lys Arg
            100                 105

<210> SEQ ID NO 41
<211> LENGTH: 123
<212> TYPE: PRT
<213> ORGANISM: Artificial Sequence
<220> FEATURE:
<223> OTHER INFORMATION: Synthetic sequence

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Leu Ala Leu Ile Asp Trp Asp Asp Asp Lys Tyr Tyr Ser Pro Ser
50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Leu Gly Asp Trp Phe Ala Tyr
            100                 105                 110

Trp Gly Gln Gly Thr Leu Val Thr Val Ser Ser
        115                 120

<210> SEQ ID NO 42
<211> LENGTH: 107
<212> TYPE: PRT
<213> ORGANISM: Artificial Sequence
<220> FEATURE:
```

<223> OTHER INFORMATION: Synthetic sequence

<400> SEQUENCE: 42

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
                85                  90                  95

Phe Gly Gln Gly Thr Lys Val Glu Ile Lys Arg
            100                 105

<210> SEQ ID NO 43
<211> LENGTH: 123
<212> TYPE: PRT
<213> ORGANISM: Artificial Sequence
<220> FEATURE:
<223> OTHER INFORMATION: Synthetic sequence

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Gly Trp Ile Arg Gln Ala Pro Gly Lys Gly Leu Glu
        35                  40                  45

Trp Leu Ala Leu Ile Asp Trp Ala Gly Asp Lys Ser Tyr Ser Thr Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Leu Gly Asp Trp Phe Ala Tyr
            100                 105                 110

Trp Gly Gln Gly Thr Leu Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: Synthetic sequence

<400> SEQUENCE: 44

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ser Thr Trp Thr
                 85                  90                  95

Phe Gly Gln Gly Thr Lys Val Glu Ile Lys Arg
                100                 105

<210> SEQ ID NO 45
<211> LENGTH: 123
<212> TYPE: PRT
<213> ORGANISM: Artificial Sequence
<220> FEATURE:
<223> OTHER INFORMATION: Synthetic sequence

<400> SEQUENCE: 45

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Ile Ser Ser Gly
                 20                  25                  30

Tyr His Trp Ala Trp Ile Arg Gln Ala Pro Gly Lys Gly Leu Glu Trp
                 35                  40                  45

Val Ser Ser Ile Ser Gly Asp Gly Ser Ser Thr Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Glu Gly Ser Asp Ala Val Thr Gly Asp Trp Phe Ala Tyr
                100                 105                 110

Trp Gly Gln Gly Thr Leu Val Thr Val Ser Ser
                115                 120

<210> SEQ ID NO 46
<211> LENGTH: 107
<212> TYPE: PRT
<213> ORGANISM: Artificial Sequence
<220> FEATURE:
<223> OTHER INFORMATION: Synthetic sequence

<400> SEQUENCE: 46

Asp Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Val Gly Thr Tyr
                 20                  25                  30

Leu Ala Trp Tyr Gln Gln Lys Pro Gly Lys Ala Pro Lys Leu Leu Ile
                 35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ser Leu Trp Thr
                 85                  90                  95

Phe Gly Gln Gly Thr Lys Val Glu Ile Lys Arg
                100                 105

<210> SEQ ID NO 47
<211> LENGTH: 123
```

```
<212> TYPE: PRT
<213> ORGANISM: Artificial Sequence
<220> FEATURE:
<223> OTHER INFORMATION: Synthetic sequence

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Gly Trp Ile Arg Gln Ala Pro Gly Lys Gly Leu Glu
        35                  40                  45

Trp Leu Ala Leu Ile Asp Trp Asp Asp Lys Tyr Tyr Ser Thr Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Thr Ala Val Ala Gly Asp Trp Phe Ala Tyr
            100                 105                 110

Trp Gly Gln Gly Thr Leu Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: Synthetic sequence

<400> SEQUENCE: 48

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Arg Thr Phe
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Trp Thr
                85                  90                  95

Phe Gly Gln Gly Thr Lys Val Glu Ile Lys Arg
            100                 105

<210> SEQ ID NO 49
<211> LENGTH: 123
<212> TYPE: PRT
<213> ORGANISM: Artificial Sequence
<220> FEATURE:
<223> OTHER INFORMATION: Synthetic sequence

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
```

```
                35                  40                  45
Trp Ile Gly Glu Ile Tyr His Ser Gly Ser Thr Tyr Tyr Ser Pro Ser
         50                  55                  60
Leu Lys Ser Arg Val Thr Ile Ser Arg Asp Asn Ser Lys Asn Thr Leu
 65                  70                  75                  80
Tyr Leu Gln Leu Asn Ser Leu Lys Ala Glu Asp Thr Ala Val Tyr Tyr
                 85                  90                  95
Cys Ala Arg Glu Gly Ser Asp Val Val Thr Gly Asp Trp Phe Ala Tyr
            100                 105                 110
Trp Gly Gln Gly Thr Leu Val Thr Val Ser Ser
            115                 120

<210> SEQ ID NO 50
<211> LENGTH: 107
<212> TYPE: PRT
<213> ORGANISM: Artificial Sequence
<220> FEATURE:
<223> OTHER INFORMATION: Synthetic sequence

<400> SEQUENCE: 50

Asp Ile Gln Leu Thr Gln Ser Pro Ser Ser Leu Ser Ala Ser Val Gly
  1               5                  10                  15
Asp Arg Val Thr Ile Thr Cys Arg Ala Ser Gln Gly Ile Ser Ser Val
             20                  25                  30
Leu Ala Trp Tyr Gln Gln Lys Pro Gly Lys Ala Pro Lys Leu Leu Ile
         35                  40                  45
Tyr Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Tyr Ser Leu Trp Thr
                 85                  90                  95
Phe Gly Gln Gly Thr Lys Val Glu Ile Lys Arg
            100                 105

<210> SEQ ID NO 51
<211> LENGTH: 123
<212> TYPE: PRT
<213> ORGANISM: Artificial Sequence
<220> FEATURE:
<223> OTHER INFORMATION: Synthetic sequence

<400> SEQUENCE: 51

Glu Val Gln Leu Val Glu Ser Gly Gly Gly Leu Val Gln Pro Gly Gly
  1               5                  10                  15
Ser Leu Arg Leu Ser Cys Ala Ala Ser Gly Tyr Ser Ile Thr Ser Gly
             20                  25                  30
His His Trp Ala Trp Ile Arg Gln Ala Pro Gly Lys Gly Leu Glu Trp
         35                  40                  45
Val Ser Ala Ile Ser Gly Asp Gly Ser Thr Thr Tyr Tyr Ala Asp Ser
 50                  55                  60
Val Lys Gly Arg Phe Thr Ile Ser Arg Asp Asn Ser Lys Asn Thr Leu
 65                  70                  75                  80
Tyr Leu Gln Leu Asn Ser Leu Arg Ala Glu Asp Thr Ala Val Tyr Tyr
                 85                  90                  95
Cys Ala Arg Glu Gly Ser Thr Ala Val Thr Gly Asp Trp Phe Ala Tyr
            100                 105                 110
```

Trp Gly Gln Gly Thr Leu Val Thr Val Ser Ser
            115                 120

<210> SEQ ID NO 52
<211> LENGTH: 106
<212> TYPE: PRT
<213> ORGANISM: Artificial Sequence
<220> FEATURE:
<223> OTHER INFORMATION: Synthetic sequence

<400> SEQUENCE: 52

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Arg Val Gly Tyr Val
            20                  25                  30

His Trp Tyr Gln Gln Lys Pro Gly Lys Ala Pro Lys Leu Leu Ile Tyr
        35                  40                  45

Asp Ala Ser Ser Leu Glu Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Gly Tyr Tyr Thr Trp Thr Phe
                85                  90                  95

Gly Gln Gly Thr Lys Val Glu Ile Lys Arg
            100                 105

<210> SEQ ID NO 53
<211> LENGTH: 123
<212> TYPE: PRT
<213> ORGANISM: Artificial Sequence
<220> FEATURE:
<223> OTHER INFORMATION: Synthetic sequence

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Gly Trp Ile Arg Gln Ala Pro Gly Lys Gly Leu Glu
        35                  40                  45

Trp Leu Ala Leu Ile Asp Trp Ala Gly Asp Lys Ser Tyr Ser Thr Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Glu Asp Ala Val Thr Gly Asp Trp Phe Ala Tyr
            100                 105                 110

Trp Gly Gln Gly Thr Leu Val Thr Val Ser Ser
            115                 120

<210> SEQ ID NO 54
<211> LENGTH: 107
<212> TYPE: PRT
<213> ORGANISM: Artificial Sequence
<220> FEATURE:
<223> OTHER INFORMATION: Synthetic sequence

<400> SEQUENCE: 54

Asp Ile Gln Leu Thr Gln Ser Pro Ser Ser Leu Ser Ala Ser Val Gly

-continued

```
            1               5                  10                 15
Asp Arg Val Thr Ile Thr Cys Gln Ala Ser Gln Asp Ile Arg Thr Tyr
                    20                  25                 30

Leu Ala Trp Tyr Gln Gln Lys Pro Gly Lys Ala Pro Lys Leu Leu Ile
            35                  40                 45

Tyr Asp Ala Ser Asn Arg Ala Thr Gly Ile Pro Ser Arg Phe Ser Gly
        50                  55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Gly Tyr Ser Ile Trp Thr
                85                  90                 95

Phe Gly Gln Gly Thr Lys Val Glu Ile Lys Arg
            100                 105
```

<210> SEQ ID NO 55
<211> LENGTH: 124
<212> TYPE: PRT
<213> ORGANISM: Artificial Sequence
<220> FEATURE:
<223> OTHER INFORMATION: Synthetic sequence

<400> SEQUENCE: 55

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Ser Leu Ser Thr Gly
            20                  25                 30

Gly Val Gly Val Gly Trp Ile Arg Gln Ala Pro Gly Lys Gly Leu Glu
        35                  40                 45

Trp Val Ser Gly Ile Ser Gly Tyr Gly Ser Thr Thr Tyr Tyr Ala Asp
    50                  55                 60

Ser Val Lys Gly Arg Phe Thr Ile Ser Arg Asp Asn Ser Lys Asn Thr
65                  70                 75                 80

Leu Tyr Leu Gln Leu Asn Ser Leu Arg Ala Glu Asp Thr Ala Val Tyr
                85                  90                 95

Tyr Cys Ala Arg Glu Gly Ser Asp Ala Val Ala Gly Asp Trp Phe Asp
            100                 105                110

Tyr Trp Gly Gln Gly Thr Leu Val Thr Val Ser Ser
        115                 120
```

<210> SEQ ID NO 56
<211> LENGTH: 107
<212> TYPE: PRT
<213> ORGANISM: Artificial Sequence
<220> FEATURE:
<223> OTHER INFORMATION: Synthetic sequence

<400> SEQUENCE: 56

```
Asp Ile Gln Leu Thr Gln Ser Pro Ser Ser Leu Ser Ala Ser Val Gly
1               5                  10                 15

Asp Arg Val Thr Ile Thr Cys Arg Ala Ser Gln Asp Ile Arg Ser Tyr
            20                  25                 30

Leu Ala Trp Tyr Gln Gln Lys Pro Gly Lys Ala Pro Lys Leu Leu Ile
            35                  40                 45

Tyr Asp Ala Ser Asn Arg Ala Thr Gly Ile Pro Ser Arg Phe Ser Gly
        50                  55                 60

Ser Gly Ser Gly Thr Asp Phe Thr Leu Thr Ile Ser Ser Leu Gln Pro
65                  70                 75                 80
```

Glu Asp Phe Ala Thr Tyr Tyr Cys Gln Gln Gly Tyr Ser Ile Trp Thr
                85                  90                  95

Phe Gly Gln Gly Thr Lys Val Glu Ile Lys Arg
            100                 105

<210> SEQ ID NO 57
<211> LENGTH: 119
<212> TYPE: PRT
<213> ORGANISM: Artificial Sequence
<220> FEATURE:
<223> OTHER INFORMATION: Synthetic sequence

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Gly Trp Ile Arg Gln Ala Pro Gly Lys Gly Leu Glu
        35                  40                  45

Trp Val Ser Gly Ile Ser Gly Asp Gly Gly Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Thr Arg Glu Asp Tyr Gly Pro His Ala Tyr Trp Gly Gln Gly
            100                 105                 110

Thr Leu Val Thr Val Ser Ser
        115

<210> SEQ ID NO 58
<211> LENGTH: 107
<212> TYPE: PRT
<213> ORGANISM: Artificial Sequence
<220> FEATURE:
<223> OTHER INFORMATION: Synthetic sequence

<400> SEQUENCE: 58

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Thr Thr Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Tyr Ser Thr
                85                  90                  95

Phe Gly Gln Gly Thr Lys Val Glu Ile Lys Arg
            100                 105

<210> SEQ ID NO 59
<211> LENGTH: 123
<212> TYPE: PRT
<213> ORGANISM: Artificial Sequence
<220> FEATURE:
<223> OTHER INFORMATION: Synthetic sequence

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

His Tyr Trp Ala Trp Ile Arg Gln Ala Pro Gly Lys Gly Leu Glu Trp
        35                  40                  45

Val Ser Ala Ile Ser Gly Ser Gly Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Leu Gly Asp Trp Phe Ala Tyr
            100                 105                 110

Trp Gly Gln Gly Thr Leu Val Thr Val Ser Ser
        115                 120

<210> SEQ ID NO 60
<211> LENGTH: 107
<212> TYPE: PRT
<213> ORGANISM: Artificial Sequence
<220> FEATURE:
<223> OTHER INFORMATION: Synthetic sequence

<400> SEQUENCE: 60

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Trp Thr
                85                  90                  95

Phe Gly Gln Gly Thr Lys Val Glu Ile Lys Arg
            100                 105

<210> SEQ ID NO 61
<211> LENGTH: 123
<212> TYPE: PRT
<213> ORGANISM: Artificial Sequence
<220> FEATURE:
<223> OTHER INFORMATION: Synthetic sequence

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

His Tyr Trp Ala Trp Ile Arg Gln Ala Pro Gly Lys Gly Leu Glu Trp
        35                  40                  45

Val Ser Ser Ile Ser Gly Tyr Gly Ser Thr Thr Tyr Tyr Ala Asp Ser
    50                  55                  60

Val Lys Gly Arg Phe Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Gly Gly Ser Asp Ala Val Leu Gly Asp Trp Phe Ala Tyr
            100                 105                 110

Trp Gly Gln Gly Thr Leu Val Thr Val Ser Ser
            115                 120

<210> SEQ ID NO 62
<211> LENGTH: 107
<212> TYPE: PRT
<213> ORGANISM: Artificial Sequence
<220> FEATURE:
<223> OTHER INFORMATION: Synthetic sequence

<400> SEQUENCE: 62

Asp Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Gly Ser Phe
                 20                  25                  30

Leu Ala Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Tyr Leu Trp Thr
                 85                  90                  95

Phe Gly Gln Gly Thr Lys Val Glu Ile Lys Arg
            100                 105

<210> SEQ ID NO 63
<211> LENGTH: 120
<212> TYPE: PRT
<213> ORGANISM: Artificial Sequence
<220> FEATURE:
<223> OTHER INFORMATION: Synthetic sequence

<400> SEQUENCE: 63

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Ile His Trp Val Arg Gln Ala Pro Gly Lys Gly Leu Glu Trp Val
             35                  40                  45

Ser Val Ile Ser Gly Asp Gly Asp Thr Thr Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                 85                  90                  95

Ala Arg Ser Arg Gly Leu Val Leu Asp Ala Phe Asp Tyr Trp Gly Gln
            100                 105                 110

Gly Thr Leu Val Thr Val Ser Ser
            115                 120

<210> SEQ ID NO 64

```
<211> LENGTH: 110
<212> TYPE: PRT
<213> ORGANISM: Artificial Sequence
<220> FEATURE:
<223> OTHER INFORMATION: Synthetic sequence

<400> SEQUENCE: 64

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Gly Arg
            20                  25                  30

Phe Leu Ala Trp Tyr Gln Gln Lys Pro Gly Lys Ala Pro Lys Leu Leu
        35                  40                  45

Ile Tyr Asp Ala Ser Ser Leu Glu Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asp Tyr Trp Pro
                85                  90                  95

Pro Tyr Thr Phe Gly Gln Gly Thr Lys Val Glu Ile Lys Arg
            100                 105                 110

<210> SEQ ID NO 65
<211> LENGTH: 123
<212> TYPE: PRT
<213> ORGANISM: Artificial Sequence
<220> FEATURE:
<223> OTHER INFORMATION: Synthetic sequence

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Ala Val Leu Gly Asp Trp Phe Ala Tyr
            100                 105                 110

Trp Gly Gln Gly Thr Leu Val Thr Val Ser Ser
        115                 120

<210> SEQ ID NO 66
<211> LENGTH: 107
<212> TYPE: PRT
<213> ORGANISM: Artificial Sequence
<220> FEATURE:
<223> OTHER INFORMATION: Synthetic sequence

<400> SEQUENCE: 66

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Tyr
            20                  25                  30
```

```
Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ser Ile Trp Thr
                 85                  90                  95

Phe Gly Gln Gly Thr Lys Val Glu Ile Lys Arg
                100                 105

<210> SEQ ID NO 67
<211> LENGTH: 123
<212> TYPE: PRT
<213> ORGANISM: Artificial Sequence
<220> FEATURE:
<223> OTHER INFORMATION: Synthetic sequence

<400> SEQUENCE: 67

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr Ser Gly
                20                  25                  30

His Tyr Trp Asn Trp Ile Arg Gln Ala Pro Gly Lys Gly Leu Glu Trp
            35                  40                  45

Val Ser Gly Ile Ser Gly Asp Gly Ser Ser Thr Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Gly Gly Ser Asp Ala Val Leu Gly Asp Trp Phe Ala Tyr
                100                 105                 110

Trp Gly Gln Gly Thr Leu Val Thr Val Ser Ser
            115                 120

<210> SEQ ID NO 68
<211> LENGTH: 107
<212> TYPE: PRT
<213> ORGANISM: Artificial Sequence
<220> FEATURE:
<223> OTHER INFORMATION: Synthetic sequence

<400> SEQUENCE: 68

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ser Thr Trp Thr
                 85                  90                  95

Phe Gly Gln Gly Thr Lys Val Glu Ile Lys Arg
                100                 105
```

<210> SEQ ID NO 69
<211> LENGTH: 123
<212> TYPE: PRT
<213> ORGANISM: Artificial Sequence
<220> FEATURE:
<223> OTHER INFORMATION: Synthetic sequence

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His Tyr Trp Thr Trp Ile Arg Gln Ala Pro Gly Lys Gly Leu Glu Trp
        35                  40                  45

Val Ser Ala Ile Ser Gly Ser Gly Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Ala Val Leu Gly Asp Trp Phe Ala Tyr
            100                 105                 110

Trp Gly Gln Gly Thr Leu Val Thr Val Ser Ser
        115                 120
```

<210> SEQ ID NO 70
<211> LENGTH: 107
<212> TYPE: PRT
<213> ORGANISM: Artificial Sequence
<220> FEATURE:
<223> OTHER INFORMATION: Synthetic sequence

<400> SEQUENCE: 70

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Gly Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gln Leu Trp Thr
                85                  90                  95

Phe Gly Gln Gly Thr Lys Val Glu Ile Lys Arg
            100                 105
```

<210> SEQ ID NO 71
<211> LENGTH: 123
<212> TYPE: PRT
<213> ORGANISM: Artificial Sequence
<220> FEATURE:
<223> OTHER INFORMATION: Synthetic sequence

<400> SEQUENCE: 71

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Ile Gly Asp Trp Phe Ala Tyr
            100                 105                 110

Trp Gly Gln Gly Thr Leu Val Thr Val Ser Ser
        115                 120

<210> SEQ ID NO 72
<211> LENGTH: 107
<212> TYPE: PRT
<213> ORGANISM: Artificial Sequence
<220> FEATURE:
<223> OTHER INFORMATION: Synthetic sequence

<400> SEQUENCE: 72

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys Arg
            100                 105

<210> SEQ ID NO 73
<211> LENGTH: 124
<212> TYPE: PRT
<213> ORGANISM: Artificial Sequence
<220> FEATURE:
<223> OTHER INFORMATION: Synthetic sequence

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Val Ser Gly Ile Ser Gly Ala Gly Asp Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
                100                 105                 110

Tyr Trp Gly Gln Gly Thr Leu Val Thr Val Ser Ser
        115                 120

<210> SEQ ID NO 74
<211> LENGTH: 107
<212> TYPE: PRT
<213> ORGANISM: Artificial Sequence
<220> FEATURE:
<223> OTHER INFORMATION: Synthetic sequence

<400> SEQUENCE: 74

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ile Trp Thr
                85                  90                  95

Phe Gly Gln Gly Thr Lys Val Glu Ile Lys Arg
            100                 105

<210> SEQ ID NO 75
<211> LENGTH: 123
<212> TYPE: PRT
<213> ORGANISM: Artificial Sequence
<220> FEATURE:
<223> OTHER INFORMATION: Synthetic sequence

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Ala Trp Ile Arg Gln Ala Pro Gly Lys Gly Leu Glu
        35                  40                  45

Trp Leu Ala Leu Ile Asp Trp Asp Asp Lys Arg Tyr Ser Thr Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Thr Val Val Gly Asp Trp Phe Asp Tyr
            100                 105                 110

Trp Gly Gln Gly Thr Leu Val Thr Val Ser Ser
        115                 120

<210> SEQ ID NO 76
<211> LENGTH: 107
<212> TYPE: PRT
<213> ORGANISM: Artificial Sequence
<220> FEATURE:
<223> OTHER INFORMATION: Synthetic sequence

```
<400> SEQUENCE: 76

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Thr Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
                85                  90                  95

Phe Gly Gln Gly Thr Lys Val Glu Ile Lys Arg
            100                 105

<210> SEQ ID NO 77
<211> LENGTH: 124
<212> TYPE: PRT
<213> ORGANISM: Artificial Sequence
<220> FEATURE:
<223> OTHER INFORMATION: Synthetic sequence

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Ala Trp Ile Arg Gln Ala Pro Gly Lys Gly Leu Glu
        35                  40                  45

Trp Val Ser Tyr Ile Ser Gly Asp Gly Ser Thr Tyr Tyr Ala Asp Ser
50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Val Val Ala Gly Asp Trp Phe Ala
            100                 105                 110

Tyr Trp Gly Gln Gly Thr Leu Val Thr Val Ser Ser
        115                 120

<210> SEQ ID NO 78
<211> LENGTH: 107
<212> TYPE: PRT
<213> ORGANISM: Artificial Sequence
<220> FEATURE:
<223> OTHER INFORMATION: Synthetic sequence

<400> SEQUENCE: 78

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Gln Ile Trp Thr
                 85                  90                  95

Phe Gly Gln Gly Thr Lys Val Glu Ile Lys Arg
            100                 105

<210> SEQ ID NO 79
<211> LENGTH: 119
<212> TYPE: PRT
<213> ORGANISM: Artificial Sequence
<220> FEATURE:
<223> OTHER INFORMATION: Synthetic sequence

<400> SEQUENCE: 79

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ser Ile Ser Ser Gly
             20                  25                  30

Tyr His Trp Ala Trp Ile Arg Gln Ala Pro Gly Lys Gly Leu Glu Trp
         35                  40                  45

Ile Gly Glu Ile Tyr His Ser Gly Ser Thr Tyr Tyr Ser Pro Ser Leu
     50                  55                  60

Lys Ser Arg Val Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                 85                  90                  95

Ala Arg Ser Pro Tyr Tyr Tyr Gly Val Phe Asp Tyr Trp Gly Gln Gly
            100                 105                 110

Thr Leu Val Thr Val Ser Ser
        115

<210> SEQ ID NO 80
<211> LENGTH: 107
<212> TYPE: PRT
<213> ORGANISM: Artificial Sequence
<220> FEATURE:
<223> OTHER INFORMATION: Synthetic sequence

<400> SEQUENCE: 80

Asp Ile Gln Leu Thr Gln Ser Pro Ser Ser Leu Ser Ala Ser Val Gly
  1               5                  10                  15

Asp Arg Val Thr Ile Thr Cys Ser Ala Ser Ser Arg Val Gly Ser Val
             20                  25                  30

Tyr Trp Tyr Gln Gln Lys Pro Gly Lys Ala Pro Lys Leu Leu Ile Tyr
         35                  40                  45

Asp Ala Ser Asn Leu Glu Thr Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Tyr Thr His Asp Pro Val Thr
                 85                  90                  95

Phe Gly Gln Gly Thr Lys Val Glu Ile Lys Arg
            100                 105

<210> SEQ ID NO 81
<211> LENGTH: 124
<212> TYPE: PRT
```

<213> ORGANISM: Artificial Sequence
<220> FEATURE:
<223> OTHER INFORMATION: Synthetic sequence

<400> SEQUENCE: 81

```
Glu Val Gln Leu Val Glu Ser Gly Gly Gly Leu Val Gln Pro Gly Ala
1               5                   10                  15

Ser Leu Arg Leu Ser Cys Ala Ala Ser Gly Phe Ser Leu Ser Thr Gly
            20                  25                  30

Gly Val Gly Val Ala Trp Ile Arg Gln Ala Pro Gly Lys Gly Leu Glu
        35                  40                  45

Trp Val Ser Ser Ile Ser Gly Tyr Gly Ser Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Ala Val Leu Gly Asp Trp Phe Gly
            100                 105                 110

Tyr Trp Gly Gln Gly Thr Leu Val Thr Val Ser Ser
        115                 120
```

<210> SEQ ID NO 82
<211> LENGTH: 107
<212> TYPE: PRT
<213> ORGANISM: Artificial Sequence
<220> FEATURE:
<223> OTHER INFORMATION: Synthetic sequence

<400> SEQUENCE: 82

```
Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Thr Thr Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys Arg
            100                 105
```

<210> SEQ ID NO 83
<211> LENGTH: 123
<212> TYPE: PRT
<213> ORGANISM: Artificial Sequence
<220> FEATURE:
<223> OTHER INFORMATION: Synthetic sequence

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr His Trp Ser Trp Ile Arg Gln Ala Pro Gly Lys Gly Leu Glu Trp
        35                  40                  45
```

Val Ser Ser Ile Ser Gly Tyr Gly Asp Thr Thr Tyr Ala Asp Ser
            50                  55                  60

Val Lys Gly Arg Phe Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Glu Gly Ser Asp Thr Val Leu Gly Asp Trp Phe Ala Tyr
            100                 105                 110

Trp Gly Gln Gly Thr Leu Val Thr Val Ser Ser
            115                 120

<210> SEQ ID NO 84
<211> LENGTH: 107
<212> TYPE: PRT
<213> ORGANISM: Artificial Sequence
<220> FEATURE:
<223> OTHER INFORMATION: Synthetic sequence

<400> SEQUENCE: 84

Asp Ile Gln Leu Thr Gln Ser Pro Ser Ser Leu Ser Ala Ser Val Gly
 1               5                  10                  15

Asp Arg Val Thr Ile Thr Cys Gln Ala Ser Gln Asp Ile Arg Thr Tyr
             20                  25                  30

Leu Ala Trp Tyr Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ser Ile Trp Thr
                 85                  90                  95

Phe Gly Gln Gly Thr Lys Val Glu Ile Lys Arg
            100                 105

<210> SEQ ID NO 85
<211> LENGTH: 123
<212> TYPE: PRT
<213> ORGANISM: Artificial Sequence
<220> FEATURE:
<223> OTHER INFORMATION: Synthetic sequence

<400> SEQUENCE: 85

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Ser Ser Gly
             20                  25                  30

His His Trp Ala Trp Ile Arg Gln Ala Pro Gly Lys Gly Leu Glu Trp
         35                  40                  45

Val Ser Val Ile Ser Gly Ser Gly Ser Ser Thr Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Glu Gly Ser Asp Thr Val Leu Gly Asp Trp Phe Ala Tyr
            100                 105                 110

Trp Gly Gln Gly Thr Leu Val Thr Val Ser Ser

<210> SEQ ID NO 86
<211> LENGTH: 107
<212> TYPE: PRT
<213> ORGANISM: Artificial Sequence
<220> FEATURE:
<223> OTHER INFORMATION: Synthetic sequence

<400> SEQUENCE: 86

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Trp Thr
                85                  90                  95

Phe Gly Gln Gly Thr Lys Val Glu Ile Lys Arg
            100                 105
```

<210> SEQ ID NO 87
<211> LENGTH: 123
<212> TYPE: PRT
<213> ORGANISM: Artificial Sequence
<220> FEATURE:
<223> OTHER INFORMATION: Synthetic sequence

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Gly Trp Ile Arg Gln Ala Pro Gly Lys Gly Leu Glu
        35                  40                  45

Trp Leu Ala Leu Ile Asp Trp Asp Gly Asp Lys Ser Tyr Ser Thr Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Thr Ala Val Val Gly Asp Trp Phe Asp Tyr
            100                 105                 110

Trp Gly Gln Gly Thr Leu Val Thr Val Ser Ser
        115                 120
```

<210> SEQ ID NO 88
<211> LENGTH: 107
<212> TYPE: PRT
<213> ORGANISM: Artificial Sequence
<220> FEATURE:
<223> OTHER INFORMATION: Synthetic sequence

<400> SEQUENCE: 88

```
Asp Ile Gln Leu Thr Gln Ser Pro Ser Ser Leu Ser Ala Ser Val Gly
1               5                   10                  15
```

Asp Arg Val Thr Ile Thr Cys Arg Ala Ser Gln Gly Ile Ser Arg Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
                85                  90                  95

Phe Gly Gln Gly Thr Lys Val Glu Ile Lys Arg
            100                 105

<210> SEQ ID NO 89
<211> LENGTH: 124
<212> TYPE: PRT
<213> ORGANISM: Artificial Sequence
<220> FEATURE:
<223> OTHER INFORMATION: Synthetic sequence

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Ala Trp Ile Arg Gln Ala Pro Gly Lys Gly Leu Glu
        35                  40                  45

Trp Val Ser Ser Ile Ser Gly Ala Gly Thr Thr Tyr Tyr Ala Asp Ser
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Gly Gly Ser Thr Ala Val Thr Gly Asp Trp Phe Asp
            100                 105                 110

Tyr Trp Gly Gln Gly Thr Leu Val Thr Val Ser Ser
        115                 120

<210> SEQ ID NO 90
<211> LENGTH: 107
<212> TYPE: PRT
<213> ORGANISM: Artificial Sequence
<220> FEATURE:
<223> OTHER INFORMATION: Synthetic sequence

<400> SEQUENCE: 90

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr

-continued

```
                85                  90                  95

Phe Gly Gln Gly Thr Lys Val Glu Ile Lys Arg
            100                 105
```

<210> SEQ ID NO 91
<211> LENGTH: 124
<212> TYPE: PRT
<213> ORGANISM: Artificial Sequence
<220> FEATURE:
<223> OTHER INFORMATION: Synthetic sequence

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Ala Trp Ile Arg Gln Ala Pro Gly Lys Gly Leu Glu
        35                  40                  45

Trp Val Ser Tyr Ile Ser Ser Gly Asp Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Val Gly Asp Trp Phe Ala
            100                 105                 110

Tyr Trp Gly Gln Gly Thr Leu Val Thr Val Ser Ser
        115                 120
```

<210> SEQ ID NO 92
<211> LENGTH: 108
<212> TYPE: PRT
<213> ORGANISM: Artificial Sequence
<220> FEATURE:
<223> OTHER INFORMATION: Synthetic sequence

<400> SEQUENCE: 92

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                85                  90                  95

Thr Phe Gly Gln Gly Thr Lys Val Glu Ile Lys Arg
            100                 105
```

<210> SEQ ID NO 93
<211> LENGTH: 124
<212> TYPE: PRT
<213> ORGANISM: Artificial Sequence
<220> FEATURE:
<223> OTHER INFORMATION: Synthetic sequence

<400> SEQUENCE: 93

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Val Ser Tyr Ile Ser Gly Asp Gly Asp Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Ala Gly Asp Trp Phe Ala
            100                 105                 110

Tyr Trp Gly Gln Gly Thr Leu Val Thr Val Ser Ser
        115                 120
```

<210> SEQ ID NO 94
<211> LENGTH: 108
<212> TYPE: PRT
<213> ORGANISM: Artificial Sequence
<220> FEATURE:
<223> OTHER INFORMATION: Synthetic sequence

<400> SEQUENCE: 94

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                85                  90                  95

Thr Phe Gly Gln Gly Thr Lys Val Glu Ile Lys Arg
            100                 105
```

<210> SEQ ID NO 95
<211> LENGTH: 124
<212> TYPE: PRT
<213> ORGANISM: Artificial Sequence
<220> FEATURE:
<223> OTHER INFORMATION: Synthetic sequence

<400> SEQUENCE: 95

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Ala Trp Ile Arg Gln Ala Pro Gly Lys Gly Leu Glu
        35                  40                  45

Trp Val Ser Ser Ile Ser Gly Tyr Gly Gly Thr Thr Tyr Tyr Ala Asp
    50                  55                  60

Ser Val Lys Gly Arg Phe Thr Ile Ser Arg Asp Asn Ser Lys Asn Thr
```

```
                65                  70                  75                  80
Leu Tyr Leu Gln Leu Asn Ser Leu Arg Ala Glu Asp Thr Ala Val Tyr
                    85                  90                  95

Tyr Cys Ala Arg Glu Gly Ser Asp Thr Val Leu Gly Asp Trp Phe Ala
                100                 105                 110

Tyr Trp Gly Gln Gly Thr Leu Val Thr Val Ser Ser
            115                 120

<210> SEQ ID NO 96
<211> LENGTH: 108
<212> TYPE: PRT
<213> ORGANISM: Artificial Sequence
<220> FEATURE:
<223> OTHER INFORMATION: Synthetic sequence

<400> SEQUENCE: 96

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                85                  90                  95

Thr Phe Gly Gln Gly Thr Lys Val Glu Ile Lys Arg
            100                 105

<210> SEQ ID NO 97
<211> LENGTH: 124
<212> TYPE: PRT
<213> ORGANISM: Artificial Sequence
<220> FEATURE:
<223> OTHER INFORMATION: Synthetic sequence

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
                20                  25                  30

Gly Val Gly Val Gly Trp Ile Arg Gln Ala Pro Gly Lys Gly Leu Glu
            35                  40                  45

Trp Val Ser Tyr Ile Ser Gly Ala Gly Thr Thr Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
                100                 105                 110

Tyr Trp Gly Gln Gly Thr Leu Val Thr Val Ser Ser
            115                 120

<210> SEQ ID NO 98
<211> LENGTH: 108
```

<212> TYPE: PRT
<213> ORGANISM: Artificial Sequence
<220> FEATURE:
<223> OTHER INFORMATION: Synthetic sequence

<400> SEQUENCE: 98

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                85                  90                  95

Thr Phe Gly Gln Gly Thr Lys Val Glu Ile Lys Arg
            100                 105
```

<210> SEQ ID NO 99
<211> LENGTH: 124
<212> TYPE: PRT
<213> ORGANISM: Artificial Sequence
<220> FEATURE:
<223> OTHER INFORMATION: Synthetic sequence

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Val Ser Tyr Ile Ser Gly Ala Gly Gly Thr Thr Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Ala Val Leu Gly Asp Trp Phe Ala
            100                 105                 110

Tyr Trp Gly Gln Gly Thr Leu Val Thr Val Ser Ser
        115                 120
```

<210> SEQ ID NO 100
<211> LENGTH: 108
<212> TYPE: PRT
<213> ORGANISM: Artificial Sequence
<220> FEATURE:
<223> OTHER INFORMATION: Synthetic sequence

<400> SEQUENCE: 100

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
```

-continued

```
                35                  40                  45
Tyr Asp Ala Ser Asn Leu Glu Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Thr Thr Pro Leu
                 85                  90                  95

Thr Phe Gly Gln Gly Thr Lys Val Glu Ile Lys Arg
                100                 105

<210> SEQ ID NO 101
<211> LENGTH: 124
<212> TYPE: PRT
<213> ORGANISM: Artificial Sequence
<220> FEATURE:
<223> OTHER INFORMATION: Synthetic sequence

<400> SEQUENCE: 101

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Thr Gly
                20                  25                  30

Gly Val Gly Val Gly Trp Ile Arg Gln Ala Pro Gly Lys Gly Leu Glu
             35                  40                  45

Trp Val Ser Tyr Ile Ser Gly Asp Gly Asp Thr Thr Tyr Tyr Ala Asp
         50                  55                  60

Ser Val Lys Gly Arg Phe Thr Ile Ser Arg Asp Asn Ser Lys Asn Thr
 65                  70                  75                  80

Leu Tyr Leu Gln Leu Asn Ser Leu Arg Ala Glu Asp Thr Ala Val Tyr
                 85                  90                  95

Tyr Cys Ala Arg Glu Gly Ser Thr Ala Val Leu Gly Asp Trp Phe Ala
                100                 105                 110

Tyr Trp Gly Gln Gly Thr Leu Val Thr Val Ser Ser
            115                 120

<210> SEQ ID NO 102
<211> LENGTH: 108
<212> TYPE: PRT
<213> ORGANISM: Artificial Sequence
<220> FEATURE:
<223> OTHER INFORMATION: Synthetic sequence

<400> SEQUENCE: 102

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Thr Thr Pro Leu
                 85                  90                  95

Thr Phe Gly Gln Gly Thr Lys Val Glu Ile Lys Arg
                100                 105
```

<210> SEQ ID NO 103
<211> LENGTH: 124
<212> TYPE: PRT
<213> ORGANISM: Artificial Sequence
<220> FEATURE:
<223> OTHER INFORMATION: Synthetic sequence

<400> SEQUENCE: 103

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Val Ser Tyr Ile Ser Gly Asp Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Thr Ala Val Val Gly Asp Trp Phe Ala
            100                 105                 110

Tyr Trp Gly Gln Gly Thr Leu Val Thr Val Ser Ser
        115                 120
```

<210> SEQ ID NO 104
<211> LENGTH: 108
<212> TYPE: PRT
<213> ORGANISM: Artificial Sequence
<220> FEATURE:
<223> OTHER INFORMATION: Synthetic sequence

<400> SEQUENCE: 104

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                85                  90                  95

Thr Phe Gly Gln Gly Thr Lys Val Glu Ile Lys Arg
            100                 105
```

<210> SEQ ID NO 105
<211> LENGTH: 124
<212> TYPE: PRT
<213> ORGANISM: Artificial Sequence
<220> FEATURE:
<223> OTHER INFORMATION: Synthetic sequence

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
```

```
                    20                  25                  30

Gly Val Gly Val Ala Trp Ile Arg Gln Ala Pro Gly Lys Gly Leu Glu
            35                  40                  45

Trp Val Ser Tyr Ile Ser Gly Tyr Gly Gly Thr Thr Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Thr Ala Val Leu Gly Asp Trp Phe Ala
            100                 105                 110

Tyr Trp Gly Gln Gly Thr Leu Val Thr Val Ser Ser
            115                 120

<210> SEQ ID NO 106
<211> LENGTH: 108
<212> TYPE: PRT
<213> ORGANISM: Artificial Sequence
<220> FEATURE:
<223> OTHER INFORMATION: Synthetic sequence

<400> SEQUENCE: 106

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 107
<211> LENGTH: 124
<212> TYPE: PRT
<213> ORGANISM: Artificial Sequence
<220> FEATURE:
<223> OTHER INFORMATION: Synthetic sequence

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Met Gly Val Gly Trp Ile Arg Gln Ala Pro Gly Lys Gly Leu Glu
        35                  40                  45

Trp Val Ser Tyr Ile Ser Gly Tyr Gly Gly Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95
```

```
Tyr Cys Ala Arg Glu Gly Ser Asp Val Val Ala Gly Asp Trp Phe Ala
                100                 105                 110

Tyr Trp Gly Gln Gly Thr Leu Val Thr Val Ser Ser
        115                 120

<210> SEQ ID NO 108
<211> LENGTH: 108
<212> TYPE: PRT
<213> ORGANISM: Artificial Sequence
<220> FEATURE:
<223> OTHER INFORMATION: Synthetic sequence

<400> SEQUENCE: 108

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 109
<211> LENGTH: 123
<212> TYPE: PRT
<213> ORGANISM: Artificial Sequence
<220> FEATURE:
<223> OTHER INFORMATION: Synthetic sequence

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His His Trp Asp Trp Ile Arg Gln Ala Pro Gly Lys Gly Leu Glu Trp
        35                  40                  45

Val Ser Tyr Ile Ser Gly Ala Gly Asp Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Asp Ala Val Leu Gly Asp Trp Phe Ala Tyr
            100                 105                 110

Trp Gly Gln Gly Thr Leu Val Thr Val Ser Ser
        115                 120

<210> SEQ ID NO 110
<211> LENGTH: 108
<212> TYPE: PRT
<213> ORGANISM: Artificial Sequence
<220> FEATURE:
<223> OTHER INFORMATION: Synthetic sequence
```

```
<400> SEQUENCE: 110

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 111
<211> LENGTH: 124
<212> TYPE: PRT
<213> ORGANISM: Artificial Sequence
<220> FEATURE:
<223> OTHER INFORMATION: Synthetic sequence

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Val Ser Tyr Ile Ser Gly Asp Gly Gly Ser Thr Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
            100                 105                 110

Tyr Trp Gly Gln Gly Thr Leu Val Thr Val Ser Ser
        115                 120

<210> SEQ ID NO 112
<211> LENGTH: 108
<212> TYPE: PRT
<213> ORGANISM: Artificial Sequence
<220> FEATURE:
<223> OTHER INFORMATION: Synthetic sequence

<400> SEQUENCE: 112

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 113
<211> LENGTH: 124
<212> TYPE: PRT
<213> ORGANISM: Artificial Sequence
<220> FEATURE:
<223> OTHER INFORMATION: Synthetic sequence

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
                20                  25                  30

Gly Val Gly Val Gly Trp Ile Arg Gln Ala Pro Gly Lys Gly Leu Glu
            35                  40                  45

Trp Val Ser Tyr Ile Ser Gly Ala Gly Ser Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
            100                 105                 110

Tyr Trp Gly Gln Gly Thr Leu Val Thr Val Ser Ser
        115                 120

<210> SEQ ID NO 114
<211> LENGTH: 108
<212> TYPE: PRT
<213> ORGANISM: Artificial Sequence
<220> FEATURE:
<223> OTHER INFORMATION: Synthetic sequence

<400> SEQUENCE: 114

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 115
<211> LENGTH: 124
<212> TYPE: PRT
<213> ORGANISM: Artificial Sequence

```
<220> FEATURE:
<223> OTHER INFORMATION: Synthetic sequence

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Ser Trp Ile Arg Gln Ala Pro Gly Lys Gly Leu Glu
        35                  40                  45

Trp Val Ser Tyr Ile Ser Gly Ser Gly Asp Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Ala Val Leu Gly Asp Trp Phe Ala
            100                 105                 110

Tyr Trp Gly Gln Gly Thr Leu Val Thr Val Ser Ser
        115                 120

<210> SEQ ID NO 116
<211> LENGTH: 108
<212> TYPE: PRT
<213> ORGANISM: Artificial Sequence
<220> FEATURE:
<223> OTHER INFORMATION: Synthetic sequence

<400> SEQUENCE: 116

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 117
<211> LENGTH: 124
<212> TYPE: PRT
<213> ORGANISM: Artificial Sequence
<220> FEATURE:
<223> OTHER INFORMATION: Synthetic sequence

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45
```

Trp Val Ser Tyr Ile Ser Gly Asp Gly Asp Thr Thr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Thr Thr Val Leu Gly Asp Trp Phe Ala
                100                 105                 110

Tyr Trp Gly Gln Gly Thr Leu Val Thr Val Ser Ser
            115                 120

<210> SEQ ID NO 118
<211> LENGTH: 108
<212> TYPE: PRT
<213> ORGANISM: Artificial Sequence
<220> FEATURE:
<223> OTHER INFORMATION: Synthetic sequence

<400> SEQUENCE: 118

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 119
<211> LENGTH: 124
<212> TYPE: PRT
<213> ORGANISM: Artificial Sequence
<220> FEATURE:
<223> OTHER INFORMATION: Synthetic sequence

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Ala Trp Ile Arg Gln Ala Pro Gly Lys Gly Leu Glu
        35                  40                  45

Trp Val Ser Tyr Ile Ser Gly Asp Gly Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
                100                 105                 110

Tyr Trp Gly Gln Gly Thr Leu Val Thr Val Ser Ser
            115                 120

<210> SEQ ID NO 120
<211> LENGTH: 108
<212> TYPE: PRT
<213> ORGANISM: Artificial Sequence
<220> FEATURE:
<223> OTHER INFORMATION: Synthetic sequence

<400> SEQUENCE: 120

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg
            100                 105
```

<210> SEQ ID NO 121
<211> LENGTH: 124
<212> TYPE: PRT
<213> ORGANISM: Artificial Sequence
<220> FEATURE:
<223> OTHER INFORMATION: Synthetic sequence

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Val Ser Tyr Ile Ser Gly Ala Gly Asp Ser Thr Tyr Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
            100                 105                 110

Tyr Trp Gly Gln Gly Thr Leu Val Thr Val Ser Ser
        115                 120
```

<210> SEQ ID NO 122
<211> LENGTH: 108
<212> TYPE: PRT
<213> ORGANISM: Artificial Sequence
<220> FEATURE:
<223> OTHER INFORMATION: Synthetic sequence

<400> SEQUENCE: 122

```
Asp Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Gly Val Ser Ser Tyr
             20                  25                  30

Leu Ala Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                 85                  90                  95

Thr Phe Gly Gln Gly Thr Lys Val Glu Ile Lys Arg
            100                 105
```

```
<210> SEQ ID NO 123
<211> LENGTH: 124
<212> TYPE: PRT
<213> ORGANISM: Artificial Sequence
<220> FEATURE:
<223> OTHER INFORMATION: Synthetic sequence

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
             20                  25                  30

Gly Val Gly Val Ala Trp Ile Arg Gln Ala Pro Gly Lys Gly Leu Glu
         35                  40                  45

Trp Val Ser Ser Ile Ser Gly Tyr Gly Gly Thr Thr Tyr Tyr Ala Asp
     50                  55                  60

Ser Val Lys Gly Arg Phe Thr Ile Ser Arg Asp Asn Ser Lys Asn Arg
65                  70                  75                  80

Leu Tyr Leu Gln Leu Asn Ser Leu Arg Ala Glu Asp Thr Ala Val Tyr
                 85                  90                  95

Tyr Cys Ala Arg Glu Gly Ser Asp Thr Val Leu Gly Asp Trp Phe Ala
            100                 105                 110

Tyr Trp Gly Gln Gly Thr Leu Val Thr Val Ser Ser
        115                 120
```

```
<210> SEQ ID NO 124
<211> LENGTH: 108
<212> TYPE: PRT
<213> ORGANISM: Artificial Sequence
<220> FEATURE:
<223> OTHER INFORMATION: Synthetic sequence

<400> SEQUENCE: 124

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Tyr
             20                  25                  30

Leu Ala Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                 85                  90                  95
```

```
Thr Phe Gly Gln Gly Thr Lys Val Glu Ile Lys Arg
            100                 105
```

```
<210> SEQ ID NO 125
<211> LENGTH: 124
<212> TYPE: PRT
<213> ORGANISM: Artificial Sequence
<220> FEATURE:
<223> OTHER INFORMATION: Synthetic sequence

<400> SEQUENCE: 125
```

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Val Ser Ser Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
            100                 105                 110

Tyr Trp Gly Gln Gly Thr Leu Val Thr Val Ser Ser
            115                 120
```

```
<210> SEQ ID NO 126
<211> LENGTH: 108
<212> TYPE: PRT
<213> ORGANISM: Artificial Sequence
<220> FEATURE:
<223> OTHER INFORMATION: Synthetic sequence

<400> SEQUENCE: 126
```

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Pro Leu
                85                  90                  95

Thr Phe Gly Gln Gly Thr Lys Val Glu Ile Lys Arg
            100                 105
```

```
<210> SEQ ID NO 127
<211> LENGTH: 123
<212> TYPE: PRT
<213> ORGANISM: Artificial Sequence
<220> FEATURE:
<223> OTHER INFORMATION: Synthetic sequence

<400> SEQUENCE: 127
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Ile Gly Asp Ile Tyr His Ser Gly Ser Thr Tyr Tyr Asn Pro Ser
    50                  55                  60

Leu Lys Ser Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Thr Ala Val Leu Gly Asp Trp Phe Ala Tyr
            100                 105                 110

Trp Gly Gln Gly Thr Leu Val Thr Val Ser Ser
            115                 120

<210> SEQ ID NO 128
<211> LENGTH: 108
<212> TYPE: PRT
<213> ORGANISM: Artificial Sequence
<220> FEATURE:
<223> OTHER INFORMATION: Synthetic sequence

<400> SEQUENCE: 128

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 129
<211> LENGTH: 123
<212> TYPE: PRT
<213> ORGANISM: Artificial Sequence
<220> FEATURE:
<223> OTHER INFORMATION: Synthetic sequence

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Thr Trp Ile Arg Gln Ala Pro Gly Lys Ser Leu Glu
        35                  40                  45

Trp Ile Gly Asp Ile Tyr His Ser Gly Ser Thr Tyr Tyr Ser Pro Ser
    50                  55                  60

Leu Lys Ser Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Asp Ala Val Ala Gly Asp Trp Phe Asp Tyr
            100                 105                 110

Trp Gly Gln Gly Thr Leu Val Thr Val Ser Ser
        115                 120

<210> SEQ ID NO 130
<211> LENGTH: 108
<212> TYPE: PRT
<213> ORGANISM: Artificial Sequence
<220> FEATURE:
<223> OTHER INFORMATION: Synthetic sequence

<400> SEQUENCE: 130

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 131
<211> LENGTH: 123
<212> TYPE: PRT
<213> ORGANISM: Artificial Sequence
<220> FEATURE:
<223> OTHER INFORMATION: Synthetic sequence

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Ala Trp Ile Arg Gln Ala Pro Gly Lys Gly Leu Glu
        35                  40                  45

Trp Ile Gly Asp Ile Tyr His Ser Gly Asn Thr Tyr Tyr Asn Pro Ser
    50                  55                  60

Leu Lys Ser Arg Val Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Val Gly Asp Trp Phe Ala Tyr
            100                 105                 110

Trp Gly Gln Gly Thr Leu Val Thr Val Ser Ser
        115                 120

<210> SEQ ID NO 132
<211> LENGTH: 108
<212> TYPE: PRT

<213> ORGANISM: Artificial Sequence
<220> FEATURE:
<223> OTHER INFORMATION: Synthetic sequence

<400> SEQUENCE: 132

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105
```

<210> SEQ ID NO 133
<211> LENGTH: 351
<212> TYPE: DNA
<213> ORGANISM: Artificial Sequence
<220> FEATURE:
<223> OTHER INFORMATION: Synthetic sequence

<400> SEQUENCE: 133

```
gaggttcagc tggtggagtc tggcggtggc ctggtgcagc caggggggctc actccgtttg    60
tcctgtgcag cttccggatt caccttcacc agctacggta ttcactgggt gcgtcaggcc   120
ccgggtaagg gcctcgagtg ggtgtctggt atctctggtg ccggtgatac tacctactac   180
gccgactctg tcaagggccg tttcactata agtcgcgaca attcgaaaaa cacactgtac   240
ctacaactga acagcttaag agctgaggac actgccgtct attattgcgc cagagaacgt   300
gattacgact cgattactg gggtcaagga acactagtca ccgtctcctc g             351
```

<210> SEQ ID NO 134
<211> LENGTH: 324
<212> TYPE: DNA
<213> ORGANISM: Artificial Sequence
<220> FEATURE:
<223> OTHER INFORMATION: Synthetic sequence

<400> SEQUENCE: 134

```
gatatccagt tgacccagtc cccgagttcc ctgtccgcct ctgtgggcga tcgggtcacc    60
atcacctgcc gtgcctctca gtctgtgtct tcttacctgg cctggtatca acagaaacca   120
ggaaaagctc cgaagcttct gatctacgac gcctctaacc tggaaaccgg tgtgccatct   180
cgcttctctg gatccggttc cgggacggat ttcactctga ccatcagcag tctgcagccg   240
gaagacttcg caacttacta ctgccagcag tcttactcta cctctcacac cttcggtcag   300
ggtaccaagg tggagatcaa acga                                          324
```

<210> SEQ ID NO 135
<211> LENGTH: 369
<212> TYPE: DNA
<213> ORGANISM: Artificial Sequence
<220> FEATURE:
<223> OTHER INFORMATION: Synthetic sequence

<400> SEQUENCE: 135

```
gaggttcagc tggtggagtc tggcggtggc ctggtgcagc cagggggctc actccgtttg    60
tcctgtgcag cttccggatt ctctctgtct accagcggtg tggctgtgag ctggattcgt   120
caggccccgg gtaagggcct cgagtggatc ggtatcatca acccaaactt cggtgatact   180
aactacgccc agaagttcca gggtcgtgtg actataagtc gcgacaattc gaaaaacaca   240
ctgtacctac aactgaacag cttaagagct gaggacactg ccgtctatta ttgcgccaga   300
gacgaatact acggtggctc ttactacttc gactactggg gtcaaggaac actagtcacc   360
gtctcctcg                                                           369
```

<210> SEQ ID NO 136
<211> LENGTH: 324
<212> TYPE: DNA
<213> ORGANISM: Artificial Sequence
<220> FEATURE:
<223> OTHER INFORMATION: Synthetic sequence

<400> SEQUENCE: 136

```
gatatccagt tgacccagtc cccgagttcc ctgtccgcct ctgtgggcga tcgggtcacc    60
atcacctgcc gtgcctctca ggacgtgcgc accgccgtgg cctggtatca acagaaacca   120
ggaaaagctc cgaagcttct gatctacgac gcctctaacc tggaaaccgg tgtgccatct   180
cgcttctctg gatccggttc cgggacggat ttcactctga ccatcagcag tctgcagccg   240
gaagacttcg caacttatta ctgccagcag tcctacgact ggcctccgac cttcggacag   300
ggtaccaagg tggagatcaa acga                                          324
```

<210> SEQ ID NO 137
<211> LENGTH: 363
<212> TYPE: DNA
<213> ORGANISM: Artificial Sequence
<220> FEATURE:
<223> OTHER INFORMATION: Synthetic sequence

<400> SEQUENCE: 137

```
gaggttcagc tggtggagtc tggcggtggc ctggtgcagc cagggggctc actccgtttg    60
tcctgtgcag cttccggatt ctctctgtct accggcggtg tgggtgtgag ctggattcgt   120
caggccccgg gtaagggcct cgagtgggtg tcttccatct ctggttccgg tggtactacc   180
tactacgccg actctgtcaa gggccgtttc actataagtc gcgacaattc gaaaaacaca   240
ctgtacctac aactgaacag cttaagagct gaggacactg ccgtctatta ttgcgccaga   300
gacgacctat actcctggta cttcgacgtg tggggtcaag gaacactagt caccgtctcc   360
tcg                                                                 363
```

<210> SEQ ID NO 138
<211> LENGTH: 321
<212> TYPE: DNA
<213> ORGANISM: Artificial Sequence
<220> FEATURE:
<223> OTHER INFORMATION: Synthetic sequence

<400> SEQUENCE: 138

```
gatatccagt tgacccagtc cccgagttcc ctgtccgcct ctgtgggcga tcgggtcacc    60
atcacctgcc gtgcctctca gggtattggc tcttccctgg cttggtatca acagaaacca   120
ggaaaagctc cgaagcttct gatctacgcc gcctcttctt tgcagtctgg tgtgccatct   180
cgcttctctg gatccggttc cgggacggat ttcactctga ccatcagcag tctgcagccg   240
```

```
gaagacttcg caacttatta ctgccagcag ggctactaca cctggacctt cggacagggt    300
accaaggtgg agatcaaacg a                                              321
```

<210> SEQ ID NO 139
<211> LENGTH: 360
<212> TYPE: DNA
<213> ORGANISM: Artificial Sequence
<220> FEATURE:
<223> OTHER INFORMATION: Synthetic sequence

<400> SEQUENCE: 139

```
gaggttcagc tggtggagtc tggcggtggc ctggtgcagc caggggggctc actccgtttg    60 tcctgtgcag cttccggata ctctatcacc tctggttacc actggggctg gattcgtcag   120
gccccgggta agggcctcga gtgggtgtct gctatctctg gtgccggtgg ttctacctac   180
tacgccgact ctgtcaaggg ccgtttcact ataagtcgcg acaattcgaa aaacacactg   240
tacctacaac tgaacagctt aagagctgag gacactgccg tctattattg cgccagagac   300
ggctacggtg gttcctactt cgactactgg ggtcaaggaa cactagtcac cgtctcctcg   360
```

<210> SEQ ID NO 140
<211> LENGTH: 321
<212> TYPE: DNA
<213> ORGANISM: Artificial Sequence
<220> FEATURE:
<223> OTHER INFORMATION: Synthetic sequence

<400> SEQUENCE: 140

```
gatatccagt tgacccagtc cccgagttcc ctgtccgcct ctgtgggcga tcgggtcacc    60
atcacctgcc aggcctctca ggacatcagc acgttcctgg cctggtatca acagaaacca   120
ggaaaagctc cgaagcttct gatctacgac gcctcttctc tggaatctgg tgtgccatct   180
cgcttctctg gatccggttc cgggacggat ttcactctga ccatcagcag tctgcagccg   240
gaagacttcg caacttatta ctgccagcag gcctactcaa tctggacctt cggacagggt   300
accaaggtgg agatcaaacg a                                              321
```

<210> SEQ ID NO 141
<211> LENGTH: 360
<212> TYPE: DNA
<213> ORGANISM: Artificial Sequence
<220> FEATURE:
<223> OTHER INFORMATION: Synthetic sequence

<400> SEQUENCE: 141

```
gaggttcagc tggtggagtc tggcggtggc ctggtgcagc caggggggctc actccgtttg    60 tcctgtgcag cttccggatt caccttcacc ggctactgga ttcactgggt cgtcaggcc   120 ccgggtaagg gcctcgagtg ggtgggtcgt atcagatcca agaccgacgg ttacactacc   180
gaatacgccg cccctgtcaa gggccgtttc actataagtc gcgacaattc gaaaaacaca   240
ctgtacctac aactgaacag cttaagagct gaggacactg ccgtctatta ttgcgccaga   300
ttgggtggtc actggtactt cgacgtctgg ggtcaaggaa cactagtcac cgtctcctcg   360
```

<210> SEQ ID NO 142
<211> LENGTH: 324
<212> TYPE: DNA
<213> ORGANISM: Artificial Sequence
<220> FEATURE:
<223> OTHER INFORMATION: Synthetic sequence

<400> SEQUENCE: 142

```
gatatccagt tgacccagtc cccgagttcc ctgtccgcct ctgtgggcga tcgggtcacc    60
atcacctgcc gtgcctctca gtccatcggc cgctacctga actggtatca acagaaacca   120
ggaaaagctc cgaagcttct gatctacgac gcctctaacc tggaaaccgg tgtgccatct   180
cgcttctctg gatccggttc cgggacggat ttcactctga ccatcagcag tctgcagccg   240
gaagacttcg caacttatta ctgcgagcaa cccctggaac tcccacgaac cttcggacag   300
ggtaccaagg tggagatcaa acga                                          324
```

<210> SEQ ID NO 143
<211> LENGTH: 366
<212> TYPE: DNA
<213> ORGANISM: Artificial Sequence
<220> FEATURE:
<223> OTHER INFORMATION: Synthetic sequence

<400> SEQUENCE: 143

```
gaggttcagc tggtggagtc tggcggtggc ctggtgcagc caggggggctc actccgtttg    60
tcctgtgcag cttccggata ctctatctcc tctggtcacc actggggctg gattcgtcag   120
gccccgggta agggcctcga gtgggtgtct ggtatctctg gttacggtga ctacctac     180
tacgccgact ctgtcaaggg ccgtttcact ataagtcgcg acaattcgaa aaacacactg   240
tacctacaac tgaacagctt aagagctgag gacactgccg tctattattg cgccagagac   300
ccatactcca gcggttccgg ttactttgac tactggggtc aaggaacact agtcaccgtc   360
tcctcg                                                              366
```

<210> SEQ ID NO 144
<211> LENGTH: 321
<212> TYPE: DNA
<213> ORGANISM: Artificial Sequence
<220> FEATURE:
<223> OTHER INFORMATION: Synthetic sequence

<400> SEQUENCE: 144

```
gatatccagt tgacccagtc cccgagttcc ctgtccgcct ctgtgggcga tcgggtcacc    60
atcacctgcc gtgcctctca gggtattagc tctgccctgg gttggtatca acagaaacca   120
ggaaaagctc cgaagcttct gatctacgcc gcctcttctt tgcagtctgg tgtgccatct   180
cgcttctctg gatccggttc cgggacggat ttcactctga ccatcagcag tctgcagccg   240
gaagacttcg caacttatta ctgccagcag agctactaca cctggacctt cggacagggt   300
accaaggtgg agatcaaacg a                                             321
```

<210> SEQ ID NO 145
<211> LENGTH: 351
<212> TYPE: DNA
<213> ORGANISM: Artificial Sequence
<220> FEATURE:
<223> OTHER INFORMATION: Synthetic sequence

<400> SEQUENCE: 145

```
gaggttcagc tggtggagtc tggcggtggc ctggtgcagc caggggggctc actccgtttg    60
tcctgtgcag cttccggata ctctatcacc tctggttact actggggctg gattcgtcag   120
gccccgggta agggcctcga gtgggtgtct ggtatctctg gttccggttc ttctacctac   180
tacgccgact ctgtcaaggg ccgtttcact ataagtcgcg acaattcgaa aaacacactg   240
tacctacaac tgaacagctt aagagctgag gacactgccg tctattattg cgccagaggt   300
```

```
acttactcct tcgacgtctg gggtcaagga acactagtca ccgtctcctc g         351
```

<210> SEQ ID NO 146
<211> LENGTH: 321
<212> TYPE: DNA
<213> ORGANISM: Artificial Sequence
<220> FEATURE:
<223> OTHER INFORMATION: Synthetic sequence

<400> SEQUENCE: 146

```
gatatccagt tgacccagtc cccgagttcc ctgtccgcct ctgtgggcga tcgggtcacc    60
atcacctgcc gtgcctctca gggtattagc tctgacctgg cttggtatca acagaaacca   120
ggaaaagctc cgaagcttct gatctacgcc gcctctacct tgcagtctgg tgtgccatct   180
cgcttctctg gatccggttc cgggacggat ttcactctga ccatcagcag tctgcagccg   240
gaagacttcg caacttatta ctgccagcag tactactctt acatcacctt cggacagggt   300
accaaggtgg agatcaaacg a                                             321
```

<210> SEQ ID NO 147
<211> LENGTH: 351
<212> TYPE: DNA
<213> ORGANISM: Artificial Sequence
<220> FEATURE:
<223> OTHER INFORMATION: Synthetic sequence

<400> SEQUENCE: 147

```
gaggttcagc tggtggagtc tggcggtggc ctggtgcagc caggggggctc actccgtttg    60
tcctgtgcag cttccggata caccttcacc ggctacgcta ttcactgggt gcgtcaggcc   120
ccgggtaagg gcctcgagtg ggtgtctgct atctctggtg acgtggttc tacctactac   180
gccgactctg tcaagggccg tttcactata agtcgcgaca attcgaaaaa cacactgtac   240
ctacaactga acagcttaag agctgaggac actgccgtct attattgcgc cagaggctat   300
aggggttact tcgactactg gggtcaagga acactagtca ccgtctcctc g             351
```

<210> SEQ ID NO 148
<211> LENGTH: 327
<212> TYPE: DNA
<213> ORGANISM: Artificial Sequence
<220> FEATURE:
<223> OTHER INFORMATION: Synthetic sequence

<400> SEQUENCE: 148

```
gatatccagt tgacccagtc cccgagttcc ctgtccgcct ctgtgggcga tcgggtcacc    60
atcacctgcc gtgcctctga gtctgttacc tctacctacc tggcctggta tcaacagaaa   120
ccaggaaaag ctccgaagct tctgatctac gacgcctcta acctggaaac cggtgtgcca   180
tctcgcttct ctggatccgg ttccgggacg gatttcactc tgaccatcag cagtctgcag   240
ccggaagact tcgcaactta ttactgccag cagtactccg actggcctcc gaccttcgga   300
cagggtacca aggtggagat caaacga                                        327
```

<210> SEQ ID NO 149
<211> LENGTH: 369
<212> TYPE: DNA
<213> ORGANISM: Artificial Sequence
<220> FEATURE:
<223> OTHER INFORMATION: Synthetic sequence

<400> SEQUENCE: 149

```
gaggttcagc tggtggagtc tggcggtggc ctggtgcagc cagggggctc actccgtttg    60
tcctgtgcag cttccggata ctctatctcc tctggttacc actggaactg gattcgtcag   120
gccccgggta agggcctcga gtgggtgtct tccatctctg gttccggtgg ttctacctac   180
tacgccgact ctgtcaaggg ccgtttcact ataagtcgcg acaattcgaa aaacacactg   240
tacctacaac tgaacagctt aagagctgag gacactgccg tctattattg cgccagagac   300
cctaattact acagtccgg ctcctacttc gactactggg gtcaaggaac actagtcacc   360
gtctcctcg                                                           369

<210> SEQ ID NO 150
<211> LENGTH: 321
<212> TYPE: DNA
<213> ORGANISM: Artificial Sequence
<220> FEATURE:
<223> OTHER INFORMATION: Synthetic sequence

<400> SEQUENCE: 150
gatatccagt tgacccagtc cccgagttcc ctgtccgcct ctgtgggcga tcgggtcacc    60
atcacctgcc gtgcctctca gggtattggc tctttcctgg ttggtatca acagaaacca   120 ggaaaagctc cgaagcttct gatctacgac gcctctaacc gtgccaccgg tatcccatct   180
cgcttctctg gatccggttc cgggacggat ttcactctga ccatcagcag tctgcagccg   240
gaagacttcg caacttatta ctgccagcag agctactccc tctggacctt cggacagggt   300
accaaggtgg agatcaaacg a                                             321

<210> SEQ ID NO 151
<211> LENGTH: 363
<212> TYPE: DNA
<213> ORGANISM: Artificial Sequence
<220> FEATURE:
<223> OTHER INFORMATION: Synthetic sequence

<400> SEQUENCE: 151
gaggttcagc tggtggagtc tggcggtggc ctggtgcagc cagggggctc actccgtttg    60
tcctgtgcag cttccggata ctctatctcc tctggttact actgggactg gattcgtcag   120
gccccgggta agggcctcga gtgggtgtct tccatctctg gtgacggtga tactacctac   180
tacgccgact ctgtcaaggg ccgtttcact ataagtcgcg acaattcgaa aaacacactg   240
tacctacaac tgaacagctt aagagctgag gacactgccg tctattattg cgccagagag   300
tactacggat acggttacgc cttggactac tggggtcaag gaacactagt caccgtctcc   360
tcg                                                                 363

<210> SEQ ID NO 152
<211> LENGTH: 324
<212> TYPE: DNA
<213> ORGANISM: Artificial Sequence
<220> FEATURE:
<223> OTHER INFORMATION: Synthetic sequence

<400> SEQUENCE: 152
gatatccagt tgacccagtc cccgagttcc ctgtccgcct ctgtgggcga tcgggtcacc    60
atcacctgcc gtgcctctca gggtatctct tcttacctgg cctggtatca acagaaacca   120
ggaaaagctc cgaagcttct gatctacgac gcctcttctc tggaatctgg tgtgccatct   180
cgcttctctg gatccggttc cgggacggat ttcactctga ccatcagcag tctgcagccg   240
gaagacttcg caacttacta ctgccagcag tactactcta ccccactgac cttcggtcag   300
```

```
ggtaccaagg tggagatcaa acga                                          324

<210> SEQ ID NO 153
<211> LENGTH: 357
<212> TYPE: DNA
<213> ORGANISM: Artificial Sequence
<220> FEATURE:
<223> OTHER INFORMATION: Synthetic sequence

<400> SEQUENCE: 153
gaggttcagc tggtggagtc tggcggtggc ctggtgcagc caggggctc actccgtttg    60 tcctgtgcag cttccggata ctctatctcc tctggtcact actggggctg gattcgtcag   120
gccccgggta agggcctcga gtggctggcc ctgatcgact ggtacggtga caagtactac   180
tctacctctc tgaagtctcg tctgactata agtcgcgaca attcgaaaaa cacactgtac   240
ctacaactga acagcttaag agctgaggac actgccgtct attattgcgc gcgttccgac   300
tactacggtt tcacttcga ctactgggt caaggaacac tagtcaccgt ctcctcg        357

<210> SEQ ID NO 154
<211> LENGTH: 336
<212> TYPE: DNA
<213> ORGANISM: Artificial Sequence
<220> FEATURE:
<223> OTHER INFORMATION: Synthetic sequence

<400> SEQUENCE: 154
gatatccagt tgacccagtc cccgagttcc ctgtccgcct ctgtgggcga tcgggtcacc    60
atcacctgcc gtgcctctga gtctgtggac ttcgacggtt tctctttcct ggcctggtat   120
caacagaaac caggaaaagc tccgaagctt ctgatctacg acgcctctaa cctggaaacc   180
ggtgtgccat ctcgcttctc tggatccggt tccgggacgg atttcactct gaccatcagc   240
agtctgcagc cggaagactt cgcaacttat tactgccagc agtacgatac tttgcctcgg   300
accttcggac agggtaccaa ggtggagatc aaacga                             336

<210> SEQ ID NO 155
<211> LENGTH: 366
<212> TYPE: DNA
<213> ORGANISM: Artificial Sequence
<220> FEATURE:
<223> OTHER INFORMATION: Synthetic sequence

<400> SEQUENCE: 155
gaggttcagc tggtggagtc tggcggtggc ctggtgcagc caggggctc actccgtttg    60 tcctgtgcag cttccggata caccttctcc aactactgga ttcactgggt gcgtcaggcc   120
ccgggtaagg gcctcgagtg ggtgtcttac atctctggtg acggtgatac tacctactac   180
gccgactctg tcaagggccg tttcactata agtcgcgaca attcgaaaaa cacactgtac   240
ctacaactga acagcttaag agctgaggac actgccgtct attattgcgc gcgtgagggt   300
tctaccaccg tggccggcga ctggttcgcc tactgggtc aaggaacact agtcaccgtc   360
tcctcg                                                             366

<210> SEQ ID NO 156
<211> LENGTH: 321
<212> TYPE: DNA
<213> ORGANISM: Artificial Sequence
<220> FEATURE:
<223> OTHER INFORMATION: Synthetic sequence
```

<400> SEQUENCE: 156

```
gatatccagt tgacccagtc cccgagttcc ctgtccgcct ctgtgggcga tcgggtcacc    60
atcacctgcc gtgcctctca gggtattggc tctttcctgg ttggtatca acagaaacca   120
ggaaaagctc cgaagcttct gatctacgac gcctcttctc tggaatctgg tgtgccatct   180
cgcttctctg gatccggttc cgggacggat ttcactctga ccatcagcag tctgcagccg   240
gaagacttcg caacttatta ctgccagcag tactactctt tggtcacctt cggacagggt   300
accaaggtgg agatcaaacg a                                             321
```

<210> SEQ ID NO 157
<211> LENGTH: 372
<212> TYPE: DNA
<213> ORGANISM: Artificial Sequence
<220> FEATURE:
<223> OTHER INFORMATION: Synthetic sequence

<400> SEQUENCE: 157

```
gaggttcagc tggtggagtc tggcggtggc ctggtgcagc caggggggctc actccgtttg    60
tcctgtgcag cttccggatt ctctctgtct accggcggtg tgggtgtggc ctggattcgt   120
caggccccgg gtaagggcct cgagtgggtg tcttccatct ctggttacgg ttctactacc   180
tactacgccg actctgtcaa gggccgtttc actataagtc gcgacaattc gaaaaacaca   240
ctgtacctac aactgaacag cttaagagct gaggacactg ccgtctatta ttgcgcgcgt   300
gagggttctg acgccgtgct cggcgactgg ttcggctact ggggtcaagg aacactagtc   360
accgtctcct cg                                                       372
```

<210> SEQ ID NO 158
<211> LENGTH: 321
<212> TYPE: DNA
<213> ORGANISM: Artificial Sequence
<220> FEATURE:
<223> OTHER INFORMATION: Synthetic sequence

<400> SEQUENCE: 158

```
gatatccagt tgacccagtc cccgagttcc ctgtccgcct ctgtgggcga tcgggtcacc    60
atcacctgcc aggcctctca ggacatcacc acgtacctgg cctggtatca acagaaacca   120
ggaaaagctc cgaagcttct gatctacgac gcctctaacc gtgccaccgg tatcccatct   180
cgcttctctg gatccggttc cgggacggat ttcactctga ccatcagcag tctgcagccg   240
gaagacttcg caacttatta ctgccagcag ggctactacc tctggacctt cggacagggt   300
accaaggtgg agatcaaacg a                                             321
```

<210> SEQ ID NO 159
<211> LENGTH: 369
<212> TYPE: DNA
<213> ORGANISM: Artificial Sequence
<220> FEATURE:
<223> OTHER INFORMATION: Synthetic sequence

<400> SEQUENCE: 159

```
gaggttcagc tggtggagtc tggcggtggc ctggtgcagc caggggggctc actccgtttg    60
tcctgtgcag cttccggatt ctctctgtct accagcggtg tggctgtggg ctggattcgt   120
caggccccgg gtaagggcct cgagtggctg gccctgatcg actgggccga tgacaagtac   180
tactctccct ctctgaagtc tcgtctgact ataagtcgcg acaattcgaa aaacacactg   240
tacctacaac tgaacagctt aagagctgag gacactgccg tctattattg cgcgcgtgag   300
```

-continued

```
ggttctgacg ccgtgctcgg cgactggttc gcctactggg gtcaaggaac actagtcacc    360
gtctcctcg                                                            369
```

<210> SEQ ID NO 160
<211> LENGTH: 321
<212> TYPE: DNA
<213> ORGANISM: Artificial Sequence
<220> FEATURE:
<223> OTHER INFORMATION: Synthetic sequence

<400> SEQUENCE: 160

```
gatatccagt tgacccagtc cccgagttcc ctgtccgcct ctgtgggcga tcgggtcacc    60
atcacctgcc gggcctctca ggacatcagc acgttcctgg cctggtatca acagaaacca   120
ggaaaagctc cgaagcttct gatctacgac gcctcttctc tggaatctgg tgtgccatct   180
cgcttctctg gatccggttc cgggacggat ttcactctga ccatcagcag tctgcagccg   240
gaagacttcg caacttatta ctgccagcag gcctactcca tctggacctt cggacagggt   300
accaaggtgg agatcaaacg a                                             321
```

<210> SEQ ID NO 161
<211> LENGTH: 369
<212> TYPE: DNA
<213> ORGANISM: Artificial Sequence
<220> FEATURE:
<223> OTHER INFORMATION: Synthetic sequence

<400> SEQUENCE: 161

```
gaggttcagc tggtggagtc tggcggtggc ctggtgcagc caggggggctc actccgtttg    60 tcctgtgcag cttccggatt ctctctgtct accagcggtg tgggtgtggg ctggattcgt   120
caggccccgg gtaagggcct cgagtggctg gccctgatcg actgggacga tgacaagtac   180
tactctccct ctctgaagtc tcgtctgact ataagtcgcg acaattcgaa aaacacactg   240
tacctacaac tgaacagctt aagagctgag gacactgccg tctattattg cgcgcgtggg   300
ggttctgaca ccgtgctcgg cgactggttc gcctactggg gtcaaggaac actagtcacc   360
gtctcctcg                                                           369
```

<210> SEQ ID NO 162
<211> LENGTH: 321
<212> TYPE: DNA
<213> ORGANISM: Artificial Sequence
<220> FEATURE:
<223> OTHER INFORMATION: Synthetic sequence

<400> SEQUENCE: 162

```
gatatccagt tgacccagtc cccgagttcc ctgtccgcct ctgtgggcga tcgggtcacc    60
atcacctgcc gtgcctctca gagcgtcagc ccttacctgg cctggtatca acagaaacca   120
ggaaaagctc cgaagcttct gatctacgac gcctcttctc tggaatctgg tgtgccatct   180
cgcttctctg gatccggttc cgggacggat ttcactctga ccatcagcag tctgcagccg   240
gaagacttcg caacttatta ctgccagcag ggctactccc tctggacctt cggacagggt   300
accaaggtgg agatcaaacg a                                             321
```

<210> SEQ ID NO 163
<211> LENGTH: 369
<212> TYPE: DNA
<213> ORGANISM: Artificial Sequence
<220> FEATURE:

<223> OTHER INFORMATION: Synthetic sequence

<400> SEQUENCE: 163

| | |
|---|---|
| gaggttcagc tggtggagtc tggcggtggc ctggtgcagc caggggggctc actccgtttg | 60 |
| tcctgtgcag cttccggatt ctctctgtct accggcggtg tggctgtggg ctggattcgt | 120 |
| caggccccgg gtaagggcct cgagtggctg gccctgatcg actgggccgg tgacaagtcc | 180 |
| tactctacct ctctgaagtc tcgtctgact ataagtcgcg acaattcgaa aaacacactg | 240 |
| tacctacaac tgaacagctt aagagctgag gacactgccg tctattattg cgcgcgtggg | 300 |
| ggttctgaca ccgtgctcgg cgactggttc gcctactggg gtcaaggaac actagtcacc | 360 |
| gtctcctcg | 369 |

<210> SEQ ID NO 164
<211> LENGTH: 321
<212> TYPE: DNA
<213> ORGANISM: Artificial Sequence
<220> FEATURE:
<223> OTHER INFORMATION: Synthetic sequence

<400> SEQUENCE: 164

| | |
|---|---|
| gatatccagt tgacccagtc cccgagttcc ctgtccgcct ctgtgggcga tcgggtcacc | 60 |
| atcacctgcc gtgcctctca gggcgtcagc ccttacctgg cctggtatca acagaaacca | 120 |
| ggaaaagctc cgaagcttct gatctacgac gcctctaacc gtgccaccgg tatcccatct | 180 |
| cgcttctctg gatccggttc cgggacggat ttcactctga ccatcagcag tctgcagccg | 240 |
| gaagacttcg caacttatta ctgccagcag ggctactcca cctggacctt cggacagggt | 300 |
| accaaggtgg agatcaaacg a | 321 |

<210> SEQ ID NO 165
<211> LENGTH: 369
<212> TYPE: DNA
<213> ORGANISM: Artificial Sequence
<220> FEATURE:
<223> OTHER INFORMATION: Synthetic sequence

<400> SEQUENCE: 165

| | |
|---|---|
| gaggttcagc tggtggagtc tggcggtggc ctggtgcagc caggggggctc actccgtttg | 60 |
| tcctgtgcag cttccggata ctctatctcc tctggttacc actgggcctg gattcgtcag | 120 |
| gccccgggta agggcctcga gtgggtgtct tccatctctg gtgacggttc ttctacctac | 180 |
| tacgccgact ctgtcaaggg ccgtttcact ataagtcgcg acaattcgaa aaacacactg | 240 |
| tacctacaac tgaacagctt aagagctgag gacactgccg tctattattg cgcgcgtgaa | 300 |
| ggttcagacg ctgtgaccgg cgactggttc gcctactggg gtcaaggaac actagtcacc | 360 |
| gtctcctcg | 369 |

<210> SEQ ID NO 166
<211> LENGTH: 321
<212> TYPE: DNA
<213> ORGANISM: Artificial Sequence
<220> FEATURE:
<223> OTHER INFORMATION: Synthetic sequence

<400> SEQUENCE: 166

| | |
|---|---|
| gatatccagt tgacccagtc cccgagttcc ctgtccgcct ctgtgggcga tcgggtcacc | 60 |
| atcacctgcc gtgcctctca gggcgtcggc acttacctgg cctggtatca acagaaacca | 120 |
| ggaaaagctc cgaagcttct gatctacgac gcctcttctc tggaatctgg tgtgccatct | 180 |

```
cgcttctctg gatccggttc cgggacggat ttcactctga ccatcagcag tctgcagccg    240
gaagacttcg caacttatta ctgccagcag ggctactcac tctggacctt cggacagggt    300
accaaggtgg agatcaaacg a                                              321
```

<210> SEQ ID NO 167
<211> LENGTH: 369
<212> TYPE: DNA
<213> ORGANISM: Artificial Sequence
<220> FEATURE:
<223> OTHER INFORMATION: Synthetic sequence

<400> SEQUENCE: 167

```
gaggttcagc tggtggagtc tggcggtggc ctggtgcagc caggggggctc actccgtttg    60 tcctgtgcag cttccggatt ctctctgtct accagcggtg tggctgtggg ctggattcgt    120
caggccccgg gtaagggcct cgagtggctg ccctgatcg actgggacga tgacaagtac    180
tactctacct ctctgaagtc tcgtctgact ataagtcgcg acaattcgaa aaacacactg    240
tacctacaac tgaacagctt aagagctgag gacactgccg tctattattg cgcgcgtgag    300
ggttctaccg ccgtggccgg cgactggttc gcctactggg gtcaaggaac actagtcacc    360
gtctcctcg                                                            369
```

<210> SEQ ID NO 168
<211> LENGTH: 321
<212> TYPE: DNA
<213> ORGANISM: Artificial Sequence
<220> FEATURE:
<223> OTHER INFORMATION: Synthetic sequence

<400> SEQUENCE: 168

```
gatatccagt tgacccagtc cccgagttcc ctgtccgcct ctgtgggcga tcgggtcacc    60
atcacctgcc aggcctctca ggacatccgc acgttcctgg cctggtatca acagaaacca    120
ggaaaagctc cgaagcttct gatctacgac gcctctaacc gtgccaccgg tatcccatct    180
cgcttctctg gatccggttc cgggacggat ttcactctga ccatcagcag tctgcagccg    240
gaagacttcg caacttatta ctgccagcag ggctactcca cctggacctt cggacagggt    300
accaaggtgg agatcaaacg a                                              321
```

<210> SEQ ID NO 169
<211> LENGTH: 369
<212> TYPE: DNA
<213> ORGANISM: Artificial Sequence
<220> FEATURE:
<223> OTHER INFORMATION: Synthetic sequence

<400> SEQUENCE: 169

```
gaggttcagc tggtggagtc tggcggtggc ctggtgcagc caggggggctc actccgtttg    60 tcctgtgcag cttccggatt ctctctgtct accagcggtg tgggtgtggg ctggattcgt    120
caggccccgg gtaagggcct cgagtggatc ggtgaaatct accactctgg ttctacctac    180
tactctccat ctctgaagtc tcgtgtgact ataagtcgcg acaattcgaa aaacacactg    240
tacctacaac tgaacagctt aaaagctgag gacactgccg tctattattg cgcgcgtgaa    300
ggttcagacg ttgtgaccgg cgactggttc gcctactggg gtcaaggaac actagtcacc    360
gtctcctcg                                                            369
```

<210> SEQ ID NO 170

```
<211> LENGTH: 321
<212> TYPE: DNA
<213> ORGANISM: Artificial Sequence
<220> FEATURE:
<223> OTHER INFORMATION: Synthetic sequence

<400> SEQUENCE: 170
gatatccagt tgacccagtc cccgagttcc ctgtccgcct ctgtgggcga tcgggtcacc      60
atcacctgcc gtgcctctca gggtattagc tctgtcctgg cttggtatca acagaaacca     120
ggaaaagctc cgaagcttct gatctacgac gcctcttctc tggaatctgg tgtgccatct     180
cgcttctctg gatccggttc cgggacggat ttcactctga ccatcagcag tctgcagccg     240
gaagacttcg caacttatta ctgccagcag ggctactccc tctggacctt cggacagggt     300
accaaggtgg agatcaaacg a                                               321

<210> SEQ ID NO 171
<211> LENGTH: 369
<212> TYPE: DNA
<213> ORGANISM: Artificial Sequence
<220> FEATURE:
<223> OTHER INFORMATION: Synthetic sequence

<400> SEQUENCE: 171
gaggttcagc tggtggagtc tggcggtggc ctggtgcagc caggggggctc actccgtttg     60 tcctgtgcag cttccggata ctctatcacc tctggtcacc actgggcctg gattcgtcag    120
gccccgggta agggcctcga gtgggtgtct gctatctctg gtgacggttc tactacctac    180
tacgccgact ctgtcaaggg ccgtttcact ataagtcgcg acaattcgaa aaacacactg    240
tacctacaac tgaacagctt aagagctgag gacactgccg tctattattg cgcgcgtgag    300
ggttctaccg ccgtgaccgg cgactggttc gcctactggg gtcaaggaac actagtcacc    360
gtctcctcg                                                            369

<210> SEQ ID NO 172
<211> LENGTH: 318
<212> TYPE: DNA
<213> ORGANISM: Artificial Sequence
<220> FEATURE:
<223> OTHER INFORMATION: Synthetic sequence

<400> SEQUENCE: 172
gatatccagt tgacccagtc cccgagttcc ctgtccgcct ctgtgggcga tcgggtcacc     60
atcacctgct ctgcctcttc tcgcgtgggc tacgtgcact ggtatcaaca gaaaccagga    120
aaagctccga agcttctgat ctacgacgcc tcttctctgg aatctggtgt gccatctcgc    180
ttctctggat ccggttccgg gacggatttc actctgacca tcagcagtct gcagccggaa    240
gacttcgcaa cttattactg ccagcagggc tactacacct ggaccttcgg acagggtacc    300
aaggtggaga tcaaacga                                                  318

<210> SEQ ID NO 173
<211> LENGTH: 369
<212> TYPE: DNA
<213> ORGANISM: Artificial Sequence
<220> FEATURE:
<223> OTHER INFORMATION: Synthetic sequence

<400> SEQUENCE: 173
gaggttcagc tggtggagtc tggcggtggc ctggtgcagc caggggggctc actccgtttg     60 tcctgtgcag cttccggatt ctctctgtct accggcggtg tggctgtggg ctggattcgt    120
```

```
caggccccgg gtaagggcct cgagtggctg gccctgatcg actgggccgg tgacaagtcc    180
tactctacct ctctgaagtc tcgtctgact ataagtcgcg acaattcgaa aaacacactg    240
tacctacaac tgaacagctt aagagctgag gacactgccg tctattattg cgcgcgtgaa    300
ggtgaagacg ctgtgaccgg cgactggttc gcctactggg gtcaaggaac actagtcacc    360
gtctcctcg                                                            369
```

<210> SEQ ID NO 174
<211> LENGTH: 321
<212> TYPE: DNA
<213> ORGANISM: Artificial Sequence
<220> FEATURE:
<223> OTHER INFORMATION: Synthetic sequence

<400> SEQUENCE: 174

```
gatatccagt tgacccagtc cccgagttcc ctgtccgcct ctgtgggcga tcgggtcacc     60
atcacctgcc aggcctctca ggacatccgc acgtacctgg cctggtatca acagaaacca    120
ggaaaagctc cgaagcttct gatctacgac gcctctaacc gtgccaccgg tatcccatct    180
cgcttctctg gatccggttc cgggacggat ttcactctga ccatcagcag tctgcagccg    240
gaagacttcg caacttatta ctgccagcag ggctactcca tctggacctt cggacagggt    300
accaaggtgg agatcaaacg a                                               321
```

<210> SEQ ID NO 175
<211> LENGTH: 372
<212> TYPE: DNA
<213> ORGANISM: Artificial Sequence
<220> FEATURE:
<223> OTHER INFORMATION: Synthetic sequence

<400> SEQUENCE: 175

```
gaggttcagc tggtggagtc tggcggtggc ctggtgcagc caggggctc actccgtttg      60 tcctgtgcag cttccggatt ctctctgtct accggcggtg tgggtgtggg ctggattcgt    120
caggccccgg gtaagggcct cgagtgggtg tctggtatct ctggttacgg ttctactacc    180
tactacgccg actctgtcaa gggccgtttc actataagtc gcgacaattc gaaaaacaca    240
ctgtacctac aactgaacag cttaagagct gaggacactg ccgtctatta ttgcgcgcgt    300
gaaggttcag acgctgtggc cggcgactgg ttcgactact ggggtcaagg aacactagtc    360
accgtctcct cg                                                        372
```

<210> SEQ ID NO 176
<211> LENGTH: 321
<212> TYPE: DNA
<213> ORGANISM: Artificial Sequence
<220> FEATURE:
<223> OTHER INFORMATION: Synthetic sequence

<400> SEQUENCE: 176

```
gatatccagt tgacccagtc cccgagttcc ctgtccgcct ctgtgggcga tcgggtcacc     60
atcacctgcc gtgcctctca ggatattcgc tcttacctgg cttggtatca acagaaacca    120
ggaaaagctc cgaagcttct gatctacgac gcctctaacc gtgccaccgg tatcccatct    180
cgcttctctg gatccggttc cgggacggat ttcactctga ccatcagcag tctgcagccg    240
gaagacttcg caacttatta ctgccagcag ggctactcca tctggacctt cggacagggt    300
accaaggtgg agatcaaacg a                                               321
```

<210> SEQ ID NO 177
<211> LENGTH: 357
<212> TYPE: DNA
<213> ORGANISM: Artificial Sequence
<220> FEATURE:
<223> OTHER INFORMATION: Synthetic sequence

<400> SEQUENCE: 177

| gaggttcagc tggtggagtc tggcggtggc ctggtgcagc caggggctc actccgtttg | 60 |
| tcctgtgcag cttccggatt ctctctgtct accggcggtg tggctgtggg ctggattcgt | 120 |
| caggccccgg gtaagggcct cgagtgggtg tctggtatct ctggtgacgg tggtactacc | 180 |
| tactacgccg actctgtcaa gggccgtttc actataagtc gcgacaattc gaaaaacaca | 240 |
| ctgtacctac aactgaacag cttaagagct gaggacactg ccgtctatta ttgcacccgt | 300 |
| gaagactacg gtccgcacgc ctactgggt caaggaacac tagtcaccgt ctcctcg | 357 |

<210> SEQ ID NO 178
<211> LENGTH: 321
<212> TYPE: DNA
<213> ORGANISM: Artificial Sequence
<220> FEATURE:
<223> OTHER INFORMATION: Synthetic sequence

<400> SEQUENCE: 178

| gatatccagt tgacccagtc cccgagttcc ctgtccgcct ctgtgggcga tcgggtcacc | 60 |
| atcacctgcc gtgcctctca gtccatcacc acgtacctga actggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttatta ctgccagcag tcctactctt actcgacctt cggacagggt | 300 |
| accaaggtgg agatcaaacg a | 321 |

<210> SEQ ID NO 179
<211> LENGTH: 369
<212> TYPE: DNA
<213> ORGANISM: Artificial Sequence
<220> FEATURE:
<223> OTHER INFORMATION: Synthetic sequence

<400> SEQUENCE: 179

| gaggttcagc tggtggagtc tggcggtggc ctggtgcagc caggggctc actccgtttg | 60 |
| tcctgtgcag cttccggata ctctatcacc tctggtcact actgggcctg gattcgtcag | 120 |
| gccccgggta agggcctcga gtgggtgtct gctatctctg gttccggttc ttctacctac | 180 |
| tacgccgact ctgtcaaggg ccgtttcact ataagtcgcg acaattcgaa aaacacactg | 240 |
| tacctacaac tgaacagctt aagagctgag gacactgccg tctattattg cgcgcgtggg | 300 |
| ggttctgaca ccgtgctcgg cgactggttc gcctactggg tcaaggaac actagtcacc | 360 |
| gtctcctcg | 369 |

<210> SEQ ID NO 180
<211> LENGTH: 321
<212> TYPE: DNA
<213> ORGANISM: Artificial Sequence
<220> FEATURE:
<223> OTHER INFORMATION: Synthetic sequence

<400> SEQUENCE: 180

| gatatccagt tgacccagtc cccgagttcc ctgtccgcct ctgtgggcga tcgggtcacc | 60 |

```
atcacctgcc gtgcctctca gggtattagc tcttccctgg cttggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttatta ctgccagcag ggctactcca cctggacctt cggacagggt    300
accaaggtgg agatcaaacg a                                              321
```

<210> SEQ ID NO 181
<211> LENGTH: 369
<212> TYPE: DNA
<213> ORGANISM: Artificial Sequence
<220> FEATURE:
<223> OTHER INFORMATION: Synthetic sequence

<400> SEQUENCE: 181

```
gaggttcagc tggtggagtc tggcggtggc ctggtgcagc caggggggctc actccgtttg    60 tcctgtgcag cttccggata ctctatcacc tctggtcact actgggcctg gattcgtcag    120
gccccgggta agggcctcga gtgggtgtct tccatctctg gttacggttc tactacctac    180
tacgccgact ctgtcaaggg ccgtttcact ataagtcgcg acaattcgaa aaacacactg    240
tacctacaac tgaacagttt aagagctgag acactgccg tctattattg cgcgcgtggg    300
ggttctgacg ccgtgctcgg cgactggttc gcctactggg gtcaaggaac actagtcacc    360
gtctcctcg                                                            369
```

<210> SEQ ID NO 182
<211> LENGTH: 321
<212> TYPE: DNA
<213> ORGANISM: Artificial Sequence
<220> FEATURE:
<223> OTHER INFORMATION: Synthetic sequence

<400> SEQUENCE: 182

```
gatatccagt tgacccagtc cccgagttcc ctgtccgcct ctgtgggcga tcgggtcacc    60
atcacctgcc gtgcctctca gggtattggc tctttcctgg cttggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttatta ctgccagcag ggctactacc tctggacctt cggacagggt    300
accaaggtgg agatcaaacg a                                              321
```

<210> SEQ ID NO 183
<211> LENGTH: 360
<212> TYPE: DNA
<213> ORGANISM: Artificial Sequence
<220> FEATURE:
<223> OTHER INFORMATION: Synthetic sequence

<400> SEQUENCE: 183

```
gaggttcagc tggtggagtc tggcggtggc ctggtgcagc caggggggctc actccgtttg    60 tcctgtgcag cttccggatt caccttctcc agctactgga ttcactgggt gcgtcaggcc    120
ccgggtaagg gcctcgagtg gtgtctgtt atctctggtg acggtgatac tacctactac    180
gccgactctg tcaagggccg tttcactata agtcgcgaca attcgaaaaa cacactgtac    240
ctacaactga acagcttaag agctgaggac actgccgtct attattgcgc gcgttcccgt    300
ggtcttgtgc tagacgccct cgactactgg ggtcaaggaa cactagtcac cgtctcctcg    360
```

<210> SEQ ID NO 184
<211> LENGTH: 330
<212> TYPE: DNA
<213> ORGANISM: Artificial Sequence
<220> FEATURE:
<223> OTHER INFORMATION: Synthetic sequence

<400> SEQUENCE: 184

```
gatatccagt tgacccagtc cccgagttcc ctgtccgcct ctgtgggcga tcgggtcacc      60
atcacctgcc gtgcctctca gtctgtgagc ggccgtttcc tggcctggta tcaacagaaa     120
ccaggaaaag ctccgaagct tctgatctac gacgcctctt ctctggaatc tggtgtgcca     180
tctcgcttct ctggatccgg ttccgggacg gatttcactc tgaccatcag cagtctgcag     240
ccggaagact cgcaactta ttactgccag cagtacgact actggccacc ttacaccttc      300
ggacagggta ccaaggtgga gatcaaacga                                       330
```

<210> SEQ ID NO 185
<211> LENGTH: 369
<212> TYPE: DNA
<213> ORGANISM: Artificial Sequence
<220> FEATURE:
<223> OTHER INFORMATION: Synthetic sequence

<400> SEQUENCE: 185

```
gaggttcagc tggtggagtc tggcggtggc ctggtgcagc caggggggctc actccgtttg    60 tcctgtgcag cttccggatt ctctctgtct accagcggtg tgggtgtggg ctggattcgt    120
caggccccgg gtaagggcct cgagtggctg gccctgatcg actgggccga tgacaagtac    180
tactctccct ctctgaagtc tcgtctgact ataagtcgcg acaattcgaa aaacacactg    240
tacctacaac tgaacagctt aagagctgag gacactgccg tctattattg cgcgcgtggg    300
ggttctgacg ccgtgctcgg cgactggttc gcctactggg gtcaaggaac actagtcacc    360
gtctcctcg                                                              369
```

<210> SEQ ID NO 186
<211> LENGTH: 321
<212> TYPE: DNA
<213> ORGANISM: Artificial Sequence
<220> FEATURE:
<223> OTHER INFORMATION: Synthetic sequence

<400> SEQUENCE: 186

```
gatatccagt tgacccagtc cccgagttcc ctgtccgcct ctgtgggcga tcgggtcacc     60
atcacctgcc gtgcctctca gggcatcggc agttacctgg cctggtatca acagaaacca   120
ggaaaagctc cgaagcttct gatctacgac gcctctaacc tggaaaccgg tgtgccatct   180
cgcttctctg gatccggttc cgggacggat ttcactctga ccatcagcag tctgcagccg   240
gaagacttcg caacttatta ctgccagcag ggctactcca tctggacctt cggacagggt   300
accaaggtgg agatcaaacg a                                               321
```

<210> SEQ ID NO 187
<211> LENGTH: 369
<212> TYPE: DNA
<213> ORGANISM: Artificial Sequence
<220> FEATURE:
<223> OTHER INFORMATION: Synthetic sequence

<400> SEQUENCE: 187

```
gaggttcagc tggtggagtc tggcggtggc ctggtgcagc caggggggctc actccgtttg    60
```

```
tcctgtgcag cttccggata ctctatcacc tctggtcact actggaactg gattcgtcag    120
gccccgggta agggcctcga gtgggtgtct ggtatctctg gtgacggttc ttctacctac    180
tacgccgact ctgtcaaggg ccgtttcact ataagtcgcg acaattcgaa aaacacactg    240
tacctacaac tgaacagctt aagagctgag gacactgccg tctattattg cgcgcgtggg    300
ggttctgacg ccgtgctcgg cgactggttc gcctactggg gtcaaggaac actagtcacc    360
gtctcctcg                                                            369
```

<210> SEQ ID NO 188
<211> LENGTH: 321
<212> TYPE: DNA
<213> ORGANISM: Artificial Sequence
<220> FEATURE:
<223> OTHER INFORMATION: Synthetic sequence

<400> SEQUENCE: 188

```
gatatccagt tgacccagtc cccgagttcc ctgtccgcct ctgtgggcga tcgggtcacc     60
atcacctgcc gtgcctctca gagcatcagc agttacctgg cctggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttatta ctgccagcag ggctactcaa cctggacctt cggacagggt    300
accaaggtgg agatcaaacg a                                              321
```

<210> SEQ ID NO 189
<211> LENGTH: 369
<212> TYPE: DNA
<213> ORGANISM: Artificial Sequence
<220> FEATURE:
<223> OTHER INFORMATION: Synthetic sequence

<400> SEQUENCE: 189

```
gaggttcagc tggtggagtc tggcggtggc ctggtgcagc caggggggctc actccgtttg     60 tcctgtgcag cttccggata ctctatctcc tctggtcact actggacctg gattcgtcag    120
gccccgggta agggcctcga gtgggtgtct gctatctctg gttccggttc ttctacctac    180
tacgccgact ctgtcaaggg ccgtttcact ataagtcgcg acaattcgaa aaacacactg    240
tacctacaac tgaacagctt aagagctgag gacactgccg tctattattg cgcgcgtggg    300
ggttctgacg ccgtgctcgg cgactggttc gcctactggg gtcaaggaac actagtcacc    360
gtctcctcg                                                            369
```

<210> SEQ ID NO 190
<211> LENGTH: 321
<212> TYPE: DNA
<213> ORGANISM: Artificial Sequence
<220> FEATURE:
<223> OTHER INFORMATION: Synthetic sequence

<400> SEQUENCE: 190

```
gatatccagt tgacccagtc cccgagttcc ctgtccgcct ctgtgggcga tcgggtcacc     60
atcacctgcc gtgcctctca gggcgtcggc agttacctgg cctggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttatta ctgccagcag ggctaccaac tctggacctt cggacagggt    300
```
accaaggtgg agatcaaacg a                                              321

<210> SEQ ID NO 191
<211> LENGTH: 369
<212> TYPE: DNA
<213> ORGANISM: Artificial Sequence
<220> FEATURE:
<223> OTHER INFORMATION: Synthetic sequence

<400> SEQUENCE: 191
gaggttcagc tggtggagtc tggcggtggc ctggtgcagc caggggggctc actccgtttg    60 tcctgtgcag cttccggatt ctctctgtct accggcggtg tgggtgtggg ctggattcgt   120
caggccccgg gtaagggcct cgagtggctg gccctgatcg actgggccga tgacaagtac   180
tactctccct ctctgaagtc tcgtctgact ataagtcgcg acaattcgaa aaacacactg   240
tacctacaac tgaacagctt aagagctgag gacactgccg tctattattg cgcgcgtggg   300
ggttctgaca ccgtgatcgg cgactggttc gcctactggg gtcaaggaac actagtcacc   360
gtctcctcg                                                           369

<210> SEQ ID NO 192
<211> LENGTH: 321
<212> TYPE: DNA
<213> ORGANISM: Artificial Sequence
<220> FEATURE:
<223> OTHER INFORMATION: Synthetic sequence

<400> SEQUENCE: 192
gatatccagt tgacccagtc cccgagttcc ctgtccgcct ctgtgggcga tcgggtcacc    60
atcacctgcc gtgcctctca gagcatcggc agttacctgg cctggtatca acagaaacca   120
ggaaaagctc cgaagcttct gatctacgac gcctctaacc tggaaaccgg tgtgccatct   180
cgcttctctg gatccggttc cgggacggat ttcactctga ccatcagcag tctgcagccg   240
gaagacttcg caacttatta ctgccagcag ggctactacc tctggacctt cggacagggt   300
accaaggtgg agatcaaacg a                                             321

<210> SEQ ID NO 193
<211> LENGTH: 372
<212> TYPE: DNA
<213> ORGANISM: Artificial Sequence
<220> FEATURE:
<223> OTHER INFORMATION: Synthetic sequence

<400> SEQUENCE: 193
gaggttcagc tggtggagtc tggcggtggc ctggtgcagc caggggggctc actccgtttg    60 tcctgtgcag cttccggatt ctctctgtct accagcggtg tgggtgtggg ctggattcgt   120
caggccccgg gtaagggcct cgagtgggtg tctggtatct ctggtgccgg tgattctacc   180
tactacgccg actctgtcaa gggccgtttc actataagtc gcgacaattc gaaaaacaca   240
ctgtacctac aactgaacag cttaagagct gaggacactg ccgtctatta ttgcgcgcgt   300
gagggttctg acaccgtgct cggcgactgg ttcgcctact ggggtcaagg aacactagtc   360
accgtctcct cg                                                       372

<210> SEQ ID NO 194
<211> LENGTH: 321
<212> TYPE: DNA
<213> ORGANISM: Artificial Sequence
<220> FEATURE:
<223> OTHER INFORMATION: Synthetic sequence

<400> SEQUENCE: 194

```
gatatccagt tgacccagtc cccgagttcc ctgtccgcct ctgtgggcga tcgggtcacc      60
atcacctgcc gtgcctctca ggatattcgc tcttacctgg cttggtatca acagaaacca     120
ggaaaagctc cgaagcttct gatctacgac gcctctaacc gtgccaccgg tatcccatct     180
cgcttctctg gatccggttc cgggacggat ttcactctga ccatcagcag tctgcagccg     240
gaagacttcg caacttatta ctgccagcag ggctactcca tctggacctt cggacagggt     300
accaaggtgg agatcaaacg a                                                321
```

<210> SEQ ID NO 195
<211> LENGTH: 369
<212> TYPE: DNA
<213> ORGANISM: Artificial Sequence
<220> FEATURE:
<223> OTHER INFORMATION: Synthetic sequence

<400> SEQUENCE: 195

```
gaggttcagc tggtggagtc tggcggtggc ctggtgcagc caggggggctc actccgtttg     60 tcctgtgcag cttccggatt ctctctgtct accagcggtg tggctgtggc ctggattcgt     120
caggccccgg gtaagggcct cgagtggctg gccctgatcg actgggacga tgacaagcgt     180
tactctacct ctctgaagtc tcgtctgact ataagtcgcg acaattcgaa aaacacactg     240
tacctacaac tgaacagctt aagagctgag gacactgccg tctattattg cgcgcgtgag     300
ggttctacca ccgtggtcgg cgactggttc gactactggg gtcaaggaac actagtcacc     360
gtctcctcg                                                             369
```

<210> SEQ ID NO 196
<211> LENGTH: 321
<212> TYPE: DNA
<213> ORGANISM: Artificial Sequence
<220> FEATURE:
<223> OTHER INFORMATION: Synthetic sequence

<400> SEQUENCE: 196

```
gatatccagt tgacccagtc cccgagttcc ctgtccgcct ctgtgggcga tcgggtcacc     60
atcacctgcc gtgcctctca gggcatcggc acttacctgg cctggtatca acagaaacca    120
ggaaaagctc cgaagcttct gatctacgac gcctctaacc gtgccaccgg tatcccatct    180
cgcttctctg gatccggttc cgggacggat ttcactctga ccatcagcag tctgcagccg    240
gaagacttcg caacttatta ctgccagcag ggctactccc tctggacctt cggacagggt    300
accaaggtgg agatcaaacg a                                              321
```

<210> SEQ ID NO 197
<211> LENGTH: 372
<212> TYPE: DNA
<213> ORGANISM: Artificial Sequence
<220> FEATURE:
<223> OTHER INFORMATION: Synthetic sequence

<400> SEQUENCE: 197

```
gaggttcagc tggtggagtc tggcggtggc ctggtgcagc caggggggctc actccgtttg     60 tcctgtgcag cttccggatt ctctctgtct accagcggtg tgggtgtggc ctggattcgt    120
caggccccgg gtaagggcct cgagtgggtg tcttacatct ctggtgacgg tggttctacc    180
tactacgccg actctgtcaa gggccgtttc actataagtc gcgacaattc gaaaaacaca    240
```
ctgtacctac aactgaacag cttaagagct gaggacactg ccgtctatta ttgcgcgcgt    300
gaaggttcag acgttgtggc cggcgactgg ttcgcctact ggggtcaagg aacactagtc    360
accgtctcct cg    372

<210> SEQ ID NO 198
<211> LENGTH: 321
<212> TYPE: DNA
<213> ORGANISM: Artificial Sequence
<220> FEATURE:
<223> OTHER INFORMATION: Synthetic sequence

<400> SEQUENCE: 198
gatatccagt tgacccagtc cccgagttcc ctgtccgcct ctgtgggcga tcgggtcacc    60
atcacctgcc gtgcctctca ggatattagc tctgtcctgg cttggtatca acagaaacca    120
ggaaaagctc cgaagcttct gatctacgac gcctcttctc tggaatctgg tgtgccatct    180
cgcttctctg gatccggttc cgggacggat ttcactctga ccatcagcag tctgcagccg    240
gaagacttcg caacttatta ctgccagcag ggctaccaaa tctggacctt cggacagggt    300
accaaggtgg agatcaaacg a    321

<210> SEQ ID NO 199
<211> LENGTH: 357
<212> TYPE: DNA
<213> ORGANISM: Artificial Sequence
<220> FEATURE:
<223> OTHER INFORMATION: Synthetic sequence

<400> SEQUENCE: 199
gaggttcagc tggtggagtc tggcggtggc ctggtgcagc caggggctc actccgtttg    60 tcctgtgcag cttccggata ctctatctcc tctggttacc actgggcctg gattcgtcag    120
gccccgggta agggcctcga gtggatcggt gaaatctacc actctggttc tacctactac    180
tctccatctc tgaagtctcg tgtgactata agtcgcgaca attcgaaaaa cacactgtac    240
ctacaactga acagcttaag agctgaggac actgccgtct attattgcgc gcgttcccca    300
tactactacg gtgtgttcga ctactgggt caaggaacac tagtcaccgt ctcctcg    357

<210> SEQ ID NO 200
<211> LENGTH: 321
<212> TYPE: DNA
<213> ORGANISM: Artificial Sequence
<220> FEATURE:
<223> OTHER INFORMATION: Synthetic sequence

<400> SEQUENCE: 200
gatatccagt tgacccagtc cccgagttcc ctgtccgcct ctgtgggcga tcgggtcacc    60
atcacctgct ctgcctcttc tcgcgtgggc agcgtgtact ggtatcaaca gaaaccagga    120
aaagctccga agcttctgat ctacgacgcc tctaacctgg aaaccggtgt gccatctcgc    180
ttctctggat ccggttccgg gacggatttc actctgacca tcagcagtct gcagccggaa    240
gacttcgcaa cttattactg ccagcagtac acccacgacc cagtcacctt cggacagggt    300
accaaggtgg agatcaaacg a    321

<210> SEQ ID NO 201
<211> LENGTH: 372
<212> TYPE: DNA
<213> ORGANISM: Artificial Sequence
<220> FEATURE:
<223> OTHER INFORMATION: Synthetic sequence

<400> SEQUENCE: 201

```
gaggttcagc tggtggagtc tggcggtggc ctggtgcagc caggggcctc actccgtttg      60
tcctgtgcag cttccggatt ctctctgtct accggcggtg tgggtgtggc ctggattcgt     120
caggccccgg gtaagggcct cgagtgggtg tcttccatct ctggttacgg ttctactacc     180
tactacgccg actctgtcaa gggccgtttc actataagtc gcgacaattc gaaaaacaca     240
ctgtacctac aactgaacag cttaagagct gaggacactg ccgtctatta ttgcgcgcgt     300
gagggttctg acgccgtgct cggcgactgg ttcggctact ggggtcaagg aacactagtc     360
accgtctcct cg                                                         372
```

<210> SEQ ID NO 202
<211> LENGTH: 321
<212> TYPE: DNA
<213> ORGANISM: Artificial Sequence
<220> FEATURE:
<223> OTHER INFORMATION: Synthetic sequence

<400> SEQUENCE: 202

```
gatatccagt tgacccagtc cccgagttcc ctgtccgcct ctgtgggcga tcgggtcacc      60
atcacctgcc aggcctctca ggacatcacc acgtacctgg cctggtatca acagaaacca     120
ggaaaagctc cgaagcttct gatctacgac gcctctaacc gtgccaccgg tatcccatct     180
cgcttctctg gatccggttc cggacggat ttcactctga ccatcagcag tctgcagccg     240
gaagacttcg caacttatta ctgccagcag ggctactacc tctggacctt cggacagggt     300
accaaggtgg agatcaaacg a                                               321
```

<210> SEQ ID NO 203
<211> LENGTH: 369
<212> TYPE: DNA
<213> ORGANISM: Artificial Sequence
<220> FEATURE:
<223> OTHER INFORMATION: Synthetic sequence

<400> SEQUENCE: 203

```
gaggttcagc tggtggagtc tggcggtggc ctggtgcagc caggggctc actccgtttg       60 tcctgtgcag cttccggata ctctatcacc tctggttacc actggagctg gattcgtcag     120
gccccgggta agggcctcga gtgggtgtct tccatctctg gttacggtga tactacctac     180
tacgccgact ctgtcaaggg ccgtttcact ataagtcgcg acaattcgaa aaacacactg     240
tacctacaac tgaacagctt aagagctgag gacactgccg tctattattg cgcgcgtgag     300
ggttctgaca ccgtgctcgg cgactggttc gcctactggg gtcaaggaac actagtcacc     360
gtctcctcg                                                             369
```

<210> SEQ ID NO 204
<211> LENGTH: 321
<212> TYPE: DNA
<213> ORGANISM: Artificial Sequence
<220> FEATURE:
<223> OTHER INFORMATION: Synthetic sequence

<400> SEQUENCE: 204

```
gatatccagt tgacccagtc cccgagttcc ctgtccgcct ctgtgggcga tcgggtcacc      60
atcacctgcc aggcctctca ggacatccgc acgtacctgg cctggtatca acagaaacca     120
ggaaaagctc cgaagcttct gatctacgac gcctctaacc tggaaaccgg tgtgccatct     180
```

| | |
|---|---|
| cgcttctctg gatccggttc cgggacggat ttcactctga ccatcagcag tctgcagccg | 240 |
| gaagacttcg caacttatta ctgccagcag ggctactcca tctggacctt cggacagggt | 300 |
| accaaggtgg agatcaaacg a | 321 |

<210> SEQ ID NO 205
<211> LENGTH: 369
<212> TYPE: DNA
<213> ORGANISM: Artificial Sequence
<220> FEATURE:
<223> OTHER INFORMATION: Synthetic sequence

<400> SEQUENCE: 205

| | |
|---|---|
| gaggttcagc tggtggagtc tggcggtggc ctggtgcagc caggggggctc actccgtttg | 60 |
| tcctgtgcag cttccggata ctctatctcc tctggtcacc actgggcctg gattcgtcag | 120 |
| gccccgggta agggcctcga gtgggtgtct gttatctctg gttccggttc ttctacctac | 180 |
| tacgccgact ctgtcaaggg ccgtttcact ataagtcgcg acaattcgaa aaacacactg | 240 |
| tacctacaac tgaacagctt aagagctgag gacactgccg tctattattg cgcgcgtgag | 300 |
| ggttctgaca ccgtgctcgg cgactggttc gcctactggg gtcaaggaac actagtcacc | 360 |
| gtctcctcg | 369 |

<210> SEQ ID NO 206
<211> LENGTH: 321
<212> TYPE: DNA
<213> ORGANISM: Artificial Sequence
<220> FEATURE:
<223> OTHER INFORMATION: Synthetic sequence

<400> SEQUENCE: 206

| | |
|---|---|
| gatatccagt tgacccagtc cccgagttcc ctgtccgcct ctgtgggcga tcgggtcacc | 60 |
| atcacctgcc gtgcctctca gggcatcagc agttacctgg cctggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttatta ctgccagcag ggctactcca cctggacctt cggacagggt | 300 |
| accaaggtgg agatcaaacg a | 321 |

<210> SEQ ID NO 207
<211> LENGTH: 369
<212> TYPE: DNA
<213> ORGANISM: Artificial Sequence
<220> FEATURE:
<223> OTHER INFORMATION: Synthetic sequence

<400> SEQUENCE: 207

| | |
|---|---|
| gaggttcagc tggtggagtc tggcggtggc ctggtgcagc caggggggctc actccgtttg | 60 |
| tcctgtgcag cttccggatt ctctctgtct accggcggtg tggctgtggg ctggattcgt | 120 |
| caggccccgg gtaagggcct cgagtggctg gccctgatcg actgggacgg tgacaagtcc | 180 |
| tactctacct ctctgaagtc tcgtctgact ataagtcgcg acaattcgaa aaacacactg | 240 |
| tacctacaac tgaacagctt aagagctgag gacactgccg tctattattg cgcgcgtgag | 300 |
| ggttctaccg ccgtggtcgg cgactggttc gactactggg gtcaaggaac actagtcacc | 360 |
| gtctcctcg | 369 |

<210> SEQ ID NO 208
<211> LENGTH: 321

<212> TYPE: DNA
<213> ORGANISM: Artificial Sequence
<220> FEATURE:
<223> OTHER INFORMATION: Synthetic sequence

<400> SEQUENCE: 208

| | | | | | |
|---|---|---|---|---|---|
| gatatccagt | tgacccagtc | cccgagttcc | ctgtccgcct | ctgtgggcga | tcgggtcacc | 60 |
| atcacctgcc | gtgcctctca | gggcatcagc | cgttacctgg | cctggtatca | acagaaacca | 120 |
| ggaaaagctc | cgaagcttct | gatctacgac | gcctctaacc | gtgccaccgg | tatcccatct | 180 |
| cgcttctctg | gatccggttc | cgggacggat | ttcactctga | ccatcagcag | tctgcagccg | 240 |
| gaagacttcg | caacttatta | ctgccagcag | ggctactcac | tctggacctt | cggacagggt | 300 |
| accaaggtgg | agatcaaacg | a | | | | 321 |

<210> SEQ ID NO 209
<211> LENGTH: 372
<212> TYPE: DNA
<213> ORGANISM: Artificial Sequence
<220> FEATURE:
<223> OTHER INFORMATION: Synthetic sequence

<400> SEQUENCE: 209

| | | | | | |
|---|---|---|---|---|---|
| gaggttcagc | tggtggagtc | tggcggtggc | ctggtgcagc | caggggctc | actccgtttg | 60 |
| tcctgtgcag | cttccggatt | ctctctgtct | accagcggtg | tgggtgtggc | ctggattcgt | 120 |
| caggccccgg | gtaagggcct | cgagtgggtg | tcttccatct | ctggtgccgg | tggtactacc | 180 |
| tactacgccg | actctgtcaa | gggccgtttc | actataagtc | gcgacaattc | gaaaaacaca | 240 |
| ctgtacctac | aactgaacag | cttaagagct | gaggacactg | ccgtctatta | ttgcgcgcgt | 300 |
| gggggttcta | ccgccgtgac | cggcgactgg | ttcgactact | ggggtcaagg | aacactagtc | 360 |
| accgtctcct | cg | | | | | 372 |

<210> SEQ ID NO 210
<211> LENGTH: 321
<212> TYPE: DNA
<213> ORGANISM: Artificial Sequence
<220> FEATURE:
<223> OTHER INFORMATION: Synthetic sequence

<400> SEQUENCE: 210

| | | | | | |
|---|---|---|---|---|---|
| gatatccagt | tgacccagtc | cccgagttcc | ctgtccgcct | ctgtgggcga | tcgggtcacc | 60 |
| atcacctgcc | gtgcctctca | gggcatcagc | ccttacctgg | cctggtatca | acagaaacca | 120 |
| ggaaaagctc | cgaagcttct | gatctacgac | gcctctaacc | gtgccaccgg | tatcccatct | 180 |
| cgcttctctg | gatccggttc | cgggacggat | ttcactctga | ccatcagcag | tctgcagccg | 240 |
| gaagacttcg | caacttatta | ctgccagcag | ggctactccc | tctggacctt | cggacagggt | 300 |
| accaaggtgg | agatcaaacg | a | | | | 321 |

<210> SEQ ID NO 211
<211> LENGTH: 372
<212> TYPE: DNA
<213> ORGANISM: Artificial Sequence
<220> FEATURE:
<223> OTHER INFORMATION: Synthetic sequence

<400> SEQUENCE: 211

| | | | | | |
|---|---|---|---|---|---|
| gaggttcagc | tggtggagtc | tggcggtggc | ctggtgcagc | caggggctc | actccgtttg | 60 |
| tcctgtgcag | cttccggatt | ctctctgtct | accggtggtg | tgggtgtggc | ctggattcgt | 120 |

```
caggccccgg gtaagggcct cgagtgggtg tcttacatct ctggttccgg tgatactacc    180
tactacgccg actctgtcaa ggccgtttc actataagtc gcgacaattc gaaaaacaca     240
ctgtacctac aactgaacag cttaagagct gaggacactg ccgtctatta ttgcgcgcgt    300
gagggttctg acaccgtggt cggcgactgg ttcgcctact ggggtcaagg aacactagtc    360
accgtctcct cg                                                       372
```

```
<210> SEQ ID NO 212
<211> LENGTH: 324
<212> TYPE: DNA
<213> ORGANISM: Artificial Sequence
<220> FEATURE:
<223> OTHER INFORMATION: Synthetic sequence

<400> SEQUENCE: 212
gatatccagt tgacccagtc cccgagttcc ctgtccgcct ctgtgggcga tcgggtcacc    60
atcacctgcc gtgcctctca gggtatctct tcttacctgg cctggtatca acagaaacca   120
ggaaaagctc cgaagcttct gatctacgac gcctctaacc tggaaaccgg tgtgccatct   180
cgcttctctg gatccggttc cgggacggat ttcactctga ccatcagcag tctgcagccg   240
gaagacttcg caacttacta ctgccagcag tactacacca ccccactgac cttcggtcag   300
ggtaccaagg tggagatcaa acga                                         324
```

```
<210> SEQ ID NO 213
<211> LENGTH: 372
<212> TYPE: DNA
<213> ORGANISM: Artificial Sequence
<220> FEATURE:
<223> OTHER INFORMATION: Synthetic sequence

<400> SEQUENCE: 213
gaggttcagc tggtggagtc tggcggtggc ctggtgcagc caggggggctc actccgtttg    60 tcctgtgcag cttccggatt ctctctgtct accggcggtg tgggtgtggg ctggattcgt   120
caggccccgg gtaagggcct cgagtgggtg tcttacatct ctggtgacgg tgatactacc   180
tactacgccg actctgtcaa ggccgtttc actataagtc gcgacaattc gaaaaacaca    240
ctgtacctac aactgaacag cttaagagct gaggacactg ccgtctatta ttgcgcgcgt   300
gagggttctg acaccgtggc cggcgactgg ttcgcctact ggggtcaagg aacactagtc   360
accgtctcct cg                                                       372
```

```
<210> SEQ ID NO 214
<211> LENGTH: 324
<212> TYPE: DNA
<213> ORGANISM: Artificial Sequence
<220> FEATURE:
<223> OTHER INFORMATION: Synthetic sequence

<400> SEQUENCE: 214
gatatccagt tgacccagtc cccgagttcc ctgtccgcct ctgtgggcga tcgggtcacc    60
atcacctgcc gtgcctctca gggtatctct tcttacctgg cctggtatca acagaaacca   120
ggaaaagctc cgaagcttct gatctacgac gcctctaacc tggaaaccgg tgtgccatct   180
cgcttctctg gatccggttc cgggacggat ttcactctga ccatcagcag tctgcagccg   240
gaagacttcg caacttacta ctgccagcag tactacacca ccccactgac cttcggtcag   300
ggtaccaagg tggagatcaa acga                                         324
```

```
<210> SEQ ID NO 215
<211> LENGTH: 372
<212> TYPE: DNA
<213> ORGANISM: Artificial Sequence
<220> FEATURE:
<223> OTHER INFORMATION: Synthetic sequence

<400> SEQUENCE: 215
gaggttcagc tggtggagtc tggcggtggc ctggtgcagc caggggggctc actccgtttg      60 tcctgtgcag cttccggatt ctctctgtct accagcggtg tgggtgtggc ctggattcgt     120
caggccccgg gtaagggcct cgagtgggtg tcttccatct ctggttacgg tggtactacc     180
tactacgccg actctgtcaa ggccgtttc actataagtc gcgacaattc gaaaaacaca     240
ctgtacctac aactgaacag cttaagagct gaggacactg ccgtctatta ttgcgcgcgt     300
gagggttctg acaccgtgct cggcgactgg ttcgcctact ggggtcaagg aacactagtc     360
accgtctcct cg                                                        372

<210> SEQ ID NO 216
<211> LENGTH: 324
<212> TYPE: DNA
<213> ORGANISM: Artificial Sequence
<220> FEATURE:
<223> OTHER INFORMATION: Synthetic sequence

<400> SEQUENCE: 216
gatatccagt tgacccagtc cccgagttcc ctgtccgcct ctgtgggcga tcgggtcacc      60
atcacctgcc gtgcctctca gggtatctct tcttacctgg cctggtatca acagaaacca     120
ggaaaagctc cgaagcttct gatctacgac gcctctaacc tggaaaccgg tgtgccatct     180
cgcttctctg gatccggttc cgggacggat ttcactctga ccatcagcag tctgcagccg     240
gaagacttcg caacttacta ctgccagcag tactacacca ccccactgac cttcggtcag     300
ggtaccaagg tggagatcaa acga                                           324

<210> SEQ ID NO 217
<211> LENGTH: 372
<212> TYPE: DNA
<213> ORGANISM: Artificial Sequence
<220> FEATURE:
<223> OTHER INFORMATION: Synthetic sequence

<400> SEQUENCE: 217
gaggttcagc tggtggagtc tggcggtggc ctggtgcagc caggggggctc actccgtttg      60 tcctgtgcag cttccggatt ctctctgtct accggcggtg tgggtgtggg ctggattcgt     120
caggccccgg gtaagggcct cgagtgggtg tcttacatct ctggtgccgg tggtactacc     180
tactacgccg actctgtcaa ggccgtttc actataagtc gcgacaattc gaaaaacaca     240
ctgtacctac aactgaacag cttaagagct gaggacactg ccgtctatta ttgcgcgcgt     300
gagggttctg acaccgtgct cggcgactgg ttcgcctact ggggtcaagg aacactagtc     360
accgtctcct cg                                                        372

<210> SEQ ID NO 218
<211> LENGTH: 324
<212> TYPE: DNA
<213> ORGANISM: Artificial Sequence
<220> FEATURE:
<223> OTHER INFORMATION: Synthetic sequence

<400> SEQUENCE: 218
```

| | |
|---|---|
| gatatccagt tgacccagtc cccgagttcc ctgtccgcct ctgtgggcga tcgggtcacc | 60 |
| atcacctgcc gtgcctctca gggtatctct tcttacctgg cctggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttacta ctgccagcag tactacacca ccccactgac cttcggtcag | 300 |
| ggtaccaagg tggagatcaa acga | 324 |

<210> SEQ ID NO 219
<211> LENGTH: 372
<212> TYPE: DNA
<213> ORGANISM: Artificial Sequence
<220> FEATURE:
<223> OTHER INFORMATION: Synthetic sequence

<400> SEQUENCE: 219

| | |
|---|---|
| gaggttcagc tggtggagtc tggcggtggc ctggtgcagc cagggggctc actccgtttg | 60 |
| tcctgtgcag cttccggatt ctctctgtct accggcggtg tgggtgtggg ctggattcgt | 120 |
| caggccccgg gtaagggcct cgagtgggtg tcttacatct ctggtgccgg tggtactacc | 180 |
| tactacgccg actctgtcaa gggccgtttc actataagtc gcgacaattc gaaaaacaca | 240 |
| ctgtacctac aactgaacag cttaagagct gaggacactg ccgtctatta ttgcgcgcgt | 300 |
| gagggttctg acgccgtgct cggcgactgg ttcgcctact ggggtcaagg aacactagtc | 360 |
| accgtctcct cg | 372 |

<210> SEQ ID NO 220
<211> LENGTH: 324
<212> TYPE: DNA
<213> ORGANISM: Artificial Sequence
<220> FEATURE:
<223> OTHER INFORMATION: Synthetic sequence

<400> SEQUENCE: 220

| | |
|---|---|
| gatatccagt tgacccagtc cccgagttcc ctgtccgcct ctgtgggcga tcgggtcacc | 60 |
| atcacctgcc gtgcctctca gggtatctct tcttacctgg cctggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttacta ctgccagcag tactacacca ccccactgac cttcggtcag | 300 |
| ggtaccaagg tggagatcaa acga | 324 |

<210> SEQ ID NO 221
<211> LENGTH: 372
<212> TYPE: DNA
<213> ORGANISM: Artificial Sequence
<220> FEATURE:
<223> OTHER INFORMATION: Synthetic sequence

<400> SEQUENCE: 221

| | |
|---|---|
| gaggttcagc tggtggagtc tggcggtggc ctggtgcagc cagggggctc actccgtttg | 60 |
| tcctgtgcag cttccggatt ctctctgtct accggcggtg tgggtgtggg ctggattcgt | 120 |
| caggccccgg gtaagggcct cgagtgggtg tcttacatct ctggtgacgg tgatactacc | 180 |
| tactacgccg actctgtcaa gggccgtttc actataagtc gcgacaattc gaaaaacaca | 240 |
| ctgtacctac aactgaacag cttaagagct gaggacactg ccgtctatta ttgcgcgcgt | 300 |
| gagggttcta ccgccgtgct cggcgactgg ttcgcctact ggggtcaagg aacactagtc | 360 |

```
accgtctcct cg                                                          372

<210> SEQ ID NO 222
<211> LENGTH: 324
<212> TYPE: DNA
<213> ORGANISM: Artificial Sequence
<220> FEATURE:
<223> OTHER INFORMATION: Synthetic sequence

<400> SEQUENCE: 222
gatatccagt tgacccagtc cccgagttcc ctgtccgcct ctgtgggcga tcgggtcacc       60
atcacctgcc gtgcctctca gggtatctct tcttacctgg cctggtatca acagaaacca      120
ggaaaagctc cgaagcttct gatctacgac gcctctaacc tggaaaccgg tgtgccatct      180
cgcttctctg gatccggttc cgggacggat ttcactctga ccatcagcag tctgcagccg      240
gaagacttcg caacttacta ctgccagcag tactacacca ccccactgac cttcggtcag      300
ggtaccaagg tggagatcaa acga                                             324

<210> SEQ ID NO 223
<211> LENGTH: 372
<212> TYPE: DNA
<213> ORGANISM: Artificial Sequence
<220> FEATURE:
<223> OTHER INFORMATION: Synthetic sequence

<400> SEQUENCE: 223
gaggttcagc tggtggagtc tggcggtggc ctggtgcagc caggggggctc actccgtttg       60 tcctgtgcag cttccggatt ctctctgtct accagcggtg tgggtgtggg ctggattcgt      120
caggccccgg gtaagggcct cgagtgggtg tcttacatct ctggtgacgg tggttctacc      180
tactacgccg actctgtcaa gggccgtttc actataagtc gcgacaattc gaaaaacaca      240
ctgtacctac aactgaacag cttaagagct gaggacactg ccgtctatta ttgcgcgcgt      300
gagggttcta ccgccgtggt cggcgactgg ttcgcctact ggggtcaagg aacactagtc      360
accgtctcct cg                                                          372

<210> SEQ ID NO 224
<211> LENGTH: 324
<212> TYPE: DNA
<213> ORGANISM: Artificial Sequence
<220> FEATURE:
<223> OTHER INFORMATION: Synthetic sequence

<400> SEQUENCE: 224
gatatccagt tgacccagtc cccgagttcc ctgtccgcct ctgtgggcga tcgggtcacc       60
atcacctgcc gtgcctctca gggtatctct tcttacctgg cctggtatca acagaaacca      120
ggaaaagctc cgaagcttct gatctacgac gcctctaacc tggaaaccgg tgtgccatct      180
cgcttctctg gatccggttc cgggacggat ttcactctga ccatcagcag tctgcagccg      240
gaagacttcg caacttacta ctgccagcag tactacacca ccccactgac cttcggtcag      300
ggtaccaagg tggagatcaa acga                                             324

<210> SEQ ID NO 225
<211> LENGTH: 372
<212> TYPE: DNA
<213> ORGANISM: Artificial Sequence
<220> FEATURE:
<223> OTHER INFORMATION: Synthetic sequence
```

```
<400> SEQUENCE: 225
gaggttcagc tggtggagtc tggcggtggc ctggtgcagc caggggctc actccgtttg      60 tcctgtgcag cttccggatt ctctctgtct accggcggtg tgggtgtggc ctggattcgt     120
caggccccgg gtaagggcct cgagtgggtg tcttacatct ctggttacgg tggtactacc     180
tactacgccg actctgtcaa gggccgtttc actataagtc gcgacaattc gaaaaacaca     240
ctgtacctac aactgaacag cttaagagct gaggacactg ccgtctatta ttgcgcgcgt     300
gagggttcta ccgccgtgct cggcgactgg ttcgcctact ggggtcaagg aacactagtc     360
accgtctcct cg                                                          372

<210> SEQ ID NO 226
<211> LENGTH: 324
<212> TYPE: DNA
<213> ORGANISM: Artificial Sequence
<220> FEATURE:
<223> OTHER INFORMATION: Synthetic sequence

<400> SEQUENCE: 226
gatatccagt tgacccagtc cccgagttcc ctgtccgcct ctgtgggcga tcgggtcacc      60
atcacctgcc gtgcctctca gggtatctct tcttacctgg cctggtatca acagaaacca     120
ggaaaagctc cgaagcttct gatctacgac gcctctaacc tggaaaccgg tgtgccatct     180
cgcttctctg gatccggttc cgggacggat ttcactctga ccatcagcag tctgcagccg     240
gaagacttcg caacttacta ctgccagcag tactactcta ccccactgac cttcggtcag     300
ggtaccaagg tggagatcaa acga                                             324

<210> SEQ ID NO 227
<211> LENGTH: 372
<212> TYPE: DNA
<213> ORGANISM: Artificial Sequence
<220> FEATURE:
<223> OTHER INFORMATION: Synthetic sequence

<400> SEQUENCE: 227
gaggttcagc tggtggagtc tggcggtggc ctggtgcagc caggggctc actccgtttg      60 tcctgtgcag cttccggatt ctctctgtct accagcggta tgggtgtggg ctggattcgt     120
caggccccgg gtaagggcct cgagtgggtg tcttacatct ctggttacgg tggtactacc     180
tactacgccg actctgtcaa gggccgtttc actataagtc gcgacaattc gaaaaacaca     240
ctgtacctac aactgaacag cttaagagct gaggacactg ccgtctatta ttgcgcgcgt     300
gaaggttcag acgttgtggc cggcgactgg ttcgcctact ggggtcaagg aacactagtc     360
accgtctcct cg                                                          372

<210> SEQ ID NO 228
<211> LENGTH: 324
<212> TYPE: DNA
<213> ORGANISM: Artificial Sequence
<220> FEATURE:
<223> OTHER INFORMATION: Synthetic sequence

<400> SEQUENCE: 228
gatatccagt tgacccagtc cccgagttcc ctgtccgcct ctgtgggcga tcgggtcacc      60
atcacctgcc gtgcctctca gggtatctct tcttacctgg cctggtatca acagaaacca     120
ggaaaagctc cgaagcttct gatctacgac gcctctaacc tggaaaccgg tgtgccatct     180
cgcttctctg gatccggttc cgggacggat ttcactctga ccatcagcag tctgcagccg     240
```

| | |
|---|---|
| gaagacttcg caacttacta ctgccagcag tactactcta ccccactgac cttcggtcag | 300 |
| ggtaccaagg tggagatcaa acga | 324 |

<210> SEQ ID NO 229
<211> LENGTH: 369
<212> TYPE: DNA
<213> ORGANISM: Artificial Sequence
<220> FEATURE:
<223> OTHER INFORMATION: Synthetic sequence

<400> SEQUENCE: 229

| | |
|---|---|
| gaggttcagc tggtggagtc tggcggtggc ctggtgcagc caggggggctc actccgtttg | 60 |
| tcctgtgcag cttccggata ctctatctcc tctggtcacc actgggactg gattcgtcag | 120 |
| gccccgggta agggcctcga gtgggtgtct tacatctctg gtgccggtga tactacctac | 180 |
| tacgccgact ctgtcaaggg ccgtttcact ataagtcgcg acaattcgaa aaacacactg | 240 |
| tacctacaac tgaacagctt aagagctgag gacactgccg tctattattg cgcgcgtgag | 300 |
| ggttctgacg ccgtgctcgg cgactggttc gcctactggg gtcaaggaac actagtcacc | 360 |
| gtctcctcg | 369 |

<210> SEQ ID NO 230
<211> LENGTH: 324
<212> TYPE: DNA
<213> ORGANISM: Artificial Sequence
<220> FEATURE:
<223> OTHER INFORMATION: Synthetic sequence

<400> SEQUENCE: 230

| | |
|---|---|
| gatatccagt tgacccagtc cccgagttcc ctgtccgcct ctgtgggcga tcgggtcacc | 60 |
| atcacctgcc gtgcctctca gggtatctct tcttacctgg cctggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttacta ctgccagcag tactactcta ccccactgac cttcggtcag | 300 |
| ggtaccaagg tggagatcaa acga | 324 |

<210> SEQ ID NO 231
<211> LENGTH: 372
<212> TYPE: DNA
<213> ORGANISM: Artificial Sequence
<220> FEATURE:
<223> OTHER INFORMATION: Synthetic sequence

<400> SEQUENCE: 231

| | |
|---|---|
| gaggttcagc tggtggagtc tggcggtggc ctggtgcagc caggggggctc actccgtttg | 60 |
| tcctgtgcag cttccggatt ctctctgtct accagcggtg tgggtgtggg ctggattcgt | 120 |
| caggcccccgg gtaagggcct cgagtgggtg tcttacatct ctggtgacgg tggttctacc | 180 |
| tactacgccg actctgtcaa ggccgtttc actataagtc gcgacaattc gaaaaacaca | 240 |
| ctgtacctac aactgaacag cttaagagct gaggacactg ccgtctatta ttgcgcgcgt | 300 |
| gagggttctg acaccgtgct cggcgactgg ttcgcctact ggggtcaagg aacactagtc | 360 |
| accgtctcct cg | 372 |

<210> SEQ ID NO 232
<211> LENGTH: 324
<212> TYPE: DNA

```
<213> ORGANISM: Artificial Sequence
<220> FEATURE:
<223> OTHER INFORMATION: Synthetic sequence

<400> SEQUENCE: 232
gatatccagt tgacccagtc cccgagttcc ctgtccgcct ctgtgggcga tcgggtcacc      60
atcacctgcc gtgcctctca gggtatctct tcttacctgg cctggtatca acagaaacca     120
ggaaaagctc cgaagcttct gatctacgac gcctctaacc tggaaaccgg tgtgccatct     180
cgcttctctg gatccggttc cgggacggat ttcactctga ccatcagcag tctgcagccg     240
gaagacttcg caacttacta ctgccagcag tactactcta ccccactgac cttcggtcag     300
ggtaccaagg tggagatcaa acga                                            324

<210> SEQ ID NO 233
<211> LENGTH: 372
<212> TYPE: DNA
<213> ORGANISM: Artificial Sequence
<220> FEATURE:
<223> OTHER INFORMATION: Synthetic sequence

<400> SEQUENCE: 233
gaggttcagc tggtggagtc tggcggtggc ctggtgcagc caggggggctc actccgtttg     60 tcctgtgcag cttccggatt ctctctgtct accggcggtg tgggtgtggg ctggattcgt    120
caggccccgg gtaagggcct cgagtgggtg tcttacatct ctggtgccgg ttctactacc    180
tactacgccg actctgtcaa gggccgtttc actataagtc gcgacaattc gaaaaacaca    240
ctgtacctac aactgaacag cttaagagct gaggacactg ccgtctatta ttgcgcgcgt    300
gagggttctg acaccgtgct cggcgactgg ttcgcctact ggggtcaagg aacactagtc    360
accgtctcct cg                                                         372

<210> SEQ ID NO 234
<211> LENGTH: 324
<212> TYPE: DNA
<213> ORGANISM: Artificial Sequence
<220> FEATURE:
<223> OTHER INFORMATION: Synthetic sequence

<400> SEQUENCE: 234
gatatccagt tgacccagtc cccgagttcc ctgtccgcct ctgtgggcga tcgggtcacc     60
atcacctgcc gtgcctctca gggtatctct tcttacctgg cctggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttacta ctgccagcag tactactcta ccccactgac cttcggtcag    300
ggtaccaagg tggagatcaa acga                                           324

<210> SEQ ID NO 235
<211> LENGTH: 372
<212> TYPE: DNA
<213> ORGANISM: Artificial Sequence
<220> FEATURE:
<223> OTHER INFORMATION: Synthetic sequence

<400> SEQUENCE: 235
gaggttcagc tggtggagtc tggcggtggc ctggtgcagc caggggggctc actccgtttg     60 tcctgtgcag cttccggatt ctctctgtct accagcggtg tgggtgtgag ctggattcgt    120
caggccccgg gtaagggcct cgagtgggtg tcttacatct ctggttccgg tgatactacc    180
```

```
tactacgccg actctgtcaa gggccgtttc actataagtc gcgacaattc gaaaaacaca    240
ctgtacctac aactgaacag cttaagagct gaggacactg ccgtctatta ttgcgcgcgt    300
gagggttctg acgccgtgct cggcgactgg ttcgcctact ggggtcaagg aacactagtc    360
accgtctcct cg                                                        372
```

<210> SEQ ID NO 236
<211> LENGTH: 324
<212> TYPE: DNA
<213> ORGANISM: Artificial Sequence
<220> FEATURE:
<223> OTHER INFORMATION: Synthetic sequence

<400> SEQUENCE: 236

```
gatatccagt tgacccagtc cccgagttcc ctgtccgcct ctgtgggcga tcgggtcacc     60
atcacctgcc gtgcctctca gggtatctct tcttacctgg cctggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttacta ctgccagcag tactactcta ccccactgac cttcggtcag    300
ggtaccaagg tggagatcaa acga                                           324
```

<210> SEQ ID NO 237
<211> LENGTH: 372
<212> TYPE: DNA
<213> ORGANISM: Artificial Sequence
<220> FEATURE:
<223> OTHER INFORMATION: Synthetic sequence

<400> SEQUENCE: 237

```
gaggttcagc tggtggagtc tggcggtggc ctggtgcagc caggggggctc actccgtttg     60 tcctgtgcag cttccggatt ctctctgtct accagcggtg tgggtgtggg ctggattcgt    120
caggccccgg gtaagggcct cgagtgggtg tcttacatct ctggtgacgg tgatactacc    180
tactacgccg actctgtcaa gggccgtttc actataagtc gcgacaattc gaaaaacaca    240
ctgtacctac aactgaacag cttaagagct gaggacactg ccgtctatta ttgcgcgcgt    300
gagggttcta ccaccgtgct cggcgactgg ttcgcctact ggggtcaagg aacactagtc    360
accgtctcct cg                                                        372
```

<210> SEQ ID NO 238
<211> LENGTH: 324
<212> TYPE: DNA
<213> ORGANISM: Artificial Sequence
<220> FEATURE:
<223> OTHER INFORMATION: Synthetic sequence

<400> SEQUENCE: 238

```
gatatccagt tgacccagtc cccgagttcc ctgtccgcct ctgtgggcga tcgggtcacc     60
atcacctgcc gtgcctctca gggtatctct tcttacctgg cctggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttacta ctgccagcag tactactcta ccccactgac cttcggtcag    300
ggtaccaagg tggagatcaa acga                                           324
```

<210> SEQ ID NO 239

```
<211> LENGTH: 372
<212> TYPE: DNA
<213> ORGANISM: Artificial Sequence
<220> FEATURE:
<223> OTHER INFORMATION: Synthetic sequence

<400> SEQUENCE: 239
gaggttcagc tggtggagtc tggcggtggc ctggtgcagc caggggggctc actccgtttg     60 tcctgtgcag cttccggatt ctctctgtct accggcggtg tgggtgtggc ctggattcgt    120
caggccccgg gtaagggcct cgagtgggtg tcttacatct ctggtgacgg tggtactacc    180
tactacgccg actctgtcaa gggccgtttc actataagtc gcgacaattc gaaaaacaca    240
ctgtacctac aactgaacag cttaagagct gaggacactg ccgtctatta ttgcgcgcgt    300
gagggttctg acaccgtgct cggcgactgg ttcgcctact ggggtcaagg aacactagtc    360
accgtctcct cg                                                        372

<210> SEQ ID NO 240
<211> LENGTH: 324
<212> TYPE: DNA
<213> ORGANISM: Artificial Sequence
<220> FEATURE:
<223> OTHER INFORMATION: Synthetic sequence

<400> SEQUENCE: 240
gatatccagt tgacccagtc cccgagttcc ctgtccgcct ctgtgggcga tcgggtcacc     60
atcacctgcc gtgcctctca gggtatctct tcttacctgg cctggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttacta ctgccagcag tcttactcta ccccactgac cttcggtcag    300
ggtaccaagg tggagatcaa acga                                           324

<210> SEQ ID NO 241
<211> LENGTH: 372
<212> TYPE: DNA
<213> ORGANISM: Artificial Sequence
<220> FEATURE:
<223> OTHER INFORMATION: Synthetic sequence

<400> SEQUENCE: 241
gaggttcagc tggtggagtc tggcggtggc ctggtgcagc caggggggctc actccgtttg     60 tcctgtgcag cttccggatt ctctctgtct accggcggtg tgggtgtggg ctggattcgt    120
caggccccgg gtaagggcct cgagtgggtg tcttacatct ctggtgccgg tgattctacc    180
tactacgccg actctgtcaa gggccgtttc actataagtc gcgacaattc gaaaaacaca    240
ctgtacctac aactgaacag cttaagagct gaggacactg ccgtctatta ttgcgcgcgt    300
gagggttctg acaccgtgct cggcgactgg ttcgcctact ggggtcaagg aacactagtc    360
accgtctcct cg                                                        372

<210> SEQ ID NO 242
<211> LENGTH: 324
<212> TYPE: DNA
<213> ORGANISM: Artificial Sequence
<220> FEATURE:
<223> OTHER INFORMATION: Synthetic sequence

<400> SEQUENCE: 242
gatatccagt tgacccagtc cccgagttcc ctgtccgcct ctgtgggcga tcgggtcacc     60
```

```
atcacctgcc gtgcctctca gggtgtgtct tcttacctgg cctggtatca acagaaacca      120
ggaaaagctc cgaagcttct gatctacgac gcctctaacc tggaaaccgg tgtgccatct      180
cgcttctctg gatccggttc cgggacggat ttcactctga ccatcagcag tctgcagccg      240
gaagacttcg caacttacta ctgccagcag tactacacca ccccactgac cttcggtcag      300
ggtaccaagg tggagatcaa acga                                             324

<210> SEQ ID NO 243
<211> LENGTH: 372
<212> TYPE: DNA
<213> ORGANISM: Artificial Sequence
<220> FEATURE:
<223> OTHER INFORMATION: Synthetic sequence

<400> SEQUENCE: 243
gaggttcagc tggtggagtc tggcggtggc ctggtgcagc caggggggctc actccgtttg      60 tcctgtgcag cttccggatt ctctctgtct accagcggtg tgggtgtggc ctggattcgt      120
caggccccgg gtaagggcct cgagtgggtg tcttccatct ctggttacgg tggtactacc      180
tactacgccg actctgtcaa gggccgtttc actataagtc gcgacaattc gaaaaacaga      240
ctgtacctac aactgaacag cttaagagct gaggacactg ccgtctatta ttgcgcgcgt      300
gagggttctg acaccgtgct cggcgactgg ttcgcctact ggggtcaagg aacactagtc      360
accgtctcct cg                                                          372

<210> SEQ ID NO 244
<211> LENGTH: 324
<212> TYPE: DNA
<213> ORGANISM: Artificial Sequence
<220> FEATURE:
<223> OTHER INFORMATION: Synthetic sequence

<400> SEQUENCE: 244
gatatccagt tgacccagtc cccgagttcc ctgtccgcct ctgtgggcga tcgggtcacc      60
atcacctgcc gtgcctctca gggtgtgtct tcttacctgg cctggtatca acagaaacca      120
ggaaaagctc cgaagcttct gatctacgac gcctctaacc tggaaaccgg tgtgccatct      180
cgcttctctg gatccggttc cgggacggat ttcactctga ccatcagcag tctgcagccg      240
gaagacttcg caacttacta ctgccagcag tactacacca ccccactgac cttcggtcag      300
ggtaccaagg tggagatcaa acga                                             324

<210> SEQ ID NO 245
<211> LENGTH: 372
<212> TYPE: DNA
<213> ORGANISM: Artificial Sequence
<220> FEATURE:
<223> OTHER INFORMATION: Synthetic sequence

<400> SEQUENCE: 245
gaggttcagc tggtggagtc tggcggtggc ctggtgcagc caggggggctc actccgtttg      60 tcctgtgcag cttccggatt ctctctgtct accggcggtg tgggtgtggg ctggattcgt      120
caggccccgg gtaagggcct cgagtgggtg tcttccatct ctggttccgg tggttctacc      180
tactacgccg actctgtcaa gggccgtttc actataagtc gcgacaattc gaaaaacaca      240
ctgtacctac aactgaacag cttaagagct gaggacactg ccgtctatta ttgcgcgcgt      300
gagggttctg acaccgtgct cggcgactgg ttcgcctact ggggtcaagg aacactagtc      360
```
accgtctcct cg					372

<210> SEQ ID NO 246
<211> LENGTH: 324
<212> TYPE: DNA
<213> ORGANISM: Artificial Sequence
<220> FEATURE:
<223> OTHER INFORMATION: Synthetic sequence

<400> SEQUENCE: 246
gatatccagt tgacccagtc cccgagttcc ctgtccgcct ctgtgggcga tcgggtcacc     60
atcacctgcc gtgcctctca gggtgtgtct tcttacctgg cctggtatca acagaaacca    120
ggaaaagctc cgaagcttct gatctacgac gcctctaacc tggaaaccgg tgtgccatct    180
cgcttctctg gatccggttc cgggacggat ttcactctga ccatcagcag tctgcagccg    240
gaagacttcg caacttacta ctgccagcag tactacacca ccccactgac cttcggtcag    300
ggtaccaagg tggagatcaa acga                                           324

<210> SEQ ID NO 247
<211> LENGTH: 369
<212> TYPE: DNA
<213> ORGANISM: Artificial Sequence
<220> FEATURE:
<223> OTHER INFORMATION: Synthetic sequence

<400> SEQUENCE: 247
gaggttcagc tggtggagtc tggcggtggc ctggtgcagc caggggggctc actccgtttg     60
tcctgtgcag cttccggatt ctctctgtct accagcggtg tgggtgtggg ctggattcgt    120
caggccccgg gtaagggcct cgagtggatt ggtgacatct accactctgg tagcacctac    180
tacaacccat ctctgaagtc tcgtgtgact ataagtcgcg acaattcgaa aaacacactg    240
tacctacaac tgaacagctt aagagctgag acactgccg tctattattg cgcgcgtgag    300
ggttctaccg ccgtgctcgg cgactggttc gcctactggg gtcaaggaac actagtcacc    360
gtctcctcg                                                            369

<210> SEQ ID NO 248
<211> LENGTH: 324
<212> TYPE: DNA
<213> ORGANISM: Artificial Sequence
<220> FEATURE:
<223> OTHER INFORMATION: Synthetic sequence

<400> SEQUENCE: 248
gatatccagt tgacccagtc cccgagttcc ctgtccgcct ctgtgggcga tcgggtcacc     60
atcacctgcc gtgcctctca gtctatctct tcttacctga actggtatca acagaaacca    120
ggaaaagctc cgaagcttct gatctacgcc gcctctacct gcagtctgg tgtgccatct    180
cgcttctctg gatccggttc cgggacggat ttcactctga ccatcagcag tctgcagccg    240
gaagacttcg caacttacta ctgccagcag tactactcta ccccactgac cttcggtcag    300
ggtaccaagg tggagatcaa acga                                           324

<210> SEQ ID NO 249
<211> LENGTH: 369
<212> TYPE: DNA
<213> ORGANISM: Artificial Sequence
<220> FEATURE:
<223> OTHER INFORMATION: Synthetic sequence

<400> SEQUENCE: 249

```
gaggttcagc tggtggagtc tggcggtggc ctggtgcagc caggggctc actccgtttg      60 tcctgtgcag cttccggatt ctctctgtct accagcggtg tgggtgtgac ctggattcgt    120
caggccccgg gtaagagcct cgagtggatc ggtgacatct accactctgg ttctacctac    180
tactctccat ctctgaagtc tcgtgtgact ataagtcgcg acaattcgaa aaacacactg    240
tacctacaac tgaacagctt aagagctgag gacactgccg tctattattg cgcgcgtgaa    300
ggttcagacg ctgtgccgg cgactggttc gactactggg gtcaaggaac actagtcacc    360
gtctcctcg                                                            369

<210> SEQ ID NO 250
<211> LENGTH: 324
<212> TYPE: DNA
<213> ORGANISM: Artificial Sequence
<220> FEATURE:
<223> OTHER INFORMATION: Synthetic sequence

<400> SEQUENCE: 250
gatatccagt tgacccagtc cccgagttcc ctgtccgcct ctgtgggcga tcgggtcacc     60
atcacctgcc gtgcctctca gtctatctct tcttacctga actggtatca acagaaacca   120
ggaaaagctc cgaagcttct gatctacgcc gcctctacct tgcagtctgg tgtgccatct   180
cgcttctctg gatccggttc cgggacggat ttcactctga ccatcagcag tctgcagccg   240
gaagacttcg caacttacta ctgccagcag tactactcta ccccactgac cttcggtcag   300
ggtaccaagg tggagatcaa acga                                            324

<210> SEQ ID NO 251
<211> LENGTH: 369
<212> TYPE: DNA
<213> ORGANISM: Artificial Sequence
<220> FEATURE:
<223> OTHER INFORMATION: Synthetic sequence

<400> SEQUENCE: 251
gaggttcagc tggtggagtc tggcggtggc ctggtgcagc caggggctc actccgtttg      60 tcctgtgcag cttccggatt ctctctgtct accagcggtg tggctgtggc ctggattcgt   120
caggccccgg gtaagggcct cgagtggatc ggtgacatct accactctgg taacacctac   180
tacaacccat ctctgaagtc tcgtgtgact ataagtcgcg acaattcgaa aaacacactg   240
tacctacaac tgaacagctt aagagctgag gacactgccg tctattattg cgcgcgtggg   300
ggttctgaca ccgtgtcgg cgactggttc gcctactggg gtcaaggaac actagtcacc    360
gtctcctcg                                                            369

<210> SEQ ID NO 252
<211> LENGTH: 324
<212> TYPE: DNA
<213> ORGANISM: Artificial Sequence
<220> FEATURE:
<223> OTHER INFORMATION: Synthetic sequence

<400> SEQUENCE: 252
gatatccagt tgacccagtc cccgagttcc ctgtccgcct ctgtgggcga tcgggtcacc     60
atcacctgcc gtgcctctca gtctatctct tcttacctga actggtatca acagaaacca   120
ggaaaagctc cgaagcttct gatctacgcc gcctctacct tgcagtctgg tgtgccatct   180
cgcttctctg gatccggttc cgggacggat ttcactctga ccatcagcag tctgcagccg   240
```

```
gaagacttcg caacttacta ctgccagcag tactactcta ccccactgac cttcggtcag    300
ggtaccaagg tggagatcaa acga                                           324
```

<210> SEQ ID NO 253
<211> LENGTH: 11
<212> TYPE: PRT
<213> ORGANISM: Artificial Sequence
<220> FEATURE:
<223> OTHER INFORMATION: Synthetic sequence

<400> SEQUENCE: 253

Phe Thr Phe Thr Ser Tyr Gly Ile His Trp Val
1               5                   10

<210> SEQ ID NO 254
<211> LENGTH: 13
<212> TYPE: PRT
<213> ORGANISM: Artificial Sequence
<220> FEATURE:
<223> OTHER INFORMATION: Synthetic sequence

<400> SEQUENCE: 254

Phe Ser Leu Ser Thr Ser Gly Val Ala Val Ser Trp Ile
1               5                   10

<210> SEQ ID NO 255
<211> LENGTH: 13
<212> TYPE: PRT
<213> ORGANISM: Artificial Sequence
<220> FEATURE:
<223> OTHER INFORMATION: Synthetic sequence

<400> SEQUENCE: 255

Phe Ser Leu Ser Thr Gly Gly Val Gly Val Ser Trp Ile
1               5                   10

<210> SEQ ID NO 256
<211> LENGTH: 12
<212> TYPE: PRT
<213> ORGANISM: Artificial Sequence
<220> FEATURE:
<223> OTHER INFORMATION: Synthetic sequence

<400> SEQUENCE: 256

Tyr Ser Ile Thr Ser Gly Tyr His Trp Gly Trp Ile
1               5                   10

<210> SEQ ID NO 257
<211> LENGTH: 11
<212> TYPE: PRT
<213> ORGANISM: Artificial Sequence
<220> FEATURE:
<223> OTHER INFORMATION: Synthetic sequence

<400> SEQUENCE: 257

Phe Thr Phe Thr Gly Tyr Trp Ile His Trp Val
1               5                   10

<210> SEQ ID NO 258
<211> LENGTH: 12
<212> TYPE: PRT
<213> ORGANISM: Artificial Sequence
<220> FEATURE:
<223> OTHER INFORMATION: Synthetic sequence

<400> SEQUENCE: 258

Tyr Ser Ile Ser Ser Gly His His Trp Gly Trp Ile
1               5                   10

<210> SEQ ID NO 259
<211> LENGTH: 12
<212> TYPE: PRT
<213> ORGANISM: Artificial Sequence
<220> FEATURE:
<223> OTHER INFORMATION: Synthetic sequence

<400> SEQUENCE: 259

Tyr Ser Ile Thr Ser Gly Tyr Tyr Trp Gly Trp Ile
1               5                   10

<210> SEQ ID NO 260
<211> LENGTH: 11
<212> TYPE: PRT
<213> ORGANISM: Artificial Sequence
<220> FEATURE:
<223> OTHER INFORMATION: Synthetic sequence

<400> SEQUENCE: 260

Tyr Thr Phe Thr Gly Tyr Ala Ile His Trp Val
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Synthetic sequence

<400> SEQUENCE: 261

Tyr Ser Ile Ser Ser Gly Tyr His Trp Asn Trp Ile
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Synthetic sequence

<400> SEQUENCE: 262

Tyr Ser Ile Ser Ser Gly Tyr Tyr Trp Asp Trp Ile
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Synthetic sequence

<400> SEQUENCE: 263

Tyr Ser Ile Ser Ser Gly His Tyr Trp Gly Trp Ile
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Synthetic sequence

<400> SEQUENCE: 264

Tyr Thr Phe Ser Asn Tyr Trp Ile His Trp Val

```
<210> SEQ ID NO 265
<211> LENGTH: 13
<212> TYPE: PRT
<213> ORGANISM: Artificial Sequence
<220> FEATURE:
<223> OTHER INFORMATION: Synthetic sequence

<400> SEQUENCE: 265

Phe Ser Leu Ser Thr Gly Gly Val Gly Val Ala Trp Ile
1               5                   10

<210> SEQ ID NO 266
<211> LENGTH: 13
<212> TYPE: PRT
<213> ORGANISM: Artificial Sequence
<220> FEATURE:
<223> OTHER INFORMATION: Synthetic sequence

<400> SEQUENCE: 266

Phe Ser Leu Ser Thr Ser Gly Val Ala Val Gly Trp Ile
1               5                   10

<210> SEQ ID NO 267
<211> LENGTH: 13
<212> TYPE: PRT
<213> ORGANISM: Artificial Sequence
<220> FEATURE:
<223> OTHER INFORMATION: Synthetic sequence

<400> SEQUENCE: 267

Phe Ser Leu Ser Thr Ser Gly Val Gly Val Gly Trp Ile
1               5                   10

<210> SEQ ID NO 268
<211> LENGTH: 13
<212> TYPE: PRT
<213> ORGANISM: Artificial Sequence
<220> FEATURE:
<223> OTHER INFORMATION: Synthetic sequence

<400> SEQUENCE: 268

Phe Ser Leu Ser Thr Gly Gly Val Ala Val Gly Trp Ile
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Synthetic sequence

<400> SEQUENCE: 269

Tyr Ser Ile Ser Ser Gly Tyr His Trp Ala Trp Ile
1               5                   10

<210> SEQ ID NO 270
<211> LENGTH: 13
<212> TYPE: PRT
<213> ORGANISM: Artificial Sequence
<220> FEATURE:
<223> OTHER INFORMATION: Synthetic sequence

<400> SEQUENCE: 270

Phe Ser Leu Ser Thr Ser Gly Val Ala Val Gly Trp Ile
1               5                   10
```

```
<210> SEQ ID NO 271
<211> LENGTH: 13
<212> TYPE: PRT
<213> ORGANISM: Artificial Sequence
<220> FEATURE:
<223> OTHER INFORMATION: Synthetic sequence

<400> SEQUENCE: 271

Phe Ser Leu Ser Thr Ser Gly Val Gly Val Gly Trp Ile
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Synthetic sequence

<400> SEQUENCE: 272

Tyr Ser Ile Thr Ser Gly His His Trp Ala Trp Ile
1               5                   10

<210> SEQ ID NO 273
<211> LENGTH: 13
<212> TYPE: PRT
<213> ORGANISM: Artificial Sequence
<220> FEATURE:
<223> OTHER INFORMATION: Synthetic sequence

<400> SEQUENCE: 273

Phe Ser Leu Ser Thr Gly Gly Val Ala Val Gly Trp Ile
1               5                   10

<210> SEQ ID NO 274
<211> LENGTH: 13
<212> TYPE: PRT
<213> ORGANISM: Artificial Sequence
<220> FEATURE:
<223> OTHER INFORMATION: Synthetic sequence

<400> SEQUENCE: 274

Phe Ser Leu Ser Thr Gly Gly Val Gly Val Gly Trp Ile
1               5                   10

<210> SEQ ID NO 275
<211> LENGTH: 13
<212> TYPE: PRT
<213> ORGANISM: Artificial Sequence
<220> FEATURE:
<223> OTHER INFORMATION: Synthetic sequence

<400> SEQUENCE: 275

Phe Ser Leu Ser Thr Gly Gly Val Ala Val Gly Trp Ile
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Synthetic sequence

<400> SEQUENCE: 276

Tyr Ser Ile Thr Ser Gly His Tyr Trp Ala Trp Ile
1               5                   10
```

<210> SEQ ID NO 277
<211> LENGTH: 12
<212> TYPE: PRT
<213> ORGANISM: Artificial Sequence
<220> FEATURE:
<223> OTHER INFORMATION: Synthetic sequence

<400> SEQUENCE: 277

Tyr Ser Ile Thr Ser Gly His Tyr Trp Ala Trp Ile
1               5                   10

<210> SEQ ID NO 278
<211> LENGTH: 11
<212> TYPE: PRT
<213> ORGANISM: Artificial Sequence
<220> FEATURE:
<223> OTHER INFORMATION: Synthetic sequence

<400> SEQUENCE: 278

Phe Thr Phe Ser Ser Tyr Trp Ile His Trp Val
1               5                   10

<210> SEQ ID NO 279
<211> LENGTH: 13
<212> TYPE: PRT
<213> ORGANISM: Artificial Sequence
<220> FEATURE:
<223> OTHER INFORMATION: Synthetic sequence

<400> SEQUENCE: 279

Phe Ser Leu Ser Thr Ser Gly Val Gly Val Gly Trp Ile
1               5                   10

<210> SEQ ID NO 280
<211> LENGTH: 12
<212> TYPE: PRT
<213> ORGANISM: Artificial Sequence
<220> FEATURE:
<223> OTHER INFORMATION: Synthetic sequence

<400> SEQUENCE: 280

Tyr Ser Ile Thr Ser Gly His Tyr Trp Asn Trp Ile
1               5                   10

<210> SEQ ID NO 281
<211> LENGTH: 12
<212> TYPE: PRT
<213> ORGANISM: Artificial Sequence
<220> FEATURE:
<223> OTHER INFORMATION: Synthetic sequence

<400> SEQUENCE: 281

Tyr Ser Ile Ser Ser Gly His Tyr Trp Thr Trp Ile
1               5                   10

<210> SEQ ID NO 282
<211> LENGTH: 13
<212> TYPE: PRT
<213> ORGANISM: Artificial Sequence
<220> FEATURE:
<223> OTHER INFORMATION: Synthetic sequence

<400> SEQUENCE: 282

Phe Ser Leu Ser Thr Gly Gly Val Gly Val Gly Trp Ile
1               5                   10

```
<210> SEQ ID NO 283
<211> LENGTH: 13
<212> TYPE: PRT
<213> ORGANISM: Artificial Sequence
<220> FEATURE:
<223> OTHER INFORMATION: Synthetic sequence

<400> SEQUENCE: 283

Phe Ser Leu Ser Thr Ser Gly Val Gly Val Gly Trp Ile
1               5                   10

<210> SEQ ID NO 284
<211> LENGTH: 13
<212> TYPE: PRT
<213> ORGANISM: Artificial Sequence
<220> FEATURE:
<223> OTHER INFORMATION: Synthetic sequence

<400> SEQUENCE: 284

Phe Ser Leu Ser Thr Ser Gly Val Ala Val Ala Trp Ile
1               5                   10

<210> SEQ ID NO 285
<211> LENGTH: 13
<212> TYPE: PRT
<213> ORGANISM: Artificial Sequence
<220> FEATURE:
<223> OTHER INFORMATION: Synthetic sequence

<400> SEQUENCE: 285

Phe Ser Leu Ser Thr Ser Gly Val Gly Val Ala Trp Ile
1               5                   10

<210> SEQ ID NO 286
<211> LENGTH: 12
<212> TYPE: PRT
<213> ORGANISM: Artificial Sequence
<220> FEATURE:
<223> OTHER INFORMATION: Synthetic sequence

<400> SEQUENCE: 286

Tyr Ser Ile Ser Ser Gly Tyr His Trp Ala Trp Ile
1               5                   10

<210> SEQ ID NO 287
<211> LENGTH: 13
<212> TYPE: PRT
<213> ORGANISM: Artificial Sequence
<220> FEATURE:
<223> OTHER INFORMATION: Synthetic sequence

<400> SEQUENCE: 287

Phe Ser Leu Ser Thr Gly Gly Val Gly Val Ala Trp Ile
1               5                   10

<210> SEQ ID NO 288
<211> LENGTH: 12
<212> TYPE: PRT
<213> ORGANISM: Artificial Sequence
<220> FEATURE:
<223> OTHER INFORMATION: Synthetic sequence

<400> SEQUENCE: 288

Tyr Ser Ile Thr Ser Gly Tyr His Trp Ser Trp Ile
1               5                   10

<210> SEQ ID NO 289
```

```
<211> LENGTH: 12
<212> TYPE: PRT
<213> ORGANISM: Artificial Sequence
<220> FEATURE:
<223> OTHER INFORMATION: Synthetic sequence

<400> SEQUENCE: 289

Tyr Ser Ile Ser Ser Gly His His Trp Ala Trp Ile
1               5                   10

<210> SEQ ID NO 290
<211> LENGTH: 13
<212> TYPE: PRT
<213> ORGANISM: Artificial Sequence
<220> FEATURE:
<223> OTHER INFORMATION: Synthetic sequence

<400> SEQUENCE: 290

Phe Ser Leu Ser Thr Gly Gly Val Ala Val Gly Trp Ile
1               5                   10

<210> SEQ ID NO 291
<211> LENGTH: 13
<212> TYPE: PRT
<213> ORGANISM: Artificial Sequence
<220> FEATURE:
<223> OTHER INFORMATION: Synthetic sequence

<400> SEQUENCE: 291

Phe Ser Leu Ser Thr Ser Gly Val Gly Val Ala Trp Ile
1               5                   10

<210> SEQ ID NO 292
<211> LENGTH: 13
<212> TYPE: PRT
<213> ORGANISM: Artificial Sequence
<220> FEATURE:
<223> OTHER INFORMATION: Synthetic sequence

<400> SEQUENCE: 292

Phe Ser Leu Ser Thr Gly Gly Val Gly Val Ala Trp Ile
1               5                   10

<210> SEQ ID NO 293
<211> LENGTH: 13
<212> TYPE: PRT
<213> ORGANISM: Artificial Sequence
<220> FEATURE:
<223> OTHER INFORMATION: Synthetic sequence

<400> SEQUENCE: 293

Phe Ser Leu Ser Thr Gly Gly Val Gly Val Gly Trp Ile
1               5                   10

<210> SEQ ID NO 294
<211> LENGTH: 13
<212> TYPE: PRT
<213> ORGANISM: Artificial Sequence
<220> FEATURE:
<223> OTHER INFORMATION: Synthetic sequence

<400> SEQUENCE: 294

Phe Ser Leu Ser Thr Ser Gly Val Gly Val Ala Trp Ile
1               5                   10

<210> SEQ ID NO 295
<211> LENGTH: 13
```

```
<212> TYPE: PRT
<213> ORGANISM: Artificial Sequence
<220> FEATURE:
<223> OTHER INFORMATION: Synthetic sequence

<400> SEQUENCE: 295

Phe Ser Leu Ser Thr Gly Gly Val Gly Val Gly Trp Ile
1               5                   10

<210> SEQ ID NO 296
<211> LENGTH: 13
<212> TYPE: PRT
<213> ORGANISM: Artificial Sequence
<220> FEATURE:
<223> OTHER INFORMATION: Synthetic sequence

<400> SEQUENCE: 296

Phe Ser Leu Ser Thr Gly Gly Val Gly Val Gly Trp Ile
1               5                   10

<210> SEQ ID NO 297
<211> LENGTH: 13
<212> TYPE: PRT
<213> ORGANISM: Artificial Sequence
<220> FEATURE:
<223> OTHER INFORMATION: Synthetic sequence

<400> SEQUENCE: 297

Phe Ser Leu Ser Thr Gly Gly Val Gly Val Gly Trp Ile
1               5                   10

<210> SEQ ID NO 298
<211> LENGTH: 13
<212> TYPE: PRT
<213> ORGANISM: Artificial Sequence
<220> FEATURE:
<223> OTHER INFORMATION: Synthetic sequence

<400> SEQUENCE: 298

Phe Ser Leu Ser Thr Ser Gly Val Gly Val Gly Trp Ile
1               5                   10

<210> SEQ ID NO 299
<211> LENGTH: 13
<212> TYPE: PRT
<213> ORGANISM: Artificial Sequence
<220> FEATURE:
<223> OTHER INFORMATION: Synthetic sequence

<400> SEQUENCE: 299

Phe Ser Leu Ser Thr Gly Gly Val Gly Val Ala Trp Ile
1               5                   10

<210> SEQ ID NO 300
<211> LENGTH: 13
<212> TYPE: PRT
<213> ORGANISM: Artificial Sequence
<220> FEATURE:
<223> OTHER INFORMATION: Synthetic sequence

<400> SEQUENCE: 300

Phe Ser Leu Ser Thr Ser Gly Met Gly Val Gly Trp Ile
1               5                   10

<210> SEQ ID NO 301
<211> LENGTH: 12
<212> TYPE: PRT
```

```
<213> ORGANISM: Artificial Sequence
<220> FEATURE:
<223> OTHER INFORMATION: Synthetic sequence

<400> SEQUENCE: 301

Tyr Ser Ile Ser Ser Gly His His Trp Asp Trp Ile
1               5                   10

<210> SEQ ID NO 302
<211> LENGTH: 13
<212> TYPE: PRT
<213> ORGANISM: Artificial Sequence
<220> FEATURE:
<223> OTHER INFORMATION: Synthetic sequence

<400> SEQUENCE: 302

Phe Ser Leu Ser Thr Ser Gly Val Gly Val Gly Trp Ile
1               5                   10

<210> SEQ ID NO 303
<211> LENGTH: 13
<212> TYPE: PRT
<213> ORGANISM: Artificial Sequence
<220> FEATURE:
<223> OTHER INFORMATION: Synthetic sequence

<400> SEQUENCE: 303

Phe Ser Leu Ser Thr Gly Gly Val Gly Val Gly Trp Ile
1               5                   10

<210> SEQ ID NO 304
<211> LENGTH: 13
<212> TYPE: PRT
<213> ORGANISM: Artificial Sequence
<220> FEATURE:
<223> OTHER INFORMATION: Synthetic sequence

<400> SEQUENCE: 304

Phe Ser Leu Ser Thr Ser Gly Val Gly Val Ser Trp Ile
1               5                   10

<210> SEQ ID NO 305
<211> LENGTH: 13
<212> TYPE: PRT
<213> ORGANISM: Artificial Sequence
<220> FEATURE:
<223> OTHER INFORMATION: Synthetic sequence

<400> SEQUENCE: 305

Phe Ser Leu Ser Thr Ser Gly Val Gly Val Gly Trp Ile
1               5                   10

<210> SEQ ID NO 306
<211> LENGTH: 13
<212> TYPE: PRT
<213> ORGANISM: Artificial Sequence
<220> FEATURE:
<223> OTHER INFORMATION: Synthetic sequence

<400> SEQUENCE: 306

Phe Ser Leu Ser Thr Gly Gly Val Gly Val Ala Trp Ile
1               5                   10

<210> SEQ ID NO 307
<211> LENGTH: 13
<212> TYPE: PRT
<213> ORGANISM: Artificial Sequence
```

```
<220> FEATURE:
<223> OTHER INFORMATION: Synthetic sequence

<400> SEQUENCE: 307

Phe Ser Leu Ser Thr Gly Gly Val Gly Val Gly Trp Ile
1               5                   10

<210> SEQ ID NO 308
<211> LENGTH: 13
<212> TYPE: PRT
<213> ORGANISM: Artificial Sequence
<220> FEATURE:
<223> OTHER INFORMATION: Synthetic sequence

<400> SEQUENCE: 308

Phe Ser Leu Ser Thr Ser Gly Val Gly Val Ala Trp Ile
1               5                   10

<210> SEQ ID NO 309
<211> LENGTH: 13
<212> TYPE: PRT
<213> ORGANISM: Artificial Sequence
<220> FEATURE:
<223> OTHER INFORMATION: Synthetic sequence

<400> SEQUENCE: 309

Phe Ser Leu Ser Thr Gly Gly Val Gly Val Gly Trp Ile
1               5                   10

<210> SEQ ID NO 310
<211> LENGTH: 13
<212> TYPE: PRT
<213> ORGANISM: Artificial Sequence
<220> FEATURE:
<223> OTHER INFORMATION: Synthetic sequence

<400> SEQUENCE: 310

Phe Ser Leu Ser Thr Ser Gly Val Gly Val Gly Trp Ile
1               5                   10

<210> SEQ ID NO 311
<211> LENGTH: 13
<212> TYPE: PRT
<213> ORGANISM: Artificial Sequence
<220> FEATURE:
<223> OTHER INFORMATION: Synthetic sequence

<400> SEQUENCE: 311

Phe Ser Leu Ser Thr Ser Gly Val Gly Val Thr Trp Ile
1               5                   10

<210> SEQ ID NO 312
<211> LENGTH: 13
<212> TYPE: PRT
<213> ORGANISM: Artificial Sequence
<220> FEATURE:
<223> OTHER INFORMATION: Synthetic sequence

<400> SEQUENCE: 312

Phe Ser Leu Ser Thr Ser Gly Val Ala Val Ala Trp Ile
1               5                   10

<210> SEQ ID NO 313
<211> LENGTH: 21
<212> TYPE: PRT
<213> ORGANISM: Artificial Sequence
<220> FEATURE:
```

```
<223> OTHER INFORMATION: Synthetic sequence

<400> SEQUENCE: 313

Val Ser Gly Ile Ser Gly Ala Gly Asp Thr Thr Tyr Tyr Ala Asp Ser
1               5                   10                  15

Val Lys Gly Arg Phe
            20

<210> SEQ ID NO 314
<211> LENGTH: 21
<212> TYPE: PRT
<213> ORGANISM: Artificial Sequence
<220> FEATURE:
<223> OTHER INFORMATION: Synthetic sequence

<400> SEQUENCE: 314

Ile Gly Ile Ile Asn Pro Asn Phe Gly Asp Thr Asn Tyr Ala Gln Lys
1               5                   10                  15

Phe Gln Gly Arg Val
            20

<210> SEQ ID NO 315
<211> LENGTH: 21
<212> TYPE: PRT
<213> ORGANISM: Artificial Sequence
<220> FEATURE:
<223> OTHER INFORMATION: Synthetic sequence

<400> SEQUENCE: 315

Val Ser Ser Ile Ser Gly Ser Gly Gly Thr Thr Tyr Tyr Ala Asp Ser
1               5                   10                  15

Val Lys Gly Arg Phe
            20

<210> SEQ ID NO 316
<211> LENGTH: 21
<212> TYPE: PRT
<213> ORGANISM: Artificial Sequence
<220> FEATURE:
<223> OTHER INFORMATION: Synthetic sequence

<400> SEQUENCE: 316

Val Ser Ala Ile Ser Gly Ala Gly Gly Ser Thr Tyr Tyr Ala Asp Ser
1               5                   10                  15

Val Lys Gly Arg Phe
            20

<210> SEQ ID NO 317
<211> LENGTH: 23
<212> TYPE: PRT
<213> ORGANISM: Artificial Sequence
<220> FEATURE:
<223> OTHER INFORMATION: Synthetic sequence

<400> SEQUENCE: 317

Val Gly Arg Ile Arg Ser Lys Thr Asp Gly Tyr Thr Thr Glu Tyr Ala
1               5                   10                  15

Ala Pro Val Lys Gly Arg Phe
            20

<210> SEQ ID NO 318
<211> LENGTH: 21
<212> TYPE: PRT
<213> ORGANISM: Artificial Sequence
```

```
<220> FEATURE:
<223> OTHER INFORMATION: Synthetic sequence

<400> SEQUENCE: 318

Val Ser Gly Ile Ser Gly Tyr Gly Asp Thr Thr Tyr Ala Asp Ser
1               5                   10                  15

Val Lys Gly Arg Phe
            20

<210> SEQ ID NO 319
<211> LENGTH: 21
<212> TYPE: PRT
<213> ORGANISM: Artificial Sequence
<220> FEATURE:
<223> OTHER INFORMATION: Synthetic sequence

<400> SEQUENCE: 319

Val Ser Gly Ile Ser Gly Ser Gly Ser Ser Thr Tyr Tyr Ala Asp Ser
1               5                   10                  15

Val Lys Gly Arg Phe
            20

<210> SEQ ID NO 320
<211> LENGTH: 21
<212> TYPE: PRT
<213> ORGANISM: Artificial Sequence
<220> FEATURE:
<223> OTHER INFORMATION: Synthetic sequence

<400> SEQUENCE: 320

Val Ser Ala Ile Ser Gly Asp Gly Gly Ser Thr Tyr Tyr Ala Asp Ser
1               5                   10                  15

Val Lys Gly Arg Phe
            20

<210> SEQ ID NO 321
<211> LENGTH: 21
<212> TYPE: PRT
<213> ORGANISM: Artificial Sequence
<220> FEATURE:
<223> OTHER INFORMATION: Synthetic sequence

<400> SEQUENCE: 321

Val Ser Ser Ile Ser Gly Ser Gly Gly Ser Thr Tyr Tyr Ala Asp Ser
1               5                   10                  15

Val Lys Gly Arg Phe
            20

<210> SEQ ID NO 322
<211> LENGTH: 21
<212> TYPE: PRT
<213> ORGANISM: Artificial Sequence
<220> FEATURE:
<223> OTHER INFORMATION: Synthetic sequence

<400> SEQUENCE: 322

Val Ser Ser Ile Ser Gly Asp Gly Asp Thr Thr Tyr Tyr Ala Asp Ser
1               5                   10                  15

Val Lys Gly Arg Phe
            20

<210> SEQ ID NO 323
<211> LENGTH: 20
<212> TYPE: PRT
```

-continued

<213> ORGANISM: Artificial Sequence
<220> FEATURE:
<223> OTHER INFORMATION: Synthetic sequence

<400> SEQUENCE: 323

Leu Ala Leu Ile Asp Trp Tyr Gly Asp Lys Tyr Tyr Ser Thr Ser Leu
1               5                   10                  15

Lys Ser Arg Leu
            20

<210> SEQ ID NO 324
<211> LENGTH: 21
<212> TYPE: PRT
<213> ORGANISM: Artificial Sequence
<220> FEATURE:
<223> OTHER INFORMATION: Synthetic sequence

<400> SEQUENCE: 324

Val Ser Tyr Ile Ser Gly Asp Gly Asp Thr Thr Tyr Tyr Ala Asp Ser
1               5                   10                  15

Val Lys Gly Arg Phe
            20

<210> SEQ ID NO 325
<211> LENGTH: 21
<212> TYPE: PRT
<213> ORGANISM: Artificial Sequence
<220> FEATURE:
<223> OTHER INFORMATION: Synthetic sequence

<400> SEQUENCE: 325

Val Ser Ser Ile Ser Gly Tyr Gly Ser Thr Thr Tyr Tyr Ala Asp Ser
1               5                   10                  15

Val Lys Gly Arg Phe
            20

<210> SEQ ID NO 326
<211> LENGTH: 20
<212> TYPE: PRT
<213> ORGANISM: Artificial Sequence
<220> FEATURE:
<223> OTHER INFORMATION: Synthetic sequence

<400> SEQUENCE: 326

Leu Ala Leu Ile Asp Trp Ala Asp Asp Lys Tyr Tyr Ser Pro Ser Leu
1               5                   10                  15

Lys Ser Arg Leu
            20

<210> SEQ ID NO 327
<211> LENGTH: 20
<212> TYPE: PRT
<213> ORGANISM: Artificial Sequence
<220> FEATURE:
<223> OTHER INFORMATION: Synthetic sequence

<400> SEQUENCE: 327

Leu Ala Leu Ile Asp Trp Asp Asp Asp Lys Tyr Tyr Ser Pro Ser Leu
1               5                   10                  15

Lys Ser Arg Leu
            20

<210> SEQ ID NO 328
<211> LENGTH: 20

```
<212> TYPE: PRT
<213> ORGANISM: Artificial Sequence
<220> FEATURE:
<223> OTHER INFORMATION: Synthetic sequence

<400> SEQUENCE: 328

Leu Ala Leu Ile Asp Trp Ala Gly Asp Lys Ser Tyr Ser Thr Ser Leu
1               5                   10                  15

Lys Ser Arg Leu
            20

<210> SEQ ID NO 329
<211> LENGTH: 21
<212> TYPE: PRT
<213> ORGANISM: Artificial Sequence
<220> FEATURE:
<223> OTHER INFORMATION: Synthetic sequence

<400> SEQUENCE: 329

Val Ser Ser Ile Ser Gly Asp Gly Ser Ser Thr Tyr Tyr Ala Asp Ser
1               5                   10                  15

Val Lys Gly Arg Phe
            20

<210> SEQ ID NO 330
<211> LENGTH: 20
<212> TYPE: PRT
<213> ORGANISM: Artificial Sequence
<220> FEATURE:
<223> OTHER INFORMATION: Synthetic sequence

<400> SEQUENCE: 330

Leu Ala Leu Ile Asp Trp Asp Asp Lys Tyr Tyr Ser Thr Ser Leu
1               5                   10                  15

Lys Ser Arg Leu
            20

<210> SEQ ID NO 331
<211> LENGTH: 20
<212> TYPE: PRT
<213> ORGANISM: Artificial Sequence
<220> FEATURE:
<223> OTHER INFORMATION: Synthetic sequence

<400> SEQUENCE: 331

Ile Gly Glu Ile Tyr His Ser Gly Ser Thr Tyr Tyr Ser Pro Ser Leu
1               5                   10                  15

Lys Ser Arg Val
            20

<210> SEQ ID NO 332
<211> LENGTH: 21
<212> TYPE: PRT
<213> ORGANISM: Artificial Sequence
<220> FEATURE:
<223> OTHER INFORMATION: Synthetic sequence

<400> SEQUENCE: 332

Val Ser Ala Ile Ser Gly Asp Gly Ser Thr Thr Tyr Tyr Ala Asp Ser
1               5                   10                  15

Val Lys Gly Arg Phe
            20

<210> SEQ ID NO 333
```

```
<211> LENGTH: 20
<212> TYPE: PRT
<213> ORGANISM: Artificial Sequence
<220> FEATURE:
<223> OTHER INFORMATION: Synthetic sequence

<400> SEQUENCE: 333

Leu Ala Leu Ile Asp Trp Ala Gly Asp Lys Ser Tyr Ser Thr Ser Leu
1               5                   10                  15

Lys Ser Arg Leu
            20

<210> SEQ ID NO 334
<211> LENGTH: 21
<212> TYPE: PRT
<213> ORGANISM: Artificial Sequence
<220> FEATURE:
<223> OTHER INFORMATION: Synthetic sequence

<400> SEQUENCE: 334

Val Ser Gly Ile Ser Gly Tyr Gly Ser Thr Thr Tyr Tyr Ala Asp Ser
1               5                   10                  15

Val Lys Gly Arg Phe
            20

<210> SEQ ID NO 335
<211> LENGTH: 21
<212> TYPE: PRT
<213> ORGANISM: Artificial Sequence
<220> FEATURE:
<223> OTHER INFORMATION: Synthetic sequence

<400> SEQUENCE: 335

Val Ser Gly Ile Ser Gly Asp Gly Gly Thr Thr Tyr Tyr Ala Asp Ser
1               5                   10                  15

Val Lys Gly Arg Phe
            20

<210> SEQ ID NO 336
<211> LENGTH: 21
<212> TYPE: PRT
<213> ORGANISM: Artificial Sequence
<220> FEATURE:
<223> OTHER INFORMATION: Synthetic sequence

<400> SEQUENCE: 336

Val Ser Ala Ile Ser Gly Ser Gly Ser Ser Thr Tyr Tyr Ala Asp Ser
1               5                   10                  15

Val Lys Gly Arg Phe
            20

<210> SEQ ID NO 337
<211> LENGTH: 21
<212> TYPE: PRT
<213> ORGANISM: Artificial Sequence
<220> FEATURE:
<223> OTHER INFORMATION: Synthetic sequence

<400> SEQUENCE: 337

Val Ser Ser Ile Ser Gly Tyr Gly Ser Thr Thr Tyr Tyr Ala Asp Ser
1               5                   10                  15

Val Lys Gly Arg Phe
            20
```

```
<210> SEQ ID NO 338
<211> LENGTH: 21
<212> TYPE: PRT
<213> ORGANISM: Artificial Sequence
<220> FEATURE:
<223> OTHER INFORMATION: Synthetic sequence

<400> SEQUENCE: 338

Val Ser Val Ile Ser Gly Asp Gly Asp Thr Thr Tyr Tyr Ala Asp Ser
1               5                   10                  15

Val Lys Gly Arg Phe
            20

<210> SEQ ID NO 339
<211> LENGTH: 20
<212> TYPE: PRT
<213> ORGANISM: Artificial Sequence
<220> FEATURE:
<223> OTHER INFORMATION: Synthetic sequence

<400> SEQUENCE: 339

Leu Ala Leu Ile Asp Trp Ala Asp Asp Lys Tyr Tyr Ser Pro Ser Leu
1               5                   10                  15

Lys Ser Arg Leu
            20

<210> SEQ ID NO 340
<211> LENGTH: 21
<212> TYPE: PRT
<213> ORGANISM: Artificial Sequence
<220> FEATURE:
<223> OTHER INFORMATION: Synthetic sequence

<400> SEQUENCE: 340

Val Ser Gly Ile Ser Gly Asp Gly Ser Ser Thr Tyr Tyr Ala Asp Ser
1               5                   10                  15

Val Lys Gly Arg Phe
            20

<210> SEQ ID NO 341
<211> LENGTH: 21
<212> TYPE: PRT
<213> ORGANISM: Artificial Sequence
<220> FEATURE:
<223> OTHER INFORMATION: Synthetic sequence

<400> SEQUENCE: 341

Val Ser Ala Ile Ser Gly Ser Gly Ser Ser Thr Tyr Tyr Ala Asp Ser
1               5                   10                  15

Val Lys Gly Arg Phe
            20

<210> SEQ ID NO 342
<211> LENGTH: 20
<212> TYPE: PRT
<213> ORGANISM: Artificial Sequence
<220> FEATURE:
<223> OTHER INFORMATION: Synthetic sequence

<400> SEQUENCE: 342

Leu Ala Leu Ile Asp Trp Ala Asp Asp Lys Tyr Tyr Ser Pro Ser Leu
1               5                   10                  15

Lys Ser Arg Leu
            20
```

<210> SEQ ID NO 343
<211> LENGTH: 21
<212> TYPE: PRT
<213> ORGANISM: Artificial Sequence
<220> FEATURE:
<223> OTHER INFORMATION: Synthetic sequence

<400> SEQUENCE: 343

Val Ser Gly Ile Ser Gly Ala Gly Asp Ser Thr Tyr Tyr Ala Asp Ser
1               5                   10                  15

Val Lys Gly Arg Phe
            20

<210> SEQ ID NO 344
<211> LENGTH: 20
<212> TYPE: PRT
<213> ORGANISM: Artificial Sequence
<220> FEATURE:
<223> OTHER INFORMATION: Synthetic sequence

<400> SEQUENCE: 344

Leu Ala Leu Ile Asp Trp Asp Asp Asp Lys Arg Tyr Ser Thr Ser Leu
1               5                   10                  15

Lys Ser Arg Leu
            20

<210> SEQ ID NO 345
<211> LENGTH: 21
<212> TYPE: PRT
<213> ORGANISM: Artificial Sequence
<220> FEATURE:
<223> OTHER INFORMATION: Synthetic sequence

<400> SEQUENCE: 345

Val Ser Tyr Ile Ser Gly Asp Gly Gly Ser Thr Tyr Tyr Ala Asp Ser
1               5                   10                  15

Val Lys Gly Arg Phe
            20

<210> SEQ ID NO 346
<211> LENGTH: 20
<212> TYPE: PRT
<213> ORGANISM: Artificial Sequence
<220> FEATURE:
<223> OTHER INFORMATION: Synthetic sequence

<400> SEQUENCE: 346

Ile Gly Glu Ile Tyr His Ser Gly Ser Thr Tyr Tyr Ser Pro Ser Leu
1               5                   10                  15

Lys Ser Arg Val
            20

<210> SEQ ID NO 347
<211> LENGTH: 21
<212> TYPE: PRT
<213> ORGANISM: Artificial Sequence
<220> FEATURE:
<223> OTHER INFORMATION: Synthetic sequence

<400> SEQUENCE: 347

Val Ser Ser Ile Ser Gly Tyr Gly Ser Thr Thr Tyr Tyr Ala Asp Ser
1               5                   10                  15

Val Lys Gly Arg Phe
            20

<210> SEQ ID NO 348
<211> LENGTH: 21
<212> TYPE: PRT
<213> ORGANISM: Artificial Sequence
<220> FEATURE:
<223> OTHER INFORMATION: Synthetic sequence

<400> SEQUENCE: 348

Val Ser Ser Ile Ser Gly Tyr Gly Asp Thr Thr Tyr Tyr Ala Asp Ser
1               5                   10                  15

Val Lys Gly Arg Phe
            20

<210> SEQ ID NO 349
<211> LENGTH: 21
<212> TYPE: PRT
<213> ORGANISM: Artificial Sequence
<220> FEATURE:
<223> OTHER INFORMATION: Synthetic sequence

<400> SEQUENCE: 349

Val Ser Val Ile Ser Gly Ser Gly Ser Ser Thr Tyr Tyr Ala Asp Ser
1               5                   10                  15

Val Lys Gly Arg Phe
            20

<210> SEQ ID NO 350
<211> LENGTH: 20
<212> TYPE: PRT
<213> ORGANISM: Artificial Sequence
<220> FEATURE:
<223> OTHER INFORMATION: Synthetic sequence

<400> SEQUENCE: 350

Leu Ala Leu Ile Asp Trp Asp Gly Asp Lys Ser Tyr Ser Thr Ser Leu
1               5                   10                  15

Lys Ser Arg Leu
            20

<210> SEQ ID NO 351
<211> LENGTH: 21
<212> TYPE: PRT
<213> ORGANISM: Artificial Sequence
<220> FEATURE:
<223> OTHER INFORMATION: Synthetic sequence

<400> SEQUENCE: 351

Val Ser Ser Ile Ser Gly Ala Gly Gly Thr Thr Tyr Tyr Ala Asp Ser
1               5                   10                  15

Val Lys Gly Arg Phe
            20

<210> SEQ ID NO 352
<211> LENGTH: 21
<212> TYPE: PRT
<213> ORGANISM: Artificial Sequence
<220> FEATURE:
<223> OTHER INFORMATION: Synthetic sequence

<400> SEQUENCE: 352

Val Ser Tyr Ile Ser Gly Ser Gly Asp Thr Thr Tyr Tyr Ala Asp Ser
1               5                   10                  15

Val Lys Gly Arg Phe

20

<210> SEQ ID NO 353
<211> LENGTH: 21
<212> TYPE: PRT
<213> ORGANISM: Artificial Sequence
<220> FEATURE:
<223> OTHER INFORMATION: Synthetic sequence

<400> SEQUENCE: 353

Val Ser Tyr Ile Ser Gly Asp Gly Asp Thr Thr Tyr Tyr Ala Asp Ser
1               5                   10                  15

Val Lys Gly Arg Phe
            20

<210> SEQ ID NO 354
<211> LENGTH: 21
<212> TYPE: PRT
<213> ORGANISM: Artificial Sequence
<220> FEATURE:
<223> OTHER INFORMATION: Synthetic sequence

<400> SEQUENCE: 354

Val Ser Ser Ile Ser Gly Tyr Gly Gly Thr Thr Tyr Tyr Ala Asp Ser
1               5                   10                  15

Val Lys Gly Arg Phe
            20

<210> SEQ ID NO 355
<211> LENGTH: 21
<212> TYPE: PRT
<213> ORGANISM: Artificial Sequence
<220> FEATURE:
<223> OTHER INFORMATION: Synthetic sequence

<400> SEQUENCE: 355

Val Ser Tyr Ile Ser Gly Ala Gly Gly Thr Thr Tyr Tyr Ala Asp Ser
1               5                   10                  15

Val Lys Gly Arg Phe
            20

<210> SEQ ID NO 356
<211> LENGTH: 21
<212> TYPE: PRT
<213> ORGANISM: Artificial Sequence
<220> FEATURE:
<223> OTHER INFORMATION: Synthetic sequence

<400> SEQUENCE: 356

Val Ser Tyr Ile Ser Gly Ala Gly Gly Thr Thr Tyr Tyr Ala Asp Ser
1               5                   10                  15

Val Lys Gly Arg Phe
            20

<210> SEQ ID NO 357
<211> LENGTH: 21
<212> TYPE: PRT
<213> ORGANISM: Artificial Sequence
<220> FEATURE:
<223> OTHER INFORMATION: Synthetic sequence

<400> SEQUENCE: 357

Val Ser Tyr Ile Ser Gly Asp Gly Asp Thr Thr Tyr Tyr Ala Asp Ser
1               5                   10                  15

-continued

Val Lys Gly Arg Phe
            20

<210> SEQ ID NO 358
<211> LENGTH: 21
<212> TYPE: PRT
<213> ORGANISM: Artificial Sequence
<220> FEATURE:
<223> OTHER INFORMATION: Synthetic sequence

<400> SEQUENCE: 358

Val Ser Tyr Ile Ser Gly Asp Gly Gly Ser Thr Tyr Tyr Ala Asp Ser
1               5                   10                  15

Val Lys Gly Arg Phe
            20

<210> SEQ ID NO 359
<211> LENGTH: 21
<212> TYPE: PRT
<213> ORGANISM: Artificial Sequence
<220> FEATURE:
<223> OTHER INFORMATION: Synthetic sequence

<400> SEQUENCE: 359

Val Ser Tyr Ile Ser Gly Tyr Gly Gly Thr Thr Tyr Tyr Ala Asp Ser
1               5                   10                  15

Val Lys Gly Arg Phe
            20

<210> SEQ ID NO 360
<211> LENGTH: 21
<212> TYPE: PRT
<213> ORGANISM: Artificial Sequence
<220> FEATURE:
<223> OTHER INFORMATION: Synthetic sequence

<400> SEQUENCE: 360

Val Ser Tyr Ile Ser Gly Tyr Gly Gly Thr Thr Tyr Tyr Ala Asp Ser
1               5                   10                  15

Val Lys Gly Arg Phe
            20

<210> SEQ ID NO 361
<211> LENGTH: 21
<212> TYPE: PRT
<213> ORGANISM: Artificial Sequence
<220> FEATURE:
<223> OTHER INFORMATION: Synthetic sequence

<400> SEQUENCE: 361

Val Ser Tyr Ile Ser Gly Ala Gly Asp Thr Thr Tyr Tyr Ala Asp Ser
1               5                   10                  15

Val Lys Gly Arg Phe
            20

<210> SEQ ID NO 362
<211> LENGTH: 21
<212> TYPE: PRT
<213> ORGANISM: Artificial Sequence
<220> FEATURE:
<223> OTHER INFORMATION: Synthetic sequence

<400> SEQUENCE: 362

Val Ser Tyr Ile Ser Gly Asp Gly Gly Ser Thr Tyr Tyr Ala Asp Ser
1               5                   10                  15

Val Lys Gly Arg Phe
            20

<210> SEQ ID NO 363
<211> LENGTH: 21
<212> TYPE: PRT
<213> ORGANISM: Artificial Sequence
<220> FEATURE:
<223> OTHER INFORMATION: Synthetic sequence

<400> SEQUENCE: 363

Val Ser Tyr Ile Ser Gly Ala Gly Ser Thr Thr Tyr Tyr Ala Asp Ser
1               5                   10                  15

Val Lys Gly Arg Phe
            20

<210> SEQ ID NO 364
<211> LENGTH: 21
<212> TYPE: PRT
<213> ORGANISM: Artificial Sequence
<220> FEATURE:
<223> OTHER INFORMATION: Synthetic sequence

<400> SEQUENCE: 364

Val Ser Tyr Ile Ser Gly Ser Gly Asp Thr Thr Tyr Tyr Ala Asp Ser
1               5                   10                  15

Val Lys Gly Arg Phe
            20

<210> SEQ ID NO 365
<211> LENGTH: 21
<212> TYPE: PRT
<213> ORGANISM: Artificial Sequence
<220> FEATURE:
<223> OTHER INFORMATION: Synthetic sequence

<400> SEQUENCE: 365

Val Ser Tyr Ile Ser Gly Asp Gly Asp Thr Thr Tyr Tyr Ala Asp Ser
1               5                   10                  15

Val Lys Gly Arg Phe
            20

<210> SEQ ID NO 366
<211> LENGTH: 21
<212> TYPE: PRT
<213> ORGANISM: Artificial Sequence
<220> FEATURE:
<223> OTHER INFORMATION: Synthetic sequence

<400> SEQUENCE: 366

Val Ser Tyr Ile Ser Gly Asp Gly Gly Thr Thr Tyr Tyr Ala Asp Ser
1               5                   10                  15

Val Lys Gly Arg Phe
            20

<210> SEQ ID NO 367
<211> LENGTH: 21
<212> TYPE: PRT
<213> ORGANISM: Artificial Sequence
<220> FEATURE:
<223> OTHER INFORMATION: Synthetic sequence

<400> SEQUENCE: 367

Val Ser Tyr Ile Ser Gly Ala Gly Asp Ser Thr Tyr Tyr Ala Asp Ser

```
1               5                   10                  15
Val Lys Gly Arg Phe
            20

<210> SEQ ID NO 368
<211> LENGTH: 21
<212> TYPE: PRT
<213> ORGANISM: Artificial Sequence
<220> FEATURE:
<223> OTHER INFORMATION: Synthetic sequence

<400> SEQUENCE: 368

Val Ser Ser Ile Ser Gly Tyr Gly Gly Thr Thr Tyr Tyr Ala Asp Ser
1               5                   10                  15
Val Lys Gly Arg Phe
            20

<210> SEQ ID NO 369
<211> LENGTH: 21
<212> TYPE: PRT
<213> ORGANISM: Artificial Sequence
<220> FEATURE:
<223> OTHER INFORMATION: Synthetic sequence

<400> SEQUENCE: 369

Val Ser Ser Ile Ser Gly Ser Gly Gly Ser Thr Tyr Tyr Ala Asp Ser
1               5                   10                  15
Val Lys Gly Arg Phe
            20

<210> SEQ ID NO 370
<211> LENGTH: 20
<212> TYPE: PRT
<213> ORGANISM: Artificial Sequence
<220> FEATURE:
<223> OTHER INFORMATION: Synthetic sequence

<400> SEQUENCE: 370

Ile Gly Asp Ile Tyr His Ser Gly Ser Thr Tyr Tyr Asn Pro Ser Leu
1               5                   10                  15
Lys Ser Arg Val
            20

<210> SEQ ID NO 371
<211> LENGTH: 20
<212> TYPE: PRT
<213> ORGANISM: Artificial Sequence
<220> FEATURE:
<223> OTHER INFORMATION: Synthetic sequence

<400> SEQUENCE: 371

Ile Gly Asp Ile Tyr His Ser Gly Ser Thr Tyr Tyr Ser Pro Ser Leu
1               5                   10                  15
Lys Ser Arg Val
            20

<210> SEQ ID NO 372
<211> LENGTH: 20
<212> TYPE: PRT
<213> ORGANISM: Artificial Sequence
<220> FEATURE:
<223> OTHER INFORMATION: Synthetic sequence

<400> SEQUENCE: 372
```

```
Ile Gly Asp Ile Tyr His Ser Gly Asn Thr Tyr Tyr Asn Pro Ser Leu
1               5                   10                  15

Lys Ser Arg Val
            20
```

<210> SEQ ID NO 373
<211> LENGTH: 10
<212> TYPE: PRT
<213> ORGANISM: Artificial Sequence
<220> FEATURE:
<223> OTHER INFORMATION: Synthetic sequence

<400> SEQUENCE: 373

```
Ala Arg Glu Arg Asp Tyr Asp Phe Asp Tyr
1               5                   10
```

<210> SEQ ID NO 374
<211> LENGTH: 14
<212> TYPE: PRT
<213> ORGANISM: Artificial Sequence
<220> FEATURE:
<223> OTHER INFORMATION: Synthetic sequence

<400> SEQUENCE: 374

```
Ala Arg Asp Glu Tyr Tyr Gly Gly Ser Tyr Tyr Phe Asp Tyr
1               5                   10
```

<210> SEQ ID NO 375
<211> LENGTH: 12
<212> TYPE: PRT
<213> ORGANISM: Artificial Sequence
<220> FEATURE:
<223> OTHER INFORMATION: Synthetic sequence

<400> SEQUENCE: 375

```
Ala Arg Asp Asp Leu Tyr Ser Trp Tyr Phe Asp Val
1               5                   10
```

<210> SEQ ID NO 376
<211> LENGTH: 12
<212> TYPE: PRT
<213> ORGANISM: Artificial Sequence
<220> FEATURE:
<223> OTHER INFORMATION: Synthetic sequence

<400> SEQUENCE: 376

```
Ala Arg Asp Gly Tyr Gly Gly Ser Tyr Phe Asp Tyr
1               5                   10
```

<210> SEQ ID NO 377
<211> LENGTH: 11
<212> TYPE: PRT
<213> ORGANISM: Artificial Sequence
<220> FEATURE:
<223> OTHER INFORMATION: Synthetic sequence

<400> SEQUENCE: 377

```
Ala Arg Leu Gly Gly His Trp Tyr Phe Asp Val
1               5                   10
```

<210> SEQ ID NO 378
<211> LENGTH: 14
<212> TYPE: PRT
<213> ORGANISM: Artificial Sequence
<220> FEATURE:
<223> OTHER INFORMATION: Synthetic sequence

<400> SEQUENCE: 378

Ala Arg Asp Pro Tyr Ser Ser Gly Ser Gly Tyr Phe Asp Tyr
1               5                   10

<210> SEQ ID NO 379
<211> LENGTH: 9
<212> TYPE: PRT
<213> ORGANISM: Artificial Sequence
<220> FEATURE:
<223> OTHER INFORMATION: Synthetic sequence

<400> SEQUENCE: 379

Ala Arg Gly Thr Tyr Ser Phe Asp Val
1               5

<210> SEQ ID NO 380
<211> LENGTH: 10
<212> TYPE: PRT
<213> ORGANISM: Artificial Sequence
<220> FEATURE:
<223> OTHER INFORMATION: Synthetic sequence

<400> SEQUENCE: 380

Ala Arg Gly Tyr Arg Gly Tyr Phe Asp Tyr
1               5                   10

<210> SEQ ID NO 381
<211> LENGTH: 15
<212> TYPE: PRT
<213> ORGANISM: Artificial Sequence
<220> FEATURE:
<223> OTHER INFORMATION: Synthetic sequence

<400> SEQUENCE: 381

Ala Arg Asp Pro Asn Tyr Tyr Ser Ser Gly Ser Tyr Phe Asp Tyr
1               5                   10                  15

<210> SEQ ID NO 382
<211> LENGTH: 13
<212> TYPE: PRT
<213> ORGANISM: Artificial Sequence
<220> FEATURE:
<223> OTHER INFORMATION: Synthetic sequence

<400> SEQUENCE: 382

Ala Arg Glu Tyr Tyr Gly Tyr Gly Tyr Ala Leu Asp Tyr
1               5                   10

<210> SEQ ID NO 383
<211> LENGTH: 12
<212> TYPE: PRT
<213> ORGANISM: Artificial Sequence
<220> FEATURE:
<223> OTHER INFORMATION: Synthetic sequence

<400> SEQUENCE: 383

Ala Arg Ser Asp Tyr Tyr Gly Ser His Phe Asp Tyr
1               5                   10

<210> SEQ ID NO 384
<211> LENGTH: 15
<212> TYPE: PRT
<213> ORGANISM: Artificial Sequence
<220> FEATURE:
<223> OTHER INFORMATION: Synthetic sequence

<400> SEQUENCE: 384

Ala Arg Glu Gly Ser Thr Thr Val Ala Gly Asp Trp Phe Ala Tyr
1               5                   10                  15

<210> SEQ ID NO 385
<211> LENGTH: 15
<212> TYPE: PRT
<213> ORGANISM: Artificial Sequence
<220> FEATURE:
<223> OTHER INFORMATION: Synthetic sequence

<400> SEQUENCE: 385

Ala Arg Glu Gly Ser Asp Ala Val Leu Gly Asp Trp Phe Gly Tyr
1               5                   10                  15

<210> SEQ ID NO 386
<211> LENGTH: 15
<212> TYPE: PRT
<213> ORGANISM: Artificial Sequence
<220> FEATURE:
<223> OTHER INFORMATION: Synthetic sequence

<400> SEQUENCE: 386

Ala Arg Glu Gly Ser Asp Ala Val Leu Gly Asp Trp Phe Ala Tyr
1               5                   10                  15

<210> SEQ ID NO 387
<211> LENGTH: 15
<212> TYPE: PRT
<213> ORGANISM: Artificial Sequence
<220> FEATURE:
<223> OTHER INFORMATION: Synthetic sequence

<400> SEQUENCE: 387

Ala Arg Gly Gly Ser Asp Thr Val Leu Gly Asp Trp Phe Ala Tyr
1               5                   10                  15

<210> SEQ ID NO 388
<211> LENGTH: 15
<212> TYPE: PRT
<213> ORGANISM: Artificial Sequence
<220> FEATURE:
<223> OTHER INFORMATION: Synthetic sequence

<400> SEQUENCE: 388

Ala Arg Gly Gly Ser Asp Thr Val Leu Gly Asp Trp Phe Ala Tyr
1               5                   10                  15

<210> SEQ ID NO 389
<211> LENGTH: 15
<212> TYPE: PRT
<213> ORGANISM: Artificial Sequence
<220> FEATURE:
<223> OTHER INFORMATION: Synthetic sequence

<400> SEQUENCE: 389

Ala Arg Glu Gly Ser Asp Ala Val Thr Gly Asp Trp Phe Ala Tyr
1               5                   10                  15

<210> SEQ ID NO 390
<211> LENGTH: 15
<212> TYPE: PRT
<213> ORGANISM: Artificial Sequence
<220> FEATURE:
<223> OTHER INFORMATION: Synthetic sequence

<400> SEQUENCE: 390

```
Ala Arg Glu Gly Ser Thr Ala Val Ala Gly Asp Trp Phe Ala Tyr
1               5                   10                  15
```

<210> SEQ ID NO 391
<211> LENGTH: 15
<212> TYPE: PRT
<213> ORGANISM: Artificial Sequence
<220> FEATURE:
<223> OTHER INFORMATION: Synthetic sequence

<400> SEQUENCE: 391

```
Ala Arg Glu Gly Ser Asp Val Val Thr Gly Asp Trp Phe Ala Tyr
1               5                   10                  15
```

<210> SEQ ID NO 392
<211> LENGTH: 15
<212> TYPE: PRT
<213> ORGANISM: Artificial Sequence
<220> FEATURE:
<223> OTHER INFORMATION: Synthetic sequence

<400> SEQUENCE: 392

```
Ala Arg Glu Gly Ser Thr Ala Val Thr Gly Asp Trp Phe Ala Tyr
1               5                   10                  15
```

<210> SEQ ID NO 393
<211> LENGTH: 15
<212> TYPE: PRT
<213> ORGANISM: Artificial Sequence
<220> FEATURE:
<223> OTHER INFORMATION: Synthetic sequence

<400> SEQUENCE: 393

```
Ala Arg Glu Gly Glu Asp Ala Val Thr Gly Asp Trp Phe Ala Tyr
1               5                   10                  15
```

<210> SEQ ID NO 394
<211> LENGTH: 15
<212> TYPE: PRT
<213> ORGANISM: Artificial Sequence
<220> FEATURE:
<223> OTHER INFORMATION: Synthetic sequence

<400> SEQUENCE: 394

```
Ala Arg Glu Gly Ser Asp Ala Val Ala Gly Asp Trp Phe Asp Tyr
1               5                   10                  15
```

<210> SEQ ID NO 395
<211> LENGTH: 10
<212> TYPE: PRT
<213> ORGANISM: Artificial Sequence
<220> FEATURE:
<223> OTHER INFORMATION: Synthetic sequence

<400> SEQUENCE: 395

```
Thr Arg Glu Asp Tyr Gly Pro His Ala Tyr
1               5                   10
```

<210> SEQ ID NO 396
<211> LENGTH: 15
<212> TYPE: PRT
<213> ORGANISM: Artificial Sequence
<220> FEATURE:
<223> OTHER INFORMATION: Synthetic sequence

<400> SEQUENCE: 396

```
Ala Arg Gly Gly Ser Asp Thr Val Leu Gly Asp Trp Phe Ala Tyr
```

```
<210> SEQ ID NO 397
<211> LENGTH: 15
<212> TYPE: PRT
<213> ORGANISM: Artificial Sequence
<220> FEATURE:
<223> OTHER INFORMATION: Synthetic sequence

<400> SEQUENCE: 397

Ala Arg Gly Gly Ser Asp Ala Val Leu Gly Asp Trp Phe Ala Tyr
1               5                   10                  15

<210> SEQ ID NO 398
<211> LENGTH: 13
<212> TYPE: PRT
<213> ORGANISM: Artificial Sequence
<220> FEATURE:
<223> OTHER INFORMATION: Synthetic sequence

<400> SEQUENCE: 398

Ala Arg Ser Arg Gly Leu Val Leu Asp Ala Phe Asp Tyr
1               5                   10

<210> SEQ ID NO 399
<211> LENGTH: 15
<212> TYPE: PRT
<213> ORGANISM: Artificial Sequence
<220> FEATURE:
<223> OTHER INFORMATION: Synthetic sequence

<400> SEQUENCE: 399

Ala Arg Gly Gly Ser Asp Ala Val Leu Gly Asp Trp Phe Ala Tyr
1               5                   10                  15

<210> SEQ ID NO 400
<211> LENGTH: 15
<212> TYPE: PRT
<213> ORGANISM: Artificial Sequence
<220> FEATURE:
<223> OTHER INFORMATION: Synthetic sequence

<400> SEQUENCE: 400

Ala Arg Gly Gly Ser Asp Ala Val Leu Gly Asp Trp Phe Ala Tyr
1               5                   10                  15

<210> SEQ ID NO 401
<211> LENGTH: 15
<212> TYPE: PRT
<213> ORGANISM: Artificial Sequence
<220> FEATURE:
<223> OTHER INFORMATION: Synthetic sequence

<400> SEQUENCE: 401

Ala Arg Gly Gly Ser Asp Ala Val Leu Gly Asp Trp Phe Ala Tyr
1               5                   10                  15

<210> SEQ ID NO 402
<211> LENGTH: 15
<212> TYPE: PRT
<213> ORGANISM: Artificial Sequence
<220> FEATURE:
<223> OTHER INFORMATION: Synthetic sequence

<400> SEQUENCE: 402

Ala Arg Gly Gly Ser Asp Thr Val Ile Gly Asp Trp Phe Ala Tyr
1               5                   10                  15
```

<210> SEQ ID NO 403
<211> LENGTH: 15
<212> TYPE: PRT
<213> ORGANISM: Artificial Sequence
<220> FEATURE:
<223> OTHER INFORMATION: Synthetic sequence

<400> SEQUENCE: 403

Ala Arg Glu Gly Ser Asp Thr Val Leu Gly Asp Trp Phe Ala Tyr
1               5                   10                  15

<210> SEQ ID NO 404
<211> LENGTH: 15
<212> TYPE: PRT
<213> ORGANISM: Artificial Sequence
<220> FEATURE:
<223> OTHER INFORMATION: Synthetic sequence

<400> SEQUENCE: 404

Ala Arg Glu Gly Ser Thr Thr Val Val Gly Asp Trp Phe Asp Tyr
1               5                   10                  15

<210> SEQ ID NO 405
<211> LENGTH: 15
<212> TYPE: PRT
<213> ORGANISM: Artificial Sequence
<220> FEATURE:
<223> OTHER INFORMATION: Synthetic sequence

<400> SEQUENCE: 405

Ala Arg Glu Gly Ser Asp Val Val Ala Gly Asp Trp Phe Ala Tyr
1               5                   10                  15

<210> SEQ ID NO 406
<211> LENGTH: 12
<212> TYPE: PRT
<213> ORGANISM: Artificial Sequence
<220> FEATURE:
<223> OTHER INFORMATION: Synthetic sequence

<400> SEQUENCE: 406

Ala Arg Ser Pro Tyr Tyr Tyr Gly Val Phe Asp Tyr
1               5                   10

<210> SEQ ID NO 407
<211> LENGTH: 15
<212> TYPE: PRT
<213> ORGANISM: Artificial Sequence
<220> FEATURE:
<223> OTHER INFORMATION: Synthetic sequence

<400> SEQUENCE: 407

Ala Arg Glu Gly Ser Asp Ala Val Leu Gly Asp Trp Phe Gly Tyr
1               5                   10                  15

<210> SEQ ID NO 408
<211> LENGTH: 15
<212> TYPE: PRT
<213> ORGANISM: Artificial Sequence
<220> FEATURE:
<223> OTHER INFORMATION: Synthetic sequence

<400> SEQUENCE: 408

Ala Arg Glu Gly Ser Asp Thr Val Leu Gly Asp Trp Phe Ala Tyr
1               5                   10                  15

<210> SEQ ID NO 409
<211> LENGTH: 15
<212> TYPE: PRT
<213> ORGANISM: Artificial Sequence
<220> FEATURE:
<223> OTHER INFORMATION: Synthetic sequence

<400> SEQUENCE: 409

Ala Arg Glu Gly Ser Asp Thr Val Leu Gly Asp Trp Phe Ala Tyr
1               5                   10                  15

<210> SEQ ID NO 410
<211> LENGTH: 15
<212> TYPE: PRT
<213> ORGANISM: Artificial Sequence
<220> FEATURE:
<223> OTHER INFORMATION: Synthetic sequence

<400> SEQUENCE: 410

Ala Arg Glu Gly Ser Thr Ala Val Val Gly Asp Trp Phe Asp Tyr
1               5                   10                  15

<210> SEQ ID NO 411
<211> LENGTH: 15
<212> TYPE: PRT
<213> ORGANISM: Artificial Sequence
<220> FEATURE:
<223> OTHER INFORMATION: Synthetic sequence

<400> SEQUENCE: 411

Ala Arg Gly Gly Ser Thr Ala Val Thr Gly Asp Trp Phe Asp Tyr
1               5                   10                  15

<210> SEQ ID NO 412
<211> LENGTH: 15
<212> TYPE: PRT
<213> ORGANISM: Artificial Sequence
<220> FEATURE:
<223> OTHER INFORMATION: Synthetic sequence

<400> SEQUENCE: 412

Ala Arg Glu Gly Ser Asp Thr Val Val Gly Asp Trp Phe Ala Tyr
1               5                   10                  15

<210> SEQ ID NO 413
<211> LENGTH: 15
<212> TYPE: PRT
<213> ORGANISM: Artificial Sequence
<220> FEATURE:
<223> OTHER INFORMATION: Synthetic sequence

<400> SEQUENCE: 413

Ala Arg Glu Gly Ser Asp Thr Val Ala Gly Asp Trp Phe Ala Tyr
1               5                   10                  15

<210> SEQ ID NO 414
<211> LENGTH: 15
<212> TYPE: PRT
<213> ORGANISM: Artificial Sequence
<220> FEATURE:
<223> OTHER INFORMATION: Synthetic sequence

<400> SEQUENCE: 414

Ala Arg Glu Gly Ser Asp Thr Val Leu Gly Asp Trp Phe Ala Tyr
1               5                   10                  15

```
<210> SEQ ID NO 415
<211> LENGTH: 15
<212> TYPE: PRT
<213> ORGANISM: Artificial Sequence
<220> FEATURE:
<223> OTHER INFORMATION: Synthetic sequence

<400> SEQUENCE: 415

Ala Arg Glu Gly Ser Asp Thr Val Leu Gly Asp Trp Phe Ala Tyr
1               5                   10                  15

<210> SEQ ID NO 416
<211> LENGTH: 15
<212> TYPE: PRT
<213> ORGANISM: Artificial Sequence
<220> FEATURE:
<223> OTHER INFORMATION: Synthetic sequence

<400> SEQUENCE: 416

Ala Arg Glu Gly Ser Asp Ala Val Leu Gly Asp Trp Phe Ala Tyr
1               5                   10                  15

<210> SEQ ID NO 417
<211> LENGTH: 15
<212> TYPE: PRT
<213> ORGANISM: Artificial Sequence
<220> FEATURE:
<223> OTHER INFORMATION: Synthetic sequence

<400> SEQUENCE: 417

Ala Arg Glu Gly Ser Thr Ala Val Leu Gly Asp Trp Phe Ala Tyr
1               5                   10                  15

<210> SEQ ID NO 418
<211> LENGTH: 15
<212> TYPE: PRT
<213> ORGANISM: Artificial Sequence
<220> FEATURE:
<223> OTHER INFORMATION: Synthetic sequence

<400> SEQUENCE: 418

Ala Arg Glu Gly Ser Thr Ala Val Val Gly Asp Trp Phe Ala Tyr
1               5                   10                  15

<210> SEQ ID NO 419
<211> LENGTH: 15
<212> TYPE: PRT
<213> ORGANISM: Artificial Sequence
<220> FEATURE:
<223> OTHER INFORMATION: Synthetic sequence

<400> SEQUENCE: 419

Ala Arg Glu Gly Ser Thr Ala Val Leu Gly Asp Trp Phe Ala Tyr
1               5                   10                  15

<210> SEQ ID NO 420
<211> LENGTH: 15
<212> TYPE: PRT
<213> ORGANISM: Artificial Sequence
<220> FEATURE:
<223> OTHER INFORMATION: Synthetic sequence

<400> SEQUENCE: 420

Ala Arg Glu Gly Ser Asp Val Val Ala Gly Asp Trp Phe Ala Tyr
1               5                   10                  15

<210> SEQ ID NO 421
```

```
<211> LENGTH: 15
<212> TYPE: PRT
<213> ORGANISM: Artificial Sequence
<220> FEATURE:
<223> OTHER INFORMATION: Synthetic sequence

<400> SEQUENCE: 421

Ala Arg Glu Gly Ser Asp Ala Val Leu Gly Asp Trp Phe Ala Tyr
1               5                   10                  15

<210> SEQ ID NO 422
<211> LENGTH: 15
<212> TYPE: PRT
<213> ORGANISM: Artificial Sequence
<220> FEATURE:
<223> OTHER INFORMATION: Synthetic sequence

<400> SEQUENCE: 422

Ala Arg Glu Gly Ser Asp Thr Val Leu Gly Asp Trp Phe Ala Tyr
1               5                   10                  15

<210> SEQ ID NO 423
<211> LENGTH: 15
<212> TYPE: PRT
<213> ORGANISM: Artificial Sequence
<220> FEATURE:
<223> OTHER INFORMATION: Synthetic sequence

<400> SEQUENCE: 423

Ala Arg Glu Gly Ser Asp Thr Val Leu Gly Asp Trp Phe Ala Tyr
1               5                   10                  15

<210> SEQ ID NO 424
<211> LENGTH: 15
<212> TYPE: PRT
<213> ORGANISM: Artificial Sequence
<220> FEATURE:
<223> OTHER INFORMATION: Synthetic sequence

<400> SEQUENCE: 424

Ala Arg Glu Gly Ser Asp Ala Val Leu Gly Asp Trp Phe Ala Tyr
1               5                   10                  15

<210> SEQ ID NO 425
<211> LENGTH: 15
<212> TYPE: PRT
<213> ORGANISM: Artificial Sequence
<220> FEATURE:
<223> OTHER INFORMATION: Synthetic sequence

<400> SEQUENCE: 425

Ala Arg Glu Gly Ser Thr Thr Val Leu Gly Asp Trp Phe Ala Tyr
1               5                   10                  15

<210> SEQ ID NO 426
<211> LENGTH: 15
<212> TYPE: PRT
<213> ORGANISM: Artificial Sequence
<220> FEATURE:
<223> OTHER INFORMATION: Synthetic sequence

<400> SEQUENCE: 426

Ala Arg Glu Gly Ser Asp Thr Val Leu Gly Asp Trp Phe Ala Tyr
1               5                   10                  15

<210> SEQ ID NO 427
<211> LENGTH: 15
```

```
<212> TYPE: PRT
<213> ORGANISM: Artificial Sequence
<220> FEATURE:
<223> OTHER INFORMATION: Synthetic sequence

<400> SEQUENCE: 427

Ala Arg Glu Gly Ser Asp Thr Val Leu Gly Asp Trp Phe Ala Tyr
1               5                   10                  15

<210> SEQ ID NO 428
<211> LENGTH: 15
<212> TYPE: PRT
<213> ORGANISM: Artificial Sequence
<220> FEATURE:
<223> OTHER INFORMATION: Synthetic sequence

<400> SEQUENCE: 428

Ala Arg Glu Gly Ser Asp Thr Val Leu Gly Asp Trp Phe Ala Tyr
1               5                   10                  15

<210> SEQ ID NO 429
<211> LENGTH: 15
<212> TYPE: PRT
<213> ORGANISM: Artificial Sequence
<220> FEATURE:
<223> OTHER INFORMATION: Synthetic sequence

<400> SEQUENCE: 429

Ala Arg Glu Gly Ser Asp Thr Val Leu Gly Asp Trp Phe Ala Tyr
1               5                   10                  15

<210> SEQ ID NO 430
<211> LENGTH: 15
<212> TYPE: PRT
<213> ORGANISM: Artificial Sequence
<220> FEATURE:
<223> OTHER INFORMATION: Synthetic sequence

<400> SEQUENCE: 430

Ala Arg Glu Gly Ser Thr Ala Val Leu Gly Asp Trp Phe Ala Tyr
1               5                   10                  15

<210> SEQ ID NO 431
<211> LENGTH: 15
<212> TYPE: PRT
<213> ORGANISM: Artificial Sequence
<220> FEATURE:
<223> OTHER INFORMATION: Synthetic sequence

<400> SEQUENCE: 431

Ala Arg Glu Gly Ser Asp Ala Val Ala Gly Asp Trp Phe Asp Tyr
1               5                   10                  15

<210> SEQ ID NO 432
<211> LENGTH: 15
<212> TYPE: PRT
<213> ORGANISM: Artificial Sequence
<220> FEATURE:
<223> OTHER INFORMATION: Synthetic sequence

<400> SEQUENCE: 432

Ala Arg Gly Gly Ser Asp Thr Val Val Gly Asp Trp Phe Ala Tyr
1               5                   10                  15

<210> SEQ ID NO 433
<211> LENGTH: 11
<212> TYPE: PRT
```

```
<213> ORGANISM: Artificial Sequence
<220> FEATURE:
<223> OTHER INFORMATION: Synthetic sequence

<400> SEQUENCE: 433

Arg Ala Ser Gln Ser Val Ser Ser Tyr Leu Ala
1               5                   10

<210> SEQ ID NO 434
<211> LENGTH: 11
<212> TYPE: PRT
<213> ORGANISM: Artificial Sequence
<220> FEATURE:
<223> OTHER INFORMATION: Synthetic sequence

<400> SEQUENCE: 434

Arg Ala Ser Gln Asp Val Arg Thr Ala Val Ala
1               5                   10

<210> SEQ ID NO 435
<211> LENGTH: 11
<212> TYPE: PRT
<213> ORGANISM: Artificial Sequence
<220> FEATURE:
<223> OTHER INFORMATION: Synthetic sequence

<400> SEQUENCE: 435

Arg Ala Ser Gln Gly Ile Gly Ser Ser Leu Ala
1               5                   10

<210> SEQ ID NO 436
<211> LENGTH: 11
<212> TYPE: PRT
<213> ORGANISM: Artificial Sequence
<220> FEATURE:
<223> OTHER INFORMATION: Synthetic sequence

<400> SEQUENCE: 436

Gln Ala Ser Gln Asp Ile Ser Thr Phe Leu Ala
1               5                   10

<210> SEQ ID NO 437
<211> LENGTH: 11
<212> TYPE: PRT
<213> ORGANISM: Artificial Sequence
<220> FEATURE:
<223> OTHER INFORMATION: Synthetic sequence

<400> SEQUENCE: 437

Arg Ala Ser Gln Ser Ile Gly Arg Tyr Leu Asn
1               5                   10

<210> SEQ ID NO 438
<211> LENGTH: 11
<212> TYPE: PRT
<213> ORGANISM: Artificial Sequence
<220> FEATURE:
<223> OTHER INFORMATION: Synthetic sequence

<400> SEQUENCE: 438

Arg Ala Ser Gln Gly Ile Ser Ser Ala Leu Gly
1               5                   10

<210> SEQ ID NO 439
<211> LENGTH: 11
<212> TYPE: PRT
<213> ORGANISM: Artificial Sequence
```

```
<220> FEATURE:
<223> OTHER INFORMATION: Synthetic sequence

<400> SEQUENCE: 439

Arg Ala Ser Gln Gly Ile Ser Ser Asp Leu Ala
1               5                   10

<210> SEQ ID NO 440
<211> LENGTH: 12
<212> TYPE: PRT
<213> ORGANISM: Artificial Sequence
<220> FEATURE:
<223> OTHER INFORMATION: Synthetic sequence

<400> SEQUENCE: 440

Arg Ala Ser Glu Ser Val Thr Ser Thr Tyr Leu Ala
1               5                   10

<210> SEQ ID NO 441
<211> LENGTH: 11
<212> TYPE: PRT
<213> ORGANISM: Artificial Sequence
<220> FEATURE:
<223> OTHER INFORMATION: Synthetic sequence

<400> SEQUENCE: 441

Arg Ala Ser Gln Gly Ile Gly Ser Phe Leu Gly
1               5                   10

<210> SEQ ID NO 442
<211> LENGTH: 11
<212> TYPE: PRT
<213> ORGANISM: Artificial Sequence
<220> FEATURE:
<223> OTHER INFORMATION: Synthetic sequence

<400> SEQUENCE: 442

Arg Ala Ser Gln Gly Ile Ser Ser Tyr Leu Ala
1               5                   10

<210> SEQ ID NO 443
<211> LENGTH: 15
<212> TYPE: PRT
<213> ORGANISM: Artificial Sequence
<220> FEATURE:
<223> OTHER INFORMATION: Synthetic sequence

<400> SEQUENCE: 443

Arg Ala Ser Glu Ser Val Asp Phe Asp Gly Phe Ser Phe Leu Ala
1               5                   10                  15

<210> SEQ ID NO 444
<211> LENGTH: 11
<212> TYPE: PRT
<213> ORGANISM: Artificial Sequence
<220> FEATURE:
<223> OTHER INFORMATION: Synthetic sequence

<400> SEQUENCE: 444

Arg Ala Ser Gln Gly Ile Gly Ser Phe Leu Gly
1               5                   10

<210> SEQ ID NO 445
<211> LENGTH: 11
<212> TYPE: PRT
<213> ORGANISM: Artificial Sequence
<220> FEATURE:
```

```
<223> OTHER INFORMATION: Synthetic sequence

<400> SEQUENCE: 445

Gln Ala Ser Gln Asp Ile Thr Thr Tyr Leu Ala
1               5                   10

<210> SEQ ID NO 446
<211> LENGTH: 11
<212> TYPE: PRT
<213> ORGANISM: Artificial Sequence
<220> FEATURE:
<223> OTHER INFORMATION: Synthetic sequence

<400> SEQUENCE: 446

Arg Ala Ser Gln Asp Ile Ser Thr Phe Leu Ala
1               5                   10

<210> SEQ ID NO 447
<211> LENGTH: 11
<212> TYPE: PRT
<213> ORGANISM: Artificial Sequence
<220> FEATURE:
<223> OTHER INFORMATION: Synthetic sequence

<400> SEQUENCE: 447

Arg Ala Ser Gln Ser Val Ser Pro Tyr Leu Ala
1               5                   10

<210> SEQ ID NO 448
<211> LENGTH: 11
<212> TYPE: PRT
<213> ORGANISM: Artificial Sequence
<220> FEATURE:
<223> OTHER INFORMATION: Synthetic sequence

<400> SEQUENCE: 448

Arg Ala Ser Gln Gly Val Ser Pro Tyr Leu Ala
1               5                   10

<210> SEQ ID NO 449
<211> LENGTH: 11
<212> TYPE: PRT
<213> ORGANISM: Artificial Sequence
<220> FEATURE:
<223> OTHER INFORMATION: Synthetic sequence

<400> SEQUENCE: 449

Arg Ala Ser Gln Gly Val Gly Thr Tyr Leu Ala
1               5                   10

<210> SEQ ID NO 450
<211> LENGTH: 11
<212> TYPE: PRT
<213> ORGANISM: Artificial Sequence
<220> FEATURE:
<223> OTHER INFORMATION: Synthetic sequence

<400> SEQUENCE: 450

Gln Ala Ser Gln Asp Ile Arg Thr Phe Leu Ala
1               5                   10

<210> SEQ ID NO 451
<211> LENGTH: 11
<212> TYPE: PRT
<213> ORGANISM: Artificial Sequence
<220> FEATURE:
<223> OTHER INFORMATION: Synthetic sequence
```

<400> SEQUENCE: 451

Arg Ala Ser Gln Gly Ile Ser Ser Val Leu Ala
1               5                   10

<210> SEQ ID NO 452
<211> LENGTH: 10
<212> TYPE: PRT
<213> ORGANISM: Artificial Sequence
<220> FEATURE:
<223> OTHER INFORMATION: Synthetic sequence

<400> SEQUENCE: 452

Ser Ala Ser Ser Arg Val Gly Tyr Val His
1               5                   10

<210> SEQ ID NO 453
<211> LENGTH: 11
<212> TYPE: PRT
<213> ORGANISM: Artificial Sequence
<220> FEATURE:
<223> OTHER INFORMATION: Synthetic sequence

<400> SEQUENCE: 453

Gln Ala Ser Gln Asp Ile Arg Thr Tyr Leu Ala
1               5                   10

<210> SEQ ID NO 454
<211> LENGTH: 11
<212> TYPE: PRT
<213> ORGANISM: Artificial Sequence
<220> FEATURE:
<223> OTHER INFORMATION: Synthetic sequence

<400> SEQUENCE: 454

Arg Ala Ser Gln Asp Ile Arg Ser Tyr Leu Ala
1               5                   10

<210> SEQ ID NO 455
<211> LENGTH: 11
<212> TYPE: PRT
<213> ORGANISM: Artificial Sequence
<220> FEATURE:
<223> OTHER INFORMATION: Synthetic sequence

<400> SEQUENCE: 455

Arg Ala Ser Gln Ser Ile Thr Thr Tyr Leu Asn
1               5                   10

<210> SEQ ID NO 456
<211> LENGTH: 11
<212> TYPE: PRT
<213> ORGANISM: Artificial Sequence
<220> FEATURE:
<223> OTHER INFORMATION: Synthetic sequence

<400> SEQUENCE: 456

Arg Ala Ser Gln Gly Ile Ser Ser Ser Leu Ala
1               5                   10

<210> SEQ ID NO 457
<211> LENGTH: 11
<212> TYPE: PRT
<213> ORGANISM: Artificial Sequence
<220> FEATURE:
<223> OTHER INFORMATION: Synthetic sequence

<400> SEQUENCE: 457

Arg Ala Ser Gln Gly Ile Gly Ser Phe Leu Ala
1               5                   10

<210> SEQ ID NO 458
<211> LENGTH: 12
<212> TYPE: PRT
<213> ORGANISM: Artificial Sequence
<220> FEATURE:
<223> OTHER INFORMATION: Synthetic sequence

<400> SEQUENCE: 458

Arg Ala Ser Gln Ser Val Ser Gly Arg Phe Leu Ala
1               5                   10

<210> SEQ ID NO 459
<211> LENGTH: 11
<212> TYPE: PRT
<213> ORGANISM: Artificial Sequence
<220> FEATURE:
<223> OTHER INFORMATION: Synthetic sequence

<400> SEQUENCE: 459

Arg Ala Ser Gln Gly Ile Gly Ser Tyr Leu Ala
1               5                   10

<210> SEQ ID NO 460
<211> LENGTH: 11
<212> TYPE: PRT
<213> ORGANISM: Artificial Sequence
<220> FEATURE:
<223> OTHER INFORMATION: Synthetic sequence

<400> SEQUENCE: 460

Arg Ala Ser Gln Ser Ile Ser Ser Tyr Leu Ala
1               5                   10

<210> SEQ ID NO 461
<211> LENGTH: 11
<212> TYPE: PRT
<213> ORGANISM: Artificial Sequence
<220> FEATURE:
<223> OTHER INFORMATION: Synthetic sequence

<400> SEQUENCE: 461

Arg Ala Ser Gln Gly Val Gly Ser Tyr Leu Ala
1               5                   10

<210> SEQ ID NO 462
<211> LENGTH: 11
<212> TYPE: PRT
<213> ORGANISM: Artificial Sequence
<220> FEATURE:
<223> OTHER INFORMATION: Synthetic sequence

<400> SEQUENCE: 462

Arg Ala Ser Gln Ser Ile Gly Ser Tyr Leu Ala
1               5                   10

<210> SEQ ID NO 463
<211> LENGTH: 11
<212> TYPE: PRT
<213> ORGANISM: Artificial Sequence
<220> FEATURE:
<223> OTHER INFORMATION: Synthetic sequence

<400> SEQUENCE: 463

```
Arg Ala Ser Gln Asp Ile Arg Ser Tyr Leu Ala
1               5                   10

<210> SEQ ID NO 464
<211> LENGTH: 11
<212> TYPE: PRT
<213> ORGANISM: Artificial Sequence
<220> FEATURE:
<223> OTHER INFORMATION: Synthetic sequence

<400> SEQUENCE: 464

Arg Ala Ser Gln Gly Ile Gly Thr Tyr Leu Ala
1               5                   10

<210> SEQ ID NO 465
<211> LENGTH: 11
<212> TYPE: PRT
<213> ORGANISM: Artificial Sequence
<220> FEATURE:
<223> OTHER INFORMATION: Synthetic sequence

<400> SEQUENCE: 465

Arg Ala Ser Gln Asp Ile Ser Ser Val Leu Ala
1               5                   10

<210> SEQ ID NO 466
<211> LENGTH: 10
<212> TYPE: PRT
<213> ORGANISM: Artificial Sequence
<220> FEATURE:
<223> OTHER INFORMATION: Synthetic sequence

<400> SEQUENCE: 466

Ser Ala Ser Ser Arg Val Gly Ser Val Tyr
1               5                   10

<210> SEQ ID NO 467
<211> LENGTH: 11
<212> TYPE: PRT
<213> ORGANISM: Artificial Sequence
<220> FEATURE:
<223> OTHER INFORMATION: Synthetic sequence

<400> SEQUENCE: 467

Gln Ala Ser Gln Asp Ile Thr Thr Tyr Leu Ala
1               5                   10

<210> SEQ ID NO 468
<211> LENGTH: 11
<212> TYPE: PRT
<213> ORGANISM: Artificial Sequence
<220> FEATURE:
<223> OTHER INFORMATION: Synthetic sequence

<400> SEQUENCE: 468

Gln Ala Ser Gln Asp Ile Arg Thr Tyr Leu Ala
1               5                   10

<210> SEQ ID NO 469
<211> LENGTH: 11
<212> TYPE: PRT
<213> ORGANISM: Artificial Sequence
<220> FEATURE:
<223> OTHER INFORMATION: Synthetic sequence

<400> SEQUENCE: 469
```

-continued

Arg Ala Ser Gln Gly Ile Ser Ser Tyr Leu Ala
1               5                   10

<210> SEQ ID NO 470
<211> LENGTH: 11
<212> TYPE: PRT
<213> ORGANISM: Artificial Sequence
<220> FEATURE:
<223> OTHER INFORMATION: Synthetic sequence

<400> SEQUENCE: 470

Arg Ala Ser Gln Gly Ile Ser Arg Tyr Leu Ala
1               5                   10

<210> SEQ ID NO 471
<211> LENGTH: 11
<212> TYPE: PRT
<213> ORGANISM: Artificial Sequence
<220> FEATURE:
<223> OTHER INFORMATION: Synthetic sequence

<400> SEQUENCE: 471

Arg Ala Ser Gln Gly Ile Ser Pro Tyr Leu Ala
1               5                   10

<210> SEQ ID NO 472
<211> LENGTH: 11
<212> TYPE: PRT
<213> ORGANISM: Artificial Sequence
<220> FEATURE:
<223> OTHER INFORMATION: Synthetic sequence

<400> SEQUENCE: 472

Arg Ala Ser Gln Gly Ile Ser Ser Tyr Leu Ala
1               5                   10

<210> SEQ ID NO 473
<211> LENGTH: 11
<212> TYPE: PRT
<213> ORGANISM: Artificial Sequence
<220> FEATURE:
<223> OTHER INFORMATION: Synthetic sequence

<400> SEQUENCE: 473

Arg Ala Ser Gln Gly Ile Ser Ser Tyr Leu Ala
1               5                   10

<210> SEQ ID NO 474
<211> LENGTH: 11
<212> TYPE: PRT
<213> ORGANISM: Artificial Sequence
<220> FEATURE:
<223> OTHER INFORMATION: Synthetic sequence

<400> SEQUENCE: 474

Arg Ala Ser Gln Gly Ile Ser Ser Tyr Leu Ala
1               5                   10

<210> SEQ ID NO 475
<211> LENGTH: 11
<212> TYPE: PRT
<213> ORGANISM: Artificial Sequence
<220> FEATURE:
<223> OTHER INFORMATION: Synthetic sequence

<400> SEQUENCE: 475

Arg Ala Ser Gln Gly Ile Ser Ser Tyr Leu Ala 1               5                   10

<210> SEQ ID NO 476
<211> LENGTH: 11
<212> TYPE: PRT
<213> ORGANISM: Artificial Sequence
<220> FEATURE:
<223> OTHER INFORMATION: Synthetic sequence

<400> SEQUENCE: 476

Arg Ala Ser Gln Gly Ile Ser Ser Tyr Leu Ala
1               5                   10

<210> SEQ ID NO 477
<211> LENGTH: 11
<212> TYPE: PRT
<213> ORGANISM: Artificial Sequence
<220> FEATURE:
<223> OTHER INFORMATION: Synthetic sequence

<400> SEQUENCE: 477

Arg Ala Ser Gln Gly Ile Ser Ser Tyr Leu Ala
1               5                   10

<210> SEQ ID NO 478
<211> LENGTH: 11
<212> TYPE: PRT
<213> ORGANISM: Artificial Sequence
<220> FEATURE:
<223> OTHER INFORMATION: Synthetic sequence

<400> SEQUENCE: 478

Arg Ala Ser Gln Gly Ile Ser Ser Tyr Leu Ala
1               5                   10

<210> SEQ ID NO 479
<211> LENGTH: 11
<212> TYPE: PRT
<213> ORGANISM: Artificial Sequence
<220> FEATURE:
<223> OTHER INFORMATION: Synthetic sequence

<400> SEQUENCE: 479

Arg Ala Ser Gln Gly Ile Ser Ser Tyr Leu Ala
1               5                   10

<210> SEQ ID NO 480
<211> LENGTH: 11
<212> TYPE: PRT
<213> ORGANISM: Artificial Sequence
<220> FEATURE:
<223> OTHER INFORMATION: Synthetic sequence

<400> SEQUENCE: 480

Arg Ala Ser Gln Gly Ile Ser Ser Tyr Leu Ala
1               5                   10

<210> SEQ ID NO 481
<211> LENGTH: 11
<212> TYPE: PRT
<213> ORGANISM: Artificial Sequence
<220> FEATURE:
<223> OTHER INFORMATION: Synthetic sequence

<400> SEQUENCE: 481

Arg Ala Ser Gln Gly Ile Ser Ser Tyr Leu Ala
1               5                   10

<210> SEQ ID NO 482
<211> LENGTH: 11
<212> TYPE: PRT
<213> ORGANISM: Artificial Sequence
<220> FEATURE:
<223> OTHER INFORMATION: Synthetic sequence

<400> SEQUENCE: 482

Arg Ala Ser Gln Gly Ile Ser Ser Tyr Leu Ala
1               5                   10

<210> SEQ ID NO 483
<211> LENGTH: 11
<212> TYPE: PRT
<213> ORGANISM: Artificial Sequence
<220> FEATURE:
<223> OTHER INFORMATION: Synthetic sequence

<400> SEQUENCE: 483

Arg Ala Ser Gln Gly Ile Ser Ser Tyr Leu Ala
1               5                   10

<210> SEQ ID NO 484
<211> LENGTH: 11
<212> TYPE: PRT
<213> ORGANISM: Artificial Sequence
<220> FEATURE:
<223> OTHER INFORMATION: Synthetic sequence

<400> SEQUENCE: 484

Arg Ala Ser Gln Gly Ile Ser Ser Tyr Leu Ala
1               5                   10

<210> SEQ ID NO 485
<211> LENGTH: 11
<212> TYPE: PRT
<213> ORGANISM: Artificial Sequence
<220> FEATURE:
<223> OTHER INFORMATION: Synthetic sequence

<400> SEQUENCE: 485

Arg Ala Ser Gln Gly Ile Ser Ser Tyr Leu Ala
1               5                   10

<210> SEQ ID NO 486
<211> LENGTH: 11
<212> TYPE: PRT
<213> ORGANISM: Artificial Sequence
<220> FEATURE:
<223> OTHER INFORMATION: Synthetic sequence

<400> SEQUENCE: 486

Arg Ala Ser Gln Gly Ile Ser Ser Tyr Leu Ala
1               5                   10

<210> SEQ ID NO 487
<211> LENGTH: 11
<212> TYPE: PRT
<213> ORGANISM: Artificial Sequence
<220> FEATURE:
<223> OTHER INFORMATION: Synthetic sequence

<400> SEQUENCE: 487

Arg Ala Ser Gln Gly Val Ser Ser Tyr Leu Ala
1               5                   10

<210> SEQ ID NO 488
<211> LENGTH: 11
<212> TYPE: PRT
<213> ORGANISM: Artificial Sequence
<220> FEATURE:
<223> OTHER INFORMATION: Synthetic sequence

<400> SEQUENCE: 488

Arg Ala Ser Gln Gly Val Ser Ser Tyr Leu Ala
1               5                   10

<210> SEQ ID NO 489
<211> LENGTH: 11
<212> TYPE: PRT
<213> ORGANISM: Artificial Sequence
<220> FEATURE:
<223> OTHER INFORMATION: Synthetic sequence

<400> SEQUENCE: 489

Arg Ala Ser Gln Gly Val Ser Ser Tyr Leu Ala
1               5                   10

<210> SEQ ID NO 490
<211> LENGTH: 11
<212> TYPE: PRT
<213> ORGANISM: Artificial Sequence
<220> FEATURE:
<223> OTHER INFORMATION: Synthetic sequence

<400> SEQUENCE: 490

Arg Ala Ser Gln Ser Ile Ser Ser Tyr Leu Asn
1               5                   10

<210> SEQ ID NO 491
<211> LENGTH: 11
<212> TYPE: PRT
<213> ORGANISM: Artificial Sequence
<220> FEATURE:
<223> OTHER INFORMATION: Synthetic sequence

<400> SEQUENCE: 491

Arg Ala Ser Gln Ser Ile Ser Ser Tyr Leu Asn
1               5                   10

<210> SEQ ID NO 492
<211> LENGTH: 11
<212> TYPE: PRT
<213> ORGANISM: Artificial Sequence
<220> FEATURE:
<223> OTHER INFORMATION: Synthetic sequence

<400> SEQUENCE: 492

Arg Ala Ser Gln Ser Ile Ser Ser Tyr Leu Asn
1               5                   10

<210> SEQ ID NO 493
<211> LENGTH: 9
<212> TYPE: PRT
<213> ORGANISM: Artificial Sequence
<220> FEATURE:
<223> OTHER INFORMATION: Synthetic sequence

<400> SEQUENCE: 493

Asp Ala Ser Asn Leu Glu Thr Gly Val
1               5

```
<210> SEQ ID NO 494
<211> LENGTH: 9
<212> TYPE: PRT
<213> ORGANISM: Artificial Sequence
<220> FEATURE:
<223> OTHER INFORMATION: Synthetic sequence

<400> SEQUENCE: 494

Asp Ala Ser Asn Leu Glu Thr Gly Val
1               5

<210> SEQ ID NO 495
<211> LENGTH: 9
<212> TYPE: PRT
<213> ORGANISM: Artificial Sequence
<220> FEATURE:
<223> OTHER INFORMATION: Synthetic sequence

<400> SEQUENCE: 495

Ala Ala Ser Ser Leu Gln Ser Gly Val
1               5

<210> SEQ ID NO 496
<211> LENGTH: 9
<212> TYPE: PRT
<213> ORGANISM: Artificial Sequence
<220> FEATURE:
<223> OTHER INFORMATION: Synthetic sequence

<400> SEQUENCE: 496

Asp Ala Ser Ser Leu Glu Ser Gly Val
1               5

<210> SEQ ID NO 497
<211> LENGTH: 9
<212> TYPE: PRT
<213> ORGANISM: Artificial Sequence
<220> FEATURE:
<223> OTHER INFORMATION: Synthetic sequence

<400> SEQUENCE: 497

Asp Ala Ser Asn Leu Glu Thr Gly Val
1               5

<210> SEQ ID NO 498
<211> LENGTH: 9
<212> TYPE: PRT
<213> ORGANISM: Artificial Sequence
<220> FEATURE:
<223> OTHER INFORMATION: Synthetic sequence

<400> SEQUENCE: 498

Ala Ala Ser Ser Leu Gln Ser Gly Val
1               5

<210> SEQ ID NO 499
<211> LENGTH: 9
<212> TYPE: PRT
<213> ORGANISM: Artificial Sequence
<220> FEATURE:
<223> OTHER INFORMATION: Synthetic sequence

<400> SEQUENCE: 499

Ala Ala Ser Thr Leu Gln Ser Gly Val
1               5

<210> SEQ ID NO 500
```

```
<211> LENGTH: 9
<212> TYPE: PRT
<213> ORGANISM: Artificial Sequence
<220> FEATURE:
<223> OTHER INFORMATION: Synthetic sequence

<400> SEQUENCE: 500

Asp Ala Ser Asn Leu Glu Thr Gly Val
1               5

<210> SEQ ID NO 501
<211> LENGTH: 9
<212> TYPE: PRT
<213> ORGANISM: Artificial Sequence
<220> FEATURE:
<223> OTHER INFORMATION: Synthetic sequence

<400> SEQUENCE: 501

Asp Ala Ser Asn Arg Ala Thr Gly Ile
1               5

<210> SEQ ID NO 502
<211> LENGTH: 9
<212> TYPE: PRT
<213> ORGANISM: Artificial Sequence
<220> FEATURE:
<223> OTHER INFORMATION: Synthetic sequence

<400> SEQUENCE: 502

Asp Ala Ser Ser Leu Glu Ser Gly Val
1               5

<210> SEQ ID NO 503
<211> LENGTH: 9
<212> TYPE: PRT
<213> ORGANISM: Artificial Sequence
<220> FEATURE:
<223> OTHER INFORMATION: Synthetic sequence

<400> SEQUENCE: 503

Asp Ala Ser Asn Leu Glu Thr Gly Val
1               5

<210> SEQ ID NO 504
<211> LENGTH: 9
<212> TYPE: PRT
<213> ORGANISM: Artificial Sequence
<220> FEATURE:
<223> OTHER INFORMATION: Synthetic sequence

<400> SEQUENCE: 504

Asp Ala Ser Ser Leu Glu Ser Gly Val
1               5

<210> SEQ ID NO 505
<211> LENGTH: 9
<212> TYPE: PRT
<213> ORGANISM: Artificial Sequence
<220> FEATURE:
<223> OTHER INFORMATION: Synthetic sequence

<400> SEQUENCE: 505

Asp Ala Ser Asn Arg Ala Thr Gly Ile
1               5

<210> SEQ ID NO 506
<211> LENGTH: 9
```

```
<212> TYPE: PRT
<213> ORGANISM: Artificial Sequence
<220> FEATURE:
<223> OTHER INFORMATION: Synthetic sequence

<400> SEQUENCE: 506

Asp Ala Ser Ser Leu Glu Ser Gly Val
1               5

<210> SEQ ID NO 507
<211> LENGTH: 9
<212> TYPE: PRT
<213> ORGANISM: Artificial Sequence
<220> FEATURE:
<223> OTHER INFORMATION: Synthetic sequence

<400> SEQUENCE: 507

Asp Ala Ser Ser Leu Glu Ser Gly Val
1               5

<210> SEQ ID NO 508
<211> LENGTH: 9
<212> TYPE: PRT
<213> ORGANISM: Artificial Sequence
<220> FEATURE:
<223> OTHER INFORMATION: Synthetic sequence

<400> SEQUENCE: 508

Asp Ala Ser Asn Arg Ala Thr Gly Ile
1               5

<210> SEQ ID NO 509
<211> LENGTH: 9
<212> TYPE: PRT
<213> ORGANISM: Artificial Sequence
<220> FEATURE:
<223> OTHER INFORMATION: Synthetic sequence

<400> SEQUENCE: 509

Asp Ala Ser Ser Leu Glu Ser Gly Val
1               5

<210> SEQ ID NO 510
<211> LENGTH: 9
<212> TYPE: PRT
<213> ORGANISM: Artificial Sequence
<220> FEATURE:
<223> OTHER INFORMATION: Synthetic sequence

<400> SEQUENCE: 510

Asp Ala Ser Asn Arg Ala Thr Gly Ile
1               5

<210> SEQ ID NO 511
<211> LENGTH: 9
<212> TYPE: PRT
<213> ORGANISM: Artificial Sequence
<220> FEATURE:
<223> OTHER INFORMATION: Synthetic sequence

<400> SEQUENCE: 511

Asp Ala Ser Ser Leu Glu Ser Gly Val
1               5

<210> SEQ ID NO 512
<211> LENGTH: 9
<212> TYPE: PRT
```

```
<213> ORGANISM: Artificial Sequence
<220> FEATURE:
<223> OTHER INFORMATION: Synthetic sequence

<400> SEQUENCE: 512

Asp Ala Ser Ser Leu Glu Ser Gly Val
1               5

<210> SEQ ID NO 513
<211> LENGTH: 9
<212> TYPE: PRT
<213> ORGANISM: Artificial Sequence
<220> FEATURE:
<223> OTHER INFORMATION: Synthetic sequence

<400> SEQUENCE: 513

Asp Ala Ser Asn Arg Ala Thr Gly Ile
1               5

<210> SEQ ID NO 514
<211> LENGTH: 9
<212> TYPE: PRT
<213> ORGANISM: Artificial Sequence
<220> FEATURE:
<223> OTHER INFORMATION: Synthetic sequence

<400> SEQUENCE: 514

Asp Ala Ser Asn Arg Ala Thr Gly Ile
1               5

<210> SEQ ID NO 515
<211> LENGTH: 9
<212> TYPE: PRT
<213> ORGANISM: Artificial Sequence
<220> FEATURE:
<223> OTHER INFORMATION: Synthetic sequence

<400> SEQUENCE: 515

Asp Ala Ser Asn Leu Glu Thr Gly Val
1               5

<210> SEQ ID NO 516
<211> LENGTH: 9
<212> TYPE: PRT
<213> ORGANISM: Artificial Sequence
<220> FEATURE:
<223> OTHER INFORMATION: Synthetic sequence

<400> SEQUENCE: 516

Asp Ala Ser Asn Leu Glu Thr Gly Val
1               5

<210> SEQ ID NO 517
<211> LENGTH: 9
<212> TYPE: PRT
<213> ORGANISM: Artificial Sequence
<220> FEATURE:
<223> OTHER INFORMATION: Synthetic sequence

<400> SEQUENCE: 517

Asp Ala Ser Asn Leu Glu Thr Gly Val
1               5

<210> SEQ ID NO 518
<211> LENGTH: 9
<212> TYPE: PRT
<213> ORGANISM: Artificial Sequence
```

```
<220> FEATURE:
<223> OTHER INFORMATION: Synthetic sequence

<400> SEQUENCE: 518

Asp Ala Ser Ser Leu Glu Ser Gly Val
1               5

<210> SEQ ID NO 519
<211> LENGTH: 9
<212> TYPE: PRT
<213> ORGANISM: Artificial Sequence
<220> FEATURE:
<223> OTHER INFORMATION: Synthetic sequence

<400> SEQUENCE: 519

Asp Ala Ser Asn Leu Glu Thr Gly Val
1               5

<210> SEQ ID NO 520
<211> LENGTH: 9
<212> TYPE: PRT
<213> ORGANISM: Artificial Sequence
<220> FEATURE:
<223> OTHER INFORMATION: Synthetic sequence

<400> SEQUENCE: 520

Asp Ala Ser Asn Leu Glu Thr Gly Val
1               5

<210> SEQ ID NO 521
<211> LENGTH: 9
<212> TYPE: PRT
<213> ORGANISM: Artificial Sequence
<220> FEATURE:
<223> OTHER INFORMATION: Synthetic sequence

<400> SEQUENCE: 521

Asp Ala Ser Asn Leu Glu Thr Gly Val
1               5

<210> SEQ ID NO 522
<211> LENGTH: 9
<212> TYPE: PRT
<213> ORGANISM: Artificial Sequence
<220> FEATURE:
<223> OTHER INFORMATION: Synthetic sequence

<400> SEQUENCE: 522

Asp Ala Ser Asn Leu Glu Thr Gly Val
1               5

<210> SEQ ID NO 523
<211> LENGTH: 9
<212> TYPE: PRT
<213> ORGANISM: Artificial Sequence
<220> FEATURE:
<223> OTHER INFORMATION: Synthetic sequence

<400> SEQUENCE: 523

Asp Ala Ser Asn Arg Ala Thr Gly Ile
1               5

<210> SEQ ID NO 524
<211> LENGTH: 9
<212> TYPE: PRT
<213> ORGANISM: Artificial Sequence
<220> FEATURE:
```

```
<223> OTHER INFORMATION: Synthetic sequence

<400> SEQUENCE: 524

Asp Ala Ser Asn Arg Ala Thr Gly Ile
1               5

<210> SEQ ID NO 525
<211> LENGTH: 9
<212> TYPE: PRT
<213> ORGANISM: Artificial Sequence
<220> FEATURE:
<223> OTHER INFORMATION: Synthetic sequence

<400> SEQUENCE: 525

Asp Ala Ser Ser Leu Glu Ser Gly Val
1               5

<210> SEQ ID NO 526
<211> LENGTH: 9
<212> TYPE: PRT
<213> ORGANISM: Artificial Sequence
<220> FEATURE:
<223> OTHER INFORMATION: Synthetic sequence

<400> SEQUENCE: 526

Asp Ala Ser Asn Leu Glu Thr Gly Val
1               5

<210> SEQ ID NO 527
<211> LENGTH: 9
<212> TYPE: PRT
<213> ORGANISM: Artificial Sequence
<220> FEATURE:
<223> OTHER INFORMATION: Synthetic sequence

<400> SEQUENCE: 527

Asp Ala Ser Asn Arg Ala Thr Gly Ile
1               5

<210> SEQ ID NO 528
<211> LENGTH: 9
<212> TYPE: PRT
<213> ORGANISM: Artificial Sequence
<220> FEATURE:
<223> OTHER INFORMATION: Synthetic sequence

<400> SEQUENCE: 528

Asp Ala Ser Asn Leu Glu Thr Gly Val
1               5

<210> SEQ ID NO 529
<211> LENGTH: 9
<212> TYPE: PRT
<213> ORGANISM: Artificial Sequence
<220> FEATURE:
<223> OTHER INFORMATION: Synthetic sequence

<400> SEQUENCE: 529

Asp Ala Ser Asn Leu Glu Thr Gly Val
1               5

<210> SEQ ID NO 530
<211> LENGTH: 9
<212> TYPE: PRT
<213> ORGANISM: Artificial Sequence
<220> FEATURE:
<223> OTHER INFORMATION: Synthetic sequence
```

<400> SEQUENCE: 530

Asp Ala Ser Asn Arg Ala Thr Gly Ile
1               5

<210> SEQ ID NO 531
<211> LENGTH: 9
<212> TYPE: PRT
<213> ORGANISM: Artificial Sequence
<220> FEATURE:
<223> OTHER INFORMATION: Synthetic sequence

<400> SEQUENCE: 531

Asp Ala Ser Asn Arg Ala Thr Gly Ile
1               5

<210> SEQ ID NO 532
<211> LENGTH: 9
<212> TYPE: PRT
<213> ORGANISM: Artificial Sequence
<220> FEATURE:
<223> OTHER INFORMATION: Synthetic sequence

<400> SEQUENCE: 532

Asp Ala Ser Asn Leu Glu Thr Gly Val
1               5

<210> SEQ ID NO 533
<211> LENGTH: 9
<212> TYPE: PRT
<213> ORGANISM: Artificial Sequence
<220> FEATURE:
<223> OTHER INFORMATION: Synthetic sequence

<400> SEQUENCE: 533

Asp Ala Ser Asn Leu Glu Thr Gly Val
1               5

<210> SEQ ID NO 534
<211> LENGTH: 9
<212> TYPE: PRT
<213> ORGANISM: Artificial Sequence
<220> FEATURE:
<223> OTHER INFORMATION: Synthetic sequence

<400> SEQUENCE: 534

Asp Ala Ser Asn Leu Glu Thr Gly Val
1               5

<210> SEQ ID NO 535
<211> LENGTH: 9
<212> TYPE: PRT
<213> ORGANISM: Artificial Sequence
<220> FEATURE:
<223> OTHER INFORMATION: Synthetic sequence

<400> SEQUENCE: 535

Asp Ala Ser Asn Leu Glu Thr Gly Val
1               5

<210> SEQ ID NO 536
<211> LENGTH: 9
<212> TYPE: PRT
<213> ORGANISM: Artificial Sequence
<220> FEATURE:
<223> OTHER INFORMATION: Synthetic sequence

<400> SEQUENCE: 536

Asp Ala Ser Asn Leu Glu Thr Gly Val
1               5

<210> SEQ ID NO 537
<211> LENGTH: 9
<212> TYPE: PRT
<213> ORGANISM: Artificial Sequence
<220> FEATURE:
<223> OTHER INFORMATION: Synthetic sequence

<400> SEQUENCE: 537

Asp Ala Ser Asn Leu Glu Thr Gly Val
1               5

<210> SEQ ID NO 538
<211> LENGTH: 9
<212> TYPE: PRT
<213> ORGANISM: Artificial Sequence
<220> FEATURE:
<223> OTHER INFORMATION: Synthetic sequence

<400> SEQUENCE: 538

Asp Ala Ser Asn Leu Glu Thr Gly Val
1               5

<210> SEQ ID NO 539
<211> LENGTH: 9
<212> TYPE: PRT
<213> ORGANISM: Artificial Sequence
<220> FEATURE:
<223> OTHER INFORMATION: Synthetic sequence

<400> SEQUENCE: 539

Asp Ala Ser Asn Leu Glu Thr Gly Val
1               5

<210> SEQ ID NO 540
<211> LENGTH: 9
<212> TYPE: PRT
<213> ORGANISM: Artificial Sequence
<220> FEATURE:
<223> OTHER INFORMATION: Synthetic sequence

<400> SEQUENCE: 540

Asp Ala Ser Asn Leu Glu Thr Gly Val
1               5

<210> SEQ ID NO 541
<211> LENGTH: 9
<212> TYPE: PRT
<213> ORGANISM: Artificial Sequence
<220> FEATURE:
<223> OTHER INFORMATION: Synthetic sequence

<400> SEQUENCE: 541

Asp Ala Ser Asn Leu Glu Thr Gly Val
1               5

<210> SEQ ID NO 542
<211> LENGTH: 9
<212> TYPE: PRT
<213> ORGANISM: Artificial Sequence
<220> FEATURE:
<223> OTHER INFORMATION: Synthetic sequence

<400> SEQUENCE: 542

Asp Ala Ser Asn Leu Glu Thr Gly Val
1               5

<210> SEQ ID NO 543
<211> LENGTH: 9
<212> TYPE: PRT
<213> ORGANISM: Artificial Sequence
<220> FEATURE:
<223> OTHER INFORMATION: Synthetic sequence

<400> SEQUENCE: 543

Asp Ala Ser Asn Leu Glu Thr Gly Val
1               5

<210> SEQ ID NO 544
<211> LENGTH: 9
<212> TYPE: PRT
<213> ORGANISM: Artificial Sequence
<220> FEATURE:
<223> OTHER INFORMATION: Synthetic sequence

<400> SEQUENCE: 544

Asp Ala Ser Asn Leu Glu Thr Gly Val
1               5

<210> SEQ ID NO 545
<211> LENGTH: 9
<212> TYPE: PRT
<213> ORGANISM: Artificial Sequence
<220> FEATURE:
<223> OTHER INFORMATION: Synthetic sequence

<400> SEQUENCE: 545

Asp Ala Ser Asn Leu Glu Thr Gly Val
1               5

<210> SEQ ID NO 546
<211> LENGTH: 9
<212> TYPE: PRT
<213> ORGANISM: Artificial Sequence
<220> FEATURE:
<223> OTHER INFORMATION: Synthetic sequence

<400> SEQUENCE: 546

Asp Ala Ser Asn Leu Glu Thr Gly Val
1               5

<210> SEQ ID NO 547
<211> LENGTH: 9
<212> TYPE: PRT
<213> ORGANISM: Artificial Sequence
<220> FEATURE:
<223> OTHER INFORMATION: Synthetic sequence

<400> SEQUENCE: 547

Asp Ala Ser Asn Leu Glu Thr Gly Val
1               5

<210> SEQ ID NO 548
<211> LENGTH: 9
<212> TYPE: PRT
<213> ORGANISM: Artificial Sequence
<220> FEATURE:
<223> OTHER INFORMATION: Synthetic sequence

<400> SEQUENCE: 548

```
Asp Ala Ser Asn Leu Glu Thr Gly Val
1               5

<210> SEQ ID NO 549
<211> LENGTH: 9
<212> TYPE: PRT
<213> ORGANISM: Artificial Sequence
<220> FEATURE:
<223> OTHER INFORMATION: Synthetic sequence

<400> SEQUENCE: 549

Asp Ala Ser Asn Leu Glu Thr Gly Val
1               5

<210> SEQ ID NO 550
<211> LENGTH: 9
<212> TYPE: PRT
<213> ORGANISM: Artificial Sequence
<220> FEATURE:
<223> OTHER INFORMATION: Synthetic sequence

<400> SEQUENCE: 550

Ala Ala Ser Thr Leu Gln Ser Gly Val
1               5

<210> SEQ ID NO 551
<211> LENGTH: 9
<212> TYPE: PRT
<213> ORGANISM: Artificial Sequence
<220> FEATURE:
<223> OTHER INFORMATION: Synthetic sequence

<400> SEQUENCE: 551

Ala Ala Ser Thr Leu Gln Ser Gly Val
1               5

<210> SEQ ID NO 552
<211> LENGTH: 9
<212> TYPE: PRT
<213> ORGANISM: Artificial Sequence
<220> FEATURE:
<223> OTHER INFORMATION: Synthetic sequence

<400> SEQUENCE: 552

Ala Ala Ser Thr Leu Gln Ser Gly Val
1               5

<210> SEQ ID NO 553
<211> LENGTH: 11
<212> TYPE: PRT
<213> ORGANISM: Artificial Sequence
<220> FEATURE:
<223> OTHER INFORMATION: Synthetic sequence

<400> SEQUENCE: 553

Tyr Cys Gln Gln Ser Tyr Ser Thr Ser His Thr
1               5                   10

<210> SEQ ID NO 554
<211> LENGTH: 11
<212> TYPE: PRT
<213> ORGANISM: Artificial Sequence
<220> FEATURE:
<223> OTHER INFORMATION: Synthetic sequence

<400> SEQUENCE: 554

Tyr Cys Gln Gln Ser Tyr Asp Trp Pro Pro Thr
```

```
1               5                   10

<210> SEQ ID NO 555
<211> LENGTH: 10
<212> TYPE: PRT
<213> ORGANISM: Artificial Sequence
<220> FEATURE:
<223> OTHER INFORMATION: Synthetic sequence

<400> SEQUENCE: 555

Tyr Cys Gln Gln Gly Tyr Tyr Thr Trp Thr
1               5                   10

<210> SEQ ID NO 556
<211> LENGTH: 10
<212> TYPE: PRT
<213> ORGANISM: Artificial Sequence
<220> FEATURE:
<223> OTHER INFORMATION: Synthetic sequence

<400> SEQUENCE: 556

Tyr Cys Gln Gln Ala Tyr Ser Ile Trp Thr
1               5                   10

<210> SEQ ID NO 557
<211> LENGTH: 11
<212> TYPE: PRT
<213> ORGANISM: Artificial Sequence
<220> FEATURE:
<223> OTHER INFORMATION: Synthetic sequence

<400> SEQUENCE: 557

Tyr Cys Glu Gln Pro Leu Glu Leu Pro Arg Thr
1               5                   10

<210> SEQ ID NO 558
<211> LENGTH: 10
<212> TYPE: PRT
<213> ORGANISM: Artificial Sequence
<220> FEATURE:
<223> OTHER INFORMATION: Synthetic sequence

<400> SEQUENCE: 558

Tyr Cys Gln Gln Ser Tyr Tyr Thr Trp Thr
1               5                   10

<210> SEQ ID NO 559
<211> LENGTH: 10
<212> TYPE: PRT
<213> ORGANISM: Artificial Sequence
<220> FEATURE:
<223> OTHER INFORMATION: Synthetic sequence

<400> SEQUENCE: 559

Tyr Cys Gln Gln Tyr Tyr Ser Tyr Ile Thr
1               5                   10

<210> SEQ ID NO 560
<211> LENGTH: 11
<212> TYPE: PRT
<213> ORGANISM: Artificial Sequence
<220> FEATURE:
<223> OTHER INFORMATION: Synthetic sequence

<400> SEQUENCE: 560

Tyr Cys Gln Gln Tyr Ser Asp Trp Pro Pro Thr
1               5                   10
```

<210> SEQ ID NO 561
<211> LENGTH: 10
<212> TYPE: PRT
<213> ORGANISM: Artificial Sequence
<220> FEATURE:
<223> OTHER INFORMATION: Synthetic sequence

<400> SEQUENCE: 561

Tyr Cys Gln Gln Ser Tyr Ser Leu Trp Thr
1               5                   10

<210> SEQ ID NO 562
<211> LENGTH: 11
<212> TYPE: PRT
<213> ORGANISM: Artificial Sequence
<220> FEATURE:
<223> OTHER INFORMATION: Synthetic sequence

<400> SEQUENCE: 562

Tyr Cys Gln Gln Tyr Tyr Ser Thr Pro Leu Thr
1               5                   10

<210> SEQ ID NO 563
<211> LENGTH: 11
<212> TYPE: PRT
<213> ORGANISM: Artificial Sequence
<220> FEATURE:
<223> OTHER INFORMATION: Synthetic sequence

<400> SEQUENCE: 563

Tyr Cys Gln Gln Tyr Asp Thr Leu Pro Arg Thr
1               5                   10

<210> SEQ ID NO 564
<211> LENGTH: 10
<212> TYPE: PRT
<213> ORGANISM: Artificial Sequence
<220> FEATURE:
<223> OTHER INFORMATION: Synthetic sequence

<400> SEQUENCE: 564

Tyr Cys Gln Gln Tyr Tyr Ser Leu Val Thr
1               5                   10

<210> SEQ ID NO 565
<211> LENGTH: 10
<212> TYPE: PRT
<213> ORGANISM: Artificial Sequence
<220> FEATURE:
<223> OTHER INFORMATION: Synthetic sequence

<400> SEQUENCE: 565

Tyr Cys Gln Gln Gly Tyr Tyr Leu Trp Thr
1               5                   10

<210> SEQ ID NO 566
<211> LENGTH: 10
<212> TYPE: PRT
<213> ORGANISM: Artificial Sequence
<220> FEATURE:
<223> OTHER INFORMATION: Synthetic sequence

<400> SEQUENCE: 566

Tyr Cys Gln Gln Ala Tyr Ser Ile Trp Thr
1               5                   10

<210> SEQ ID NO 567
<211> LENGTH: 10
<212> TYPE: PRT
<213> ORGANISM: Artificial Sequence
<220> FEATURE:
<223> OTHER INFORMATION: Synthetic sequence

<400> SEQUENCE: 567

Tyr Cys Gln Gln Gly Tyr Ser Leu Trp Thr
1               5                   10

<210> SEQ ID NO 568
<211> LENGTH: 10
<212> TYPE: PRT
<213> ORGANISM: Artificial Sequence
<220> FEATURE:
<223> OTHER INFORMATION: Synthetic sequence

<400> SEQUENCE: 568

Tyr Cys Gln Gln Gly Tyr Ser Thr Trp Thr
1               5                   10

<210> SEQ ID NO 569
<211> LENGTH: 10
<212> TYPE: PRT
<213> ORGANISM: Artificial Sequence
<220> FEATURE:
<223> OTHER INFORMATION: Synthetic sequence

<400> SEQUENCE: 569

Tyr Cys Gln Gln Gly Tyr Ser Leu Trp Thr
1               5                   10

<210> SEQ ID NO 570
<211> LENGTH: 10
<212> TYPE: PRT
<213> ORGANISM: Artificial Sequence
<220> FEATURE:
<223> OTHER INFORMATION: Synthetic sequence

<400> SEQUENCE: 570

Tyr Cys Gln Gln Gly Tyr Ser Thr Trp Thr
1               5                   10

<210> SEQ ID NO 571
<211> LENGTH: 10
<212> TYPE: PRT
<213> ORGANISM: Artificial Sequence
<220> FEATURE:
<223> OTHER INFORMATION: Synthetic sequence

<400> SEQUENCE: 571

Tyr Cys Gln Gln Gly Tyr Ser Leu Trp Thr
1               5                   10

<210> SEQ ID NO 572
<211> LENGTH: 10
<212> TYPE: PRT
<213> ORGANISM: Artificial Sequence
<220> FEATURE:
<223> OTHER INFORMATION: Synthetic sequence

<400> SEQUENCE: 572

Tyr Cys Gln Gln Gly Tyr Tyr Thr Trp Thr
1               5                   10

```
<210> SEQ ID NO 573
<211> LENGTH: 10
<212> TYPE: PRT
<213> ORGANISM: Artificial Sequence
<220> FEATURE:
<223> OTHER INFORMATION: Synthetic sequence

<400> SEQUENCE: 573

Tyr Cys Gln Gln Gly Tyr Ser Ile Trp Thr
1               5                   10

<210> SEQ ID NO 574
<211> LENGTH: 10
<212> TYPE: PRT
<213> ORGANISM: Artificial Sequence
<220> FEATURE:
<223> OTHER INFORMATION: Synthetic sequence

<400> SEQUENCE: 574

Tyr Cys Gln Gln Gly Tyr Ser Ile Trp Thr
1               5                   10

<210> SEQ ID NO 575
<211> LENGTH: 10
<212> TYPE: PRT
<213> ORGANISM: Artificial Sequence
<220> FEATURE:
<223> OTHER INFORMATION: Synthetic sequence

<400> SEQUENCE: 575

Tyr Cys Gln Gln Ser Tyr Ser Tyr Ser Thr
1               5                   10

<210> SEQ ID NO 576
<211> LENGTH: 10
<212> TYPE: PRT
<213> ORGANISM: Artificial Sequence
<220> FEATURE:
<223> OTHER INFORMATION: Synthetic sequence

<400> SEQUENCE: 576

Tyr Cys Gln Gln Gly Tyr Ser Thr Trp Thr
1               5                   10

<210> SEQ ID NO 577
<211> LENGTH: 10
<212> TYPE: PRT
<213> ORGANISM: Artificial Sequence
<220> FEATURE:
<223> OTHER INFORMATION: Synthetic sequence

<400> SEQUENCE: 577

Tyr Cys Gln Gln Gly Tyr Tyr Leu Trp Thr
1               5                   10

<210> SEQ ID NO 578
<211> LENGTH: 12
<212> TYPE: PRT
<213> ORGANISM: Artificial Sequence
<220> FEATURE:
<223> OTHER INFORMATION: Synthetic sequence

<400> SEQUENCE: 578

Tyr Cys Gln Gln Tyr Asp Tyr Trp Pro Pro Tyr Thr
1               5                   10

<210> SEQ ID NO 579
```

```
<211> LENGTH: 10
<212> TYPE: PRT
<213> ORGANISM: Artificial Sequence
<220> FEATURE:
<223> OTHER INFORMATION: Synthetic sequence

<400> SEQUENCE: 579

Tyr Cys Gln Gln Gly Tyr Ser Ile Trp Thr
1               5                   10

<210> SEQ ID NO 580
<211> LENGTH: 10
<212> TYPE: PRT
<213> ORGANISM: Artificial Sequence
<220> FEATURE:
<223> OTHER INFORMATION: Synthetic sequence

<400> SEQUENCE: 580

Tyr Cys Gln Gln Gly Tyr Ser Thr Trp Thr
1               5                   10

<210> SEQ ID NO 581
<211> LENGTH: 10
<212> TYPE: PRT
<213> ORGANISM: Artificial Sequence
<220> FEATURE:
<223> OTHER INFORMATION: Synthetic sequence

<400> SEQUENCE: 581

Tyr Cys Gln Gln Gly Tyr Gln Leu Trp Thr
1               5                   10

<210> SEQ ID NO 582
<211> LENGTH: 10
<212> TYPE: PRT
<213> ORGANISM: Artificial Sequence
<220> FEATURE:
<223> OTHER INFORMATION: Synthetic sequence

<400> SEQUENCE: 582

Tyr Cys Gln Gln Gly Tyr Tyr Leu Trp Thr
1               5                   10

<210> SEQ ID NO 583
<211> LENGTH: 10
<212> TYPE: PRT
<213> ORGANISM: Artificial Sequence
<220> FEATURE:
<223> OTHER INFORMATION: Synthetic sequence

<400> SEQUENCE: 583

Tyr Cys Gln Gln Gly Tyr Ser Ile Trp Thr
1               5                   10

<210> SEQ ID NO 584
<211> LENGTH: 10
<212> TYPE: PRT
<213> ORGANISM: Artificial Sequence
<220> FEATURE:
<223> OTHER INFORMATION: Synthetic sequence

<400> SEQUENCE: 584

Tyr Cys Gln Gln Gly Tyr Ser Leu Trp Thr
1               5                   10

<210> SEQ ID NO 585
<211> LENGTH: 10
```

```
<212> TYPE: PRT
<213> ORGANISM: Artificial Sequence
<220> FEATURE:
<223> OTHER INFORMATION: Synthetic sequence

<400> SEQUENCE: 585

Tyr Cys Gln Gln Gly Tyr Gln Ile Trp Thr
1               5                   10

<210> SEQ ID NO 586
<211> LENGTH: 11
<212> TYPE: PRT
<213> ORGANISM: Artificial Sequence
<220> FEATURE:
<223> OTHER INFORMATION: Synthetic sequence

<400> SEQUENCE: 586

Tyr Cys Gln Gln Tyr Thr His Asp Pro Val Thr
1               5                   10

<210> SEQ ID NO 587
<211> LENGTH: 10
<212> TYPE: PRT
<213> ORGANISM: Artificial Sequence
<220> FEATURE:
<223> OTHER INFORMATION: Synthetic sequence

<400> SEQUENCE: 587

Tyr Cys Gln Gln Gly Tyr Tyr Leu Trp Thr
1               5                   10

<210> SEQ ID NO 588
<211> LENGTH: 10
<212> TYPE: PRT
<213> ORGANISM: Artificial Sequence
<220> FEATURE:
<223> OTHER INFORMATION: Synthetic sequence

<400> SEQUENCE: 588

Tyr Cys Gln Gln Gly Tyr Ser Ile Trp Thr
1               5                   10

<210> SEQ ID NO 589
<211> LENGTH: 10
<212> TYPE: PRT
<213> ORGANISM: Artificial Sequence
<220> FEATURE:
<223> OTHER INFORMATION: Synthetic sequence

<400> SEQUENCE: 589

Tyr Cys Gln Gln Gly Tyr Ser Thr Trp Thr
1               5                   10

<210> SEQ ID NO 590
<211> LENGTH: 10
<212> TYPE: PRT
<213> ORGANISM: Artificial Sequence
<220> FEATURE:
<223> OTHER INFORMATION: Synthetic sequence

<400> SEQUENCE: 590

Tyr Cys Gln Gln Gly Tyr Ser Leu Trp Thr
1               5                   10

<210> SEQ ID NO 591
<211> LENGTH: 10
<212> TYPE: PRT
```

<213> ORGANISM: Artificial Sequence
<220> FEATURE:
<223> OTHER INFORMATION: Synthetic sequence

<400> SEQUENCE: 591

Tyr Cys Gln Gln Gly Tyr Ser Leu Trp Thr
1               5                   10

<210> SEQ ID NO 592
<211> LENGTH: 11
<212> TYPE: PRT
<213> ORGANISM: Artificial Sequence
<220> FEATURE:
<223> OTHER INFORMATION: Synthetic sequence

<400> SEQUENCE: 592

Tyr Cys Gln Gln Tyr Tyr Thr Thr Pro Leu Thr
1               5                   10

<210> SEQ ID NO 593
<211> LENGTH: 11
<212> TYPE: PRT
<213> ORGANISM: Artificial Sequence
<220> FEATURE:
<223> OTHER INFORMATION: Synthetic sequence

<400> SEQUENCE: 593

Tyr Cys Gln Gln Tyr Tyr Thr Thr Pro Leu Thr
1               5                   10

<210> SEQ ID NO 594
<211> LENGTH: 11
<212> TYPE: PRT
<213> ORGANISM: Artificial Sequence
<220> FEATURE:
<223> OTHER INFORMATION: Synthetic sequence

<400> SEQUENCE: 594

Tyr Cys Gln Gln Tyr Tyr Thr Thr Pro Leu Thr
1               5                   10

<210> SEQ ID NO 595
<211> LENGTH: 11
<212> TYPE: PRT
<213> ORGANISM: Artificial Sequence
<220> FEATURE:
<223> OTHER INFORMATION: Synthetic sequence

<400> SEQUENCE: 595

Tyr Cys Gln Gln Tyr Tyr Thr Thr Pro Leu Thr
1               5                   10

<210> SEQ ID NO 596
<211> LENGTH: 11
<212> TYPE: PRT
<213> ORGANISM: Artificial Sequence
<220> FEATURE:
<223> OTHER INFORMATION: Synthetic sequence

<400> SEQUENCE: 596

Tyr Cys Gln Gln Tyr Tyr Thr Thr Pro Leu Thr
1               5                   10

<210> SEQ ID NO 597
<211> LENGTH: 11
<212> TYPE: PRT
<213> ORGANISM: Artificial Sequence

```
<220> FEATURE:
<223> OTHER INFORMATION: Synthetic sequence

<400> SEQUENCE: 597

Tyr Cys Gln Gln Tyr Tyr Thr Thr Pro Leu Thr
1               5                   10

<210> SEQ ID NO 598
<211> LENGTH: 11
<212> TYPE: PRT
<213> ORGANISM: Artificial Sequence
<220> FEATURE:
<223> OTHER INFORMATION: Synthetic sequence

<400> SEQUENCE: 598

Tyr Cys Gln Gln Tyr Tyr Thr Thr Pro Leu Thr
1               5                   10

<210> SEQ ID NO 599
<211> LENGTH: 11
<212> TYPE: PRT
<213> ORGANISM: Artificial Sequence
<220> FEATURE:
<223> OTHER INFORMATION: Synthetic sequence

<400> SEQUENCE: 599

Tyr Cys Gln Gln Tyr Tyr Ser Thr Pro Leu Thr
1               5                   10

<210> SEQ ID NO 600
<211> LENGTH: 11
<212> TYPE: PRT
<213> ORGANISM: Artificial Sequence
<220> FEATURE:
<223> OTHER INFORMATION: Synthetic sequence

<400> SEQUENCE: 600

Tyr Cys Gln Gln Tyr Tyr Ser Thr Pro Leu Thr
1               5                   10

<210> SEQ ID NO 601
<211> LENGTH: 11
<212> TYPE: PRT
<213> ORGANISM: Artificial Sequence
<220> FEATURE:
<223> OTHER INFORMATION: Synthetic sequence

<400> SEQUENCE: 601

Tyr Cys Gln Gln Tyr Tyr Ser Thr Pro Leu Thr
1               5                   10

<210> SEQ ID NO 602
<211> LENGTH: 11
<212> TYPE: PRT
<213> ORGANISM: Artificial Sequence
<220> FEATURE:
<223> OTHER INFORMATION: Synthetic sequence

<400> SEQUENCE: 602

Tyr Cys Gln Gln Tyr Tyr Ser Thr Pro Leu Thr
1               5                   10

<210> SEQ ID NO 603
<211> LENGTH: 11
<212> TYPE: PRT
<213> ORGANISM: Artificial Sequence
<220> FEATURE:
```

```
<223> OTHER INFORMATION: Synthetic sequence

<400> SEQUENCE: 603

Tyr Cys Gln Gln Tyr Tyr Ser Thr Pro Leu Thr
1               5                   10

<210> SEQ ID NO 604
<211> LENGTH: 11
<212> TYPE: PRT
<213> ORGANISM: Artificial Sequence
<220> FEATURE:
<223> OTHER INFORMATION: Synthetic sequence

<400> SEQUENCE: 604

Tyr Cys Gln Gln Tyr Tyr Ser Thr Pro Leu Thr
1               5                   10

<210> SEQ ID NO 605
<211> LENGTH: 11
<212> TYPE: PRT
<213> ORGANISM: Artificial Sequence
<220> FEATURE:
<223> OTHER INFORMATION: Synthetic sequence

<400> SEQUENCE: 605

Tyr Cys Gln Gln Tyr Tyr Ser Thr Pro Leu Thr
1               5                   10

<210> SEQ ID NO 606
<211> LENGTH: 11
<212> TYPE: PRT
<213> ORGANISM: Artificial Sequence
<220> FEATURE:
<223> OTHER INFORMATION: Synthetic sequence

<400> SEQUENCE: 606

Tyr Cys Gln Gln Ser Tyr Ser Thr Pro Leu Thr
1               5                   10

<210> SEQ ID NO 607
<211> LENGTH: 11
<212> TYPE: PRT
<213> ORGANISM: Artificial Sequence
<220> FEATURE:
<223> OTHER INFORMATION: Synthetic sequence

<400> SEQUENCE: 607

Tyr Cys Gln Gln Tyr Tyr Thr Thr Pro Leu Thr
1               5                   10

<210> SEQ ID NO 608
<211> LENGTH: 11
<212> TYPE: PRT
<213> ORGANISM: Artificial Sequence
<220> FEATURE:
<223> OTHER INFORMATION: Synthetic sequence

<400> SEQUENCE: 608

Tyr Cys Gln Gln Tyr Tyr Thr Thr Pro Leu Thr
1               5                   10

<210> SEQ ID NO 609
<211> LENGTH: 11
<212> TYPE: PRT
<213> ORGANISM: Artificial Sequence
<220> FEATURE:
<223> OTHER INFORMATION: Synthetic sequence
```

<400> SEQUENCE: 609

Tyr Cys Gln Gln Tyr Tyr Thr Thr Pro Leu Thr
1               5                   10

<210> SEQ ID NO 610
<211> LENGTH: 11
<212> TYPE: PRT
<213> ORGANISM: Artificial Sequence
<220> FEATURE:
<223> OTHER INFORMATION: Synthetic sequence

<400> SEQUENCE: 610

Tyr Cys Gln Gln Tyr Tyr Ser Thr Pro Leu Thr
1               5                   10

<210> SEQ ID NO 611
<211> LENGTH: 11
<212> TYPE: PRT
<213> ORGANISM: Artificial Sequence
<220> FEATURE:
<223> OTHER INFORMATION: Synthetic sequence

<400> SEQUENCE: 611

Tyr Cys Gln Gln Tyr Tyr Ser Thr Pro Leu Thr
1               5                   10

<210> SEQ ID NO 612
<211> LENGTH: 11
<212> TYPE: PRT
<213> ORGANISM: Artificial Sequence
<220> FEATURE:
<223> OTHER INFORMATION: Synthetic sequence

<400> SEQUENCE: 612

Tyr Cys Gln Gln Tyr Tyr Ser Thr Pro Leu Thr
1               5                   10

<210> SEQ ID NO 613
<211> LENGTH: 450
<212> TYPE: PRT
<213> ORGANISM: Artificial Sequence
<220> FEATURE:
<223> OTHER INFORMATION: Synthetic sequence

<400> SEQUENCE: 613

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Ser Trp Ile Arg Gln Ala Pro Gly Lys Gly Leu Glu
        35                  40                  45

Trp Ile Gly Ile Ile Asn Pro Asn Phe Gly Asp Thr Asn Tyr Ala Gln
    50                  55                  60

Lys Phe Gln Gly Arg Val Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Asp Glu Tyr Tyr Gly Gly Ser Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
    450

<210> SEQ ID NO 614
<211> LENGTH: 214
<212> TYPE: PRT
<213> ORGANISM: Artificial Sequence
<220> FEATURE:
<223> OTHER INFORMATION: Synthetic sequence

<400> SEQUENCE: 614

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Val Arg Thr Ala
                20                  25                  30

Val Ala Trp Tyr Gln Gln Lys Pro Gly Lys Ala Pro Lys Leu Leu Ile
              35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
65                   70                  75                  80

Glu Asp Phe Ala Thr Tyr Tyr Cys Gln Gln Ser Tyr Asp Trp Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 615
<211> LENGTH: 450
<212> TYPE: PRT
<213> ORGANISM: Artificial Sequence
<220> FEATURE:
<223> OTHER INFORMATION: Synthetic sequence

<400> SEQUENCE: 615

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
 50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Asp Ala Val Leu Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

```
Pro Ala Val Leu Gln Ser Ser Gly Leu Tyr Ser Leu Ser Ser Val Val
            180                 185                 190

Thr Val Pro Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
    450

<210> SEQ ID NO 616
<211> LENGTH: 213
<212> TYPE: PRT
<213> ORGANISM: Artificial Sequence
<220> FEATURE:
<223> OTHER INFORMATION: Synthetic sequence

<400> SEQUENCE: 616

Asp Ile Gln Leu Thr Gln Ser Pro Ser Leu Ser Ala Ser Val Gly
1               5                   10                  15

Asp Arg Val Thr Ile Thr Cys Arg Ala Ser Gln Asp Ile Ser Thr Phe
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ala Tyr Ser Ile Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 617
<211> LENGTH: 450
<212> TYPE: PRT
<213> ORGANISM: Artificial Sequence
<220> FEATURE:
<223> OTHER INFORMATION: Synthetic sequence

<400> SEQUENCE: 617

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Leu Ala Leu Ile Asp Trp Asp Asp Lys Tyr Tyr Ser Pro Ser
50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Leu Gly Asp Trp Phe Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
450

<210> SEQ ID NO 618
<211> LENGTH: 213
<212> TYPE: PRT
<213> ORGANISM: Artificial Sequence
<220> FEATURE:
<223> OTHER INFORMATION: Synthetic sequence

<400> SEQUENCE: 618

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
            85                  90                  95

Phe Gly Gln Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 619
<211> LENGTH: 450
<212> TYPE: PRT
<213> ORGANISM: Artificial Sequence
<220> FEATURE:
<223> OTHER INFORMATION: Synthetic sequence

<400> SEQUENCE: 619

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
                20                  25                  30

His Tyr Trp Ala Trp Ile Arg Gln Ala Pro Gly Lys Gly Leu Glu Trp
                35                  40                  45

Val Ser Ser Ile Ser Gly Tyr Gly Ser Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Ala Val Leu Gly Asp Trp Phe Ala Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270
```

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 620
<211> LENGTH: 213
<212> TYPE: PRT
<213> ORGANISM: Artificial Sequence
<220> FEATURE:
<223> OTHER INFORMATION: Synthetic sequence

<400> SEQUENCE: 620

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Phe
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 621
<211> LENGTH: 450
<212> TYPE: PRT
<213> ORGANISM: Artificial Sequence
<220> FEATURE:
<223> OTHER INFORMATION: Synthetic sequence

<400> SEQUENCE: 621

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Ala Val Leu Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 622
<211> LENGTH: 213
<212> TYPE: PRT
<213> ORGANISM: Artificial Sequence
<220> FEATURE:
<223> OTHER INFORMATION: Synthetic sequence

<400> SEQUENCE: 622

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ile Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 623
<211> LENGTH: 450
<212> TYPE: PRT
<213> ORGANISM: Artificial Sequence
<220> FEATURE:
<223> OTHER INFORMATION: Synthetic sequence

<400> SEQUENCE: 623

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Ala Trp Ile Arg Gln Ala Pro Gly Lys Gly Leu Glu
        35                  40                  45

Trp Leu Ala Leu Ile Asp Trp Asp Asp Lys Arg Tyr Ser Thr Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Thr Thr Val Val Gly Asp Trp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Leu
                435                 440                 445
Gly Lys
    450
```

<210> SEQ ID NO 624
<211> LENGTH: 213
<212> TYPE: PRT
<213> ORGANISM: Artificial Sequence
<220> FEATURE:
<223> OTHER INFORMATION: Synthetic sequence

<400> SEQUENCE: 624

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Gly Thr Tyr
                20                  25                  30
Leu Ala Trp Tyr Gln Gln Lys Pro Gly Lys Ala Pro Lys Leu Leu Ile
                35                  40                  45
Tyr Asp Ala Ser Asn Arg Ala Thr Gly Ile Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Ser Leu Trp Thr
                85                  90                  95
Phe Gly Gln Gly Thr Lys Val Glu Ile Lys Arg Thr Val Ala Ala Pro
                100                 105                 110
Ser Val Phe Ile Phe Pro Pro Ser Asp Glu Gln Leu Lys Ser Gly Thr
                115                 120                 125
Ala Ser Val Val Cys Leu Leu Asn Asn Phe Tyr Pro Arg Glu Ala Lys
                130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
                180                 185                 190
Cys Glu Val Thr His Gln Gly Leu Ser Ser Pro Val Thr Lys Ser Phe
                195                 200                 205
Asn Arg Gly Glu Cys
    210
```

<210> SEQ ID NO 625
<211> LENGTH: 446
<212> TYPE: PRT
<213> ORGANISM: Artificial Sequence
<220> FEATURE:
<223> OTHER INFORMATION: Synthetic sequence

<400> SEQUENCE: 625

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Tyr Ser Ile Ser Ser Gly
            20                  25                  30

Tyr His Trp Ala Trp Ile Arg Gln Ala Pro Gly Lys Gly Leu Glu Trp
        35                  40                  45

Ile Gly Glu Ile Tyr His Ser Gly Ser Thr Tyr Tyr Ser Pro Ser Leu
 50                  55                  60

Lys Ser Arg Val Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                85                  90                  95

Ala Arg Ser Pro Tyr Tyr Gly Val Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
 210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
 290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415
```

-continued

```
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
            435                 440                 445

<210> SEQ ID NO 626
<211> LENGTH: 213
<212> TYPE: PRT
<213> ORGANISM: Artificial Sequence
<220> FEATURE:
<223> OTHER INFORMATION: Synthetic sequence

<400> SEQUENCE: 626

Asp Ile Gln Leu Thr Gln Ser Pro Ser Ser Leu Ser Ala Ser Val Gly
1               5                   10                  15
Asp Arg Val Thr Ile Thr Cys Ser Ala Ser Ser Arg Val Gly Ser Val
            20                  25                  30
Tyr Trp Tyr Gln Gln Lys Pro Gly Lys Ala Pro Lys Leu Leu Ile Tyr
        35                  40                  45
Asp Ala Ser Asn Leu Glu Thr Gly Val Pro Ser Arg Phe Ser Gly Ser
    50                  55                  60
Gly Ser Gly Thr Asp Phe Thr Leu Thr Ile Ser Ser Leu Gln Pro Glu
65                  70                  75                  80
Asp Phe Ala Thr Tyr Tyr Cys Gln Gln Tyr Thr His Asp Pro Val Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 627
<211> LENGTH: 450
<212> TYPE: PRT
<213> ORGANISM: Artificial Sequence
<220> FEATURE:
<223> OTHER INFORMATION: Synthetic sequence

<400> SEQUENCE: 627

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Ser Thr Gly
            20                  25                  30
Gly Val Ala Val Gly Trp Ile Arg Gln Ala Pro Gly Lys Gly Leu Glu
        35                  40                  45
Trp Leu Ala Leu Ile Asp Trp Asp Gly Asp Lys Ser Tyr Ser Thr Ser
    50                  55                  60
```

Leu Lys Ser Arg Leu Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
             85                  90                  95

Cys Ala Arg Glu Gly Ser Thr Ala Val Val Gly Asp Trp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 628
<211> LENGTH: 213

```
<212> TYPE: PRT
<213> ORGANISM: Artificial Sequence
<220> FEATURE:
<223> OTHER INFORMATION: Synthetic sequence

<400> SEQUENCE: 628
```

| | | | | | | | | | | | | | | |
|---|---|---|---|---|---|---|---|---|---|---|---|---|---|---|
| Asp | Ile | Gln | Leu | Thr | Gln | Ser | Pro | Ser | Ser | Leu | Ser | Ala | Ser | Val | Gly |
| 1 | | | | 5 | | | | | 10 | | | | | 15 | |

Asp Arg Val Thr Ile Thr Cys Arg Ala Ser Gln Gly Ile Ser Arg Tyr
                20                  25                  30

Leu Ala Trp Tyr Gln Gln Lys Pro Gly Lys Ala Pro Lys Leu Leu Ile
             35                  40                  45

Tyr Asp Ala Ser Asn Arg Ala Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ser Leu Trp Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

```
<210> SEQ ID NO 629
<211> LENGTH: 448
<212> TYPE: PRT
<213> ORGANISM: Artificial Sequence
<220> FEATURE:
<223> OTHER INFORMATION: Synthetic sequence

<400> SEQUENCE: 629
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Thr Gly
            20                  25                  30

Gly Val Gly Val Ser Trp Ile Arg Gln Ala Pro Gly Lys Gly Leu Glu
         35                  40                  45

Trp Val Ser Ser Ile Ser Gly Ser Gly Gly Thr Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Leu Asn Ser Leu Arg Ala Glu Asp Thr Ala Val Tyr
                 85                  90                  95

Tyr Cys Ala Arg Asp Asp Leu Tyr Ser Trp Tyr Phe Asp Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 630
<211> LENGTH: 213
<212> TYPE: PRT
<213> ORGANISM: Artificial Sequence
<220> FEATURE:
<223> OTHER INFORMATION: Synthetic sequence

<400> SEQUENCE: 630

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ser
            20                  25                  30

-continued

```
Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Tyr Thr Trp Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
210

<210> SEQ ID NO 631
<211> LENGTH: 448
<212> TYPE: PRT
<213> ORGANISM: Artificial Sequence
<220> FEATURE:
<223> OTHER INFORMATION: Synthetic sequence

<400> SEQUENCE: 631

Glu Val Gln Leu Val Glu Ser Gly Gly Gly Leu Val Gln Pro Gly Gly
1                5                  10                  15

Ser Leu Arg Leu Ser Cys Ala Ala Ser Gly Tyr Ser Ile Ser Ser Gly
             20                  25                  30

Tyr Tyr Trp Asp Trp Ile Arg Gln Ala Pro Gly Lys Gly Leu Glu Trp
         35                  40                  45

Val Ser Ser Ile Ser Gly Asp Gly Asp Thr Thr Tyr Tyr Ala Asp Ser
 50                  55                  60

Val Lys Gly Arg Phe Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Glu Tyr Tyr Gly Tyr Gly Tyr Ala Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175
```

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 632
<211> LENGTH: 214
<212> TYPE: PRT
<213> ORGANISM: Artificial Sequence
<220> FEATURE:
<223> OTHER INFORMATION: Synthetic sequence

<400> SEQUENCE: 632

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 633
<211> LENGTH: 446
<212> TYPE: PRT
<213> ORGANISM: Artificial Sequence
<220> FEATURE:
<223> OTHER INFORMATION: Synthetic sequence

<400> SEQUENCE: 633

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His Tyr Trp Gly Trp Ile Arg Gln Ala Pro Gly Lys Gly Leu Glu Trp
        35                  40                  45

Leu Ala Leu Ile Asp Trp Tyr Gly Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Asp Tyr Tyr Gly Ser His Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240
```

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 634
<211> LENGTH: 218
<212> TYPE: PRT
<213> ORGANISM: Artificial Sequence
<220> FEATURE:
<223> OTHER INFORMATION: Synthetic sequence

<400> SEQUENCE: 634

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Asp
            20                  25                  30

Gly Phe Ser Phe Leu Ala Trp Tyr Gln Gln Lys Pro Gly Lys Ala Pro
        35                  40                  45

Lys Leu Leu Ile Tyr Asp Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Asp
                85                  90                  95

Thr Leu Pro Arg Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

```
Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 635
<211> LENGTH: 449
<212> TYPE: PRT
<213> ORGANISM: Artificial Sequence
<220> FEATURE:
<223> OTHER INFORMATION: Synthetic sequence

<400> SEQUENCE: 635

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Asn Tyr
            20                  25                  30

Trp Ile His Trp Val Arg Gln Ala Pro Gly Lys Gly Leu Glu Trp Val
        35                  40                  45

Ser Tyr Ile Ser Gly Asp Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
            85                  90                  95

Ala Arg Glu Gly Ser Thr Thr Val Ala Gly Asp Trp Phe Ala Tyr Trp
        100                 105                 110

Gly Gln Gly Thr Leu Val Thr Val Ser Ser Ala Ser Thr Lys Gly Pro
    115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 636
<211> LENGTH: 213
<212> TYPE: PRT
<213> ORGANISM: Artificial Sequence
<220> FEATURE:
<223> OTHER INFORMATION: Synthetic sequence

<400> SEQUENCE: 636

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Phe
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Leu Val Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 637
<211> LENGTH: 450
<212> TYPE: PRT
<213> ORGANISM: Artificial Sequence
<220> FEATURE:
<223> OTHER INFORMATION: Synthetic sequence

<400> SEQUENCE: 637

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Gly Val Gly Trp Ile Arg Gln Ala Pro Gly Lys Gly Leu Glu
        35                  40                  45

Trp Ile Gly Glu Ile Tyr His Ser Gly Ser Thr Tyr Tyr Ser Pro Ser
    50                  55                  60

Leu Lys Ser Arg Val Thr Ile Ser Arg Asp Asn Ser Lys Asn Thr Leu
65                  70                  75                  80

Tyr Leu Gln Leu Asn Ser Leu Lys Ala Glu Asp Thr Ala Val Tyr Tyr
                85                  90                  95

Cys Ala Arg Glu Gly Ser Asp Val Val Thr Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 638
<211> LENGTH: 213
<212> TYPE: PRT
<213> ORGANISM: Artificial Sequence
<220> FEATURE:
<223> OTHER INFORMATION: Synthetic sequence

<400> SEQUENCE: 638

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 639
<211> LENGTH: 450
<212> TYPE: PRT
<213> ORGANISM: Artificial Sequence
<220> FEATURE:

<223> OTHER INFORMATION: Synthetic sequence

<400> SEQUENCE: 639

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

His Tyr Trp Asn Trp Ile Arg Gln Ala Pro Gly Lys Gly Leu Glu Trp
        35                  40                  45

Val Ser Gly Ile Ser Gly Asp Gly Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Ala Val Leu Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

-continued

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
            435                 440                 445

Gly Lys
    450

<210> SEQ ID NO 640
<211> LENGTH: 213
<212> TYPE: PRT
<213> ORGANISM: Artificial Sequence
<220> FEATURE:
<223> OTHER INFORMATION: Synthetic sequence

<400> SEQUENCE: 640

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 641
<211> LENGTH: 451
<212> TYPE: PRT
<213> ORGANISM: Artificial Sequence
<220> FEATURE:
<223> OTHER INFORMATION: Synthetic sequence

<400> SEQUENCE: 641

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

```
Gly Val Gly Val Gly Trp Ile Arg Gln Ala Pro Gly Lys Gly Leu Glu
            35                  40                  45

Trp Val Ser Gly Ile Ser Gly Ala Gly Asp Ser Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Thr Val Leu Gly Asp Trp Phe Ala
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
            435                 440                 445
```

Leu Gly Lys
    450

<210> SEQ ID NO 642
<211> LENGTH: 213
<212> TYPE: PRT
<213> ORGANISM: Artificial Sequence
<220> FEATURE:
<223> OTHER INFORMATION: Synthetic sequence

<400> SEQUENCE: 642

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ile Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 643
<211> LENGTH: 450
<212> TYPE: PRT
<213> ORGANISM: Artificial Sequence
<220> FEATURE:
<223> OTHER INFORMATION: Synthetic sequence

<400> SEQUENCE: 643

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

His His Trp Ala Trp Ile Arg Gln Ala Pro Gly Lys Gly Leu Glu Trp
        35                  40                  45

Val Ser Val Ile Ser Gly Ser Gly Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
            85                  90                  95

Cys Ala Arg Glu Gly Ser Asp Thr Val Leu Gly Asp Trp Phe Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 644
<211> LENGTH: 213
<212> TYPE: PRT
<213> ORGANISM: Artificial Sequence
<220> FEATURE:

<223> OTHER INFORMATION: Synthetic sequence

<400> SEQUENCE: 644

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 645
<211> LENGTH: 451
<212> TYPE: PRT
<213> ORGANISM: Artificial Sequence
<220> FEATURE:
<223> OTHER INFORMATION: Synthetic sequence

<400> SEQUENCE: 645

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Ala Trp Ile Arg Gln Ala Pro Gly Lys Gly Leu Glu
        35                  40                  45

Trp Val Ser Ser Ile Ser Gly Tyr Gly Ser Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Leu Asn Ser Leu Arg Ala Glu Asp Thr Ala Val Tyr
                85                  90                  95

Tyr Cys Ala Arg Glu Gly Ser Asp Ala Val Leu Gly Asp Trp Phe Gly
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 646
<211> LENGTH: 213
<212> TYPE: PRT
<213> ORGANISM: Artificial Sequence
<220> FEATURE:
<223> OTHER INFORMATION: Synthetic sequence

<400> SEQUENCE: 646

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Thr Thr Tyr
            20                  25                  30

```
Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Tyr Leu Trp Thr
                 85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
210

<210> SEQ ID NO 647
<211> LENGTH: 450
<212> TYPE: PRT
<213> ORGANISM: Artificial Sequence
<220> FEATURE:
<223> OTHER INFORMATION: Synthetic sequence

<400> SEQUENCE: 647

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Thr Gly
             20                  25                  30

Gly Val Ala Val Gly Trp Ile Arg Gln Ala Pro Gly Lys Gly Leu Glu
         35                  40                  45

Trp Leu Ala Leu Ile Asp Trp Ala Gly Asp Lys Ser Tyr Ser Thr Ser
 50                  55                  60

Leu Lys Ser Arg Leu Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Gly Gly Ser Asp Thr Val Leu Gly Asp Trp Phe Ala Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 648
<211> LENGTH: 213
<212> TYPE: PRT
<213> ORGANISM: Artificial Sequence
<220> FEATURE:
<223> OTHER INFORMATION: Synthetic sequence

<400> SEQUENCE: 648

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Pro Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Gly Tyr Ser Thr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 649
<211> LENGTH: 450
<212> TYPE: PRT
<213> ORGANISM: Artificial Sequence
<220> FEATURE:
<223> OTHER INFORMATION: Synthetic sequence

<400> SEQUENCE: 649

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Ala Trp Ile Arg Gln Ala Pro Gly Lys Gly Leu Glu Trp
        35                  40                  45

Val Ser Ser Ile Ser Gly Asp Gly Ser Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Asp Ala Val Thr Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

```
Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
    450

<210> SEQ ID NO 650
<211> LENGTH: 213
<212> TYPE: PRT
<213> ORGANISM: Artificial Sequence
<220> FEATURE:
<223> OTHER INFORMATION: Synthetic sequence

<400> SEQUENCE: 650

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Gly Thr Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Leu Trp Thr
            85                  90                  95

Phe Gly Gln Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125
```

```
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 651
<211> LENGTH: 450
<212> TYPE: PRT
<213> ORGANISM: Artificial Sequence
<220> FEATURE:
<223> OTHER INFORMATION: Synthetic sequence

<400> SEQUENCE: 651

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Val Ala Val Gly Trp Ile Arg Gln Ala Pro Gly Lys Gly Leu Glu
        35                  40                  45

Trp Leu Ala Leu Ile Asp Trp Asp Asp Lys Tyr Tyr Ser Thr Ser
50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Ser Thr Ala Val Ala Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270
```

-continued

```
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
        435                 440                 445
Gly Lys
    450

<210> SEQ ID NO 652
<211> LENGTH: 213
<212> TYPE: PRT
<213> ORGANISM: Artificial Sequence
<220> FEATURE:
<223> OTHER INFORMATION: Synthetic sequence

<400> SEQUENCE: 652

Asp Ile Gln Leu Thr Gln Ser Pro Ser Ser Leu Ser Ala Ser Val Gly
1               5                   10                  15
Asp Arg Val Thr Ile Thr Cys Gln Ala Ser Gln Asp Ile Arg Thr Phe
            20                  25                  30
Leu Ala Trp Tyr Gln Gln Lys Pro Gly Lys Ala Pro Lys Leu Leu Ile
        35                  40                  45
Tyr Asp Ala Ser Asn Arg Ala Thr Gly Ile Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Ser Thr Trp Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
```

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 653
<211> LENGTH: 450
<212> TYPE: PRT
<213> ORGANISM: Artificial Sequence
<220> FEATURE:
<223> OTHER INFORMATION: Synthetic sequence

<400> SEQUENCE: 653

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Ala Val Gly Trp Ile Arg Gln Ala Pro Gly Lys Gly Leu Glu
        35                  40                  45

Trp Leu Ala Leu Ile Asp Trp Ala Gly Asp Lys Ser Tyr Ser Thr Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Glu Gly Glu Asp Ala Val Thr Gly Asp Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 654
<211> LENGTH: 213
<212> TYPE: PRT
<213> ORGANISM: Artificial Sequence
<220> FEATURE:
<223> OTHER INFORMATION: Synthetic sequence

<400> SEQUENCE: 654

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Arg Thr Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ile Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 655
<211> LENGTH: 447
<212> TYPE: PRT
<213> ORGANISM: Artificial Sequence
<220> FEATURE:
<223> OTHER INFORMATION: Synthetic sequence

<400> SEQUENCE: 655

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ser Val Ile Ser Gly Asp Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Arg Gly Leu Val Leu Asp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365
```

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 656
<211> LENGTH: 216
<212> TYPE: PRT
<213> ORGANISM: Artificial Sequence
<220> FEATURE:
<223> OTHER INFORMATION: Synthetic sequence

<400> SEQUENCE: 656

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Gly Arg
            20                  25                  30

Phe Leu Ala Trp Tyr Gln Gln Lys Pro Gly Lys Ala Pro Lys Leu Leu
        35                  40                  45

Ile Tyr Asp Ala Ser Ser Leu Glu Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Asp Tyr Trp Pro
                85                  90                  95

Pro Tyr Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 657
<211> LENGTH: 450
<212> TYPE: PRT
<213> ORGANISM: Artificial Sequence
<220> FEATURE:
<223> OTHER INFORMATION: Synthetic sequence

<400> SEQUENCE: 657

Glu Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Ser Leu Ser Thr Gly
            20                  25                  30
Gly Val Gly Val Gly Trp Ile Arg Gln Ala Pro Gly Lys Gly Leu Glu
            35                  40                  45
Trp Leu Ala Leu Ile Asp Trp Ala Asp Asp Lys Tyr Tyr Ser Pro Ser
50                  55                  60
Leu Lys Ser Arg Leu Thr Ile Ser Arg Asp Asn Ser Lys Asn Thr Leu
65                  70                  75                  80
Tyr Leu Gln Leu Asn Ser Leu Arg Ala Glu Asp Thr Ala Val Tyr Tyr
                85                  90                  95
Cys Ala Arg Gly Gly Ser Asp Thr Val Ile Gly Asp Trp Phe Ala Tyr
            100                 105                 110
Trp Gly Gln Gly Thr Leu Val Thr Val Ser Ser Ala Ser Thr Lys Gly
            115                 120                 125
Pro Ser Val Phe Pro Leu Ala Pro Cys Ser Arg Ser Thr Ser Glu Ser
        130                 135                 140
Thr Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
            195                 200                 205
Asp His Lys Pro Ser Asn Thr Lys Val Asp Lys Arg Val Glu Ser Lys
        210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
```

```
Glu Ala Leu His Asn His Tyr Thr Gln Lys Ser Leu Ser Leu Ser Leu
        435                 440                 445

Gly Lys
    450

<210> SEQ ID NO 658
<211> LENGTH: 213
<212> TYPE: PRT
<213> ORGANISM: Artificial Sequence
<220> FEATURE:
<223> OTHER INFORMATION: Synthetic sequence

<400> SEQUENCE: 658

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 659
<211> LENGTH: 450
<212> TYPE: PRT
<213> ORGANISM: Artificial Sequence
<220> FEATURE:
<223> OTHER INFORMATION: Synthetic sequence

<400> SEQUENCE: 659

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr His Trp Ser Trp Ile Arg Gln Ala Pro Gly Lys Gly Leu Glu Trp
        35                  40                  45

Val Ser Ser Ile Ser Gly Tyr Gly Asp Thr Thr Tyr Tyr Ala Asp Ser
```

```
            50                  55                  60
Val Lys Gly Arg Phe Thr Ile Ser Arg Asp Asn Ser Lys Asn Thr Leu
 65                  70                  75                  80

Tyr Leu Gln Leu Asn Ser Leu Arg Ala Glu Asp Thr Ala Val Tyr Tyr
                 85                  90                  95

Cys Ala Arg Glu Gly Ser Asp Thr Val Leu Gly Asp Trp Phe Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
450

<210> SEQ ID NO 660
```

<211> LENGTH: 213
<212> TYPE: PRT
<213> ORGANISM: Artificial Sequence
<220> FEATURE:
<223> OTHER INFORMATION: Synthetic sequence

<400> SEQUENCE: 660

Asp Ile Gln Leu Thr Gln Ser Pro Ser Ser Leu Ser Ala Ser Val Gly
1               5                   10                  15
Asp Arg Val Thr Ile Thr Cys Gln Ala Ser Gln Asp Ile Arg Thr Tyr
            20                  25                  30
Leu Ala Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Ser Ile Trp Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 661
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 661
gaggttcagc tggtggagtc tggcggtggc ctggtgcagc cagggggctc actccgtttg      60
tcctgtgcag cttccggatt ctctctgtct accagcggtg tggctgtgag ctggattcgt     120
caggccccgg gtaagggcct cgagtggatc ggtatcatca cccaaacttc ggtgatact      180
aactacgccc agaagttcca gggtcgtgtg actataagtc gcgacaattc gaaaaacaca     240
ctgtacctac aactgaacag cttaagagct gaggacactg ccgtctatta ttgcgccaga     300
gacgaatact acggtggctc ttactacttc gactactggg gtcaaggaac actagtcacc     360
gtctcctcgg cttccaccaa gggcccatcg gtcttccccc tggcgccctg ctccaggagc     420
acctccgaga gcacagccgc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600

| | |
|---|---|
| acgaagacct acacctgcaa cgtagatcac aagcccagca acaccaaggt ggacaagaga | 660 |
| gttgagtcca aatatggtcc cccatgccca ccatgcccag cacctgagtt cctgggggga | 720 |
| ccatcagtct tcctgttccc cccaaaaccc aaggacactc tcatgatctc ccggacccct | 780 |
| gaggtcacgt gcgtggtggt ggacgtgagc caggaagacc ccgaggtcca gttcaactgg | 840 |
| tacgtggatg gcgtggaggt gcataatgcc aagacaaagc cgcgggagga gcagttcaac | 900 |
| agcacgtacc gtgtggtcag cgtcctcacc gtcctgcacc aggactggct gaacggcaag | 960 |
| gagtacaagt gcaaggtctc caacaaaggc ctcccgtcct ccatcgagaa aaccatctcc | 1020 |
| aaagccaaag ggcagccccg agagccacag gtgtacaccc tgcccccatc ccaggaggag | 1080 |
| atgaccaaga accaggtcag cctgacctgc ctggtcaaag gcttctaccc cagcgacatc | 1140 |
| gccgtggagt gggagagcaa tgggcagccg gagaacaact acaagaccac gcctcccgtg | 1200 |
| ctggactccg acggctcctt cttcctctac agcaggctaa ccgtggacaa gagcaggtgg | 1260 |
| caggagggga atgtcttctc atgctccgtg atgcatgagg ctctgcacaa ccactacaca | 1320 |
| cagaagagcc tctccctgtc tctgggtaaa | 1350 |

<210> SEQ ID NO 662
<211> LENGTH: 642
<212> TYPE: DNA
<213> ORGANISM: Artificial Sequence
<220> FEATURE:
<223> OTHER INFORMATION: Synthetic sequence

<400> SEQUENCE: 662

| | |
|---|---|
| gatatccagt tgacccagtc cccgagttcc ctgtccgcct ctgtgggcga tcgggtcacc | 60 |
| atcacctgcc gtgcctctca ggacgtgcgc accgccgtgg cctggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttatta ctgccagcag tcctacgact ggcctccgac cttcggacag | 300 |
| ggtaccaagg tggagatcaa acgaaccgtg gccgctccct ccgtcttcat tttteeccct | 360 |
| tctgacgaac agctgaagag tggaacagcc agcgtggtct gtctgctgaa caatttctac | 420 |
| cctagagagg caaaagtgca gtggaaggtc gataacgccc tgcagagcgg caattcccag | 480 |
| gagtctgtga ctgaacagga cagtaaagat tcaacctata gcctgtcctc tacactgact | 540 |
| ctgtccaagg ctgattacga aaagcataaa gtctatgcat gtgaggtcac ccatcagggg | 600 |
| ctgtccagtc cagtcacaaa gtcattcaat aggggggagt gt | 642 |

<210> SEQ ID NO 663
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 663

| | |
|---|---|
| gaggttcagc tggtggagtc tggcggtggc ctggtgcagc caggggggctc actccgtttg | 60 |
| tcctgtgcag cttccggatt ctctctgtct accagcggtg tggctgtggg ctggattcgt | 120 |
| caggccccgg gtaagggcct cgagtggctg gccctgatcg actgggccga tgacaagtac | 180 |
| tactctccct ctctgaagtc tcgtctgact ataagtcgcg acaattcgaa aaacacactg | 240 |
| tacctacaac tgaacagctt aagagctgag gacactgccg tctattattg cgcgcgtgag | 300 |

| | |
|---|---|
| ggttctgacg ccgtgctcgg cgactggttc gcctactggg gtcaaggaac actagtcacc | 360 |
| gtctcctcgg cttccaccaa gggcccatcg gtcttccccc tggcgccctg ctccaggagc | 420 |
| acctccgaga gcacagccgc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acgaagacct acacctgcaa cgtagatcac aagcccagca acaccaaggt ggacaagaga | 660 |
| gttgagtcca aatatggtcc cccatgccca ccatgcccag cacctgagtt cctgggggga | 720 |
| ccatcagtct tcctgttccc cccaaaaccc aaggacactc tcatgatctc ccggacccct | 780 |
| gaggtcacgt gcgtggtggt ggacgtgagc caggaagacc ccgaggtcca gttcaactgg | 840 |
| tacgtggatg gcgtggaggt gcataatgcc aagacaaagc cgcggagga gcagttcaac | 900 |
| agcacgtacc gtgtggtcag cgtcctcacc gtcctgcacc aggactggct gaacggcaag | 960 |
| gagtacaagt gcaaggtctc caacaaaggc ctcccgtcct ccatcgagaa aaccatctcc | 1020 |
| aaagccaaag ggcagccccg agagccacag gtgtacaccc tgcccccatc ccaggaggag | 1080 |
| atgaccaaga accaggtcag cctgacctgc ctggtcaaag gcttctaccc cagcgacatc | 1140 |
| gccgtggagt gggagagcaa tgggcagccg gagaacaact acaagaccac gcctcccgtg | 1200 |
| ctggactccg acggctcctt cttcctctac agcaggctaa ccgtggacaa gagcaggtgg | 1260 |
| caggagggga atgtcttctc atgctccgtg atgcatgagg ctctgcacaa ccactacaca | 1320 |
| cagaagagcc tctccctgtc tctgggtaaa | 1350 |

<210> SEQ ID NO 664
<211> LENGTH: 639
<212> TYPE: DNA
<213> ORGANISM: Artificial Sequence
<220> FEATURE:
<223> OTHER INFORMATION: Synthetic sequence

<400> SEQUENCE: 664

| | |
|---|---|
| gatatccagt tgacccagtc cccgagttcc ctgtccgcct ctgtgggcga tcgggtcacc | 60 |
| atcacctgcc gggcctctca ggacatcagc acgttcctgg cctggtatca acagaaacca | 120 |
| ggaaaagctc cgaagcttct gatctacgac gcctcttctc tggaatctgg tgtgccatct | 180 |
| cgcttctctg gatccggttc cgggacggat ttcactctga ccatcagcag tctgcagccg | 240 |
| gaagacttcg caacttatta ctgccagcag gcctactcca tctggacctt cggacagggt | 300 |
| accaaggtgg agatcaaacg aaccgtggcc gctccctccg tcttcatttt tccccttct | 360 |
| gacgaacagc tgaagagtgg gacagccagc gtggtctgtc tgctgaacaa tttctaccct | 420 |
| agagaggcaa aagtgcagtg gaaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcagggctg | 600 |
| tccagtccag tcacaaagtc attcaatagg ggggagtgt | 639 |

<210> SEQ ID NO 665
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 665

| | |
|---|---|
| gaggttcagc tggtggagtc tggcggtggc ctggtgcagc cagggggctc actccgtttg | 60 |

```
tcctgtgcag cttccggatt ctctctgtct accagcggtg tgggtgtggg ctggattcgt    120
caggccccgg gtaagggcct cgagtggctg ccctgatcg actgggacga tgacaagtac    180
tactctccct ctctgaagtc tcgtctgact ataagtcgcg acaattcgaa aaacacactg    240
tacctacaac tgaacagctt aagagctgag gacactgccg tctattattg cgcgcgtggg    300
ggttctgaca ccgtgctcgg cgactggttc gcctactggg gtcaaggaac actagtcacc    360
gtctcctcgg cttccaccaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acgaagacct acacctgcaa cgtagatcac aagcccagca acaccaaggt ggacaagaga    660
gttgagtcca aatatggtcc cccatgccca ccatgcccag cacctgagtt cctgggggga    720
ccatcagtct tcctgttccc cccaaaaccc aaggacactc tcatgatctc ccggaccct    780 gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc    1020
aaagccaaag ggcagccccg agagccacag gtgtacaccc tgcccccatc ccaggaggag    1080
atgaccaaga accaggtcag cctgacctgc ctggtcaaag gcttctaccc cagcgacatc    1140
gccgtggagt gggagagcaa tgggcagccg gagaacaact acaagaccac gcctcccgtg    1200
ctggactccg acggctcctt cttcctctac agcaggctaa ccgtggacaa gagcaggtgg    1260 caggaggga atgtcttctc atgctccgtg atgcatgagg ctctgcacaa ccactacaca    1320
cagaagagcc tctccctgtc tctgggtaaa                                     1350
```

<210> SEQ ID NO 666
<211> LENGTH: 639
<212> TYPE: DNA
<213> ORGANISM: Artificial Sequence
<220> FEATURE:
<223> OTHER INFORMATION: Synthetic sequence

<400> SEQUENCE: 666

```
gatatccagt tgacccagtc cccgagttcc ctgtccgcct ctgtgggcga tcgggtcacc     60
atcacctgcc gtgcctctca gagcgtcagc ccttacctgg cctggtatca acagaaacca    120
ggaaaagctc cgaagcttct gatctacgac gcctcttctc tggaatctgg tgtgccatct    180
cgcttctctg gatccggttc cgggacggat ttcactctga ccatcagcag tctgcagccg    240
gaagacttcg caacttatta ctgccagcag ggctactccc tctggacctt cggacagggt    300
accaaggtgg agatcaaacg aaccgtggcc gctcccctccg tcttcatttt tcccccttct    360
gacgaacagc tgaagagtgg gacagccagc gtggtctgtc tgctgaacaa tttctaccct    420
agagaggcaa aagtgcagtg gaaggtcgat aacgccctgc agagcggcaa ttcccaggag    480
tctgtgactg aacaggacag taaagattca acctatagcc tgtcctctac actgactctg    540
tccaaggctg attacgaaaa gcataaagtc tatgcatgtg aggtcaccca tcaggggctg    600
tccagtccag tcacaaagtc attcaatagg ggggagtgt                           639
```

<210> SEQ ID NO 667

<211> LENGTH: 1350
<212> TYPE: DNA
<213> ORGANISM: Artificial Sequence
<220> FEATURE:
<223> OTHER INFORMATION: Synthetic sequence

<400> SEQUENCE: 667

| gaggttcagc | tggtggagtc | tggcggtggc | ctggtgcagc | caggggctc | actccgtttg | 60 |
| tcctgtgcag | cttccggata | ctctatcacc | tctggtcact | actgggcctg | gattcgtcag | 120 |
| gccccgggta | agggcctcga | gtgggtgtct | tccatctctg | gttacggttc | tactacctac | 180 |
| tacgccgact | ctgtcaaggg | ccgtttcact | ataagtcgcg | acaattcgaa | aaacacactg | 240 |
| tacctacaac | tgaacagttt | aagagctgag | gacactgccg | tctattattg | cgcgcgtggg | 300 |
| ggttctgacg | ccgtgctcgg | cgactggttc | gcctactggg | gtcaaggaac | actagtcacc | 360 |
| gtctcctcgg | cttccaccaa | gggcccatcg | gtcttccccc | tggcgccctg | ctccaggagc | 420 |
| acctccgaga | gcacagccgc | cctgggctgc | ctggtcaagg | actacttccc | cgaaccggtg | 480 |
| acggtgtcgt | ggaactcagg | cgccctgacc | agcggcgtgc | acaccttccc | ggctgtccta | 540 |
| cagtcctcag | gactctactc | cctcagcagc | gtggtgaccg | tgccctccag | cagcttgggc | 600 |
| acgaagacct | acacctgcaa | cgtagatcac | aagcccagca | acaccaaggt | ggacaagaga | 660 |
| gttgagtcca | aatatggtcc | cccatgccca | ccatgcccag | cacctgagtt | cctgggggga | 720 |
| ccatcagtct | tcctgttccc | cccaaaaccc | aaggacactc | tcatgatctc | ccggaccct | 780 |
| gaggtcacgt | gcgtggtggt | ggacgtgagc | caggaagacc | ccgaggtcca | gttcaactgg | 840 |
| tacgtggatg | gcgtggaggt | gcataatgcc | aagacaaagc | cgcgggagga | gcagttcaac | 900 |
| agcacgtacc | gtgtggtcag | cgtcctcacc | gtcctgcacc | aggactggct | gaacggcaag | 960 |
| gagtacaagt | gcaaggtctc | caacaaaggc | ctcccgtcct | ccatcgagaa | aaccatctcc | 1020 |
| aaagccaaag | ggcagccccg | agagccacag | gtgtacaccc | tgcccccatc | ccaggaggag | 1080 |
| atgaccaaga | accaggtcag | cctgacctgc | ctggtcaaag | gcttctaccc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctac | agcaggctaa | ccgtggacaa | gagcaggtgg | 1260 |
| caggaggga | atgtcttctc | atgctccgtg | atgcatgagg | ctctgcacaa | ccactacaca | 1320 |
| cagaagagcc | tctccctgtc | tctgggtaaa | | | | 1350 |

<210> SEQ ID NO 668
<211> LENGTH: 639
<212> TYPE: DNA
<213> ORGANISM: Artificial Sequence
<220> FEATURE:
<223> OTHER INFORMATION: Synthetic sequence

<400> SEQUENCE: 668

| gatatccagt | tgacccagtc | cccgagttcc | ctgtccgcct | ctgtgggcga | tcgggtcacc | 60 |
| atcacctgcc | gtgcctctca | gggtattggc | tctttcctgg | cttggtatca | acagaaacca | 120 |
| ggaaaagctc | cgaagcttct | gatctacgac | gcctctaacc | tggaaaccgg | tgtgccatct | 180 |
| cgcttctctg | gatccggttc | cggacggat | ttcactctga | ccatcagcag | tctgcagccg | 240 |
| gaagacttcg | caacttatta | ctgccagcag | ggctactacc | tctggacctt | cggacagggt | 300 |
| accaaggtgg | agatcaaacg | aactgtggcc | gctcccctccg | tcttcatttt | tccccttct | 360 |
| gacgaacagc | tgaagagtgg | acagccagc | gtggtctgtc | tgctgaacaa | tttctaccct | 420 |
| agagaggcaa | aagtgcagtg | gaaggtcgat | aacgccctgc | agagcggcaa | ttcccaggag | 480 |

| | |
|---|---|
| tctgtgactg aacaggacag taaagattca acctatagcc tgtcctctac actgactctg | 540 |
| tccaaggctg attacgaaaa gcataaagtc tatgcatgtg aggtcaccca tcagggctg | 600 |
| tccagtccag tcacaaagtc attcaatagg ggggagtgt | 639 |

<210> SEQ ID NO 669
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 669

| | |
|---|---|
| gaggttcagc tggtggagtc tggcggtggc ctggtgcagc caggggctc actccgtttg | 60 |
| tcctgtgcag cttccggatt ctctctgtct accagcggtg tgggtgtggg ctggattcgt | 120 |
| caggccccgg gtaagggcct cgagtggctg ccctgatcg actgggccga tgacaagtac | 180 |
| tactctccct ctctgaagtc tcgtctgact ataagtcgcg acaattcgaa aaacacactg | 240 |
| tacctacaac tgaacagctt aagagctgag gacactgccg tctattattg cgcgcgtggg | 300 |
| ggttctgacg ccgtgctcgg cgactggttc gcctactggg gtcaaggaac actagtcacc | 360 |
| gtctcctcgg cttccaccaa gggcccatcg gtcttccccc tggcgccctg ctccaggagc | 420 |
| acctccgaga gcacagccgc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acgaagacct acacctgcaa cgtagatcac aagcccagca acaccaaggt ggacaagaga | 660 |
| gttgagtcca aatatggtcc cccatgccca ccatgcccag cacctgagtt cctgggggga | 720 |
| ccatcagtct tcctgttccc cccaaaaccc aaggacactc tcatgatctc ccggacccct | 780 |
| gaggtcacgt gcgtggtggt ggacgtgagc caggaagacc ccgaggtcca gttcaactgg | 840 |
| tacgtggatg gcgtggaggt gcataatgcc aagacaaagc cgcgggagga gcagttcaac | 900 |
| agcacgtacc gtgtggtcag cgtcctcacc gtcctgcacc aggactggct gaacggcaag | 960 |
| gagtacaagt gcaaggtctc caacaaaggc ctcccgtcct ccatcgagaa aaccatctcc | 1020 |
| aaagccaaag gcagccccg agagccacag gtgtacaccc tgcccccatc ccaggaggag | 1080 |
| atgaccaaga accaggtcag cctgacctgc ctggtcaaag gcttctaccc cagcgacatc | 1140 |
| gccgtggagt gggagagcaa tgggcagccg gagaacaact acaagaccac gcctcccgtg | 1200 |
| ctggactccg acggctcctt cttcctctac agcaggctaa ccgtggacaa gagcaggtgg | 1260 |
| caggagggga atgtcttctc atgctccgtg atgcatgagg ctctgcacaa ccactacaca | 1320 |
| cagaagagcc tctccctgtc tctgggtaaa | 1350 |

<210> SEQ ID NO 670
<211> LENGTH: 639
<212> TYPE: DNA
<213> ORGANISM: Artificial Sequence
<220> FEATURE:
<223> OTHER INFORMATION: Synthetic sequence

<400> SEQUENCE: 670

| | |
|---|---|
| gatatccagt tgacccagtc cccgagttcc ctgtccgcct ctgtgggcga tcgggtcacc | 60 |
| atcacctgcc gtgcctctca gggcatcggc agttacctgg cctggtatca acagaaacca | 120 |
| ggaaaagctc cgaagcttct gatctacgac gcctctaacc tggaaaccgg tgtgccatct | 180 |

```
cgcttctctg gatccggttc cgggacggat ttcactctga ccatcagcag tctgcagccg    240
gaagacttcg caacttatta ctgccagcag ggctactcca tctggacctt cggacagggt    300
accaaggtgg agatcaaacg aaccgtggcc gctccctccg tcttcatttt tccccttct     360 gacgaacagc tgaagagtgg gacagccagc gtggtctgtc tgctgaacaa tttctaccct    420
agagaggcaa aagtgcagtg gaaggtcgat aacgccctgc agagcggcaa ttcccaggag    480
tctgtgactg aacaggacag taaagattca acctatagcc tgtcctctac actgactctg    540
tccaaggctg attacgaaaa gcataaagtc tatgcatgtg aggtcaccca tcaggggctg    600
tccagtccag tcacaaagtc attcaatagg ggggagtgt                           639
```

<210> SEQ ID NO 671
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 671

```
gaggttcagc tggtggagtc tggcggtggc ctggtgcagc cagggggctc actccgtttg     60
tcctgtgcag cttccggatt ctctctgtct accagcggtg tggctgtggc ctggattcgt    120
caggccccgg gtaagggcct cgagtggctg gccctgatcg actgggacga tgacaagcgt    180
tactctacct ctctgaagtc tcgtctgact ataagtcgcg acaattcgaa aaacacactg    240
tacctacaac tgaacagctt aagagctgag gacactgccg tctattattg cgcgcgtgag    300
ggttctacca ccgtggtcgg cgactggttc gactactggg gtcaaggaac actagtcacc    360
gtctcctcgg cttccaccaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acgaagacct acacctgcaa cgtagatcac aagcccagca acaccaaggt ggacaagaga    660
gttgagtcca aatatggtcc cccatgccca ccatgcccag cacctgagtt cctgggggga    720
ccatcagtct tcctgttccc cccaaaaccc aaggacactc tcatgatctc ccggacccct    780
gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc   1020
aaagccaaag gcagccccg agagccacag gtgtacaccc tgcccccatc ccaggaggag   1080
atgaccaaga accaggtcag cctgacctgc ctggtcaaag gcttctaccc cagcgacatc   1140
gccgtggagt gggagagcaa tgggcagccg gagaacaact acaagaccac gcctcccgtg   1200
ctggactccg acggctcctt cttcctctac agcaggctaa ccgtggacaa gagcaggtgg   1260
caggagggga atgtcttctc atgctccgtg atgcatgagg ctctgcacaa ccactacaca   1320
cagaagagcc tctccctgtc tctgggtaaa                                    1350
```

<210> SEQ ID NO 672
<211> LENGTH: 639
<212> TYPE: DNA
<213> ORGANISM: Artificial Sequence
<220> FEATURE:
<223> OTHER INFORMATION: Synthetic sequence

<400> SEQUENCE: 672

```
gatatccagt tgacccagtc cccgagttcc ctgtccgcct ctgtgggcga tcgggtcacc    60
atcacctgcc gtgcctctca gggcatcggc acttacctgg cctggtatca acagaaacca   120
ggaaaagctc cgaagcttct gatctacgac gcctctaacc gtgccaccgg tatcccatct   180
cgcttctctg gatccggttc cgggacggat ttcactctga ccatcagcag tctgcagccg   240
gaagacttcg caacttatta ctgccagcag ggctactccc tctggacctt cggacagggt   300
accaaggtgg agatcaaacg aaccgtggcc gctccctccg tcttcatttt tccccttct    360
gacgaacagc tgaagagtgg acagccagc gtggtctgtc tgctgaacaa tttctaccct   420
agagaggcaa aagtgcagtg gaaggtcgat aacgccctgc agagcggcaa ttcccaggag   480
tctgtgactg aacaggacag taaagattca acctatagcc tgtcctctac actgactctg   540
tccaaggctg attacgaaaa gcataaagtc tatgcatgtg aggtcaccca tcagggggctg   600
tccagtccag tcacaaagtc attcaatagg ggggagtgt                           639
```

<210> SEQ ID NO 673
<211> LENGTH: 1338
<212> TYPE: DNA
<213> ORGANISM: Artificial Sequence
<220> FEATURE:
<223> OTHER INFORMATION: Synthetic sequence

<400> SEQUENCE: 673

```
gaggttcagc tggtggagtc tggcggtggc ctggtgcagc caggggggctc actccgtttg    60
tcctgtgcag cttccggata tctatctcc tctggttacc actgggcctg gattcgtcag   120
gccccgggta agggcctcga gtggatcggt gaaatctacc actctggttc tacctactac   180
tctccatctc tgaagtctcg tgtgactata agtcgcgaca attcgaaaaa cacactgtac   240
ctacaactga acagcttaag agctgaggac actgccgtct attattgcgc gcgttcccca   300
tactactacg gtgtgttcga ctactggggt caaggaacac tagtcaccgt ctcctcggct   360
tccaccaagg gcccatcggt cttccccctg gcgccctgct ccaggagcac ctccgagagc   420
acagccgccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac gaagacctac   600
acctgcaacg tagatcacaa gcccagcaac accaaggtgg acaagagagt tgagtccaaa   660
tatggtcccc catgcccacc atgcccagca cctgagttcc tggggggacc atcagtcttc   720
ctgttccccc caaaacccaa ggacactctc atgatctccc ggacccctga ggtcacgtgc   780
gtggtggtgg acgtgagcca ggaagacccc gaggtccagt tcaactggta cgtggatggc   840
gtggaggtgc ataatgccaa gacaaagccg cgggaggagc agttcaacag cacgtaccgt   900
gtggtcagcg tcctcaccgt cctgcaccag gactggctga acggcaagga gtacaagtgc   960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctaacc gtggacaaga gcaggtggca ggaggggaat  1260
gtcttctcat gctccgtgat gcatgaggct ctgcacaacc actacacaca gaagagcctc  1320
```

```
tccctgtctc tggg taaa                                           1338
```

<210> SEQ ID NO 674
<211> LENGTH: 639
<212> TYPE: DNA
<213> ORGANISM: Artificial Sequence
<220> FEATURE:
<223> OTHER INFORMATION: Synthetic sequence

<400> SEQUENCE: 674

```
gatatccagt tgacccagtc cccgagttcc ctgtccgcct ctgtgggcga tcgggtcacc      60
atcacctgct ctgcctcttc tcgcgtgggc agcgtgtact ggtatcaaca gaaaccagga     120
aaagctccga agcttctgat ctacgacgcc tctaacctgg aaaccggtgt gccatctcgc    180
ttctctggat ccggttccgg gacggatttc actctgacca tcagcagtct gcagccggaa    240
gacttcgcaa cttattactg ccagcagtac acccacgacc cagtcacctt cggacagggt    300
accaaggtgg agatcaaacg aaccgtggcc gctcccctccg tcttcatttt tcccccttct   360
gacgaacagc tgaagagtgg acagccagc gtggtctgtc tgctgaacaa tttctaccct    420
agagaggcaa aagtgcagtg gaaggtcgat aacgccctgc agagcggcaa ttcccaggag   480
tctgtgactg aacaggacag taaagattca acctatagcc tgtcctctac actgactctg   540
tccaaggctg attacgaaaa gcataaagtc tatgcatgtg aggtcaccca tcaggggctg   600
tccagtccag tcacaaagtc attcaatagg ggggagtgt                            639
```

<210> SEQ ID NO 675
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 675

```
gaggttcagc tggtggagtc tggcggtggc ctggtgcagc cagggggctc actccgtttg      60
tcctgtgcag cttccggatt ctctctgtct accggcggtg tggctgtggg ctggattcgt     120
caggccccgg gtaagggcct cgagtggctg gccctgatcg actgggacgg tgacaagtcc    180
tactctacct ctctgaagtc tcgtctgact ataagtcgcg acaattcgaa aaacacactg    240
tacctacaac tgaacagctt aagagctgag gacactgccg tctattattg cgcgcgtgag   300
ggttctaccg ccgtggtcgg cgactggttc gactactggg gtcaaggaac actagtcacc   360
gtctcctcgg cttccaccaa gggcccatcg gtcttcccc tggcgccctg ctccaggagc    420
acctccgaga gcacagccgc cctgggctgc ctggtcaagg actacttccc cgaaccggtg   480
acggtgtcgt ggaactcagg cgccctgacc agcggcgtgc acaccttccc ggctgtccta    540
cagtcctcag gactctactc cctcagcagc gtggtgaccg tgccctccag cagcttgggc   600
acgaagacct acacctgcaa cgtagatcac aagcccagca acaccaaggt ggacaagaga   660
gttgagtcca aatatggtcc cccatgccca ccatgcccag cacctgagtt cctggggga    720
ccatcagtct tcctgttccc cccaaaaccc aaggacactc tcatgatctc ccggaccct    780
gaggtcacgt gcgtggtggt ggacgtgagc caggaagacc ccgaggtcca gttcaactgg   840
tacgtggatg gcgtggaggt gcataatgcc aagacaaagc cgcgggagga gcagttcaac   900
agcacgtacc gtgtggtcag cgtcctcacc gtcctgcacc aggactggct gaacggcaag   960
gagtacaagt gcaaggtctc caacaaaggc ctcccgtcct ccatcgagaa aaccatctcc   1020
aaagccaaag ggcagccccg agagccacag gtgtacaccc tgcccccatc ccaggaggag  1080
```

| | |
|---|---|
| atgaccaaga accaggtcag cctgacctgc ctggtcaaag gcttctaccc cagcgacatc | 1140 |
| gccgtggagt gggagagcaa tgggcagccg gagaacaact acaagaccac gcctcccgtg | 1200 |
| ctggactccg acggctcctt cttcctctac agcaggctaa ccgtggacaa gagcaggtgg | 1260 |
| caggagggga atgtcttctc atgctccgtg atgcatgagg ctctgcacaa ccactacaca | 1320 |
| cagaagagcc tctccctgtc tctgggtaaa | 1350 |

<210> SEQ ID NO 676
<211> LENGTH: 639
<212> TYPE: DNA
<213> ORGANISM: Artificial Sequence
<220> FEATURE:
<223> OTHER INFORMATION: Synthetic sequence

<400> SEQUENCE: 676

| | |
|---|---|
| gatatccagt tgacccagtc cccgagttcc ctgtccgcct ctgtgggcga tcgggtcacc | 60 |
| atcacctgcc gtgcctctca gggcatcagc cgttacctgg cctggtatca acagaaacca | 120 |
| ggaaaagctc cgaagcttct gatctacgac gcctctaacc gtgccaccgg tatcccatct | 180 |
| cgcttctctg gatccggttc cgggacggat ttcactctga ccatcagcag tctgcagccg | 240 |
| gaagacttcg caacttatta ctgccagcag ggctactcac tctggacctt cggacagggt | 300 |
| accaaggtgg agatcaaacg aaccgtggcc gctcccctcc gtcttcatttt tccccccttct | 360 |
| gacgaacagc tgaagagtgg acagccagc gtggtctgtc tgctgaacaa tttctaccct | 420 |
| agagaggcaa aagtgcagtg gaaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcagggctg | 600 |
| tccagtccag tcacaaagtc attcaatagg ggggagtgt | 639 |

<210> SEQ ID NO 677
<211> LENGTH: 1344
<212> TYPE: DNA
<213> ORGANISM: Artificial Sequence
<220> FEATURE:
<223> OTHER INFORMATION: Synthetic sequence

<400> SEQUENCE: 677

| | |
|---|---|
| gaggttcagc tggtggagtc tggcggtggc ctggtgcagc caggggggctc actccgtttg | 60 |
| tcctgtgcag cttccggatt ctctctgtct accggcggtg tgggtgtgag ctggattcgt | 120 |
| caggcccccg gtaagggcct cgagtgggtg tcttccatct ctggttccgg tggtactacc | 180 |
| tactacgccg actctgtcaa gggccgtttc actataagtc gcgacaattc gaaaaacaca | 240 |
| ctgtacctac aactgaacag cttaagagct gaggacactg ccgtctatta ttgcgccaga | 300 |
| gacgacctat actcctggta cttcgacgtg tggggtcaag aacactagt caccgtctcc | 360 |
| tcggcttcca ccaagggccc atcggtcttc cccctggcgc cctgctccag gagcacctcc | 420 |
| gagagcacag ccgccctggg ctgcctggtc aaggactact ccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgcccc cagcagctt gggcacgaag | 600 |
| acctacacct gcaacgtaga tcacaagccc agcaacacca aggtggacaa gagagttgag | 660 |
| tccaaatatg gtccccatg cccaccatgc ccagcacctg agttcctggg ggaccatca | 720 |
| gtcttcctgt tccccccaaa acccaaggac actctcatga tctcccggac ccctgaggtc | 780 |

| | |
|---|---|
| acgtgcgtgg tggtggacgt gagccaggaa gaccccgagg tccagttcaa ctggtacgtg | 840 |
| gatggcgtgg aggtgcataa tgccaagaca aagccgcggg aggagcagtt caacagcacg | 900 |
| taccgtgtgg tcagcgtcct caccgtcctg caccaggact ggctgaacgg caaggagtac | 960 |
| aagtgcaagg tctccaacaa aggcctcccg tcctccatcg agaaaaccat ctccaaagcc | 1020 |
| aaagggcagc cccgagagcc acaggtgtac accctgcccc catcccagga ggagatgacc | 1080 |
| aagaaccagg tcagcctgac ctgcctggtc aaaggcttct accccagcga catcgccgtg | 1140 |
| gagtgggaga gcaatgggca gccggagaac aactacaaga ccacgcctcc cgtgctggac | 1200 |
| tccgacggct ccttcttcct ctacagcagg ctaaccgtgg acaagagcag gtggcaggag | 1260 |
| gggaatgtct tctcatgctc cgtgatgcat gaggctctgc acaaccacta cacacagaag | 1320 |
| agcctctccc tgtctctggg taaa | 1344 |

```
<210> SEQ ID NO 678
<211> LENGTH: 639
<212> TYPE: DNA
<213> ORGANISM: Artificial Sequence
<220> FEATURE:
<223> OTHER INFORMATION: Synthetic sequence

<400> SEQUENCE: 678
```

| | |
|---|---|
| gatatccagt tgacccagtc cccgagttcc ctgtccgcct ctgtgggcga tcgggtcacc | 60 |
| atcacctgcc gtgcctctca gggtattggc tcttccctgg cttggtatca acagaaacca | 120 |
| ggaaaagctc cgaagcttct gatctacgcc gcctcttctt tgcagtctgg tgtgccatct | 180 |
| cgcttctctg gatccggttc cgggacggat ttcactctga ccatcagcag tctgcagccg | 240 |
| gaagacttcg caacttatta ctgccagcag ggctactaca cctggacctt cggacagggt | 300 |
| accaaggtgg agatcaaacg aaccgtggcc gctcccccg tcttcatttt tccccttct | 360 |
| gacgaacagc tgaagagtgg acagccagc gtggtctgtc tgctgaacaa tttctaccct | 420 |
| agagaggcaa aagtgcagtg gaaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcagggctg | 600 |
| tccagtccag tcacaaagtc attcaatagg ggggagtgt | 639 |

```
<210> SEQ ID NO 679
<211> LENGTH: 1344
<212> TYPE: DNA
<213> ORGANISM: Artificial Sequence
<220> FEATURE:
<223> OTHER INFORMATION: Synthetic sequence

<400> SEQUENCE: 679
```

| | |
|---|---|
| gaggttcagc tggtggagtc tggcggtggc ctggtgcagc cagggggctc actccgtttg | 60 |
| tcctgtgcag cttccggata ctctatctcc tctggttact actgggactg gattcgtcag | 120 |
| gccccgggta agggcctcga gtgggtgtct tccatctctg gtgacggtga atactaccta | 180 |
| tacgccgact ctgtcaaggg ccgtttcact ataagtcgcg acaattcgaa aaacacactg | 240 |
| tacctacaac tgaacagctt aagagctgag gacactgccg tctattattg cgccagagag | 300 |
| tactacggat acggttacgc cttggactac tggggtcaag aacactagt caccgtctcc | 360 |
| tcggcttcca ccaagggccc atcggtcttc cccctggcgc cctgctccag gagcacctcc | 420 |
| gagagcacag ccgccctggg ctgcctggtc aaggactact ccccgaacc ggtgacggtg | 480 |
| tcgtggaact caggcgccct gaccagcggc gtgcacacct tcccggctgt cctacagtcc | 540 |

```
tcaggactct actccctcag cagcgtggtg accgtgccct ccagcagctt gggcacgaag    600
acctacacct gcaacgtaga tcacaagccc agcaacacca aggtggacaa gagagttgag    660
tccaaatatg gtcccccatg cccaccatgc ccagcacctg agttcctggg gggaccatca    720
gtcttcctgt tccccccaaa acccaaggac actctcatga tctcccggac ccctgaggtc    780
acgtgcgtgg tggtggacgt gagccaggaa gaccccgagg tccagttcaa ctggtacgtg    840
gatggcgtgg aggtgcataa tgccaagaca aagccgcggg aggagcagtt caacagcacg    900
taccgtgtgg tcagcgtcct caccgtcctg caccaggact ggctgaacgg caaggagtac    960
aagtgcaagg tctccaacaa aggcctcccg tcctccatcg agaaaaccat ctccaaagcc   1020
aaagggcagc cccgagagcc acaggtgtac accctgcccc catcccagga ggagatgacc   1080
aagaaccagg tcagcctgac ctgcctggtc aaaggcttct accccagcga catcgccgtg   1140
gagtgggaga gcaatgggca gccggagaac aactacaaga ccacgcctcc cgtgctggac   1200
tccgacggct ccttcttcct ctacagcagg ctaaccgtgg acaagagcag gtggcaggag   1260
gggaatgtct tctcatgctc cgtgatgcat gaggctctgc acaaccacta cacacagaag   1320
agcctctccc tgtctctggg taaa                                          1344
```

<210> SEQ ID NO 680
<211> LENGTH: 642
<212> TYPE: DNA
<213> ORGANISM: Artificial Sequence
<220> FEATURE:
<223> OTHER INFORMATION: Synthetic sequence

<400> SEQUENCE: 680

```
gatatccagt tgacccagtc cccgagttcc ctgtccgcct ctgtgggcga tcgggtcacc     60
atcacctgcc gtgcctctca gggtatctct tcttacctgg cctggtatca acagaaacca    120
ggaaaagctc cgaagcttct gatctacgac gcctcttctc tggaatctgg tgtgccatct    180
cgcttctctg gatccggttc cgggacggat ttcactctga ccatcagcag tctgcagccg    240
gaagacttcg caacttacta ctgccagcag tactactcta ccccactgac cttcggtcag    300
ggtaccaagg tggagatcaa acgaaccgtg gccgctcccc ccgtcttcat tttccccct    360 tctgacgaac agctgaagag tggaacagcc agcgtggtct gtctgctgaa caatttctac    420
cctagagagg caaaagtgca gtggaaggtc gataacgccc tgcagagcgg caattcccag    480
gagtctgtga ctgaacagga cagtaaagat tcaacctata gcctgtcctc tacactgact    540
ctgtccaagg ctgattacga aaagcataaa gtctatgcat gtgaggtcac ccatcagggg    600
ctgtccagtc cagtcacaaa gtcattcaat aggggggagt gt                       642
```

<210> SEQ ID NO 681
<211> LENGTH: 1338
<212> TYPE: DNA
<213> ORGANISM: Artificial Sequence
<220> FEATURE:
<223> OTHER INFORMATION: Synthetic sequence

<400> SEQUENCE: 681

```
gaggttcagc tggtggagtc tggcggtggc ctggtgcagc cagggggctc actccgtttg     60
tcctgtgcag cttccggata ctctatctcc tctggtcact actgggctg gattcgtcag    120 gccccgggta agggcctcga gtggctggcc ctgatcgact ggtacggtga caagtactac    180
tctacctctc tgaagtctcg tctgactata agtcgcgaca attcgaaaaa cacactgtac    240
```

```
ctacaactga acagcttaag agctgaggac actgccgtct attattgcgc gcgttccgac    300
tactacggtt ctcacttcga ctactggggt caaggaacac tagtcaccgt ctcctcggct    360
tccaccaagg gcccatcggt cttccccctg gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaagacctac    600
acctgcaacg tagatcacaa gcccagcaac accaaggtgg acaagagagt tgagtccaaa    660
tatggtcccc catgcccacc atgcccagca cctgagttcc tggggggacc atcagtcttc    720
ctgttccccc caaaacccaa ggacactctc atgatctccc ggacccctga ggtcacgtgc    780
gtggtggtgg acgtgagcca ggaagacccc gaggtccagt tcaactggta cgtggatggc    840
gtggaggtgc ataatgccaa gacaaagccg cgggaggagc agttcaacag cacgtaccgt    900
gtggtcagcg tcctcaccgt cctgcaccag gactggctga acggcaagga gtacaagtgc    960
aaggtctcca acaaaggcct cccgtcctcc atcgagaaaa ccatctccaa agccaaaggg   1020
cagccccgag agccacaggt gtacaccctg cccccatccc aggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacgc ctcccgtgct ggactccgac   1200
ggctccttct cctctacag caggctaacc gtggacaaga gcaggtggca ggaggggaat   1260
gtcttctcat gctccgtgat gcatgaggct ctgcacaacc actacacaca gaagagcctc   1320
tccctgtctc tgggtaaa                                                 1338
```

<210> SEQ ID NO 682
<211> LENGTH: 654
<212> TYPE: DNA
<213> ORGANISM: Artificial Sequence
<220> FEATURE:
<223> OTHER INFORMATION: Synthetic sequence

<400> SEQUENCE: 682

```
gatatccagt tgacccagtc cccgagttcc ctgtccgcct ctgtgggcga tcgggtcacc     60
atcacctgcc gtgcctctga gtctgtggac ttcgacggtt tctctttcct ggcctggtat    120
caacagaaac caggaaaagc tccgaagctt ctgatctacg acgcctctaa cctggaaacc    180
ggtgtgccat ctcgcttctc tggatccggt tccgggacgg atttcactct gaccatcagc    240
agtctgcagc cggaagactt cgcaacttat tactgccagc agtacgatac tttgcctcgg    300
accttcggac agggtaccaa ggtggagatc aaacgaaccg tggccgctcc ctccgtcttc    360
attttccccc cttctgacga acagctgaag agtgggacag ccagcgtggt ctgtctgctg    420
aacaatttct accctagaga ggcaaaagtg cagtggaagg tcgataacgc cctgcagagc    480
ggcaattccc aggagtctgt gactgaacag gacagtaaag attcaaccta tagcctgtcc    540
tctacactga ctctgtccaa ggctgattac gaaaagcata aagtctatgc atgtgaggtc    600
acccatcagg ggctgtccag tccagtcaca aagtcattca taggggga gtgt           654
```

<210> SEQ ID NO 683
<211> LENGTH: 1347
<212> TYPE: DNA
<213> ORGANISM: Artificial Sequence
<220> FEATURE:
<223> OTHER INFORMATION: Synthetic sequence

<400> SEQUENCE: 683

```
gaggttcagc tggtggagtc tggcggtggc ctggtgcagc caggggctc actccgtttg      60 tcctgtgcag cttccggata caccttctcc aactactgga ttcactgggt gcgtcaggcc    120
ccgggtaagg gcctcgagtg ggtgtcttac atctctggtg acggtgatac tacctactac    180
gccgactctg tcaagggccg tttcactata agtcgcgaca attcgaaaaa cacactgtac    240
ctacaactga acagcttaag agctgaggac actgccgtct attattgcgc gcgtgagggt    300
tctaccaccg tggccggcga ctggttcgcc tactggggtc aaggaacact agtcaccgtc    360
tcctcggctt ccaccaaggg cccatcggtc ttccccctgg cgcctgctc caggagcacc     420 tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcct ggggggacca    720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc    1140 gtggagtggg agagcaatgg gcagccggag aacaactaca agaccacgcc tcccgtgctg   1200
gactccgacg gctccttctt cctctacagc aggctaaccg tggacaagag caggtggcag   1260 gagggggaatg tcttctcatg ctccgtgatg catgaggctc tgcacaacca ctacacacag   1320
aagagcctct ccctgtctct gggtaaa                                        1347

<210> SEQ ID NO 684
<211> LENGTH: 639
<212> TYPE: DNA
<213> ORGANISM: Artificial Sequence
<220> FEATURE:
<223> OTHER INFORMATION: Synthetic sequence

<400> SEQUENCE: 684
gatatccagt tgacccagtc cccgagttcc ctgtccgcct ctgtgggcga tcgggtcacc      60
atcacctgcc gtgcctctca gggtattggc tctttcctgg gttggtatca acagaaacca    120
ggaaaagctc cgaagcttct gatctacgac gcctcttctc tggaatctgg tgtgccatct    180
cgcttctctg gatccggttc cgggacggat ttcactctga ccatcagcag tctgcagccg    240
gaagacttcg caacttatta ctgccagcag tactactctt tggtcacctt cggacagggt    300
accaaggtgg agatcaaacg aaccgtggcc gctccctccg tcttcatttt tccccttct     360 gacgaacagc tgaagagtgg acagccagc gtggtctgtc tgctgaacaa tttctaccct    420
agagaggcaa aagtgcagtg gaaggtcgat aacgccctgc agagcggcaa ttcccaggag   480
tctgtgactg aacaggacag taaagattca acctatagcc tgtcctctac actgactctg    540
tccaaggctg attacgaaaa gcataaagtc tatgcatgtg aggtcaccca tcagggggctg   600 tccagtccag tcacaaaagtc attcaatagg ggggagtgt                           639
```

<210> SEQ ID NO 685
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 685

| | | | | | |
|---|---|---|---|---|---|
| gaggttcagc | tggtggagtc | tggcggtggc | ctggtgcagc | caggggctc | actccgtttg | 60 |
| tcctgtgcag | cttccggatt | ctctctgtct | accagcggtg | tgggtgtggg | ctggattcgt | 120 |
| caggccccgg | gtaagggcct | cgagtggatc | ggtgaaatct | accactctgg | ttctacctac | 180 |
| tactctccat | ctctgaagtc | tcgtgtgact | ataagtcgcg | acaattcgaa | aaacacactg | 240 |
| tacctacaac | tgaacagctt | aaaagctgag | gacactgccg | tctattattg | cgcgcgtgaa | 300 |
| ggttcagacg | ttgtgaccgg | cgactggttc | gcctactggg | gtcaaggaac | actagtcacc | 360 |
| gtctcctcgg | cttccaccaa | gggcccatcg | gtcttccccc | tggcgccctg | ctccaggagc | 420 |
| acctccgaga | gcacagccgc | cctgggctgc | ctggtcaagg | actacttccc | cgaaccggtg | 480 |
| acggtgtcgt | ggaactcagg | cgccctgacc | agcggcgtgc | acaccttccc | ggctgtccta | 540 |
| cagtcctcag | gactctactc | cctcagcagc | gtggtgaccg | tgccctccag | cagcttgggc | 600 |
| acgaagacct | acacctgcaa | cgtagatcac | aagcccagca | acaccaaggt | ggacaagaga | 660 |
| gttgagtcca | aatatggtcc | cccatgccca | ccatgcccag | cacctgagtt | cctgggggga | 720 |
| ccatcagtct | tcctgttccc | cccaaaaccc | aaggacactc | tcatgatctc | ccggaccct | 780 |
| gaggtcacgt | gcgtggtggt | ggacgtgagc | caggaagacc | ccgaggtcca | gttcaactgg | 840 |
| tacgtggatg | gcgtggaggt | gcataatgcc | aagacaaagc | cgcgggagga | gcagttcaac | 900 |
| agcacgtacc | gtgtggtcag | cgtcctcacc | gtcctgcacc | aggactggct | gaacggcaag | 960 |
| gagtacaagt | gcaaggtctc | caacaaaggc | ctcccgtcct | ccatcgagaa | aaccatctcc | 1020 |
| aaagccaaag | gcagccccg | agagccacag | gtgtacaccc | tgcccccatc | ccaggaggag | 1080 |
| atgaccaaga | accaggtcag | cctgacctgc | ctggtcaaag | gcttctaccc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctac | agcaggctaa | ccgtggacaa | gagcaggtgg | 1260 |
| caggagggga | atgtcttctc | atgctccgtg | atgcatgagg | ctctgcacaa | ccactacaca | 1320 |
| cagaagagcc | tctccctgtc | tctgggtaaa | | | | 1350 |

<210> SEQ ID NO 686
<211> LENGTH: 639
<212> TYPE: DNA
<213> ORGANISM: Artificial Sequence
<220> FEATURE:
<223> OTHER INFORMATION: Synthetic sequence

<400> SEQUENCE: 686

| | | | | | |
|---|---|---|---|---|---|
| gatatccagt | tgacccagtc | cccgagttcc | ctgtccgcct | ctgtgggcga | tcgggtcacc | 60 |
| atcacctgcc | gtgcctctca | gggtattagc | tctgtcctgg | cttggtatca | acagaaacca | 120 |
| ggaaaagctc | cgaagcttct | gatctacgac | gcctcttctc | tggaatctgg | tgtgccatct | 180 |
| cgcttctctg | gatccggttc | cgggacggat | ttcactctga | ccatcagcag | tctgcagccg | 240 |
| gaagacttcg | caacttatta | ctgccagcag | ggctactccc | tctggacctt | cggacagggt | 300 |
| accaaggtgg | agatcaaacg | aaccgtggcc | gctcccctccg | tcttcatttt | tcccccttct | 360 |
| gacgaacagc | tgaagagtgg | gacagccagc | gtggtctgtc | tgctgaacaa | tttctaccct | 420 |

```
agagaggcaa aagtgcagtg gaaggtcgat aacgccctgc agagcggcaa ttcccaggag    480
tctgtgactg aacaggacag taaagattca acctatagcc tgtcctctac actgactctg    540
tccaaggctg attacgaaaa gcataaagtc tatgcatgtg aggtcaccca tcaggggctg    600
tccagtccag tcacaaagtc attcaatagg ggggagtgt                          639

<210> SEQ ID NO 687
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 687
gaggttcagc tggtggagtc tggcggtggc ctggtgcagc cagggggctc actccgtttg     60
tcctgtgcag cttccggata ctctatcacc tctggtcact actggaactg gattcgtcag    120
gccccgggta agggcctcga gtgggtgtct ggtatctctg gtgacggttc ttctacctac    180
tacgccgact ctgtcaaggg ccgtttcact ataagtcgcg acaattcgaa aaacacactg    240
tacctacaac tgaacagctt aagagctgag gacactgccg tctattattg cgcgcgtggg    300
ggttctgacg ccgtgctcgg cgactggttc gcctactggg gtcaaggaac actagtcacc    360
gtctcctcgg cttccaccaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acgaagacct acacctgcaa cgtagatcac aagcccagca acaccaaggt ggacaagaga    660
gttgagtcca aatatggtcc cccatgccca ccatgcccag cacctgagtt cctggggggga    720 ccatcagtct tcctgttccc cccaaaaccc aaggacactc tcatgatctc ccggacccct    780
gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc   1020
aaagccaaag ggcagccccg agagccacag gtgtacaccc tgcccccatc ccaggaggag   1080
atgaccaaga accaggtcag cctgacctgc ctggtcaaag gcttctaccc cagcgacatc   1140
gccgtggagt gggagagcaa tgggcagccg gagaacaact acaagaccac gcctcccgtg   1200
ctggactccg acggctcctt cttcctctac agcaggctaa ccgtggacaa gagcaggtgg   1260
caggagggga atgtcttctc atgctccgtg atgcatgagg ctctgcacaa ccactacaca   1320
cagaagagcc tctccctgtc tctgggtaaa                                   1350

<210> SEQ ID NO 688
<211> LENGTH: 639
<212> TYPE: DNA
<213> ORGANISM: Artificial Sequence
<220> FEATURE:
<223> OTHER INFORMATION: Synthetic sequence

<400> SEQUENCE: 688
gatatccagt tgacccagtc cccgagttcc ctgtccgcct ctgtgggcga tcgggtcacc     60
atcacctgcc gtgcctctca gagcatcagc agttacctgg cctggtatca acagaaacca    120
```

| | |
|---|---|
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttatta ctgccagcag ggctactcaa cctggacctt cggacagggt | 300 |
| accaaggtgg agatcaaacg aaccgtggcc gctcccctccg tcttcatttt tcccccttct | 360 |
| gacgaacagc tgaagagtgg acagccagc gtggtctgtc tgctgaacaa tttctaccct | 420 |
| agagaggcaa aagtgcagtg gaaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcagggctg | 600 |
| tccagtccag tcacaaagtc attcaatagg ggggagtgt | 639 |

<210> SEQ ID NO 689
<211> LENGTH: 1353
<212> TYPE: DNA
<213> ORGANISM: Artificial Sequence
<220> FEATURE:
<223> OTHER INFORMATION: Synthetic sequence
<400> SEQUENCE: 689

| | |
|---|---|
| gaggttcagc tggtggagtc tggcggtggc ctggtgcagc caggggggctc actccgtttg | 60 |
| tcctgtgcag cttccggatt ctctctgtct accagcggtg tgggtgtggg ctggattcgt | 120 |
| caggccccgg gtaagggcct cgagtgggtg tctggtatct ctggtgccgg tgattctacc | 180 |
| tactacgccg actctgtcaa gggccgtttc actataagtc gcgacaattc gaaaaacaca | 240 |
| ctgtacctac aactgaacag cttaagagct gaggacactg ccgtctatta ttgcgcgcgt | 300 |
| gagggttctg acaccgtgct cggcgactgg ttcgcctact ggggtcaagg aacactagtc | 360 |
| accgtctcct cggcttccac caagggccca tcggtcttcc ccctggcgcc ctgctccagg | 420 |
| agcacctccg agagcacagc cgccctgggc tgcctggtca aggactactt ccccgaaccg | 480 |
| gtgacggtgt cgtggaactc aggcgccctg accagcggcg tgcacacctt cccggctgtc | 540 |
| ctacagtcct caggactcta ctccctcagc agcgtggtga ccgtgccctc cagcagcttg | 600 |
| ggcacgaaga cctacacctg caacgtagat cacaagccca gcaacaccaa ggtggacaag | 660 |
| agagttgagt ccaaatatgg tccccccatgc ccaccatgcc cagcacctga gttcctgggg | 720 |
| ggaccatcag tcttcctgtt ccccccaaaa cccaaggaca ctctcatgat ctcccggacc | 780 |
| cctgaggtca cgtgcgtggt ggtggacgtg agccaggaag accccgaggt ccagttcaac | 840 |
| tggtacgtgg atggcgtgga ggtgcataat gccaagacaa agccgcggga ggagcagttc | 900 |
| aacagcacgt accgtgtggt cagcgtcctc accgtcctgc accaggactg gctgaacggc | 960 |
| aaggagtaca agtgcaaggt ctccaacaaa ggcctcccgt cctccatcga gaaaaccatc | 1020 |
| tccaaagcca aagggcagcc ccgagagcca caggtgtaca ccctgccccc atcccaggag | 1080 |
| gagatgacca agaaccaggt cagcctgacc tgcctggtca aaggcttcta ccccagcgac | 1140 |
| atcgccgtgg agtgggagag caatgggcag ccggagaaca actacaagac cacgcctccc | 1200 |
| gtgctggact ccgacggctc cttcttcctc tacagcaggc taaccgtgga caagagcagg | 1260 |
| tggcaggagg ggaatgtctt ctcatgctcc gtgatgcatg aggctctgca caaccactac | 1320 |
| acacagaaga gcctctcccct gtctctgggt aaa | 1353 |

<210> SEQ ID NO 690
<211> LENGTH: 639
<212> TYPE: DNA
<213> ORGANISM: Artificial Sequence
<220> FEATURE:
<223> OTHER INFORMATION: Synthetic sequence

<400> SEQUENCE: 690

```
gatatccagt tgacccagtc cccgagttcc ctgtccgcct ctgtgggcga tcgggtcacc      60
atcacctgcc gtgcctctca ggatattcgc tcttacctgg cttggtatca acagaaacca     120
ggaaaagctc cgaagcttct gatctacgac gcctctaacc gtgccaccgg tatcccatct     180
cgcttctctg gatccggttc cgggacggat ttcactctga ccatcagcag tctgcagccg     240
gaagacttcg caacttatta ctgccagcag ggctactcca tctggacctt cggacagggt     300
accaaggtgg agatcaaacg aaccgtggcc gctcccctcg tcttcatttt tccccttct     360
gacgaacagc tgaagagtgg acagccagc gtggtctgtc tgctgaacaa tttctaccct     420
agagaggcaa aagtgcagtg gaaggtcgat aacgccctgc agagcggcaa ttcccaggag     480
tctgtgactg aacaggacag taaagattca acctatagcc tgtcctctac actgactctg     540
tccaaggcta ttacgaaaaa gcataaagtc tatgcatgtg aggtcaccca tcagggctg     600
tccagtccag tcacaaagtc attcaatagg ggggagtgt                            639
```

<210> SEQ ID NO 691
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 691

```
gaggttcagc tggtggagtc tggcggtggc ctggtgcagc cagggggctc actccgtttg      60
tcctgtgcag cttccggata ctctatctcc tctggtcacc actgggcctg gattcgtcag     120
gccccgggta agggcctcga gtgggtgtct gttatctctg gttccggttc ttctacctac     180
tacgccgact ctgtcaaggg ccgtttcact ataagtcgcg acaattcgaa aaacacactg     240
tacctacaac tgaacagctt aagagctgag gacactgccg tctattattg cgcgcgtgag     300
ggttctgaca ccgtgctcgg cgactggttc gcctactggg gtcaaggaac actagtcacc     360
gtctcctcgg cttccaccaa gggcccatcg gtcttcccc tggcgccctg ctccaggagc     420
acctccgaga gcacagccgc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acgaagacct acacctgcaa cgtagatcac aagcccagca acaccaaggt ggacaagaga     660
gttgagtcca aatatggtcc cccatgccca ccatgcccag cacctgagtt cctggggga     720
ccatcagtct tcctgttccc cccaaaaccc aaggacactc tcatgatctc ccggacccct     780
gaggtcacgt gcgtggtggt ggacgtgagc caggaagacc ccgaggtcca gttcaactgg     840
tacgtggatg gcgtggaggt gcataatgcc aagacaaagc cgcgggagga gcagttcaac     900
agcacgtacc gtgtggtcag cgtcctcacc gtcctgcacc aggactggct gaacggcaag     960
gagtacaagt gcaaggtctc caacaaaggc ctcccgtcct ccatcgagaa aaccatctcc    1020
aaagccaaag gcagccccg agagccacag gtgtacaccc tgcccccatc ccaggaggag    1080
atgaccaaga accaggtcag cctgacctgc ctggtcaaag gcttctaccc cagcgacatc    1140
gccgtggagt gggagagcaa tgggcagccg gagaacaact acaagaccac gcctcccgtg    1200
ctggactccg acggctcctt cttcctctac agcaggctaa ccgtggacaa gagcaggtgg    1260
```

| | |
|---|---|
| caggagggga atgtcttctc atgctccgtg atgcatgagg ctctgcacaa ccactacaca | 1320 |
| cagaagagcc tctccctgtc tctgggtaaa | 1350 |

<210> SEQ ID NO 692
<211> LENGTH: 639
<212> TYPE: DNA
<213> ORGANISM: Artificial Sequence
<220> FEATURE:
<223> OTHER INFORMATION: Synthetic sequence

<400> SEQUENCE: 692

| | |
|---|---|
| gatatccagt tgacccagtc cccgagttcc ctgtccgcct ctgtgggcga tcgggtcacc | 60 |
| atcacctgcc gtgcctctca gggcatcagc agttacctgg cctggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttatta ctgccagcag ggctactcca cctggacctt cggacagggt | 300 |
| accaaggtgg agatcaaacg aaccgtggcc gctccctccg tcttcatttt tcccccttct | 360 |
| gacgaacagc tgaagagtgg acagccagc gtggtctgtc tgctgaacaa tttctaccct | 420 |
| agagaggcaa aagtgcagtg gaaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcagggctg | 600 |
| tccagtccag tcacaaagtc attcaatagg ggggagtgt | 639 |

<210> SEQ ID NO 693
<211> LENGTH: 1353
<212> TYPE: DNA
<213> ORGANISM: Artificial Sequence
<220> FEATURE:
<223> OTHER INFORMATION: Synthetic sequence

<400> SEQUENCE: 693

| | |
|---|---|
| gaggttcagc tggtggagtc tggcggtggc ctggtgcagc caggggctc actccgtttg | 60 |
| tcctgtgcag cttccggatt ctctctgtct accggcggtg tgggtgtggc ctggattcgt | 120 |
| caggccccgg gtaagggcct cgagtgggtg tcttccatct ctggttacgg ttctactacc | 180 |
| tactacgccg actctgtcaa gggccgtttc actataagtc gcgacaattc gaaaaacaca | 240 |
| ctgtacctac aactgaacag cttaagagct gaggacactg ccgtctatta ttgcgcgcgt | 300 |
| gagggttctg acgccgtgct cggcgactgg ttcggctact ggggtcaagg aacactagtc | 360 |
| accgtctcct cggcttccac caagggccca tcggtcttcc cctggcgcc ctgctccagg | 420 |
| agcacctccg agagcacagc cgccctgggc tgcctggtca aggactactt ccccgaaccg | 480 |
| gtgacggtgt cgtggaactc aggcgccctg accagcggcg tgcacacctt cccggctgtc | 540 |
| ctacagtcct caggactcta ctccctcagc agcgtggtga ccgtgccctc agcagcttg | 600 |
| ggcacgaaga cctacacctg caacgtagat cacaagccca gcaacaccaa ggtggacaag | 660 |
| agagttgagt ccaaatatgg tccccccatgc ccaccatgcc cagcacctga gttcctgggg | 720 |
| ggaccatcag tcttcctgtt ccccccaaaa cccaaggaca ctctcatgat ctcccggacc | 780 |
| cctgaggtca cgtgcgtggt ggtggacgtg agccaggaag accccgaggt ccagttcaac | 840 |
| tggtacgtgg atggcgtgga ggtgcataat gccaagacaa agccgcggga ggagcagttc | 900 |
| aacagcacgt accgtgtggt cagcgtcctc accgtcctgc accaggactg gctgaacggc | 960 |
| aaggagtaca agtgcaaggt ctccaacaaa ggcctcccgt cctccatcga gaaaaccatc | 1020 |

| | |
|---|---|
| tccaaagcca aagggcagcc ccgagagcca caggtgtaca ccctgccccc atcccaggag | 1080 |
| gagatgacca agaaccaggt cagcctgacc tgcctggtca aaggcttcta ccccagcgac | 1140 |
| atcgccgtgg agtgggagag caatgggcag ccggagaaca actacaagac cacgcctccc | 1200 |
| gtgctggact ccgacggctc cttcttcctc tacagcaggc taaccgtgga caagagcagg | 1260 |
| tggcaggagg ggaatgtctt ctcatgctcc gtgatgcatg aggctctgca caaccactac | 1320 |
| acacagaaga gcctctccct gtctctgggt aaa | 1353 |

<210> SEQ ID NO 694
<211> LENGTH: 639
<212> TYPE: DNA
<213> ORGANISM: Artificial Sequence
<220> FEATURE:
<223> OTHER INFORMATION: Synthetic sequence

<400> SEQUENCE: 694

| | |
|---|---|
| gatatccagt tgacccagtc cccgagttcc ctgtccgcct ctgtgggcga tcgggtcacc | 60 |
| atcacctgcc aggcctctca ggacatcacc acgtacctgg cctggtatca acagaaacca | 120 |
| ggaaaagctc cgaagcttct gatctacgac gcctctaacc gtgccaccgg tatcccatct | 180 |
| cgcttctctg gatccggttc cgggacggat ttcactctga ccatcagcag tctgcagccg | 240 |
| gaagacttcg caacttatta ctgccagcag ggctactacc tctggacctt cggacagggt | 300 |
| accaaggtgg agatcaaacg aaccgtggcc gctccctccg tcttcatttt tccccttct | 360 |
| gacgaacagc tgaagagtgg acagccagc gtggtctgtc tgctgaacaa tttctaccct | 420 |
| agagaggcaa aagtgcagtg aaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcaggggctg | 600 |
| tccagtccag tcacaaagtc attcaatagg ggggagtgt | 639 |

<210> SEQ ID NO 695
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 695

| | |
|---|---|
| gaggttcagc tggtggagtc tggcggtggc ctggtgcagc caggggggctc actccgtttg | 60 |
| tcctgtgcag cttccggatt ctctctgtct accggcggtg tggctgtggg ctggattcgt | 120 |
| caggccccgg gtaagggcct cgagtggctg gccctgatcg actgggccgg tgacaagtcc | 180 |
| tactctacct ctctgaagtc tcgtctgact ataagtcgcg acaattcgaa aaacacactg | 240 |
| tacctacaac tgaacagctt aagagctgag gacactgccg tctattattg cgcgcgtggg | 300 |
| ggttctgaca ccgtgctcgg cgactggttc gcctactggg gtcaaggaac actagtcacc | 360 |
| gtctcctcgg cttccaccaa gggcccatcg gtcttccccc tggcgccctg ctccaggagc | 420 |
| acctccgaga gcacagccgc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acgaagacct acacctgcaa cgtagatcac aagcccagca acaccaaggt ggacaagaga | 660 |
| gttgagtcca aatatggtcc cccatgccca ccatgcccag cacctgagtt cctggggga | 720 |

| | |
|---|---|
| ccatcagtct tcctgttccc cccaaaaccc aaggacactc tcatgatctc ccggaccct | 780 |
| gaggtcacgt gcgtggtggt ggacgtgagc caggaagacc ccgaggtcca gttcaactgg | 840 |
| tacgtggatg gcgtggaggt gcataatgcc aagacaaagc cgcgggagga gcagttcaac | 900 |
| agcacgtacc gtgtggtcag cgtcctcacc gtcctgcacc aggactggct gaacggcaag | 960 |
| gagtacaagt gcaaggtctc caacaaaggc ctcccgtcct ccatcgagaa aaccatctcc | 1020 |
| aaagccaaag gcagccccg agagccacag gtgtacaccc tgcccccatc ccaggaggag | 1080 |
| atgaccaaga accaggtcag cctgacctgc ctggtcaaag gcttctaccc cagcgacatc | 1140 |
| gccgtggagt gggagagcaa tgggcagccg gagaacaact acaagaccac gcctcccgtg | 1200 |
| ctggactccg acggctcctt cttcctctac agcaggctaa ccgtggacaa gagcaggtgg | 1260 |
| caggagggga atgtcttctc atgctccgtg atgcatgagg ctctgcacaa ccactacaca | 1320 |
| cagaagagcc tctccctgtc tctgggtaaa | 1350 |

<210> SEQ ID NO 696
<211> LENGTH: 639
<212> TYPE: DNA
<213> ORGANISM: Artificial Sequence
<220> FEATURE:
<223> OTHER INFORMATION: Synthetic sequence

<400> SEQUENCE: 696

| | |
|---|---|
| gatatccagt tgacccagtc cccgagttcc ctgtccgcct ctgtgggcga tcgggtcacc | 60 |
| atcacctgcc gtgcctctca gggcgtcagc ccttacctgg cctggtatca acagaaacca | 120 |
| ggaaaagctc cgaagcttct gatctacgac gcctctaacc gtgccaccgg tatcccatct | 180 |
| cgcttctctg gatccggttc cgggacggat ttcactctga ccatcagcag tctgcagccg | 240 |
| gaagacttcg caacttatta ctgccagcag ggctactcca cctggacctt cggacagggt | 300 |
| accaaggtgg agatcaaacg aaccgtggcc gctccctccg tcttcatttt tccccttct | 360 |
| gacgaacagc tgaagagtgg acagccagc gtggtctgtc tgctgaacaa tttctaccct | 420 |
| agagaggcaa aagtgcagtg gaaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcagggctg | 600 |
| tccagtccag tcacaaagtc attcaatagg ggggagtgt | 639 |

<210> SEQ ID NO 697
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 697

| | |
|---|---|
| gaggttcagc tggtggagtc tggcggtggc ctggtgcagc caggggctc actccgtttg | 60 |
| tcctgtgcag cttccggata tctctatctc ctctggttacc actgggcctg gattcgtcag | 120 |
| gccccgggta agggcctcga gtgggtgtct tccatctctg gtgacggttc ttctacctac | 180 |
| tacgccgact ctgtcaaggg ccgtttcact ataagtcgcg acaattcgaa aaacacactg | 240 |
| tacctacaac tgaacagctt aagagctgag gacactgccg tctattattg cgcgcgtgaa | 300 |
| ggttcagacg ctgtgaccgg cgactggttc gcctactggg gtcaaggaac actagtcacc | 360 |
| gtctcctcgg cttccaccaa gggcccatcg gtcttccccc tggcgccctg ctccaggagc | 420 |
| acctccgaga gcacagccgc cctgggctgc ctggtcaagg actacttccc cgaaccggtg | 480 |

```
acggtgtcgt ggaactcagg cgccctgacc agcggcgtgc acaccttccc ggctgtccta    540
cagtcctcag gactctactc cctcagcagc gtggtgaccg tgcccccag cagcttgggc     600 acgaagacct acacctgcaa cgtagatcac aagcccagca acaccaaggt ggacaagaga    660
gttgagtcca aatatggtcc cccatgccca ccatgcccag cacctgagtt cctgggggga    720
ccatcagtct tcctgttccc cccaaaaccc aaggacactc tcatgatctc ccggacccct    780
gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc    1020
aaagccaaag gcagccccg agagccacag gtgtacaccc tgcccccatc ccaggaggag    1080
atgaccaaga accaggtcag cctgacctgc ctggtcaaag gcttctaccc cagcgacatc    1140
gccgtggagt gggagagcaa tgggcagccg gagaacaact acaagaccac gcctcccgtg    1200
ctggactccg acggctcctt cttcctctac agcaggctaa ccgtggacaa gagcaggtgg    1260
caggagggga atgtcttctc atgctccgtg atgcatgagg ctctgcacaa ccactacaca    1320
cagaagagcc tctccctgtc tctgggtaaa                                    1350
```

<210> SEQ ID NO 698
<211> LENGTH: 639
<212> TYPE: DNA
<213> ORGANISM: Artificial Sequence
<220> FEATURE:
<223> OTHER INFORMATION: Synthetic sequence

<400> SEQUENCE: 698

```
gatatccagt tgacccagtc cccgagttcc ctgtccgcct ctgtgggcga tcgggtcacc     60
atcacctgcc gtgcctctca gggcgtcggc acttacctgg cctggtatca acagaaacca    120
ggaaaagctc cgaagcttct gatctacgac gcctcttctc tggaatctgg tgtgccatct    180
cgcttctctg gatccggttc cgggacggat ttcactctga ccatcagcag tctgcagccg    240
gaagacttcg caacttatta ctgccagcag ggctactcac tctggacctt cggacagggt    300
accaaggtgg agatcaaacg aaccgtggcc gctccctccg tcttcatttt tccccctcct    360
gacgaacagc tgaagagtgg acagccagc gtggtctgtc tgctgaacaa tttctaccct    420
agagaggcaa aagtgcagtg gaaggtcgat aacgccctgc agagcggcaa ttcccaggag    480
tctgtgactg aacaggacag taaagattca acctatagcc tgtcctctac actgactctg    540
tccaaggctg attacgaaaa gcataaagtc tatgcatgtg aggtcaccca tcagggctg    600 tccagtccag tcacaaagtc attcaatagg ggggagtgt                            639
```

<210> SEQ ID NO 699
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 699

```
gaggttcagc tggtggagtc tggcggtggc ctggtgcagc caggggctc actccgtttg     60 tcctgtgcag cttccggatt ctctctgtct accagcggtg tggctgtggg ctggattcgt    120
caggccccgg gtaagggcct cgagtggctg gccctgatcg actgggacga tgacaagtac    180
```

```
tactctacct ctctgaagtc tcgtctgact ataagtcgcg acaattcgaa aaacacactg    240
tacctacaac tgaacagctt aagagctgag gacactgccg tctattattg cgcgcgtgag    300
ggttctaccg ccgtggccgg cgactggttc gcctactggg gtcaaggaac actagtcacc    360
gtctcctcgg cttccaccaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acgaagacct acacctgcaa cgtagatcac aagcccagca acaccaaggt ggacaagaga    660
gttgagtcca aatatggtcc cccatgccca ccatgcccag cacctgagtt cctgggggga    720
ccatcagtct tcctgttccc cccaaaaccc aaggacactc tcatgatctc ccggacccct    780
gaggtcacgt gcgtggtggt ggacgtgagc caggaagacc ccgaggtcca gttcaactgg    840
tacgtggatg gcgtggaggt gcataatgcc aagacaaagc cgcgggagga gcagttcaac    900
agcacgtacc gtgtggtcag cgtcctcacc gtcctgcacc aggactggct gaacggcaag    960
gagtacaagt gcaaggtctc caacaaaggc ctcccgtcct ccatcgagaa aaccatctcc   1020
aaagccaaag gcagccccg agagccacag gtgtacaccc tgcccccatc ccaggaggag   1080
atgaccaaga accaggtcag cctgacctgc ctggtcaaag gcttctaccc cagcgacatc   1140
gccgtggagt gggagagcaa tgggcagccg gagaacaact acaagaccac gcctcccgtg   1200
ctggactccg acggctcctt cttcctctac agcaggctaa ccgtggacaa gagcaggtgg   1260
caggagggga atgtcttctc atgctccgtg atgcatgagg ctctgcacaa ccactacaca   1320
cagaagagcc tctccctgtc tctgggtaaa                                   1350

<210> SEQ ID NO 700
<211> LENGTH: 639
<212> TYPE: DNA
<213> ORGANISM: Artificial Sequence
<220> FEATURE:
<223> OTHER INFORMATION: Synthetic sequence

<400> SEQUENCE: 700
gatatccagt tgacccagtc cccgagttcc ctgtccgcct ctgtgggcga tcgggtcacc     60
atcacctgcc aggcctctca ggacatccgc acgttcctgg cctggtatca acagaaacca    120
ggaaaagctc cgaagcttct gatctacgac gcctctaacc gtgccaccgg tatcccatct    180
cgcttctctg gatccggttc cgggacggat ttcactctga ccatcagcag tctgcagccg    240
gaagacttcg caacttatta ctgccagcag ggctactcca cctggacctt cggacagggt    300
accaaggtgg agatcaaacg aaccgtggcc gctcccctccg tcttcatttt tccccctctct    360 gacgaacagc tgaagagtgg aacagccagc gtggtctgtc tgctgaacaa tttctacccc    420
agagaggcaa agtcagtg gaaggtcgat aacgccctgc agagcggcaa ttcccaggag    480
tctgtgactg aacaggacag taaagattca acctatagcc tgtcctctac actgactctg    540
tccaaggctg attacgaaaa gcataaagtc tatgcatgtg aggtcaccca tcaggggctg    600
tccagtccag tcacaaagtc attcaatagg ggggagtgt                           639

<210> SEQ ID NO 701
<211> LENGTH: 1350
<212> TYPE: DNA
<213> ORGANISM: Artificial Sequence
<220> FEATURE:
<223> OTHER INFORMATION: Synthetic sequence
```

<400> SEQUENCE: 701

| | | | | | |
|---|---|---|---|---|---|
| gaggttcagc | tggtggagtc | tggcggtggc | ctggtgcagc | caggggggctc | actccgtttg | 60 |
| tcctgtgcag | cttccggatt | ctctctgtct | accggcggtg | tggctgtggg | ctggattcgt | 120 |
| caggccccgg | gtaagggcct | cgagtggctg | gccctgatcg | actgggccgg | tgacaagtcc | 180 |
| tactctacct | ctctgaagtc | tcgtctgact | ataagtcgcg | acaattcgaa | aaacacactg | 240 |
| tacctacaac | tgaacagctt | aagagctgag | gacactgccg | tctattattg | cgcgcgtgaa | 300 |
| ggtgaagacg | ctgtgaccgg | cgactggttc | gcctactggg | gtcaaggaac | actagtcacc | 360 |
| gtctcctcgg | cttccaccaa | gggcccatcg | gtcttcccccc | tggcgccctg | ctccaggagc | 420 |
| acctccgaga | gcacagccgc | cctgggctgc | ctggtcaagg | actacttccc | cgaaccggtg | 480 |
| acggtgtcgt | ggaactcagg | cgccctgacc | agcggcgtgc | acaccttccc | ggctgtccta | 540 |
| cagtcctcag | gactctactc | cctcagcagc | gtggtgaccg | tgccctccag | cagcttgggc | 600 |
| acgaagacct | acacctgcaa | cgtagatcac | aagcccagca | acaccaaggt | ggacaagaga | 660 |
| gttgagtcca | aatatggtcc | cccatgccca | ccatgcccag | cacctgagtt | cctgggggga | 720 |
| ccatcagtct | tcctgttccc | cccaaaaccc | aaggacactc | tcatgatctc | ccggacccct | 780 |
| gaggtcacgt | gcgtggtggt | ggacgtgagc | caggaagacc | ccgaggtcca | gttcaactgg | 840 |
| tacgtggatg | gcgtggaggt | gcataatgcc | aagacaaagc | cgcgggagga | gcagttcaac | 900 |
| agcacgtacc | gtgtggtcag | cgtcctcacc | gtcctgcacc | aggactggct | gaacggcaag | 960 |
| gagtacaagt | gcaaggtctc | caacaaaggc | ctcccgtcct | ccatcgagaa | aaccatctcc | 1020 |
| aaagccaaag | ggcagccccg | agagccacag | gtgtacaccc | tgcccccatc | ccaggaggag | 1080 |
| atgaccaaga | accaggtcag | cctgacctgc | ctggtcaaag | gcttctaccc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctac | agcaggctaa | ccgtggacaa | gagcaggtgg | 1260 |
| caggagggga | atgtcttctc | atgctccgtg | atgcatgagg | ctctgcacaa | ccactacaca | 1320 |
| cagaagagcc | tctccctgtc | tctgggtaaa | | | | 1350 |

<210> SEQ ID NO 702
<211> LENGTH: 639
<212> TYPE: DNA
<213> ORGANISM: Artificial Sequence
<220> FEATURE:
<223> OTHER INFORMATION: Synthetic sequence

<400> SEQUENCE: 702

| | | | | | |
|---|---|---|---|---|---|
| gatatccagt | tgacccagtc | cccgagttcc | ctgtccgcct | ctgtgggcga | tcgggtcacc | 60 |
| atcacctgcc | aggcctctca | ggacatccgc | acgtacctgg | cctggtatca | acagaaacca | 120 |
| ggaaaagctc | cgaagcttct | gatctacgac | gcctctaacc | gtgccaccgg | tatcccatct | 180 |
| cgcttctctg | gatccggttc | cgggacggat | ttcactctga | ccatcagcag | tctgcagccg | 240 |
| gaagacttcg | caacttatta | ctgccagcag | ggctactcca | tctggacctt | cggacagggt | 300 |
| accaaggtgg | agatcaaacg | aaccgtggcc | gctcccctccg | tcttcatttt | tccccccttct | 360 |
| gacgaacagc | tgaagagtgg | cacagccagc | gtggtctgtc | tgctgaacaa | tttctaccct | 420 |
| agagaggcaa | aagtgcagtg | gaaggtcgat | aacgccctgc | agagcggcaa | ttcccaggag | 480 |
| tctgtgactg | aacaggacag | taaagattca | acctatagcc | tgtcctctac | actgactctg | 540 |
| tccaaggctg | attacgaaaa | gcataaagtc | tatgcatgtg | aggtcaccca | tcagggggctg | 600 |

```
tccagtccag tcacaaagtc attcaatagg ggggagtgt                              639
```

<210> SEQ ID NO 703
<211> LENGTH: 1341
<212> TYPE: DNA
<213> ORGANISM: Artificial Sequence
<220> FEATURE:
<223> OTHER INFORMATION: Synthetic sequence

<400> SEQUENCE: 703

```
gaggttcagc tggtggagtc tggcggtggc ctggtgcagc caggggggctc actccgtttg      60
tcctgtgcag cttccggatt caccttctcc agctactgga ttcactgggt gcgtcaggcc     120
ccgggtaagg gcctcgagtg ggtgtctgtt atctctggtg acggtgatac tacctactac     180
gccgactctg tcaagggccg tttcactata agtcgcgaca attcgaaaaa cacactgtac     240
ctacaactga acagcttaag agctgaggac actgccgtct attattgcgc gcgttcccgt     300
ggtcttgtgc tagacgcctt cgactactgg ggtcaaggaa cactagtcac cgtctcctcg     360
gcttccacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accatgccca gcacctgagt tcctgggggg accatcagtc     720
ttcctgttcc cccaaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa a                                              1341
```

<210> SEQ ID NO 704
<211> LENGTH: 648
<212> TYPE: DNA
<213> ORGANISM: Artificial Sequence
<220> FEATURE:
<223> OTHER INFORMATION: Synthetic sequence

<400> SEQUENCE: 704

```
gatatccagt tgacccagtc cccgagttcc ctgtccgcct ctgtgggcga tcgggtcacc      60
atcacctgcc gtgcctctca gtctgtgagc ggccgtttcc tggcctggta tcaacagaaa     120
ccaggaaaag ctccgaagct tctgatctac gacgcctctt ctctggaatc tggtgtgcca     180
tctcgcttct ctggatccgg ttccgggacg gatttcactc tgaccatcag cagtctgcag     240
ccggaagact tcgcaactta ttactgccag cagtacgact actggccacc ttacaccttc     300
ggacagggta ccaaggtgga gatcaaacga accgtggccg ctcccctccgt cttcatttt     360
```

```
cccccttctg acgaacagct gaagagtggg acagccagcg tggtctgtct gctgaacaat      420
ttctacccta gagaggcaaa agtgcagtgg aaggtcgata acgccctgca gagcggcaat      480
tcccaggagt ctgtgactga acaggacagt aaagattcaa cctatagcct gtcctctaca      540
ctgactctgt ccaaggctga ttacgaaaag cataaagtct atgcatgtga ggtcacccat      600
caggggctgt ccagtccagt cacaaagtca ttcaataggg gggagtgt                   648
```

<210> SEQ ID NO 705
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 705

```
gaggttcagc tggtggagtc tggcggtggc ctggtgcagc caggggggctc actccgtttg      60 tcctgtgcag cttccggatt ctctctgtct accggcggtg tgggtgtggg ctggattcgt      120
caggccccgg gtaagggcct cgagtggctg gccctgatcg actgggccga tgacaagtac      180
tactctccct ctctgaagtc tcgtctgact ataagtcgcg acaattcgaa aaacacactg      240
tacctacaac tgaacagctt aagagctgag acactgccg tctattattg cgcgcgtggg      300
ggttctgaca ccgtgatcgg cgactggttc gcctactggg gtcaaggaac actagtcacc      360
gtctcctcgg cttccaccaa gggcccatcg gtcttccccc tggcgccctg ctccaggagc      420
acctccgaga gcacagccgc cctgggctgc ctggtcaagg actacttccc cgaaccggtg      480
acggtgtcgt ggaactcagg cgccctgacc agcggcgtgc acaccttccc ggctgtccta      540
cagtcctcag gactctactc cctcagcagc gtggtgaccg tgccctccag cagcttgggc      600
acgaagacct acacctgcaa cgtagatcac aagcccagca caccaaggt ggacaagaga      660 gttgagtcca aatatggtcc cccatgccca ccatgcccag cacctgagtt cctgggggga      720
ccatcagtct tcctgttccc cccaaaaccc aaggacactc tcatgatctc ccggacccct      780
gaggtcacgt gcgtggtggt ggacgtgagc caggaagacc ccgaggtcca gttcaactgg      840
tacgtggatg gcgtggaggt gcataatgcc aagacaaagc cgcgggagga gcagttcaac      900
agcacgtacc gtgtggtcag cgtcctcacc gtcctgcacc aggactggct gaacggcaag      960
gagtacaagt gcaaggtctc caacaaaggc ctcccgtcct ccatcgagaa aaccatctcc      1020
aaagccaaag gcagccccg agagccacag gtgtacaccc tgcccccatc ccaggaggag      1080
atgaccaaga accaggtcag cctgacctgc ctggtcaaag gcttctaccc cagcgacatc      1140
gccgtggagt gggagagcaa tgggcagccg gagaacaact acaagaccac gcctcccgtg      1200
ctggactccg acggctcctt cttcctctac agcaggctaa ccgtggacaa gagcaggtgg      1260 caggaggga atgtcttctc atgctccgtg atgcatgagg ctctgcacaa ccactacaca      1320
cagaagagcc tctccctgtc tctgggtaaa                                      1350
```

<210> SEQ ID NO 706
<211> LENGTH: 639
<212> TYPE: DNA
<213> ORGANISM: Artificial Sequence
<220> FEATURE:
<223> OTHER INFORMATION: Synthetic sequence

<400> SEQUENCE: 706

```
gatatccagt tgacccagtc cccgagttcc ctgtccgcct ctgtgggcga tcgggtcacc      60
```

-continued

| | |
|---|---:|
| atcacctgcc gtgcctctca gagcatcggc agttacctgg cctggtatca acagaaacca | 120 |
| ggaaaagctc cgaagcttct gatctacgac gcctctaacc tggaaaccgg tgtgccatct | 180 |
| cgcttctctg gatccggttc cgggacggat ttcactctga ccatcagcag tctgcagccg | 240 |
| gaagacttcg caacttatta ctgccagcag ggctactacc tctggacctt cggacagggt | 300 |
| accaaggtgg agatcaaacg aaccgtggcc gctccctccg tcttcatttt tccccttct | 360 |
| gacgaacagc tgaagagtgg acagccagc gtggtctgtc tgctgaacaa tttctaccct | 420 |
| agagaggcaa aagtgcagtg aaggtcgat aacgccctgc agagcggcaa ttcccaggag | 480 |
| tctgtgactg aacaggacag taaagattca acctatagcc tgtcctctac actgactctg | 540 |
| tccaaggctg attacgaaaa gcataaagtc tatgcatgtg aggtcaccca tcaggggctg | 600 |
| tccagtccag tcacaaagtc attcaatagg ggggagtgt | 639 |

<210> SEQ ID NO 707
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 707

| | |
|---|---:|
| gaggttcagc tggtggagtc tggcggtggc ctggtgcagc caggggctc actccgtttg | 60 |
| tcctgtgcag cttccggata ctctatcacc tctggttacc actggagctg gattcgtcag | 120 |
| gccccgggta agggcctcga gtgggtgtct tccatctctg gttacggtga tactacctac | 180 |
| tacgccgact ctgtcaaggg ccgtttcact ataagtcgcg acaattcgaa aaacacactg | 240 |
| tacctacaac tgaacagctt aagagctgag gacactgccg tctattattg cgcgcgtgag | 300 |
| ggttctgaca ccgtgctcgg cgactggttc gcctactggg gtcaaggaac actagtcacc | 360 |
| gtctcctcgg cttccaccaa gggcccatcg gtcttccccc tggcgccctg ctccaggagc | 420 |
| acctccgaga gcacagccgc cctgggctgc ctggtcaagg actacttccc cgaaccggtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acgaagacct acacctgcaa cgtagatcac aagcccagca acaccaaggt ggacaagaga | 660 |
| gttgagtcca aatatggtcc cccatgccca ccatgcccag cacctgagtt cctggggggga | 720 |
| ccatcagtct tcctgttccc cccaaaaccc aaggacactc tcatgatctc ccggaccct | 780 |
| gaggtcacgt gcgtggtggt ggacgtgagc caggaagacc ccgaggtcca gttcaactgg | 840 |
| tacgtggatg gcgtggaggt gcataatgcc aagacaaagc cgcgggagga gcagttcaac | 900 |
| agcacgtacc gtgtggtcag cgtcctcacc gtcctgcacc aggactggct gaacggcaag | 960 |
| gagtacaagt gcaaggtctc caacaaaggc ctcccgtcct ccatcgagaa aaccatctcc | 1020 |
| aaagccaaag gcagccccg agagccacag gtgtacaccc tgcccccatc ccaggaggag | 1080 |
| atgaccaaga accaggtcag cctgacctgc ctggtcaaag gcttctaccc cagcgacatc | 1140 |
| gccgtggagt gggagagcaa tgggcagccg gagaacaact acaagaccac gcctcccgtg | 1200 |
| ctggactccg acggctcctt cttcctctac agcaggctaa ccgtggacaa gagcaggtgg | 1260 |
| caggaggga atgtcttctc atgctccgtg atgcatgagg ctctgcacaa ccactacaca | 1320 |
| cagaagagcc tctccctgtc tctgggtaaa | 1350 |

<210> SEQ ID NO 708
<211> LENGTH: 639

```
<212> TYPE: DNA
<213> ORGANISM: Artificial Sequence
<220> FEATURE:
<223> OTHER INFORMATION: Synthetic sequence

<400> SEQUENCE: 708
gatatccagt tgacccagtc cccgagttcc ctgtccgcct ctgtgggcga tcgggtcacc      60
atcacctgcc aggcctctca ggacatccgc acgtacctgg cctggtatca acagaaacca     120
ggaaaagctc cgaagcttct gatctacgac gcctctaacc tggaaaccgg tgtgccatct     180
cgcttctctg gatccggttc cgggacggat ttcactctga ccatcagcag tctgcagccg     240
gaagacttcg caacttatta ctgccagcag ggctactcca tctggacctt cggacagggt     300
accaaggtgg agatcaaacg aaccgtggcc gctcccccg tcttcatttt tcccccttct      360
gacgaacagc tgaagagtgg gacagccagc gtggtctgtc tgctgaacaa tttctaccct     420
agagaggcaa aagtgcagtg gaaggtcgat aacgccctgc agagcggcaa ttcccaggag     480
tctgtgactg aacaggacag taaagattca acctatagcc tgtcctctac actgactctg     540
tccaaggctg attacgaaaa gcataaagtc tatgcatgtg aggtcaccca tcaggggctg     600
tccagtccag tcacaaagtc attcaatagg ggggagtgt                           639
```

```
<210> SEQ ID NO 709
<211> LENGTH: 13
<212> TYPE: PRT
<213> ORGANISM: Artificial Sequence
<220> FEATURE:
<223> OTHER INFORMATION: Synthetic sequence

<400> SEQUENCE: 709

Phe Ser Leu Ser Thr Ser Gly Val Ala Val Ser Trp Ile
1               5                  10
```

```
<210> SEQ ID NO 710
<211> LENGTH: 13
<212> TYPE: PRT
<213> ORGANISM: Artificial Sequence
<220> FEATURE:
<223> OTHER INFORMATION: Synthetic sequence

<400> SEQUENCE: 710

Phe Ser Leu Ser Thr Ser Gly Val Ala Val Gly Trp Ile
1               5                  10
```

```
<210> SEQ ID NO 711
<211> LENGTH: 13
<212> TYPE: PRT
<213> ORGANISM: Artificial Sequence
<220> FEATURE:
<223> OTHER INFORMATION: Synthetic sequence

<400> SEQUENCE: 711

Phe Ser Leu Ser Thr Ser Gly Val Gly Val Gly Trp Ile
1               5                  10
```

```
<210> SEQ ID NO 712
<211> LENGTH: 12
<212> TYPE: PRT
<213> ORGANISM: Artificial Sequence
<220> FEATURE:
<223> OTHER INFORMATION: Synthetic sequence

<400> SEQUENCE: 712

Tyr Ser Ile Thr Ser Gly His Tyr Trp Ala Trp Ile
```

```
1               5                   10
```

<210> SEQ ID NO 713
<211> LENGTH: 13
<212> TYPE: PRT
<213> ORGANISM: Artificial Sequence
<220> FEATURE:
<223> OTHER INFORMATION: Synthetic sequence

<400> SEQUENCE: 713

```
Phe Ser Leu Ser Thr Ser Gly Val Gly Val Gly Trp Ile
1               5                   10
```

<210> SEQ ID NO 714
<211> LENGTH: 13
<212> TYPE: PRT
<213> ORGANISM: Artificial Sequence
<220> FEATURE:
<223> OTHER INFORMATION: Synthetic sequence

<400> SEQUENCE: 714

```
Phe Ser Leu Ser Thr Ser Gly Val Ala Val Ala Trp Ile
1               5                   10
```

<210> SEQ ID NO 715
<211> LENGTH: 12
<212> TYPE: PRT
<213> ORGANISM: Artificial Sequence
<220> FEATURE:
<223> OTHER INFORMATION: Synthetic sequence

<400> SEQUENCE: 715

```
Tyr Ser Ile Ser Ser Gly Tyr His Trp Ala Trp Ile
1               5                   10
```

<210> SEQ ID NO 716
<211> LENGTH: 13
<212> TYPE: PRT
<213> ORGANISM: Artificial Sequence
<220> FEATURE:
<223> OTHER INFORMATION: Synthetic sequence

<400> SEQUENCE: 716

```
Phe Ser Leu Ser Thr Gly Gly Val Ala Val Gly Trp Ile
1               5                   10
```

<210> SEQ ID NO 717
<211> LENGTH: 13
<212> TYPE: PRT
<213> ORGANISM: Artificial Sequence
<220> FEATURE:
<223> OTHER INFORMATION: Synthetic sequence

<400> SEQUENCE: 717

```
Phe Ser Leu Ser Thr Gly Gly Val Gly Val Ser Trp Ile
1               5                   10
```

<210> SEQ ID NO 718
<211> LENGTH: 12
<212> TYPE: PRT
<213> ORGANISM: Artificial Sequence
<220> FEATURE:
<223> OTHER INFORMATION: Synthetic sequence

<400> SEQUENCE: 718

```
Tyr Ser Ile Ser Ser Gly Tyr Tyr Trp Asp Trp Ile
1               5                   10
```

```
<210> SEQ ID NO 719
<211> LENGTH: 12
<212> TYPE: PRT
<213> ORGANISM: Artificial Sequence
<220> FEATURE:
<223> OTHER INFORMATION: Synthetic sequence

<400> SEQUENCE: 719

Tyr Ser Ile Ser Ser Gly His Tyr Trp Gly Trp Ile
1               5                   10

<210> SEQ ID NO 720
<211> LENGTH: 11
<212> TYPE: PRT
<213> ORGANISM: Artificial Sequence
<220> FEATURE:
<223> OTHER INFORMATION: Synthetic sequence

<400> SEQUENCE: 720

Tyr Thr Phe Ser Asn Tyr Trp Ile His Trp Val
1               5                   10

<210> SEQ ID NO 721
<211> LENGTH: 13
<212> TYPE: PRT
<213> ORGANISM: Artificial Sequence
<220> FEATURE:
<223> OTHER INFORMATION: Synthetic sequence

<400> SEQUENCE: 721

Phe Ser Leu Ser Thr Ser Gly Val Gly Val Gly Trp Ile
1               5                   10

<210> SEQ ID NO 722
<211> LENGTH: 12
<212> TYPE: PRT
<213> ORGANISM: Artificial Sequence
<220> FEATURE:
<223> OTHER INFORMATION: Synthetic sequence

<400> SEQUENCE: 722

Tyr Ser Ile Thr Ser Gly His Tyr Trp Asn Trp Ile
1               5                   10

<210> SEQ ID NO 723
<211> LENGTH: 13
<212> TYPE: PRT
<213> ORGANISM: Artificial Sequence
<220> FEATURE:
<223> OTHER INFORMATION: Synthetic sequence

<400> SEQUENCE: 723

Phe Ser Leu Ser Thr Ser Gly Val Gly Val Gly Trp Ile
1               5                   10

<210> SEQ ID NO 724
<211> LENGTH: 12
<212> TYPE: PRT
<213> ORGANISM: Artificial Sequence
<220> FEATURE:
<223> OTHER INFORMATION: Synthetic sequence

<400> SEQUENCE: 724

Tyr Ser Ile Ser Ser Gly His His Trp Ala Trp Ile
1               5                   10
```

<210> SEQ ID NO 725
<211> LENGTH: 13
<212> TYPE: PRT
<213> ORGANISM: Artificial Sequence
<220> FEATURE:
<223> OTHER INFORMATION: Synthetic sequence

<400> SEQUENCE: 725

Phe Ser Leu Ser Thr Gly Gly Val Gly Val Ala Trp Ile
1               5                   10

<210> SEQ ID NO 726
<211> LENGTH: 13
<212> TYPE: PRT
<213> ORGANISM: Artificial Sequence
<220> FEATURE:
<223> OTHER INFORMATION: Synthetic sequence

<400> SEQUENCE: 726

Phe Ser Leu Ser Thr Gly Gly Val Ala Val Gly Trp Ile
1               5                   10

<210> SEQ ID NO 727
<211> LENGTH: 12
<212> TYPE: PRT
<213> ORGANISM: Artificial Sequence
<220> FEATURE:
<223> OTHER INFORMATION: Synthetic sequence

<400> SEQUENCE: 727

Tyr Ser Ile Ser Ser Gly Tyr His Trp Ala Trp Ile
1               5                   10

<210> SEQ ID NO 728
<211> LENGTH: 13
<212> TYPE: PRT
<213> ORGANISM: Artificial Sequence
<220> FEATURE:
<223> OTHER INFORMATION: Synthetic sequence

<400> SEQUENCE: 728

Phe Ser Leu Ser Thr Ser Gly Val Ala Val Gly Trp Ile
1               5                   10

<210> SEQ ID NO 729
<211> LENGTH: 13
<212> TYPE: PRT
<213> ORGANISM: Artificial Sequence
<220> FEATURE:
<223> OTHER INFORMATION: Synthetic sequence

<400> SEQUENCE: 729

Phe Ser Leu Ser Thr Gly Gly Val Ala Val Gly Trp Ile
1               5                   10

<210> SEQ ID NO 730
<211> LENGTH: 11
<212> TYPE: PRT
<213> ORGANISM: Artificial Sequence
<220> FEATURE:
<223> OTHER INFORMATION: Synthetic sequence

<400> SEQUENCE: 730

Phe Thr Phe Ser Ser Tyr Trp Ile His Trp Val
1               5                   10

```
<210> SEQ ID NO 731
<211> LENGTH: 13
<212> TYPE: PRT
<213> ORGANISM: Artificial Sequence
<220> FEATURE:
<223> OTHER INFORMATION: Synthetic sequence

<400> SEQUENCE: 731

Phe Ser Leu Ser Thr Gly Gly Val Gly Val Gly Trp Ile
1               5                   10

<210> SEQ ID NO 732
<211> LENGTH: 12
<212> TYPE: PRT
<213> ORGANISM: Artificial Sequence
<220> FEATURE:
<223> OTHER INFORMATION: Synthetic sequence

<400> SEQUENCE: 732

Tyr Ser Ile Thr Ser Gly Tyr His Trp Ser Trp Ile
1               5                   10

<210> SEQ ID NO 733
<211> LENGTH: 21
<212> TYPE: PRT
<213> ORGANISM: Artificial Sequence
<220> FEATURE:
<223> OTHER INFORMATION: Synthetic sequence

<400> SEQUENCE: 733

Ile Gly Ile Ile Asn Pro Asn Phe Gly Asp Thr Asn Tyr Ala Gln Lys
1               5                   10                  15

Phe Gln Gly Arg Val
            20

<210> SEQ ID NO 734
<211> LENGTH: 20
<212> TYPE: PRT
<213> ORGANISM: Artificial Sequence
<220> FEATURE:
<223> OTHER INFORMATION: Synthetic sequence

<400> SEQUENCE: 734

Leu Ala Leu Ile Asp Trp Ala Asp Asp Lys Tyr Tyr Ser Pro Ser Leu
1               5                   10                  15

Lys Ser Arg Leu
            20

<210> SEQ ID NO 735
<211> LENGTH: 20
<212> TYPE: PRT
<213> ORGANISM: Artificial Sequence
<220> FEATURE:
<223> OTHER INFORMATION: Synthetic sequence

<400> SEQUENCE: 735

Leu Ala Leu Ile Asp Trp Asp Asp Asp Lys Tyr Tyr Ser Pro Ser Leu
1               5                   10                  15

Lys Ser Arg Leu
            20

<210> SEQ ID NO 736
<211> LENGTH: 21
<212> TYPE: PRT
<213> ORGANISM: Artificial Sequence
<220> FEATURE:
```

<223> OTHER INFORMATION: Synthetic sequence

<400> SEQUENCE: 736

Val Ser Ser Ile Ser Gly Tyr Gly Ser Thr Thr Tyr Tyr Ala Asp Ser
1               5                   10                  15

Val Lys Gly Arg Phe
            20

<210> SEQ ID NO 737
<211> LENGTH: 20
<212> TYPE: PRT
<213> ORGANISM: Artificial Sequence
<220> FEATURE:
<223> OTHER INFORMATION: Synthetic sequence

<400> SEQUENCE: 737

Leu Ala Leu Ile Asp Trp Ala Asp Asp Lys Tyr Tyr Ser Pro Ser Leu
1               5                   10                  15

Lys Ser Arg Leu
            20

<210> SEQ ID NO 738
<211> LENGTH: 20
<212> TYPE: PRT
<213> ORGANISM: Artificial Sequence
<220> FEATURE:
<223> OTHER INFORMATION: Synthetic sequence

<400> SEQUENCE: 738

Leu Ala Leu Ile Asp Trp Asp Asp Asp Lys Arg Tyr Ser Thr Ser Leu
1               5                   10                  15

Lys Ser Arg Leu
            20

<210> SEQ ID NO 739
<211> LENGTH: 20
<212> TYPE: PRT
<213> ORGANISM: Artificial Sequence
<220> FEATURE:
<223> OTHER INFORMATION: Synthetic sequence

<400> SEQUENCE: 739

Ile Gly Glu Ile Tyr His Ser Gly Ser Thr Tyr Tyr Ser Pro Ser Leu
1               5                   10                  15

Lys Ser Arg Val
            20

<210> SEQ ID NO 740
<211> LENGTH: 20
<212> TYPE: PRT
<213> ORGANISM: Artificial Sequence
<220> FEATURE:
<223> OTHER INFORMATION: Synthetic sequence

<400> SEQUENCE: 740

Leu Ala Leu Ile Asp Trp Asp Gly Asp Lys Ser Tyr Ser Thr Ser Leu
1               5                   10                  15

Lys Ser Arg Leu
            20

<210> SEQ ID NO 741
<211> LENGTH: 21
<212> TYPE: PRT
<213> ORGANISM: Artificial Sequence

```
<220> FEATURE:
<223> OTHER INFORMATION: Synthetic sequence

<400> SEQUENCE: 741

Val Ser Ser Ile Ser Gly Ser Gly Gly Thr Thr Tyr Tyr Ala Asp Ser
1               5                   10                  15

Val Lys Gly Arg Phe
            20

<210> SEQ ID NO 742
<211> LENGTH: 21
<212> TYPE: PRT
<213> ORGANISM: Artificial Sequence
<220> FEATURE:
<223> OTHER INFORMATION: Synthetic sequence

<400> SEQUENCE: 742

Val Ser Ser Ile Ser Gly Asp Gly Asp Thr Thr Tyr Tyr Ala Asp Ser
1               5                   10                  15

Val Lys Gly Arg Phe
            20

<210> SEQ ID NO 743
<211> LENGTH: 20
<212> TYPE: PRT
<213> ORGANISM: Artificial Sequence
<220> FEATURE:
<223> OTHER INFORMATION: Synthetic sequence

<400> SEQUENCE: 743

Leu Ala Leu Ile Asp Trp Tyr Gly Asp Lys Tyr Tyr Ser Thr Ser Leu
1               5                   10                  15

Lys Ser Arg Leu
            20

<210> SEQ ID NO 744
<211> LENGTH: 21
<212> TYPE: PRT
<213> ORGANISM: Artificial Sequence
<220> FEATURE:
<223> OTHER INFORMATION: Synthetic sequence

<400> SEQUENCE: 744

Val Ser Tyr Ile Ser Gly Asp Gly Asp Thr Thr Tyr Tyr Ala Asp Ser
1               5                   10                  15

Val Lys Gly Arg Phe
            20

<210> SEQ ID NO 745
<211> LENGTH: 20
<212> TYPE: PRT
<213> ORGANISM: Artificial Sequence
<220> FEATURE:
<223> OTHER INFORMATION: Synthetic sequence

<400> SEQUENCE: 745

Ile Gly Glu Ile Tyr His Ser Gly Ser Thr Tyr Tyr Ser Pro Ser Leu
1               5                   10                  15

Lys Ser Arg Val
            20

<210> SEQ ID NO 746
<211> LENGTH: 21
<212> TYPE: PRT
```

-continued

```
<213> ORGANISM: Artificial Sequence
<220> FEATURE:
<223> OTHER INFORMATION: Synthetic sequence

<400> SEQUENCE: 746

Val Ser Gly Ile Ser Gly Asp Gly Ser Ser Thr Tyr Tyr Ala Asp Ser
1               5                   10                  15

Val Lys Gly Arg Phe
            20

<210> SEQ ID NO 747
<211> LENGTH: 21
<212> TYPE: PRT
<213> ORGANISM: Artificial Sequence
<220> FEATURE:
<223> OTHER INFORMATION: Synthetic sequence

<400> SEQUENCE: 747

Val Ser Gly Ile Ser Gly Ala Gly Asp Ser Thr Tyr Tyr Ala Asp Ser
1               5                   10                  15

Val Lys Gly Arg Phe
            20

<210> SEQ ID NO 748
<211> LENGTH: 21
<212> TYPE: PRT
<213> ORGANISM: Artificial Sequence
<220> FEATURE:
<223> OTHER INFORMATION: Synthetic sequence

<400> SEQUENCE: 748

Val Ser Val Ile Ser Gly Ser Gly Ser Ser Thr Tyr Tyr Ala Asp Ser
1               5                   10                  15

Val Lys Gly Arg Phe
            20

<210> SEQ ID NO 749
<211> LENGTH: 21
<212> TYPE: PRT
<213> ORGANISM: Artificial Sequence
<220> FEATURE:
<223> OTHER INFORMATION: Synthetic sequence

<400> SEQUENCE: 749

Val Ser Ser Ile Ser Gly Tyr Gly Ser Thr Thr Tyr Tyr Ala Asp Ser
1               5                   10                  15

Val Lys Gly Arg Phe
            20

<210> SEQ ID NO 750
<211> LENGTH: 20
<212> TYPE: PRT
<213> ORGANISM: Artificial Sequence
<220> FEATURE:
<223> OTHER INFORMATION: Synthetic sequence

<400> SEQUENCE: 750

Leu Ala Leu Ile Asp Trp Ala Gly Asp Lys Ser Tyr Ser Thr Ser Leu
1               5                   10                  15

Lys Ser Arg Leu
            20

<210> SEQ ID NO 751
<211> LENGTH: 21
```

```
<212> TYPE: PRT
<213> ORGANISM: Artificial Sequence
<220> FEATURE:
<223> OTHER INFORMATION: Synthetic sequence

<400> SEQUENCE: 751

Val Ser Ser Ile Ser Gly Asp Gly Ser Ser Thr Tyr Tyr Ala Asp Ser
1               5                   10                  15

Val Lys Gly Arg Phe
            20

<210> SEQ ID NO 752
<211> LENGTH: 20
<212> TYPE: PRT
<213> ORGANISM: Artificial Sequence
<220> FEATURE:
<223> OTHER INFORMATION: Synthetic sequence

<400> SEQUENCE: 752

Leu Ala Leu Ile Asp Trp Asp Asp Asp Lys Tyr Tyr Ser Thr Ser Leu
1               5                   10                  15

Lys Ser Arg Leu
            20

<210> SEQ ID NO 753
<211> LENGTH: 20
<212> TYPE: PRT
<213> ORGANISM: Artificial Sequence
<220> FEATURE:
<223> OTHER INFORMATION: Synthetic sequence

<400> SEQUENCE: 753

Leu Ala Leu Ile Asp Trp Ala Gly Asp Lys Ser Tyr Ser Thr Ser Leu
1               5                   10                  15

Lys Ser Arg Leu
            20

<210> SEQ ID NO 754
<211> LENGTH: 21
<212> TYPE: PRT
<213> ORGANISM: Artificial Sequence
<220> FEATURE:
<223> OTHER INFORMATION: Synthetic sequence

<400> SEQUENCE: 754

Val Ser Val Ile Ser Gly Asp Gly Asp Thr Thr Tyr Tyr Ala Asp Ser
1               5                   10                  15

Val Lys Gly Arg Phe
            20

<210> SEQ ID NO 755
<211> LENGTH: 20
<212> TYPE: PRT
<213> ORGANISM: Artificial Sequence
<220> FEATURE:
<223> OTHER INFORMATION: Synthetic sequence

<400> SEQUENCE: 755

Leu Ala Leu Ile Asp Trp Ala Asp Asp Lys Tyr Tyr Ser Pro Ser Leu
1               5                   10                  15

Lys Ser Arg Leu
            20

<210> SEQ ID NO 756
```

```
<211> LENGTH: 21
<212> TYPE: PRT
<213> ORGANISM: Artificial Sequence
<220> FEATURE:
<223> OTHER INFORMATION: Synthetic sequence

<400> SEQUENCE: 756

Val Ser Ser Ile Ser Gly Tyr Gly Asp Thr Thr Tyr Tyr Ala Asp Ser
1               5                   10                  15

Val Lys Gly Arg Phe
            20

<210> SEQ ID NO 757
<211> LENGTH: 14
<212> TYPE: PRT
<213> ORGANISM: Artificial Sequence
<220> FEATURE:
<223> OTHER INFORMATION: Synthetic sequence

<400> SEQUENCE: 757

Ala Arg Asp Glu Tyr Tyr Gly Gly Ser Tyr Tyr Phe Asp Tyr
1               5                   10

<210> SEQ ID NO 758
<211> LENGTH: 15
<212> TYPE: PRT
<213> ORGANISM: Artificial Sequence
<220> FEATURE:
<223> OTHER INFORMATION: Synthetic sequence

<400> SEQUENCE: 758

Ala Arg Glu Gly Ser Asp Ala Val Leu Gly Asp Trp Phe Ala Tyr
1               5                   10                  15

<210> SEQ ID NO 759
<211> LENGTH: 15
<212> TYPE: PRT
<213> ORGANISM: Artificial Sequence
<220> FEATURE:
<223> OTHER INFORMATION: Synthetic sequence

<400> SEQUENCE: 759

Ala Arg Gly Gly Ser Asp Thr Val Leu Gly Asp Trp Phe Ala Tyr
1               5                   10                  15

<210> SEQ ID NO 760
<211> LENGTH: 15
<212> TYPE: PRT
<213> ORGANISM: Artificial Sequence
<220> FEATURE:
<223> OTHER INFORMATION: Synthetic sequence

<400> SEQUENCE: 760

Ala Arg Gly Gly Ser Asp Ala Val Leu Gly Asp Trp Phe Ala Tyr
1               5                   10                  15

<210> SEQ ID NO 761
<211> LENGTH: 15
<212> TYPE: PRT
<213> ORGANISM: Artificial Sequence
<220> FEATURE:
<223> OTHER INFORMATION: Synthetic sequence

<400> SEQUENCE: 761

Ala Arg Gly Gly Ser Asp Ala Val Leu Gly Asp Trp Phe Ala Tyr
1               5                   10                  15
```

<210> SEQ ID NO 762
<211> LENGTH: 15
<212> TYPE: PRT
<213> ORGANISM: Artificial Sequence
<220> FEATURE:
<223> OTHER INFORMATION: Synthetic sequence

<400> SEQUENCE: 762

Ala Arg Glu Gly Ser Thr Thr Val Val Gly Asp Trp Phe Asp Tyr
1               5                   10                  15

<210> SEQ ID NO 763
<211> LENGTH: 12
<212> TYPE: PRT
<213> ORGANISM: Artificial Sequence
<220> FEATURE:
<223> OTHER INFORMATION: Synthetic sequence

<400> SEQUENCE: 763

Ala Arg Ser Pro Tyr Tyr Tyr Gly Val Phe Asp Tyr
1               5                   10

<210> SEQ ID NO 764
<211> LENGTH: 15
<212> TYPE: PRT
<213> ORGANISM: Artificial Sequence
<220> FEATURE:
<223> OTHER INFORMATION: Synthetic sequence

<400> SEQUENCE: 764

Ala Arg Glu Gly Ser Thr Ala Val Val Gly Asp Trp Phe Asp Tyr
1               5                   10                  15

<210> SEQ ID NO 765
<211> LENGTH: 12
<212> TYPE: PRT
<213> ORGANISM: Artificial Sequence
<220> FEATURE:
<223> OTHER INFORMATION: Synthetic sequence

<400> SEQUENCE: 765

Ala Arg Asp Asp Leu Tyr Ser Trp Tyr Phe Asp Val
1               5                   10

<210> SEQ ID NO 766
<211> LENGTH: 13
<212> TYPE: PRT
<213> ORGANISM: Artificial Sequence
<220> FEATURE:
<223> OTHER INFORMATION: Synthetic sequence

<400> SEQUENCE: 766

Ala Arg Glu Tyr Tyr Gly Tyr Gly Tyr Ala Leu Asp Tyr
1               5                   10

<210> SEQ ID NO 767
<211> LENGTH: 12
<212> TYPE: PRT
<213> ORGANISM: Artificial Sequence
<220> FEATURE:
<223> OTHER INFORMATION: Synthetic sequence

<400> SEQUENCE: 767

Ala Arg Ser Asp Tyr Tyr Gly Ser His Phe Asp Tyr
1               5                   10

```
<210> SEQ ID NO 768
<211> LENGTH: 15
<212> TYPE: PRT
<213> ORGANISM: Artificial Sequence
<220> FEATURE:
<223> OTHER INFORMATION: Synthetic sequence

<400> SEQUENCE: 768

Ala Arg Glu Gly Ser Thr Thr Val Ala Gly Asp Trp Phe Ala Tyr
1               5                   10                  15

<210> SEQ ID NO 769
<211> LENGTH: 15
<212> TYPE: PRT
<213> ORGANISM: Artificial Sequence
<220> FEATURE:
<223> OTHER INFORMATION: Synthetic sequence

<400> SEQUENCE: 769

Ala Arg Glu Gly Ser Asp Val Val Thr Gly Asp Trp Phe Ala Tyr
1               5                   10                  15

<210> SEQ ID NO 770
<211> LENGTH: 15
<212> TYPE: PRT
<213> ORGANISM: Artificial Sequence
<220> FEATURE:
<223> OTHER INFORMATION: Synthetic sequence

<400> SEQUENCE: 770

Ala Arg Gly Gly Ser Asp Ala Val Leu Gly Asp Trp Phe Ala Tyr
1               5                   10                  15

<210> SEQ ID NO 771
<211> LENGTH: 15
<212> TYPE: PRT
<213> ORGANISM: Artificial Sequence
<220> FEATURE:
<223> OTHER INFORMATION: Synthetic sequence

<400> SEQUENCE: 771

Ala Arg Glu Gly Ser Asp Thr Val Leu Gly Asp Trp Phe Ala Tyr
1               5                   10                  15

<210> SEQ ID NO 772
<211> LENGTH: 15
<212> TYPE: PRT
<213> ORGANISM: Artificial Sequence
<220> FEATURE:
<223> OTHER INFORMATION: Synthetic sequence

<400> SEQUENCE: 772

Ala Arg Glu Gly Ser Asp Thr Val Leu Gly Asp Trp Phe Ala Tyr
1               5                   10                  15

<210> SEQ ID NO 773
<211> LENGTH: 15
<212> TYPE: PRT
<213> ORGANISM: Artificial Sequence
<220> FEATURE:
<223> OTHER INFORMATION: Synthetic sequence

<400> SEQUENCE: 773

Ala Arg Glu Gly Ser Asp Ala Val Leu Gly Asp Trp Phe Gly Tyr
1               5                   10                  15

<210> SEQ ID NO 774
```

```
<211> LENGTH: 15
<212> TYPE: PRT
<213> ORGANISM: Artificial Sequence
<220> FEATURE:
<223> OTHER INFORMATION: Synthetic sequence

<400> SEQUENCE: 774

Ala Arg Gly Gly Ser Asp Thr Val Leu Gly Asp Trp Phe Ala Tyr
1               5                   10                  15

<210> SEQ ID NO 775
<211> LENGTH: 15
<212> TYPE: PRT
<213> ORGANISM: Artificial Sequence
<220> FEATURE:
<223> OTHER INFORMATION: Synthetic sequence

<400> SEQUENCE: 775

Ala Arg Glu Gly Ser Asp Ala Val Thr Gly Asp Trp Phe Ala Tyr
1               5                   10                  15

<210> SEQ ID NO 776
<211> LENGTH: 15
<212> TYPE: PRT
<213> ORGANISM: Artificial Sequence
<220> FEATURE:
<223> OTHER INFORMATION: Synthetic sequence

<400> SEQUENCE: 776

Ala Arg Glu Gly Ser Thr Ala Val Ala Gly Asp Trp Phe Ala Tyr
1               5                   10                  15

<210> SEQ ID NO 777
<211> LENGTH: 15
<212> TYPE: PRT
<213> ORGANISM: Artificial Sequence
<220> FEATURE:
<223> OTHER INFORMATION: Synthetic sequence

<400> SEQUENCE: 777

Ala Arg Glu Gly Glu Asp Ala Val Thr Gly Asp Trp Phe Ala Tyr
1               5                   10                  15

<210> SEQ ID NO 778
<211> LENGTH: 13
<212> TYPE: PRT
<213> ORGANISM: Artificial Sequence
<220> FEATURE:
<223> OTHER INFORMATION: Synthetic sequence

<400> SEQUENCE: 778

Ala Arg Ser Arg Gly Leu Val Leu Asp Ala Phe Asp Tyr
1               5                   10

<210> SEQ ID NO 779
<211> LENGTH: 15
<212> TYPE: PRT
<213> ORGANISM: Artificial Sequence
<220> FEATURE:
<223> OTHER INFORMATION: Synthetic sequence

<400> SEQUENCE: 779

Ala Arg Gly Gly Ser Asp Thr Val Ile Gly Asp Trp Phe Ala Tyr
1               5                   10                  15

<210> SEQ ID NO 780
<211> LENGTH: 15
```

```
<212> TYPE: PRT
<213> ORGANISM: Artificial Sequence
<220> FEATURE:
<223> OTHER INFORMATION: Synthetic sequence

<400> SEQUENCE: 780

Ala Arg Glu Gly Ser Asp Thr Val Leu Gly Asp Trp Phe Ala Tyr
1               5                   10                  15

<210> SEQ ID NO 781
<211> LENGTH: 11
<212> TYPE: PRT
<213> ORGANISM: Artificial Sequence
<220> FEATURE:
<223> OTHER INFORMATION: Synthetic sequence

<400> SEQUENCE: 781

Arg Ala Ser Gln Asp Val Arg Thr Ala Val Ala
1               5                   10

<210> SEQ ID NO 782
<211> LENGTH: 11
<212> TYPE: PRT
<213> ORGANISM: Artificial Sequence
<220> FEATURE:
<223> OTHER INFORMATION: Synthetic sequence

<400> SEQUENCE: 782

Arg Ala Ser Gln Asp Ile Ser Thr Phe Leu Ala
1               5                   10

<210> SEQ ID NO 783
<211> LENGTH: 11
<212> TYPE: PRT
<213> ORGANISM: Artificial Sequence
<220> FEATURE:
<223> OTHER INFORMATION: Synthetic sequence

<400> SEQUENCE: 783

Arg Ala Ser Gln Ser Val Ser Pro Tyr Leu Ala
1               5                   10

<210> SEQ ID NO 784
<211> LENGTH: 11
<212> TYPE: PRT
<213> ORGANISM: Artificial Sequence
<220> FEATURE:
<223> OTHER INFORMATION: Synthetic sequence

<400> SEQUENCE: 784

Arg Ala Ser Gln Gly Ile Gly Ser Phe Leu Ala
1               5                   10

<210> SEQ ID NO 785
<211> LENGTH: 11
<212> TYPE: PRT
<213> ORGANISM: Artificial Sequence
<220> FEATURE:
<223> OTHER INFORMATION: Synthetic sequence

<400> SEQUENCE: 785

Arg Ala Ser Gln Gly Ile Gly Ser Tyr Leu Ala
1               5                   10

<210> SEQ ID NO 786
<211> LENGTH: 11
<212> TYPE: PRT
```

<213> ORGANISM: Artificial Sequence
<220> FEATURE:
<223> OTHER INFORMATION: Synthetic sequence

<400> SEQUENCE: 786

Arg Ala Ser Gln Gly Ile Gly Thr Tyr Leu Ala
1               5                   10

<210> SEQ ID NO 787
<211> LENGTH: 10
<212> TYPE: PRT
<213> ORGANISM: Artificial Sequence
<220> FEATURE:
<223> OTHER INFORMATION: Synthetic sequence

<400> SEQUENCE: 787

Ser Ala Ser Ser Arg Val Gly Ser Val Tyr
1               5                   10

<210> SEQ ID NO 788
<211> LENGTH: 11
<212> TYPE: PRT
<213> ORGANISM: Artificial Sequence
<220> FEATURE:
<223> OTHER INFORMATION: Synthetic sequence

<400> SEQUENCE: 788

Arg Ala Ser Gln Gly Ile Ser Arg Tyr Leu Ala
1               5                   10

<210> SEQ ID NO 789
<211> LENGTH: 11
<212> TYPE: PRT
<213> ORGANISM: Artificial Sequence
<220> FEATURE:
<223> OTHER INFORMATION: Synthetic sequence

<400> SEQUENCE: 789

Arg Ala Ser Gln Gly Ile Gly Ser Ser Leu Ala
1               5                   10

<210> SEQ ID NO 790
<211> LENGTH: 11
<212> TYPE: PRT
<213> ORGANISM: Artificial Sequence
<220> FEATURE:
<223> OTHER INFORMATION: Synthetic sequence

<400> SEQUENCE: 790

Arg Ala Ser Gln Gly Ile Ser Ser Tyr Leu Ala
1               5                   10

<210> SEQ ID NO 791
<211> LENGTH: 15
<212> TYPE: PRT
<213> ORGANISM: Artificial Sequence
<220> FEATURE:
<223> OTHER INFORMATION: Synthetic sequence

<400> SEQUENCE: 791

Arg Ala Ser Glu Ser Val Asp Phe Asp Gly Phe Ser Phe Leu Ala
1               5                   10                  15

<210> SEQ ID NO 792
<211> LENGTH: 11
<212> TYPE: PRT
<213> ORGANISM: Artificial Sequence

```
<220> FEATURE:
<223> OTHER INFORMATION: Synthetic sequence

<400> SEQUENCE: 792

Arg Ala Ser Gln Gly Ile Gly Ser Phe Leu Gly
1               5                   10

<210> SEQ ID NO 793
<211> LENGTH: 11
<212> TYPE: PRT
<213> ORGANISM: Artificial Sequence
<220> FEATURE:
<223> OTHER INFORMATION: Synthetic sequence

<400> SEQUENCE: 793

Arg Ala Ser Gln Gly Ile Ser Ser Val Leu Ala
1               5                   10

<210> SEQ ID NO 794
<211> LENGTH: 11
<212> TYPE: PRT
<213> ORGANISM: Artificial Sequence
<220> FEATURE:
<223> OTHER INFORMATION: Synthetic sequence

<400> SEQUENCE: 794

Arg Ala Ser Gln Ser Ile Ser Ser Tyr Leu Ala
1               5                   10

<210> SEQ ID NO 795
<211> LENGTH: 11
<212> TYPE: PRT
<213> ORGANISM: Artificial Sequence
<220> FEATURE:
<223> OTHER INFORMATION: Synthetic sequence

<400> SEQUENCE: 795

Arg Ala Ser Gln Asp Ile Arg Ser Tyr Leu Ala
1               5                   10

<210> SEQ ID NO 796
<211> LENGTH: 11
<212> TYPE: PRT
<213> ORGANISM: Artificial Sequence
<220> FEATURE:
<223> OTHER INFORMATION: Synthetic sequence

<400> SEQUENCE: 796

Arg Ala Ser Gln Gly Ile Ser Ser Tyr Leu Ala
1               5                   10

<210> SEQ ID NO 797
<211> LENGTH: 11
<212> TYPE: PRT
<213> ORGANISM: Artificial Sequence
<220> FEATURE:
<223> OTHER INFORMATION: Synthetic sequence

<400> SEQUENCE: 797

Gln Ala Ser Gln Asp Ile Thr Thr Tyr Leu Ala
1               5                   10

<210> SEQ ID NO 798
<211> LENGTH: 11
<212> TYPE: PRT
<213> ORGANISM: Artificial Sequence
<220> FEATURE:
```

<223> OTHER INFORMATION: Synthetic sequence

<400> SEQUENCE: 798

Arg Ala Ser Gln Gly Val Ser Pro Tyr Leu Ala
1               5                   10

<210> SEQ ID NO 799
<211> LENGTH: 11
<212> TYPE: PRT
<213> ORGANISM: Artificial Sequence
<220> FEATURE:
<223> OTHER INFORMATION: Synthetic sequence

<400> SEQUENCE: 799

Arg Ala Ser Gln Gly Val Gly Thr Tyr Leu Ala
1               5                   10

<210> SEQ ID NO 800
<211> LENGTH: 11
<212> TYPE: PRT
<213> ORGANISM: Artificial Sequence
<220> FEATURE:
<223> OTHER INFORMATION: Synthetic sequence

<400> SEQUENCE: 800

Gln Ala Ser Gln Asp Ile Arg Thr Phe Leu Ala
1               5                   10

<210> SEQ ID NO 801
<211> LENGTH: 11
<212> TYPE: PRT
<213> ORGANISM: Artificial Sequence
<220> FEATURE:
<223> OTHER INFORMATION: Synthetic sequence

<400> SEQUENCE: 801

Gln Ala Ser Gln Asp Ile Arg Thr Tyr Leu Ala
1               5                   10

<210> SEQ ID NO 802
<211> LENGTH: 12
<212> TYPE: PRT
<213> ORGANISM: Artificial Sequence
<220> FEATURE:
<223> OTHER INFORMATION: Synthetic sequence

<400> SEQUENCE: 802

Arg Ala Ser Gln Ser Val Ser Gly Arg Phe Leu Ala
1               5                   10

<210> SEQ ID NO 803
<211> LENGTH: 11
<212> TYPE: PRT
<213> ORGANISM: Artificial Sequence
<220> FEATURE:
<223> OTHER INFORMATION: Synthetic sequence

<400> SEQUENCE: 803

Arg Ala Ser Gln Ser Ile Gly Ser Tyr Leu Ala
1               5                   10

<210> SEQ ID NO 804
<211> LENGTH: 11
<212> TYPE: PRT
<213> ORGANISM: Artificial Sequence
<220> FEATURE:
<223> OTHER INFORMATION: Synthetic sequence

```
<400> SEQUENCE: 804

Gln Ala Ser Gln Asp Ile Arg Thr Tyr Leu Ala
1               5                   10

<210> SEQ ID NO 805
<211> LENGTH: 9
<212> TYPE: PRT
<213> ORGANISM: Artificial Sequence
<220> FEATURE:
<223> OTHER INFORMATION: Synthetic sequence

<400> SEQUENCE: 805

Asp Ala Ser Asn Leu Glu Thr Gly Val
1               5

<210> SEQ ID NO 806
<211> LENGTH: 9
<212> TYPE: PRT
<213> ORGANISM: Artificial Sequence
<220> FEATURE:
<223> OTHER INFORMATION: Synthetic sequence

<400> SEQUENCE: 806

Asp Ala Ser Ser Leu Glu Ser Gly Val
1               5

<210> SEQ ID NO 807
<211> LENGTH: 9
<212> TYPE: PRT
<213> ORGANISM: Artificial Sequence
<220> FEATURE:
<223> OTHER INFORMATION: Synthetic sequence

<400> SEQUENCE: 807

Asp Ala Ser Ser Leu Glu Ser Gly Val
1               5

<210> SEQ ID NO 808
<211> LENGTH: 9
<212> TYPE: PRT
<213> ORGANISM: Artificial Sequence
<220> FEATURE:
<223> OTHER INFORMATION: Synthetic sequence

<400> SEQUENCE: 808

Asp Ala Ser Asn Leu Glu Thr Gly Val
1               5

<210> SEQ ID NO 809
<211> LENGTH: 9
<212> TYPE: PRT
<213> ORGANISM: Artificial Sequence
<220> FEATURE:
<223> OTHER INFORMATION: Synthetic sequence

<400> SEQUENCE: 809

Asp Ala Ser Asn Leu Glu Thr Gly Val
1               5

<210> SEQ ID NO 810
<211> LENGTH: 9
<212> TYPE: PRT
<213> ORGANISM: Artificial Sequence
<220> FEATURE:
<223> OTHER INFORMATION: Synthetic sequence
```

<400> SEQUENCE: 810

Asp Ala Ser Asn Arg Ala Thr Gly Ile
1               5

<210> SEQ ID NO 811
<211> LENGTH: 9
<212> TYPE: PRT
<213> ORGANISM: Artificial Sequence
<220> FEATURE:
<223> OTHER INFORMATION: Synthetic sequence

<400> SEQUENCE: 811

Asp Ala Ser Asn Leu Glu Thr Gly Val
1               5

<210> SEQ ID NO 812
<211> LENGTH: 9
<212> TYPE: PRT
<213> ORGANISM: Artificial Sequence
<220> FEATURE:
<223> OTHER INFORMATION: Synthetic sequence

<400> SEQUENCE: 812

Asp Ala Ser Asn Arg Ala Thr Gly Ile
1               5

<210> SEQ ID NO 813
<211> LENGTH: 9
<212> TYPE: PRT
<213> ORGANISM: Artificial Sequence
<220> FEATURE:
<223> OTHER INFORMATION: Synthetic sequence

<400> SEQUENCE: 813

Ala Ala Ser Ser Leu Gln Ser Gly Val
1               5

<210> SEQ ID NO 814
<211> LENGTH: 9
<212> TYPE: PRT
<213> ORGANISM: Artificial Sequence
<220> FEATURE:
<223> OTHER INFORMATION: Synthetic sequence

<400> SEQUENCE: 814

Asp Ala Ser Ser Leu Glu Ser Gly Val
1               5

<210> SEQ ID NO 815
<211> LENGTH: 9
<212> TYPE: PRT
<213> ORGANISM: Artificial Sequence
<220> FEATURE:
<223> OTHER INFORMATION: Synthetic sequence

<400> SEQUENCE: 815

Asp Ala Ser Asn Leu Glu Thr Gly Val
1               5

<210> SEQ ID NO 816
<211> LENGTH: 9
<212> TYPE: PRT
<213> ORGANISM: Artificial Sequence
<220> FEATURE:
<223> OTHER INFORMATION: Synthetic sequence

<400> SEQUENCE: 816

Asp Ala Ser Ser Leu Glu Ser Gly Val
1               5

<210> SEQ ID NO 817
<211> LENGTH: 9
<212> TYPE: PRT
<213> ORGANISM: Artificial Sequence
<220> FEATURE:
<223> OTHER INFORMATION: Synthetic sequence

<400> SEQUENCE: 817

Asp Ala Ser Ser Leu Glu Ser Gly Val
1               5

<210> SEQ ID NO 818
<211> LENGTH: 9
<212> TYPE: PRT
<213> ORGANISM: Artificial Sequence
<220> FEATURE:
<223> OTHER INFORMATION: Synthetic sequence

<400> SEQUENCE: 818

Asp Ala Ser Asn Leu Glu Thr Gly Val
1               5

<210> SEQ ID NO 819
<211> LENGTH: 9
<212> TYPE: PRT
<213> ORGANISM: Artificial Sequence
<220> FEATURE:
<223> OTHER INFORMATION: Synthetic sequence

<400> SEQUENCE: 819

Asp Ala Ser Asn Arg Ala Thr Gly Ile
1               5

<210> SEQ ID NO 820
<211> LENGTH: 9
<212> TYPE: PRT
<213> ORGANISM: Artificial Sequence
<220> FEATURE:
<223> OTHER INFORMATION: Synthetic sequence

<400> SEQUENCE: 820

Asp Ala Ser Asn Leu Glu Thr Gly Val
1               5

<210> SEQ ID NO 821
<211> LENGTH: 9
<212> TYPE: PRT
<213> ORGANISM: Artificial Sequence
<220> FEATURE:
<223> OTHER INFORMATION: Synthetic sequence

<400> SEQUENCE: 821

Asp Ala Ser Asn Arg Ala Thr Gly Ile
1               5

<210> SEQ ID NO 822
<211> LENGTH: 9
<212> TYPE: PRT
<213> ORGANISM: Artificial Sequence
<220> FEATURE:
<223> OTHER INFORMATION: Synthetic sequence

<400> SEQUENCE: 822

Asp Ala Ser Asn Arg Ala Thr Gly Ile
1               5

<210> SEQ ID NO 823
<211> LENGTH: 9
<212> TYPE: PRT
<213> ORGANISM: Artificial Sequence
<220> FEATURE:
<223> OTHER INFORMATION: Synthetic sequence

<400> SEQUENCE: 823

Asp Ala Ser Ser Leu Glu Ser Gly Val
1               5

<210> SEQ ID NO 824
<211> LENGTH: 9
<212> TYPE: PRT
<213> ORGANISM: Artificial Sequence
<220> FEATURE:
<223> OTHER INFORMATION: Synthetic sequence

<400> SEQUENCE: 824

Asp Ala Ser Asn Arg Ala Thr Gly Ile
1               5

<210> SEQ ID NO 825
<211> LENGTH: 9
<212> TYPE: PRT
<213> ORGANISM: Artificial Sequence
<220> FEATURE:
<223> OTHER INFORMATION: Synthetic sequence

<400> SEQUENCE: 825

Asp Ala Ser Asn Arg Ala Thr Gly Ile
1               5

<210> SEQ ID NO 826
<211> LENGTH: 9
<212> TYPE: PRT
<213> ORGANISM: Artificial Sequence
<220> FEATURE:
<223> OTHER INFORMATION: Synthetic sequence

<400> SEQUENCE: 826

Asp Ala Ser Ser Leu Glu Ser Gly Val
1               5

<210> SEQ ID NO 827
<211> LENGTH: 9
<212> TYPE: PRT
<213> ORGANISM: Artificial Sequence
<220> FEATURE:
<223> OTHER INFORMATION: Synthetic sequence

<400> SEQUENCE: 827

Asp Ala Ser Asn Leu Glu Thr Gly Val
1               5

<210> SEQ ID NO 828
<211> LENGTH: 9
<212> TYPE: PRT
<213> ORGANISM: Artificial Sequence
<220> FEATURE:
<223> OTHER INFORMATION: Synthetic sequence

<400> SEQUENCE: 828

Asp Ala Ser Asn Leu Glu Thr Gly Val

```
1               5

<210> SEQ ID NO 829
<211> LENGTH: 11
<212> TYPE: PRT
<213> ORGANISM: Artificial Sequence
<220> FEATURE:
<223> OTHER INFORMATION: Synthetic sequence

<400> SEQUENCE: 829

Tyr Cys Gln Gln Ser Tyr Asp Trp Pro Pro Thr
1               5                   10

<210> SEQ ID NO 830
<211> LENGTH: 10
<212> TYPE: PRT
<213> ORGANISM: Artificial Sequence
<220> FEATURE:
<223> OTHER INFORMATION: Synthetic sequence

<400> SEQUENCE: 830

Tyr Cys Gln Gln Ala Tyr Ser Ile Trp Thr
1               5                   10

<210> SEQ ID NO 831
<211> LENGTH: 10
<212> TYPE: PRT
<213> ORGANISM: Artificial Sequence
<220> FEATURE:
<223> OTHER INFORMATION: Synthetic sequence

<400> SEQUENCE: 831

Tyr Cys Gln Gln Gly Tyr Ser Leu Trp Thr
1               5                   10

<210> SEQ ID NO 832
<211> LENGTH: 10
<212> TYPE: PRT
<213> ORGANISM: Artificial Sequence
<220> FEATURE:
<223> OTHER INFORMATION: Synthetic sequence

<400> SEQUENCE: 832

Tyr Cys Gln Gln Gly Tyr Tyr Leu Trp Thr
1               5                   10

<210> SEQ ID NO 833
<211> LENGTH: 10
<212> TYPE: PRT
<213> ORGANISM: Artificial Sequence
<220> FEATURE:
<223> OTHER INFORMATION: Synthetic sequence

<400> SEQUENCE: 833

Tyr Cys Gln Gln Gly Tyr Ser Ile Trp Thr
1               5                   10

<210> SEQ ID NO 834
<211> LENGTH: 10
<212> TYPE: PRT
<213> ORGANISM: Artificial Sequence
<220> FEATURE:
<223> OTHER INFORMATION: Synthetic sequence

<400> SEQUENCE: 834

Tyr Cys Gln Gln Gly Tyr Ser Leu Trp Thr
1               5                   10
```

<210> SEQ ID NO 835
<211> LENGTH: 11
<212> TYPE: PRT
<213> ORGANISM: Artificial Sequence
<220> FEATURE:
<223> OTHER INFORMATION: Synthetic sequence

<400> SEQUENCE: 835

Tyr Cys Gln Gln Tyr Thr His Asp Pro Val Thr
1               5                   10

<210> SEQ ID NO 836
<211> LENGTH: 10
<212> TYPE: PRT
<213> ORGANISM: Artificial Sequence
<220> FEATURE:
<223> OTHER INFORMATION: Synthetic sequence

<400> SEQUENCE: 836

Tyr Cys Gln Gln Gly Tyr Ser Leu Trp Thr
1               5                   10

<210> SEQ ID NO 837
<211> LENGTH: 10
<212> TYPE: PRT
<213> ORGANISM: Artificial Sequence
<220> FEATURE:
<223> OTHER INFORMATION: Synthetic sequence

<400> SEQUENCE: 837

Tyr Cys Gln Gln Gly Tyr Tyr Thr Trp Thr
1               5                   10

<210> SEQ ID NO 838
<211> LENGTH: 11
<212> TYPE: PRT
<213> ORGANISM: Artificial Sequence
<220> FEATURE:
<223> OTHER INFORMATION: Synthetic sequence

<400> SEQUENCE: 838

Tyr Cys Gln Gln Tyr Tyr Ser Thr Pro Leu Thr
1               5                   10

<210> SEQ ID NO 839
<211> LENGTH: 11
<212> TYPE: PRT
<213> ORGANISM: Artificial Sequence
<220> FEATURE:
<223> OTHER INFORMATION: Synthetic sequence

<400> SEQUENCE: 839

Tyr Cys Gln Gln Tyr Asp Thr Leu Pro Arg Thr
1               5                   10

<210> SEQ ID NO 840
<211> LENGTH: 10
<212> TYPE: PRT
<213> ORGANISM: Artificial Sequence
<220> FEATURE:
<223> OTHER INFORMATION: Synthetic sequence

<400> SEQUENCE: 840

Tyr Cys Gln Gln Tyr Tyr Ser Leu Val Thr
1               5                   10

<210> SEQ ID NO 841
<211> LENGTH: 10
<212> TYPE: PRT
<213> ORGANISM: Artificial Sequence
<220> FEATURE:
<223> OTHER INFORMATION: Synthetic sequence

<400> SEQUENCE: 841

Tyr Cys Gln Gln Gly Tyr Ser Leu Trp Thr
1               5                   10

<210> SEQ ID NO 842
<211> LENGTH: 10
<212> TYPE: PRT
<213> ORGANISM: Artificial Sequence
<220> FEATURE:
<223> OTHER INFORMATION: Synthetic sequence

<400> SEQUENCE: 842

Tyr Cys Gln Gln Gly Tyr Ser Thr Trp Thr
1               5                   10

<210> SEQ ID NO 843
<211> LENGTH: 10
<212> TYPE: PRT
<213> ORGANISM: Artificial Sequence
<220> FEATURE:
<223> OTHER INFORMATION: Synthetic sequence

<400> SEQUENCE: 843

Tyr Cys Gln Gln Gly Tyr Ser Ile Trp Thr
1               5                   10

<210> SEQ ID NO 844
<211> LENGTH: 10
<212> TYPE: PRT
<213> ORGANISM: Artificial Sequence
<220> FEATURE:
<223> OTHER INFORMATION: Synthetic sequence

<400> SEQUENCE: 844

Tyr Cys Gln Gln Gly Tyr Ser Thr Trp Thr
1               5                   10

<210> SEQ ID NO 845
<211> LENGTH: 10
<212> TYPE: PRT
<213> ORGANISM: Artificial Sequence
<220> FEATURE:
<223> OTHER INFORMATION: Synthetic sequence

<400> SEQUENCE: 845

Tyr Cys Gln Gln Gly Tyr Tyr Leu Trp Thr
1               5                   10

<210> SEQ ID NO 846
<211> LENGTH: 10
<212> TYPE: PRT
<213> ORGANISM: Artificial Sequence
<220> FEATURE:
<223> OTHER INFORMATION: Synthetic sequence

<400> SEQUENCE: 846

Tyr Cys Gln Gln Gly Tyr Ser Thr Trp Thr
1               5                   10

```
<210> SEQ ID NO 847
<211> LENGTH: 10
<212> TYPE: PRT
<213> ORGANISM: Artificial Sequence
<220> FEATURE:
<223> OTHER INFORMATION: Synthetic sequence

<400> SEQUENCE: 847

Tyr Cys Gln Gln Gly Tyr Ser Leu Trp Thr
1               5                   10

<210> SEQ ID NO 848
<211> LENGTH: 10
<212> TYPE: PRT
<213> ORGANISM: Artificial Sequence
<220> FEATURE:
<223> OTHER INFORMATION: Synthetic sequence

<400> SEQUENCE: 848

Tyr Cys Gln Gln Gly Tyr Ser Thr Trp Thr
1               5                   10

<210> SEQ ID NO 849
<211> LENGTH: 10
<212> TYPE: PRT
<213> ORGANISM: Artificial Sequence
<220> FEATURE:
<223> OTHER INFORMATION: Synthetic sequence

<400> SEQUENCE: 849

Tyr Cys Gln Gln Gly Tyr Ser Ile Trp Thr
1               5                   10

<210> SEQ ID NO 850
<211> LENGTH: 12
<212> TYPE: PRT
<213> ORGANISM: Artificial Sequence
<220> FEATURE:
<223> OTHER INFORMATION: Synthetic sequence

<400> SEQUENCE: 850

Tyr Cys Gln Gln Tyr Asp Tyr Trp Pro Pro Tyr Thr
1               5                   10

<210> SEQ ID NO 851
<211> LENGTH: 10
<212> TYPE: PRT
<213> ORGANISM: Artificial Sequence
<220> FEATURE:
<223> OTHER INFORMATION: Synthetic sequence

<400> SEQUENCE: 851

Tyr Cys Gln Gln Gly Tyr Tyr Leu Trp Thr
1               5                   10

<210> SEQ ID NO 852
<211> LENGTH: 10
<212> TYPE: PRT
<213> ORGANISM: Artificial Sequence
<220> FEATURE:
<223> OTHER INFORMATION: Synthetic sequence

<400> SEQUENCE: 852

Tyr Cys Gln Gln Gly Tyr Ser Ile Trp Thr
1               5                   10

<210> SEQ ID NO 853
```

```
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 1
<223> OTHER INFORMATION: Xaa = F or Y
<220> FEATURE:
<221> NAME/KEY: VARIANT
<222> LOCATION: 5
<223> OTHER INFORMATION: Xaa = G, N, or S

<400> SEQUENCE: 853

Xaa Thr Phe Ser Xaa Tyr Trp Ile His Trp Val
1               5                   10

<210> SEQ ID NO 854
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 4
<223> OTHER INFORMATION: Xaa = S or T
<220> FEATURE:
<221> NAME/KEY: VARIANT
<222> LOCATION: 7
<223> OTHER INFORMATION: Xaa = H or Y
<220> FEATURE:
<221> NAME/KEY: VARIANT
<222> LOCATION: 8
<223> OTHER INFORMATION: Xaa = H or Y
<220> FEATURE:
<221> NAME/KEY: VARIANT
<222> LOCATION: 10
<223> OTHER INFORMATION: Xaa = A, D, G, N, or S

<400> SEQUENCE: 854

Tyr Ser Ile Xaa Ser Gly Xaa Xaa Trp Xaa Trp Ile
1               5                   10

<210> SEQ ID NO 855
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 6
<223> OTHER INFORMATION: Xaa = G or S
<220> FEATURE:
<221> NAME/KEY: VARIANT
<222> LOCATION: 9
<223> OTHER INFORMATION: Xaa = A or G
<220> FEATURE:
<221> NAME/KEY: VARIANT
<222> LOCATION: 11
<223> OTHER INFORMATION: Xaa = A, G, or S

<400> SEQUENCE: 855

Phe Ser Leu Ser Thr Xaa Gly Val Xaa Val Xaa Trp Ile
1               5                   10

<210> SEQ ID NO 856
<211> LENGTH: 21
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: VARIANT
<222> LOCATION: 3
<223> OTHER INFORMATION: Xaa = G, S, V, or Y
<220> FEATURE:
<221> NAME/KEY: VARIANT
<222> LOCATION: 7
<223> OTHER INFORMATION: Xaa = A, D, S, or Y
<220> FEATURE:
<221> NAME/KEY: VARIANT
<222> LOCATION: 9
<223> OTHER INFORMATION: Xaa = D, G, or S
<220> FEATURE:
<221> NAME/KEY: VARIANT
<222> LOCATION: 10
<223> OTHER INFORMATION: Xaa = S or T

<400> SEQUENCE: 856

Val Ser Xaa Ile Ser Gly Xaa Gly Xaa Xaa Thr Tyr Tyr Ala Asp Ser
1               5                   10                  15

Val Lys Gly Arg Phe
            20

<210> SEQ ID NO 857
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 1
<223> OTHER INFORMATION: Xaa = Q or R
<220> FEATURE:
<221> NAME/KEY: VARIANT
<222> LOCATION: 5
<223> OTHER INFORMATION: Xaa = D, G, or S
<220> FEATURE:
<221> NAME/KEY: VARIANT
<222> LOCATION: 6
<223> OTHER INFORMATION: Xaa = I or V
<220> FEATURE:
<221> NAME/KEY: VARIANT
<222> LOCATION: 7
<223> OTHER INFORMATION: Xaa = G, R, S, or T
<220> FEATURE:
<221> NAME/KEY: VARIANT
<222> LOCATION: 8
<223> OTHER INFORMATION: Xaa = P, R, S, or T
<220> FEATURE:
<221> NAME/KEY: VARIANT
<222> LOCATION: 9
<223> OTHER INFORMATION: Xaa = A, F, S, V, or Y
<220> FEATURE:
<221> NAME/KEY: VARIANT
<222> LOCATION: 10
<223> OTHER INFORMATION: Xaa = L or V
<220> FEATURE:
<221> NAME/KEY: VARIANT
<222> LOCATION: 11
<223> OTHER INFORMATION: Xaa = A or G

<400> SEQUENCE: 857

Xaa Ala Ser Gln Xaa Xaa Xaa Xaa Xaa Xaa Xaa
1               5                   10

<210> SEQ ID NO 858
<211> LENGTH: 9
<212> TYPE: PRT
<213> ORGANISM: Artificial Sequence
<220> FEATURE:
<223> OTHER INFORMATION: Synthetic sequence
<220> FEATURE:
```

```
<221> NAME/KEY: VARIANT
<222> LOCATION: 1
<223> OTHER INFORMATION: Xaa = A or D
<220> FEATURE:
<221> NAME/KEY: VARIANT
<222> LOCATION: 4
<223> OTHER INFORMATION: Xaa = N or S
<220> FEATURE:
<221> NAME/KEY: VARIANT
<222> LOCATION: 5
<223> OTHER INFORMATION: Xaa = L or R
<220> FEATURE:
<221> NAME/KEY: VARIANT
<222> LOCATION: 6
<223> OTHER INFORMATION: Xaa = A, E, or Q
<220> FEATURE:
<221> NAME/KEY: VARIANT
<222> LOCATION: 7
<223> OTHER INFORMATION: Xaa = S or T
<220> FEATURE:
<221> NAME/KEY: VARIANT
<222> LOCATION: 9
<223> OTHER INFORMATION: Xaa = I or V

<400> SEQUENCE: 858

Xaa Ala Ser Xaa Xaa Xaa Xaa Gly Xaa
1               5

<210> SEQ ID NO 859
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 5
<223> OTHER INFORMATION: Xaa = A or G
<220> FEATURE:
<221> NAME/KEY: VARIANT
<222> LOCATION: 7
<223> OTHER INFORMATION: Xaa = S or Y
<220> FEATURE:
<221> NAME/KEY: VARIANT
<222> LOCATION: 8
<223> OTHER INFORMATION: Xaa = I, L, or T

<400> SEQUENCE: 859

Tyr Cys Gln Gln Xaa Tyr Xaa Xaa Trp Thr
1               5                   10

<210> SEQ ID NO 860
<211> LENGTH: 156
<212> TYPE: PRT
<213> ORGANISM: Macaca fascicularis

<400> SEQUENCE: 860

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95
```

Cys Cys Phe Gly Thr Phe Asn Asp Gln Lys Arg Gly Ile Cys Arg Pro
                100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
130                 135                 140

Gly Ala Ser Ser Ala Thr Pro Pro Ala Pro Arg
145                 150                 155

<210> SEQ ID NO 861
<211> LENGTH: 178
<212> TYPE: PRT
<213> ORGANISM: Mus musculus

<400> SEQUENCE: 861

Met Gly Asn Asn Cys Tyr Asn Val Val Ile Val Leu Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly

<210> SEQ ID NO 862
<211> LENGTH: 116
<212> TYPE: PRT
<213> ORGANISM: Artificial Sequence
<220> FEATURE:
<223> OTHER INFORMATION: Synthetic sequence

<400> SEQUENCE: 862

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr

```
                    65                  70                  75                  80
Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 863
<211> LENGTH: 108
<212> TYPE: PRT
<213> ORGANISM: Artificial Sequence
<220> FEATURE:
<223> OTHER INFORMATION: Synthetic sequence

<400> SEQUENCE: 863

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 864
<211> LENGTH: 121
<212> TYPE: PRT
<213> ORGANISM: Artificial Sequence
<220> FEATURE:
<223> OTHER INFORMATION: Synthetic sequence

<400> SEQUENCE: 864

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120

<210> SEQ ID NO 865
<211> LENGTH: 109
```

<212> TYPE: PRT
<213> ORGANISM: Artificial Sequence
<220> FEATURE:
<223> OTHER INFORMATION: Synthetic sequence

<400> SEQUENCE: 865

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 866
<211> LENGTH: 12
<212> TYPE: PRT
<213> ORGANISM: Artificial Sequence
<220> FEATURE:
<223> OTHER INFORMATION: Synthetic sequence

<400> SEQUENCE: 866

Gly Phe Ser Leu Ser Thr Ser Gly Val Gly Val Gly
1               5                   10

<210> SEQ ID NO 867
<211> LENGTH: 16
<212> TYPE: PRT
<213> ORGANISM: Artificial Sequence
<220> FEATURE:
<223> OTHER INFORMATION: Synthetic sequence

<400> SEQUENCE: 867

Leu Ile Asp Trp Asp Asp Asp Lys Tyr Tyr Ser Pro Ser Leu Lys Ser
1               5                   10                  15

<210> SEQ ID NO 868
<211> LENGTH: 13
<212> TYPE: PRT
<213> ORGANISM: Artificial Sequence
<220> FEATURE:
<223> OTHER INFORMATION: Synthetic sequence

<400> SEQUENCE: 868

Gly Gly Ser Asp Thr Val Leu Gly Asp Trp Phe Ala Tyr
1               5                   10

<210> SEQ ID NO 869
<211> LENGTH: 11
<212> TYPE: PRT
<213> ORGANISM: Artificial Sequence
<220> FEATURE:
<223> OTHER INFORMATION: Synthetic sequence

<400> SEQUENCE: 869

Arg Ala Ser Gln Ser Val Ser Pro Tyr Leu Ala
1               5                   10

```
<210> SEQ ID NO 870
<211> LENGTH: 7
<212> TYPE: PRT
<213> ORGANISM: Artificial Sequence
<220> FEATURE:
<223> OTHER INFORMATION: Synthetic sequence

<400> SEQUENCE: 870

Asp Ala Ser Ser Leu Glu Ser
1               5

<210> SEQ ID NO 871
<211> LENGTH: 8
<212> TYPE: PRT
<213> ORGANISM: Artificial Sequence
<220> FEATURE:
<223> OTHER INFORMATION: Synthetic sequence

<400> SEQUENCE: 871

Gln Gln Gly Tyr Ser Leu Trp Thr
1               5

<210> SEQ ID NO 872
<211> LENGTH: 11
<212> TYPE: PRT
<213> ORGANISM: Artificial Sequence
<220> FEATURE:
<223> OTHER INFORMATION: Synthetic sequence

<400> SEQUENCE: 872

Gly Tyr Ser Ile Thr Ser Gly His Tyr Trp Ala
1               5                   10

<210> SEQ ID NO 873
<211> LENGTH: 17
<212> TYPE: PRT
<213> ORGANISM: Artificial Sequence
<220> FEATURE:
<223> OTHER INFORMATION: Synthetic sequence

<400> SEQUENCE: 873

Ser Ile Ser Gly Tyr Gly Ser Thr Thr Tyr Tyr Ala Asp Ser Val Lys
1               5                   10                  15

Gly

<210> SEQ ID NO 874
<211> LENGTH: 13
<212> TYPE: PRT
<213> ORGANISM: Artificial Sequence
<220> FEATURE:
<223> OTHER INFORMATION: Synthetic sequence

<400> SEQUENCE: 874

Gly Gly Ser Asp Ala Val Leu Gly Asp Trp Phe Ala Tyr
1               5                   10

<210> SEQ ID NO 875
<211> LENGTH: 11
<212> TYPE: PRT
<213> ORGANISM: Artificial Sequence
<220> FEATURE:
<223> OTHER INFORMATION: Synthetic sequence

<400> SEQUENCE: 875

Arg Ala Ser Gln Gly Ile Gly Ser Phe Leu Ala
```

1               5                  10

<210> SEQ ID NO 876
<211> LENGTH: 7
<212> TYPE: PRT
<213> ORGANISM: Artificial Sequence
<220> FEATURE:
<223> OTHER INFORMATION: Synthetic sequence

<400> SEQUENCE: 876

Asp Ala Ser Asn Leu Glu Thr
1               5

<210> SEQ ID NO 877
<211> LENGTH: 8
<212> TYPE: PRT
<213> ORGANISM: Artificial Sequence
<220> FEATURE:
<223> OTHER INFORMATION: Synthetic sequence

<400> SEQUENCE: 877

Gln Gln Gly Tyr Tyr Leu Trp Thr
1               5

<210> SEQ ID NO 878
<211> LENGTH: 12
<212> TYPE: PRT
<213> ORGANISM: Artificial Sequence
<220> FEATURE:
<223> OTHER INFORMATION: Synthetic sequence

<400> SEQUENCE: 878

Gly Phe Ser Leu Ser Thr Gly Gly Val Gly Val Gly
1               5                  10

<210> SEQ ID NO 879
<211> LENGTH: 16
<212> TYPE: PRT
<213> ORGANISM: Artificial Sequence
<220> FEATURE:
<223> OTHER INFORMATION: Synthetic sequence

<400> SEQUENCE: 879

Leu Ile Asp Trp Ala Asp Asp Lys Tyr Tyr Ser Pro Ser Leu Lys Ser
1               5                  10                  15

<210> SEQ ID NO 880
<211> LENGTH: 13
<212> TYPE: PRT
<213> ORGANISM: Artificial Sequence
<220> FEATURE:
<223> OTHER INFORMATION: Synthetic sequence

<400> SEQUENCE: 880

Gly Gly Ser Asp Thr Val Ile Gly Asp Trp Phe Ala Tyr
1               5                  10

<210> SEQ ID NO 881
<211> LENGTH: 11
<212> TYPE: PRT
<213> ORGANISM: Artificial Sequence
<220> FEATURE:
<223> OTHER INFORMATION: Synthetic sequence

<400> SEQUENCE: 881

Arg Ala Ser Gln Ser Ile Gly Ser Tyr Leu Ala
1               5                  10

```
<210> SEQ ID NO 882
<211> LENGTH: 7
<212> TYPE: PRT
<213> ORGANISM: Artificial Sequence
<220> FEATURE:
<223> OTHER INFORMATION: Synthetic sequence

<400> SEQUENCE: 882

Asp Ala Ser Asn Leu Glu Thr
1               5

<210> SEQ ID NO 883
<211> LENGTH: 8
<212> TYPE: PRT
<213> ORGANISM: Artificial Sequence
<220> FEATURE:
<223> OTHER INFORMATION: Synthetic sequence

<400> SEQUENCE: 883

Gln Gln Gly Tyr Tyr Leu Trp Thr
1               5
```